(12) United States Patent
Palese et al.

(10) Patent No.: US 10,736,956 B2
(45) Date of Patent: Aug. 11, 2020

(54) INFLUENZA VIRUS VACCINATION REGIMENS

(71) Applicant: ICAHN SCHOOL OF MEDICINE AT MOUNT SINAI, New York, NY (US)

(72) Inventors: Peter Palese, New York, NY (US); Adolfo Garcia-Sastre, New York, NY (US); Florian Krammer, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 15/545,548

(22) PCT Filed: Jan. 22, 2016

(86) PCT No.: PCT/US2016/014640
§ 371 (c)(1),
(2) Date: Jul. 21, 2017

(87) PCT Pub. No.: WO2016/118937
PCT Pub. Date: Jul. 28, 2016

(65) Prior Publication Data
US 2018/0008696 A1   Jan. 11, 2018

Related U.S. Application Data

(60) Provisional application No. 62/215,277, filed on Sep. 8, 2015, provisional application No. 62/107,166, filed on Jan. 23, 2015.

(51) Int. Cl.
| | |
|---|---|
| *A61K 39/145* | (2006.01) |
| *A61K 39/12* | (2006.01) |
| *C07K 14/005* | (2006.01) |
| *C07K 14/11* | (2006.01) |
| *C12N 7/04* | (2006.01) |
| *A61K 39/00* | (2006.01) |

(52) U.S. Cl.
CPC ............ *A61K 39/145* (2013.01); *A61K 39/12* (2013.01); *C07K 14/005* (2013.01); *C07K 14/11* (2013.01); *C12N 7/04* (2013.01); *A61K 2039/543* (2013.01); *A61K 2039/575* (2013.01); *C07K 2319/00* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,522,811 A | 6/1985 | Eppstein et al. |
| 4,603,112 A | 7/1986 | Paoletti et al. |
| 4,693,981 A | 9/1987 | Wiesehahn et al. |
| 4,716,111 A | 12/1987 | Osband et al. |
| 4,722,848 A | 2/1988 | Paoletti et al. |
| 4,769,330 A | 9/1988 | Paoletti et al. |
| 5,057,540 A | 10/1991 | Kensil et al. |
| 5,106,619 A | 4/1992 | Wiesehahn et al. |
| 5,110,587 A | 5/1992 | Paoletti et al. |
| 5,166,057 A | 11/1992 | Palese et al. |
| 5,174,993 A | 12/1992 | Paoletti |
| 5,182,192 A | 1/1993 | Steplewski et al. |
| 5,413,923 A | 5/1995 | Kucherlapati et al. |
| 5,484,719 A | 1/1996 | Lam et al. |
| 5,545,806 A | 8/1996 | Lonberg et al. |
| 5,569,825 A | 10/1996 | Lonberg et al. |
| 5,571,709 A | 11/1996 | Devauchelle et al. |
| 5,573,916 A | 11/1996 | Cheronis et al. |
| 5,589,174 A | 12/1996 | Okuno et al. |
| 5,612,487 A | 3/1997 | Lam et al. |
| 5,625,126 A | 4/1997 | Lonberg et al. |
| 5,631,350 A | 5/1997 | Okuno et al. |
| 5,633,425 A | 5/1997 | Lonberg et al. |
| 5,643,576 A | 7/1997 | Johnston et al. |
| 5,661,016 A | 8/1997 | Lonberg et al. |
| 5,820,871 A | 10/1998 | Palese et al. |
| 5,854,037 A | 12/1998 | Palese et al. |
| 5,885,793 A | 3/1999 | Griffiths et al. |
| 5,891,705 A | 4/1999 | Budowsky et al. |
| 5,916,771 A | 6/1999 | Hori et al. |

(Continued)

FOREIGN PATENT DOCUMENTS

| | | |
|---|---|---|
| CA | 2121559 A1 | 10/1994 |
| CA | 2718923 A1 | 9/2009 |

(Continued)

OTHER PUBLICATIONS

Air, "Influenza virus antigenicity and broadly neutralizing epitopes," Curr. Opin. Virol. 11:113-121 (2015).

(Continued)

*Primary Examiner* — Benjamin P Blumel
(74) *Attorney, Agent, or Firm* — Jones Day

(57) ABSTRACT

Provided herein are immunization regimens for inducing an immune response (e.g., an antibody response) against influenza virus. In specific aspects, the immunization regimens involve the administration of a chimeric hemagglutinin (HA), a headless HA or another influenza virus stem domain based construct (e.g., the HA stem domain or a fragment thereof) to a subject. In certain aspects, the immunization regimens also involve the administration of an influenza virus neuraminidase immunogen.

Figure 2A:
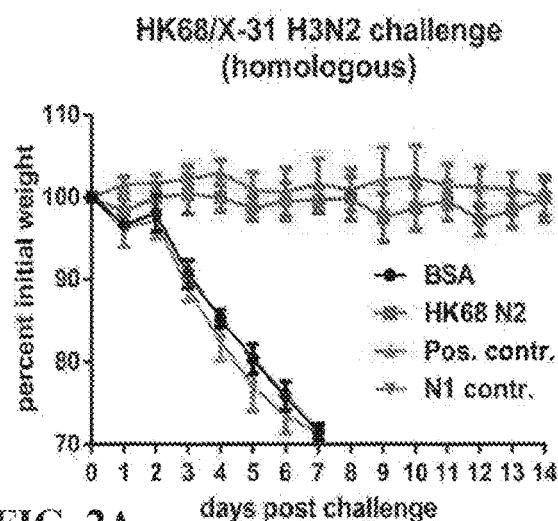

24 Claims, 25 Drawing Sheets
Specification includes a Sequence Listing.

(56) References Cited

U.S. PATENT DOCUMENTS

| | | |
|---|---|---|
| 5,929,304 A | 7/1999 | Radin et al. |
| 6,001,634 A | 12/1999 | Palese et al. |
| 6,034,298 A | 3/2000 | Lam et al. |
| 6,136,320 A | 10/2000 | Arntzen et al. |
| 6,146,642 A | 11/2000 | Garcia-Sastre et al. |
| 6,165,476 A | 12/2000 | Strom et al. |
| 6,265,189 B1 | 7/2001 | Paoletti et al. |
| 6,337,070 B1 | 1/2002 | Okuno et al. |
| 6,468,544 B1 | 10/2002 | Egorov et al. |
| 6,544,785 B1 | 4/2003 | Palese et al. |
| 6,551,820 B1 | 4/2003 | Mason et al. |
| 6,573,079 B1 | 6/2003 | Palese et al. |
| 6,635,246 B1 | 10/2003 | Barrett et al. |
| 6,649,372 B1 | 11/2003 | Palese et al. |
| 6,669,943 B1 | 12/2003 | Palese et al. |
| 6,720,409 B2 | 4/2004 | Okuno et al. |
| 6,770,799 B2 | 8/2004 | Mor et al. |
| 6,852,522 B1 | 2/2005 | Palese et al. |
| 6,867,293 B2 | 3/2005 | Andrews et al. |
| 6,887,699 B1 | 5/2005 | Palese et al. |
| 6,942,861 B2 | 9/2005 | McKee et al. |
| 6,951,754 B2 | 10/2005 | Hoffmann |
| 7,312,064 B2 | 12/2007 | Hoffmann |
| 7,384,774 B2 | 6/2008 | Palese et al. |
| 7,442,379 B2 | 10/2008 | Garcia-Sastre et al. |
| 7,494,808 B2 | 2/2009 | Palese et al. |
| 7,504,560 B2 | 3/2009 | Arntzen et al. |
| 7,566,458 B2 | 7/2009 | Yang et al. |
| 8,367,077 B2 | 2/2013 | Zurbriggen et al. |
| 8,603,467 B2 | 12/2013 | Chen et al. |
| 8,673,314 B2 | 3/2014 | Garcia Sastre et al. |
| 8,828,406 B2 | 9/2014 | Garcia-Sastre et al. |
| 9,051,359 B2 | 6/2015 | Garcia-Sastre et al. |
| 9,175,069 B2 | 11/2015 | Garcia-Sastre et al. |
| 9,371,366 B2 | 6/2016 | Garcia-Sastre et al. |
| 9,452,211 B2 | 9/2016 | Meijberg et al. |
| 9,701,723 B2 | 7/2017 | Garcia-Sastre et al. |
| 9,707,288 B2 | 7/2017 | Schrader |
| 9,708,373 B2 | 7/2017 | Garcia-Sastre et al. |
| 9,849,172 B2 | 12/2017 | Garcia-Sastre et al. |
| 9,908,930 B2 | 3/2018 | Palese et al. |
| 9,968,670 B2 | 5/2018 | Garcia-Sastre et al. |
| 10,131,695 B2 | 11/2018 | Garcia-Sastre et al. |
| 10,137,189 B2 | 11/2018 | Garcia-Sastre et al. |
| 10,179,806 B2 | 1/2019 | Garcia-Sastre et al. |
| 10,544,207 B2 | 1/2020 | Palese et al. |
| 10,583,188 B2 | 3/2020 | Garcia-Sastre et al. |
| 2002/0164770 A1 | 11/2002 | Hoffman |
| 2003/0134338 A1 | 7/2003 | Makarocskiy |
| 2004/0002061 A1 | 1/2004 | Kawaoka |
| 2004/0073011 A1 | 4/2004 | Hagay et al. |
| 2005/0009008 A1 | 1/2005 | Robinson et al. |
| 2005/0042229 A1 | 2/2005 | Yang et al. |
| 2005/0048074 A1 | 3/2005 | Cardineau et al. |
| 2005/0064391 A1 | 3/2005 | Segal et al. |
| 2005/0106178 A1 | 5/2005 | O'Hagan et al. |
| 2005/0201946 A1 | 9/2005 | Friede et al. |
| 2006/0008473 A1 | 1/2006 | Yana et al. |
| 2006/0204487 A1 | 9/2006 | Shaaltiel et al. |
| 2006/0217338 A1 | 9/2006 | Lu et al. |
| 2006/0280754 A1 | 12/2006 | Garry et al. |
| 2007/0020238 A1 | 1/2007 | Baltimore et al. |
| 2007/0036809 A1 | 2/2007 | Michl et al. |
| 2007/0207171 A1 | 9/2007 | Dubensky et al. |
| 2007/0275014 A1 | 11/2007 | Yusibov et al. |
| 2008/0019998 A1 | 1/2008 | Wang et al. |
| 2008/0032921 A1 | 2/2008 | Alexander et al. |
| 2008/0038232 A1 | 2/2008 | Shaaltiel et al. |
| 2008/0152657 A1 | 6/2008 | Horowitz et al. |
| 2008/0176247 A1 | 7/2008 | Chou et al. |
| 2008/0193455 A1 | 8/2008 | Stassen et al. |
| 2008/0248066 A1 | 10/2008 | Dubensky et al. |
| 2009/0053762 A1 | 2/2009 | Shaaltiel |
| 2009/0068221 A1 | 3/2009 | Morrison |
| 2009/0081255 A1 | 3/2009 | Bublot et al. |
| 2009/0082548 A1 | 3/2009 | Shaaltiel et al. |
| 2009/0169547 A1 | 7/2009 | Sahin et al. |
| 2009/0208477 A1 | 8/2009 | Shaaltiel et al. |
| 2009/0291472 A1 | 11/2009 | Lu et al. |
| 2009/0304730 A1 | 12/2009 | Amon et al. |
| 2009/0304739 A1 | 12/2009 | Rappouli et al. |
| 2009/0311265 A1 | 12/2009 | Van Den Brink et al. |
| 2009/0311669 A1 | 12/2009 | Kawaoka |
| 2010/0184192 A1 | 7/2010 | Smith et al. |
| 2010/0297165 A1 | 11/2010 | Berzofsky et al. |
| 2010/0297174 A1 | 11/2010 | Garcia-Sastre et al. |
| 2011/0027270 A1 | 2/2011 | Garcia-Sastre et al. |
| 2011/0111494 A1 | 5/2011 | Hill et al. |
| 2011/0182938 A1 | 7/2011 | Weiner et al. |
| 2012/0039898 A1 | 2/2012 | Throsby et al. |
| 2012/0122185 A1 | 5/2012 | Palese et al. |
| 2012/0189658 A1 | 7/2012 | Couture et al. |
| 2012/0244183 A1 | 9/2012 | Garcia-Sastre et al. |
| 2013/0129747 A1 | 5/2013 | Schrader |
| 2013/0129761 A1 | 5/2013 | Garcia-Sastre et al. |
| 2013/0209499 A1 | 8/2013 | Garcia-Sastre et al. |
| 2013/0224187 A1 | 8/2013 | Rother et al. |
| 2014/0170163 A1 | 6/2014 | Garcia Sastre et al. |
| 2014/0193484 A1 | 7/2014 | Bertholet Girardin et al. |
| 2014/0328875 A1 | 11/2014 | Garcia Sastre et al. |
| 2015/0132330 A1 | 5/2015 | Garcia-Sastre et al. |
| 2015/0239960 A1 | 8/2015 | Garcia-Sastre et al. |
| 2015/0252103 A1 | 9/2015 | Sahin et al. |
| 2015/0266951 A1 | 9/2015 | Song |
| 2015/0297712 A1 | 10/2015 | Garcia-Sastre et al. |
| 2015/0299270 A1 | 10/2015 | Galarza et al. |
| 2015/0335729 A1 | 11/2015 | Garcia-Sastre et al. |
| 2016/0015828 A1 | 1/2016 | Torgov et al. |
| 2016/0017025 A1 | 1/2016 | Samira et al. |
| 2016/0022806 A1 | 1/2016 | Weiner et al. |
| 2016/0038585 A1 | 2/2016 | Dormitzer et al. |
| 2016/0137721 A1 | 5/2016 | Palese et al. |
| 2016/0185860 A1 | 6/2016 | Sahin et al. |
| 2016/0355553 A1 | 12/2016 | Meijberg et al. |
| 2016/0355590 A1 | 12/2016 | Epstein |
| 2016/0361408 A1 | 12/2016 | Garcia-Sastre et al. |
| 2016/0362455 A1 | 12/2016 | Meijberg et al. |
| 2016/0376347 A1 | 12/2016 | Saelens et al. |
| 2017/0327565 A1 | 11/2017 | Schrader |
| 2018/0002385 A1 | 1/2018 | Garcia-Sastre et al. |
| 2018/0008696 A1 | 1/2018 | Palese et al. |
| 2018/0265573 A1 | 9/2018 | Palese et al. |
| 2018/0333479 A1 | 11/2018 | Garcia-Sastre et al. |
| 2019/0099484 A1 | 4/2019 | Garcia-Sastre et al. |
| 2019/0106461 A1 | 4/2019 | Garcia-Sastre et al. |
| 2019/0125859 A1 | 5/2019 | Palese et al. |
| 2019/0314485 A1 | 10/2019 | Palese et al. |

FOREIGN PATENT DOCUMENTS

| | | |
|---|---|---|
| CN | 1196788 C | 4/2005 |
| CN | 103665155 A | 3/2014 |
| EP | 0621339 A2 | 10/1994 |
| EP | 0702085 A1 | 3/1996 |
| EP | 0780475 A1 | 6/1997 |
| EP | 2540312 A1 | 1/2013 |
| JP | A-H7-89992 | 4/1995 |
| JP | H 10-502168 A | 2/1998 |
| JP | 2004-258814 A | 9/2004 |
| JP | 2006-347922 A | 12/2006 |
| JP | 2008-249712 A | 10/2008 |
| JP | 2009022186 A | 2/2009 |
| JP | 2009131237 A | 6/2009 |
| JP | 2012521786 A | 10/2010 |
| JP | 2011-057653 A | 3/2011 |
| JP | 2012-530499 A | 12/2012 |
| WO | WO 1984/000687 | 3/1984 |
| WO | WO 1991010741 A1 | 7/1991 |
| WO | WO 1992/001047 | 1/1992 |
| WO | WO 1994/009136 | 4/1994 |
| WO | WO 1994012629 A1 | 6/1994 |
| WO | WO 1994/016109 | 7/1994 |
| WO | WO 1994/017826 | 8/1994 |
| WO | WO 1995/034324 | 12/1994 |

(56) References Cited

FOREIGN PATENT DOCUMENTS

| | | |
|---|---|---|
| WO | WO 1996011279 A2 | 4/1996 |
| WO | WO 1996/033735 | 10/1996 |
| WO | WO 1996/034096 | 10/1996 |
| WO | WO 1996034625 A1 | 11/1996 |
| WO | WO 1997006270 A1 | 2/1997 |
| WO | WO 1997012032 A1 | 4/1997 |
| WO | WO 1997/040177 | 10/1997 |
| WO | WO 1997040161 A1 | 10/1997 |
| WO | WO 1998002530 A1 | 1/1998 |
| WO | WO 1998013501 A2 | 4/1998 |
| WO | WO 1998016654 A1 | 4/1998 |
| WO | WO 1998/024893 | 6/1998 |
| WO | WO 1998046645 A2 | 10/1998 |
| WO | WO 1998050433 A2 | 11/1998 |
| WO | WO 1998053078 A1 | 11/1998 |
| WO | WO 1999002657 A1 | 1/1999 |
| WO | WO 1999015672 A1 | 4/1999 |
| WO | WO 2001004333 A1 | 1/2001 |
| WO | WO 2002000885 A2 | 1/2002 |
| WO | WO 2005000901 A2 | 1/2005 |
| WO | WO 2007/045674 | 4/2007 |
| WO | WO 2007/064802 | 6/2007 |
| WO | WO 2007/103322 | 9/2007 |
| WO | WO 2007109812 A2 | 9/2007 |
| WO | WO 2007109813 A1 | 9/2007 |
| WO | WO 2007110776 A1 | 10/2007 |
| WO | WO 2007/134327 | 11/2007 |
| WO | WO 2007134237 A2 | 11/2007 |
| WO | WO 2008/005777 | 1/2008 |
| WO | WO 2008/028946 | 3/2008 |
| WO | WO 2008/032219 | 3/2008 |
| WO | WO 2009001217 A2 | 12/2008 |
| WO | WO 2009/009876 | 1/2009 |
| WO | WO 2009012489 A1 | 1/2009 |
| WO | WO 2009/025770 | 2/2009 |
| WO | WO 2009/036157 | 3/2009 |
| WO | WO 2009/068992 | 6/2009 |
| WO | WO 2009/076778 | 6/2009 |
| WO | WO 2009/079259 | 6/2009 |
| WO | WO 2009/092038 | 7/2009 |
| WO | WO 2009/121004 | 10/2009 |
| WO | WO 2009/150532 | 12/2009 |
| WO | WO 2009/156405 | 12/2009 |
| WO | WO 2010/003235 | 1/2010 |
| WO | WO 2010/036948 | 4/2010 |
| WO | WO 2010036170 A1 | 4/2010 |
| WO | WO 2010/117786 | 10/2010 |
| WO | WO 2010/130636 | 11/2010 |
| WO | WO 2010/138564 | 12/2010 |
| WO | WO 2010/148511 | 12/2010 |
| WO | WO 2011/014645 | 2/2011 |
| WO | WO 2011/044152 | 4/2011 |
| WO | WO 2011/087092 | 7/2011 |
| WO | WO 2011/103453 | 8/2011 |
| WO | WO 2011/111966 | 9/2011 |
| WO | WO 2011/123495 | 10/2011 |
| WO | WO 2011126370 A1 | 10/2011 |
| WO | WO 2012/009790 | 1/2012 |
| WO | WO 2013/043729 | 3/2013 |
| WO | WO 2013/079473 | 6/2013 |
| WO | WO 2014/159960 | 1/2014 |
| WO | WO 2014/099931 | 6/2014 |
| WO | WO 2014/152841 | 9/2014 |
| WO | WO 2015/199564 | 12/2015 |
| WO | WO 2016005480 A1 | 1/2016 |
| WO | WO 2016005482 A1 | 1/2016 |
| WO | WO 2016118937 A1 | 7/2016 |
| WO | WO 2016/205347 | 12/2016 |
| WO | WO 2017021893 A1 | 2/2017 |
| WO | WO 2017035479 A1 | 3/2017 |
| WO | WO 2017053413 A1 | 3/2017 |
| WO | WO 2017136575 A1 | 8/2017 |
| WO | WO 2017210445 A1 | 12/2017 |
| WO | WO 2017218624 A1 | 12/2017 |
| WO | WO 2018187706 A2 | 10/2018 |
| WO | WO 2019032463 A1 | 2/2019 |
| WO | WO 2019246363 A1 | 12/2019 |

OTHER PUBLICATIONS

Anonymous, "alignment" IBIS—Integrated Biotechnological Information, European Patent Office, retrieved from ibis.internal.epo.org/exam/jobResult?id=285344, on Sep. 26, 2014 (1 page).

Anonymous, "Amino Acids Reference Chart—Sigma-Aldrich" retreived from www.sigmaaldrich.com/life-science/metabolomics/learning-center/amino-acid-reference-chart.html, on Jul. 17, 2015 (3 pages).

Doyle et al., "A monoclonal antibody targeting a highly conserved epitope in influenza B neuraminidase provides protection against drug resistant strains," Biochem. Biophys. Res. Commun. 441(1):226-229 (2013).

Ermler et al., "Chimeric Hemagglutinin Constructs Induce Broad Protection against Influenza B Virus Challenge in the Mouse Model," J. Virol. 91(12): e00286-17 (2017).

Extended European Search Report for European Application No. 11763347.9, dated Feb. 2, 2015.

Fleury, et al., 2007, GenBank Acc. No: P03437, Updated Apr. 3, 2007.

Georgiev et al., 2018, "Two-Component Ferritin Nanoparticles for Multimerization of Diverse Trimeric Antigens," ACS Infect Dis., 4(5):788-796.

Gravel et al., "Qualitative and quantitative analyses of virtually all subtypes of influenza A and B viral neuraminidases using antibodies targeting the universally conserved sequences," Vaccine 28(36):5774-5784 (2010).

Harvey et al., 2011, "Improved antigen yield in pandemic H1N1 (2009) candidate vaccine viruses with chimeric hemagglutinin molecules," J Virol., 85(12):6086-6090.

Hu et al., "Fully human broadly neutralizing monoclonal antibodies against influenza A viruses generated from the memory B cells of a 2009 pandemic H1N1 influenza vaccine recipient," Virology 435(2):320-328 (2013) (Epub Oct. 16, 2012).

Impagliazzo et al., 2015, "A stable trimeric influenza hemagglutinin stem as a broadly protective immunogen." Science, 349(6254):1301-1306 and supplemental materials.

International Preliminary Report on Patentability of International application No. PCT/US2011/030441, dated Oct. 2, 2012.

International Search Report of International Application No. PCT/US2018/026489, dated Aug. 27, 2018.

Krammer, 2017, "Annex I: Sequence comparison of the J&J, VRC and MSSM headless HA constructs (tentative H3 numbering included)" (3 pages).

Nelson et al., 2008, "Lehninger Principles of Biochemistry—Fifth Edition," Chapter 4.3, p. 123, W.H. Freeman and Company.

Singleton et al., 1995, "Dictionary of Microbiology and Molecular Biology—Second Edition." A Wiley-Interscience Publication (3 pages).

Van Der Lubbe, 2018, "Mini-HA Is Superior to Full Length Hemagglutinin Immunization in Inducing Stem-Specific Antibodies and Protection Against Group 1 Influenza Virus Challenges in Mice," Front Immunol., 9:2350.

Wohlbold et al., "Broadly protective murine monoclonal antibodies against influenza B virus target highly conserved neuraminidase epitopes," Nat. Microbiol. 2(10):1415-1424 (2017).

Written Opinion of the International Searching Authority for International Application No. PCT/US2018/026489, dated Aug. 27, 2018.

Babai et al., "A novel liposomal influenza vaccine (INFLUSOME-VAC) containing hemagglutinin-neuraminidase and IL-2 or GM-CSF induces protective anti-neuraminidase antibodies cross-reacting with a wide spectrum of influenza A viral strains." Vaccine. 20(3-4);505-15.

Babu et al., 2014, "Live attenuated H7N7 influenza vaccine primes for a vigorous antibody response to inactivated H7N7 influenza vaccine," Vaccine, 32:6798-6804.

(56) References Cited

OTHER PUBLICATIONS

Berry, 2007, "Cross-reactive MAb to the binding domain of botulinum neurotoxin A, B, and E developed using a sequential immunization strategy: anti-botulinum neurotoxin", Hybridoma, 26(6).

Bianchi et al., 2005, "Universal influenza B vaccine based on the maturational cleavage site of the hemagglutinin precursor", Journal of Virology; 79(12):7380-7388.

Bommakanti et al., 2010, "Design of an HA2-based *Escherichia coli* expressed influenza immunogen that protects mice from pathogenic challenge", Proc Natl Acad Sci USA, 107:13701-13706.

Bommakanti et al., 2012, "Design of *Eschericia coli*-Expressed Stalk Domain Immunogens of H1N1 Hemagglutinin That Protect Mice from Lethal Challenge." J. Virol., 86(24):13434-13444.

Boni et al., 2010, "Guidelines for identifying homologous recombination events in influenza A virus", PLoS One, 5(5):e10434.

Boni et al., 2012, "no. evidence for intra-segment recombination of 2009 H1N1 influenza virus in swine", Gene, 494(2):242-245.

Bowie, et al., 1990, "Deciphering the Message in Protein Sequences: Tolerance to Amino Acid Substitutions." Science, 247: 1306-1310.

Bullough et al., 1994, "Structure of influenza haemagglutinin at the pH of membrane fusion." Nature, 371:37-43.

Casali et al., 2008, "Site-directed mutagenesis of the hinge peptide from the hemagglutinin protein: enhancement of the pH-responsive conformational change." Protein Engineering Design & Selection, 21(6):395-404.

Centers for Disease Control and Prevention Metropolitan Atlanta Congenital Defects Program (CDC MACDP) guidelines. Birth defects and genetic diseases branch 6-digit code for reportable congenital anomalies; http://www.cdc.gov/ncbddd/birthdefects/documents/MACDPcode0807.pdf.

Chen et al., 1999, "N- and C-terminal residues combine in the fusion-pH influenza hemagglutinin HA2 subunit to form an N cap that terminates the triple-stranded coiled coil." Proc. Natl. Acad Sci., 91:8967-8972.

Chen et al., 2007, "Influenza Virus Hemagglutinin and Neuraminidase, but Not the Matrix Protein, Are Required for Assembly and Budding of Plasmid-Derived Virus-Like Particles", J. Virol. 81(13):7111-7123.

Chen et al., 2010, "Generation of Live Attenuated Novel Influenza Virus A/California/7/09 (H1N1) Vaccines with High Yield in Embryonated Chicken Eggs." J. Virol. 84(1):44-51.

Chen et al., 2011, "Vaccine design of hemagglutinin glycoprotein against influenza", Trends in Biotechnology, 29(9):426-434.

Chen et al., 2016, "Influenza A viruses expressing intra- or intergroup chimeric hemagglutinins", doi:10.1128/JVI.03060-15.

Clementi et al., 2011, "A Human Monoclonal Antibody with Neutralizing Activity against Highly Divergent Influenza Subtypes". PLoS ONE, 6(12):e28001.

Copeland et al., 2005, "Functional chimeras of human immunodeficiency virus type 1 Gp120 and influenza A virus (H3) hemagglutinin", Journal of Virology; 79:6459-6471.

Corti et al., 2011, "A neutralizing antibody selected from plasma cells that binds to group 1 and group 2 influenza A hemagglutinins", Science. 333(6044):850-856.

Cotter et al., 2014, "A Single Amino Acid in the Stalk Region of the H1N1pdm Influenza Virus HA Protein Affects Viral Fusion, Stability and Infectivity." PLoS Pathogens, 10(1):e1003831.

Cox and Fukuda, 1998, "Influenza," Infect.Dis.Clin.North Am, 12:27-38.

Crotty et al., 2004, "Tracking human antigen-specific memory B cells: a sensitive and generalized ELISPOT system," *J. Immunol. Methods*, 286 (1-2): 111-122.

D'Aoust et al., 2008, "Influenza virus-like particles produced by transient expression in Nicotiana benthaminana induce a protective immune response against a lethal viral challenge in mice", J. Plant Biotechnology, 6(9):930-940.

D'Aoust et al., 2010, "The production of hemagglutinin-based virus-like particles in plants: a rapid, efficient and safe response to pandemic influenza", Plant Biotechnology, 8(5):607-619.

Das et al., 2010, "Glycosylation Focuses Sequence Variation in the Influenza A Virus H1 Hemagglutinin Globular Domain." PLoS Pathogens, 6(11):e1001211.

Database Geneseq "Influenza A virus hemagglutinin protein, 1-11PR8", Accession No. AJG95109, dated Nov. 15, 2007.

Database GenPept "Hemagglutinin precursor [Contains. Hemagglutinin HA1 chain; Hemagglutinin HA2 chain]", Accession No. P03437, dated Jul. 21, 1986.

Dillon et al., 1992, "Induction of protective class I MHC-restricted CTL in mice by a recombinant influenza vaccine in aluminum hydroxide adjuvant", Vaccine, 10(5):309-318.

Doms RW & Moore JP, 2000, "HIV-1 Membrane Fusion: Targets of Opportunity," JCB, 151(2): F9-F13.

Doyle et al., 1986, "Analysis of Progressive Deletions of the Transmembrane and Cytoplasmic Domains of Influenza Hemagglutinin", JCB, 103:1193-1204.

Dunand et al., 2016, "Both Neutralizing and Non-Neutralizing Human H7N9 Influenza Vaccine-Induced Monoclonal Antibodies Confer Protection," Cell Host & Microbe, 19:1-14.

Eda et al., 2006, "Sequential immunization with V3 peptides from primary human immunodeficiency virus type 1 produces cross-neutralizing antibodies against primary isolates with a matching narrow-neutralization sequence motif" J Virol, 80(11):5552-5562.

Ekiert et al., 2009, "Antibody recognition of a highly conserved influenza virus epitope", Science; 324(5924):246-251.

Ekiert et al., 2011, "A highly conserved neutralizing epitope on group 2 influenza A viruses", Science 333:843-850.

Ekiert et al., 2012, "Cross-neutralization of influenza A viruses mediated by a single antibody loop", Nature, 489:526-532.

EMA Guideline on the exposure to medicinal products during pregnancy: need for post-authorization data (Doc. Ref. EMEA/CHMP/313666/2005 ) adopted at Community level in May 2006); http://www.ema.europa.eu/docs/en_GB/document_library/Regulatory_and_procedural_guideline/2009/11/WC500011303.pdf.

Flandorfer et al., 2003, "Chimeric Influenza A Viruses with a Functional Influenza B Virus Neuraminidase or Hemagglutinin", J. Virol., 77(17):9116-9123.

Fluzone®, 2009-2010 Fluzone Seasonal influenza vaccine package insert, 2009.

Fodor et al., 1999, "Rescue of influenza A virus from recombinant DNA", J Virol 73:9679-9682.

Fujii et al., 2002, "Selective incorporation of influenza virus RNA segments into virions", Proc. Natl. Acad. Sci. USA 100:2002-2007.

Gao & Palese, 2009, "Rewiring the RNAs of influenza virus to prevent reassortment", PNAS 106:15891-15896.

Gao et al., 2013, "Human infection with a novel avian-origin influenza A(H7N9) virus", N. Engl. J. Med. 368:1888-1897.

García-Sastre et al., 1994, "Introduction of foreign sequences into the genome of influenza A virus", Dev. Biol. Stand, 82:237-246.

García-Sastre et al., 1994, "Use of a mammalian internal ribosomal entry site element for expression of a foreign protein by a transfectant influenza virus", J. Virol. 68:6254-6261.

Gauger et al., 2011, "Enhanced pneumonia and disease in pigs vaccinated with an inactivated human-like (δ-cluster) H1N2 vaccine and challenged with pandemic 2009 H1N1 influenza virus." Vaccine., 29(15): 2712-2719.

Genbank, NCBI Reference Sequence: YP_163736.1, HA2 [Influenza A virus (A/Puerto Rico/8/1934(H1N1))].

Gerhard et al., 2006, "Prospects for universal influenza virus vaccine", Emerging Infectious Diseases; 12(4):569-574.

Gibbs et al., 2001, "Recombination in the hemagglutinin gene of the 1918 Spanish Flu". Science, 293(5536):1842-1845.

Giddings et al., 2000, "Transgenic plants as factories for biopharmaceuticals", Nature Biotechnology, 18:1151-1155.

Gocnik et al., 2008, "Antibodies Induced by the HA2 Glycopolypeptide of Influenza Virus Haemagglutinin Improve Recovery from Influenza A Virus Infection," J Gen Virol., 89:958-967.

Goff et al., 2013, "Induction of cross-reactive antibodies to novel H7N9 influenza virus by recombinant Newcastle disease virus expressing a North American lineage H7 subtype hemagglutinin," *J. Virol.*, 87(14): 8235-40.

Goff et al., 2013, "Adjuvants and immunization strategies to induce influenza virus hemagglutinin stalk antibodies", PLoS One 8:e79194.

(56) References Cited

OTHER PUBLICATIONS

Gomord et al., 2005, "Biopharmaceutical production in plants: problems, solutions and opportunities." TRENDS in Biotechnology, 23(11):559-565.
Gould et al., 1987, "Mouse H-2k-Restricted Cytotoxic T Cells Recognize Antigenic Determinants in Both the HA1 and HA2 Subunits of the Influenza A/PR/8/34 Hemagglutinin," J. Exp. Med., 166:693-701.
Graham et al., 2013, "DNA Vaccine Delivered by a Needle-Free Injection Device Improves Potency of Priming for Antibody and CD8+ TCell Responses after rAd5 Boost in a Randomized Clinical Trial," PLoS ONE, 8(4): 1-11, e59340.
Graves et al., 1983, "Preparation of influenza virus subviral particles lacking the HAI subunit of hemagglutinin: unmasking of cross-reactive HA2 determinants," Virology, 126(1):106-1 16).
Hai et al., 2008, "Influenza B virus NS1-truncated mutants: live-attenuated vaccine approach", J Virol 82:10580-10590.
Hai et al., 2011, "A reassortment-incompetent live attenuated influenza virus vaccine for protection against pandemic virus strains", Journal of virology 85:6832-6843.
Hai et al., 2012, "Influenza viruses expressing chimeric hemagglutinins: globular head and stalk domains derived from different subtypes", J. Virol. 86:5774-5781.
Hallily et al., 2015, "High-Affinity H7 Head and Stalk Domain-Specific Antibody Response to an Inactivated Influenza H7N7 Vaccine After Priming With Live Attenuated Influenza Vaccine," Journal of Infectious Diseases, 212: 1270-1278.
Haynes, 2009, "Influenza virus-like particle vaccines", Expert Rev. Vaccines, 8(4): 435-445.
Heaton et al., "In Vivo Bioluminescent Imaging of Influenza A Virus Infection and Characterization of Novel Cross-Protective Monoclonal Antibodies," J. Virol. 87(15):8272-8281 (2013).
Hong et al., "Antibody recognition of the pandemic H1N1 Influenza virus hemagglutinin receptor binding site," J. Virol. 87(22):12471-12480 (2013) (Epub Sep. 11, 2013).
Horimoto et al., 2003, "Generation of influenza A viruses with chimeric (type A/B) hemagglutinins." J Virol. 77(14):8031-8038.
Horimoto et al., 2004, "Influenza A viruses possessing type B hemagglutinin and neuraminidase: potential as vaccine components." Microbes and Infection, 6(6): 579-583.
Horvath et al., 1998, "Hemagglutinin-based multipeptide construct elicits enhanced protective immune response in mice against influenza A virus infection", Immunology Letters; 60(2/03):127-136.
Igarashi et al.: 2008, "Genetically destined potentials for N-linked glycosylation of influenza virus hemagglutinin" Virology, 376:323-329.
Impagliazzo et al., 2015, "A stable trimeric influenza hemagglutinin stem as a broadly protective immunogen." Science, 349(6254):1301-1306.
International Search Report dated Feb. 19, 2013 or PCT Application No. PCT/US2012/056122, Published as WO 2013/043729.
International Search Report dated Apr. 28, 2014 of PCT Application No. PCT/US2013/075697, Published as WO 2014/099931.
International Search Report dated Jun. 26, 2014 for PCT Application No. PCT/US2014/025526, Published as WO 2014/159960.
International Search Report dated Jul. 13, 2011 of PCT Application No. PCT/US2011/030441, Published as WO 2011/123495.
International Search Report dated Aug. 24, 2010 or PCT Application No. PCT/US2010/029202, Published as WO 2010/117786.
International Search Report dated Nov. 3, 2017, for International Application No. PCT/US2017/037384.
International Search Report dated Oct. 25, 2017, for International Application No. PCT/US2017/035479.
International Search Report dated Sep. 15, 2016, for International Application No. PCT/US2016/037595.
International Search Report of International Application No. PCT/US2016/014640, dated Jun. 3, 2016.
International Search Report of International application No. PCT/US2011/025467, dated Oct. 19, 2011.
International Search Report of International application No. PCT/US2010/036170, dated Aug. 17, 2010.
Izurieta et al., 2000, "Influenza and the rates of hospitalization for respiratory disease among infants and young children," NEJM,342(4):232-239.
Kanekiyo et al., 2013, "Self-assembling influenza nanoparticle vaccines elicit broadly neutralizing H1N1 antibodies." Nature, 499(7456):102-6.
Kashyap et al., 2008, "Combinatorial antibody libraries from survivors of the Turkish H5N1 avian influenza outbreak reveal virus neutralization strategies", Proc Natl Acad Sci USA; 105:5986-5991.
Kaverin et al., 2004, "Structural Differences Among Hemagglutinins of Influenza A Virus Subtypes Are Reflected in Their Antigenic Architecture: Analysis of H9 Escape Mutants", Journal of Virology, 78(1):240-249.
Khurana et al., 2013, "DNA Priming Prior to Inactivated Influenza A(H5N1) Vaccination Expands the Antibody Epitope Repertoire and Increases Affinity Maturation in a Boost-Interval-Dependent Manner in Adults," Journal of Infectious Disease, 208:413-417.
Kistner et al., 2007, "Cell culture (Vero) derived whole virus (H5N1) vaccine based on wild-type virus strain induces cross-protective immune responses," Vaccine, 25(32):6028-6036.
Krammer and Palese, 2013, "Influenza virus hemagglutinin stalk-based antibodies and vaccines," Curr. Opin. Virol., 3, 521-530.
Krammer et al., 2010, "Trichoplusia ni cells (High Five) are highly efficient for the production of influenza A virus-like particles: a comparison of two insect cell lines as production platforms for influenza vaccines", Mol Biotechnol; 45:226-34.
Krammer et al., 2012, "A carboxy-terminal trimerization domain stabilizes conformational epitopes on the stalk domain of soluble recombinant hemagglutinin substrates", PLoS One. 7:e43603, doi:10.1371/journal.pone.0043603.
Krammer et al., 2012, "Hemagglutinin stalk-reactive antibodies are boosted following sequential infection with seasonal and pandemic H1N1 influenza virus in mice", J Virol, 86:10302-10307.
Krammer et al., 2013, "Chimeric hemagglutinin influenza virus vaccine constructs elicit broadly protective stalk-specific antibodies", J Virol. 87:6542-6550.
Krammer et al., 2013, "Influenza virus hemagglutinin stalk-based antibodies and vaccines", Current Opinion in Virology 3:521-530.
Krammer et al., 2014, "Assessment of influenza virus hemagglutinin stalk-based immunity in ferrets", J Virol, 88:3432-3442.
Krammer et al., 2014, "H3 stalk-based chimeric hemagglutinin influenza virus constructs protect mice from H7N9 challenge", J Virol, 88:2340-2343.
Krammer, 2015, "The quest for a universal flu vaccine: headless HA 2.0", Cell Host Microbe, 18:395-397.
Krammer, 2016, "Novel universal influenza virus vaccine approaches", Current Opinion in Virology, 17:95-103.
Krause et al., 2011, "A broadly neutralizing human monoclonal antibody that recognizes a conserved, novel epitope on the globular head of the influenza H1N1 virus hemagglutinin", J. Virol., 85(20):10905-10908.
Krause et al., 2012, "Human monoclonal antibodies to pandemic 1957 H2N2 and pandemic 1968 H3N2 influenza viruses", J. Virol. 86:6334-6340.
Landry et al., 2008, "Three-dimensional structure determines the pattern of CD4+ T-cell epitope dominance in influenza virus hemagglutinin", Journal of Virology; 82(3):1238-1248.
Landry et al., 2010, "Preclinical and Clinical Development of Plant-Made Virus-Like Particle Vaccine against Avian H5N1 Influenza", PLoS One, 5(12): e15559.
Lebendiker M. "Purification Protocols." The Wolfson Centre for Applied Structural Biology, http://wolfson.huji.ac.il/purification/Purification_Protocols.html. Apr. 5, 2006.
Ledgerwood, et al., 2013, "Prime-Boost Interval Matters: A Randomized Phase 1 Study to Identify the Minimum Interval Necessary to Observe the H5 DNA Influenza Vaccine Priming Effect," Journal of Infectious Diseases, 208:418-422.
Lee et al. 2012, "Heterosubtypic antibody recognition of the influenza virus hemagglutinin receptor binding site enhanced by avidity", Proc. Natl. Acad. Sci. U.S.A. 109:17040-17045.

(56) References Cited

OTHER PUBLICATIONS

Leroux-Roels, et al. 2008. "Broad Glade 2 cross-reactive immunity induced by an adjuvanted Glade 1 rH5N1 pandemic influenza vaccine", PLOS One; 3(2):1-5.
Li et al., 1992, "Influenza A virus transfectants with chimaeric haemagglutinins containing epitopes from different subytpes", Journal of Virology, 67:399-404.
Lorieau, et al., 2010, "The complete influenza hemagglutinin fusion domain adopts a tight helical hairpin arrangement at the lipid:water interface." PNAS, 107(25):11341-11346.
Lowen et al. 2009, "Blocking interhost transmission of influenza virus by vaccination in the guinea pig model", Journal of Virology; 8307):2803-2818.
Lu et al., 2013, "Production and stabilization of the trimeric influenza hemagglutinin stem domain for potentially broadly protective influenza vaccines." PNAS, 111(1):125-130.
Luke et al., 2014, "Improving pandemic H5N1 influenza vaccines by combining different vaccine platforms," Expert Review of Vaccines 13(7):873-883.
Mallajosyula et al., 2014, "Influenza hemagglutinin stem-fragment immunogen elicits broadly neutralizing antibodies and confers heterologous protection." PNAS, 111(25):E2514-23.
Marasco et al.. 2007, "The growth and potential of human antiviral monoclonal antibody therapeutics", Nat. Biotechnol: 25(12):1421-1434.
Margine et al., 2013, "H3N2 influenza virus infection induces broadly reactive hemagglutinin stalk antibodies in humans and mice", J. Virol. 87:4728-4737.
Margine et al., 2013, "Hemagglutinin stalk-based universal vaccine constructs protect against group 2 influenza A viruses", J Virol, 10435-10446.
Mbawuike et al., 1994, "Influenza A subtype cross-protection after immunization of outbred mice with purified chimeric NS1/HA2 influenza virus protein", Vaccine, 1994: 12(14):1340-1348.
Mett et al., 2008, "A plant-produced influenza subunit vaccine protects ferrets against virus challenge", Influenza and Other Respiratory Viruses, 2(1):33-40.
Miller et al., 2013, "1976 and 2009 H1N1 influenza virus vaccines boost anti-hemagglutinin stalk antibodies in humans", J. Infect. Dis. 207:98-105.
Mo et al., 2003. "Coexpression of complementary fragments of CIC-5 and restoration of chloride channel function in a Dent's disease mutation", Am J Physiol Cell Physiol; 286:C79-C89.
Mok et al., 2008, "Enhancement of the CD8<+> T cell response to a subdominant epitope respiratory syncytial virus by deletion of an immunodominant epitope", Vaccine: 26(37):4775-4782.
Montgomery et al., "Heterologous and homologous protection against influenza A by DNA vaccination: optimization of DNA vectors," DNA Cell Biol. 12(9):777-783 (1993).
Montplaisir et al., 2009, "Risk of narcolepsy associated with inactivated adjuvanted (AS03) A/H1N1 (2009) pandemic influenza vaccine in Quebec," *PLoS One*, 9 (9): e108489. doi: 10.1371/journal.pone.0108489.
Nachbagauer et al., 2014, "Induction of broadly reactive anti-hemagglutinin stalk antibodies by an H5N1 vaccine in humans," *J. Virol.*, 88 (22): 13260-8.
Nachbagauer et al., 2015, "Hemagglutinin stalk immunity reduces influenza virus replication and transmission in ferrets", J. Virol., doi:10.1128/JVI.02481-15.
Nachbagauer et al., 2016, "A chimeric haemagglutinin-based influenza split virion vaccine adjuvanted with AS03 induces protective stalk-reactive antibodies in mice." *Nature Partner Journals (NPJ) Vaccines*, Article No. 16015 (2016) doi:10.1038/npjvaccines.2016.15.
NCT01676402, Clinical Trial, Seasonal Influenza HA DNA With Trivalent Inactivated Vaccine (TIV) Administered ID or IM in Healthy Adults 18-70 Years.
Neumann et al., 1999, "Generation of influenza A viruses entirely from cloned cDNAs", PNAS 96:9345-9350.
Ni et al, "Structural basis for the divergent evolution of influenza B virus hemagglutinin," Virology 446(1-2):112-122 (2013) (Epub Aug. 27, 2013).
O'Brien MA, Uyeki TM, Shay DK, Thompson WW, Kleinman K, McAdam A, Yu XJ, Platt R, Lieu TA. Incidence of outpatient visits and hospitalizations related to influenza in infants and young children. *Pediatrics*. 2004; 113: 585-93.
Ohkura et al., "Epitope mapping of neutralizing monoclonal antibody in avian influenza A H5N1 virus hemagglutinin," Biochem. Biophys. Res. Commun. 418(1):38-43 (2012) (Epub Dec. 27, 2011).
Okuno et al., 1993, "A common neutralizing epitope conserved between the hemagglutinins of influenza A virus H1 and H2 strains," J. Virol., 67(5):2552-2558.
Okuno et al., 1994, "Protection against the mouse-adapted A/FM/1/47 strain of influenza A virus in mice by a monoclonal antibody with cross-neutralizing activity among Ell and H2 strains," J. Virol., 68(1):517-520.
Oshima et al., 2011, "Naturally Occurring Antibodies in Humans Can Neutralize a Variety of Influenza Virus Strains, Including H3, H1, H2, and H5". Journal of Virology, 85(21):11048-11057.
Ott et al., 2000. The Adjuvant MF59: A 10-Year Perspective, p. 211-228. In O'Hagan DT (ed.), Vaccine Adjuvants, vol. 42. Springer.
Palese P & Shaw M (2007). Orthomyxoviridae: The Viruses and Their Replication. In D.M. Knipe, & P.M. Howley (Eds.), Fields Virology (pp. 1647-1689). Philadelphia, PA: Wolters Kluwer Lippincott Williams & Wilkins.
Papanikolopoulou et al., 2004, "Formation of highly stable chimeric trimers by fusion of an adenovirus fiber shaft fragment with the foldon domain of bacteriophage t4 fibritin", J. Biol. Chem. 279(10):8991-8998.
Perricone et al., 2013, "Autoimmune/inflammatory syndrome induced by adjuvants (ASIA) 2013: Unveiling the pathogenic, clinical and diagnostic aspects," *J Autoimmun.*, 47:1-16.
Pica et al., "Hemagglutinin stalk antibodies elicited by the 2009 pandemic influenza virus as a mechanism for the extinction or seasonal H1N1 viruses." Proc Nat Acad Sci U S A. 2012; 109(7):2573-8.
Pleschka et al., 1996, "A plasmid-based reverse genetics system for influenza A virus", J Virol 70:4188-92.
Ponomarenko et al., "B-Cell Epitope Prediction" Chap. 35 in Structural Bioinformatics, 2nd Edition, Gu and Bourne. Editors; 2009 John Wiley & Sons. Inc. pp. 849-879.
Q0PZR5, UniProtKB Accession No. Q0PZR5, Oct. 29, 2014 [online]. http://www.uniprot.org/uniprot/Q0PZR5.txt?version=53>.
Reid et al., Hemagglutinin [Influenza A virus (A/South Carolina/1/1918(H1N1))]. GenBank Acc. No. AAD17229.1. Dep. Oct. 11, 2000.
Rivera et al., "Probing the structure of influenza B hemagglutinin using site-directed mutagenesis," Virology 206(2):787-795 (1995).
Roberts el al., 1993, "Role of conserved glycosylation sites in maturation and transport of influenza A virus hemagglutinin." J Virol, 67(6):3048-60.
Robertson, 1987, "Sequence Analysis of the Haemagglutinin of A/Taiwan/1/86, a New Variant of Human Influenza A(H1/N1) Virus," J. Gen. Virol., 68:1205-1208.
Rudenko et al., 2015, "Assessment of immune responses to H5N1 inactivated influenza vaccine among individuals previously primed with H5N2 live attenuated influenza vaccine," Human Vaccines & Immunotherapeutics, 11(12):2839-2848.
Rudikoff et al., 1982, "Single amino acid substitution altering antigen-binding specificity." Proc Nat Acad Sci U S A., 79(6): I 979-83.
Ryder et al., 2016, "Vaccination with VSV-vectored chimeric hemagglutinins protects mice against divergent influenza virus challenge strains", J. Virol., 90(5):2544-2550.
Sagawa et al., 1996, "The immunological activity of a deletion mutant of influenza virus haemagglutinin lacking the globular region", J Gen Virol; 77:1483-1487.
Salem, 2000, "In vivo acute depletion of CD8(+) T cells before murine cytomegalovirus infection upregulated innate antiviral activity of natural killer cells", Int. J. Immunopharmacol. 22:707-718.
Santak, M., "Old and new ways to combat human influenza virus." Periodicus Biologorum, 2012; 114(2):221-34.

(56) References Cited

OTHER PUBLICATIONS

Schneeman et al., 2012, "A Virus-Like Particle That Elicits Cross-Reactive Antibodies to the Conserved Stem of Influenza Virus Hemagglutinin," J. Virol., 86(21): 11686-22697.
Schulze, 1997, "Effects of Glycosylation on the Properites and Functions of Influenza Virus Hemagglutinin", The Journal of Infectious Diseases, 176(S1):S24-S28.
Shoji et al., 2008, "Plant-expressed HA as a seasonal influenza vaccine candidate", Vaccine, 26(23):2930-2934.
Simmons et al., 2007. "Prophylactic and therapeutic efficacy of human monoclonal antibodies against H5N1 Influenza", PLOS Medicine; 4(5):928-936.
Song et al., 2007, "Influenza A Virus Hemagglutinin Protein, H1PR8," GENESEQ, XP002595511.
Sparrow et al., 2016, "Passive immunization for influenza through antibody therapies, a review of the pipeline, challenges, and potential applications." Vaccine, 34: 5442-5448.
Stech et al., 2005, "A new approach to an influenza live vaccine: modification of the cleavage site of hemagglutinin", Nature Med. 11(6):683-689.
Steel et al., 2010. "Influenza Virus Vaccine Based on the Conserved Hemagglutinin Stalk Domain," mBIO, 1(0:1-9, pii: e00018-10.
Stephenson et al., 2005, "Cross-reactivity to highly pathogenic avian influenza H5N1 viruses alter vaccination with nonadjuvanted and MF59-adjuvanted influenza A/Duck/Singapore/97 (H5N3) vaccine: a potential priming strategy." J Infect Dis., 191(8):1210-1215.
Stevens et al., 2006, "Structure and Receptor Specificity of the Hemagglutinin from an H5N1 Influenza Virus" Science, 312:404-409.
Strobel et al., 2000, "Efficient Expression of the Tumor-Associated Antigen MAGE-3 in Human Dendritic Cells, Using an Avian Influenza Virus Vector", Human Gene Therapy 11:2207-2218.
Sui et al.. 2009, "Structural and functional bases for broad-spectrum neutralization of avian and human influenza A viruses", Nat Struct Mol Biol; 16(3):265-273.
Sui et al.. 2009, "Structural and functional bases for broad-spectrum neutralization of avian and human influenza A viruses", Nat Struct Mol Biol; 16(3):265-273; Supplementary Information.
Sun et al., 2011, "Glycosylation Site Alteration in the Evolution of Influenza A (H1N1) Viruses." PLoS Pathogens, 6(7):e22844.
Talaat et al., 2014, "A Live Attenuated Influenza A(H5N1) Vaccine Induces Long-Term Immunity in the Absence of a Primary Antibody Response," Journal of Infectious Disease; 208:1860-1869.
Tamura et al., 1998, "Definition of amino acid residues on the epitope responsible for recognition by influenza a virus H1-specific, H2-specific, and H1- and H2-cross-reactive murine cytotoxic T-lymphocyte clones", J. Virol. 72:9404-9406.
Tan et al., 2012, "A pan-H1 anti-hemagglutinin monoclonal antibody with potent broad-spectrum efficacyin vivo", J. Virol. 86:6179-6188.
Tao et al., 2009, "Enhanced protective immunity against H5N1 influenza virus challenge by vaccination with DNA expressing a chimeric hemagglutinin in combination with an MHC class I-restricted epitope of nucleoprotein in mice", Antiviral research. 2009; 81(3): 253-260.
Tate et al., 2011, "Specific Sites of N-Linked Glycosylation on the Hemagglutinin of H1N1 Subtype Influenza A Virus Determine Sensitivity to Inhibitors of the Innate Immune Systema nd Virulence in Mice." Journal of Immunology, 187(4):1884-1894.
Tete et al., 2016, "Dissecting the hemagglutinin head and stalk-specific IgG antibody response in healthcare workers following pandemic H1N1 vaccination," *Nature Partner Journals (NPJ) Vaccine*, Article No. 16001 doi:10.1038/npjvaccines.2016.1.
Thoennes et al., 2008, "Analysis of residues near the fusion peptide in the influenza hemagglutinin structure for roles in triggering membrane fusion", Virology; 370(2):403-414.
Thomson et al., 2012, "Pandemic H1N1 Influenza Infection and Vaccination in Humans Induces Cross-Protective Antibodies that Target the Hemagglutinin Stem", Front. Immunol. 3:87.

Throsby et al., 2008, "Heterosubtypic neutralizing monoclonal antibodies cross-protective against H5N1 and H1N1 recovered from human IgM+ memory B cells", PLoS ONE; 3(12):e3942.
Tong et al., 2013. "New world bats harbor diverse influenza A viruses," PLoS Pathog. 9: e1003657.
Tran et al., 2016, "Cryo-electron microscopy structures of chimeric hemagglutinin displayed on a universal influenza vaccine candidate", MBio, 7(2): e00257-16.
Vajdos et al., 2002, "Comprehensive Functional Maps of the Antigenbinding Site of an Anti-ErbB2 Antibody Obtained with Shotgun Scanning Mutagenesis," Journal of Molecular Biology, 320:415-428.
Vanlandschoot et al., 1995. "A fairly conserved epitope on the hemagglutinin of influenza A (H3N2) virus with variable accessibility to neutralizing antibody." Virology, 212(2)526-34.
Vanlandschoot et al., 1998. "An antibody which binds to the membrane-proximal end of influenza virus haemagglutinin (1-13 subtype) inhibits the low-pH-induced conformational change and cell-cell fusion but does not neutralize virus", Journal of General Virology; 79:1781-1791.
Vareckova et al., 2008, "HA2-specific monoclonal antibodies as tools for differential recognition of influenza A virus antigenic subtypes," Virus Research, 132:181-186.
Vigerust et al., 2007, "N-Linked Glycosylation Attenuates H3N2 Influenza Viruses", Journal of Virology, 81(16): 8593-8600.
Vincent et al., 2008, "Failure of protection and enhanced pneumonia with a US H1N2 swine influenza virus in pigs vaccinated with an inactivated classical swine H1N1 vaccine," *Vet Microbiol.*, 126 (4): 310-23.
Wang et al., "Crystal structure of unliganded influenza B virus hemagglutinin," J. Virol. 82(6):3011-3020 (2008) (Epub Jan. 9, 2008).
Wang et al., 2007, "Incorporation of High Levels of Chimeric Human Immunodeficiency Virus Envelope Glycoproteins into Virus-Like Particles", J. Virol., 81(20):10869-10878.
Wang et al., 2008, "Simplified recombinational approach for influenza A virus reverse genetics", J. Virol. Methods 151:74-78.
Wang et al., 2009, "Characterization of cross-reactive antibodies against the influenza virus hemagglutinin", American Society for Virology 28th Annual Meeting, University of British Columbia, Vancouver, BC, Canada dated Jul. 11-15, 2009; Abstract W30-6.
Wang et al., 2009, "Glycans on influenza hemagglutinin affect receptor binding and immune response." PNAS, 106(43): 18137-18142.
Wang et al., 2009, "Universal epitopes of influenza virus hemagglutinins?", Nature Structural and Molecular Biology; 16(3):233-234.
Wang et al., 2010, "Broadly protective monoclonal antibodies against H3 influenza viruses following sequential immunization with different hemagglutinins", PLOS Pathogens; 6(2):1-9.
Wang et al., 2010, "Vaccination with a synthetic peptide from the influenza virus hemagglutinin provides protection against distinct viral subtypes". PNAS. 107(44): 18979-18984.
Wang et al., 2012, "Generation of recombinant pandemic H1N1 influenza virus with the HA cleavable by bromelain and identification of the residues influencing HA bromelain cleavage." Vaccine, 30(4):872-8.
Webby et al., 2010, Hemagglutinin [Influenza A virus (A/Brisbane/59/2007(H1N1))]. GenBank Acc. No. ADE28750.1. Dep. Mar. 29, 2010.
Wei et al., 2010, "Induction of Broadly Neutralizing H1N1 Influenza Antibodies by Vaccination," Science; 329: 1060-1064.
Weis and Brunger, 1990, "Refinement of the Influenza Virus Hemagglutinin by Simulated Annealing." J. Mol. Biol. 212:737-761.
Weis et al., 1988, "Structure of the influenza virus haemagglutinin complexed with its receptor, sialic acid." Nature, 333:426-431.
Weldon et al., 2010, "Enhanced immunogenicity of stabilized trimeric soluble influenza hemagglutinin", PLoSONE 5(9): e12466.
WHO World Health Organization Factsheet No. 211. Influenza Nov. 2016. https://www.who.int/mediacentre/factsheets/fs211/en.
Wiley and Skehel, 1983, "The three-dimensional structure and antigenic variation of the influenza virus haemagglutinin." Division of Virology, 107-111.

(56) References Cited

OTHER PUBLICATIONS

Wiley, 1987, "The Structure and Function of the Hemagglutinin Membrane Glycoprotein of Influenza Virus." Ann. Rev. Biochem., 56:365-94.
Wilson et al., 1981, "Structure of the haemagglutinin membrane glycoprotein of influenza virus at 3 A resolution." Nature, 289:366-373.
Winter et al., 1981, "Nucleotide Sequence of the Haemagglutinin Gene of a Human Influenza Virus H1 Subtype" Nature, 292:72-75.
Wohlbold et al., "In the Shadow of Hemagglutinin: A Growing Interest in Influenza Viral N euraminidase and Its Role as a Vaccine Antigen," Viruses 6(6):2465-2494 (2014).
Wohlbold et al., 2015, "Vaccination with soluble headless hemagglutinin protects mice from challenge with divergent influenza viruses." Vaccine, 33(29):3314-3321.
Wohlbold et al., 2015, "Vaccination with adjuvanted recombinant neuraminidase induces broad heterologous, but not heterosubtypic, cross-protection against influenza virus infection in mice." MBio, 6(2):e02556.
Worobey et al., 2002, "Questioning the Evidence for Genetic Recombination in the 1918 "Spanish Flu" Virus", Science, 296(5566): 211a.
Wrammert et al., 2011, "Broadly cross-reactive antibodies dominate the human B cell response against 2009 pandemic H1N1 influenza virus infection", J. Exp. Med. 208:181-193.
Written Opinion dated Feb. 19, 2013 for PCT Application No. PCT/US2012/056122, Published as WO 2013/043729.
Written Opinion dated Apr. 28, 2014 for PCT Application No. PCT/US2013/075697, Published as WO 2014/099931.
Written Opinion dated Jun. 26, 2014 for PCT Application No. PCT/US2014/025526, Published as WO 2014/159960.
Written Opinion dated Jul. 13, 2011 for PCT Application No. PCT/US2011/030441, Published as WO 2011/123495.
Written Opinion dated Sep. 30, 2011 for PCT Application No. PCT/US2010/029202, Published as WO 2010/117786.
Written Opinion of International Application No. PCT/US2010/036170, dated Aug. 17, 2010.
Written Opinion of International Application No. PCT/US2011/25467, dated Oct. 19, 2011.
Written Opinion of the International Searching Authority for International Application No. PCT/US2017/037384, dated Nov. 3, 2017.
Written Opinion of the International Searching Authority for International Application No. PCT/US2016/037595, dated Sep. 15, 2016.
Written Opinion of the International Searching Authority for International Application No. PCT/US2016/014640, dated Jun. 3, 2016.
Written Opinion of the International Searching Authority for International Application No. PCT/US2017/035479, dated Oct. 25, 2017.
Yang et al., 2006, "Targeting lentiviral vectors to specific cell types in vivo", PNAS 103: 11479-11484.
Yang et al., 2007, "Immunization by Avian H5 Influenza Hemagglutinin Mutants with Altered Receptor Binding Specificity", Science, 317(5839):825-828.
Yang et al., 2014, "Structural stability of influenza A(H1N1)pdm09 virus hemagglutinins." J. Virol., 88(9):4828-4838.
Yassine et al., 2015, "Hemagglutinin-stem nanoparticles generate heterosubtypic influenza protection." Nat. Med. 21(9):1065-70.
Yasugi et al., 2013, "Human monoclonal antibodies broadly neutralizing against influenza B virus", PLoS Pathog. 9(2): e1003150.
Yoshida et al., A. "Cross-protective potential of a novel monoclonal antibody directed against antigenic site B of the hemagglutinin of influenza A viruses." PLoS Pathog. 2009; 5(3);e1000350.
Zamarin et al., 2006, "Influenza a virus PB1-F2 protein contributes to viral pathogenesis in mice". J Virol. 80(16):7976-7983.
Zhang et al., "Crystal structure of the swine-origin A (H1N1)-2009 influenza a virus hemagglutinin (HA) reveals similar antigenicity to that of the 1918 pandemic virus," Protein Cell 1(5):459-467 (2010) (Epub Jun. 4, 2010).

Zhang et al., 2011, "Determination of serum neutralization antibodies against seasonal influenza A strain H3N2 and the emerging strains 2009 H1N1 and avian H5N1". Scandinavian Journal of Infectious Diseases, 43:216-220.
Zheng, et al., 1996, "Nonconserved nucleotides at the 3' and 5' ends of an influenza A virus RNA play an important role in viral RNA replication", Virology 217:242-251.
Anthony et al., 2012, "Emergence of fatal avian influenza in New England harbor seals," MBio., 3(4):e00166-12.
Arzey et al., 2012, "Influenza virus A (H10N7) in chickens and poultry abattoir workers, Australia," Emerg Infect Dis., 18(5):814-816.
Baker et al., 1976, "Effect of Ca++ on the stability of influenza virus neuraminidase," Arch Virol., 52(1-2):7-18.
Baker et al., 2013, "Protection against lethal influenza with a viral mimic," J Virol., 87(15):8591-8605.
Basler et al., 1999, "Mutation of neuraminidase cysteine residues yields temperature-sensitive influenza viruses," J Virol., 73(10):8095-8103.
Baz et al., 2013, "Replication and immunogenicity of swine, equine, and avian h3 subtype influenza viruses in mice and ferrets," J Virol., 87(12):6901-6910.
Belshe, 2007, "Translational research on vaccines: influenza as an example," Clin Pharmacol Ther., 82(6):745-749.
Bett et al., 1993, "Packaging capacity and stability of human adenovirus type 5 vectors," J Virol., 67(10):5911-5921.
Bouvier et al., 2008, "Oseltamivir-resistant influenza A viruses are transmitted efficiently among guinea pigs by direct contact but not by aerosol," J Virol., 82(20):10052-10058.
Bright et al., 2007, "Influenza virus-like particles elicit broader immune responses than whole inactivated virion influenza virus or recombinant hemagglutinin," Vaccine, 25(19):3871-3878.
Broecker et al., 2018, "Immunodominance of Antigenic Site B in the Hemagglutinin of the Current H3N2 Influenza Virus in Humans and Mice," J Virol., 92(20):e01100-18.
Carter et al., 2016, "Design and Characterization of a Computationally Optimized Broadly Reactive Hemagglutinin Vaccine for H1N1 Influenza Viruses," J Virol., 90(9):4720-4734.
Centers for Disease Control and Prevention (CDC), 2009, "Swine influenza A (H1N1) infection in two children—Southern California, Mar.-Apr. 2009," MMWR Morb Mortal Wkly Rep., 58(15):400-402.
Centers for Disease Control and Prevention (CDC), 2009, "Update on influenza A (H1N1) 2009 monovalent vaccines," MMWR Morb Mortal Wkly Rep., 58(39):1100-1101.
Centers for Disease Control and Prevention (CDC), 2010, "Estimates of deaths associated with seasonal influenza—United States, 1976-2007," MMWR Morb Mortal Wkly Rep., 59(33):1057-1062.
Centers for Disease Control and Prevention (CDC), 2012, "Notes from the field: Highly pathogenic avian influenza A (H7N3) virus infection in two poultry workers—Jalisco, Mexico, Jul. 2012," MMWR Morb Mortal Wkly Rep., 61(36):726-727.
Centers for Disease Control and Prevention (CDC), 2012, "Notes from the field: Outbreak of influenza A (H3N2) virus among persons and swine at a county fair—Indiana, Jul. 2012," MMWR Morb Mortal Wkly Rep., 61(29):561.
Chen et al., 2000, "Cross-protection against a lethal influenza virus infection by DNA vaccine to neuraminidase," Vaccine, 18(28):3214-3222.
Chen et al., 2009, "Evaluation of live attenuated influenza a virus h6 vaccines in mice and ferrets," J Virol., 83(1):65-72.
Chen et al., 2012, "The 2009 pandemic H1N1 virus induces anti-neuraminidase (NA) antibodies that cross-react with the NA of H5N1 viruses in ferrets," Vaccine, 30(15):2516-2522.
Claas et al., 1998, "Human influenza A H5N1 virus related to a highly pathogenic avian influenza virus," Lancet, 351(9101):472-477.
Corti et al., 2010, "Heterosubtypic neutralizing antibodies are produced by individuals immunized with a seasonal influenza vaccine," J Clin Invest., 120(5):1663-1673.
Couch et al., 1974, "Induction of partial immunity to influenza by a neuraminidase-specific vaccine," J Infect Dis., 129(4):411-420.

(56) References Cited

OTHER PUBLICATIONS

De Jong et al., 2000, "Mismatch between the 1997/1998 influenza vaccine and the major epidemic A(H3N2) virus strain as the cause of an inadequate vaccine-induced antibody response to this strain in the elderly," J Med Virol., 61(1):94-99.
Deroo et al., 1996, "Recombinant neuraminidase vaccine protects against lethal influenza," Vaccine, 14(6):561-569.
Desselberger et al., 1978, "Biochemical evidence that "new" influenza virus strains in nature may arise by recombination (reassortment)," Proc Natl Acad Sci USA, 75(7):3341-3345.
Dowdle et al., 1973, "Inactivated influenza vaccines. 2. Laboratory indices of protection," Postgrad Med J., 49(569):159-163.
Doyle et al., 2013, "Universal anti-neuraminidase antibody inhibiting all influenza A subtypes," Antiviral Res., 100(2):567-574.
Dreyfus et al., 2012, "Highly conserved protective epitopes on influenza B viruses," Science, 337(6100):1343-1348.
Dubensky et al., 1996, "Sindbis virus DNA-based expression vectors: utility for in vitro and in vivo gene transfer," J Virol., 70(1):508-519.
Easterbrook et al., 2012, "Protection against a lethal H5N1 influenza challenge by intranasal immunization with virus-like particles containing 2009 pandemic H1N1 neuraminidase in mice," Virology, 432(1):39-44.
Ekiert et al., 2012, ,"Broadly neutralizing antibodies against influenza virus and prospects for universal therapies," Curr Opin Virol., 2(2):134-141.
Ellebedy et al., 2014, "Induction of broadly cross-reactive antibody responses to the influenza HA stem region following H5N1 vaccination in humans," Proc Natl Acad Sci USA, 111(36):13133-13138.
Eriksson et al., 2007, "Local and systemic cytokine and chemokine responses after parenteral influenza vaccination," Influenza Other Respir Viruses, 1(4):139-146.
Fouchier et al., 2004, "Avian influenza A virus (H7N7) associated with human conjunctivitis and a fatal case of acute respiratory distress syndrome," Proc Natl Acad Sci USA, 101(5):1356-1361.
Garcon et al., 2012, "Development and evaluation of AS03, an Adjuvant System containing α-tocopherol and squalene in an oil-in-water emulsion," Expert Rev Vaccines, 11(3):349-366.
GenBan Accession No. AAA43397.1, neuraminidase [Influenza A virus (A/WSN/1933(H1N1))], 1982.
GenBan Accession No. ABG23658.1, neuraminidase, partial [Influenza A virus (A/Zhejiang/16/2006(H5N1))], 2007.
GenBank Accession No. AAA43412.1, neuraminidase [Influenza A virus (A/Puerto Rico/8/1934(H1N1))], 1981.
GenBank Accession No. AAQ90293.1, neuraminidase [Influenza A virus (A/equine/Santiago/77(H7N7))], 2003.
GenBank Accession No. AAS89005.1, neuraminidase [Influenza A virus (A/Thailand/3(SP-83)/2004(H5N1))], 2005.
GenBank Accession No. ABE97718.1, neuraminidase [Influenza A virus (A/Vietnam/CL100/2004(H5N1))], 2006.
GenBank Accession No. ABE97719.1, neuraminidase [Influenza A virus (A/Vietnam/CL105/2005(H5N1))], 2006.
GenBank Accession No. ABE97720.1, neuraminidase [Influenza A virus (A/Vietnam/CL115/2005(H5N1))], 2006.
GenBank Accession No. ACS71642, haemagglutinin [Influenza A virus (A/Perth/16/2009(H3N2))], 2009.
GenBank Accession No. AEX30531.1, neuraminidase [Influenza A virus (A/chicken/N101/Iran/2011(H9N2))], 2011.
GenBank Accession No. AEX30532.1, neuraminidase [Influenza A virus (A/chicken/N102/Iran/2011(H9N2))], 2011.
GenBank Accession No. AG018161.1, *Homo sapiens* genomic DNA, 21q region, clone: B396A17A4a015, genomic survey sequence, 1999.
GenBank Accession No. AIA62041.1, neuraminidase [Influenza A virus (A/goose/Guangxi/020G/2009(H3N8))], 2014.
GenBank Accession No. AI130325.1, neuraminidase [Influenza A virus (A/pigeon/Guangxi/020P/2009(H3N6))], 2015.
GenBank Accession No. BAF48478-2007, haemagglutinin [Influenza A virus (A/duck/Czech/1956(H4N6))], 2007.
GenBank Accession No. CRI06477.1, neuraminidase [Influenza A virus (A/England/10740685/2010(H1N1))], 2015.
GenBank Accession No. DQ017504.1, Influenza A virus (A/mallard/Alberta/24/01(H7N3)) from Canada segment 4, complete sequence, 2005.
GenBank Accession No. NP_040981.1, neuraminidase [Influenza A virus (A/Puerto Rico/8/1934(H1N1))], 1981.
Gerdil, 2003, "The annual production cycle for influenza vaccine," Vaccine, 21(16):1776-1779.
Gerhard et al., 1981, "Antigenic structure of influenza virus haemagglutinin defined by hybridoma antibodies," Nature, 290(5808):713-717.
Giles et al., 2012, "Computationally optimized antigens to overcome influenza viral diversity," Expert Rev Vaccines, 11(3):267-269.
Halbherr et al., 2015, "Biological and protective properties of immune sera directed to the influenza virus neuraminidase," J Virol., 89(3):1550-1563 (Epub Nov. 12, 2014).
Hamilton et al., 2016, "Club cells surviving influenza A virus infection induce temporary nonspecific antiviral immunity," Proc Natl Acad Sci USA, 113(14):3861-3866.
Harris et al., 2006, "Influenza virus pleiomorphy characterized by cryoelectron tomography," Proc Natl Acad Sci USA, 103(50):19123-19127.
He et al., 2014, "Infection of influenza virus neuraminidase-vaccinated mice with homologous influenza virus leads to strong protection against heterologous influenza viruses," J Gen Virol., 95(Pt 12):2627-2637.
Heaton et al., 2013, "Genome-wide mutagenesis of influenza virus reveals unique plasticity of the hemagglutinin and NS1 proteins," Proc Natl Acad Sci USA, 110(50):20248-20253.
Hobson et al., 1972, "The role of serum haemagglutination-inhibiting antibody in protection against challenge infection with influenza A2 and B viruses," J Hyg (Lond), 70(4):767-777.
Hoffmann et al., 2000, "A DNA transfection system for generation of influenza a virus from eight plasmids," Proc Natl Acad Sci USA, 97(11):6108-6113.
International Search Report of International Application No. PCT/US2018/045399, dated Nov. 29, 2018.
Isakova-Sivak et al., 2011, "Genetic bases of the temperature-sensitive phenotype of a master donor virus used in live attenuated influenza vaccines: A/Leningrad/134/17/57 (H2N2)," Virology, 412(2):297-305.
Isakova-Sivak et al., 2015, "Safety, immunogenicity and infectivity of new live attenuated influenza vaccines," Expert Rev Vaccines, 14(10):1313-1329.
Jayasundara et al., 2014, "Natural attack rate of influenza in unvaccinated children and adults: a meta-regression analysis," BMC Infect Dis., 14:670.
Jin et al., 2003, "Multiple amino acid residues confer temperature sensitivity to human influenza virus vaccine strains (FluMist) derived from cold-adapted A/Ann Arbor/6/60," Virology, 306(1):18-24.
Joh Hira et al., 2004, "Production of monoclonal antibodies against a conserved region of Hemagglutinin of Influenza A virus and enzymatic activity of the light chain," Lectures in the Chemical Society of Japan, 84(2):1156, 2 J6-15 in Japanese with English translation of Abstract (4 pages).
Johansson et al., 1987, "Antigen-presenting B cells and helper T cells cooperatively mediate intravirionic antigenic competition between influenza A virus surface glycoproteins," Proc Natl Acad Sci USA, 84(19):6869-6873.
Johansson et al., 1993, "Dissociation of influenza virus hemagglutinin and neuraminidase eliminates their intravirionic antigenic competition," J Virol., 67(10):5721-5723.
Johansson et al., 1994, "Immunization with purified N1 and N2 influenza virus neuraminidases demonstrates cross-reactivity without antigenic competition," Proc Natl Acad Sci USA, 91(6):2358-2361.
Johnson et al., 2002, "Updating the accounts: global mortality of the 1918-1920 "Spanish" influenza pandemic," Bull Hist Med., 76(1):105-115.

(56) References Cited

OTHER PUBLICATIONS

Joseph et al., 2007, "Evaluation of replication and pathogenicity of avian influenza a H7 subtype viruses in a mouse model," J Virol., 81(19):10558-10566.
Kayali et al., 2011, "Evidence of infection with H4 and H11 avian influenza viruses among Lebanese chicken growers," PLoS One, 6(10):e26818.
Khurana et al., 2013, "Vaccine-induced anti-HA2 antibodies promote virus fusion and enhance influenza virus respiratory disease," Sci Transl Med., 5(200):200ra114.
Kilbourne et al., 1987, "Immunologic response to the influenza virus neuraminidase is influenced by prior experience with the associated viral hemagglutinin I Studies in human vaccinees," J Immunol., 138(9):3010-3013.
Krammer et al., 2014, "An H7N1 influenza virus vaccine induces broadly reactive antibody responses against H7N9 in humans," Clin Vaccine Immunol., 21(8):1153-1163.
Krammer et al., 2015, "Advances in the development of influenza virus vaccines," Nat Rev Drug Discov., 14(3):167-182.
Lambe et al., 2013, "Immunity against heterosubtypic influenza virus induced by adenovirus and MVA expressing nucleoprotein and matrix protein-1," Sci Rep., 3:1443.
Ledgerwood et al., 2011, "DNA priming and influenza vaccine immunogenicity: two phase 1 open label randomised clinical trials," Lancet Infect Dis., 11(12):916-924.
Li et al., 1999, "Recombinant influenza A virus vaccines for the pathogenic human A/Hong Kong/97 (H5N1) viruses," J Infect Dis., 179(5):1132-1138.
Li et al., 2012, "Pandemic H1N1 influenza vaccine induces a recall response in humans that favors broadly cross-reactive memory B cells," Proc Natl Acad Sci USA, 109(23):9047-9052.
Liang et al., 1994, "Heterosubtypic immunity to influenza type A virus in mice. Effector mechanisms and their longevity," J Immunol., 152(4):1653-1661.
Lowen et al., 2006, "The guinea pig as a transmission model for human influenza viruses," Proc Natl Acad Sci USA, 103(26):9988-9992.
Margine et al., 2013, "Expression of functional recombinant hemagglutinin and neuraminidase proteins from the novel H7N9 influenza virus using the baculovirus expression system," J Vis Exp., 6(81):e51112.
Martinez-Romero et al., 2013, "Substitutions T200A and E227A in the hemagglutinin of pandemic 2009 influenza A virus increase lethality but decrease transmission," J Virol., 87(11):6507-6511.
Monto et al., 2015, "Antibody to Influenza Virus Neuraminidase an Independent Correlate of Protection," J Infect Dis., 212(8):1191-1199.
Moody et al., 2011, "H3N2 influenza infection elicits more cross-reactive and less clonally expanded anti-hemagglutinin antibodies than influenza vaccination," PLoS One, 6(10):e25797.
Nachbagauer et al., 2016, "Age Dependence and Isotype Specificity of Influenza Virus Hemagglutinin Stalk-Reactive Antibodies in Humans," MBio., 7(1):e01996-15.
Nakaya et al., 2001, "Recombinant Newcastle disease virus as a vaccine vector," J Virol., 75(23):11868-11873.
Ohmit et al., 2011, "Influenza hemagglutination-inhibition antibody titer as a correlate of vaccine-induced protection," J Infect Dis., 204(12):1879-1885.
Oxford, 2013, "Towards a universal influenza vaccine: volunteer virus challenge studies in quarantine to speed the development and subsequent licensing," Br J Clin Pharmacol., 76(2):210-216.
Palese, 2004, "Influenza: old and new threats," Nat Med., 10(12 Suppl):S82-87.
Park et al., 2006, "Engineered viral vaccine constructs with dual specificity: avian influenza and Newcastle disease," Proc Natl Acad Sci USA, 103(21):8203-8208.
Ridenour et al., 2015, "Development of influenza A(H7N9) candidate vaccine viruses with improved hemagglutinin antigen yield in eggs," Influenza Other Respir Viruses, 9(5):263-270.

Rockman et al., 2013, "Neuraminidase-inhibiting antibody is a correlate of cross-protection against lethal H5N1 influenza virus in ferrets immunized with seasonal influenza vaccine," J Virol., 87(6):3053-3061.
Rolfes et al., 2014, "Update: influenza activity—United States, Sep. 28-Dec. 6, 2014," MMWR Morb Mortal Wkly Rep., 63(50):1189-1194.
Runstadler et al., 2013, "Connecting the study of wild influenza with the potential for pandemic disease," Infect Genet Evol., 17:162-187.
Sandbulte et al., 2007, "Cross-reactive neuraminidase antibodies afford partial protection against H5N1 in mice and are present in unexposed humans," PLoS Med., 4(2):e59.
Scheiffele et al., 1997, "Interaction of influenza virus haemagglutinin with sphingolipid-cholesterol membrane domains via its transmembrane domain," EMBO J., 16(18):5501-5508.
Schuind et al., 2015, "Immunogenicity and Safety of an EB66 Cell-Culture-Derived Influenza A/Indonesia/5/2005(H5N1) AS03-Adjuvanted Vaccine: A Phase 1 Randomized Trial," J Infect Dis., 212(4):531-541.
Schulman et al., 1968, "Protective effects of specific immunity to viral neuraminidase on influenza virus infection of mice," J Virol., 2(8):778-786.
Seibert et al., 2010, "Oseltamivir-resistant variants of the 2009 pandemic H1N1 influenza A virus are not attenuated in the guinea pig and ferret transmission models," J Virol., 84(21):11219-11226.
Seibert et al., 2013, "Recombinant IgA is sufficient to prevent influenza virus transmission in guinea pigs," J Virol., 87(14):7793-7804.
Shoji et al., 2011, "An influenza N1 neuraminidase-specific monoclonal antibody with broad neuraminidase inhibition activity against H5N1 HPAI viruses," Hum Vaccin., 7 Suppl:199-204.
Steel et al., 2009, "Live attenuated influenza viruses containing NS1 truncations as vaccine candidates against H5N1 highly pathogenic avian influenza," J Virol., 83(4):1742-1753.
Subbarao et al., 2013, "The prospects and challenges of universal vaccines for influenza," Trends Microbiol., 21(7):350-358.
Sui et al., 2011, "Wide prevalence of heterosubtypic broadly neutralizing human anti-influenza A antibodies," Clin Infect Dis., 52(8):1003-1009.
Skowronski et al., 2013, "Virus-host interactions and the unusual age and sex distribution of human cases of influenza A(H7N9) in China, Apr. 2013," Euro Surveill., 18(17):20465.
Sylte et al. 2007, "Influenza neuraminidase antibodies provide partial protection for chickens against high pathogenic avian influenza infection," Vaccine, 25(19):3763-3772.
Thompson et al., 2003, "Mortality associated with influenza and respiratory syncytial virus in the United States," JAMA, 289(2):179-186.
Treanor et al., 2007, "Safety and immunogenicity of a baculovirus-expressed hemagglutinin influenza vaccine: a randomized controlled trial," JAMA, 297(14):1577-1582.
Tricco et al., 2013, "Comparing influenza vaccine efficacy against mismatched and matched strains: a systematic review and meta-analysis," BMC Med., 11:153.
Tscherne et al., 2010, "An enzymatic virus-like particle assay for sensitive detection of virus entry," J Virol Methods, 163(2):336-343.
Tweed et al., 2004, "Human illness from avian influenza H7N3, British Columbia," Emerg Infect Dis., 10(12):2196-2199.
Van Der Brand et al., 2011, "Efficacy of vaccination with different combinations of MF59-adjuvanted and nonadjuvanted seasonal and pandemic influenza vaccines against pandemic H1N1 (2009) influenza virus infection in ferrets," J Virol., 85(6):2851-2858.
Van Der Most et al., 2014, "Seeking help: B cells adapting to flu variability," Sci Transl Med., 6(246):246ps8.
Van Reeth et al., 2009, "Prior infection with an H1N1 swine influenza virus partially protects pigs against a low pathogenic H5N1 avian influenza virus," Vaccine, 27(45):6330-6339.
Wan et al., 2013, "Molecular basis for broad neuraminidase immunity: conserved epitopes in seasonal and pandemic H1N1 as well as H5N1 influenza viruses," J Virol., 87(16):9290-9300.
Wang et al., 2006, "Hemagglutinin (HA) proteins from H1 and H3 serotypes of influenza A viruses require different antigen designs for

(56) References Cited

OTHER PUBLICATIONS the induction of optimal protective antibody responses as studied by codon-optimized HA DNA vaccines," J Virol., 80(23):11628-11637.
Wang et al., 2010, "Broadly protective monoclonal antibodies against H3 influenza viruses following sequential immunization with different hemagglutinins," PLoS Pathog., 6(2):e1000796.
Wang et al., 2011, "Biochemistry. Catching a moving target," Science, 333(6044):834-835.
Weir et al., 2016, "An overview of the regulation of influenza vaccines in the United States," Influenza Other Respir Viruses, 10(5):354-360.
Wrammert et al., 2008, "Rapid cloning of high-affinity human monoclonal antibodies against influenza virus," Nature, 453(7195):667-671.
Written Opinion of the International Searching Authority for International Application No. PCT/US2018/045399, dated Nov. 29, 2018.
Xu et al., 2008, "Structural characterization of the 1918 influenza virus H1N1 neuraminidase," J Virol., 82(21):10493-10501.
Yang et al., 2014, "A beneficiary role for neuraminidase in influenza virus penetration through the respiratory mucus," PLoS One, 9(10):e110026.
Yewdell., 2013, "To dream the impossible dream: universal influenza vaccination," Curr Opin Virol., 3(3):316-321.
Yoshida et al., 2007, "Preparation of monoclonal antibodies against common region of influenza A virus hemagglutinin (HA)," Lectures in the Chemical Society of Japan, 87(2):1307, 2 J3-02 in Japanese with English translation of Abstract (4 pages).
Zerangue et al., 2000, "An artificial tetramerization domain restores efficient assembly of functional Shaker channels lacking T1," Proc Natl Acad Sci USA, 97(7):3591-3595.
Ziegler et al., 1995, "Type- and subtype-specific detection of influenza viruses in clinical specimens by rapid culture assay," J Clin Microbiol., 33(2):318-321.
Abe et al., 2004, "Effect of the addition of oligosaccharides on the biological activities and antigenicity of influenza A/H3N2 virus hemagglutinin," J Virol., 78(18):9605-9611.
Altschul et al., 1997, "Gapped BLAST and PSI-BLAST: A new generation of protein database search programs," Nucleic Acids Res., 25(17):3389-3402.
Angeletti et al., 2017, "Defining B cell immunodominance to viruses," Nat Immunol., 18(4):456-463.
Antoine et al., 1998, "The complete genomic sequence of the modified vaccinia Ankara strain: comparison with other orthopoxviruses," Virology, 244(2):365-396.
Beare et al., 1975, "Trials in man with live recombinants made from A/PR/8/34 (HO N1) and wild H3 N2 influenza viruses," Lancet, 2(7938):729-732.
Fox et al., 1982, "Influenzavirus infections in Seattle families, 1975-1979. II. Pattern of infection in invaded households and relation of age and prior antibody to occurrence of infection and related illness," Am J Epidemiol., 116(2):228-242.
GenBank Accession No. ACQ76318, hemagglutinin [Influenza A virus (A/California/04/2009(H1N1))], 2009.
Glezen et al., 1978, "Interpandemic influenza in the Houston area, 1974-76," N Engl J Med., 298(11):587-592.
Haffer et al., 1990, "Human immunodeficiency virus-like, nonreplicating, gag-env particles assemble in a recombinant vaccinia virus expression system," J Virol., 64(6):2653-2659.
Hagnesee et al., 1991, "Self-assembly of human papillomavirus type 1 capsids by expression of the L1 protein alone or by coexpression of the L1 and L2 capsid proteins," J Virol., 67(1):315-322.
Hanks et al., 2005, "Re-engineered CD40 receptor enables potent pharmacological activation of dendritic-cell cancer vaccines in vivo," Nat Med., 11(2):130-137 and supplemental materials.
International Search Report and Written Opinion dated Oct. 29, 2019 of International Patent Application No. PCT/US2019/038178 (16 pages).

Jeoung et al., 1995, "Effects of tumor necrosis factor-alpha on antimitogenicity and cell cycle-related proteins in MCF-7 cells." J Biol Chem., 270(31):18367-18373.
Jerne et al., 1982, "Recurrent idiotopes and internal images," Embo J., 1(2):243-247.
Karlin et al., 1990, "Methods for assessing the statistical significance of molecular sequence features by using general scoring schemes," Proc Natl Acad Sci USA, 87(6):2264-2268.
Karlin et al., 1993, "Applications and statistics for multiple high-scoring segments in molecular sequences," Proc Natl Acad Sci USA, 90(12):5873-5877.
Kirnbauer et al., 1992, "Papillomavirus L1 major capsid protein self-assembles into virus-like particles that are highly immunogenic," Proc Natl Acad Sci USA, 89(24):12180-12184.
Laver et al., 1981, "Mechanism of antigenic drift in influenza virus. Amino acid sequence changes in an antigenically active region of Hong Kong (H3N2) influenza virus hemagglutinin," J Mol Biol., 145(2):339-361.
Liu et al., 2019, "Sequential Immunization With Live-Attenuated Chimeric Hemagglutinin-Based Vaccines Confers Heterosubtypic Immunity Against Influenza A Viruses in a Preclinical Ferret Model," Front. Immunol., 10:756 and Supplemental Figs. S1 to S7 (25 pages).
Martínez-Sobrido et al., 2010, "Generation of recombinant influenza virus from plasmid DNA," J Vis Exp., (42), 5 pages.
Morel et al., 2011, "Adjuvant System AS03 containing a-tocopherol modulates innate immune response and leads to improved adaptive immunity," Vaccine, 29(13):2461-2473.
Nachbagauer et al., 2017, "A universal influenza virus vaccine candidate confers protection against pandemic H1N1 infection in preclinical ferret studies," NPJ Vaccines, 2:26 (13 pages).
Pan et al., 2011, "Selective pressure to increase charge in immunodominant epitopes of the H3 hemagglutinin influenza protein," J Mol Evol., 72(1):90-103.
Pantua et al., 2006, "Requirements for the assembly and release of Newcastle disease virus-like particles," J Virol, 80(22):11062-11073.
Pearson et al., 1988, "Improved tools for biological sequence comparison," Proc Natl Acad Sci USA, 85(8):2444-2448.
Popova et al., 2012, "Immunodominance of antigenic site B over site A of hemagglutinin of recent H3N2 influenza viruses," PLoS One, 7(7):e41895 (11 pages).
Quinlivan et al., 2005, "Attenuation of equine influenza viruses through truncations of the NS1 protein," J Virol., 79(13):8431-8439.
Rasala et al., 2010, "Production of therapeutic proteins in algae, analysis of expression of seven human proteins in the chloroplast of Chlamydomonas reinhardtii," Plant Biotechnol J., 8(6):719-733.
Smith et al., 1981, "Comparison of biosequences," Advances in Applied Mathematics, 2(4):482-489.
Stoute et al., 1997, "A preliminary evaluation of a recombinant circumsporozoite protein vaccine against Plasmodium falciparum malaria RTS,S Malaria Vaccine Evaluation Group," N Engl J Med., 336(2):86-91.
Sutter et al., 1992, "Nonreplicating vaccinia vector efficiently expresses recombinant genes," Proc Natl Acad Sci USA, 89(22):10847-10851.
Swayne et al., 2003, "Recombinant paramyxovirus type 1-avian influenza-H7 virus as a vaccine for protection of chickens against influenza and Newcastle disease," Avian Dis., 47(3 Suppl):1047-1050.
Wang et al., 1992, "High-affinity laminin receptor is a receptor for Sindbis virus in mammalian cells," J Virol., 66(8):4992-5001.
Winokur et al., 1991, "The hepatitis A virus polyprotein expressed by a recombinant vaccinia virus undergoes proteolytic processing and assembly into viruslike particles," J Virol., 65(9):5029-5036.
Xiao et al., 1996, "High efficiency, long-term clinical expression of cottontail rabbit papillomavirus (CRPV) DNA in rabbit skin following particle-mediated DNA transfer," Nucleic Acids Res., 24(13):2620-2622.
Zhou et al., 1994, "Adeno-associated virus 2-mediated high efficiency gene transfer into immature and mature subsets of hematopoietic progenitor cells in human umbilical cord blood," J Exp Med., 179(6):1867-1875.

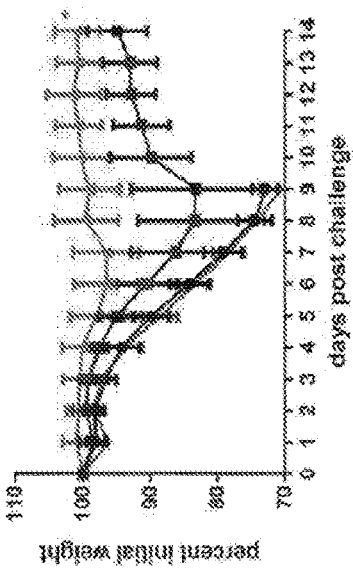
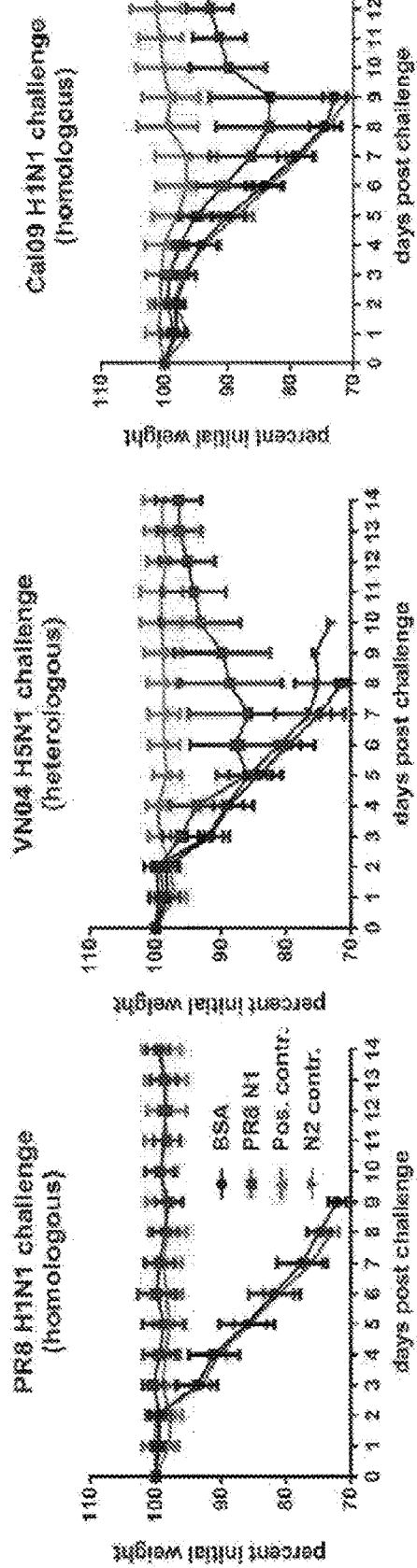
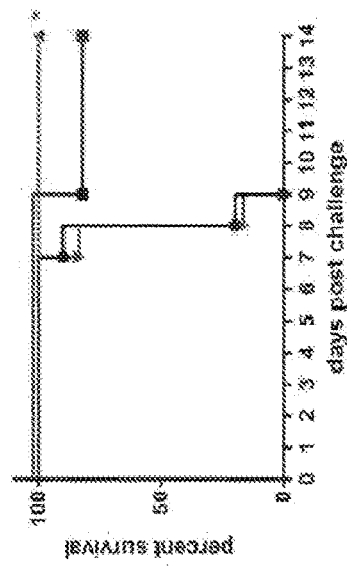
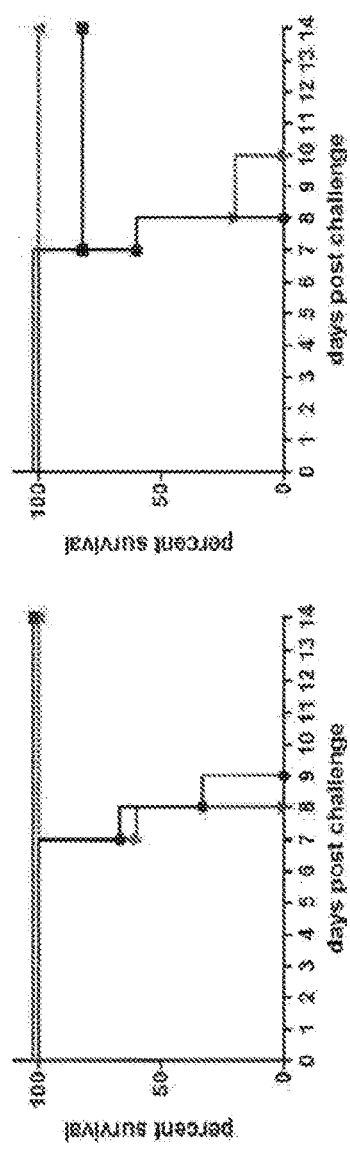
FIG. 1A   FIG. 1B   FIG. 1C
FIG. 1D   FIG. 1E   FIG. 1F

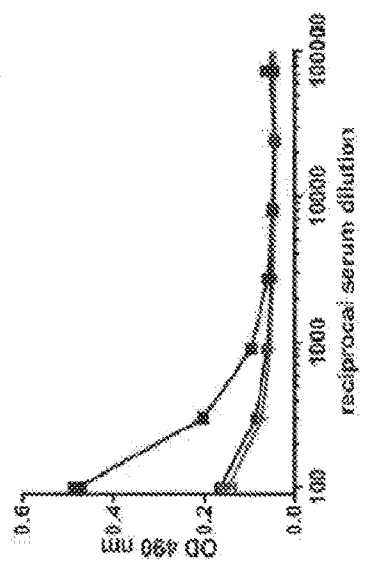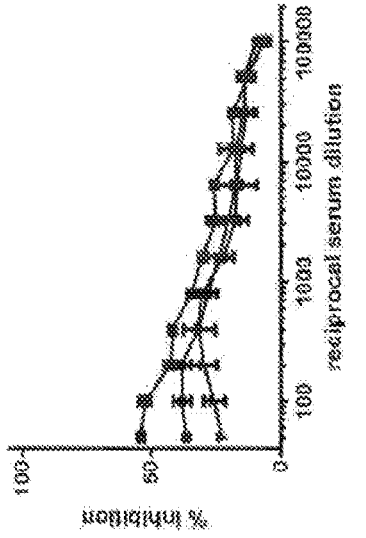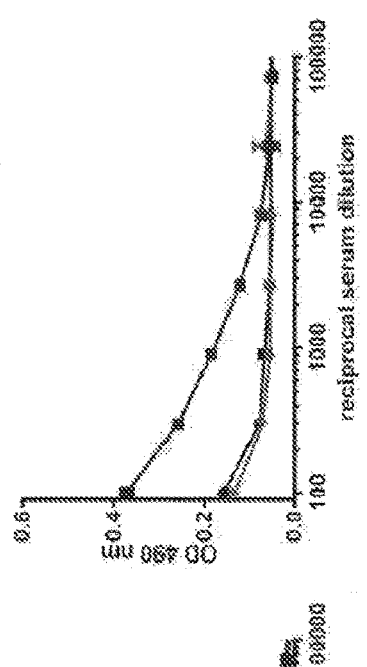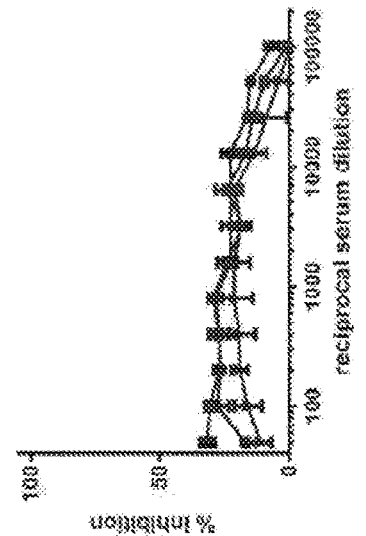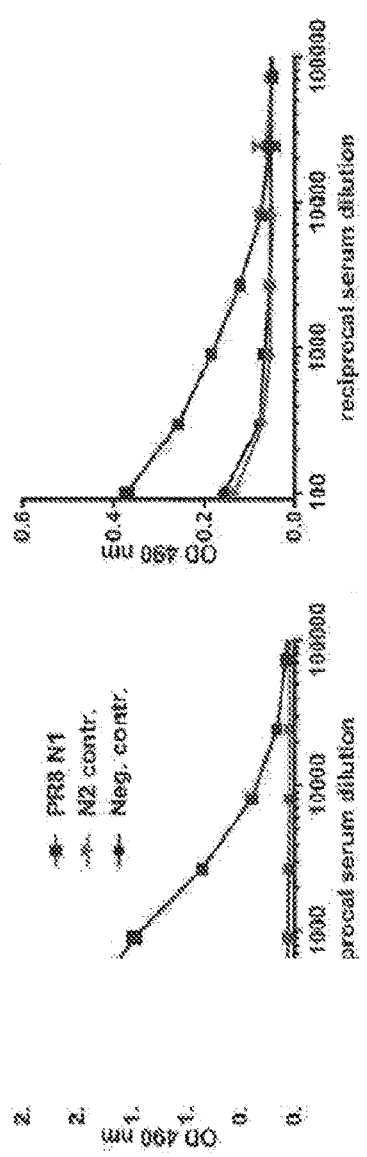
FIG. 1G FIG. 1H FIG. 1I
FIG. 1J FIG. 1K FIG. 1L

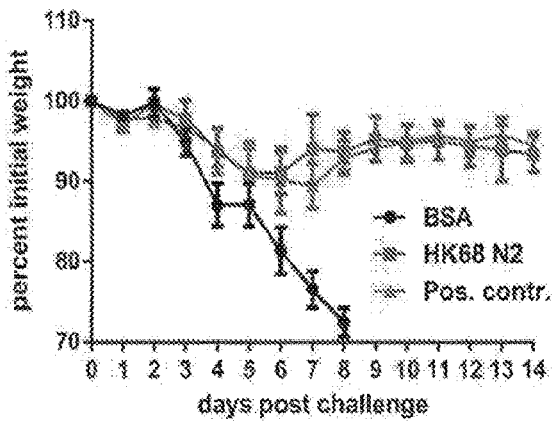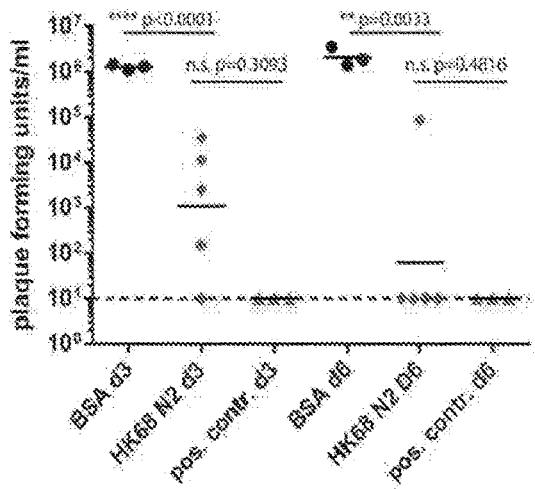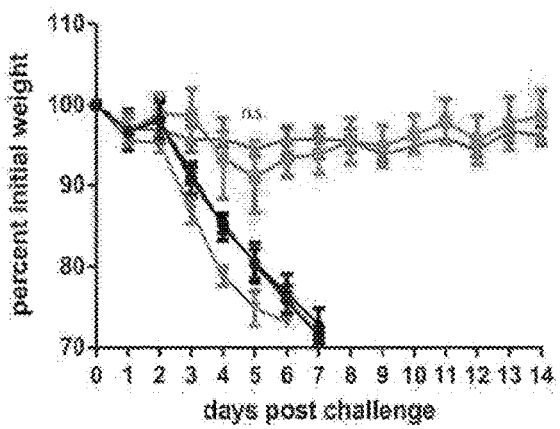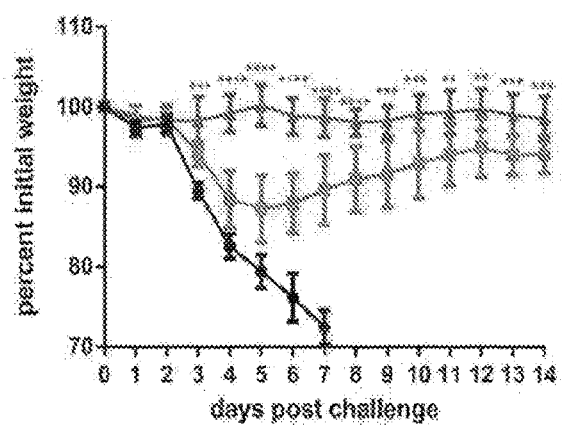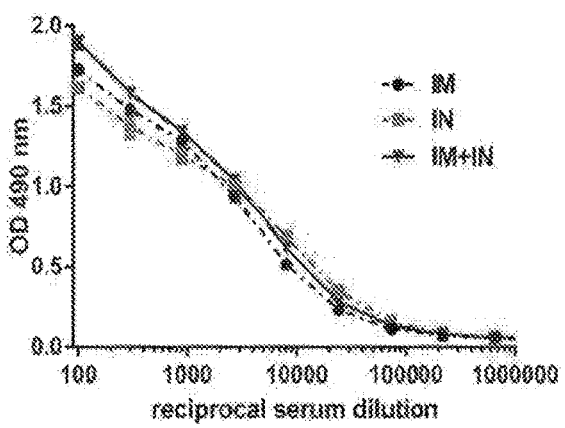

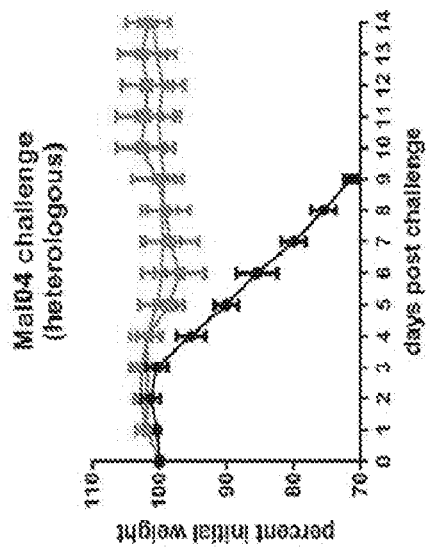
FIG. 4A
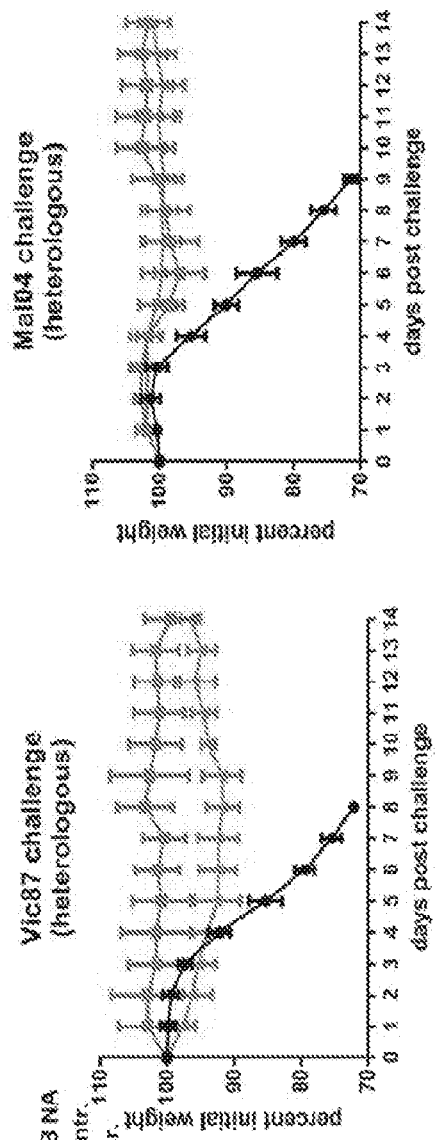
FIG. 4B
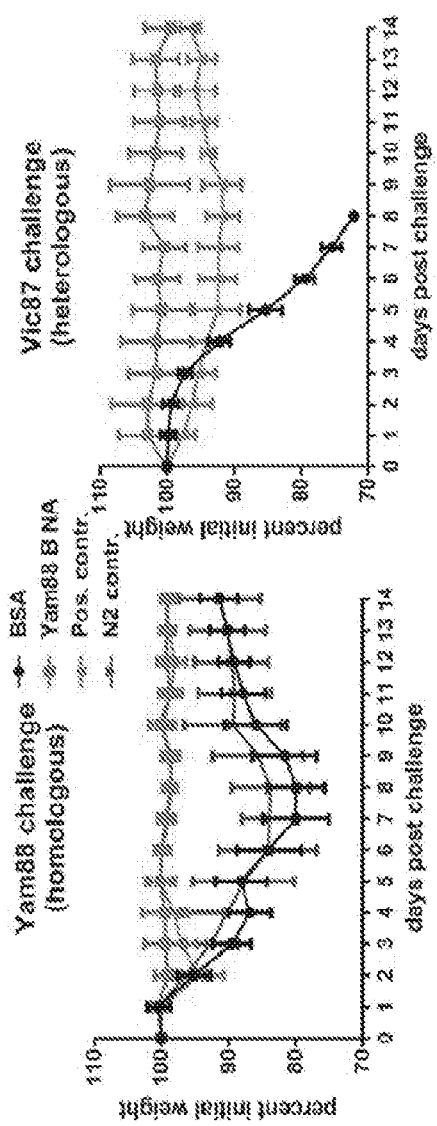
FIG. 4C
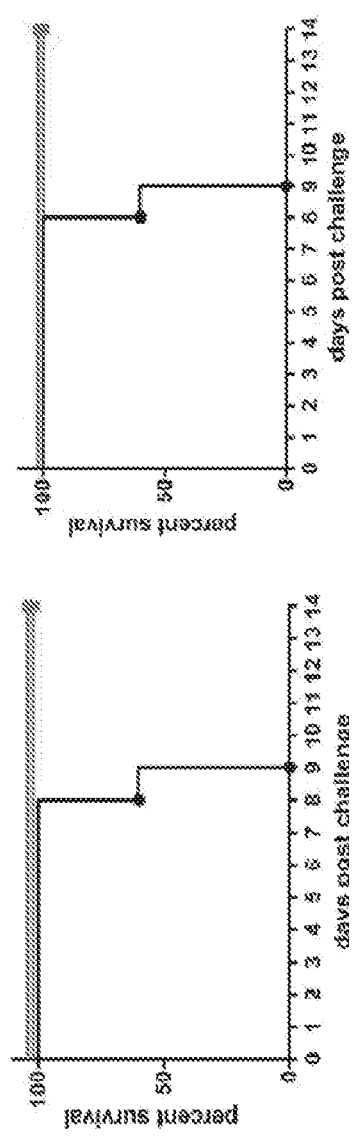
FIG. 4D
FIG. 4E
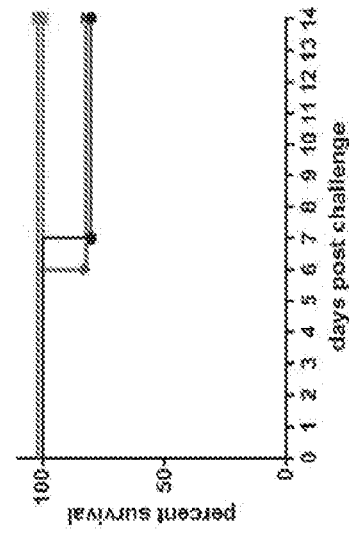
FIG. 4F

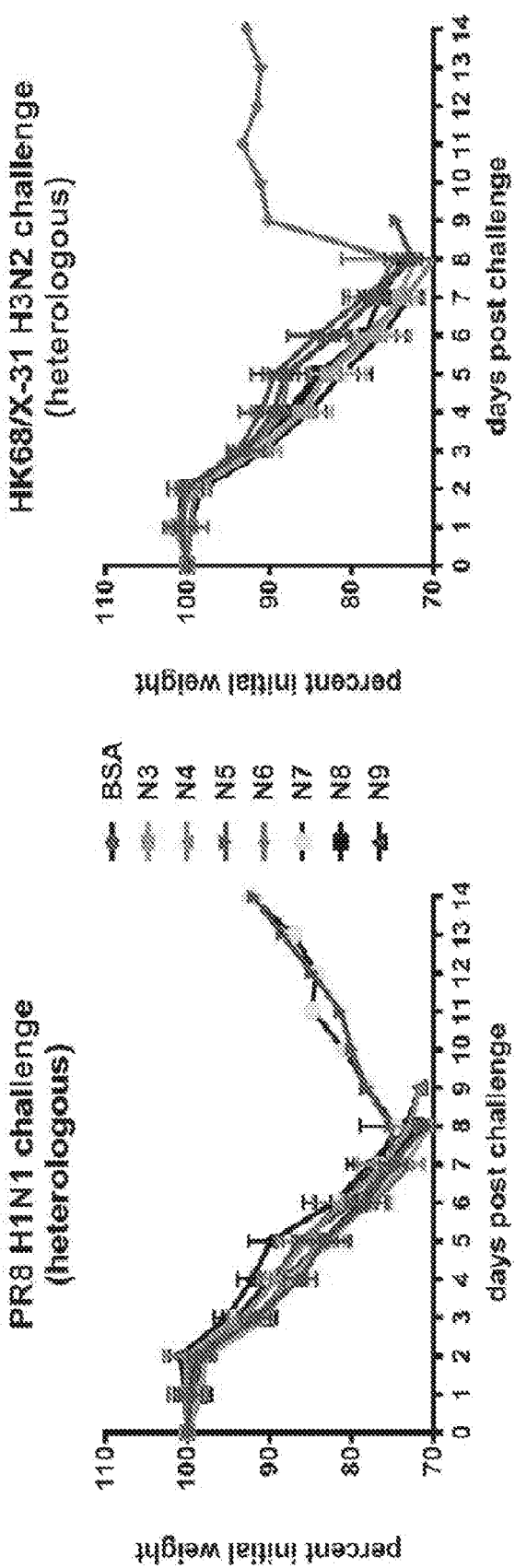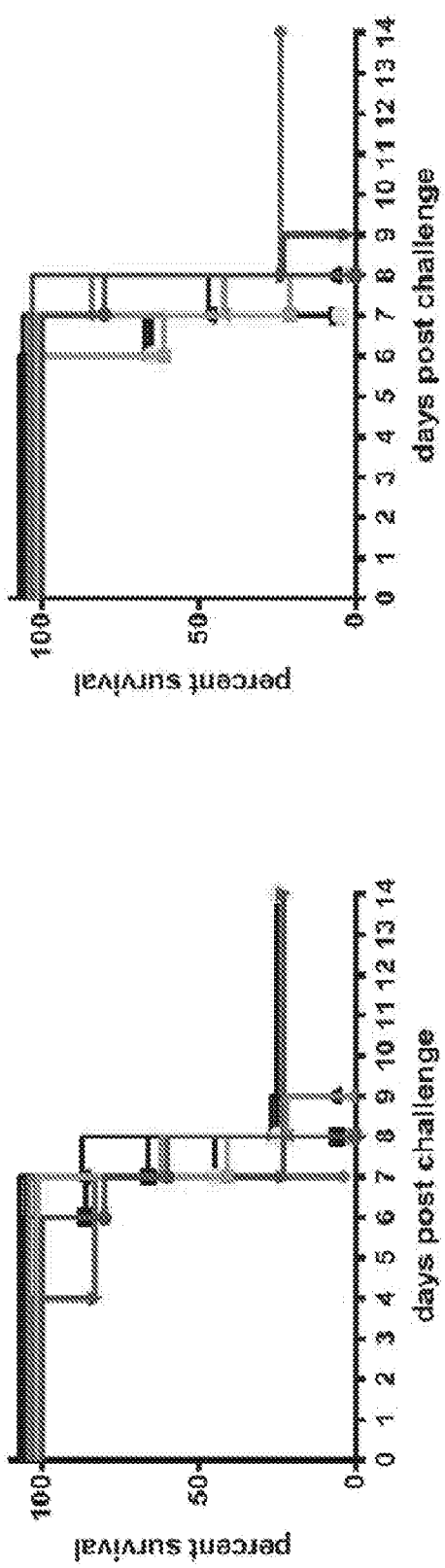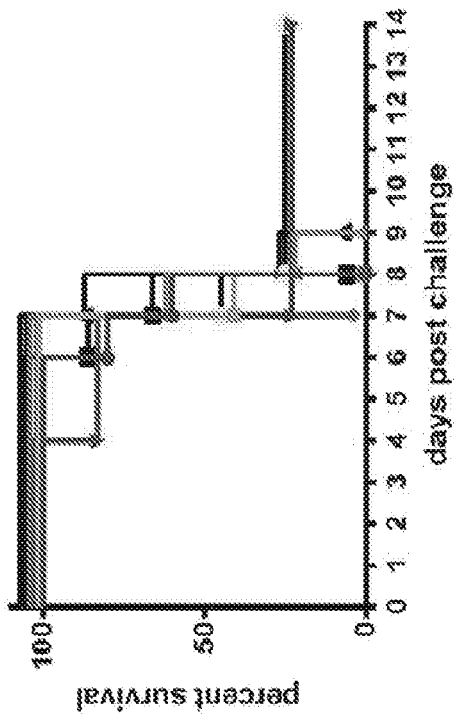
FIG. 5A  FIG. 5B  FIG. 5C  FIG. 5D

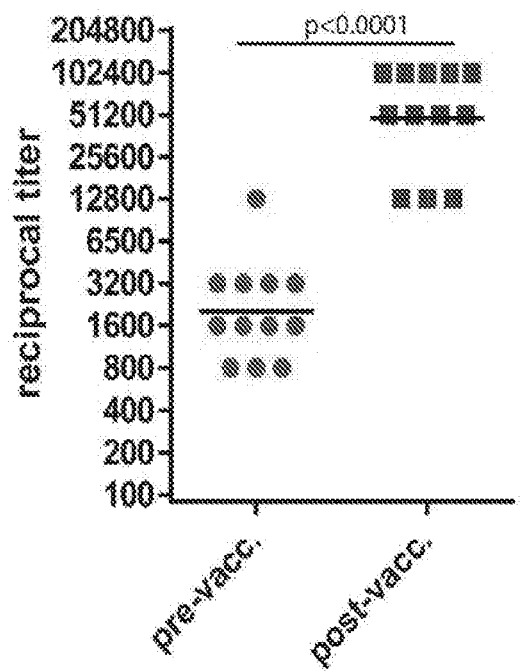
FIG. 6A H1 HA
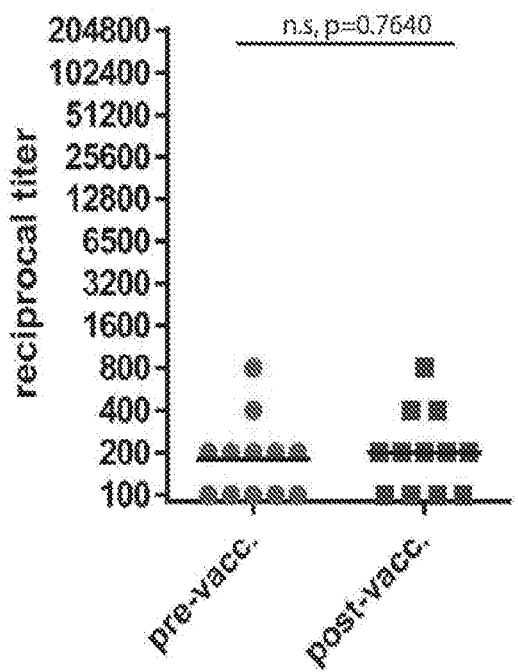
FIG. 6B N1 NA
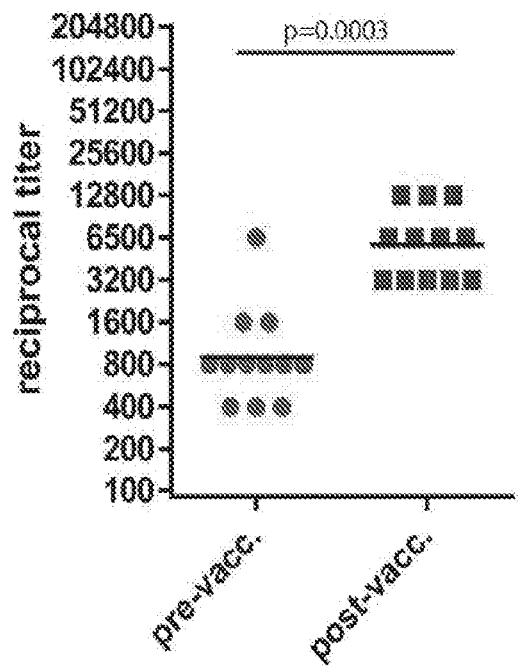
FIG. 6C H3 HA
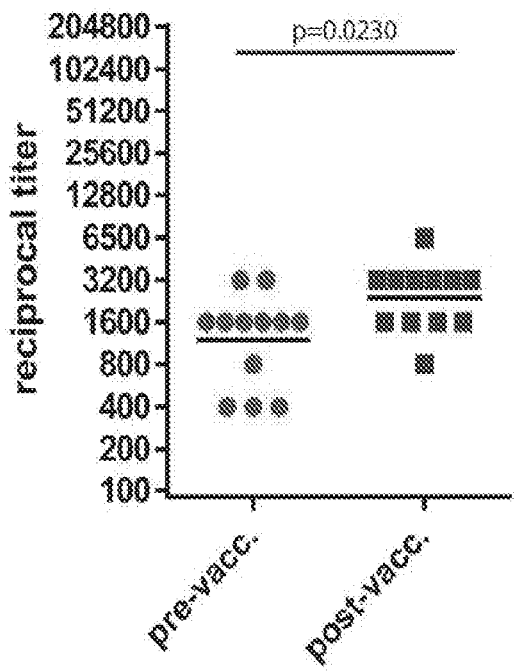
FIG. 6D N2 NA

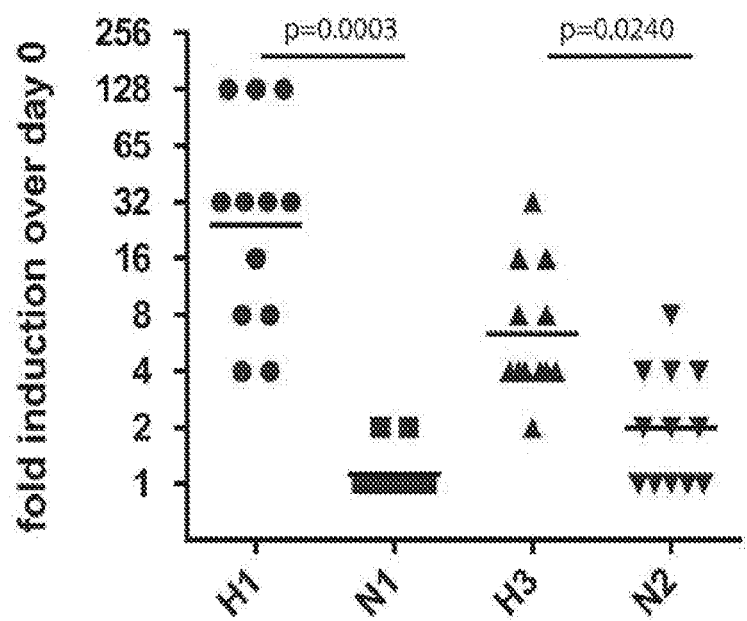

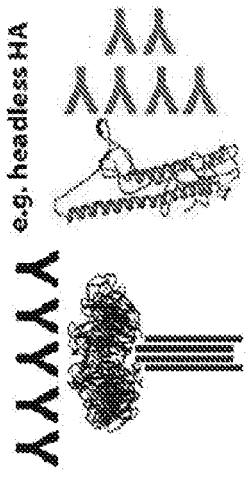
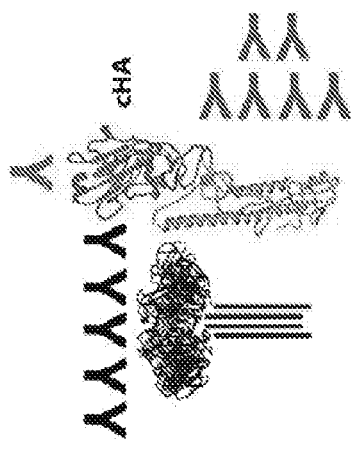
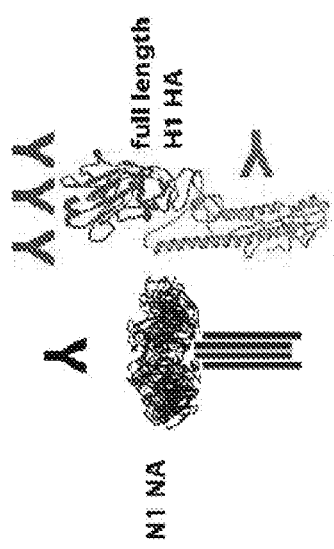
FIG. 8A regular seasonal vaccination
FIG. 8B vaccination with cHA vaccines (st

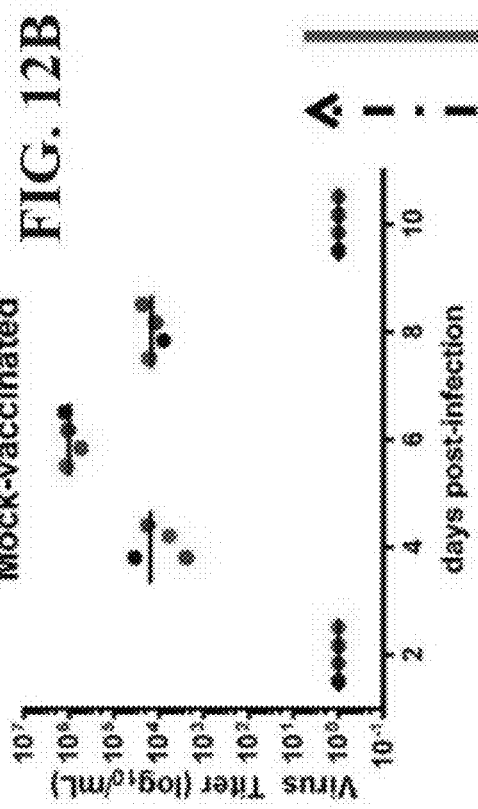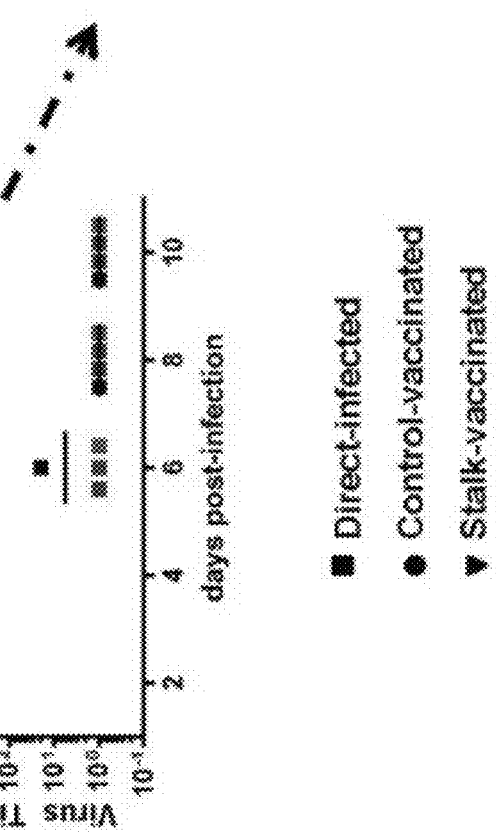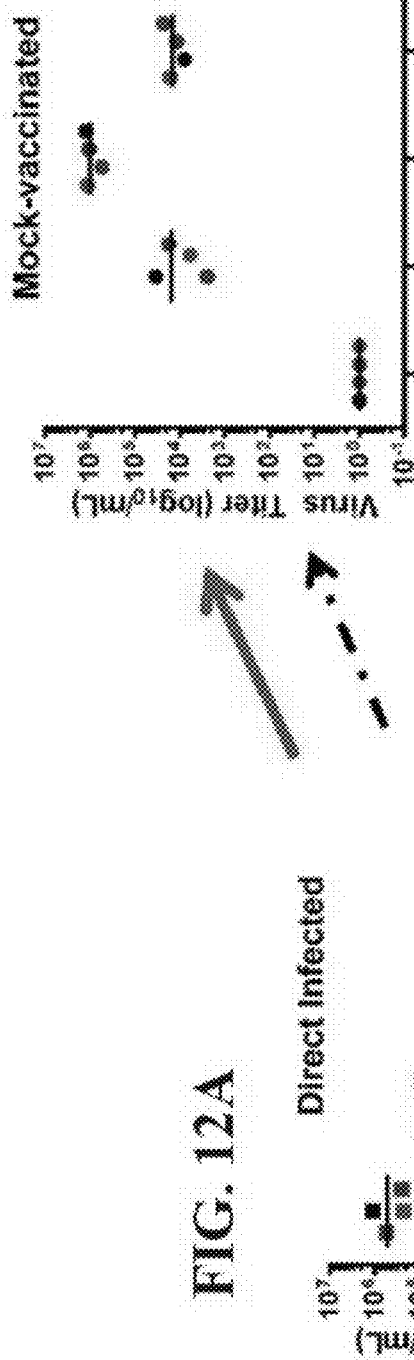

```
                             ▼(Mature residue 1)
    H1    -MKANLLVLLCALA--AAD---------ADTICIGYHANNSTDTVDTVLEKNVTVTHSVNL
    H2    ----MAIIYLILLFT--AVR--------GDQICIGYHSNNSTEKVDTILERNVTVTHAQNI
    H3    --MKTIIALSYIFCLALGQDLPGNDNSTATLCLGHHAVPNGTLVKTITDDQIEVTNATEL
    H4    --MLSIVILFLLIAENS----SQNYTGNPVICMGHHAVANGTMVKTLADDQVEVVTAQEL
    H5    ---MERIVLLLAIVS--LVK--------SDQICIGYHANKSTKQVDTIMEKNVTVTHAQDI
    H6    --MIAIIVVAILAT--AGR---------SDKICIGYHANNSTTQIDTILEKNVTVTHSVEL
    H7    --MNTQILVPALVAVIPTN---------ADKICLGHHAVSNGTKVNTLTERGVEVVNATET
    H8    --MEKFIAIAT-LASTNA----------YDRICIGYQSNNSTDTVNTLIEQNVPVTQTMEL
    H9    --METKAIIAALLMVTAAN---------ADKICIGYQSTNSTETVDTLTESNVPVTHTKEL
    H10   --MYKVVVIIALLGAVKG----------LDRICLGHHAVANGTIVKTLTNEQEEVTNATET
    H11   --MEKTLLFAAIFL--CVK--------ADEICIGYLSNNSTDKVDTIIENNVTVTSSVEL
    H12   --MEKFIILSTVLAASFA----------YDKICIGYQTNNSTETVNTLSEQNVPVTQVEEL
    H13   -MALNVIATLTLIS-VCVH--------ADRICVGYLSTNSSERVDTLLENGVPVTSSIDL
    H14   --MIALILVALALSHIAYSQITNGTTGNPIICLGHHAVENGTSVKTLTDNHVEVVSAKEL
    H15   --MNTQIIVILVLGLSMVK--------SDKICLGHHAVANGTKVNTLTERGVEVVNATET
    H16   -MMIKVLYFLIIVLGRYSK--------ADKICIGYLSNNSSDTVDTLTENGVPVTSSVDL
    H17   MELIVLLILLNPYT--FVL--------GDRICIGYQANQNNQTVNTLLEQNVPVTGAQEI
                             ▲(Mature residue 1)
              ▼(Residue Ap)                        (Residue Cp)▼
    H1    LEDSHNGKLCRLKGIAPLQLGKCNIAGWLLGNPECDPLLPVRSWSYIVETPNSENGICYP
    H2    LEKTHNGKLCKLNGIPPLELGDCSIAGWLLGNPECDRLLTVPEWSYIMEKENPRNGLCYP
    H3    VQSSSTGKICNN-PHRILDGIDCTLIDALLGDPHCDVFQNET-WDLFVERSKAFS-NCYP
    H4    VESQNLPELCPS-PLRLVDGQTCDIINGALGSPGCDHLNGAE-WDVFIERPNAVD-TCYP
    H5    LERTHNGKLCSLNGVKPLILRDCSVAGWLLGNPMCDEFLNLPEWLYIVEKDNPINSLCYP
    H6    LENQKEERFCKILKKAFLDKGCTIEGWILGNPQCDLLLGDQSWSYIVERPTAQNGICYP
    H7    VERTNIPKICSK-GKRTTDLGQCGLLGTITGPPQCDQPLEFS-ADLIIERREGND-VCYP
    H8    VETEKHPAYCNTDLGAPLELRDCKIEAVIYGNPKCDIHLKDQGWSYIVERPSAPEGMCYP
    H9    LHTEHNGMLCATDLGHPLILDTCTIEGLIYGNPSCDILLGGKEWSYIVERSSAVNGMCYP
    H10   VESTNLNKLCMK-GRSYKDLGNCHPVGMLIGTPVCDPHLTGT-WDTLIERENAIA-ECYP
    H11   VETEHTGSFCSINGKQPISLGDCSFAGWILGNPMCDELIGKTSWSYIVEKPNPTNGICYP
    H12   VHRGIDPILCGTELGSPLVLDDCSLEGLILGNPKCDLYLNGREWSYIVERPKEMEGVCYP
    H13   IETNHTGTYCSLNGVSPVHLGDCSFEGWIVGNPACTSNFGIREWSYLIEDPAAPHGLCYP
    H14   VETNHTDELCPS-PLKLVDGQDCHLINGALGSPGCDRLQDTT-WDVFIERPTAVD-TCYP
    H15   VEITGIDKVCTK-GKKAVDLGSCGILGTIIGPPQCDLHLEFK-ADLIIERRNSSD-ICYP
    H16   VETNHTGTYCSLNGISPIHLGDCSFEGWIVGNPSCATNINIREWSYLIEDPNAPNKFCYP
    H17   LETNHNGKLCSLNGVPPLDLQSCTLAGWLLGNPNCDSLLEAEEWSYIKINESAPDDLCFP
              ▲(Residue Ap)                        (Residue Cp)▲

H1    GDFIDYEELREQLSSVSSFERFEIFPKESSWPNHNTNGVTAACSHE-GKSSFYRNLLWLT
    H2    GSFNDYEELKHLLSSVTHPEKVKILFKDRWTQHTTTGG-SRACAVS-GNPSFFRNMVWLT
    H3    YDVPDYASLRSLVASSGTLE--FITEGFTW-TGVTQNGGSNACKRG-PGNGFFSRLNWLT
    H4    FDVPEYQSLRSILANNGKFE--FIAEEFQW-NTVKQNGKSGACKRA-NVDDFFNRLNWLV
    H5    GDFNDYEELKYLLSSTNHPEKIRIIPRSSWSNHDASSGVSSACPYI-GRSSFLRNVVWLI
    H6    GVLNEVEELKALIGSSGERVERFEMFPKSTWTGVDTSSGVTRACPYN-SGSSFYRNLLWII
    H7    GKFVNEEALRQILRGSGGID--KETMGFTY-SGIRTNGTTSACRRS-G-SSFYAEMEWLL
    H8    GSVENLEELRFVFSSAASYKRIRLFDYSRWNVTRS--GTSKACNASTGGQSFYRSINWLT
    H9    GNVENLEELRSLFSSAKSYKRIQIFPDKTWNVTYS--GTSRACSN-----SPFYRSMRWLT
    H10   GATINEEALRQKIMESGGIS--KMSTGFTYGSSITSAGTTKACMRN-GGDSFYAELKWLV
    H11   GTLESEEELRLKFSGVLEFNKFEVFTSNGWGAVNSGVGVTAACKFG-GSNSFFRNMVWLI
    H12   GSIENQEELRSLFSSIKKYERVKMFDFTKWNVTYT--GTSKACNNTSNQGSFYRSMRWLT
    H13   GELNNNGELRHLFSGIRSFSRTELIPPTSWGEVLD--GTTSACRDNTGTNSFYRNLVWFI
    H14   FDVPDYQSLRSILASSGSLE--FIAEQFTW-NGVKVDGSSSACLRG-GRNSFFSRLNWLT
    H15   GRFTNEEALRQIIRESGGID--KESMGFRY-SGIRTDGATSACKRT-V-SSFYSEMKWLS
    H16   GELDNNGELRHLFSGVNSFSRTELINPSKWGNVLD--GVTASCLDR-GASSFYRNLVWIV
    H17   GNFENLQDLLLEMSGVQNFTKVKLFNPQSMTG-VTTNNVDQTCPFE-GKPSFYRNLNWIQ
```

FIG. 14A

```
H1   E-K-EGSYPKLKNSYVNKKGKEVLVLWGIHHPPNSKEQQNLYQNENAYVSVVTSNYNRRF
H2   K-K-GSNYPIAKGSYNNTSGEQMLIIWGVHHPNDETEQRTLYQNVGTYVSIGTSTLNKRS
H3   KS--GSTYPVLNVTMPNNDNFDKLYIWGVHHPSTNQEQTSLYVQESGRVTVSTRRSQQSI
H4   KSD-GNAYPLQNLTKINNGDYARLYIWGVHHPSTSTEQTNLYKNNPGRVTVSTKTSQTSV
H5   K-K-NNTYPTIKRSYNNTNQEDLLILWGIHHPNDAAEQTKLYQNPTTYVSVGTSTLNQRS
H6   KTK-SAAYSVIKGAYNNTGNQPILYFWGVHHPPDTNEQNTLYGSGDRYVRMGTESMNFAK
H7   SNTDNASFPQMTKSYKNTRRESALIVWGIHHSGSTTEQTKLYGSGNKLITVGSSKYHQSF
H8   KKE-PDTYDFNEGAYVNNEDGDIIFLWGIHHPPDTKEQTTLYKNANTLSSVTTNTINRSF
H9   HK--SNSYPFQNAHYTNNERENILFMWGIHHPPTDTEQTDLYKNADTTTSVTTEDINRTF
H10  SKTKGQNFPQTTNTYRNTDTAEHLIIWGIHHPSSTQEKNDLYGTQSLSISVESSTYQNNF
H11  H-Q-SGTYPVIKRTFNNTKGRDVLIVWGIHHPATLTEHQDLYKKDSSYVAVGSETYNRRF
H12  LK--SGQFPVQTDEYKNTRDSDIVFTWAIHHPPTSDEQVKLYKNPDTLSSVTTVEINRSF
H13  K-K-NTRYPVISKTYNNFTGRDVLVLWGIHHPVSVDETKTLYVNSDPYTLVSTKSWSEKY
H14  KAT-NGNYGPINVTKENTGSYVRLYLWGVHHPSSDNEQTDLYKVATGRVTVSTRSDQISI
H15  SSMNNQVFPQLNQTYRNTRKEPALIVWGVHHSSSLDEQNKLYGTGNKLITVGSSKYQQSF
H16  K-K-DEKYPVIKGDYNNTTGRDVLVLWGIHHPDTETTATNLYVNKNPYTLVSTKEWSKRY
H17  G----NSGLPFNIEIKNPTSNPLLLLWGIHNTKDAAQQRNLYGNDYSYTIFNFGEKSEEF

▼(Residue Cq)
H1   TPEIAERPKVRDQAGRMNYYWTLLKPGDTIIFEANGNLIAPMYAFALSRGFG--------
H2   IPVIATRPKVNGQGGRMEFSWTILDIWDTINFESTGNLIAPEYGFRISKRGS--------
H3   IPNIGSRPWVRGQSSRISIYWTIVKPGDLVINSNGNLIAPRGYFKMRTG---------K
H4   VPDIGSRPLVRGQSGRVSFYWTIVEPGDLIVFNTIGNLIAPRGHYKLNNQK--------K
H5   IPEIATRPKVNGQGGRMEFFWTILKPNDAINFESNGNFIAPRYAYKIVKKGD--------
H6   SPEIAARPAVNGQRGIDYYWSILKPGETLNVESNGNLIAPWYAFRFVSTSNK--------
H7   VPSPGTRPQINGQSGRIDFHWLILDPNDTVTFSFNGAFIAPNRASFLR---------GK
H8   QPNIGPRPLVRGQQGRMDYYWGILKRGETLKIRTNGNLIAPEFGYLLKGESY--------
H9   KPVIGPRPLVNGQQGRIDYYWSVLKPGQTLRIRSNGNLIAPWYGHVLTGESH--------
H10  VPVVGARPQVNGQSGRIDFHWTLVQPGDNITFSDNGGLIAPSRVSKLT----------GR
H11  TPEINTRPRVNGQAGRMTFYWKIVKPGESITFESNGAFLAPRYAFEIVSVGN--------
H12  KPNIGPRPLVRGQQGRMDYYWAVLKPGQTVKIQTNGNLIAPEYGHLITGKSH--------
H13  KLETGVRPGYNGQRSWMKIYWSLIHPGEMITFESNGGFLAPRYGYIIEEYGK--------
H14  VPNIGSRPRVRNQSGRISIYWTLVNPGDSIIFNSIGNLIAPRGHYKISKST--------K
H15  SPSPGARPKVNGQAGRIDFHWMLLDPGDTVTFTFNGAFIAPDRATFLRSNAPSGIEYNGK
H16  ELEIGTRIG-DGQRSWMKLYWHLMHFGERIMFESNGGLIAPRYGYIIEKYGT--------
H17  RPEIGQRDEVKAHQDRIDYYWGSLPAQSTLRIESTGNLIAPEYGFYYKRKEGK--------
                                              ▲(Residue Cq)

▼(Residue Aq)                  ▼(Residue Bq)
H1   SGIITS-NASMHECNTKCQTPLGAINSSLPYQNIHPVTIGECPKYVRSAKLRMVTGLRNN
H2   SGIMKT-EGTLENCETKCQTPLGAINTTLPFHNVHPLTIGECPKYVKSERLVLATGLRNV
H3   SSIMSSDAPIDT-CISECITPNGSIPNDKPFQNVNKITYGACPKYVKQNTLKLATGMRNV
H4   STILNTAIPIGS-CVSKCHTDKGSLSTTKPFQNISRIAVGDCPRYVKQGSLKLATGMRNI
H5   SAIMKS-GLAYGNCDTKCQTPVGEINSSMPFHNIHPHTIGECPKYVKSDRLVLATGLRNV
H6   GAVFKS-NLPIENCDATCQTVAGVLRTNKTFQNVSPLWIGECPKYVKSESLRLATGLRNV
H7   SMGIQSDVQVDANCEGECYHSGGTITSRLPFQNINSRAVGKCPRYVKQESLLLATGMKNV
H8   GRIIQNEDIPIGNCNTKCQTYAGAINSSKPFQNASRHYMGECPKYVKKASLRLAVGLRNT
H9   GRILKT-DLNNGNCVVQCQTEKGGLNTTLPFHNISKYAFGNCPKYVGVKSLKLPVGLRNV
H10  DLGIQSEALIDNSCESKCFWRGGSINTKLPFQNLSPRTVGQCPKYVNQRSLLLATGMRNV
H11  GKLFRS-ELNIESCSTKCQTEIGGINTNKSFHNVHRNTIGDCPKYVNVKSLKLATGPRNV
H12  GRILKN-NLPMGQCVTECQLNEGVMNTSKPFQNTSKHYIGKCPKYIPSGSLKLAIGLRNV
H13  GRIFQS-RIRMSRCNTKCQTSVGGINTNRTFQNIDKNALGDCPKYIKSGQLKLATGLRNV
H14  STVLKSDKRIGS-CTSPCLTDKGSIQSDKPFQNVSRIAIGNCPKYVKQGSLMLATGMRNI
H15  SLGIQSDAQIDESCEGECFYSGGTINSPLPFQNIDSRAVGKCPRYVKQSSLPLALGMKNV
H16  GRIFQS-GVRMARCNTKCQTSLGGINTNKTFQNIERNALGDCPKYIKSGQLKLATGLRNV
H17  GGLMKS-KLPISDCSTKCQTPLGALNSTLPFQNVHQQTIGNCPKYVKATSLMLATGLRNN
         ▲(Residue Aq)                  ▲(Residue Bq)
```

FIG. 14B

```
                        ▼(HA2 domain starts)
H1    P----SIQSRGLFGAIAGFIEGGWTGMIDGWYGYHHQNEQGSGYAADQKSTQNAINGITN
H2    P----QIESRGLFGAIAGFIEGGWQGMIDGWYGYHHSNDQGSGYAADKESTQKAIDGITN
H3    P----EKQTRGLFGAIAGFIENGWEGMIDGWYGFRHQNSEGTGQAADLKSTQAAIDQING
H4    P----EKASRGLFGAIAGFIENGWQGLIDGWYGFRHQNAEGTGTAADLKSTQAAIDQING
H5    P----QKKKRGLFGAIAGFIEGGWQGMVDGWYGYHHSNEQGSGYAADKESTQKAIDGITN
H6    P----QIETRGLFGAIAGFIEGGWTGMIDGWYGYHHENSQGSGYAADRESTQKAVDGITN
H7    PEPSKERKYRGLFGAIAGFIENGWEGLVDGWYGFRHQNAQGEGTAADYKSTQSAIDQITG
H8    P----SVEPRGLFGAIAGFIEGGWSGMIDGWYGFHHSNSEGTGMAADQKSTQEAIDKITN
H9    P----AVSSRGLFGAIAGFIEGGWPGLVAGWYGFQHSNDQGVGMAADKGSTQKAIDKITS
H10   P---EVVQGRGLFGAIAGFIENGWEGMVDGWYGFRHQNAQGTGQAADYKSTQAAIDQITG
H11   P----AIASRGLFGAIAGFIEGGWPGLINGWYGFQHRDEEGTGIAADKESTQKAIDQITS
H12   P----QVQDRGLFGAIAGFIEGGWPGLVAGWYGFQHNAEGTGIAADRDSTQRAIDNMQN
H13   P----AISNRGLFGAIAGFIEGGWPGLINGWYGFQHQNEQGTGIAADKESTQKAIDQITT
H14   P----GKQAKGLFGAIAGFIENGWQGLIDGWYGFRHQNAEGTGTAADLKSTQAAIDQING
H15   P----EKIRTRGLFGAIAGFIENGWEGLIDGWYGFRHQNAQGQGTAADYKSTQAAIDQITG
H16   P----SIGERGLFGAIAGFIEGGWPGLINGWYGFQHQNEQGTGIAADKASTQKAINEITT
H17   P----QMEGRGLFGAIAGFIEGGWQGMIDGWYGYHHENQEGSGYAADKEATQKAVDAITN
                        ▲(HA2 domain starts)

H1    KVNTVIEKMNIQFTAVGKEFNKLEKRMENLNKKVDGFLDIWTYNAELLVLLENERTLDF
H2    RVNSVIEKMNTQFEAVGKEFSNLERRLENLNKKMEDGFLDVWTYNAELLVLMENERTLDF
H3    KLNRVIEKTNEKFHQIEKEFSEVEGRIQDLEKYVEDTKIDLWSYNAELLVALENQHTIDL
H4    KLNRLIEKTNDKYHQIEKEFEQVEGRIQDLENYVEDTKIDLWSYNAELLVALENQHTIDV
H5    KVNSIIDKMNTRFEAVGKEFNNLERRVENLNKKMEDGFLDWWTYNVELLVLMENERTLDF
H6    KVNSIIDKMNTQFEAVDHEFSNLERRIDNLNKRMEDGFLDWWTYNAELLVLLENERTLDL
H7    KLNRLIEKTNQQFELIDNEFTEVEKQIGNLINWPKDSITEVWSYNAELIVAMENQHTIDL
H8    KVNNIVDKMNREFEVVNHEFSEVEKRINMINDKIDDQIEDLWAYNAELLVLLENQKTLDE
H9    KVNNIIDKMNKQYEVIDHEFNELEARLNMINNKIDDQIQDIWAYNAELLVLLENQKTLDE
H10   KLNRLIEKTNTEFESIESEFSETEHQIGNVINWPKDSITDIWTYNAELLVAMENQHTIDM
H11   KVNNIVDRMNTNFESVQHEFSEIEERINQLSKHVLDSVVDIWSYNAQLLVLLENEKTLDL
H12   KLNNVIDKMNKQFEVVNHEFSEVESRINMINSKIDDQITDIWAYNAELLVLLENQKTLDE
H13   KINNIIDKMNGNYDSIRGEFNQVEKRINMLADRIDDAVTDIWSYNAKLLVLLENDKTLDM
H14   KLNRLIEKTNEKYHQIEKEFEQVEGRIQDLEKYVEDTKIDLWSYNAELLVALENQHTIDV
H15   KLNRLIEKTNKQFELIDNEFTEVEQQIGNVINWTRDSLTEIWSYNAELLVAMENQHTIDL
H16   KINNIIEKMNGNYDSIRGEFNQVEKRINMLADRVDDAVTDIWSYNAKLLVLLENDRTLDL
H17   KVNSIIDKMNSQFESNIKEFNKLELRIQHLSDRVDDALLDIWSYNTELLVLLENERTLDF

H1    HDSNVKNLYEKVKSQLKNNAKEIGNGCFEFYHKCDNECMESVRNGTYDYPKYSEESKLNR
H2    HDSNVKNLYDRVKMQLRDNAKELGNGCFEFYHKCDDECMNSVKNGTYDYPKYEEESKLNR
H3    TDSEMNKLFEKTRRQLRENAEDMGNGCFKIYHKCDNACIESIRNGTYDHDVYRDEALNNR
H4    TDSEMNKLFERVRRQLRENAEDKGNGCFEIPHKCDNNCIESIRMGTYDHDIYRDEAINNR
H5    HDSNVRNLYDKVRLQLKDNAKELGNGCFEFYHKCDNECMESVRNGTYDPQYSEEARLNR
H6    HDANVKNLYERVKSQLRDNAMILGNGCFEFWHKCDDECMESVKNGTYDYPKYQDESKLNR
H7    ADSEMNRLYERVRKQLRENAEEDGTGCFEIPEKCDDDCMASIRNNTYDHSKYREEAMQNR
H8    HDSNVKNLFDEVKRRLSANAIDQGNGCFDILHKCDNECMETIKMGTYDHKEYEEEAKLER
H9    HDANVNNLYNKVKRALGSNAVEDGNGCFELYHKCDDQCMETIRNGTYDRQKYQEESRLER
H10   ADGEMLNLYERVRKQLRQNAEEDGKGCFEIYHTCDSCMESIRMNTYDHSQYREEALLNR
H11   HDSNVRNLHEKVRRMLKDNAKDEGNGCFTFYHKCDNKCIERVRNGTYDHKEFEEESKINR
H12   HDANVRNLHEDRVRRVLRENAIDTGDGCFEILHKCDNNCMDTIRNGTYNHKEYEEESKIER
H13   HDANVKNLHEQVRRELKDNAIDEGNGCFELLHKCNDSCMETIRMGTYDHTEYAEESKLKR
H14   TDSEMNKLFERVRRQLRENAEDQGNGCFEIPHQCDNNCIESIRMGTYDHNIYRDEAINNR
H15   ADGEMNKLYERVRRQLRENAEEDGTGCFEIFHRCTDDQCMESIRMNTYMHTEYRQEALQNR
H16   HDANVRNLHDQVKRALKSNAIDEGDGCFNLLHKCNDSCMETIRMGTYMHEDYREESQLKR
H17   HDANVKNLFEKVKAQLKDNAIDEGNGCFLLHKCNNSCMDDIKMGTYKYMDYREESHIEK
```

FIG. 14C

```
H1   EKVDGVKLESMG-IYQILAIYSTVASSLVLLVSLGAISFWMCSNGSLQCRICI
H2   NEIKGVKLSNMG-VYQILAIYATVAGSLSLAIMIAGISLWMCSNGSLQCRICI
H3   FQIKGVELKSGY--KDWILWISFAISCFLLCVVLLGFIMWACQRGNIRCNICI
H4   FQIQGVKLTQGY--KDIILWISFSISCFLLVALLLAFILWACQNGNIRCQICI
H5   EEISGVKLESMG-VYQILSIYSTVASSLALAIMIAGLSFWMCSNGSLQCRICI
H6   QEIESVKLESLG-VYQILAIYSTVSSSLVLVGLIIAVGLWMCSNGSMQCRICI
H7   IQIDPVKLSSGY--KDVILWFSFGASCFLLLAIAMGLVFICVKNGNMRCTICI
H8   SKINGVKLEENT-TYKILSIYSTVAASLCLAILIAGGLILGMQNGSCRCMFCI
H9   QKIEGVKLESEG-TYKILTIYSTVASSLVLAMGFAAFLFWAMSNGSCRCNICI
H10  LNINPVKLSSGY--KDIILWFSFGESCFVLLAVVMGLVFFCLKNGNMRCTICI
H11  QEIEGVKLDSSGNVYKILSIYSCIASSLVLAALIMGFMFWACSNGSCRCTICI
H12  QKVNGVKLEENS-TYKILSIYSSVASSLVLLLMIIGGFIFGCQNGNVRCTFCI
H13  QEIDGIKLKSEDNVYKALSIYSCIASSVVLVGLILSFIMWACSSGNCRFNVCI
H14  IKINPVTLTMGY--KDIILWISFSMSCFVFVALILGFVLWACQNGNIRCQICI
H15  IMINPVKLSSGY--KDVILWFSFGASCVMLLAIAMGLIFMCVKNGNLRCTICI
H16  QEIEGIKLKTEDNVYKVLSIYSCIASSIVLVGLILAFIMWACSNGSCRFNVCI
H17  QKIDGVKLTDYS-RYYIMTLYSTIASSVVLGSLIIAAFLWGCQKGSIQCKICI
```

FIG. 14D

SEQUENCE LISTING

```
<160> NUMBER OF SEQ ID NOS: 107

<210> SEQ ID NO 1
<211> LENGTH: 565
<212> TYPE: PRT
<213> ORGANISM: Artificial Sequence
<220> FEATURE:
<223> OTHER INFORMATION: Exemplary H1 HA

<400> SEQUENCE: 1

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
```

```
            85                  90                  95
Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
            130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
                180                 185                 190

Trp Gly Ile His His Pro Pro Asn Ser Lys Glu Gln Gln Asn Leu Tyr
                195                 200                 205

Gln Asn Glu Asn Ala Tyr Val Ser Val Val Thr Ser Asn Tyr Asn Arg
            210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
            290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Asn Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
                500                 505                 510
```

```
Arg Glu Lys Val Asp Gly Val Lys Leu Glu Ser Met Gly Ile Tyr Gln
            515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 2
<211> LENGTH: 563
<212> TYPE: PRT
<213> ORGANISM: Artificial Sequence
<220> FEATURE:
<223> OTHER INFORMATION: Exemplary H2 HA

<400> SEQUENCE: 2

Met Ala Ile Ile Tyr Leu Ile Leu Leu Phe Thr Ala Val Arg Gly Asp
1               5                   10                  15

Gln Ile Cys Ile Gly Tyr His Ser Asn Asn Ser Thr Glu Lys Val Asp
            20                  25                  30

Thr Ile Leu Glu Arg Asn Val Thr Val Thr His Ala Gln Asn Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Thr Val Pro Glu Trp Ser Tyr Ile Met Glu
                85                  90                  95

Lys Glu Asn Pro Arg Asn Gly Leu Cys Tyr Pro Gly Ser Phe Asn Asp
            100                 105                 110

Tyr Glu Glu Leu Lys His Leu Leu Ser Ser Val Thr His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Ile Ala Lys Gly
                165                 170                 175

Ser Tyr Asn Asn Thr Ser Gly Glu Gln Met Leu Ile Ile Trp Gly Val
            180                 185                 190

His His Pro Ser Asn Asp Glu Thr Glu Gln Arg Thr Leu Tyr Gln Asn
        195                 200                 205

Val Gly Thr Tyr Val Ser Ile Gly Thr Ser Thr Leu Asn Lys Arg Ser
    210                 215                 220

Ile Pro Val Ile Ala Thr Arg Pro Lys Val Asn Gly Gln Gly Gly Arg
225                 230                 235                 240

Met Glu Phe Ser Trp Thr Ile Leu Asp Ile Trp Asp Thr Ile Asn Phe
                245                 250                 255

Glu Ser Thr Gly Asn Leu Ile Ala Pro Glu Tyr Gly Phe Arg Ile Ser
            260                 265                 270

Lys Arg Gly Ser Ser Gly Ile Met Lys Thr Glu Gly Thr Leu Glu Asn
        275                 280                 285

Cys Glu Thr Lys Cys Gln Thr Pro Leu Gly Ala Ile Asn Thr Thr Leu
    290                 295                 300
```

```
Pro Phe His Asn Val His Pro Leu Thr Ile Gly Glu Cys Pro Lys Tyr
305                 310                 315                 320

Val Lys Ser Glu Arg Leu Val Leu Ala Thr Gly Leu Arg Asn Val Pro
            325                 330                 335

Gln Ile Glu Ser Arg Gly Leu Phe Gly Ala Ile Ala Gly Phe Ile Glu
            340                 345                 350

Gly Gly Trp Gln Gly Met Ile Asp Gly Trp Tyr Gly Tyr His His Ser
            355                 360                 365

Asn Asp Gln Gly Ser Gly Tyr Ala Ala Asp Lys Glu Ser Thr Gln Lys
370                 375                 380

Ala Ile Asp Gly Ile Thr Asn Arg Val Asn Ser Val Ile Glu Lys Met
385                 390                 395                 400

Asn Thr Gln Phe Glu Ala Val Gly Lys Glu Phe Ser Asn Leu Glu Lys
                405                 410                 415

Arg Leu Glu Asn Leu Asn Lys Lys Met Glu Asp Gly Phe Leu Asp Val
            420                 425                 430

Trp Thr Tyr Asn Ala Glu Leu Leu Val Leu Met Glu Asn Glu Arg Thr
            435                 440                 445

Leu Asp Phe His Asp Ser Asn Val Lys Asn Leu Tyr Asp Arg Val Arg
450                 455                 460

Met Gln Leu Arg Asp Asn Ala Lys Glu Leu Gly Asn Gly Cys Phe Glu
465                 470                 475                 480

Phe Tyr His Lys Cys Asp Asp Glu Cys Met Asn Ser Val Lys Asn Gly
                485                 490                 495

Thr Tyr Asp Tyr Pro Lys Tyr Glu Glu Ser Lys Leu Asn Arg Asn
            500                 505                 510

Glu Ile Lys Gly Val Lys Leu Ser Asn Met Gly Val Tyr Gln Ile Leu
            515                 520                 525

Ala Ile Tyr Ala Thr Val Ala Gly Ser Leu Ser Leu Ala Ile Met Ile
530                 535                 540

Ala Gly Ile Ser Leu Trp Met Cys Ser Asn Gly Ser Leu Gln Cys Arg
545                 550                 555                 560

Ile Cys Ile

<210> SEQ ID NO 3
<211> LENGTH: 566
<212> TYPE: PRT
<213> ORGANISM: Artificial Sequence
<220> FEATURE:
<223> OTHER INFORMATION: Exemplary H3 HA

<400> SEQUENCE: 3

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Ile Asp Cys
65              70                  75                  80

Thr Leu Ile Asp Ala Leu Leu Gly Asp Pro His Cys Asp Val Phe Gln
                85                  90                  95
```

```
Asn Glu Thr Trp Asp Leu Phe Val Glu Arg Ser Lys Ala Phe Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Ile Thr Glu Gly Phe Thr Trp Thr
        130                 135                 140

Gly Val Thr Gln Asn Gly Gly Ser Asn Ala Cys Lys Arg Gly Pro Gly
145                 150                 155                 160

Asn Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Glu Ser Gly Arg Val Thr Val Ser Thr Arg Arg
210                 215                 220

Ser Gln Gln Ser Ile Ile Pro Asn Ile Gly Ser Arg Pro Trp Val Arg
225                 230                 235                 240

Gly Gln Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Ser Ser Asp Ala
        275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
```

```
                515                 520                 525
Asp Trp Ile Leu Trp Ile Ser Phe Ala Ile Ser Cys Phe Leu Leu Cys
            530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 4
<211> LENGTH: 564
<212> TYPE: PRT
<213> ORGANISM: Artificial Sequence
<220> FEATURE:
<223> OTHER INFORMATION: Exemplary H4 HA

<400> SEQUENCE: 4

Met Leu Ser Ile Val Ile Leu Phe Leu Leu Ile Ala Glu Asn Ser Ser
1               5                   10                  15

Gln Asn Tyr Thr Gly Asn Pro Val Ile Cys Met Gly His His Ala Val
            20                  25                  30

Ala Asn Gly Thr Met Val Lys Thr Leu Ala Asp Asp Gln Val Glu Val
        35                  40                  45

Val Thr Ala Gln Glu Leu Val Glu Ser Gln Asn Leu Pro Glu Leu Cys
    50                  55                  60

Pro Ser Pro Leu Arg Leu Val Asp Gly Gln Thr Cys Asp Ile Ile Asn
65                  70                  75                  80

Gly Ala Leu Gly Ser Pro Gly Cys Asp His Leu Asn Gly Ala Glu Trp
                85                  90                  95

Asp Val Phe Ile Glu Arg Pro Asn Ala Val Asp Thr Cys Tyr Pro Phe
            100                 105                 110

Asp Val Pro Glu Tyr Gln Ser Leu Arg Ser Ile Leu Ala Asn Asn Gly
        115                 120                 125

Lys Phe Glu Phe Ile Ala Glu Glu Phe Gln Trp Asn Thr Val Lys Gln
    130                 135                 140

Asn Gly Lys Ser Gly Ala Cys Lys Arg Ala Asn Val Asp Asp Phe Phe
145                 150                 155                 160

Asn Arg Leu Asn Trp Leu Val Lys Ser Asp Gly Asn Ala Tyr Pro Leu
                165                 170                 175

Gln Asn Leu Thr Lys Ile Asn Asn Gly Asp Tyr Ala Arg Leu Tyr Ile
            180                 185                 190

Trp Gly Val His His Pro Ser Thr Ser Thr Glu Gln Thr Asn Leu Tyr
        195                 200                 205

Lys Asn Asn Pro Gly Arg Val Thr Val Ser Thr Lys Thr Ser Gln Thr
    210                 215                 220

Ser Val Val Pro Asp Ile Gly Ser Arg Pro Leu Val Arg Gly Gln Ser
225                 230                 235                 240

Gly Arg Val Ser Phe Tyr Trp Thr Ile Val Glu Pro Gly Asp Leu Ile
                245                 250                 255

Val Phe Asn Thr Ile Gly Asn Leu Ile Ala Pro Arg Gly His Tyr Lys
            260                 265                 270

Leu Asn Asn Gln Lys Lys Ser Thr Ile Leu Asn Thr Ala Ile Pro Ile
        275                 280                 285

Gly Ser Cys Val Ser Lys Cys His Thr Asp Lys Gly Ser Leu Ser Thr
    290                 295                 300

Thr Lys Pro Phe Gln Asn Ile Ser Arg Ile Ala Val Gly Asp Cys Pro
```

```
            305                 310                 315                 320
Arg Tyr Val Lys Gln Gly Ser Leu Lys Leu Ala Thr Gly Met Arg Asn
                325                 330                 335
Ile Pro Glu Lys Ala Ser Arg Gly Leu Phe Gly Ala Ile Ala Gly Phe
                340                 345                 350
Ile Glu Asn Gly Trp Gln Gly Leu Ile Asp Gly Trp Tyr Gly Phe Arg
                355                 360                 365
His Gln Asn Ala Glu Gly Thr Gly Thr Ala Ala Asp Leu Lys Ser Thr
                370                 375                 380
Gln Ala Ala Ile Asp Gln Ile Asn Gly Lys Leu Asn Arg Leu Ile Glu
385                 390                 395                 400
Lys Thr Asn Asp Lys Tyr His Gln Ile Glu Lys Glu Phe Glu Gln Val
                405                 410                 415
Glu Gly Arg Ile Gln Asp Leu Glu Asn Tyr Val Glu Asp Thr Lys Ile
                420                 425                 430
Asp Leu Trp Ser Tyr Asn Ala Glu Leu Leu Val Ala Leu Glu Asn Gln
                435                 440                 445
His Thr Ile Asp Val Thr Asp Ser Glu Met Asn Lys Leu Phe Glu Arg
                450                 455                 460
Val Arg Arg Gln Leu Arg Glu Asn Ala Glu Asp Lys Gly Asn Gly Cys
465                 470                 475                 480
Phe Glu Ile Phe His Lys Cys Asp Asn Cys Ile Glu Ser Ile Arg
                485                 490                 495
Asn Gly Thr Tyr Asp His Asp Ile Tyr Arg Asp Glu Ala Ile Asn Asn
                500                 505                 510
Arg Phe Gln Ile Gln Gly Val Lys Leu Thr Gln Gly Tyr Lys Asp Ile
                515                 520                 525
Ile Leu Trp Ile Ser Phe Ser Ile Ser Cys Phe Leu Leu Val Ala Leu
                530                 535                 540
Leu Leu Ala Phe Ile Leu Trp Ala Cys Gln Asn Gly Asn Ile Arg Cys
545                 550                 555                 560
Gln Ile Cys Ile

<210> SEQ ID NO 5
<211> LENGTH: 564
<212> TYPE: PRT
<213> ORGANISM: Artificial Sequence
<220> FEATURE:
<223> OTHER INFORMATION: Exemplary H5 HA

<400> SEQUENCE: 5

Met Glu Arg Ile Val Leu Leu Leu Ala Ile Val Ser Leu Val Lys Ser
1               5                   10                  15
Asp Gln Ile Cys Ile Gly Tyr His Ala Asn Lys Ser Thr Lys Gln Val
                20                  25                  30
Asp Thr Ile Met Glu Lys Asn Val Thr Val Thr His Ala Gln Asp Ile
                35                  40                  45
Leu Glu Arg Thr His Asn Gly Lys Leu Cys Ser Leu Asn Gly Val Lys
                50                  55                  60
Pro Leu Ile Leu Arg Asp Cys Ser Val Ala Gly Trp Leu Leu Gly Asn
65                  70                  75                  80
Pro Met Cys Asp Glu Phe Leu Asn Leu Pro Glu Trp Leu Tyr Ile Val
                85                  90                  95
Glu Lys Asp Asn Pro Ile Asn Ser Leu Cys Tyr Pro Gly Asp Phe Asn
                100                 105                 110
```

```
Asp Tyr Glu Glu Leu Lys Tyr Leu Leu Ser Ser Thr Asn His Phe Glu
        115                 120                 125
Lys Ile Arg Ile Ile Pro Arg Ser Ser Trp Ser Asn His Asp Ala Ser
130                 135                 140
Ser Gly Val Ser Ser Ala Cys Pro Tyr Ile Gly Arg Ser Ser Phe Leu
145                 150                 155                 160
Arg Asn Val Val Trp Leu Ile Lys Lys Asn Asn Thr Tyr Pro Thr Ile
                165                 170                 175
Lys Arg Ser Tyr Asn Asn Thr Asn Gln Glu Asp Leu Leu Ile Leu Trp
            180                 185                 190
Gly Ile His His Pro Asn Asp Ala Ala Glu Gln Thr Lys Leu Tyr Gln
        195                 200                 205
Asn Pro Thr Thr Tyr Val Ser Val Gly Thr Ser Thr Leu Asn Gln Arg
    210                 215                 220
Ser Ile Pro Glu Ile Ala Thr Arg Pro Lys Val Asn Gly Gln Ser Gly
225                 230                 235                 240
Arg Met Glu Phe Phe Trp Thr Ile Leu Lys Pro Asn Asp Ala Ile Asn
                245                 250                 255
Phe Glu Ser Asn Gly Asn Phe Ile Ala Pro Arg Tyr Ala Tyr Lys Ile
            260                 265                 270
Val Lys Lys Gly Asp Ser Ala Ile Met Lys Ser Gly Leu Ala Tyr Gly
        275                 280                 285
Asn Cys Asp Thr Lys Cys Gln Thr Pro Val Gly Glu Ile Asn Ser Ser
    290                 295                 300
Met Pro Phe His Asn Ile His Pro His Thr Ile Gly Glu Cys Pro Lys
305                 310                 315                 320
Tyr Val Lys Ser Asp Arg Leu Val Leu Ala Thr Gly Leu Arg Asn Val
                325                 330                 335
Pro Gln Arg Lys Lys Arg Gly Leu Phe Gly Ala Ile Ala Gly Phe Ile
            340                 345                 350
Glu Gly Gly Trp Gln Gly Met Val Asp Gly Trp Tyr Gly Tyr His His
        355                 360                 365
Ser Asn Glu Gln Gly Ser Gly Tyr Ala Ala Asp Lys Glu Ser Thr Gln
    370                 375                 380
Lys Ala Ile Asp Gly Ile Thr Asn Lys Val Asn Ser Ile Ile Asp Lys
385                 390                 395                 400
Met Asn Thr Arg Phe Glu Ala Val Gly Lys Glu Phe Asn Asn Leu Glu
                405                 410                 415
Arg Arg Val Glu Asn Leu Asn Lys Lys Met Glu Asp Gly Phe Leu Asp
            420                 425                 430
Val Trp Thr Tyr Asn Val Glu Leu Leu Val Leu Met Glu Asn Glu Arg
        435                 440                 445
Thr Leu Asp Phe His Asp Ser Asn Val Asn Asn Leu Tyr Asp Lys Val
    450                 455                 460
Arg Leu Gln Leu Lys Asp Asn Ala Arg Glu Leu Gly Asn Gly Cys Phe
465                 470                 475                 480
Glu Phe Tyr His Lys Cys Asp Asn Glu Cys Met Glu Ser Val Arg Asn
                485                 490                 495
Gly Thr Tyr Asp Tyr Pro Gln Tyr Ser Glu Glu Ala Arg Leu Asn Arg
            500                 505                 510
Glu Glu Ile Ser Gly Val Lys Leu Glu Ser Met Gly Val Tyr Gln Ile
        515                 520                 525
```

```
Leu Ser Ile Tyr Ser Thr Val Ala Ser Ser Leu Ala Leu Ala Ile Met
    530                 535                 540

Ile Ala Gly Leu Ser Phe Trp Met Cys Ser Asn Gly Ser Leu Gln Cys
545                 550                 555                 560

Arg Ile Cys Ile

<210> SEQ ID NO 6
<211> LENGTH: 566
<212> TYPE: PRT
<213> ORGANISM: Artificial Sequence
<220> FEATURE:
<223> OTHER INFORMATION: Exemplary H6 HA

<400> SEQUENCE: 6

Met Ile Ala Ile Ile Val Val Ala Ile Leu Ala Thr Ala Gly Arg Ser
1               5                   10                  15

Asp Lys Ile Cys Ile Gly Tyr His Ala Asn Asn Ser Thr Thr Gln Ile
            20                  25                  30

Asp Thr Ile Leu Glu Lys Asn Val Thr Val Thr His Ser Val Glu Leu
        35                  40                  45

Leu Glu Asn Gln Lys Glu Glu Arg Phe Cys Lys Ile Leu Lys Lys Ala
    50                  55                  60

Pro Leu Asp Leu Lys Gly Cys Thr Ile Glu Gly Trp Ile Leu Gly Asn
65                  70                  75                  80

Pro Gln Cys Asp Leu Leu Leu Gly Asp Gln Ser Trp Ser Tyr Ile Val
                85                  90                  95

Glu Arg Pro Thr Ala Gln Asn Gly Ile Cys Tyr Pro Gly Val Leu Asn
            100                 105                 110

Glu Val Glu Glu Leu Lys Ala Leu Ile Gly Ser Gly Glu Arg Val Glu
        115                 120                 125

Arg Phe Glu Met Phe Pro Lys Ser Thr Trp Thr Gly Val Asp Thr Ser
    130                 135                 140

Ser Gly Val Thr Arg Ala Cys Pro Tyr Asn Ser Gly Ser Ser Phe Tyr
145                 150                 155                 160

Arg Asn Leu Leu Trp Ile Ile Lys Thr Lys Ser Ala Ala Tyr Ser Val
                165                 170                 175

Ile Lys Gly Ala Tyr Asn Asn Thr Gly Asn Gln Pro Ile Leu Tyr Phe
            180                 185                 190

Trp Gly Val His His Pro Pro Asp Thr Asn Glu Gln Asn Thr Leu Tyr
        195                 200                 205

Gly Ser Gly Asp Arg Tyr Val Arg Met Gly Thr Glu Ser Met Asn Phe
    210                 215                 220

Ala Lys Ser Pro Glu Ile Ala Ala Arg Pro Ala Val Asn Gly Gln Arg
225                 230                 235                 240

Gly Arg Ile Asp Tyr Tyr Trp Ser Ile Leu Lys Pro Gly Glu Thr Leu
                245                 250                 255

Asn Val Glu Ser Asn Gly Asn Leu Ile Ala Pro Trp Tyr Ala Phe Arg
            260                 265                 270

Phe Val Ser Thr Ser Asn Lys Gly Ala Val Phe Lys Ser Asn Leu Pro
        275                 280                 285

Ile Glu Asn Cys Asp Ala Thr Cys Gln Thr Val Ala Gly Val Leu Arg
    290                 295                 300

Thr Asn Lys Thr Phe Gln Asn Val Ser Pro Leu Trp Ile Gly Glu Cys
305                 310                 315                 320

Pro Lys Tyr Val Lys Ser Glu Ser Leu Arg Leu Ala Thr Gly Leu Arg
```

325 330 335

Asn Val Pro Gln Ile Glu Thr Arg Gly Leu Phe Gly Ala Ile Ala Gly
340 345 350

Phe Ile Glu Gly Gly Trp Thr Gly Met Ile Asp Gly Trp Tyr Gly Tyr
355 360 365

His His Glu Asn Ser Gln Gly Ser Gly Tyr Ala Ala Asp Arg Glu Ser
370 375 380

Thr Gln Lys Ala Val Asp Gly Ile Thr Asn Lys Val Asn Ser Ile Ile
385 390 395 400

Asp Lys Met Asn Thr Gln Phe Glu Ala Val Asp His Glu Phe Ser Asn
405 410 415

Leu Glu Arg Arg Ile Asp Asn Leu Asn Lys Arg Met Glu Asp Gly Phe
420 425 430

Leu Asp Val Trp Thr Tyr Asn Ala Glu Leu Leu Val Leu Leu Glu Asn
435 440 445

Glu Arg Thr Leu Asp Leu His Asp Ala Asn Val Lys Asn Leu Tyr Glu
450 455 460

Arg Val Lys Ser Gln Leu Arg Asp Asn Ala Met Ile Leu Gly Asn Gly
465 470 475 480

Cys Phe Glu Phe Trp His Lys Cys Asp Asp Glu Cys Met Glu Ser Val
485 490 495

Lys Asn Gly Thr Tyr Asp Tyr Pro Lys Tyr Gln Asp Glu Ser Lys Leu
500 505 510

Asn Arg Gln Glu Ile Glu Ser Val Lys Leu Glu Ser Leu Gly Val Tyr
515 520 525

Gln Ile Leu Ala Ile Tyr Ser Thr Val Ser Ser Ser Leu Val Leu Val
530 535 540

Gly Leu Ile Ile Ala Val Gly Leu Trp Met Cys Ser Asn Gly Ser Met
545 550 555 560

Gln Cys Arg Ile Cys Ile
565

<210> SEQ ID NO 7
<211> LENGTH: 563
<212> TYPE: PRT
<213> ORGANISM: Artificial Sequence
<220> FEATURE:
<223> OTHER INFORMATION: Exemplary H7 HA

<400> SEQUENCE: 7

Met Asn Thr Gln Ile Leu Val Phe Ala Leu Val Ala Val Ile Pro Thr
1 5 10 15

Asn Ala Asp Lys Ile Cys Leu Gly His His Ala Val Ser Asn Gly Thr
20 25 30

Lys Val Asn Thr Leu Thr Glu Arg Gly Val Glu Val Val Asn Ala Thr
35 40 45

Glu Thr Val Glu Arg Thr Asn Ile Pro Lys Ile Cys Ser Lys Gly Lys
50 55 60

Arg Thr Thr Asp Leu Gly Gln Cys Gly Leu Leu Gly Thr Ile Thr Gly
65 70 75 80

Pro Pro Gln Cys Asp Gln Phe Leu Glu Phe Ser Ala Asp Leu Ile Ile
85 90 95

Glu Arg Arg Glu Gly Asn Asp Val Cys Tyr Pro Gly Lys Phe Val Asn
100 105 110

Glu Glu Ala Leu Arg Gln Ile Leu Arg Gly Ser Gly Gly Ile Asp Lys

-continued

```
            115                 120                 125
Glu Thr Met Gly Phe Thr Tyr Ser Gly Ile Arg Thr Asn Gly Thr Thr
130                 135                 140

Ser Ala Cys Arg Arg Ser Gly Ser Ser Phe Tyr Ala Glu Met Glu Trp
145                 150                 155                 160

Leu Leu Ser Asn Thr Asp Asn Ala Ser Phe Pro Gln Met Thr Lys Ser
                165                 170                 175

Tyr Lys Asn Thr Arg Arg Glu Ser Ala Leu Ile Val Trp Gly Ile His
                180                 185                 190

His Ser Gly Ser Thr Thr Glu Gln Thr Lys Leu Tyr Gly Ser Gly Asn
                195                 200                 205

Lys Leu Ile Thr Val Gly Ser Ser Lys Tyr His Gln Ser Phe Val Pro
210                 215                 220

Ser Pro Gly Thr Arg Pro Gln Ile Asn Gly Gln Ser Gly Arg Ile Asp
225                 230                 235                 240

Phe His Trp Leu Ile Leu Asp Pro Asn Asp Thr Val Thr Phe Ser Phe
                245                 250                 255

Asn Gly Ala Phe Ile Ala Pro Asn Arg Ala Ser Phe Leu Arg Gly Lys
                260                 265                 270

Ser Met Gly Ile Gln Ser Asp Val Gln Val Asp Ala Asn Cys Glu Gly
                275                 280                 285

Glu Cys Tyr His Ser Gly Gly Thr Ile Thr Ser Arg Leu Pro Phe Gln
                290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Pro Ser
                325                 330                 335

Lys Lys Arg Lys Lys Arg Gly Leu Phe Gly Ala Ile Ala Gly Phe Ile
                340                 345                 350

Glu Asn Gly Trp Glu Gly Leu Val Asp Gly Trp Tyr Gly Phe Arg His
                355                 360                 365

Gln Asn Ala Gln Gly Glu Gly Thr Ala Ala Asp Tyr Lys Ser Thr Gln
370                 375                 380

Ser Ala Ile Asp Gln Ile Thr Gly Lys Leu Asn Arg Leu Ile Glu Lys
385                 390                 395                 400

Thr Asn Gln Gln Phe Glu Leu Ile Asp Asn Glu Phe Thr Glu Val Glu
                405                 410                 415

Lys Gln Ile Gly Asn Leu Ile Asn Trp Thr Lys Asp Ser Ile Thr Glu
                420                 425                 430

Val Trp Ser Tyr Asn Ala Glu Leu Ile Val Ala Met Glu Asn Gln His
                435                 440                 445

Thr Ile Asp Leu Ala Asp Ser Glu Met Asn Arg Leu Tyr Glu Arg Val
                450                 455                 460

Arg Lys Gln Leu Arg Glu Asn Ala Glu Glu Asp Gly Thr Gly Cys Phe
465                 470                 475                 480

Glu Ile Phe His Lys Cys Asp Asp Cys Met Ala Ser Ile Arg Asn
                485                 490                 495

Asn Thr Tyr Asp His Ser Lys Tyr Arg Glu Glu Ala Met Gln Asn Arg
                500                 505                 510

Ile Gln Ile Asp Pro Val Lys Leu Ser Ser Gly Tyr Lys Asp Val Ile
                515                 520                 525

Leu Trp Phe Ser Phe Gly Ala Ser Cys Phe Leu Leu Leu Ala Ile Ala
530                 535                 540
```

Met Gly Leu Val Phe Ile Cys Val Lys Asn Gly Asn Met Arg Cys Thr
545                 550                 555                 560

Ile Cys Ile

<210> SEQ ID NO 8
<211> LENGTH: 565
<212> TYPE: PRT
<213> ORGANISM: Artificial Sequence
<220> FEATURE:
<223> OTHER INFORMATION: Exemplary H8 HA

<400> SEQUENCE: 8

Met Glu Lys Phe Ile Ala Ile Ala Thr Leu Ala Ser Thr Asn Ala Tyr
1               5                   10                  15

Asp Arg Ile Cys Ile Gly Tyr Gln Ser Asn Asn Ser Asp Thr Val
            20                  25                  30

Asn Thr Leu Ile Glu Gln Asn Val Pro Val Thr Gln Thr Met Glu Leu
            35                  40                  45

Val Glu Thr Glu Lys His Pro Ala Tyr Cys Asn Thr Asp Leu Gly Ala
        50                  55                  60

Pro Leu Glu Leu Arg Asp Cys Lys Ile Glu Ala Val Ile Tyr Gly Asn
65                  70                  75                  80

Pro Lys Cys Asp Ile His Leu Lys Asp Gln Gly Trp Ser Tyr Ile Val
                85                  90                  95

Glu Arg Pro Ser Ala Pro Glu Gly Met Cys Tyr Pro Gly Ser Val Glu
            100                 105                 110

Asn Leu Glu Glu Leu Arg Phe Val Phe Ser Ser Ala Ser Tyr Lys
            115                 120                 125

Arg Ile Arg Leu Phe Asp Tyr Ser Arg Trp Asn Val Thr Arg Ser Gly
130                 135                 140

Thr Ser Lys Ala Cys Asn Ala Ser Thr Gly Gly Gln Ser Phe Tyr Arg
145                 150                 155                 160

Ser Ile Asn Trp Leu Thr Lys Lys Glu Pro Asp Thr Tyr Asp Phe Asn
                165                 170                 175

Glu Gly Ala Tyr Val Asn Asn Glu Asp Gly Asp Ile Ile Phe Leu Trp
            180                 185                 190

Gly Ile His His Pro Pro Asp Thr Lys Glu Gln Thr Thr Leu Tyr Lys
            195                 200                 205

Asn Ala Asn Thr Leu Ser Ser Val Thr Thr Asn Thr Ile Asn Arg Ser
210                 215                 220

Phe Gln Pro Asn Ile Gly Pro Arg Pro Leu Val Arg Gly Gln Gln Gly
225                 230                 235                 240

Arg Met Asp Tyr Tyr Trp Gly Ile Leu Lys Arg Gly Glu Thr Leu Lys
                245                 250                 255

Ile Arg Thr Asn Gly Asn Leu Ile Ala Pro Glu Phe Gly Tyr Leu Leu
            260                 265                 270

Lys Gly Glu Ser Tyr Gly Arg Ile Gln Asn Glu Asp Ile Pro Ile
            275                 280                 285

Gly Asn Cys Asn Thr Lys Cys Gln Thr Tyr Ala Gly Ala Ile Asn Ser
290                 295                 300

Ser Lys Pro Phe Gln Asn Ala Ser Arg His Tyr Met Gly Glu Cys Pro
305                 310                 315                 320

Lys Tyr Val Lys Lys Ala Ser Leu Arg Leu Ala Val Gly Leu Arg Asn
                325                 330                 335

Thr Pro Ser Val Glu Pro Arg Gly Leu Phe Gly Ala Ile Ala Gly Phe
340 345 350

Ile Glu Gly Gly Trp Ser Gly Met Ile Asp Gly Trp Tyr Gly Phe His
355 360 365

His Ser Asn Ser Glu Gly Thr Gly Met Ala Ala Asp Gln Lys Ser Thr
370 375 380

Gln Glu Ala Ile Asp Lys Ile Thr Asn Lys Val Asn Asn Ile Val Asp
385 390 395 400

Lys Met Asn Arg Glu Phe Glu Val Val Asn His Glu Phe Ser Glu Val
405 410 415

Glu Lys Arg Ile Asn Met Ile Asn Asp Lys Ile Asp Asp Gln Ile Glu
420 425 430

Asp Leu Trp Ala Tyr Asn Ala Glu Leu Leu Val Leu Leu Glu Asn Gln
435 440 445

Lys Thr Leu Asp Glu His Asp Ser Asn Val Lys Asn Leu Phe Asp Glu
450 455 460

Val Lys Arg Arg Leu Ser Ala Asn Ala Ile Asp Ala Gly Asn Gly Cys
465 470 475 480

Phe Asp Ile Leu His Lys Cys Asp Asn Glu Cys Met Glu Thr Ile Lys
485 490 495

Asn Gly Thr Tyr Asp His Lys Glu Tyr Glu Glu Glu Ala Lys Leu Glu
500 505 510

Arg Ser Lys Ile Asn Gly Val Lys Leu Glu Glu Asn Thr Thr Tyr Lys
515 520 525

Ile Leu Ser Ile Tyr Ser Thr Val Ala Ala Ser Leu Cys Leu Ala Ile
530 535 540

Leu Ile Ala Gly Gly Leu Ile Leu Gly Met Gln Asn Gly Ser Cys Arg
545 550 555 560

Cys Met Phe Cys Ile
565

<210> SEQ ID NO 9
<211> LENGTH: 560
<212> TYPE: PRT
<213> ORGANISM: Artificial Sequence
<220> FEATURE:
<223> OTHER INFORMATION: Exemplary H9 HA

<400> SEQUENCE: 9

Met Glu Thr Lys Ala Ile Ile Ala Ala Leu Leu Met Val Thr Ala Ala
1 5 10 15

Asn Ala Asp Lys Ile Cys Ile Gly Tyr Gln Ser Thr Asn Ser Thr Glu
20 25 30

Thr Val Asp Thr Leu Thr Glu Ser Asn Val Pro Val Thr His Thr Lys
35 40 45

Glu Leu Leu His Thr Glu His Asn Gly Met Leu Cys Ala Thr Asp Leu
50 55 60

Gly His Pro Leu Ile Leu Asp Thr Cys Thr Ile Glu Gly Leu Ile Tyr
65 70 75 80

Gly Asn Pro Ser Cys Asp Ile Leu Leu Gly Gly Lys Glu Trp Ser Tyr
85 90 95

Ile Val Glu Arg Ser Ser Ala Val Asn Gly Met Cys Tyr Pro Gly Asn
100 105 110

Val Glu Asn Leu Glu Glu Leu Arg Ser Leu Phe Ser Ser Ala Lys Ser
115 120 125

Tyr Lys Arg Ile Gln Ile Phe Pro Asp Lys Thr Trp Asn Val Thr Tyr
130                 135                 140

Ser Gly Thr Ser Arg Ala Cys Ser Asn Ser Phe Tyr Arg Ser Met Arg
145                 150                 155                 160

Trp Leu Thr His Lys Ser Asn Ser Tyr Pro Phe Gln Asn Ala His Tyr
                165                 170                 175

Thr Asn Asn Glu Arg Glu Asn Ile Leu Phe Met Trp Gly Ile His His
            180                 185                 190

Pro Pro Thr Asp Thr Glu Gln Thr Asp Leu Tyr Lys Asn Ala Asp Thr
        195                 200                 205

Thr Thr Ser Val Thr Thr Glu Asp Ile Asn Arg Thr Phe Lys Pro Val
210                 215                 220

Ile Gly Pro Arg Pro Leu Val Asn Gly Gln Gln Gly Arg Ile Asp Tyr
225                 230                 235                 240

Tyr Trp Ser Val Leu Lys Pro Gly Gln Thr Leu Arg Ile Arg Ser Asn
                245                 250                 255

Gly Asn Leu Ile Ala Pro Trp Tyr Gly His Val Leu Thr Gly Glu Ser
            260                 265                 270

His Gly Arg Ile Leu Lys Thr Asp Leu Asn Asn Gly Asn Cys Val Val
        275                 280                 285

Gln Cys Gln Thr Glu Lys Gly Gly Leu Asn Thr Thr Leu Pro Phe His
290                 295                 300

Asn Ile Ser Lys Tyr Ala Phe Gly Asn Cys Pro Lys Tyr Val Gly Val
305                 310                 315                 320

Lys Ser Leu Lys Leu Pro Val Gly Leu Arg Asn Val Pro Ala Val Ser
                325                 330                 335

Ser Arg Gly Leu Phe Gly Ala Ile Ala Gly Phe Ile Glu Gly Gly Trp
            340                 345                 350

Pro Gly Leu Val Ala Gly Trp Tyr Gly Phe Gln His Ser Asn Asp Gln
        355                 360                 365

Gly Val Gly Met Ala Ala Asp Lys Gly Ser Thr Gln Lys Ala Ile Asp
370                 375                 380

Lys Ile Thr Ser Lys Val Asn Asn Ile Ile Asp Lys Met Asn Lys Gln
385                 390                 395                 400

Tyr Glu Val Ile Asp His Glu Phe Asn Glu Leu Glu Ala Arg Leu Asn
                405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
        435                 440                 445

His Asp Ala Asn Val Asn Asn Leu Tyr Asn Lys Val Lys Arg Ala Leu
450                 455                 460

Gly Ser Asn Ala Val Glu Asp Gly Asn Gly Cys Phe Glu Leu Tyr His
465                 470                 475                 480

Lys Cys Asp Asp Gln Cys Met Glu Thr Ile Arg Asn Gly Thr Tyr Asp
                485                 490                 495

Arg Gln Lys Tyr Gln Glu Glu Ser Arg Leu Glu Arg Gln Lys Ile Glu
            500                 505                 510

Gly Val Lys Leu Glu Ser Glu Gly Thr Tyr Lys Ile Leu Thr Ile Tyr
        515                 520                 525

Ser Thr Val Ala Ser Ser Leu Val Leu Ala Met Gly Phe Ala Ala Phe
530                 535                 540

Leu Phe Trp Ala Met Ser Asn Gly Ser Cys Arg Cys Asn Ile Cys Ile 545 550 555 560

<210> SEQ ID NO 10
<211> LENGTH: 561
<212> TYPE: PRT
<213> ORGANISM: Artificial Sequence
<220> FEATURE:
<223> OTHER INFORMATION: Exemplary H10 HA

<400> SEQUENCE: 10

Met Tyr Lys Val Val Val Ile Ile Ala Leu Leu Gly Ala Val Lys Gly
1 5 10 15

Leu Asp Arg Ile Cys Leu Gly His His Ala Val Ala Asn Gly Thr Ile
20 25 30

Val Lys Thr Leu Thr Asn Glu Gln Glu Glu Val Thr Asn Ala Thr Glu
35 40 45

Thr Val Glu Ser Thr Asn Leu Asn Lys Leu Cys Met Lys Gly Arg Ser
50 55 60

Tyr Lys Asp Leu Gly Asn Cys His Pro Val Gly Met Leu Ile Gly Thr
65 70 75 80

Pro Val Cys Asp Pro His Leu Thr Gly Thr Trp Asp Thr Leu Ile Glu
85 90 95

Arg Glu Asn Ala Ile Ala His Cys Tyr Pro Gly Ala Thr Ile Asn Glu
100 105 110

Glu Ala Leu Arg Gln Lys Ile Met Glu Ser Gly Gly Ile Ser Lys Met
115 120 125

Ser Thr Gly Phe Thr Tyr Gly Ser Ser Ile Thr Ser Ala Gly Thr Thr
130 135 140

Lys Ala Cys Met Arg Asn Gly Gly Asp Ser Phe Tyr Ala Glu Leu Lys
145 150 155 160

Trp Leu Val Ser Lys Thr Lys Gly Gln Asn Phe Pro Gln Thr Thr Asn
165 170 175

Thr Tyr Arg Asn Thr Asp Thr Ala Glu His Leu Ile Ile Trp Gly Ile
180 185 190

His His Pro Ser Ser Thr Gln Glu Lys Asn Asp Leu Tyr Gly Thr Gln
195 200 205

Ser Leu Ser Ile Ser Val Glu Ser Ser Thr Tyr Gln Asn Asn Phe Val
210 215 220

Pro Val Val Gly Ala Arg Pro Gln Val Asn Gly Gln Ser Gly Arg Ile
225 230 235 240

Asp Phe His Trp Thr Leu Val Gln Pro Gly Asp Asn Ile Thr Phe Ser
245 250 255

Asp Asn Gly Gly Leu Ile Ala Pro Ser Arg Val Ser Lys Leu Thr Gly
260 265 270

Arg Asp Leu Gly Ile Gln Ser Glu Ala Leu Ile Asp Asn Ser Cys Glu
275 280 285

Ser Lys Cys Phe Trp Arg Gly Gly Ser Ile Asn Thr Lys Leu Pro Phe
290 295 300

Gln Asn Leu Ser Pro Arg Thr Val Gly Gln Cys Pro Lys Tyr Val Asn
305 310 315 320

Gln Arg Ser Leu Leu Leu Ala Thr Gly Met Arg Asn Val Pro Glu Val
325 330 335

Val Gln Gly Arg Gly Leu Phe Gly Ala Ile Ala Gly Phe Ile Glu Asn
340 345 350

Gly Trp Glu Gly Met Val Asp Gly Trp Tyr Gly Phe Arg His Gln Asn

```
                355                 360                 365
Ala Gln Gly Thr Gly Gln Ala Ala Asp Tyr Lys Ser Thr Gln Ala Ala
            370                 375                 380

Ile Asp Gln Ile Thr Gly Lys Leu Asn Arg Leu Ile Glu Lys Thr Asn
385                 390                 395                 400

Thr Glu Phe Glu Ser Ile Glu Ser Glu Phe Ser Glu Thr Glu His Gln
                405                 410                 415

Ile Gly Asn Val Ile Asn Trp Thr Lys Asp Ser Ile Thr Asp Ile Trp
            420                 425                 430

Thr Tyr Asn Ala Glu Leu Leu Val Ala Met Glu Asn Gln His Thr Ile
                435                 440                 445

Asp Met Ala Asp Ser Glu Met Leu Asn Leu Tyr Glu Arg Val Arg Lys
            450                 455                 460

Gln Leu Arg Gln Asn Ala Glu Glu Asp Gly Lys Gly Cys Phe Glu Ile
465                 470                 475                 480

Tyr His Thr Cys Asp Asp Ser Cys Met Glu Ser Ile Arg Asn Asn Thr
                485                 490                 495

Tyr Asp His Ser Gln Tyr Arg Glu Glu Ala Leu Leu Asn Arg Leu Asn
            500                 505                 510

Ile Asn Pro Val Lys Leu Ser Ser Gly Tyr Lys Asp Ile Ile Leu Trp
                515                 520                 525

Phe Ser Phe Gly Glu Ser Cys Phe Val Leu Leu Ala Val Val Met Gly
            530                 535                 540

Leu Val Phe Phe Cys Leu Lys Asn Gly Asn Met Arg Cys Thr Ile Cys
545                 550                 555                 560

Ile

<210> SEQ ID NO 11
<211> LENGTH: 565
<212> TYPE: PRT
<213> ORGANISM: Artificial Sequence
<220> FEATURE:
<223> OTHER INFORMATION: Exemplary H11 HA

<400> SEQUENCE: 11

Met Glu Lys Thr Leu Leu Phe Ala Ala Ile Phe Leu Cys Val Lys Ala
1               5                   10                  15

Asp Glu Ile Cys Ile Gly Tyr Leu Ser Asn Asn Ser Thr Asp Lys Val
            20                  25                  30

Asp Thr Ile Ile Glu Asn Asn Val Thr Val Thr Ser Val Glu Leu
            35                  40                  45

Val Glu Thr Glu His Thr Gly Ser Phe Cys Ser Ile Asn Gly Lys Gln
50                  55                  60

Pro Ile Ser Leu Gly Asp Cys Ser Phe Ala Gly Trp Ile Leu Gly Asn
65                  70                  75                  80

Pro Met Cys Asp Glu Leu Ile Gly Lys Thr Ser Trp Ser Tyr Ile Val
                85                  90                  95

Glu Lys Pro Asn Pro Thr Asn Gly Ile Cys Tyr Pro Gly Thr Leu Glu
            100                 105                 110

Ser Glu Glu Glu Leu Arg Leu Lys Phe Ser Gly Val Leu Glu Phe Asn
            115                 120                 125

Lys Phe Glu Val Phe Thr Ser Asn Gly Trp Gly Ala Val Asn Ser Gly
        130                 135                 140

Val Gly Val Thr Ala Ala Cys Lys Phe Gly Gly Ser Asn Ser Phe Phe
145                 150                 155                 160
```

```
Arg Asn Met Val Trp Leu Ile His Gln Ser Gly Thr Tyr Pro Val Ile
            165                 170                 175

Lys Arg Thr Phe Asn Asn Thr Lys Gly Arg Asp Val Leu Ile Val Trp
        180                 185                 190

Gly Ile His His Pro Ala Thr Leu Thr Glu His Gln Asp Leu Tyr Lys
        195                 200                 205

Lys Asp Ser Ser Tyr Val Ala Val Gly Ser Glu Thr Tyr Asn Arg Arg
210                 215                 220

Phe Thr Pro Glu Ile Asn Thr Arg Pro Arg Val Asn Gly Gln Ala Gly
225                 230                 235                 240

Arg Met Thr Phe Tyr Trp Lys Ile Val Lys Pro Gly Glu Ser Ile Thr
                245                 250                 255

Phe Glu Ser Asn Gly Ala Phe Leu Ala Pro Arg Tyr Ala Phe Glu Ile
                260                 265                 270

Val Ser Val Gly Asn Gly Lys Leu Phe Arg Ser Glu Leu Asn Ile Glu
            275                 280                 285

Ser Cys Ser Thr Lys Cys Gln Thr Glu Ile Gly Gly Ile Asn Thr Asn
        290                 295                 300

Lys Ser Phe His Asn Val His Arg Asn Thr Ile Gly Asp Cys Pro Lys
305                 310                 315                 320

Tyr Val Asn Val Lys Ser Leu Lys Leu Ala Thr Gly Pro Arg Asn Val
                325                 330                 335

Pro Ala Ile Ala Ser Arg Gly Leu Phe Gly Ala Ile Ala Gly Phe Ile
                340                 345                 350

Glu Gly Gly Trp Pro Gly Leu Ile Asn Gly Trp Tyr Gly Phe Gln His
            355                 360                 365

Arg Asp Glu Glu Gly Thr Gly Ile Ala Ala Asp Lys Glu Ser Thr Gln
370                 375                 380

Lys Ala Ile Asp Gln Ile Thr Ser Lys Val Asn Asn Ile Val Asp Arg
385                 390                 395                 400

Met Asn Thr Asn Phe Glu Ser Val Gln His Glu Phe Ser Glu Ile Glu
                405                 410                 415

Glu Arg Ile Asn Gln Leu Ser Lys His Val Asp Asp Ser Val Val Asp
                420                 425                 430

Ile Trp Ser Tyr Asn Ala Gln Leu Leu Val Leu Leu Glu Asn Glu Lys
            435                 440                 445

Thr Leu Asp Leu His Asp Ser Asn Val Arg Asn Leu His Glu Lys Val
    450                 455                 460

Arg Arg Met Leu Lys Asp Asn Ala Lys Asp Glu Gly Asn Gly Cys Phe
465                 470                 475                 480

Thr Phe Tyr His Lys Cys Asp Asn Lys Cys Ile Glu Arg Val Arg Asn
                485                 490                 495

Gly Thr Tyr Asp His Lys Glu Phe Glu Glu Ser Lys Ile Asn Arg
                500                 505                 510

Gln Glu Ile Glu Gly Val Lys Leu Asp Ser Ser Gly Asn Val Tyr Lys
        515                 520                 525

Ile Leu Ser Ile Tyr Ser Cys Ile Ala Ser Ser Leu Val Leu Ala Ala
    530                 535                 540

Leu Ile Met Gly Phe Met Phe Trp Ala Cys Ser Asn Gly Ser Cys Arg
545                 550                 555                 560

Cys Thr Ile Cys Ile
            565
```

<210> SEQ ID NO 12
<211> LENGTH: 564
<212> TYPE: PRT
<213> ORGANISM: Artificial Sequence
<220> FEATURE:
<223> OTHER INFORMATION: Exemplary H12 HA

<400> SEQUENCE: 12

```
Met Glu Lys Phe Ile Ile Leu Ser Thr Val Leu Ala Ala Ser Phe Ala
1               5                   10                  15

Tyr Asp Lys Ile Cys Ile Gly Tyr Gln Thr Asn Asn Ser Thr Glu Thr
            20                  25                  30

Val Asn Thr Leu Ser Glu Gln Asn Val Pro Val Thr Gln Val Glu Glu
        35                  40                  45

Leu Val His Arg Gly Ile Asp Pro Ile Leu Cys Gly Thr Glu Leu Gly
    50                  55                  60

Ser Pro Leu Val Leu Asp Asp Cys Ser Leu Glu Gly Leu Ile Leu Gly
65                  70                  75                  80

Asn Pro Lys Cys Asp Leu Tyr Leu Asn Gly Arg Glu Trp Ser Tyr Ile
                85                  90                  95

Val Glu Arg Pro Lys Glu Met Glu Gly Val Cys Tyr Pro Gly Ser Ile
            100                 105                 110

Glu Asn Gln Glu Glu Leu Arg Ser Leu Phe Ser Ser Ile Lys Lys Tyr
        115                 120                 125

Glu Arg Val Lys Met Phe Asp Phe Thr Lys Trp Asn Val Thr Tyr Thr
    130                 135                 140

Gly Thr Ser Lys Ala Cys Asn Asn Thr Ser Asn Gln Gly Ser Phe Tyr
145                 150                 155                 160

Arg Ser Met Arg Trp Leu Thr Leu Lys Ser Gly Gln Phe Pro Val Gln
                165                 170                 175

Thr Asp Glu Tyr Lys Asn Thr Arg Asp Ser Asp Ile Val Phe Thr Trp
            180                 185                 190

Ala Ile His His Pro Pro Thr Ser Asp Glu Gln Val Lys Leu Tyr Lys
        195                 200                 205

Asn Pro Asp Thr Leu Ser Ser Val Thr Thr Val Glu Ile Asn Arg Ser
    210                 215                 220

Phe Lys Pro Asn Ile Gly Pro Arg Pro Leu Val Arg Gly Gln Gln Gly
225                 230                 235                 240

Arg Met Asp Tyr Tyr Trp Ala Val Leu Lys Pro Gly Gln Thr Val Lys
                245                 250                 255

Ile Gln Thr Asn Gly Asn Leu Ile Ala Pro Glu Tyr Gly His Leu Ile
            260                 265                 270

Thr Gly Lys Ser His Gly Arg Ile Leu Lys Asn Asn Leu Pro Met Gly
        275                 280                 285

Gln Cys Val Thr Glu Cys Gln Leu Asn Glu Gly Val Met Asn Thr Ser
    290                 295                 300

Lys Pro Phe Gln Asn Thr Ser Lys His Tyr Ile Gly Lys Cys Pro Lys
305                 310                 315                 320

Tyr Ile Pro Ser Gly Ser Leu Lys Leu Ala Ile Gly Leu Arg Asn Val
                325                 330                 335

Pro Gln Val Gln Asp Arg Gly Leu Phe Gly Ala Ile Ala Gly Phe Ile
            340                 345                 350

Glu Gly Gly Trp Pro Gly Leu Val Ala Gly Trp Tyr Gly Phe Gln His
        355                 360                 365
```

```
Gln Asn Ala Glu Gly Thr Gly Ile Ala Ala Asp Arg Asp Ser Thr Gln
    370                 375                 380

Arg Ala Ile Asp Asn Met Gln Asn Lys Leu Asn Asn Val Ile Asp Lys
385                 390                 395                 400

Met Asn Lys Gln Phe Glu Val Val Asn His Glu Phe Ser Glu Val Glu
                405                 410                 415

Ser Arg Ile Asn Met Ile Asn Ser Lys Ile Asp Asp Gln Ile Thr Asp
            420                 425                 430

Ile Trp Ala Tyr Asn Ala Glu Leu Leu Val Leu Leu Glu Asn Gln Lys
                435                 440                 445

Thr Leu Asp Glu His Asp Ala Asn Val Arg Asn Leu His Asp Arg Val
450                 455                 460

Arg Arg Val Leu Arg Glu Asn Ala Ile Asp Thr Gly Asp Gly Cys Phe
465                 470                 475                 480

Glu Ile Leu His Lys Cys Asp Asn Asn Cys Met Asp Thr Ile Arg Asn
                485                 490                 495

Gly Thr Tyr Asn His Lys Glu Tyr Glu Glu Ser Lys Ile Glu Arg
                500                 505                 510

Gln Lys Val Asn Gly Val Lys Leu Glu Glu Asn Ser Thr Tyr Lys Ile
                515                 520                 525

Leu Ser Ile Tyr Ser Ser Val Ala Ser Ser Leu Val Leu Leu Leu Met
            530                 535                 540

Ile Ile Gly Gly Phe Ile Phe Gly Cys Gln Asn Gly Asn Val Arg Cys
545                 550                 555                 560

Thr Phe Cys Ile

<210> SEQ ID NO 13
<211> LENGTH: 566
<212> TYPE: PRT
<213> ORGANISM: Artificial Sequence
<220> FEATURE:
<223> OTHER INFORMATION: Exemplary H13 HA

<400> SEQUENCE: 13

Met Ala Leu Asn Val Ile Ala Thr Leu Thr Leu Ile Ser Val Cys Val
1               5                   10                  15

His Ala Asp Arg Ile Cys Val Gly Tyr Leu Ser Thr Asn Ser Ser Glu
                20                  25                  30

Arg Val Asp Thr Leu Leu Glu Asn Gly Val Pro Val Thr Ser Ser Ile
            35                  40                  45

Asp Leu Ile Glu Thr Asn His Thr Gly Thr Tyr Cys Ser Leu Asn Gly
    50                  55                  60

Val Ser Pro Val His Leu Gly Asp Cys Ser Phe Glu Gly Trp Ile Val
65                  70                  75                  80

Gly Asn Pro Ala Cys Thr Ser Asn Phe Gly Ile Arg Glu Trp Ser Tyr
                85                  90                  95

Leu Ile Glu Asp Pro Ala Ala Pro His Gly Leu Cys Tyr Pro Gly Glu
                100                 105                 110

Leu Asn Asn Asn Gly Glu Leu Arg His Leu Phe Ser Gly Ile Arg Ser
            115                 120                 125

Phe Ser Arg Thr Glu Leu Ile Pro Pro Thr Ser Trp Gly Glu Val Leu
    130                 135                 140

Asp Gly Thr Thr Ser Ala Cys Arg Asp Asn Thr Gly Thr Asn Ser Phe
145                 150                 155                 160

Tyr Arg Asn Leu Val Trp Phe Ile Lys Lys Asn Thr Arg Tyr Pro Val
```

```
                165                 170                 175
Ile Ser Lys Thr Tyr Asn Asn Thr Thr Gly Arg Asp Val Leu Val Leu
            180                 185                 190
Trp Gly Ile His His Pro Val Ser Val Asp Glu Thr Lys Thr Leu Tyr
            195                 200                 205
Val Asn Ser Asp Pro Tyr Thr Leu Val Ser Thr Lys Ser Trp Ser Glu
            210                 215                 220
Lys Tyr Lys Leu Glu Thr Gly Val Arg Pro Gly Tyr Asn Gly Gln Arg
225                 230                 235                 240
Ser Trp Met Lys Ile Tyr Trp Ser Leu Ile His Pro Gly Glu Met Ile
            245                 250                 255
Thr Phe Glu Ser Asn Gly Gly Phe Leu Ala Pro Arg Tyr Gly Tyr Ile
            260                 265                 270
Ile Glu Glu Tyr Gly Lys Gly Arg Ile Phe Gln Ser Arg Ile Arg Met
            275                 280                 285
Ser Arg Cys Asn Thr Lys Cys Gln Thr Ser Val Gly Gly Ile Asn Thr
            290                 295                 300
Asn Arg Thr Phe Gln Asn Ile Asp Lys Asn Ala Leu Gly Asp Cys Pro
305                 310                 315                 320
Lys Tyr Ile Lys Ser Gly Gln Leu Lys Leu Ala Thr Gly Leu Arg Asn
            325                 330                 335
Val Pro Ala Ile Ser Asn Arg Gly Leu Phe Gly Ala Ile Ala Gly Phe
            340                 345                 350
Ile Glu Gly Gly Trp Pro Gly Leu Ile Asn Gly Trp Tyr Gly Phe Gln
            355                 360                 365
His Gln Asn Glu Gln Gly Thr Gly Ile Ala Ala Asp Lys Glu Ser Thr
            370                 375                 380
Gln Lys Ala Ile Asp Gln Ile Thr Thr Lys Ile Asn Asn Ile Ile Asp
385                 390                 395                 400
Lys Met Asn Gly Asn Tyr Asp Ser Ile Arg Gly Glu Phe Asn Gln Val
            405                 410                 415
Glu Lys Arg Ile Asn Met Leu Ala Asp Arg Ile Asp Asp Ala Val Thr
            420                 425                 430
Asp Ile Trp Ser Tyr Asn Ala Lys Leu Leu Val Leu Leu Glu Asn Asp
            435                 440                 445
Lys Thr Leu Asp Met His Asp Ala Asn Val Lys Asn Leu His Glu Gln
            450                 455                 460
Val Arg Arg Glu Leu Lys Asp Asn Ala Ile Asp Glu Gly Asn Gly Cys
465                 470                 475                 480
Phe Glu Leu Leu His Lys Cys Asn Asp Ser Cys Met Glu Thr Ile Arg
            485                 490                 495
Asn Gly Thr Tyr Asp His Thr Glu Tyr Ala Glu Glu Ser Lys Leu Lys
            500                 505                 510
Arg Gln Glu Ile Asp Gly Ile Lys Leu Lys Ser Glu Asp Asn Val Tyr
            515                 520                 525
Lys Ala Leu Ser Ile Tyr Ser Cys Ile Ala Ser Ser Val Val Leu Val
            530                 535                 540
Gly Leu Ile Leu Ser Phe Ile Met Trp Ala Cys Ser Ser Gly Asn Cys
545                 550                 555                 560
Arg Phe Asn Val Cys Ile
            565

<210> SEQ ID NO 14
```

```
<211> LENGTH: 568
<212> TYPE: PRT
<213> ORGANISM: Artificial Sequence
<220> FEATURE:
<223> OTHER INFORMATION: Exemplary H14 HA

<400> SEQUENCE: 14

Met Ile Ala Leu Ile Leu Val Ala Leu Ala Leu Ser His Thr Ala Tyr
1               5                   10                  15

Ser Gln Ile Thr Asn Gly Thr Thr Gly Asn Pro Ile Ile Cys Leu Gly
            20                  25                  30

His His Ala Val Glu Asn Gly Thr Ser Val Lys Thr Leu Thr Asp Asn
        35                  40                  45

His Val Glu Val Val Ser Ala Lys Glu Leu Val Glu Thr Asn His Thr
    50                  55                  60

Asp Glu Leu Cys Pro Ser Pro Leu Lys Leu Val Asp Gly Gln Asp Cys
65                  70                  75                  80

His Leu Ile Asn Gly Ala Leu Gly Ser Pro Gly Cys Asp Arg Leu Gln
                85                  90                  95

Asp Thr Thr Trp Asp Val Phe Ile Glu Arg Pro Thr Ala Val Asp Thr
            100                 105                 110

Cys Tyr Pro Phe Asp Val Pro Asp Tyr Gln Ser Leu Arg Ser Ile Leu
        115                 120                 125

Ala Ser Ser Gly Ser Leu Glu Phe Ile Ala Glu Gln Phe Thr Trp Asn
    130                 135                 140

Gly Val Lys Val Asp Gly Ser Ser Ser Ala Cys Leu Arg Gly Gly Arg
145                 150                 155                 160

Asn Ser Phe Phe Ser Arg Leu Asn Trp Leu Thr Lys Ala Thr Asn Gly
                165                 170                 175

Asn Tyr Gly Pro Ile Asn Val Thr Lys Glu Asn Thr Gly Ser Tyr Val
            180                 185                 190

Arg Leu Tyr Leu Trp Gly Val His His Pro Ser Ser Asp Asn Glu Gln
        195                 200                 205

Thr Asp Leu Tyr Lys Val Ala Thr Gly Arg Val Thr Val Ser Thr Arg
    210                 215                 220

Ser Asp Gln Ile Ser Ile Val Pro Asn Ile Gly Ser Arg Pro Arg Val
225                 230                 235                 240

Arg Asn Gln Ser Gly Arg Ile Ser Ile Tyr Trp Thr Leu Val Asn Pro
                245                 250                 255

Gly Asp Ser Ile Ile Phe Asn Ser Ile Gly Asn Leu Ile Ala Pro Arg
            260                 265                 270

Gly His Tyr Lys Ile Ser Lys Ser Thr Lys Ser Thr Val Leu Lys Ser
        275                 280                 285

Asp Lys Arg Ile Gly Ser Cys Thr Ser Pro Cys Leu Thr Asp Lys Gly
    290                 295                 300

Ser Ile Gln Ser Asp Lys Pro Phe Gln Asn Val Ser Arg Ile Ala Ile
305                 310                 315                 320

Gly Asn Cys Pro Lys Tyr Val Lys Gln Gly Ser Leu Met Leu Ala Thr
                325                 330                 335

Gly Met Arg Asn Ile Pro Gly Lys Gln Ala Lys Gly Leu Phe Gly Ala
            340                 345                 350

Ile Ala Gly Phe Ile Glu Asn Gly Trp Gln Gly Leu Ile Asp Gly Trp
        355                 360                 365

Tyr Gly Phe Arg His Gln Asn Ala Glu Gly Thr Gly Thr Ala Ala Asp
    370                 375                 380
```

Leu Lys Ser Thr Gln Ala Ala Ile Asp Gln Ile Asn Gly Lys Leu Asn
385                 390                 395                 400

Arg Leu Ile Glu Lys Thr Asn Glu Lys Tyr His Gln Ile Glu Lys Glu
            405                 410                 415

Phe Glu Gln Val Glu Gly Arg Ile Gln Asp Leu Glu Lys Tyr Val Glu
            420                 425                 430

Asp Thr Lys Ile Asp Leu Trp Ser Tyr Asn Ala Glu Leu Leu Val Ala
            435                 440                 445

Leu Glu Asn Gln His Thr Ile Asp Val Thr Asp Ser Glu Met Asn Lys
450                 455                 460

Leu Phe Glu Arg Val Arg Arg Gln Leu Arg Glu Asn Ala Glu Asp Gln
465                 470                 475                 480

Gly Asn Gly Cys Phe Glu Ile Phe His Gln Cys Asp Asn Asn Cys Ile
            485                 490                 495

Glu Ser Ile Arg Asn Gly Thr Tyr Asp His Asn Ile Tyr Arg Asp Glu
            500                 505                 510

Ala Ile Asn Asn Arg Ile Lys Ile Asn Pro Val Thr Leu Thr Met Gly
            515                 520                 525

Tyr Lys Asp Ile Ile Leu Trp Ile Ser Phe Ser Met Ser Cys Phe Val
530                 535                 540

Phe Val Ala Leu Ile Leu Gly Phe Val Leu Trp Ala Cys Gln Asn Gly
545                 550                 555                 560

Asn Ile Arg Cys Gln Ile Cys Ile
            565

<210> SEQ ID NO 15
<211> LENGTH: 570
<212> TYPE: PRT
<213> ORGANISM: Artificial Sequence
<220> FEATURE:
<223> OTHER INFORMATION: Exemplary H15 HA

<400> SEQUENCE: 15

Met Asn Thr Gln Ile Ile Val Ile Leu Val Leu Gly Leu Ser Met Val
1               5                   10                  15

Lys Ser Asp Lys Ile Cys Leu Gly His His Ala Val Ala Asn Gly Thr
            20                  25                  30

Lys Val Asn Thr Leu Thr Glu Arg Gly Val Glu Val Val Asn Ala Thr
        35                  40                  45

Glu Thr Val Glu Ile Thr Gly Ile Asp Lys Val Cys Thr Lys Gly Lys
    50                  55                  60

Lys Ala Val Asp Leu Gly Ser Cys Gly Ile Leu Gly Thr Ile Ile Gly
65                  70                  75                  80

Pro Pro Gln Cys Asp Leu His Leu Glu Phe Lys Ala Asp Leu Ile Ile
                85                  90                  95

Glu Arg Arg Asn Ser Ser Asp Ile Cys Tyr Pro Gly Arg Phe Thr Asn
            100                 105                 110

Glu Glu Ala Leu Arg Gln Ile Ile Arg Glu Ser Gly Gly Ile Asp Lys
        115                 120                 125

Glu Ser Met Gly Phe Arg Tyr Ser Gly Ile Arg Thr Asp Gly Ala Thr
    130                 135                 140

Ser Ala Cys Lys Arg Thr Val Ser Ser Phe Tyr Ser Glu Met Lys Trp
145                 150                 155                 160

Leu Ser Ser Ser Met Asn Asn Gln Val Phe Pro Gln Leu Asn Gln Thr
                165                 170                 175

Tyr Arg Asn Thr Arg Lys Glu Pro Ala Leu Ile Val Trp Gly Val His
                180                 185                 190

His Ser Ser Ser Leu Asp Glu Gln Asn Lys Leu Tyr Gly Thr Gly Asn
            195                 200                 205

Lys Leu Ile Thr Val Gly Ser Ser Lys Tyr Gln Gln Ser Phe Ser Pro
210                 215                 220

Ser Pro Gly Ala Arg Pro Lys Val Asn Gly Gln Ala Gly Arg Ile Asp
225                 230                 235                 240

Phe His Trp Met Leu Leu Asp Pro Gly Asp Thr Val Thr Phe Thr Phe
                245                 250                 255

Asn Gly Ala Phe Ile Ala Pro Asp Arg Ala Thr Phe Leu Arg Ser Asn
            260                 265                 270

Ala Pro Ser Gly Ile Glu Tyr Asn Gly Lys Ser Leu Gly Ile Gln Ser
        275                 280                 285

Asp Ala Gln Ile Asp Glu Ser Cys Glu Gly Glu Cys Phe Tyr Ser Gly
    290                 295                 300

Gly Thr Ile Asn Ser Pro Leu Pro Phe Gln Asn Ile Asp Ser Arg Ala
305                 310                 315                 320

Val Gly Lys Cys Pro Arg Tyr Val Lys Gln Ser Ser Leu Pro Leu Ala
                325                 330                 335

Leu Gly Met Lys Asn Val Pro Glu Lys Ile Arg Thr Arg Gly Leu Phe
            340                 345                 350

Gly Ala Ile Ala Gly Phe Ile Glu Asn Gly Trp Glu Gly Leu Ile Asp
        355                 360                 365

Gly Trp Tyr Gly Phe Arg His Gln Asn Ala Gln Gly Gln Gly Thr Ala
    370                 375                 380

Ala Asp Tyr Lys Ser Thr Gln Ala Ala Ile Asp Gln Ile Thr Gly Lys
385                 390                 395                 400

Leu Asn Arg Leu Ile Glu Lys Thr Asn Lys Gln Phe Glu Leu Ile Asp
                405                 410                 415

Asn Glu Phe Thr Glu Val Glu Gln Gln Ile Gly Asn Val Ile Asn Trp
            420                 425                 430

Thr Arg Asp Ser Leu Thr Glu Ile Trp Ser Tyr Asn Ala Glu Leu Leu
        435                 440                 445

Val Ala Met Glu Asn Gln His Thr Ile Asp Leu Ala Asp Ser Glu Met
450                 455                 460

Asn Lys Leu Tyr Glu Arg Val Arg Arg Gln Leu Arg Glu Asn Ala Glu
465                 470                 475                 480

Glu Asp Gly Thr Gly Cys Phe Glu Ile Phe His Arg Cys Asp Asp Gln
                485                 490                 495

Cys Met Glu Ser Ile Arg Asn Asn Thr Tyr Asn His Thr Glu Tyr Arg
            500                 505                 510

Gln Glu Ala Leu Gln Asn Arg Ile Met Ile Asn Pro Val Lys Leu Ser
        515                 520                 525

Ser Gly Tyr Lys Asp Val Ile Leu Trp Phe Ser Phe Gly Ala Ser Cys
    530                 535                 540

Val Met Leu Leu Ala Ile Ala Met Gly Leu Ile Phe Met Cys Val Lys
545                 550                 555                 560

Asn Gly Asn Leu Arg Cys Thr Ile Cys Ile
                565                 570

<210> SEQ ID NO 16
<211> LENGTH: 565

<212> TYPE: PRT
<213> ORGANISM: Artificial Sequence
<220> FEATURE:
<223> OTHER INFORMATION: Exemplary H16 HA

<400> SEQUENCE: 16

```
Met Met Ile Lys Val Leu Tyr Phe Leu Ile Ile Val Leu Gly Arg Tyr
1               5                   10                  15

Ser Lys Ala Asp Lys Ile Cys Ile Gly Tyr Leu Ser Asn Asn Ser Ser
            20                  25                  30

Asp Thr Val Asp Thr Leu Thr Glu Asn Gly Val Pro Val Thr Ser Ser
        35                  40                  45

Val Asp Leu Val Glu Thr Asn His Thr Gly Thr Tyr Cys Ser Leu Asn
    50                  55                  60

Gly Ile Ser Pro Ile His Leu Gly Asp Cys Ser Phe Glu Gly Trp Ile
65                  70                  75                  80

Val Gly Asn Pro Ser Cys Ala Thr Asn Ile Asn Ile Arg Glu Trp Ser
                85                  90                  95

Tyr Leu Ile Glu Asp Pro Asn Ala Pro Asn Lys Phe Cys Tyr Pro Gly
            100                 105                 110

Glu Leu Asp Asn Asn Gly Glu Leu Arg His Leu Phe Ser Gly Val Asn
        115                 120                 125

Ser Phe Ser Arg Thr Glu Leu Ile Asn Pro Ser Lys Trp Gly Asn Val
    130                 135                 140

Leu Asp Gly Val Thr Ala Ser Cys Leu Asp Arg Gly Ala Ser Ser Phe
145                 150                 155                 160

Tyr Arg Asn Leu Val Trp Ile Val Lys Lys Asp Glu Lys Tyr Pro Val
                165                 170                 175

Ile Lys Gly Asp Tyr Asn Asn Thr Thr Gly Arg Asp Val Leu Val Leu
            180                 185                 190

Trp Gly Ile His His Pro Asp Thr Glu Thr Thr Ala Thr Asn Leu Tyr
        195                 200                 205

Val Asn Lys Asn Pro Tyr Thr Leu Val Ser Thr Lys Glu Trp Ser Lys
    210                 215                 220

Arg Tyr Glu Leu Glu Ile Gly Thr Arg Ile Gly Asp Gly Gln Arg Ser
225                 230                 235                 240

Trp Met Lys Leu Tyr Trp His Leu Met His Pro Gly Glu Arg Ile Met
                245                 250                 255

Phe Glu Ser Asn Gly Gly Leu Ile Ala Pro Arg Tyr Gly Tyr Ile Ile
            260                 265                 270

Glu Lys Tyr Gly Thr Gly Arg Ile Phe Gln Ser Gly Val Arg Met Ala
        275                 280                 285

Arg Cys Asn Thr Lys Cys Gln Thr Ser Leu Gly Gly Ile Asn Thr Asn
    290                 295                 300

Lys Thr Phe Gln Asn Ile Glu Arg Asn Ala Leu Gly Asp Cys Pro Lys
305                 310                 315                 320

Tyr Ile Lys Ser Gly Gln Leu Lys Leu Ala Thr Gly Leu Arg Asn Val
                325                 330                 335

Pro Ser Ile Gly Glu Arg Gly Leu Phe Gly Ala Ile Ala Gly Phe Ile
            340                 345                 350

Glu Gly Gly Trp Pro Gly Leu Ile Asn Gly Trp Tyr Gly Phe Gln His
        355                 360                 365

Gln Asn Glu Gln Gly Thr Gly Ile Ala Ala Asp Lys Ala Ser Thr Gln
    370                 375                 380
```

Lys Ala Ile Asn Glu Ile Thr Thr Lys Ile Asn Asn Ile Glu Lys
385                 390                 395                 400

Met Asn Gly Asn Tyr Asp Ser Ile Arg Gly Glu Phe Asn Gln Val Glu
            405                 410                 415

Lys Arg Ile Asn Met Leu Ala Asp Arg Val Asp Asp Ala Val Thr Asp
            420                 425                 430

Ile Trp Ser Tyr Asn Ala Lys Leu Leu Val Leu Leu Glu Asn Asp Arg
            435                 440                 445

Thr Leu Asp Leu His Asp Ala Asn Val Arg Asn Leu His Asp Gln Val
    450                 455                 460

Lys Arg Ala Leu Lys Ser Asn Ala Ile Asp Glu Gly Asp Gly Cys Phe
465                 470                 475                 480

Asn Leu Leu His Lys Cys Asn Asp Ser Cys Met Glu Thr Ile Arg Asn
            485                 490                 495

Gly Thr Tyr Asn His Glu Asp Tyr Arg Glu Glu Ser Gln Leu Lys Arg
            500                 505                 510

Gln Glu Ile Glu Gly Ile Lys Leu Lys Thr Glu Asp Asn Val Tyr Lys
            515                 520                 525

Val Leu Ser Ile Tyr Ser Cys Ile Ala Ser Ser Ile Val Leu Val Gly
            530                 535                 540

Leu Ile Leu Ala Phe Ile Met Trp Ala Cys Ser Asn Gly Ser Cys Arg
545                 550                 555                 560

Phe Asn Val Cys Ile
            565

<210> SEQ ID NO 17
<211> LENGTH: 342
<212> TYPE: PRT
<213> ORGANISM: Artificial Sequence
<220> FEATURE:
<223> OTHER INFORMATION: Exemplary H17 HA

<400> SEQUENCE: 17

Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Gln
            35                  40                  45

Thr Arg Gly Lys Leu Cys Pro Asn Cys Leu Asn Cys Thr Asp Leu Asp
    50                  55                  60

Val Ala Leu Gly Arg Pro Lys Cys Met Gly Thr Ile Pro Ser Ala Lys
65                  70                  75                  80

Ala Ser Ile Leu His Glu Val Lys Pro Val Thr Ser Gly Cys Phe Pro
            85                  90                  95

Ile Met His Asp Arg Thr Lys Ile Arg Gln Leu Pro Asn Leu Leu Arg
            100                 105                 110

Gly Tyr Glu Asn Ile Arg Leu Ser Ala Arg Asn Val Thr Asn Ala Glu
            115                 120                 125

Thr Ala Pro Gly Gly Pro Tyr Ile Val Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asn Lys Thr Ala Thr Asn Pro Leu Thr Val Glu Val Pro Tyr
            165                 170                 175

```
Ile Cys Thr Lys Gly Glu Asp Gln Ile Thr Val Trp Gly Phe His Ser
            180                 185                 190

Asp Asp Glu Thr Gln Met Val Lys Leu Tyr Gly Asp Ser Lys Pro Gln
            195                 200                 205

Lys Phe Thr Ser Ser Ala Asn Gly Val Thr Thr His Tyr Val Ser Gln
        210                 215                 220

Ile Gly Gly Phe Pro Asn Gln Ala Glu Asp Glu Gly Leu Pro Gln Ser
225                 230                 235                 240

Gly Arg Ile Val Val Asp Tyr Met Val Gln Lys Pro Gly Lys Thr Gly
                245                 250                 255

Thr Ile Ala Tyr Gln Arg Gly Val Leu Leu Pro Gln Lys Val Trp Cys
            260                 265                 270

Ala Ser Gly Arg Ser Lys Val Ile Lys Gly Ser Leu Pro Leu Ile Gly
        275                 280                 285

Glu Ala Asp Cys Leu His Glu Lys Tyr Gly Gly Leu Asn Lys Ser Lys
290                 295                 300

Pro Tyr Tyr Thr Gly Glu His Ala Lys Ala Ile Gly Asn Cys Pro Ile
305                 310                 315                 320

Trp Val Lys Thr Pro Leu Lys Leu Ala Asn Gly Thr Lys Tyr Arg Pro
                325                 330                 335

Pro Ala Lys Leu Leu Lys
                340
```

<210> SEQ ID NO 18
<211> LENGTH: 17
<212> TYPE: PRT
<213> ORGANISM: Artificial Sequence
<220> FEATURE:
<223> OTHER INFORMATION: Exemplary influenza A HA subtype H1 signal
      peptide

<400> SEQUENCE: 18

```
Met Lys Ala Asn Leu Leu Val Leu Leu Cys Ala Leu Ala Ala Ala Asp
1               5                   10                  15

Ala
```

<210> SEQ ID NO 19
<211> LENGTH: 15
<212> TYPE: PRT
<213> ORGANISM: Artificial Sequence
<220> FEATURE:
<223> OTHER INFORMATION: Exemplary influenza A HA subtype H2 signal
      peptide

<400> SEQUENCE: 19

```
Met Ala Ile Ile Tyr Leu Ile Leu Leu Phe Thr Ala Val Arg Gly
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: Exemplary influenza A HA subtype H3 signal
      peptide

<400> SEQUENCE: 20

```
Met Lys Thr Ile Ile Ala Leu Ser Tyr Ile Phe Cys Leu Ala Leu Gly
1               5                   10                  15
```

<210> SEQ ID NO 21

-continued

```
<211> LENGTH: 16
<212> TYPE: PRT
<213> ORGANISM: Artificial Sequence
<220> FEATURE:
<223> OTHER INFORMATION: Exemplary influenza A HA subtype H4 signal
      peptide

<400> SEQUENCE: 21

Met Leu Ser Ile Val Ile Leu Phe Leu Leu Ile Ala Glu Asn Ser

```
<400> SEQUENCE: 26

Met Glu Thr Lys Ala Ile Ile Ala Ala Leu Leu Met Val Thr Ala Ala
1 5 10 15

<210> SEQ ID NO 27
<211> LENGTH: 16
<212> TYPE: PRT
<213> ORGANISM: Artificial Sequence
<220> FEATURE:
<223> OTHER INFORMATION: Exemplary influenza A HA subtype H10 signal peptide

<400> SEQUENCE: 27

Met Tyr Lys Val Val Val Ile Ile Ala Leu Leu Gly Ala Val Lys Gly
1 5 10 15

<210> SEQ ID NO 28
<211> LENGTH: 16
<212> TYPE: PRT
<213> ORGANISM: Artificial Sequence
<220> FEATURE:
<223> OTHER INFORMATION: Exemplary influenza A HA subtype H11 signal peptide

<400> SEQUENCE: 28

Met Glu Lys Thr Leu Leu Phe Ala Ala Ile Phe Leu Cys Val Lys Ala
1 5 10 15

<210> SEQ ID NO 29
<211> LENGTH: 17
<212> TYPE: PRT
<213> ORGANISM: Artificial Sequence
<220> FEATURE:
<223> OTHER INFORMATION: Exemplary influenza A HA subtype H12 signal peptide

<400> SEQUENCE: 29

Met Glu Lys Phe Ile Ile Leu Ser Thr Val Leu Ala Ala Ser Phe Ala
1 5 10 15

Tyr

<210> SEQ ID NO 30
<211> LENGTH: 18
<212> TYPE: PRT
<213> ORGANISM: Artificial Sequence
<220> FEATURE:
<223> OTHER INFORMATION: Exemplary influenza A HA subtype H13 signal peptide

<400> SEQUENCE: 30

Met Ala Leu Asn Val Ile Ala Thr Leu Thr Leu Ile Ser Val Cys Val
1 5 10 15

His Ala

<210> SEQ ID NO 31
<211> LENGTH: 17
<212> TYPE: PRT
<213> ORGANISM: Artificial Sequence
<220> FEATURE:
<223> OTHER INFORMATION: Exemplary influenza A HA subtype H14 signal peptide

<400> SEQUENCE: 31

Met Ile Ala Leu Ile Leu Val Ala Leu Ala Leu Ser His Thr Ala Tyr
1 5 10 15

Ser

<210> SEQ ID NO 32
<211> LENGTH: 18
<212> TYPE: PRT
<213> ORGANISM: Artificial Sequence
<220> FEATURE:
<223> OTHER INFORMATION: Exemplary influenza A HA subtype H15 signal
      peptide

<400> SEQUENCE: 32

Met Asn Thr Gln Ile Ile Val Ile Leu Val Leu Gly Leu Ser Met Val
1 5 10 15

Lys Ser

<210> SEQ ID NO 33
<211> LENGTH: 19
<212> TYPE: PRT
<213> ORGANISM: Artificial Sequence
<220> FEATURE:
<223> OTHER INFORMATION: Exemplary influenza A HA subtype H16 signal peptide

<400> SEQUENCE: 33

Met Met Ile Lys Val Leu Tyr Phe Leu Ile Ile Val Leu Gly Arg Tyr
1 5 10 15

Ser Lys Ala

<210> SEQ ID NO 34
<211> LENGTH: 180
<212> TYPE: PRT
<213> ORGANISM: Artificial Sequence
<220> FEATURE:
<223> OTHER INFORMATION: Exemplary influenza A HA2 domain subtype H1 stem domain

<400> SEQUENCE: 34

Gly Leu Phe Gly Ala Ile Ala Gly Phe Ile Glu Gly Gly Trp Thr Gly
1 5 10 15

Met Ile Asp Gly Trp Tyr Gly Tyr His His Gln Asn Glu Gln Gly Ser
20 25 30

Gly Tyr Ala Ala Asp Gln Lys Ser Thr Gln Asn Ala Ile Asn Gly Ile
35 40 45

Thr Asn Lys Val Asn Thr Val Ile Glu Lys Met Asn Ile Gln Phe Thr
50 55 60

Ala Val Gly Lys Glu Phe Asn Lys Leu Glu Lys Arg Met Glu Asn Leu
65 70 75 80

Asn Lys Lys Val Asp Asp Gly Phe Leu Asp Ile Trp Thr Tyr Asn Ala
85 90 95

Glu Leu Leu Val Leu Leu Glu Asn Glu Arg Thr Leu Asp Phe His Asp
100 105 110

Ser Asn Val Lys Asn Leu Tyr Glu Lys Val Lys Ser Gln Leu Lys Asn
115 120 125

Asn Ala Lys Glu Ile Gly Asn Gly Cys Phe Glu Phe Tyr His Lys Cys
130 135 140

Asp Asn Glu Cys Met Glu Ser Val Arg Asn Gly Thr Tyr Asp Tyr Pro
145 150 155 160

Lys Tyr Ser Glu Glu Ser Lys Leu Asn Arg Glu Lys Val Asp Gly Val
165 170 175

Lys Leu Glu Ser

<210> SEQ ID NO 35
<211> LENGTH: 180
<212> TYPE: PRT
<213> ORGANISM: Artificial Sequence
<220> FEATURE:
<223> OTHER INFORMATION: Exemplary influenza A HA2 domain subtype H2
      stem domain

<400> SEQUENCE: 35

```
Gly Leu Phe Gly Ala Ile Ala Gly Phe Ile Glu Gly Gly Trp Gln Gly
1               5                   10                  15

Met Ile Asp Gly Trp Tyr Gly Tyr His His Ser Asn Asp Gln Gly Ser
            20                  25                  30

Gly Tyr Ala Ala Asp Lys Glu Ser Thr Gln Lys Ala Ile Asp Gly Ile
        35                  40                  45

Thr Asn Arg Val Asn Ser Val Ile Glu Lys Met Asn Thr Gln Phe Glu
    50                  55                  60

Ala Val Gly Lys Glu Phe Ser Asn Leu Glu Lys Arg Leu Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Arg Val Arg Met Gln Leu Arg Asp
        115                 120                 125

Asn Ala Lys Glu Leu Gly Asn Gly Cys Phe Glu Phe Tyr His Lys Cys
130                 135                 140

Asp Asp Glu Cys Met Asn Ser Val Lys Asn Gly Thr Tyr Asp Tyr Pro
145                 150                 155                 160

Lys Tyr Glu Glu Glu Ser Lys Leu Asn Arg Asn Glu Ile Lys Gly Val
                165                 170                 175

Lys Leu Ser Asn
            180
```

<210> SEQ ID NO 36
<211> LENGTH: 179
<212> TYPE: PRT
<213> ORGANISM: Artificial Sequence
<220> FEATURE:
<223> OTHER INFORMATION: Exemplary influenza A HA2 domain subtype H3
      stem domain

<400> SEQUENCE: 36

```
Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
```

```
                 100                 105                 110
Ser Glu Met Asn Lys Leu Phe Glu Lys Thr Arg Arg Gln Leu Arg Glu
            115                 120                 125

Asn Ala Glu Asp Met Gly Asn Gly Cys Phe Lys Ile Tyr His Lys Cys
            130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys

<210> SEQ ID NO 37
<211> LENGTH: 179
<212> TYPE: PRT
<213> ORGANISM: Artificial Sequence
<220> FEATURE:
<223> OTHER INFORMATION: Exemplary influenza A HA2 domain subtype H4
      stem domain

<400> SEQUENCE: 37

Gly Leu Phe Gly Ala Ile Ala Gly Phe Ile Glu Asn Gly Trp Gln Gly
1               5                   10                  15

Leu Ile Asp Gly Trp Tyr Gly Phe Arg His Gln Asn Ala Glu Gly Thr
            20                  25                  30

Gly Thr Ala Ala Asp Leu Lys Ser Thr Gln Ala Ala Ile Asp Gln Ile
        35                  40                  45

Asn Gly Lys Leu Asn Arg Leu Ile Glu Lys Thr Asn Asp Lys Tyr His
50                  55                  60

Gln Ile Glu Lys Glu Phe Glu Gln Val Glu Gly Arg Ile Gln Asp Leu
65                  70                  75                  80

Glu Asn Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Val Thr Asp
            100                 105                 110

Ser Glu Met Asn Lys Leu Phe Glu Arg Val Arg Arg Gln Leu Arg Glu
            115                 120                 125

Asn Ala Glu Asp Lys Gly Asn Gly Cys Phe Glu Ile Phe His Lys Cys
            130                 135                 140

Asp Asn Asn Cys Ile Glu Ser Ile Arg Asn Gly Thr Tyr Asp His Asp
145                 150                 155                 160

Ile Tyr Arg Asp Glu Ala Ile Asn Asn Arg Phe Gln Ile Gln Gly Val
                165                 170                 175

Lys Leu Thr

<210> SEQ ID NO 38
<211> LENGTH: 180
<212> TYPE: PRT
<213> ORGANISM: Artificial Sequence
<220> FEATURE:
<223> OTHER INFORMATION: Exemplary influenza A HA2 domain subtype H5
      stem domain

<400> SEQUENCE: 38

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30
```

Gly Tyr Ala Ala Asp Lys Glu Ser Thr Gln Lys Ala Ile Asp Gly Ile
                35                  40                  45

Thr Asn Lys Val Asn Ser Ile Ile Asp Lys Met Asn Thr Arg Phe Glu
 50                  55                  60

Ala Val Gly Lys Glu Phe Asn Asn Leu Glu Arg Arg Val Glu Asn Leu
 65                  70                  75                  80

Asn Lys Lys Met Glu Asp Gly Phe Leu Asp Val Trp Thr Tyr Asn Val
                 85                  90                  95

Glu Leu Leu Val Leu Met Glu Asn Glu Arg Thr Leu Asp Phe His Asp
                100                 105                 110

Ser Asn Val Asn Asn Leu Tyr Asp Lys Val Arg Leu Gln Leu Lys Asp
                115                 120                 125

Asn Ala Arg Glu Leu Gly Asn Gly Cys Phe Glu Phe Tyr His Lys Cys
130                 135                 140

Asp Asn Glu Cys Met Glu Ser Val Arg Asn Gly Thr Tyr Asp Tyr Pro
145                 150                 155                 160

Gln Tyr Ser Glu Glu Ala Arg Leu Asn Arg Glu Ile Ser Gly Val
                165                 170                 175

Lys Leu Glu Ser
            180

<210> SEQ ID NO 39
<211> LENGTH: 180
<212> TYPE: PRT
<213> ORGANISM: Artificial Sequence
<220> FEATURE:
<223> OTHER INFORMATION: Exemplary influenza A HA2 domain subtype H6
      stem domain

<400> SEQUENCE: 39

Gly Leu Phe Gly Ala Ile Ala Gly Phe Ile Glu Gly Gly Trp Thr Gly
 1               5                  10                  15

Met Ile Asp Gly Trp Tyr Gly Tyr His His Glu Asn Ser Gln Gly Ser
                20                  25                  30

Gly Tyr Ala Ala Asp Arg Glu Ser Thr Gln Lys Ala Val Asp Gly Ile
                35                  40                  45

Thr Asn Lys Val Asn Ser Ile Ile Asp Lys Met Asn Thr Gln Phe Glu
 50                  55                  60

Ala Val Asp His Glu Phe Ser Asn Leu Glu Arg Arg Ile Asp Asn Leu
 65                  70                  75                  80

Asn Lys Arg Met Glu Asp Gly Phe Leu Asp Val Trp Thr Tyr Asn Ala
                 85                  90                  95

Glu Leu Leu Val Leu Leu Glu Asn Glu Arg Thr Leu Asp Leu His Asp
                100                 105                 110

Ala Asn Val Lys Asn Leu Tyr Glu Arg Val Lys Ser Gln Leu Arg Asp
                115                 120                 125

Asn Ala Met Ile Leu Gly Asn Gly Cys Phe Glu Phe Trp His Lys Cys
130                 135                 140

Asp Asp Glu Cys Met Glu Ser Val Lys Asn Gly Thr Tyr Asp Tyr Pro
145                 150                 155                 160

Lys Tyr Gln Asp Glu Ser Lys Leu Asn Arg Gln Glu Ile Glu Ser Val
                165                 170                 175

Lys Leu Glu Ser
            180

<210> SEQ ID NO 40

```
<211> LENGTH: 179
<212> TYPE: PRT
<213> ORGANISM: Artificial Sequence
<220> FEATURE:
<223> OTHER INFORMATION: Exemplary influenza A HA2 domain subtype H7
      stem domain

<400> SEQUENCE: 40

Gly Leu Phe Gly Ala Ile Ala Gly Phe Ile Glu Asn Gly Trp Glu Gly
1               5                   10                  15

Leu Val Asp Gly Trp Tyr Gly Phe Arg His Gln Asn Ala Gln Gly Glu
                20                  25                  30

Gly Thr Ala Ala Asp Tyr Lys Ser Thr Gln Ser Ala Ile Asp Gln Ile
            35                  40                  45

Thr Gly Lys Leu Asn Arg Leu Ile Glu Lys Thr Asn Gln Gln Phe Glu
    50                  55                  60

Leu Ile Asp Asn Glu Phe Thr Glu Val Glu Lys Gln Ile Gly Asn Leu
65                  70                  75                  80

Ile Asn Trp Thr Lys Asp Ser Ile Thr Glu Val Trp Ser Tyr Asn Ala
                85                  90                  95

Glu Leu Ile Val Ala Met Glu Asn Gln His Thr Ile Asp Leu Ala Asp
                100                 105                 110

Ser Glu Met Asn Arg Leu Tyr Glu Arg Val Arg Lys Gln Leu Arg Glu
            115                 120                 125

Asn Ala Glu Glu Asp Gly Thr Gly Cys Phe Glu Ile Phe His Lys Cys
    130                 135                 140

Asp Asp Asp Cys Met Ala Ser Ile Arg Asn Asn Thr Tyr Asp His Ser
145                 150                 155                 160

Lys Tyr Arg Glu Glu Ala Met Gln Asn Arg Ile Gln Ile Asp Pro Val
                165                 170                 175

Lys Leu Ser

<210> SEQ ID NO 41
<211> LENGTH: 180
<212> TYPE: PRT
<213> ORGANISM: Artificial Sequence
<220> FEATURE:
<223> OTHER INFORMATION: Exemplary influenza A HA2 domain subtype H8
      stem domain

<400> SEQUENCE: 41

Gly Leu Phe Gly Ala Ile Ala Gly Phe Ile Glu Gly Gly Trp Ser Gly
1               5                   10                  15

Met Ile Asp Gly Trp Tyr Gly Phe His His Ser Asn Ser Glu Gly Thr
                20                  25                  30

Gly Met Ala Ala Asp Gln Lys Ser Thr Gln Glu Ala Ile Asp Lys Ile
            35                  40                  45

Thr Asn Lys Val Asn Asn Ile Val Asp Lys Met Asn Arg Glu Phe Glu
    50                  55                  60

Val Val Asn His Glu Phe Ser Glu Val Glu Lys Arg Ile Asn Met Ile
65                  70                  75                  80

Asn Asp Lys Ile Asp Asp Gln Ile Glu Asp Leu Trp Ala Tyr Asn Ala
                85                  90                  95

Glu Leu Leu Val Leu Leu Glu Asn Gln Lys Thr Leu Asp Glu His Asp
                100                 105                 110

Ser Asn Val Lys Asn Leu Phe Asp Glu Val Lys Arg Arg Leu Ser Ala
            115                 120                 125
```

Asn Ala Ile Asp Ala Gly Asn Gly Cys Phe Asp Ile Leu His Lys Cys
            130                 135                 140

Asp Asn Glu Cys Met Glu Thr Ile Lys Asn Gly Thr Tyr Asp His Lys
145                 150                 155                 160

Glu Tyr Glu Glu Glu Ala Lys Leu Glu Arg Ser Lys Ile Asn Gly Val
                165                 170                 175

Lys Leu Glu Glu
            180

<210> SEQ ID NO 42
<211> LENGTH: 180
<212> TYPE: PRT
<213> ORGANISM: Artificial Sequence
<220> FEATURE:
<223> OTHER INFORMATION: Exemplary influenza A HA2 domain subtype H9
      stem domain

<400> SEQUENCE: 42

Gly Leu Phe Gly Ala Ile Ala Gly Phe Ile Glu Gly Gly Trp Pro Gly
1               5                   10                  15

Leu Val Ala Gly Trp Tyr Gly Phe Gln His Ser Asn Asp Gln Gly Val
                20                  25                  30

Gly Met Ala Ala Asp Lys Gly Ser Thr Gln Lys Ala Ile Asp Lys Ile
            35                  40                  45

Thr Ser Lys Val Asn Asn Ile Ile Asp Lys Met Asn Lys Gln Tyr Glu
50                  55                  60

Val Ile Asp His Glu Phe Asn Glu Leu Glu Ala Arg Leu Asn Met Ile
65                  70                  75                  80

Asn Asn Lys Ile Asp Asp Gln Ile Gln Asp Ile Trp Ala Tyr Asn Ala
                85                  90                  95

Glu Leu Leu Val Leu Leu Glu Asn Gln Lys Thr Leu Asp Glu His Asp
            100                 105                 110

Ala Asn Val Asn Asn Leu Tyr Asn Lys Val Lys Arg Ala Leu Gly Ser
        115                 120                 125

Asn Ala Val Glu Asp Gly Asn Gly Cys Phe Glu Leu Tyr His Lys Cys
            130                 135                 140

Asp Asp Gln Cys Met Glu Thr Ile Arg Asn Gly Thr Tyr Asp Arg Gln
145                 150                 155                 160

Lys Tyr Gln Glu Glu Ser Arg Leu Glu Arg Gln Lys Ile Glu Gly Val
                165                 170                 175

Lys Leu Glu Ser
            180

<210> SEQ ID NO 43
<211> LENGTH: 179
<212> TYPE: PRT
<213> ORGANISM: Artificial Sequence
<220> FEATURE:
<223> OTHER INFORMATION: Exemplary influenza A HA2 domain subtype H10
      stem domain

<400> SEQUENCE: 43

Gly Leu Phe Gly Ala Ile Ala Gly Phe Ile Glu Asn Gly Trp Glu Gly
1               5                   10                  15

Met Val Asp Gly Trp Tyr Gly Phe Arg His Gln Asn Ala Gln Gly Thr
                20                  25                  30

Gly Gln Ala Ala Asp Tyr Lys Ser Thr Gln Ala Ala Ile Asp Gln Ile
            35                  40                  45

Thr Gly Lys Leu Asn Arg Leu Ile Glu Lys Thr Asn Thr Glu Phe Glu
    50                  55                  60

Ser Ile Glu Ser Glu Phe Ser Glu Thr Glu His Gln Ile Gly Asn Val
65                  70                  75                  80

Ile Asn Trp Thr Lys Asp Ser Ile Thr Asp Ile Trp Thr Tyr Asn Ala
                85                  90                  95

Glu Leu Leu Val Ala Met Glu Asn Gln His Thr Ile Asp Met Ala Asp
            100                 105                 110

Ser Glu Met Leu Asn Leu Tyr Glu Arg Val Arg Lys Gln Leu Arg Gln
            115                 120                 125

Asn Ala Glu Glu Asp Gly Lys Gly Cys Phe Glu Ile Tyr His Thr Cys
130                 135                 140

Asp Asp Ser Cys Met Glu Ser Ile Arg Asn Asn Thr Tyr Asp His Ser
145                 150                 155                 160

Gln Tyr Arg Glu Glu Ala Leu Leu Asn Arg Leu Asn Ile Asn Pro Val
                165                 170                 175

Lys Leu Ser

<210> SEQ ID NO 44
<211> LENGTH: 181
<212> TYPE: PRT
<213> ORGANISM: Artificial Sequence
<220> FEATURE:
<223> OTHER INFORMATION: Exemplary influenza A HA2 domain subtype H11
      stem domain

<400> SEQUENCE: 44

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Arg Asp Glu Glu Gly Thr
            20                  25                  30

Gly Ile Ala Ala Asp Lys Glu Ser Thr Gln Lys Ala Ile Asp Gln Ile
        35                  40                  45

Thr Ser Lys Val Asn Asn Ile Val Asp Arg Met Asn Thr Asn Phe Glu
    50                  55                  60

Ser Val Gln His Glu Phe Ser Glu Ile Glu Glu Arg Ile Asn Gln Leu
65                  70                  75                  80

Ser Lys His Val Asp Asp Ser Val Val Asp Ile Trp Ser Tyr Asn Ala
                85                  90                  95

Gln Leu Leu Val Leu Leu Glu Asn Glu Lys Thr Leu Asp Leu His Asp
            100                 105                 110

Ser Asn Val Arg Asn Leu His Glu Lys Val Arg Arg Met Leu Lys Asp
            115                 120                 125

Asn Ala Lys Asp Glu Gly Asn Gly Cys Phe Thr Phe Tyr His Lys Cys
130                 135                 140

Asp Asn Lys Cys Ile Glu Arg Val Arg Asn Gly Thr Tyr Asp His Lys
145                 150                 155                 160

Glu Phe Glu Glu Glu Ser Lys Ile Asn Arg Gln Glu Ile Glu Gly Val
                165                 170                 175

Lys Leu Asp Ser Ser
            180

<210> SEQ ID NO 45
<211> LENGTH: 180
<212> TYPE: PRT
<213> ORGANISM: Artificial Sequence
<220> FEATURE:

<223> OTHER INFORMATION: Exemplary influenza A HA2 domain subtype H12
     stem domain

<400> SEQUENCE: 45

Gly Leu Phe Gly Ala Ile Ala Gly Phe Ile Glu Gly Gly Trp Pro Gly
1               5                   10                  15

Leu Val Ala Gly Trp Tyr Gly Phe Gln His Gln Asn Ala Glu Gly Thr
            20                  25                  30

Gly Ile Ala Ala Asp Arg Asp Ser Thr Gln Arg Ala Ile Asp Asn Met
        35                  40                  45

Gln Asn Lys Leu Asn Asn Val Ile Asp Lys Met Asn Lys Gln Phe Glu
    50                  55                  60

Val Val Asn His Glu Phe Ser Glu Val Glu Ser Arg Ile Asn Met Ile
65                  70                  75                  80

Asn Ser Lys Ile Asp Asp Gln Ile Thr Asp Ile Trp Ala Tyr Asn Ala
                85                  90                  95

Glu Leu Leu Val Leu Leu Glu Asn Gln Lys Thr Leu Asp Glu His Asp
            100                 105                 110

Ala Asn Val Arg Asn Leu His Asp Arg Val Arg Arg Val Leu Arg Glu
        115                 120                 125

Asn Ala Ile Asp Thr Gly Asp Gly Cys Phe Glu Ile Leu His Lys Cys
    130                 135                 140

Asp Asn Asn Cys Met Asp Thr Ile Arg Asn Gly Thr Tyr Asn His Lys
145                 150                 155                 160

Glu Tyr Glu Glu Glu Ser Lys Ile Glu Arg Gln Lys Val Asn Gly Val
                165                 170                 175

Lys Leu Glu Glu
            180

<210> SEQ ID NO 46
<211> LENGTH: 181
<212> TYPE: PRT
<213> ORGANISM: Artificial Sequence
<220> FEATURE:
<223> OTHER INFORMATION: Exemplary influenza A HA2 domain subtype H13
     stem domain

<400> SEQUENCE: 46

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Gln Asn Glu Gln Gly Thr
            20                  25                  30

Gly Ile Ala Ala Asp Lys Glu Ser Thr Gln Lys Ala Ile Asp Gln Ile
        35                  40                  45

Thr Thr Lys Ile Asn Asn Ile Ile Asp Lys Met Asn Gly Asn Tyr Asp
    50                  55                  60

Ser Ile Arg Gly Glu Phe Asn Gln Val Glu Lys Arg Ile Asn Met Leu
65                  70                  75                  80

Ala Asp Arg Ile Asp Asp Ala Val Thr Asp Ile Trp Ser Tyr Asn Ala
                85                  90                  95

Lys Leu Leu Val Leu Leu Glu Asn Asp Lys Thr Leu Asp Met His Asp
            100                 105                 110

Ala Asn Val Lys Asn Leu His Glu Gln Val Arg Arg Glu Leu Lys Asp
        115                 120                 125

Asn Ala Ile Asp Glu Gly Asn Gly Cys Phe Glu Leu Leu His Lys Cys
    130                 135                 140

```
Asn Asp Ser Cys Met Glu Thr Ile Arg Asn Gly Thr Tyr Asp His Thr
145                 150                 155                 160

Glu Tyr Ala Glu Glu

```
                65                  70                  75                  80
Ile Asn Trp Thr Arg Asp Ser Leu Thr Glu Ile Trp Ser Tyr Asn Ala
                    85                  90                  95

Glu Leu Leu Val Ala Met Glu Asn Gln His Thr Ile Asp Leu Ala Asp
                100                 105                 110

Ser Glu Met Asn Lys Leu Tyr Glu Arg Val Arg Gln Leu Arg Glu
                115                 120                 125

Asn Ala Glu Glu Asp Gly Thr Gly Cys Phe Glu Ile Phe His Arg Cys
130                 135                 140

Asp Gln Cys Met Glu Ser Ile Arg Asn Asn Thr Tyr Asn His Thr
145                 150                 155                 160

Glu Tyr Arg Gln Glu Ala Leu Gln Asn Arg Ile Met Ile Asn Pro Val
                165                 170                 175

Lys Leu Ser

<210> SEQ ID NO 49
<211> LENGTH: 181
<212> TYPE: PRT
<213> ORGANISM: Artificial Sequence
<220> FEATURE:
<223> OTHER INFORMATION: Exemplary influenza A HA2 domain subtype H16
      stem domain

<400> SEQUENCE: 49

Gly Leu Phe Gly Ala Ile Ala Gly Phe Ile Glu Gly Gly Trp Pro Gly
1               5                   10                  15

Leu Ile Asn Gly Trp Tyr Gly Phe Gln His Gln Asn Glu Gln

<223> OTHER INFORMATION: Xaa = Gly or Ser

<400> SEQUENCE: 50

Glu Asn Leu Tyr Phe Gln Xaa
1 5

<210> SEQ ID NO 51
<211> LENGTH: 5
<212> TYPE: PRT
<213> ORGANISM: Artificial Sequence
<220> FEATURE:
<223> OTHER INFORMATION: Exemplary influenza A HA2 domain subtype H1
Luminal domain

<400> SEQUENCE: 51

Met Gly Ile Tyr Gln
1 5

<210> SEQ ID NO 52
<211> LENGTH: 5
<212> TYPE: PRT
<213> ORGANISM: Artificial Sequence
<220> FEATURE:
<223> OTHER INFORMATION: Exemplary influenza A HA2 domain subtype H2
Luminal domain

<400> SEQUENCE: 52

Met Gly Val Tyr Gln
1 5

<210> SEQ ID NO 53
<211> LENGTH: 5
<212> TYPE: PRT
<213> ORGANISM: Artificial Sequence
<220> FEATURE:
<223> OTHER INFORMATION: Exemplary influenza A HA2 domain subtype H3
Luminal domain

<400> SEQUENCE: 53

Ser Gly Tyr Lys Asp
1 5

<210> SEQ ID NO 54
<211> LENGTH: 5
<212> TYPE: PRT
<213> ORGANISM: Artificial Sequence
<220> FEATURE:
<223> OTHER INFORMATION: Exemplary influenza A HA2 domain subtype H4
Luminal domain

<400> SEQUENCE: 54

Gln Gly Tyr Lys Asp
1 5

<210> SEQ ID NO 55
<211> LENGTH: 5
<212> TYPE: PRT
<213> ORGANISM: Artificial Sequence
<220> FEATURE:
<223> OTHER INFORMATION: Exemplary influenza A HA2 domain subtype H5
Luminal domain

<400> SEQUENCE: 55

Met Gly Val Tyr Gln
1 5

<210> SEQ ID NO 56

```
<211> LENGTH: 5
<212> TYPE: PRT
<213> ORGANISM: Artificial Sequence
<220> FEATURE:
<223> OTHER INFORMATION: Exemplary influenza A HA2 domain subtype H6
      Luminal domain

<400> SEQUENCE: 56

Leu Gly Val Tyr Gln
1               5

<210> SEQ ID NO 57
<211> LENGTH: 5
<212> TYPE: PRT
<213> ORGANISM: Artificial Sequence
<220> FEATURE:
<223> OTHER INFORMATION: Exemplary influenza A HA2 domain subtype H7
      Luminal domain

<400> SEQUENCE: 57

Ser Gly Tyr Lys Asp
1               5

<210> SEQ ID NO 58
<211> LENGTH: 5
<212> TYPE: PRT
<213> ORGANISM: Artificial Sequence
<220> FEATURE:
<223> OTHER INFORMATION: Exemplary influenza A HA2 domain subtype H8
      Luminal domain

<400> SEQUENCE: 58

Asn Thr Thr Tyr Lys
1               5

<210> SEQ ID NO 59
<211> LENGTH: 5
<212> TYPE: PRT
<213> ORGANISM: Artificial Sequence
<220> FEATURE:
<223> OTHER INFORMATION: Exemplary influenza A HA2 domain subtype H9
      Luminal domain

<400> SEQUENCE: 59

Glu Gly Thr Tyr Lys
1               5

<210> SEQ ID NO 60
<211> LENGTH: 5
<212> TYPE: PRT
<213> ORGANISM: Artificial Sequence
<220> FEATURE:
<223> OTHER INFORMATION: Exemplary influenza A HA2 domain subtype H10
      Luminal domain

<400> SEQUENCE: 60

Ser Gly Tyr Lys Asp
1               5

<210> SEQ ID NO 61
<211> LENGTH: 5
<212> TYPE: PRT
<213> ORGANISM: Artificial Sequence
<220> FEATURE:
<223> OTHER INFORMATION: Exemplary influenza A HA2 domain subtype H11
      Luminal domain

<400> SEQUENCE: 61
```

Gly Asn Val Tyr Lys
1               5

<210> SEQ ID NO 62
<211> LENGTH: 5
<212> TYPE: PRT
<213> ORGANISM: Artificial Sequence
<220> FEATURE:
<223> OTHER INFORMATION: Exemplary influenza A HA2 domain subtype H12
      Luminal domain

<400> SEQUENCE: 62

Asn Ser Thr Tyr Lys
1 5

<210> SEQ ID NO 63
<211> LENGTH: 5
<212> TYPE: PRT
<213> ORGANISM: Artificial Sequence
<220> FEATURE:
<223> OTHER INFORMATION: Exemplary influenza A HA2 domain subtype H13 Luminal domain

<400> SEQUENCE: 63

Asp Asn Val Tyr Lys
1 5

<210> SEQ ID NO 64
<211> LENGTH: 5
<212> TYPE: PRT
<213> ORGANISM: Artificial Sequence
<220> FEATURE:
<223> OTHER INFORMATION: Exemplary influenza A HA2 domain subtype H14 Luminal domain

<400> SEQUENCE: 64

Met Gly Tyr Lys Asp
1 5

<210> SEQ ID NO 65
<211> LENGTH: 5
<212> TYPE: PRT
<213> ORGANISM: Artificial Sequence
<220> FEATURE:
<223> OTHER INFORMATION: Exemplary influenza A HA2 domain subtype H15 Luminal domain

<400> SEQUENCE: 65

Ser Gly Tyr Lys Asp
1 5

<210> SEQ ID NO 66
<211> LENGTH: 5
<212> TYPE: PRT
<213> ORGANISM: Artificial Sequence
<220> FEATURE:
<223> OTHER INFORMATION: Exemplary influenza A HA2 domain subtype H16 Luminal domain

<400> SEQUENCE: 66

Asp Asn Val Tyr Lys
1 5

<210> SEQ ID NO 67
<211> LENGTH: 27
<212> TYPE: PRT
<213> ORGANISM: Artificial Sequence
<220> FEATURE:

<223> OTHER INFORMATION: Exemplary influenza A HA2 domain subtype H2
     Transmembrane domain

<400> SEQUENCE: 67

Ile Leu Ala Ile Tyr Ser Thr Val Ala Ser Ser Leu Val Leu Leu Val
1               5                   10                  15

Ser Leu Gly Ala Ile Ser Phe Trp Met Cys Ser
            20                  25

<210> SEQ ID NO 68
<211> LENGTH: 27
<212> TYPE: PRT
<213> ORGANISM: Artificial Sequence
<220> FEATURE:
<223> OTHER INFORMATION: Exemplary influenza A HA2 domain subtype H2
     Transmembrane domain

<400> SEQUENCE: 68

Ile Leu Ala Ile Tyr Ala Thr Val Ala Gly Ser Leu Ser Leu Ala Ile
1               5                   10                  15

Met Ile Ala Gly Ile Ser Leu Trp Met Cys Ser
            20                  25

<210> SEQ ID NO 69
<211> LENGTH: 27
<212> TYPE: PRT
<213> ORGANISM: Artificial Sequence
<220> FEATURE:
<223> OTHER INFORMATION: Exemplary influenza A HA2 domain subtype H3
     Transmembrane domain

<400> SEQUENCE: 69

Trp Ile Leu Trp Ile Ser Phe Ala Ile Ser Cys Phe Leu Leu Cys Val
1               5                   10                  15

Val Leu Leu Gly Phe Ile Met Trp Ala Cys Gln
            20                  25

<210> SEQ ID NO 70
<211> LENGTH: 27
<212> TYPE: PRT
<213> ORGANISM: Artificial Sequence
<220> FEATURE:
<223> OTHER INFORMATION: Exemplary influenza A HA2 domain subtype H4
     Transmembrane domain

<400> SEQUENCE: 70

Ile Ile Leu Trp Ile Ser Phe Ser Ile Ser Cys Phe Leu Leu Val Ala
1               5                   10                  15

Leu Leu Leu Ala Phe Ile Leu Trp Ala Cys Gln
            20                  25

<210> SEQ ID NO 71
<211> LENGTH: 27
<212> TYPE: PRT
<213> ORGANISM: Artificial Sequence
<220> FEATURE:
<223> OTHER INFORMATION: Exemplary influenza A HA2 domain subtype H5
     Transmembrane domain

<400> SEQUENCE: 71

Ile Leu Ser Ile Tyr Ser Thr Val Ala Ser Ser Leu Ala Leu Ala Ile
1               5                   10                  15

Met Ile Ala Gly Leu Ser Phe Trp Met Cys Ser
            20                  25

<210> SEQ ID NO 72
<211> LENGTH: 27
<212> TYPE: PRT
<213> ORGANISM: Artificial Sequence
<220> FEATURE:
<223> OTHER INFORMATION: Exemplary influenza A HA2 domain subtype H6
Transmembrane domain

<400> SEQUENCE: 72

Ile Leu Ala Ile Tyr Ser Thr Val Ser Ser Ser Leu Val Leu Val Gly
1 5 10 15

Leu Ile Ile Ala Val Gly Leu Trp Met Cys Ser
20 25

<210> SEQ ID NO 73
<211> LENGTH: 27
<212> TYPE: PRT
<213> ORGANISM: Artificial Sequence
<220> FEATURE:
<223> OTHER INFORMATION: Exemplary influenza A HA2 domain subtype H7
Transmembrane domain

<400> SEQUENCE: 73

Val Ile Leu Trp Phe Ser Phe Gly Ala Ser Cys Phe Leu Leu Leu Ala
1 5 10 15

Ile Ala Met Gly Leu Val Phe Ile Cys Val Lys
20 25

<210> SEQ ID NO 74
<211> LENGTH: 27
<212> TYPE: PRT
<213> ORGANISM: Artificial Sequence
<220> FEATURE:
<223> OTHER INFORMATION: Exemplary influenza A HA2 domain subtype H8
Transmembrane domain

<400> SEQUENCE: 74

Ile Leu Ser Ile Tyr Ser Thr Val Ala Ala Ser Leu Cys Leu Ala Ile
1 5 10 15

Leu Ile Ala Gly Gly Leu Ile Leu Gly Met Gln
20 25

<210> SEQ ID NO 75
<211> LENGTH: 27
<212> TYPE: PRT
<213> ORGANISM: Artificial Sequence
<220> FEATURE:
<223> OTHER INFORMATION: Exemplary influenza A HA2 domain subtype H9
Transmembrane domain

<400> SEQUENCE: 75

Ile Leu Thr Ile Tyr Ser Thr Val Ala Ser Ser Leu Val Leu Ala Met
1 5 10 15

Gly Phe Ala Ala Phe Leu Phe Trp Ala Met Ser
20 25

<210> SEQ ID NO 76
<211> LENGTH: 27
<212> TYPE: PRT
<213> ORGANISM: Artificial Sequence
<220> FEATURE:
<223> OTHER INFORMATION: Exemplary influenza A HA2 domain subtype H10
Transmembrane domain

<400> SEQUENCE: 76

-continued

```
Ile Ile Leu Trp Phe Ser Phe Gly Glu Ser Cys Phe Val Leu Leu Ala
1               5                   10                  15

Val Val Met Gly Leu Val Phe Phe Cys Leu Lys
            20                  25

<210> SEQ ID NO 77
<211> LENGTH: 27
<212> TYPE: PRT
<213> ORGANISM: Artificial Sequence
<220> FEATURE:
<223> OTHER INFORMATION: Exemplary influenza A HA2 domain subtype H11
      Transmembrane domain

<400> SEQUENCE: 77

Ile Leu Ser Ile Tyr Ser Cys Ile Ala Ser Ser Leu Val Leu Ala Ala
1               5                   10                  15

Leu Ile Met Gly Phe Met Phe Trp Ala Cys Ser
            20                  25

<210> SEQ ID NO 78
<211> LENGTH: 28
<212> TYPE: PRT
<213> ORGANISM: Artificial Sequence
<220> FEATURE:
<223> OTHER INFORMATION: Exemplary influenza A HA2 domain subtype H12
      Transmembrane domain

<400> SEQUENCE: 78

Ile Leu Ser Ile Tyr Ser Ser Val Ala Ser Ser Leu Val Leu Leu Leu
1               5                   10                  15

Met Ile Ile Gly Gly Phe Ile Phe Gly Cys Gln Asn
            20                  25

<210> SEQ ID NO 79
<211> LENGTH: 28
<212> TYPE: PRT
<213> ORGANISM: Artificial Sequence
<220> FEATURE:
<223> OTHER INFORMATION: Exemplary influenza A HA2 domain subtype H13
      Transmembrane domain

<400> SEQUENCE: 79

Ala Leu Ser Ile Tyr Ser Cys Ile Ala Ser Ser Val Val Leu Val Gly
1               5                   10                  15

Leu Ile Leu Ser Phe Ile Met Trp Ala Cys Ser Ser
            20                  25

<210> SEQ ID NO 80
<211> LENGTH: 27
<212> TYPE: PRT
<213> ORGANISM: Artificial Sequence
<220> FEATURE:
<223> OTHER INFORMATION: Exemplary influenza A HA2 domain subtype H14
      Transmembrane domain

<400> SEQUENCE: 80

Ile Ile Leu Trp Ile Ser Phe Ser Met Ser Cys Phe Val Phe Val Ala
1               5                   10                  15

Leu Ile Leu Gly Phe Val Leu Trp Ala Cys Gln
            20                  25

<210> SEQ ID NO 81
<211> LENGTH: 28
<212> TYPE: PRT
<213> ORGANISM: Artificial Sequence
```

-continued

```
<220> FEATURE:
<223> OTHER INFORMATION: Exemplary influenza A HA2 domain subtype H15
      Transmembrane domain

<400> SEQUENCE: 81

Val Ile Leu Trp Phe Ser Phe Gly Ala Ser Cys Val Met Leu Leu Ala
1               5                   10                  15

Ile Ala Met Gly Leu Ile Phe Met Cys Val Lys Asn
            20                  25

<210> SEQ ID NO 82
<211> LENGTH: 27
<212> TYPE: PRT
<213> ORGANISM: Artificial Sequence
<220> FEATURE:
<223> OTHER INFORMATION: Exemplary influenza A HA2 domain subtype H16
      Transmembrane domain

<400> SEQUENCE: 82

Val Leu Ser Ile Tyr Ser Cys Ile Ala Ser Ser Ile Val Leu Val Gly
1               5                   10                  15

Leu Ile Leu Ala Phe Ile Met Trp Ala Cys Ser
            20                  25

<210> SEQ ID NO 83
<211> LENGTH: 10
<212> TYPE: PRT
<213> ORGANISM: Artificial Sequence
<220> FEATURE:
<223> OTHER INFORMATION: Exemplary influenza A HA2 domain subtype H1
      Cytoplasmic domain

<400> SEQUENCE: 83

Asn Gly Ser Leu Gln Cys Arg Ile Cys Ile
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Exemplary influenza A HA2 domain subtype H2
      Cytoplasmic domain

<400> SEQUENCE: 84

Asn Gly Ser Leu Gln Cys Arg Ile Cys Ile
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Exemplary influenza A HA2 domain subtype H3
      Cytoplasmic domain

<400> SEQUENCE: 85

Arg Gly Asn Ile Arg Cys Asn Ile Cys Ile
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Exemplary influenza A HA2 domain subtype H4
      Cytoplasmic domain
```

```
<400> SEQUENCE: 86

Asn Gly Asn Ile Arg Cys Gln Ile Cys Ile
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Exemplary influenza A HA2 domain subtype H5
      Cytoplasmic domain

<400> SEQUENCE: 87

Asn Gly Ser Leu Gln Cys Arg Ile Cys Ile
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Exemplary influenza A HA2 domain subtype H6
      Cytoplasmic domain

<400> SEQUENCE: 88

Asn Gly Ser Met Gln Cys Arg Ile Cys Ile
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Exemplary influenza A HA2 domain subtype H7
      Cytoplasmic domain

<400> SEQUENCE: 89

Asn Gly Asn Met Arg Cys Thr Ile Cys Ile
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Exemplary influenza A HA2 domain subtype H8
      Cytoplasmic domain

<400> SEQUENCE: 90

Asn Gly Ser Cys Arg Cys Met Phe Cys Ile
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Exemplary influenza A HA2 domain subtype H9
      Cytoplasmic domain

<400> SEQUENCE: 91

Asn Gly Ser Cys Arg Cys Asn Ile Cys Ile
1               5                   10

<210> SEQ ID NO 92
<211> LENGTH: 10
```

```
<212> TYPE: PRT
<213> ORGANISM: Artificial Sequence
<220> FEATURE:
<223> OTHER INFORMATION: Exemplary influenza A HA2 domain subtype H10
      Cytoplasmic domain

<400> SEQUENCE: 92

Asn Gly Asn Met Arg Cys Thr Ile Cys Ile
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Exemplary influenza A HA2 domain subtype H11
      Cytoplasmic domain

<400> SEQUENCE: 93

Asn Gly Ser Cys Arg Cys Thr Ile Cys Ile
1               5                   10

<210> SEQ ID NO 94
<211> LENGTH: 9
<212> TYPE: PRT
<213> ORGANISM: Artificial Sequence
<220> FEATURE:
<223> OTHER INFORMATION: Exemplary influenza A HA2 domain subtype H12
      Cytoplasmic domain

<400> SEQUENCE: 94

Gly Asn Val Arg Cys Thr Phe Cys Ile
1               5

<210> SEQ ID NO 95
<211> LENGTH: 9
<212> TYPE: PRT
<213> ORGANISM: Artificial Sequence
<220> FEATURE:
<223> OTHER INFORMATION: Exemplary influenza A HA2 domain subtype H13
      Cytoplasmic domain

<400> SEQUENCE: 95

Gly Asn Cys Arg Phe Asn Val Cys Ile
1               5

<210> SEQ ID NO 96
<211> LENGTH: 10
<212> TYPE: PRT
<213> ORGANISM: Artificial Sequence
<220> FEATURE:
<223> OTHER INFORMATION: Exemplary influenza A HA2 domain subtype H14
      Cytoplasmic domain

<400> SEQUENCE: 96

Asn Gly Asn Ile Arg Cys Gln Ile Cys Ile
1               5                   10

<210> SEQ ID NO 97
<211> LENGTH: 9
<212> TYPE: PRT
<213> ORGANISM: Artificial Sequence
<220> FEATURE:
<223> OTHER INFORMATION: Exemplary influenza A HA2 domain subtype H15
      Cytoplasmic domain

<400> SEQUENCE: 97

Gly Asn Leu Arg Cys Thr Ile Cys Ile
```

<210> SEQ ID NO 98
<211> LENGTH: 10
<212> TYPE: PRT
<213> ORGANISM: Artificial Sequence
<220> FEATURE:
<223> OTHER INFORMATION: Exemplary influenza A HA2 domain subtype H16
      Cytoplasmic domain

<400> SEQUENCE: 98

Asn Gly Ser Cys Arg Phe Asn Val Cys Ile
1               5                   10

<210> SEQ ID NO 99
<211> LENGTH: 223
<212> TYPE: PRT
<213> ORGANISM: Artificial Sequence
<220> FEATURE:
<223> OTHER INFORMATION: HA2 Domain of Influenza B HA construct variant
      Arg50-Ser277

<400> SEQUENCE: 99

Gly Phe Phe Gly Ala Ile Ala Gly Phe Leu Glu Gly Gly Trp Glu Gly
1               5                   10                  15

Met Ile Ala Gly Trp His Gly Tyr Thr Ser His Gly Ala His Gly Val
                20                  25                  30

Ala Val Ala Ala Asp Leu Lys Ser Thr Gln Glu Ala Ile Asn Lys Ile
            35                  40                  45

Thr Lys Asn Leu Asn Ser Leu Ser Glu Leu Glu Val Lys Asn Leu Gln
50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg Lys Leu Lys Lys Met Leu Gly Pro
        115                 120                 125

Ser Ala Val Glu Ile Gly Asn Gly Cys Phe Glu Thr Lys His Lys Cys
130                 135                 140

Asn Gln Thr Cys Leu Asp Arg Ile Ala Ala Gly Thr Phe Asp Ala Gly
145                 150                 155                 160

Glu Phe Ser Leu Pro Thr Phe Asp Ser Leu Asn Ile Thr Ala Ala Ser
                165                 170                 175

Leu Asn Asp Asp Gly Leu Asp Asn His Thr Ile Leu Leu Tyr Tyr Ser
            180                 185                 190

Thr Ala Ala Ser Ser Leu Ala Val Thr Leu Met Ile Ala Ile Phe Val
        195                 200                 205

Val Tyr Met Val Ser Arg Asp Asn Val Ser Cys Ser Ile Cys Leu
210                 215                 220

<210> SEQ ID NO 100
<211> LENGTH: 23
<212> TYPE: PRT
<213> ORGANISM: Artificial Sequence
<220> FEATURE:
<223> OTHER INFORMATION: 281 turn loop linker

<400> SEQUENCE: 100

```
Ile Thr Pro Asn Gly Ser Ile Pro Asn Asp Lys Pro Phe Gln Asn Val
1               5                   10                  15

Asn Lys Ile Thr Tyr Gly Ala
            20
```

<210> SEQ ID NO 101
<211> LENGTH: 6
<212> TYPE: PRT
<213> ORGANISM: Artificial Sequence
<220> FEATURE:
<223> OTHER INFORMATION: 6xHistag

<400> SEQUENCE: 101

```
His His His His His His
1               5
```

<210> SEQ ID NO 102
<211> LENGTH: 29
<212> TYPE: PRT
<213> ORGANISM: Artificial Sequence
<220> FEATURE:
<223> OTHER INFORMATION: Exemplary foldon domain sequence

<400> SEQUENCE: 102

```
Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu
            20                  25
```

<210> SEQ ID NO 103
<211> LENGTH: 7
<212> TYPE: PRT
<213> ORGANISM: Artificial Sequence
<220> FEATURE:
<223> OTHER INFORMATION: Exemplary thrombin cleavage site

<400> SEQUENCE: 103

```
Leu Val Pro Arg Gly Ser Pro
1               5
```

<210> SEQ ID NO 104
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 104

```
Lys Leu Asn Gly Ser Gly Ile Met Lys Thr Glu Gly Thr Leu Glu Asn
1               5                   10                  15
```

<210> SEQ ID NO 105
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 105

```
Asn Asn Ile Asp Thr
1               5
```

<210> SEQ ID NO 106
<211> LENGTH: 16
<212> TYPE: PRT
<213> ORGANISM: Artificial Sequence

```
<220> FEATURE:
<223> OTHER INFORMATION: Exemplary linker sequence

<400> SEQUENCE: 106

Lys Leu Asn Gly Ser Gly Ile Met Lys Thr Glu Gly Thr Leu Glu Asn
1               5                   10                  15

<210> SEQ ID NO 107
<211> LENGTH: 9
<212> TYPE: PRT
<213> ORGANISM: Artificial Sequence
<220> FEATURE:
<223> OTHER INFORMATION: Conserved NA epitope

<400> SEQUENCE: 107

Ile Leu Arg Thr Gln Glu Ser Glu Cys
1               5
```

INFLUENZA VIRUS VACCINATION REGIMENS

This invention was made with government support under HHSN272201400008C, HHSN266200700010C, AI109946, and AI097092 awarded by the National Institutes of Health. The government has certain rights in the invention.

This application is a national stage entry of International Patent Application No. PCT/US2016/014640, filed Jan. 22, 2016, which claims the benefit of U.S. Provisional Application Nos. 62/107,166, filed Jan. 23, 2015, and 62/215,277, filed Sept. 8, 2015, each of which is incorporated herein by reference in its entirety.

This application incorporates by reference a Sequence Listing submitted with this application as text file entitled "Sequence_Listing_6923-238-228.txt" created on Jan. 20, 2016 and having a size of 126,541 bytes.

1. INTRODUCTION

Provided herein are immunization/vaccination regimens for inducing an immune response (e.g., an antibody response) against influenza virus. In specific aspects, the immunization regimens involve the administration of a chimeric hemagglutinin (HA), a headless HA or another influenza virus stem domain based construct (e.g., the HA stem domain or a fragment thereof) to a subject. In certain aspects, the immunization regimens also involve the administration of an influenza virus neuraminidase immunogen.

2. BACKGROUND

Influenza viruses are enveloped RNA viruses that belong to the family of Orthomyxoviridae (Palese and Shaw (2007) Orthomyxoviridae: The Viruses and Their Replication, 5th ed. Fields' Virology, edited by B. N. Fields, D. M. Knipe and P. M. Howley. Wolters Kluwer Health/Lippincott Williams & Wilkins, Philadelphia, USA, p 1647-1689). The natural host of influenza A viruses are mainly avians, but influenza A viruses (including those of avian origin) also can infect and cause illness in humans and other animal hosts (bats, canines, pigs, horses, sea mammals, and mustelids). For example, the H5N1 avian influenza A virus circulating in Asia has been found in pigs in China and Indonesia and has also expanded its host range to include cats, leopards, and tigers, which generally have not been considered susceptible to influenza A (CIDRAP—Avian Influenza: Agricultural and Wildlife Considerations). The occurrence of influenza virus infections in animals could potentially give rise to human pandemic influenza strains.

Influenza A and B viruses are major human pathogens, causing a respiratory disease that ranges in severity from sub-clinical infection to primary viral pneumonia which can result in death. The clinical effects of infection vary with the virulence of the influenza strain and the exposure, history, age, and immune status of the host. The cumulative morbidity and mortality caused by seasonal influenza is substantial due to the relatively high attack rate. In a normal season, influenza can cause between 3-5 million cases of severe illness and up to 500,000 deaths worldwide (World Health Organization (2003) Influenza: Overview; March 2003). In the United States, influenza viruses infect an estimated 10-15% of the population (Glezen and Couch RB (1978) Interpandemic influenza in the Houston area, 1974-76. N Engl J Med 298: 587-592; Fox et al. (1982) Influenza virus infections in Seattle families, 1975-1979. II. Pattern of infection in invaded households and relation of age and prior antibody to occurrence of infection and related illness. Am J Epidemiol 116: 228-242) and are associated with approximately 30,000 deaths each year (Thompson W W et al. (2003) Mortality Associated with Influenza and Respiratory Syncytial Virus in the United States. JAMA 289: 179-186; Belshe (2007) Translational research on vaccines: influenza as an example. Clin Pharmacol Ther 82: 745-749).

In addition to annual epidemics, influenza viruses are the cause of infrequent pandemics. For example, influenza A viruses can cause pandemics such as those that occurred in 1918, 1957, 1968, and 2009. Due to the lack of pre-formed immunity against the major viral antigen, hemagglutinin (HA), pandemic influenza can affect greater than 50% of the population in a single year and often causes more severe disease than epidemic influenza. A stark example is the pandemic of 1918, in which an estimated 50-100 million people were killed (Johnson and Mueller (2002) Updating the Accounts: Global Mortality of the 1918-1920 "Spanish" Influenza Pandemic Bulletin of the History of Medicine 76: 105-115). Since the emergence of the highly pathogenic avian H5N1 influenza virus in the late 1990s (Claas et al. (1998) Human influenza A H5N1 virus related to a highly pathogenic avian influenza virus. Lancet 351: 472-7), there have been concerns that it may be the next pandemic virus. Further, H7 and H9 strains are candidates for new pandemics since these strains infect humans on occasion.

An effective way to protect against influenza virus infection is through vaccination; however, current vaccination approaches rely on achieving a good match between circulating strains and the isolates included in the vaccine. Such a match is often difficult to attain due to a combination of factors. First, influenza viruses are constantly undergoing change: every 3-5 years the predominant strain of influenza A virus is replaced by a variant that has undergone sufficient antigenic drift to evade existing antibody responses. Isolates to be included in vaccine preparations must therefore be selected each year based on the intensive surveillance efforts of the World Health Organization (WHO) collaborating centers. Second, to allow sufficient time for vaccine manufacture and distribution, strains must be selected approximately six months prior to the initiation of the influenza season. Often, the predictions of the vaccine strain selection committee are inaccurate, resulting in a substantial drop in the efficacy of vaccination.

The possibility of a novel subtype of influenza A virus entering the human population also presents a significant challenge to current vaccination strategies. Since it is impossible to predict what subtype and strain of influenza virus will cause the next pandemic, current, strain-specific approaches cannot be used to prepare a pandemic influenza vaccine in advance of a pandemic. Thus, there is a need for vaccines that cross-protect subjects against different strains and/or subtypes of influenza virus.

3. SUMMARY

In one aspect, provided herein are regimens for immunization/vaccination of a subject (e.g., a human or other animal, such as a pig, horse, cow, dog, cat, and bird) against influenza virus. These immunization/vaccination regimens are designed to elicit highly potent and broadly neutralizing antibodies against the stem domain of an influenza virus hemagglutinin (HA) polypeptide. In specific embodiments, these immunization/vaccination regimens are designed to elicit highly potent and broadly neutralizing antibodies against the stem domain of an influenza virus HA polypeptide and elicit highly potent antibodies against an influenza virus neuraminidase (NA) polypeptide. In a specific embodiment, the immunization/vaccination regimens involve the use of a headless HA, chimeric HA, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). See, e.g., U.S. Pat. Nos. 8,673,314, 9,175,069, and 9,051,359, U.S. Patent Application Publication Nos. 20110027270, 20130129761, 20150297712, 20130209499, 20140328875, 20150335729 and 20150132330, and International Patent Publication Nos. WO 2010/117786, WO 2011/123495, WO 2011/103453, WO 2013/043729 and WO 2014/099931, which are incorporated herein by reference in their entirety, for examples of such constructs. In certain embodiments, the immunization/vaccination regimens involve supplementing a seasonal influenza vaccine with a headless HA, chimeric HA, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system).

In certain embodiments, the immunization/vaccinating regimens also involve the use of an NA immunogen. In some embodiments, the immunization/vaccinating regimens involve supplementing a seasonal influenza vaccine with NA immunogen. In certain embodiments, the immunization/vaccinating regimens involve supplementing a seasonal vaccine with a fragment of NA. In certain embodiments, the immunization/vaccinating regimens involve supplementing a seasonal influenza virus vaccine with an (i) NA immunogen, and (ii) a headless HA, chimeric HA, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system).

In certain embodiments, the immunization/vaccinating regimens involve a combination of (i) a headless HA, a chimeric HA, or another influenza virus stem domain-based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system), and (ii) an NA immunogen.

The headless HA, chimeric HA, another influenza virus stem domain based construct, such as an influenza virus HA stem domain or a fragment of the stem domain of an influenza virus HA (e.g., the long alpha helix e.g., amino acids 76-130 of A/Hong Kong/1/1968, numbered according to the classic H3 subtype numbering system) and/or an NA immunogen may be administered to a subject (e.g., a human or other animal, such as a pig, horse, cow, dog, cat, and bird) in various forms, such as a live influenza viruses, inactivated influenza viruses, virus/viral-like particles ("VLPs"), subunit vaccines, split vaccines, DNA virus, polypeptides, etc. Without being bound by any theory, it is believed that the use of a chimeric HA, headless HA or other HA stem domain based construct breaks the immunodominance of the globular head domain of influenza virus HA and induces a more robust antibody response against the conserved HA stem domain of influenza virus (sometimes referred to herein as the "stalk domain") and, in certain embodiments, the influenza virus NA polypeptide.

In another aspect, provided herein is a method for immunizing against influenza virus in a human subject, comprising (a) administering to the subject a live attenuated influenza virus engineered to express a first chimeric hemagglutinin (HA), wherein the first chimeric HA comprises a first influenza virus HA globular head domain and an influenza virus HA stem domain, wherein the HA globular head domain is heterologous to the HA stem domain; and (b) a certain time after the administration of the live attenuated influenza virus, administering to the subject an inactivated influenza virus comprising a second chimeric HA, wherein the second chimeric HA comprises a second influenza virus HA globular head domain and the HA stem domain, wherein the second globular head domain is heterologous to the HA stem domain, and wherein the first HA globular head domain is different than the second HA globular head domain. In some aspects, the method further comprises administering a neuraminidase immunogen or a vector comprising such a construct concurrently with or within 1 hour of the administration of the live attenuated influenza virus. In some aspects, the method further comprises administering an NA immunogen or a vector comprising such a construct concurrently with or within 1 hour of the administration of the inactivated influenza virus. In some aspects, the first globular head domain comprises one or more antigenic regions from influenza virus NA. In some aspects, the second globular head domain comprises one or more antigenic regions from influenza virus NA.

In another aspect, provided herein is a method for immunizing against influenza virus in a human subject, comprising (a) administering to the subject a chimeric HA, a headless HA or another influenza virus stem domain based construct (e.g., the HA stem domain or a fragment thereof), or an influenza virus hemagglutinin core polypeptide or a vector comprising such a construct; and (b) subsequently administering to the subject an inactivated influenza virus vaccine, which may be supplemented with an NA immunogen(s) or a vector comprising such a construct.

In another aspect, provided herein is a method for immunizing against influenza virus in a human subject, comprising administering to the subject (a) a chimeric HA, a headless HA or another influenza virus stem domain based construct (e.g., the HA stem domain or a fragment thereof), or an influenza virus hemagglutinin core polypeptide or a vector comprising such a construct; and (b) an NA immunogen(s) or a vector comprising such a construct.

In another aspect, provided herein is a method for immunizing against influenza virus in a human subject, comprising administering to the subject (a) an inactivated influenza virus vaccine; and (b) an NA immunogen(s) or a vector comprising such a construct.

In another aspect, provided herein is a method for immunizing against influenza virus in a human subject, comprising (a) administering to the subject a chimeric HA or a vector comprising such a construct; (b) subsequently administering to the subject a first headless HA or a vector comprising such a construct; and (c) subsequently administering to the subject a second headless HA or a vector comprising such a construct, wherein the first headless HA and the second headless HA are the same; wherein the chimeric HA, the first headless HA, and/or the second headless HA is administered to the subject in combination with an NA immunogen(s) or a vector comprising such a construct. In another aspect, provided herein is a method for immunizing against influenza virus in a human subject, comprising (a) administering to the subject a chimeric HA or a vector comprising such a construct; (b) subsequently administering to the subject a first headless HA or a vector comprising such a construct; and (c) subsequently administering to the subject a second headless HA or a vector comprising such a construct, wherein the first headless HA and the second headless HA are different; wherein the chimeric HA, the first headless HA, and/or the second headless HA is administered to the subject in combination with an NA immunogen(s) or a vector comprising such a construct. In certain embodiments, an NA immunogen is administered to a subject using a vector described herein. In certain embodiments, a vector comprising a construct such as, e.g., a chimeric HA, a headless HA, or an NA immunogen, described herein is a vector as described in Section 5.8-Section 5.12.

In another aspect, provided herein is a method for immunizing against influenza virus in a human subject, comprising (a) administering to the subject a first headless HA or a vector comprising such a construct; and (b) subsequently administering to the subject a second headless HA or a vector comprising such a construct, wherein the first headless HA and the second headless HA are the same; and wherein the first headless HA and/or the second headless HA is administered to the subject in combination with an NA immunogen(s) or a vector comprising such a construct. In another aspect, provided herein is a method for immunizing against influenza virus in a human subject, comprising (a) administering to the subject a first headless HA or a vector comprising such a construct; and (b) subsequently administering to the subject a second headless HA or a vector comprising such a construct, wherein the first headless HA and the second headless HA are different or a vector comprising such a construct; wherein the first headless HA and/or the second headless HA is administered to the subject in combination with an NA immunogen(s) or a vector comprising such a construct. In certain embodiments, a vector comprising a construct such as, e.g., a chimeric HA, a headless HA, or an NA immunogen, described herein is a vector as described in Section 5.8-Section 5.12.

In another aspect, provided herein is a method for immunizing against influenza virus in a human subject, comprising: (a) administering to the subject a live attenuated influenza virus engineered to express a first chimeric hemagglutinin (HA), wherein the first chimeric HA comprises a first influenza virus HA globular head domain and an influenza virus HA stem domain polypeptide, wherein the HA globular head domain is heterologous to the HA stem domain; and (b) a certain time after the administration of the live attenuated influenza virus, administering to the subject an inactivated influenza virus comprising a second chimeric HA, wherein the second chimeric HA comprises a second influenza virus HA globular head domain and the HA stem domain polypeptide, wherein the second HA globular head domain is heterologous to the HA stem domain polypeptide, and wherein the first influenza virus HA globular head domain is different than the second influenza virus HA globular head domain. In specific embodiments, the method further comprises administering to the subject a neuraminidase (NA) polypeptide concurrently with or within 1 hour of the administration of the live attenuated influenza virus. In specific embodiments, the method further comprises administering a neuraminidase (NA) polypeptide concurrently with or within 1 hour of the administration of the inactivated influenza virus.

In specific embodiments, the influenza virus HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In specific embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In specific embodiments, the first influenza virus HA globular head domain comprises one or more antigenic peptides from influenza virus neuraminidase (NA). In specific embodiments, the second influenza virus HA globular head domain comprises one or more antigenic peptides from influenza virus NA. In specific embodiments, the antigenic region of NA is ILRTQESEC (SEQ ID NO:107).

Also provided herein is a method for immunizing against influenza virus in a human subject, comprising: (a) administering to the subject a live attenuated influenza virus engineered to express a chimeric HA, wherein the chimeric HA comprises an influenza virus HA globular head domain and an influenza virus HA stem domain polypeptide, wherein the HA globular head domain is heterologous to the HA stem domain polypeptide; and (b) a certain time after the administration of the live attenuated influenza virus, administering to the subject an inactivated virus. In specific embodiments, the method further comprises administering to the subject a neuraminidase (NA) polypeptide concurrently with or within 1 hour of the administration of the live attenuated influenza virus. In specific embodiments, the method further comprises administering a neuraminidase (NA) polypeptide concurrently with or within 1 hour of the administration of the inactivated influenza virus.

In specific embodiments, the influenza virus HA globular head domain consists of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In specific embodiments, the influenza virus HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}terms}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In specific embodiments, the HA globular head domain comprises one or more antigenic peptides from influenza virus neuraminidase (NA). In specific embodiments, the antigenic region of NA is ILRTQESEC (SEQ ID NO:107)

Also provided herein is a method for immunizing against influenza virus in a human subject, comprising: (a) administering to the subject a chimeric HA or a vector comprising such a construct, wherein the chimeric HA comprises an influenza virus HA globular head domain heterologous to the influenza virus HA stem domain polypeptide of the chimeric HA; and (b) administering to the subject an influenza virus neuraminidase polypeptide or a vector comprising such a construct.

In specific embodiments, the influenza virus HA globular head domain consists of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In specific embodiments, the influenza virus HA stem domain comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In another aspect, provided herein is a method for immunizing against influenza virus in a human subject, comprising: (a) administering to the subject a first vaccine formulation comprising an influenza virus neuraminidase polypeptide and a live attenuated influenza virus engineered to express a first chimeric hemagglutinin (HA), wherein the first chimeric HA comprises a first influenza virus HA globular head domain and an influenza virus HA stem domain polypeptide, wherein the first influenza virus HA globular head domain is heterologous to the HA stem domain polypeptide; and (b) a certain time after the administration of the first vaccine formulation, administering to the subject a second vaccine formulation comprising an inactivated influenza virus comprising a second chimeric HA, wherein the second chimeric HA comprises a second influenza virus HA globular head domain and the HA stem domain polypeptide, wherein the second influenza virus HA globular head domain is heterologous to the HA stem domain polypeptide, and wherein the first influenza virus HA globular head domain is different than the second influenza virus HA globular head domain. In certain embodiments, the the second vaccine formulation further comprises an influenza virus neuraminidase polypeptide.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first influenza virus HA globular head domain comprises one or more antigenic peptides from influenza virus neuraminidase (NA). In certain embodiments, the second influenza virus HA globular head domain comprises one or more antigenic peptides from influenza virus NA. In certain embodiments, the antigenic peptide from NA is ILRTQESEC (SEQ ID NO:107).

In certain embodiments, the certain time is about 3 to about 6 months after the administration of the first vaccine formulation.

In another aspect, provided herein is a method for immunizing against influenza virus in a human subject, comprising: (a) administering to the subject a first vaccine formulation comprising a live attenuated influenza virus engineered to express a first chimeric hemagglutinin (HA), wherein the first chimeric HA comprises a first influenza virus HA globular head domain and an influenza virus HA stem domain polypeptide, wherein the first influenza virus HA globular head domain is heterologous to the HA stem domain polypeptide; and (b) a certain time after the administration of the first vaccine formulation, administering to the subject a second vaccine formulation comprising an influenza virus neuraminidase polypeptide and an inactivated influenza virus comprising a second chimeric HA, wherein the second chimeric HA comprises a second influenza virus HA globular head domain and the HA stem domain polypeptide, wherein the second influenza virus HA globular head domain is heterologous to the HA stem domain polypeptide, and wherein the first influenza virus HA globular head domain is different than the second influenza virus HA globular head domain.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first influenza virus HA globular head domain comprises one or more antigenic peptides from influenza virus neuraminidase (NA). In certain embodiments, the second influenza virus HA globular head domain comprises one or more antigenic peptides from influenza virus NA. In certain embodiments, the antigenic peptide from NA is ILRTQESEC (SEQ ID NO:107).

In certain embodiments, the certain time is about 3 to about 6 months after the administration of the first vaccine formulation.

In another aspect, provided herein is a method for immunizing against influenza virus in a human subject, comprising: (a) administering to the subject a first vaccine formulation comprising an influenza virus neuraminidase polypeptide and a live attenuated influenza virus engineered to express a chimeric HA, wherein the chimeric HA comprises an influenza virus HA globular head domain and an influenza virus HA stem domain polypeptide, wherein the influenza virus HA globular head domain is heterologous to the HA stem domain polypeptide; and (b) a certain time after the administration of the first vaccine formulation, administering to the subject a second vaccine formulation comprising an inactivated virus, wherein inactivated virus comprises a stem domain that is of the same subtype or strain as the influenza virus HA stem domain polypeptide.

In certain embodiments, the second vaccine formulation further comprises an influenza virus neuraminidase polypeptide.

In certain embodiments, the HA stem domain polypeptide comprises an HA1 N-terminal stem segment and an HA1 C-terminal stem segment, wherein the HA1 N-terminal stem segment consists of amino acid residues $HA_{N-term}$ through $A_p$ of an influenza virus hemagglutinin HA1 domain, and wherein the HA1 C-terminal stem segment consists of amino acid residues $A_q$ through $HA_{C-term}$ of an influenza virus hemagglutinin HA1 domain, wherein $HA_{N-term}$ is the N-terminal amino acid of a mature HA0 protein lacking a signal peptide, wherein $HA_{C-term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the influenza virus HA globular head domain consists of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the influenza virus HA globular head domain comprises one or more antigenic peptides from influenza virus neuraminidase (NA). In certain embodiments, the antigenic peptide from NA is ILRTQESEC (SEQ ID NO:107).

In certain embodiments, the certain time is about 3 to about 6 months after the administration of the first vaccine formulation.

In another aspect, provided herein is a method for immunizing against influenza virus in a human subject, comprising: (a) administering to the subject a first vaccine formulation comprising a live attenuated influenza virus engineered to express a chimeric HA, wherein the chimeric HA comprises a influenza virus HA globular head domain and an influenza virus HA stem domain polypeptide, wherein the influenza virus HA globular head domain is heterologous to the HA stem domain polypeptide; and (b) a certain time after the administration of the first vaccine formulation, administering to the subject a second vaccine formulation comprising an inactivated virus and an influenza virus neuraminidase polypeptide, wherein inactivated virus comprises a stem domain that is of the same subtype or strain as the influenza virus HA stem domain polypeptide.

In certain embodiments, the HA stem domain polypeptide comprises an HA1 N-terminal stem segment and an HA1 C-terminal stem segment, wherein the HA1 N-terminal stem segment consists of amino acid residues $HA_{N-term}$ through $A_p$ of an influenza virus hemagglutinin HA1 domain, and wherein the HA1 C-terminal stem segment consists of amino acid residues $A_q$ through $HA_{C-term}$ of an influenza virus hemagglutinin HA1 domain, wherein $HA_{N-term}$ is the N-terminal amino acid of a mature HA0 protein lacking a signal peptide, wherein $HA_{C-term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the influenza virus HA globular head domain consists of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the influenza virus HA globular head domain comprises one or more antigenic peptides from influenza virus neuraminidase (NA). In certain embodiments, the antigenic peptide from NA is ILRTQESEC (SEQ ID NO:107).

In certain embodiments, the certain time is about 3 to about 6 months after the administration of the first vaccine formulation.

In another aspect, provided herein is a method for immunizing against influenza virus in a human subject, comprising: (a) administering to the subject a first vaccine formulation comprising an influenza virus neuraminidase polypeptide and a first chimeric hemagglutinin (HA), wherein the first chimeric HA comprises a first influenza virus HA globular head domain and an influenza virus HA stem domain polypeptide, wherein the first influenza virus HA globular head domain is heterologous to the HA stem domain polypeptide; and (b) a certain time after the administration of the first vaccine formulation, administering to the subject a second vaccine formulation comprising a second chimeric HA, wherein the second chimeric HA comprises a second influenza virus HA globular head domain and the HA stem domain polypeptide, wherein the second influenza virus HA globular head domain is heterologous to the HA stem domain polypeptide, and wherein the first influenza virus HA globular head domain is different than the second influenza virus HA globular head domain.

In certain embodiments, the second vaccine formulation further comprises an influenza virus neuraminidase polypeptide.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the second vaccine formulation further comprises an influenza virus neuraminidase polypeptide. In certain embodiments, the first vaccine formulation further comprises an influenza virus neuraminidase polypeptide.

In certain embodiments, the one of the antigenic peptides comprises the amino acid sequence of SEQ ID NO:107.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the certain time is about 3 to about 6 months after the administration of the first vaccine formulation.

In another aspect, provided herein is a method for immunizing against influenza virus in a human subject, comprising (a) administering to the subject a first vaccine formulation comprising a first chimeric hemagglutinin (HA), wherein the first chimeric HA comprises a first influenza virus HA globular head domain and an influenza virus HA stem domain polypeptide, wherein the first influenza virus HA globular head domain is heterologous to the HA stem domain polypeptide; and (b) a certain time after the administration of the first vaccine formulation, administering to the subject a second vaccine formulation comprising an influenza virus neuraminidase polypeptide and a second chimeric HA, wherein the second chimeric HA comprises a second influenza virus HA globular head domain and the HA stem domain polypeptide, wherein the second influenza virus HA globular head domain is heterologous to the HA stem domain polypeptide, and wherein the first influenza virus HA globular head domain is different than the second influenza virus HA globular head domain.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the second vaccine formulation further comprises an influenza virus neuraminidase polypeptide. In certain embodiments, the first vaccine formulation further comprises an influenza virus neuraminidase polypeptide.

In certain embodiments, the one of the antigenic peptides comprises the amino acid sequence of SEQ ID NO:107.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the certain time is about 3 to about 6 months after the administration of the first vaccine formulation.

In another aspect, provided herein is a method for immunizing against influenza virus in a human subject, comprising: (a) administering to the subject a first vaccine formulation comprising a first chimeric hemagglutinin (HA), wherein the first chimeric HA comprises a first influenza virus HA globular head domain and an influenza virus HA stem domain polypeptide, wherein the first influenza virus HA globular head domain is heterologous to the HA stem domain polypeptide, and wherein the first influenza virus HA globular head domain comprises one or more antigenic peptides from influenza virus neuraminidase; and (b) a certain time after the administration of the first vaccine formulation, administering to the subject a second vaccine formulation comprising a second chimeric HA, wherein the second chimeric HA comprises a second influenza virus HA globular head domain and the HA stem domain polypeptide, wherein the second influenza virus HA globular head domain is heterologous to the HA stem domain polypeptide, and wherein the first influenza virus HA globular head domain is different than the second influenza virus HA globular head domain.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the certain time is about 3 to about 6 months after the administration of the first vaccine formulation.

In another aspect, provided herein is a method for immunizing against influenza virus in a human subject, comprising: (a) administering to the subject a first vaccine formulation comprising a first chimeric hemagglutinin (HA), wherein the first chimeric HA comprises a first influenza virus HA globular head domain and an influenza virus HA stem domain polypeptide, wherein the first influenza virus HA globular head domain is heterologous to the HA stem domain; and (b) a certain time after the administration of the first vaccine formulation, administering to the subject a second vaccine formulation comprising a second chimeric HA, wherein the second chimeric HA comprises a second influenza virus HA globular head domain and the HA stem domain polypeptide, wherein the second influenza virus HA globular head domain is heterologous to the HA stem domain polypeptide, and wherein the second influenza virus HA globular head domain comprises one or more antigenic peptides from influenza virus neuraminidase, and wherein the first influenza virus HA globular head domain is different than the second influenza virus HA globular head domain.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the first and second influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the certain time is about 3 to about 6 months after the administration of the first vaccine formulation.

In another aspect, provided herein is a method for immunizing against influenza virus in a human subject, comprising: (a) administering to the subject a first vaccine formulation comprising a chimeric hemagglutinin (HA), wherein the chimeric HA comprises an influenza virus HA globular head domain and an influenza virus HA stem domain polypeptide, wherein the influenza virus HA globular head domain is heterologous to the HA stem domain polypeptide; and (b) a certain time after the administration of the first vaccine formulation, administering to the subject a second vaccine comprising an influenza virus neuraminidase polypeptide.

In certain embodiments, the HA stem domain polypeptide comprises an HA1 N-terminal stem segment and an HA1 C-terminal stem segment, wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the influenza virus HA globular head domains consist of the amino acid residues intervening $A_p$ and $A_q$, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

In certain embodiments, the certain time is about 3 to about 6 months after the administration of the first vaccine formulation.

In another aspect, provided herein is a method for immunizing against influenza virus in a human subject, comprising administering to the subject a vaccine formulation comprising three chimeric HAs, an influenza virus neuraminidase polypeptide from an N1, an influenza virus neuraminidase polypeptide from an N2, and an influenza virus neuraminidase polypeptide from an influenza B virus, wherein the first chimeric HA comprises a stem domain polypeptide from an H1 influenza virus and a first HA globular head domain, the second chimeric HA comprises a stem domain polypeptide from an H3 influenza virus and a second HA globular head domain, and the third chimeric HA comprises a stem domain polypeptide from an influenza B virus and a third HA globular head domain, wherein the first, second and third HA globular head domains are each from a different subtype or strain of influenza virus hemagglutinin, and wherein the HA globular head domain of each chimeric HA is heterologous to the stem domain polypeptide of each chimeric HA.

In another aspect, provided herein is a method for immunizing against influenza virus in a human subject, comprising administering to the subject a vaccine formulation comprises three vectors, an influenza virus neuraminidase polypeptide from an N1, an influenza virus neuraminidase polypeptide from an N2, and an influenza virus neuraminidase polypeptide from an influenza B virus, wherein each vector comprises a chimeric HA, wherein the first vector comprises a first chimeric HA comprising a stem domain polypeptide from an H1 influenza virus and a first HA globular head domain, the second vector comprises a second chimeric HA comprising a stem domain polypeptide from an H3 influenza virus and a second HA globular head domain, and the third vector comprises a third chimeric HA comprising a stem domain polypeptide from an influenza B virus and a third HA globular head domain, wherein the first, second and third HA globular head domains are each from a different subtype or strain of influenza virus hemagglutinin, and wherein the HA globular head domain of each chimeric HA is heterologous to the stem domain polypeptide of each chimeric HA.

In certain embodiments, one or more of the vectors is an influenza virus. In certain embodiments, one or more of the vectors is a Newcastle disease virus, an adeno-associated virus, vesicular stomatitis virus, or an adenovirus. In certain embodiments, each vector is an influenza virus. In certain embodiments, each vector is a Newcastle disease virus, an adeno-associated virus, vesicular stomatitis virus, or an adenovirus.

3.1 Terminology

The terms "about" or "approximate," when used in reference to an amino acid position refer to the particular amino acid position in a sequence or any amino acid that is within five, four, three, two, or one residues of that amino acid position, either in an N-terminal direction or a C-terminal direction. As used herein, the term "about" or "approximately" when used in conjunction with a number refers to any number within 1, 5 or 10% of the referenced number. In certain embodiments, the term "about" encompasses the exact number recited.

The term "amino acid sequence identity" refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide after aligning the sequences and introducing gaps, if necessary, to achieve the maximum percent sequence homology. Sequence homology, including percentages of sequence identity and similarity, may be determined using sequence alignment techniques well-known in the art, preferably computer algorithms designed for this purpose, using the default parameters of said computer algorithms or the software packages containing them. Non-limiting examples of computer algorithms and software packages incorporating such algorithms include the following. The BLAST family of programs exemplify a particular, non-limiting example of a mathematical algorithm utilized for the comparison of two sequences (e.g., Karlin & Altschul, 1990, *Proc. Natl. Acad. Sci. USA* 87:2264-2268 (modified as in Karlin & Altschul, 1993, *Proc. Natl. Acad. Sci. USA* 90:5873-5877), Altschul et al., 1990, *J. Mol. Biol.* 215:403-410, (describing NBLAST and) (BLAST), Altschul et al., 1997, *Nucleic Acids Res.* 25:3389-3402 (describing Gapped BLAST, and PSI-Blast). Another particular example is the algorithm of Myers and Miller (1988 *CABIOS* 4:11-17) which is incorporated into the ALIGN program (version 2.0) and is available as part of the GCG sequence alignment software package. Also particular is the FASTA program (Pearson W. R. and Lipman D. J., *Proc. Nat. Acad. Sci. USA,* 85:2444-2448, 1988), available as part of the Wisconsin Sequence Analysis Package. Additional examples include BESTFIT, which uses the "local homology" algorithm of Smith and Waterman (Advances in Applied Mathematics, 2:482-489, 1981) to find best single region of similarity between two sequences, and which is preferable where the two sequences being compared are dissimilar in length; and GAP, which aligns two sequences by finding a "maximum similarity" according to the algorithm of Neddleman and Wunsch (*J. Mol. Biol.* 48:443-354, 1970), and is preferable where the two sequences are approximately the same length and an alignment is expected over the entire length.

As used herein, the term "core polypeptide", in the context of an influenza virus hemagglutinin, refers to a polypeptide segment that corresponds to a region of an influenza hemagglutinin HA2 polypeptide, i.e., core polypeptides as referred to herein do not comprise an entire influenza hemagglutinin HA2 polypeptide. In a specific embodiment, the term refers to a polypeptide segment that corresponds to a region of the long alpha helix region of an influenza hemagglutinin HA2 polypeptide. See Section 5.3.2, infra, and Section 5.1.1 of International Publication No. WO 2011/103453 and US Application No. 2013/0209499, which are incorporated herein by reference in their entirety, for examples of core polypeptides.

As used herein, the terms "chimeric influenza virus hemagglutinin polypeptide," "chimeric influenza virus HA polypeptide," "chimeric hemagglutinin polypeptide," "chimeric HA," "chimeric hemagglutinin," and "chimeric influenza hemagglutinin polypeptide" refer to an influenza hemagglutinin that comprises an influenza virus hemagglutinin stem domain and an influenza virus hemagglutinin head domain, wherein the influenza virus hemagglutinin head domain is heterologous to the influenza virus hemagglutinin stem domain. See, e.g., Section 5.1, infra, for a discussion of chimeric influenza virus polypeptides. In certain embodiments, the influenza virus hemagglutinin head domain of a chimeric influenza virus hemagglutinin polypeptide is from a different strain or subtype of influenza virus than the influenza virus hemagglutinin stem domain. In certain embodiments, in the context of the chimeric influenza virus hemagglutinin polypeptides described herein, a heterologous influenza virus hemagglutinin head domain refers to an influenza virus hemagglutinin head that is at least 5%, at least 10%, at least 15%, at least 20%, at least 25%, at least 5-10%, at least 10-15%, at least 10-20%, at least 15-20%, or at least 20-25% different from the homologous head (i.e., the head domain that would normally be associated with the stem domain of the chimeric influenza virus hemagglutinin polypeptide). Those of skill in the art will recognize that such a difference can be measured using approaches known in the art and described herein, e.g., comparing sequence identity or sequence homology of the head domains. In certain embodiments, in the context of the chimeric influenza virus hemagglutinin polypeptides described herein, a heterologous influenza virus hemagglutinin head domain refers to an influenza virus hemagglutinin head that, in a hemagglutination inhibition assay, results in antisera with at least 2, at least 3, at least 4, at least 5, or at least 6 times less hemagglutination inhibition titers relative to the hemagglutination inhibition titers of the antisera raised against the homologous heads (i.e., the head domain that would normally be associated with the stem domain of the chimeric influenza virus hemagglutinin polypeptide). Those of skill in the art will recognize that such a difference can be measured using approaches known in the art and described herein (see, e.g., Section 5.19, infra). Exemplary chimeric HA are described herein and in International Publication No. WO 2013/043729, International Publication No. WO 2014/099931, U.S. Publication No. 2014/0328875 and U.S. application Ser. No. 14/345,816, which published as U.S. Patent Publication No. 20150132330, which are incorporated herein by reference in their entirety.

"Conservative substitution" refers to replacement of an amino acid of one class is with another amino acid of the same class. In particular embodiments, a conservative substitution does not alter the structure or function, or both, of a polypeptide. Classes of amino acids for the purposes of conservative substitution include hydrophobic (Met, Ala, Val, Leu, Ile), neutral hydrophilic (Cys, Ser, Thr), acidic (Asp, Glu), basic (Asn, Gln, His, Lys, Arg), conformation disrupters (Gly, Pro) and aromatic (Trp, Tyr, Phe).

As used herein, the term "derivative" in the context of an influenza virus flu HA polypeptide or an NA polypeptide means (i) a polypeptide with 1, 2, 3, 4, or 5 amino acid changes as compared to a wild-type influenza virus flu HA polypeptide or NA polypeptide, respectively, or fragment thereof, for example, a conservative amino acid residue is substituted for one or more of the residues, and/or (ii) a polypeptide that is shorter or longer at the N- and/or C-terminus by 1, 2, 3, 4, 5, 7, or 8 amino acid residues.

As used herein, the terms "disease" and "disorder" are used interchangeably to refer to a condition in a subject. In some embodiments, the condition is a viral infection. In specific embodiments, a term "disease" refers to the pathological state resulting from the presence of the virus in a cell or a subject, or by the invasion of a cell or subject by the virus. In certain embodiments, the condition is a disease in a subject, the severity of which is decreased by inducing an immune response in the subject through the administration of an immunogenic composition.

As used herein, the term "effective amount" in the context of administering a therapy to a subject refers to the amount of a therapy which has a prophylactic and/or therapeutic effect(s). In certain embodiments, an "effective amount" in the context of administration of a therapy to a subject refers to the amount of a therapy which is sufficient to achieve one, two, three, four, or more of the following effects: (i) reduce or ameliorate the severity of an influenza virus infection, disease or symptom associated therewith; (ii) reduce the duration of an influenza virus infection, disease or symptom associated therewith; (iii) prevent the progression of an influenza virus infection, disease or symptom associated therewith; (iv) cause regression of an influenza virus infection, disease or symptom associated therewith; (v) prevent the development or onset of an influenza virus infection, disease or symptom associated therewith; (vi) prevent the recurrence of an influenza virus infection, disease or symptom associated therewith; (vii) reduce or prevent the spread of an influenza virus from one cell to another cell, one tissue to another tissue, or one organ to another organ; (viii) prevent or reduce the spread of an influenza virus from one subject to another subject; (ix) reduce organ failure associated with an influenza virus infection; (x) reduce hospitalization of a subject; (xi) reduce hospitalization length; (xii) increase the survival of a subject with an influenza virus infection or disease associated therewith; (xiii) eliminate an influenza virus infection or disease associated therewith; (xiv) inhibit or reduce influenza virus replication; (xv) inhibit or reduce the entry of an influenza virus into a host cell(s); (xvi) inhibit or reduce replication of the influenza virus genome; (xvii) inhibit or reduce synthesis of influenza virus proteins; (xviii) inhibit or reduce assembly of influenza virus particles; (xix) inhibit or reduce release of influenza virus particles from a host cell(s); (xx) reduce influenza virus titer; and/or (xxi) enhance or improve the prophylactic or therapeutic effect(s) of another therapy.

In certain embodiments, the effective amount does not result in complete protection from an influenza virus disease, but results in a lower titer or reduced number of influenza viruses compared to an untreated subject with an influenza virus infection. In certain embodiments, the effective amount results in a 0.5 fold, 1 fold, 1.5 fold, 2 fold, 3 fold, 4 fold, 5 fold, 6 fold, 7 fold, 8 fold, 9 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject with an influenza virus infection. In some embodiments, the effective amount results in a reduction in titer of influenza virus relative to an untreated subject with an influenza virus infection of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs. Benefits of a reduction in the titer, number or total burden of influenza virus include, but are not limited to, less severe symptoms of the infection, fewer symptoms of the infection and a reduction in the length of the disease associated with the infection.

As used herein, the term "elderly human" refers to a human 65 years or older.

As used herein, the term "flu hemagglutinin polypeptide" and "flu HA polypeptide" refer to (i) the chimeric influenza hemagglutinin (HA) polypeptides disclosed herein; (ii) any of the polypeptides disclosed herein that comprise an influenza virus hemagglutinin head domain, an influenza virus hemagglutinin stem domain or fragment thereof, and/or an influenza virus hemagglutinin core polypeptide; and (iii) any of the polypeptides disclosed herein that comprise an influenza virus hemagglutinin head domain and/or an influenza virus hemagglutinin stem domain or fragment thereof, wherein either the influenza virus hemagglutinin stem domain comprises one or more modified glycosylation sites; the influenza virus hemagglutinin head domain comprises one or more non-naturally occurring glycosylation sites; or both. Flu HA polypeptides include, but are not limited to, chimeric influenza virus hemagglutinin polypeptides, non-chimeric influenza virus hemagglutinin polypeptides, influenza virus hemagglutinin head domain polypeptides and influenza virus hemagglutinin stem domain polypeptides. In a specific embodiment, the flu HA polypeptide is a chimeric influenza virus hemagglutinin polypeptide that comprises either one or more modified glycosylation sites in the influenza virus hemagglutinin stem domain that disrupts glycan binding to the stem domain; an influenza virus hemagglutinin globular head domain comprising one or more non-naturally occurring glycosylation sites; or both. In another embodiment, the flu HA polypeptide is an influenza hemagglutinin polypeptide (of or from any strain, subtype, or type of influenza virus) that comprises one or more modified glycosylation sites in the influenza virus hemagglutinin stem domain that disrupts glycan binding to the stem domain, an influenza virus hemagglutinin globular head domain comprising one or more non-naturally occurring glycosylation sites; or both. See, e.g., Example 11 of International Publication No. WO 2013/043729, which is incorporated herein by reference in its entirety, for such a flu polypeptide. In another embodiment, the flu HA polypeptide is a headless HA.

The term "fragment" in the context of a nucleic acid sequence refers to a nucleotide sequence comprising a portion of consecutive nucleotides from a parent sequence. In a specific embodiment, the term refers to a nucleotide sequence of 5 to 15, 5 to 25, 10 to 30, 15 to 30, 10 to 60, 25 to 100, 150 to 300 or more consecutive nucleotides from a parent sequence. In another embodiment, the term refers to a nucleotide sequence of at least 5, 10, 15, 20, 25, 30, 35, 40, 45, 50, 55, 60, 65, 70, 75, 80, 85, 90, 95, 100, 110, 125, 150, 175, 200, 250, 275, 300, 325, 350, 375, 400, 425, 450 or 475 consecutive nucleotides of a parent sequence. The term "fragment" in the context of an amino acid sequence refers to an amino acid sequence comprising a portion of consecutive amino acid residues from a parent sequence. In a specific embodiment, the term refers to an amino acid sequence of 8 to 15, 10 to 20, 2 to 30, 5 to 30, 10 to 60, 25 to 100, 150 to 300 or more consecutive amino acid residues from a parent sequence. In another embodiment, the term refers to an amino acid sequence of at least 5, 10, 15, 20, 25, 30, 35, 40, 45, 50, 55, 60, 65, 70, 75, 80, 85, 90, 95, 100, 110, 125, 150, 175, or 200 consecutive amino acid residues of a parent sequence.

"HA" and "hemagglutinin" refer to any hemagglutinin known to those of skill in the art. In certain embodiments, the hemagglutinin is influenza hemagglutinin, such as an influenza A hemagglutinin, an influenza B hemagglutinin, or an influenza C hemagglutinin. A typical hemagglutinin comprises domains known to those of skill in the art including a signal peptide (optional herein), a stem domain, a globular head domain, a luminal domain (optional herein), a transmembrane domain (optional herein) and a cytoplasmic domain (optional herein). In certain embodiments, a hemagglutinin consists of a single polypeptide chain, such as HA0. In certain embodiments, a hemagglutinin consists of more than one polypeptide chain in quaternary association, e.g. HA1 and HA2. Those of skill in the art will recognize that an immature HA0 might be cleaved to release a signal peptide (approximately 20 amino acids) yielding a mature hemagglutinin HA0. A hemagglutinin HA0 might be cleaved at another site to yield HA1 polypeptide (approximately 320 amino acids, including the globular head domain and a portion of the stem domain) and HA2 polypeptide (approximately 220 amino acids, including the remainder of the stem domain, a luminal domain, a transmembrane domain and a cytoplasmic domain). In certain embodiments, a hemagglutinin comprises a signal peptide, a transmembrane domain and a cytoplasmic domain. In certain embodiments, a hemagglutinin lacks a signal peptide, i.e. the hemagglutinin is a mature hemagglutinin. In certain embodiments, a hemagglutinin lacks a transmembrane domain or cytoplasmic domain, or both. As used herein, the terms "hemagglutinin" and "HA" encompass hemagglutinin polypeptides that are modified by post-translational processing such as signal peptide cleavage, disulfide bond formation, glycosylation (e.g., N-linked glycosylation), protease cleavage and lipid modification (e.g. S-palmitoylation).

"HA2" refers to a polypeptide domain that corresponds to the HA2 domain of an influenza hemagglutinin polypeptide known to those of skill in the art. In certain embodiments, an HA2 consists of a stem domain, a luminal domain, a transmembrane domain and a cytoplasmic domain (see, e.g., Scheiffle et al., 2007, *EMBO J.* 16(18):5501-5508, the contents of which are incorporated by reference in their entirety). In certain embodiments, an HA2 consists of a stem domain, a luminal domain and a transmembrane domain. In certain embodiments, an HA2 consists of a stem domain and a luminal domain; in such embodiments, the HA2 might be soluble. In certain embodiments, an HA2 consists of a stem domain; in such embodiments, the HA2 might be soluble.

The term "HA1 C-terminal stem segment" refers to a polypeptide segment that corresponds to the carboxy-terminal portion of the stem domain of an influenza hemagglutinin HA1 polypeptide. In certain embodiments, an HA1 C-terminal stem segment consists of amino acid residues corresponding approximately to amino acids Aq through AC term of an HA1 domain. Aq is the cysteine residue in the HA1 C-terminal stem segment that forms or is capable of forming a disulfide bond with a cysteine residue in an HA1 N-terminal stem segment. AC term or otherwise referred to herein as $HA1_{C-term}$ is the C-terminal amino acid of the HA1 domain as recognized by those of skill in the art. Residue Aq is identified in influenza A hemagglutinin polypeptides in FIG. 14. Exemplary HA1 C-terminal stem segments are described herein and in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety. In certain embodiments, an HA1 C-terminal stem segment consists of amino acid residues corresponding approximately to amino acids 277-329 of HA1 from an H3 hemagglutinin (i.e., according to H3 numbering). Note that, in this numbering system, 1 refers to the N-terminal amino acid of the mature HA0 protein, from which the signal peptide has been removed. Those of skill in the art will readily be able to recognize the amino acid residues that correspond to the HA1 C-terminal stem segment of other influenza HA polypeptides, e.g., the amino acid residues that correspond to the HA1 C-terminal stem segment of HA1 from an H1 hemagglutinin (see, e.g., FIG. 14).

"HA1 C-terminal long stem segment" refers to a polypeptide segment that corresponds to the carboxyl-terminal portion of the stem domain of an influenza hemagglutinin HA1 polypeptide. In certain embodiments, an HA1 C-terminal long stem segment consists of amino acid residues corresponding approximately to amino acids $C_q$ through $HA1_{C-term}$ of an HA1 domain. $C_q$ is an alanine residue in the HA1 C-terminal long stem segment that is or is capable of being linked to a cysteine residue in an HA1 N-terminal long stem segment. Residue $C_q$ is identified in influenza A hemagglutinin polypeptides in FIG. 14. Exemplary HA1 C-terminal long stem segments are described herein and in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety. In certain embodiments, an HA1 C-terminal long stem segment consists of amino acid residues corresponding approximately to amino acids 253-329 of HA1 from an H3 hemagglutinin (i.e., according to H3 numbering). Note that, in this numbering system, 1 refers to the N-terminal amino acid of the mature HA0 protein, from which the signal peptide has been removed.

"HA1 C-terminal short stem segment" refers to a polypeptide segment that corresponds to the carboxyl-terminal portion of the stem domain of an influenza hemagglutinin HA1 polypeptide. In certain embodiments, an HA1 C-terminal short stem segment consists of amino acid residues corresponding approximately to amino acids $B_q$ through $HA1_{C-term}$ of an HA1 domain. Residue $B_q$ is identified in influenza A hemagglutinin polypeptides in FIG. 14. Exemplary HA1 C-terminal short stem segments are described herein. In certain embodiments, an HA1 C-terminal short stem segment consists of amino acid residues corresponding approximately to amino acids 305-329 of HA1 from an H3 hemagglutinin (i.e., according to H3 numbering). Note that, in this numbering system, 1 refers to the N-terminal amino acid of the mature HA0 protein, from which the signal peptide has been removed.

The term "HA1 N-terminal stem segment" refers to a polypeptide segment that corresponds to the amino-terminal portion of the stem domain of an influenza virus hemagglutinin HA1 polypeptide. In certain embodiments, an HA1 N-terminal stem segment consists of amino acid residues corresponding approximately to amino acids AN-term through Ap of an HA1 domain. AN-term otherwise referred to herein as $HA1_{N-term}$ is the N-terminal amino acid of HA1 as recognized by those of skill in the art. $A_p$ is the cysteine residue in the HA1 N-terminal stem segment that forms or is capable of forming a disulfide bond with a cysteine residue in an HA1 C-terminal stem segment. Residue Ap is identified in influenza A hemagglutinin polypeptides in FIG. 14. Exemplary HA1 N-terminal stem segments are described herein or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety. In certain embodiments, an HA1 N-terminal stem segment consists of amino acid residues corresponding approximately to amino acids 1-52 of HA1 from an H3 hemagglutinin (i.e., according to H3 numbering). Note that, in this numbering system, 1 refers to the N-terminal amino acid of the mature HA0 protein, from which the signal peptide has been removed. Those of skill in the art will readily be able to recognize the amino acid residues that correspond to the HA1 N-terminal stem segment of other influenza HA polypeptides, e.g., the amino acid residues that correspond to the HA1 N-terminal stem segment of HA1 from an H1 hemagglutinin (see, e.g., FIG. 14).

"HA1 N-terminal long stem segment" refers to a polypeptide segment that corresponds to the amino-terminal portion of the stem domain of an influenza hemagglutinin HA1 polypeptide. In certain embodiments, an HA1 N-terminal long stem segment consists of amino acid residues corresponding approximately to amino acids $HA1_{N-term}$ through $c_p$ of an HA1 domain. $C_p$ is a cysteine residue in the HA1 N-terminal long stem segment that is or is capable of being linked to an alanine residue in an HA1 C-terminal long stem segment. Residue $C_p$ is identified in influenza A hemagglutinin polypeptides in FIG. 14. Exemplary HA1 N-terminal long stem segments are described herein or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety. In certain embodiments, an HA1 N-terminal long stem segment consists of amino acid residues corresponding approximately to amino acids 1-97 of HA1 from an H3 hemagglutinin (i.e., according to H3 numbering). Note that, in this numbering system, 1 refers to the N-terminal amino acid of the mature HA0 protein, from which the signal peptide has been removed.

As used herein, the term "heterologous" in the context of a polypeptide, nucleic acid or virus refers to a polypeptide, nucleic acid or virus, respectively, that is not normally found in nature or not normally associated in nature with a polypeptide, nucleic acid or virus of interest. For example, a "heterologous polypeptide" may refer to a polypeptide derived from a different virus, e.g., a different influenza strain or subtype, or an unrelated virus or different species. In specific embodiments, when used in the context of a globular head domain of a chimeric influenza virus hemagglutinin described herein, the term heterologous refers to an influenza HA globular head domain that is associated with an influenza HA stem domain that it would not normally be found associated with (e.g., the head and stem domains of the HA would not be found together in nature). In specific embodiments, the heterologous HA globular head domain has a different amino acid sequence than that found normally associated with the influenza virus HA stem domain. As described above, in certain embodiments, a heterologous influenza HA globular head domain of a chimeric influenza virus hemagglutinin described herein is at least 5%, at least 10%, at least 15%, at least 20%, at least 25%, at least 5-10%, at least 10-15%, at least 10-20%, at least 15-20%, or at least 20-25% different from the homologous head of the hemagglutinin (i.e., the head domain that would normally be associated with the stem domain of the chimeric influenza virus hemagglutinin polypeptide).

As used herein, the term "human infant" refers to a newborn to 1 year old human.

As used herein, the term "human child" refers to a human that is 1 year to 18 years old.

As used herein, the term "human adult" refers to a human that is 18 years or older.

As used herein, the term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, the term "infection" means the invasion by, multiplication and/or presence of a virus in a cell or a subject. In one embodiment, an infection is an "active" infection, i.e., one in which the virus is replicating in a cell or a subject. Such an infection is characterized by the spread of the virus to other cells, tissues, and/or organs, from the cells, tissues, and/or organs initially infected by the virus. An infection may also be a latent infection, i.e., one in which the virus is not replicating. In certain embodiments, an infection refers to the pathological state resulting from the presence of the virus in a cell or a subject, or by the invasion of a cell or subject by the virus.

As used herein, the term "influenza virus disease" refers to the pathological state resulting from the presence of an influenza (e.g., influenza A or B virus) virus in a cell or subject or the invasion of a cell or subject by an influenza virus. In specific embodiments, the term refers to a respiratory illness caused by an influenza virus.

As used herein, the terms "influenza virus hemagglutinin head domain polypeptide," "influenza virus hemagglutinin head domain," "HA globular head domain," and "HA head domain" refer to the globular head domain of an influenza hemagglutinin polypeptide. An influenza virus hemagglutinin head domain polypeptide or influenza virus hemagglutinin head domain may comprise or consist of a known (e.g., wild-type) influenza virus hemagglutinin head domain or may comprise or consist of a derivative, e.g. an engineered derivative, of a known (e.g., wild-type) influenza virus hemagglutinin head domain. Those of skill in the art will recognize that an influenza virus HA globular head domain typically comprises the amino acid residues intervening Cys that corresponds to amino acid position 52 of an influenza virus hemagglutinin HA1 domain of an H3 hemagglutinin (i.e., according to H3 numbering) and Cys that corresponds to amino acid position 277 of an influenza virus hemagglutinin HA1 domain of an H3 hemagglutinin (i.e., according to H3 numbering), e.g., $A_p$ and $A_q$ of FIG. 14, respectively. See Section 5.2, infra, for information regarding influenza virus HA globular head domain polypeptides.

As used herein, the phrases "IFN deficient system" or "IFN-deficient substrate" refer to systems, e.g., cells, cell lines and animals, such as pigs, mice, chickens, turkeys, rabbits, rats, etc., which do not produce interferon (IFN) or produce low levels of IFN (i.e., a reduction in IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to IFN, and/or are deficient in the activity of one or more antiviral genes induced by IFN.

As used herein, the numeric term "log" refers to $\log_{10}$.

As used herein, the term "modified glycosylation site" refers to a naturally-occurring glycosylation site in an influenza virus hemagglutinin polypeptide or neuraminidase polypeptide that has been modified by the addition, substitution or deletion of one or more amino acids. In certain embodiments, the modified glycosylation site is unable to bind glycan. In certain embodiments, the modified glycosylation site disrupts or interferes with the glycosylation at the modified glycosylation site. In certain embodiments, the modified glycosylation site does not interfere with the proper folding of a flu HA polypeptide (e.g., a chimeric influenza virus HA polypeptide) described herein or of a NA polypeptide described herein. In certain embodiments, the modified glycosylation site comprises a modification of a naturally occurring glycosylation site having the amino acid motif Asn-Xaa-Ser/Thr/Cys, wherein Xaa is any amino acid. In particular embodiments, the modified glycosylation site comprises one or more amino acid substitutions in a naturally occurring glycosylation site having the amino acid motif Asn-Xaa-Ser/Thr/Cys, wherein Xaa is any amino acid.

As used herein, the phrase "multiplicity of infection" or "MOI" is the average number of infectious virus particles per infected cell. The MOI is determined by dividing the number of infectious virus particles added (ml added×PFU/ml) by the number of cells added (ml added×cells/ml).

"NA" and "neuraminidase" refer to any neuraminidase known to those of skill in the art. In certain embodiments, the neuraminidase is influenza neuraminidase, such as an influenza A neuraminidase, an influenza B neuraminidase, or an influenza C neuraminidase. A typical neuraminidase comprises domains known to those of skill in the art including a cytoplasmic domain, a transmembrane domain, a stalk domain, and a globular head domain. As used herein, the terms "neuraminidase" and "NA" encompass neuraminidase polypeptides that are modified by post-translational processing such as disulfide bond formation, glycosylation (e.g., N-linked glycosylation), protease cleavage and lipid modification (e.g. S-palmitoylation).

As used herein, the term "non-chimeric influenza virus hemagglutinin polypeptide" refers to an influenza virus hemagglutinin polypeptide comprising an HA stem domain and an HA head domain from the same subtype or strain, and wherein the polypeptide comprises one or more non-naturally occurring glycosylation sites as discussed in Section 5.4.2, infra, and/or one or more modified glycosylation sites as discussed in Section 5.4.1, infra. In certain embodiments, the non-chimeric influenza virus hemagglutinin polypeptide comprises an HA stem domain and HA globular head domain from the same influenza virus subtype. In specific embodiments, the influenza virus subtype is an H1, H2, H3, H4, H5, H6, H7, H8, H9, H10, H11, H12, H13, H14, H15, H16, H17, or H18 subtype. In certain embodiments, the non-chimeric influenza virus hemagglutinin polypeptide comprises an HA stem domain and HA globular head domain from the same influenza virus strain. In certain embodiments, the influenza virus strain is A/Netherlands/602/2009.

As used herein, the term "non-naturally occurring glycosylation site" refers to a glycosylation site that is located at any amino acid positions within a particular globular head domain where a naturally occurring glycosylation site, with respect to a particular HA subtype or strain, is not located. One example of a non-naturally occurring glycosylation site is the addition of a glycosylation site to the globular head domain of an influenza virus hemagglutinin of one subtype, wherein the glycosylation is naturally found in the globular head domain of a hemagglutinin from an influenza virus of another subtype. Another example of a non-naturally occurring glycosylation is the addition of a glycosylation site to the globular head domain of an influenza virus hemagglutinin from one strain, wherein the glycosylation site is naturally found in the globular head of a hemagglutinin from another influenza virus strain. Yet another example of a non-naturally occurring glycosylation site is the addition of a glycosylation site to the globular head domain of an influenza virus hemagglutinin from one strain, wherein the glycosylation site is not naturally found in the globular head of a hemagglutinin from another subtype or strain of influenza virus. In preferred embodiments, the non-naturally occurring glycosylation site has the amino acid motif Asn-Xaa-Ser/Thr/Cys, wherein Xaa is any amino acid, or, in certain embodiments, wherein Xaa is any amino acid except Pro.

As used herein, the term "nucleic acid" is intended to include DNA molecules (e.g., cDNA or genomic DNA) and RNA molecules (e.g., mRNA) and analogs of the DNA or RNA generated using nucleotide analogs. The nucleic acid can be single-stranded or double-stranded.

"Polypeptide" refers to a polymer of amino acids linked by amide bonds as is known to those of skill in the art. As used herein, the term can refer to a single polypeptide chain linked by covalent amide bonds. The term can also refer to multiple polypeptide chains associated by non-covalent interactions such as ionic contacts, hydrogen bonds, Van der Waals contacts and hydrophobic contacts. Those of skill in the art will recognize that the term includes polypeptides that have been modified, for example by post-translational processing such as signal peptide cleavage, disulfide bond formation, glycosylation (e.g., N-linked glycosylation), protease cleavage and lipid modification (e.g. S-palmitoylation).

As used herein, the term "premature human infant" refers to a human infant born at less than 37 weeks of gestational age.

As used herein, the terms "prevent," "preventing" and "prevention" in the context of the administration of a therapy(ies) to a subject to prevent an influenza virus disease refer to one or more of the prophylactic/beneficial effects resulting from the administration of a therapy or a combination of therapies. In a specific embodiment, the terms "prevent," "preventing" and "prevention" in the context of the administration of a therapy(ies) to a subject to prevent an influenza virus disease refer to one or more of the following effects resulting from the administration of a therapy or a combination of therapies: (i) the inhibition of the development or onset of an influenza virus disease or a symptom thereof; (ii) the inhibition of the recurrence of an influenza virus disease or a symptom associated therewith; and (iii) the reduction or inhibition in influenza virus infection and/or replication.

As used herein, the terms "purified" and "isolated" when used in the context of a polypeptide (including an antibody) that is obtained from a natural source, e.g., cells, refers to a polypeptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%, 5%, 2%, or 1% (by dry weight) of cellular materials and/or contaminating materials. As used herein, the terms "purified" and "isolated" when used in the context of a polypeptide (including an antibody) that is chemically synthesized refers to a polypeptide which is substantially free of chemical precursors or other chemicals which are involved in the syntheses of the polypeptide. In a specific embodiment, a flu HA polypeptide (e.g., an influenza hemagglutinin stem domain polypeptide, an influenza hemagglutinin head domain polypeptide, a chimeric influenza hemagglutinin polypeptide and/or a non-chimeric influenza hemagglutinin polypeptide) is chemically synthesized. In another specific embodiment, an influenza hemagglutinin stem domain polypeptide, an influenza hemagglutinin head domain polypeptide, non-chimeric HA polypeptide, and/or a chimeric influenza hemagglutinin polypeptide is isolated.

As used herein, the terms "replication," "viral replication" and "virus replication" in the context of a virus refer to one or more, or all, of the stages of a viral life cycle which result in the propagation of virus. The steps of a viral life cycle include, but are not limited to, virus attachment to the host cell surface, penetration or entry of the host cell (e.g., through receptor mediated endocytosis or membrane fusion), uncoating (the process whereby the viral capsid is removed and degraded by viral enzymes or host enzymes thus releasing the viral genomic nucleic acid), genome replication, synthesis of viral messenger RNA (mRNA), viral protein synthesis, and assembly of viral ribonucleoprotein complexes for genome replication, assembly of virus particles, post-translational modification of the viral proteins, and release from the host cell by lysis or budding and acquisition of a phospholipid envelope which contains embedded viral glycoproteins. In some embodiments, the terms "replication," "viral replication" and "virus replication" refer to the replication of the viral genome. In other embodiments, the terms "replication," "viral replication" and "virus replication" refer to the synthesis of viral proteins.

As used herein, the terms "stem domain polypeptide" and "influenza virus hemagglutinin stem domain polypeptide" refer to a derivative, e.g. an engineered derivative, of a hemagglutinin polypeptide that comprises one or more polypeptide chains that make up a stem domain of hemagglutinin. A stem domain polypeptide might be a single polypeptide chain, two polypeptide chains or more polypeptide chains. Typically, a stem domain polypeptide is a single polypeptide chain (i.e. corresponding to the stem domain of a hemagglutinin HA0 polypeptide) or two polypeptide chains (i.e. corresponding to the stem domain of a hemagglutinin HA1 polypeptide in association with a hemagglutinin HA2 polypeptide). In certain embodiments, a stem domain polypeptide is derived from an influenza hemagglutinin. In specific embodiments, a stem domain polypeptide is derived from an H1 or H3 influenza virus hemagglutinin. Engineered stem domain polypeptides can comprise one or more linkers as described below. See Section 5.3.1, infra, for information regarding influenza virus HA stem domain polypeptides.

Those of skill in the art will recognize that an influenza virus HA stem domain typically comprises an HA1 N-terminal stem segment and an HA1 C-terminal stem segment, wherein the HA1 N-terminal stem segment consists of amino acid residues $HA_{N-term}$ through $A_p$ of an influenza virus hemagglutinin HA1L domain, and wherein the HA1L C-terminal stem segment consists of amino acid residues $A_q$ through $HA_{C-term}$ of an influenza virus hemagglutinin HA1 domain, wherein $HA_{N-term}$ is the N-terminal amino acid of a mature HA0 protein lacking a signal peptide, wherein $HA_{C-term}$ is the C-terminal amino acid of the HA1 domain, wherein $A_p$ is Cys that corresponds to amino acid position 52 of an influenza virus hemagglutinin HA1L domain according to H3 numbering, and wherein $A_q$ is Cys that corresponds to amino acid position 277 of an influenza virus hemagglutinin HA1L domain of an H3 hemagglutinin according to H3 numbering.

As used herein, terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g., a monkey, chimpanzee, and a human). In certain embodiments, a subject is a non-human animal. In some embodiments, a subject is a farm animal or pet. In another embodiment, a subject is a human. In another embodiment, a subject is a human infant. In another embodiment, a subject is a human child. In another embodiment, a subject is a human adult. In another embodiment, a subject is an elderly human. In another embodiment, a subject is a premature human infant.

As used herein, the term "seasonal influenza virus strain" refers to a strain of influenza virus to which a subject population is exposed to on a seasonal basis. In specific embodiments, the term seasonal influenza virus strain refers to a strain of influenza A virus. In specific embodiments, the term seasonal influenza virus strain refers to a strain of influenza virus that belongs to the H1 or the H3 subtype, i.e., the two subtypes that presently persist in the human subject population. In other embodiments, the term seasonal influenza virus strain refers to a strain of influenza B virus.

The terms "tertiary structure" and "quaternary structure" have the meanings understood by those of skill in the art. Tertiary structure refers to the three-dimensional structure of a single polypeptide chain. Quaternary structure refers to the three dimensional structure of a polypeptide having multiple polypeptide chains.

As used herein, the terms "therapies" and "therapy" can refer to any protocol(s), method(s), compound(s), composition(s), formulation(s), and/or agent(s) that can be used in the prevention or treatment of a viral infection or a disease or symptom associated therewith. In certain embodiments, the terms "therapies" and "therapy" refer to biological therapy, supportive therapy, and/or other therapies useful in treatment or prevention of a viral infection or a disease or symptom associated therewith known to one of skill in the art. In some embodiments, the term "therapy" refers to (i) a nucleic acid encoding a flu HA polypeptide (e.g., an chimeric influenza virus hemagglutinin polypeptide), (ii) a flu HA polypeptide (e.g., chimeric influenza virus hemagglutinin polypeptide), (iii) a vector or composition comprising a nucleic acid encoding a flu HA polypeptide (e.g., chimeric influenza virus hemagglutinin polypeptide) or comprising a flu HA polypeptide, (iv) a nucleic acid encoding an NA immunogen, (v) an NA immunogen, or (vi) a vector or composition comprising a nucleic acid encoding an NA immunogen or comprising an NA immunogen. In some embodiments, the term "therapy" refers to an antibody that specifically binds to a chimeric influenza virus hemagglutinin polypeptide.

As used herein, the terms "treat," "treatment," and "treating" refer in the context of administration of a therapy(ies) to a subject to treat an influenza virus disease or infection to obtain a beneficial or therapeutic effect of a therapy or a combination of therapies. In specific embodiments, such terms refer to one, two, three, four, five or more of the following effects resulting from the administration of a therapy or a combination of therapies: (i) the reduction or amelioration of the severity of an influenza virus infection or a disease or a symptom associated therewith; (ii) the reduction in the duration of an influenza virus infection or a disease or a symptom associated therewith; (iii) the regression of an influenza virus infection or a disease or a symptom associated therewith; (iv) the reduction of the titer of an influenza virus; (v) the reduction in organ failure associated with an influenza virus infection or a disease associated therewith; (vi) the reduction in hospitalization of a subject; (vii) the reduction in hospitalization length; (viii) the increase in the survival of a subject; (ix) the elimination of an influenza virus infection or a disease or symptom associated therewith; (x) the inhibition of the progression of an influenza virus infection or a disease or a symptom associated therewith; (xi) the prevention of the spread of an influenza virus from a cell, tissue, organ or subject to another cell, tissue, organ or subject; (xii) the inhibition or reduction in the entry of an influenza virus into a host cell(s); (xiii) the inhibition or reduction in the replication of an influenza virus genome; (xiv) the inhibition or reduction in the synthesis of influenza virus proteins; (xv) the inhibition or reduction in the release of influenza virus particles from a host cell(s); and/or (xvi) the enhancement or improvement the therapeutic effect of another therapy.

As used herein, in some embodiments, the phrase "wild-type" in the context of a viral polypeptide refers to a viral polypeptide that is found in nature and is associated with a naturally occurring virus.

As used herein, in some embodiments, the phrase "wild-type" in the context of a virus refers to the types of a virus that are prevalent, circulating naturally and producing typical outbreaks of disease. In other embodiments, the term "wild-type" in the context of a virus refers to a parental virus.

4. BRIEF DESCRIPTION OF THE DRAWINGS

FIG. 1. Vaccination with recombinant N1 protects mice from homologous and heterologous viral challenge. FIG. 1A, FIG. 1B, and FIG. 1C: 6-8 week old naive BALB/c mice (n=5 for all experimental groups, except in FIG. 1A, FIG. 1B, and FIG. 1C, in which n=10 for BSA and positive control groups, and FIG. 3D, in which n=10 for N2 IM and IN only groups) were primed and boosted with 10 μg rNA from PR8 (5 μg delivered IM, 5 μg delivered IN) adjuvanted with polyI:C. Negative control mice were primed and boosted with 10 μg BSA (5 delivered IM, 5 μg delivered IN) adjuvanted with polyI:C. Positive control mice received a 1 μg IM prime and boost of a formalin-inactivated, unadjuvanted virus matching the challenge strain. Additionally, one experimental group was primed and boosted with rN2 in an identical fashion to the N1-vaccinated mice. Upon challenge weight loss was monitored for 14 days post infection as a measure of morbidity. Graphs plot the average weight loss as percentage of initial weight with standard errors of the means (SEM). FIG. 1D, FIG. 1E, and FIG. 1F: Survival curves corresponding to the above challenge experiments. FIG. 1G, FIG. 1H, and FIG. 1I: Pooled sera from individual mice (PR8 N1 vaccinated, rN2 vaccinated or naive) in each experimental group were tested in triplicate for reactivity to purified virus via ELISA. FIG. 1J, FIG. 1K, and FIG. 1L: The same sera from FIG. 1G, FIG. 1H, and FIG. 1I was tested in triplicate for NI activity against the respective challenge viruses. *Positive control data shown in FIG. 1C and FIG. 1F was collected from the high challenge dose group (10 mLD50).

FIG. 2. Vaccination with recombinant N2 protects mice from homologous and heterologous viral challenge. The experimental design for these challenge studies was identical to that detailed in FIG. 1, except mice were primed and boosted with rNA from HK68 (H3N2) and challenged with homologous H3N2 re-assortant strain HK68/X-31 or the heterologous H3N2 strain Phil82/X-79. Control mice were primed and boosted with rNA from PR8 or BSA. Weight loss and survival of mice challenged with HK68/X-31 (FIG. 2A and FIG. 2C, respectively) or Phil82/X-79 (FIG. 2B and FIG. 2D, respectively). FIG. 2E and FIG. 2F: Pooled sera from individual mice (HK68 N2 vaccinated, rN1 vaccinated or naive) in each experimental group were tested in triplicate for reactivity to purified virus via ELISA. The same sera were tested in triplicate for NI activity against HK68/X-31 (FIG. 2G) and Phil82/X-79 (FIG. 2H).

Figure 4G:
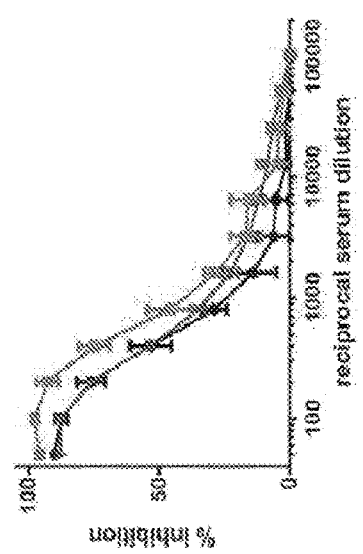
Figure 4H:
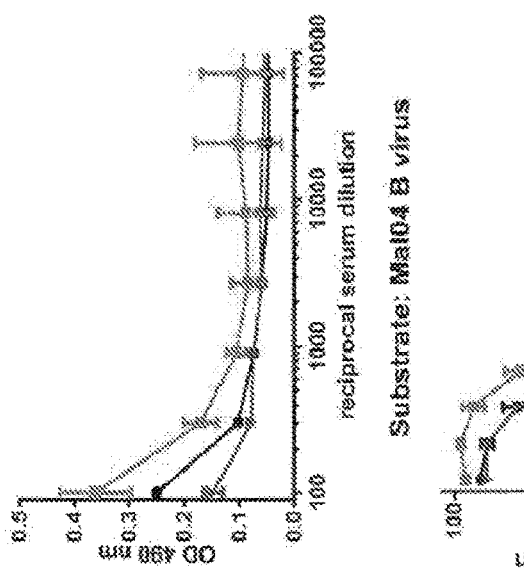
Figure 4I:
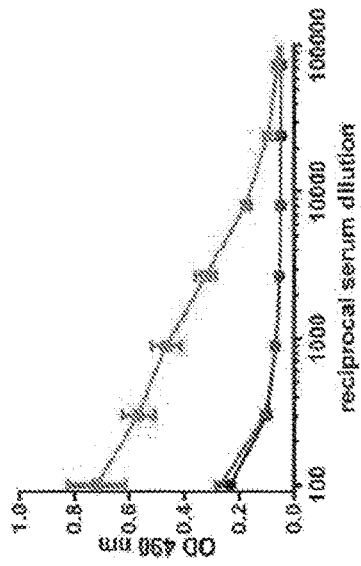
Figure 4J:
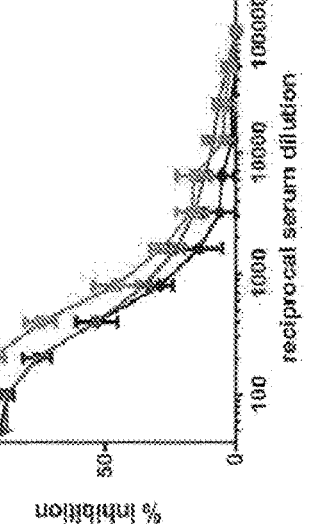
Figure 4K:
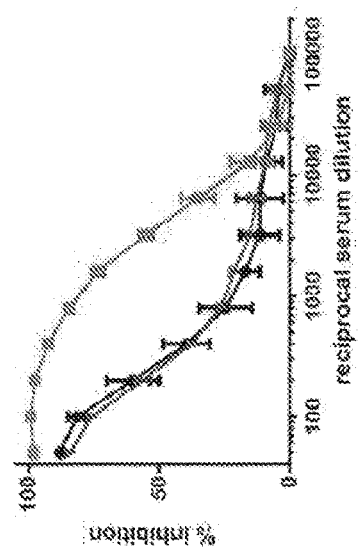
Figure 4L:
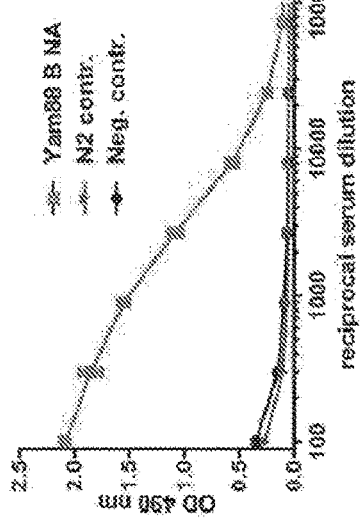

FIG. 3. Passive transfer of sera from vaccinated mice and IM vs. IN vaccination. To demonstrate that humoral immunity against NA is sufficient for protection, passive transfer experiments were performed. Sera from animals vaccinated with HK68 N2, whole inactivated HK68/X-31 virus or BSA was transferred into naive mice, which were subsequently challenged with HK68/X-31 virus. Weight loss post challenge is shown in (FIG. 3A). All mice that received HK68 N2 or the whole inactivated virus vaccine survived the challenge. FIG. 3B: Lung titers of animals vaccinated with HK68 N2, BSA or whole inactivated HK68/X-31 virus on day 3 and day 6 post-challenge with HK68/X-31. FIG. 3C: To assess whether the route of vaccine administration impacted protection, a challenge experiment identical to that in FIG. 2A was performed, except the mice in one group (n=10) were primed and boosted with 10 μg N2 (adjuvanted with polyI:C) exclusively intramuscularly (IM) while those in the other (n=10) were primed and boosted exclusively intranasally (IN). Initially, a difference in weight loss was slight but not very distinguishable. FIG. 3D: However, upon repeating the experiment with a higher challenge dose (25 LD50) a clear difference in weight loss was resolved, with the IN-vaccinated mice displaying significantly less weight loss than the IM-vaccinated mice. Survival was 100% in both groups. FIG. 3E: Reactivity to HK68/X-31 virus was similar for mice that received HK68 N2 via the IM, the IN or both routes at the same time (IM+IN). n.s.=not significant, $p>0.05$; $*=p\leq0.05$; $=p\leq0.01$; $*=p\leq0.001$; $****=p\leq0.0001$ FIG. 4. Vaccination with recombinant B-NA protects mice from homologous and heterologous viral challenge. The experimental design for these challenge studies was identical to that detailed in FIGS. 1 and 2, except mice were primed and boosted with rNA from B Yam88 and challenged with the homologous Yam88 virus or the heterologous influenza B virus strains Vic87 and Ma104. The mice in the N2 control group were primed and boosted with rNA from HK68. Weight loss and survival after homologous challenge with Yam88 (FIG. 4A and FIG. 4D, respectively) or after heterologous challenge with Vic87 (FIG. 4B and FIG. 4E, respectively) or Ma104 (FIG. 4C and FIG. 4F, respectivley). Seroreactivity of Yam88 B NA vaccinated mice to Yam88 (FIG. 4G), Vic87 (FIG. 4H) or Ma104 (FIG. 4I) virus. The same sera from FIG. 4G, FIG. 4H, and FIG. 4I were tested in triplicate for NI activity against the respective challenge viruses (FIG. 4J, FIG. 4K, and FIG. 4L, respectively).

FIG. 5. Vaccination with rNA does not induce heterosubtypic immunity in mice. To test the possibility of NA-induced, heterosubtypic cross-protection, a sizeable challenge study was performed in which mice were separated into groups (n=5) and primed and boosted with representative rNA from subtypes N39. Similar to the study in FIG. 1, animals received identical primes and boosts of 10 μg rNA (5 μg delivered IM, 5 μg delivered IN) adjuvanted with polyI:C. Negative control mice were primed and boosted with 10 μg BSA (5 delivered IM, 5 μg delivered IN) adjuvanted with polyI:C. No reduction in weight loss was observed upon lethal (5 LD50) challenge with (FIG. 5A) PR8 or (FIG. 5B) X-31. FIG. 5C and FIG. 5D: Survival curves corresponding to the above challenge experiments. No appreciable protection from mortality was observed.

FIG. 6. Seasonal IIV vaccination is inefficient at inducing NA reactive antibodies in humans. HA and NA reactivity of human pre- and post vaccination sera from 12 individuals who received the 2004-2005 inactivated seasonal vaccine. FIG. 6A: The geometric mean H1 titer was relatively high at baseline (~1600) and was induced upon vaccination approximately 24-fold (p<0.0001) while (FIG. 6B) the geometric mean N1 baseline titer was low (~200) and did not increase upon vaccination. (FIG. 6C) The geometric mean H3 baseline titer (~800) was lower than that of H1 and vaccination induced a 6.4-fold induction (p=0.0003) while (FIG. 6D) the geometric mean N2 baseline titer was higher than that of N1 and increased 2-fold upon vaccination (p=0.0230). (FIG. 6E) IIV induced significantly higher endpoint titers against HA than against NA for both influenza A subtypes included in the vaccine (p=0.0003 for H1N1; p=0.0240 for H3N2).

Figure 7B:
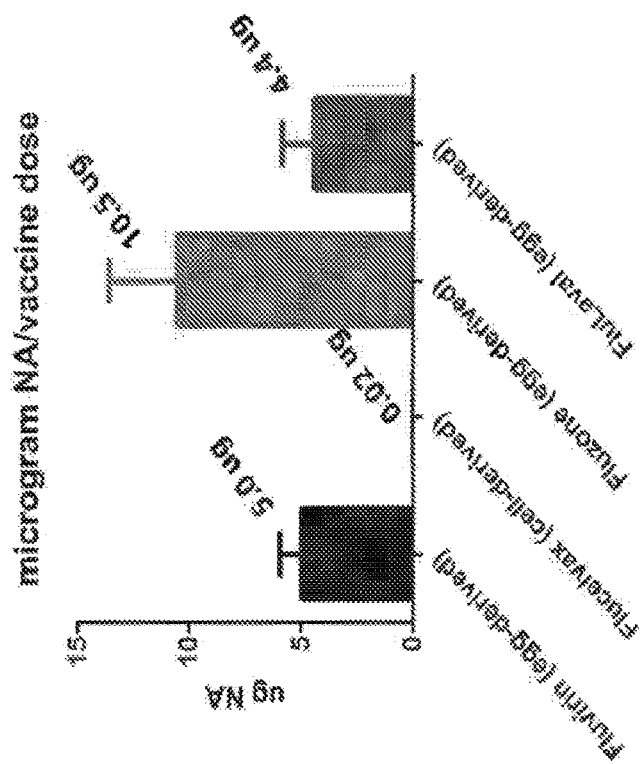
Figure 7A:
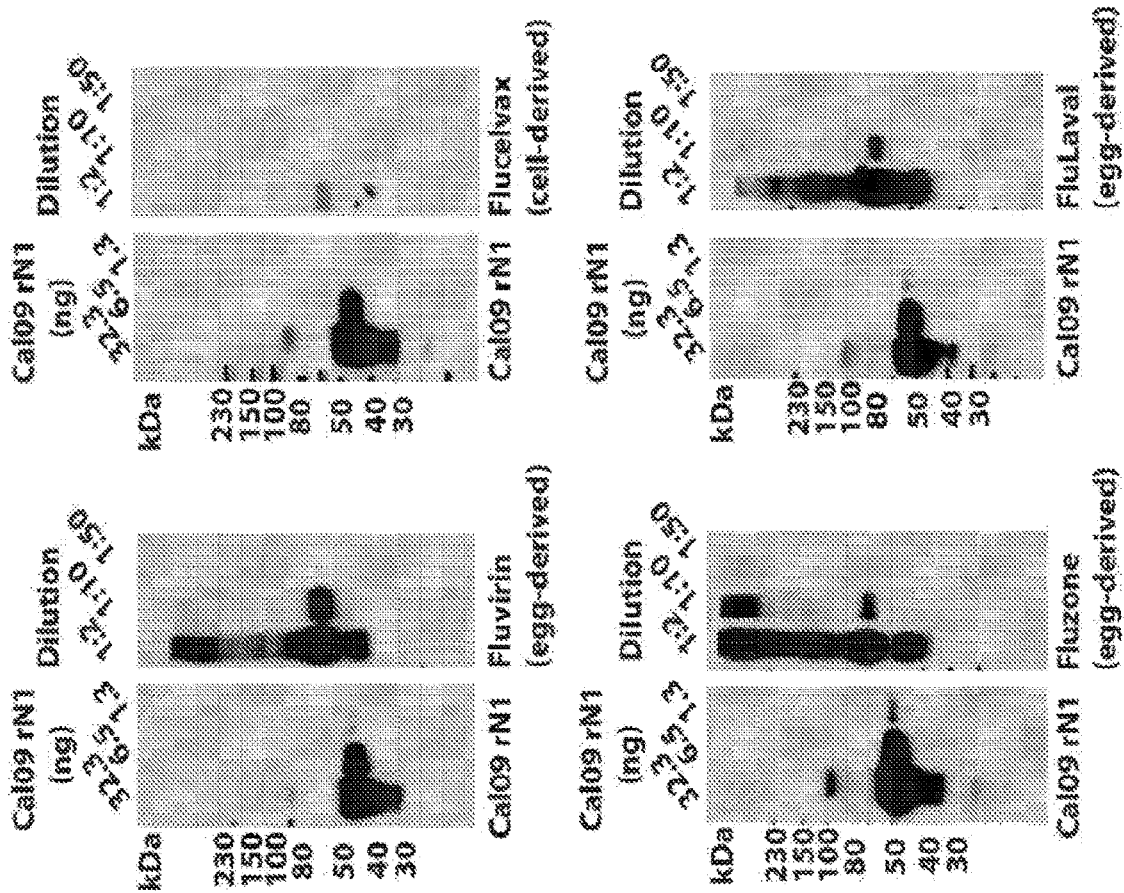

FIG. 7. The amount of Ca109 NA contained in seasonal IIVs from the 2013-2014 influenza season is variable. FIG. 7A: 5 fold serial dilutions of 4 IIVs recommended for the 2013-2014 influenza season were analyzed via Western blot for Ca109 N1 NA content. Membranes were blotted with 4A5 (monoclonal antibody specific for Ca109 NA). Each panel represents a separately run Western blot of a unique vaccine brand. Dilutions of recombinant, baculovirus-expressed Ca109 rN1 (shown on the left blot in every panel) of known concentrations were run alongside every vaccine sample on the same gel. Dilutions of vaccines and amounts of standard are displayed on the top of the gel, and the name of the vaccine is displayed on the bottom, with the company name in parentheses. FIG. 7B: Quantities of N1 NA (in μg) per adult vaccine dose (0.5 mL) as measured by ELISA. Bar graphs show the mean quantification and standard errors of the means (SEM), with mean values displayed above each corresponding bar.

FIG. 8. Strategies to enhance neuraminidase (NA)-based immunity. FIG. 8A depicts that the regular seasonal influenza virus vaccine can produce antibodies against hemagglutinin (HA) and neuraminidase (NA). N1 refers to the NA subtype. H1 refers to the HA subtype. FIG. 8B depicts that, without being bound by any theory, NA-based immunity can be enhanced with influenza virus vaccines comprising neuraminidase and chimeric HA (cHA), allowing for an antibody response against the NA and the HA stalk. FIG. 8C depicts that, without being bound by any theory, NA-based immunity can be enhanced with influenza virus vaccines comprising HA stalk-based constructs, e.g., headless HA, supplemented with NA, allowing for an antibody response against the NA and the HA stalk. FIG. 8D depicts that immunization with NA only allows for anti-NA antibody generation. FIG. 8E depicts that, without being bound by any theory, NA-based immunity can be enhanced with the regular seasonal influenza virus vaccine supplemented with additional NA. Structures are based on PDB#1RU7 (HA) and 3B7E (NA) and were visualized using Protein Workshop (Gamblin et al., 2004, Science, 202:1838-1842; Xu et al., 2008, J Virol, 82:10493-10501).

Figure 9:
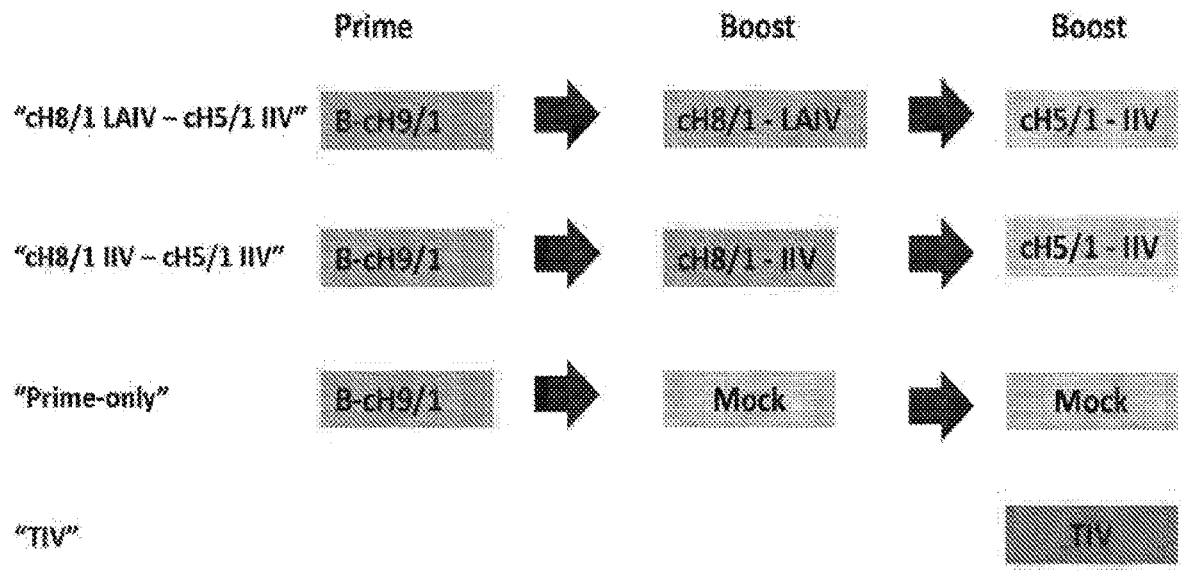

FIG. 9. Ferret vaccination schemes. In the "cH8/1 LAIV-cH5/1 IIV" vaccination scheme, ferrets are primed with an influenza B virus expressing cH9/1 (B-cH9/1), boosted with a LAIV expressing cH8/1 (cH8/1-LAIV), and boosted with an IIV expressing cH5/1 (cH5/1-IIV). In the "cH8/1 IIV-cH5/1 IIV" vaccination scheme, ferrets are primed with B-cH9/1, boosted with an IIV expressing cH8/1 (cH8/1-IIV), and boosted with cH5/1-IIV. In the "prime only" vaccination scheme, ferrets are primed with B-cH9/1 and are mock boosted twice. In the "TIV" vaccination scheme, ferrets are vaccinated with the TIV once. cHX/Y refers to a chimeric HA, wherein X is the HA subtype of the chimeric HA head, and wherein Y is the HA subtype of the chimeric HA stalk. IIV refers to an inactivated influenza virus. LAIV refers to a live attenuated influenza virus. TW refers to a trivalent influenza virus.

Figure 10:
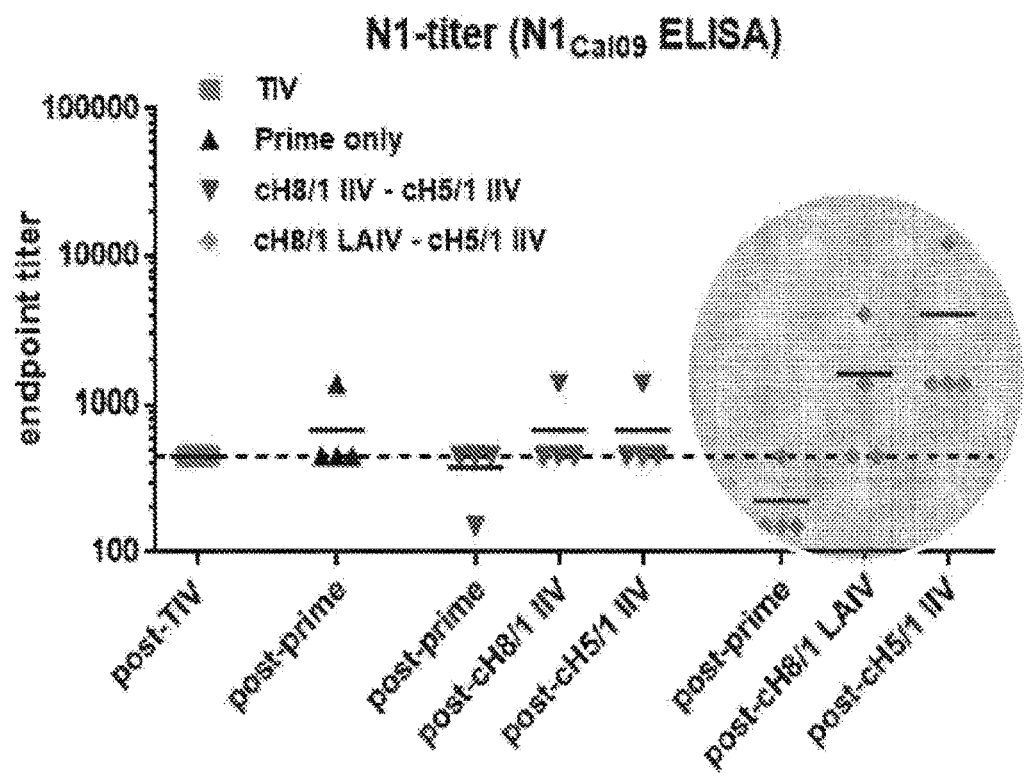

FIG. 10. Induction of anti-N1 antibodies in ferrets vaccinated with chimeric HA constructs as described in FIG. 9. Animals received a prime with an influenza B virus expressing a cH9/1 HA (prime-only, cH8/1 IIV-cH5/1 IIV and cH8/1 LAIV-cH5/1 IIV groups). The cH8/1 IIV-cH5/1 IIV group was then boosted with an inactivated vaccine based on cH8/1Ca109N1Ca109 virus (cH8/1 IIV) and was then boosted again with a cH5/1Ca109N1Ca109 inactivated vaccine (cH5/1 IIV). The cH8/1 LAIV-cH5/1 IIV group was boosted with a live attenuated vaccine based on cH8/1Ca109N1Ca109 virus (cH8/1 LAIV) and was then also boosted again with cH5/1 IIV. Control animals received mock booster vaccination (prime-only group) or were vaccinated with regular trivalent inactivated influenza virus vaccine (TIV group). Anti-N1 titers were then measured after the respective vaccinations via an endpoint titer ELISA.

Figure 11:
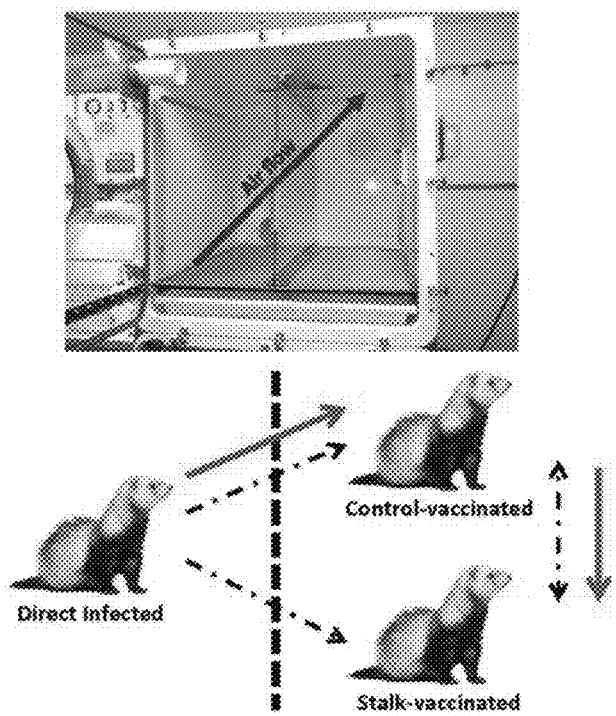

FIG. 11. Experimental model to measure influenza virus transmission in ferrets. Top panel of FIG. 11: Poultry isolation units (Plas-Labs, Lansing, Mich.) that were modified with a perforated plexiglass divider that separates directly infected ferrets from the immunized aerosol contact ferrets. The arrow indicates directional air flow across the plexiglass divider. Bottom panel of FIG. 11: Schematic of the design of the transmission experiment. The direct infected ferret was housed on the left site of the cage separated from the control and stalk vaccinated animals by a perforated divider that allowed for air flow (as indicated by dashed arrows) but prevented direct contact of the animals. One control vaccinated and one stalk vaccinated ferret were co-housed on the right side, a setting that allowed for direct contact transmission between these two ferrets (as indicated by the dashed bidirectional arrow). The most likely infection route for the stalk vaccinated animals in this experiment is indicated by solid arrows.

FIG. 12. Stalk immunization reduced viral titers following infection by aerosol route of transmission. On day 0, a ferret was directly infected by the intranasal route with pandemic H1N1 influenza virus. On day 1 post direct infection, stalk immunized and control immunized ferrets were housed adjacently to the directly infected ferret under conditions that permitted only aerosol transmission to occur between the direct infected and the control or stalk vaccinated animals. However, direct contact transmission was possible between control and stalk vaccinated ferrets. On days 2, 4, 6, 8, and 10 post-infection (days 1, 3, 5, 7, and 9 post-aerosol contact), all ferrets were anesthetized with ketamine and xylazine for collection of nasal wash samples to determine virus titers by plaque assay. FIG. 12A shows nasal wash virus titers of directly infected ferrets, FIG. 12B shows titers of control vaccinated ferrets and FIG. 12C shows the nasal wash titers of stalk vaccinated animals. Horizontal bars indicate average nasal wash titers for the four inoculated animals. Without being bound by any theory, dashed arrows show possible directions of transmission and solid arrows show the most likely direction of transmission. Each specific square represents an individual animal.

Figure 13:
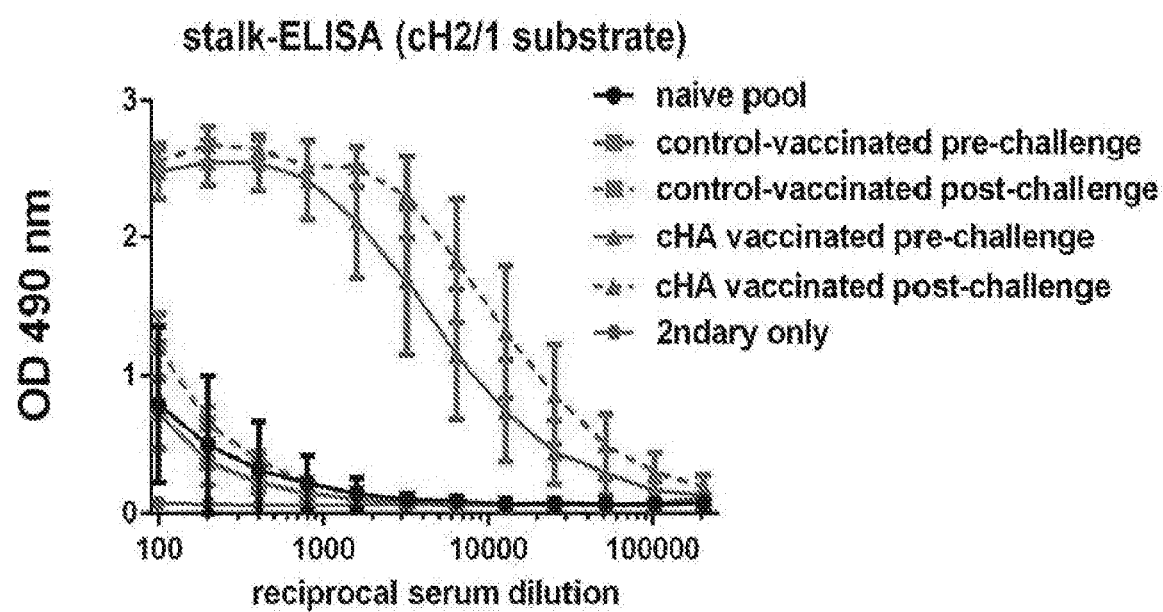

FIG. 13. Induction of H1 stalk-specific antibody responses in ferrets immunized repeatedly immunized with viral vectors expressing cHAs. Ferrets (n=4) were immunized with influenza B virus expressing cH9/1 HA, boosted with VSV-cH5/1 HA, and boosted a second time with an adenovirus 5 vector expressing the cH6/1 protein. Control ferrets (n=4) were immunized with corresponding empty viral vectors. Immunized ferrets were then exposed to ferrets directly infected with pandemic H1N1 under conditions that specifically allowed for aerosol transmission. The development of H1 stalk-reactive antibody responses was assessed by ELISA with baculovirus-produced cH2/1 HA. Enzyme linked immunosorbent assays (ELISA) were performed as described before (See, References 6 and 7 in Section 6.1.5).

FIG. 14. Sequence alignment by CLUSTALW of representative sequences of 17 subtypes of influenza virus A hemagglutinin (SEQ ID NOS:1-17, H1-H17, respectively). The residue designated Ap is the cysteine residue in the HA1 N-terminal stem segment that forms or is capable of forming a disulfide bond with the residue designated Aq, a cysteine residue in an HA1 C-terminal stem segment. The residue designated Bq represents the approximate N-terminal amino acid of the HA1 C-terminal short stem segments described herein. The residue designated Cq represents the approximate N-terminal amino acid of the HA1 C-terminal long stem segments described herein. The residue designated Cp represents the approximate C-terminal amino acid of the HA1 N-terminal long stem segments described herein. Due to size limitations, the sequence alignment is split between FIG. 14A, FIG. 14B, FIG. 14C and FIG. 14D.

Figure 15A:
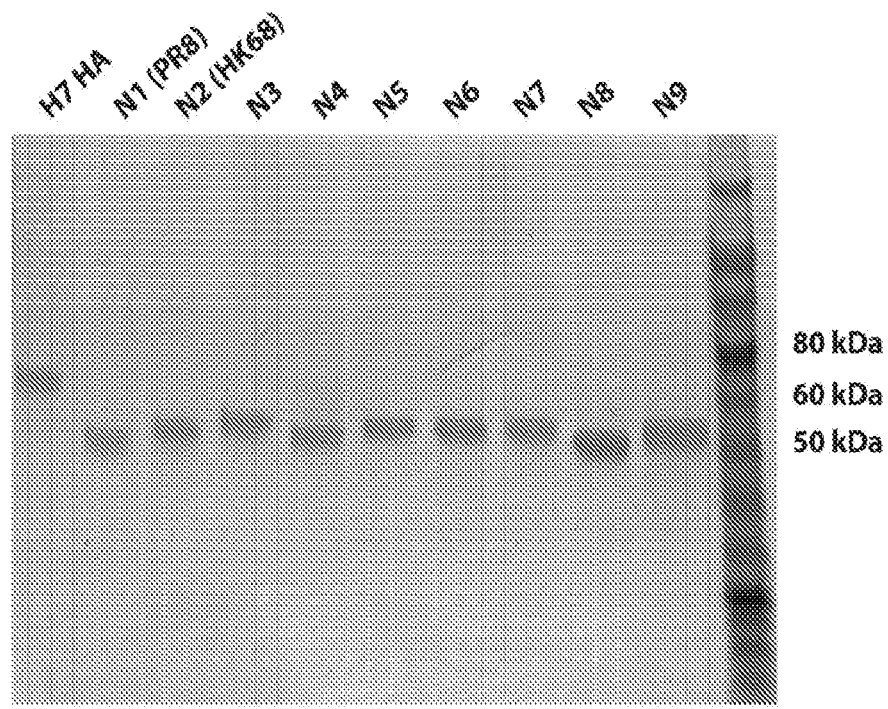
Figure 15B:
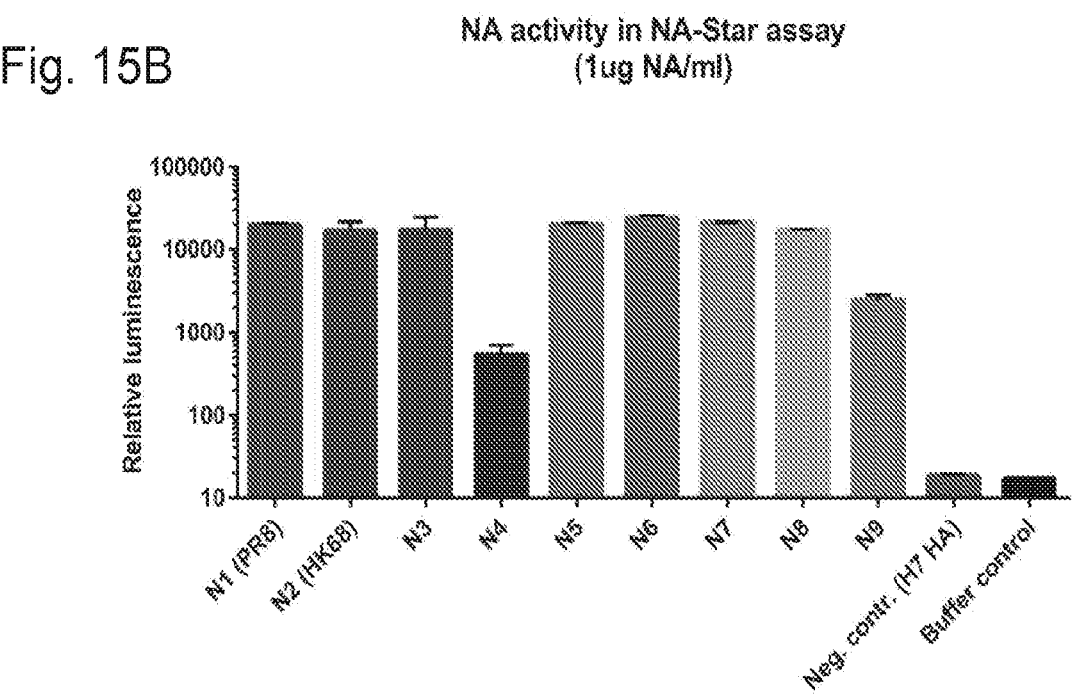

FIG. 15. Characterization of recombinant influenza A NAs. FIG. 15A depicts a Coomassie-stained reducing SDS PAGE that was loaded with approximately 500 ng of N1, N2, N3, N4, N5, N6, N7, N8 and N9 NA and an H7 HA as size control. FIG. 15B depicts the activity of the same NAs at a concentration of 1 ug/ml in an NA*Star assay. H7 HA was included as control.

Figure 16A:
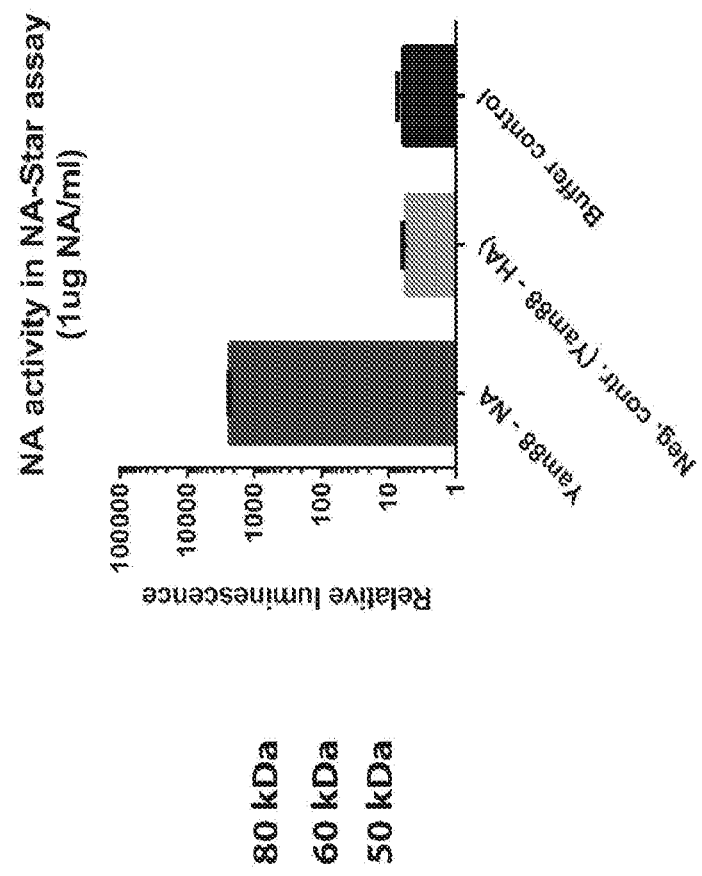
Figure 16B:
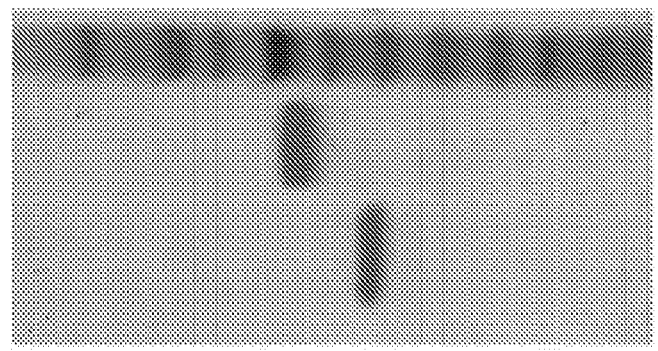

FIG. 16. Characterization of recombinant Influenza B NA. FIG. 16A depicts a Coomassie-stained reducing SDS PAGE with approximately 500 ng Yam88 B NA. Yam88 HA was included as a control for size. FIG. 16B depicts activity of recombinant B NA at 1 ug/ml in an NA*Star assay. Yam88 HA was used as a control.

Figures 17A, 17B, 17C:
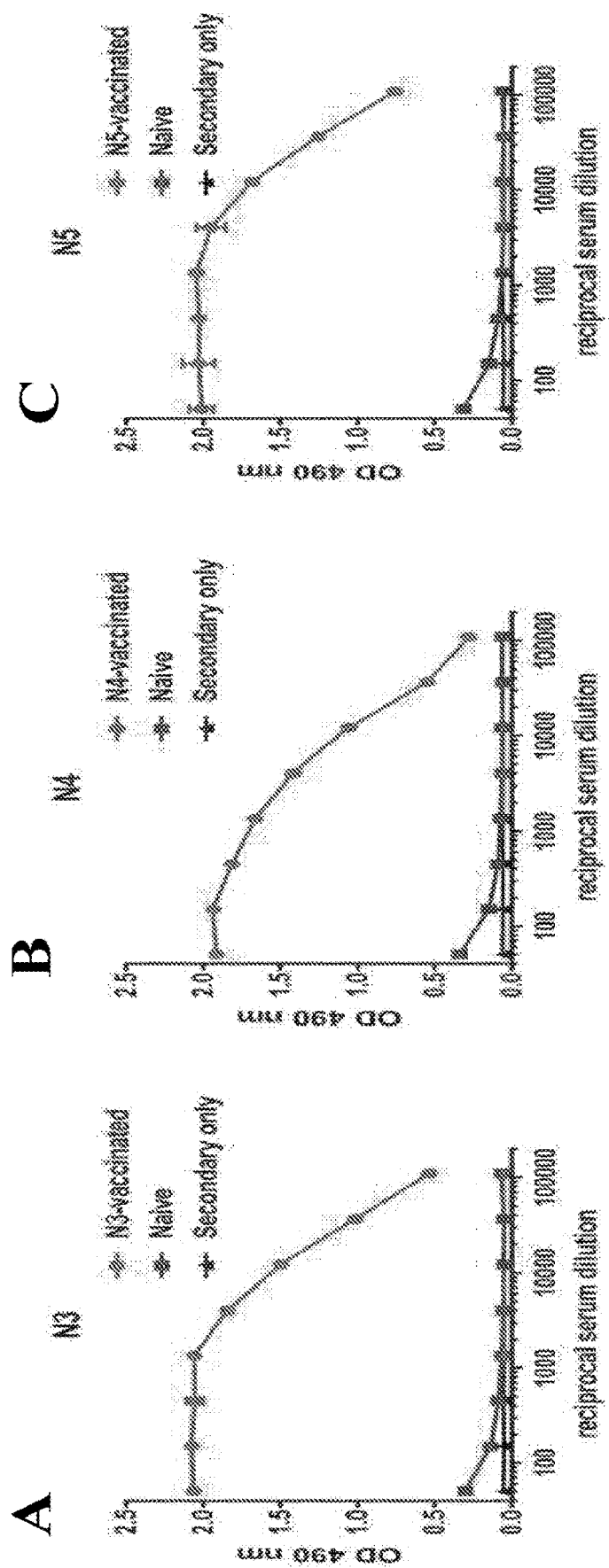
Figures 17D, 17E, 17F, 17G:
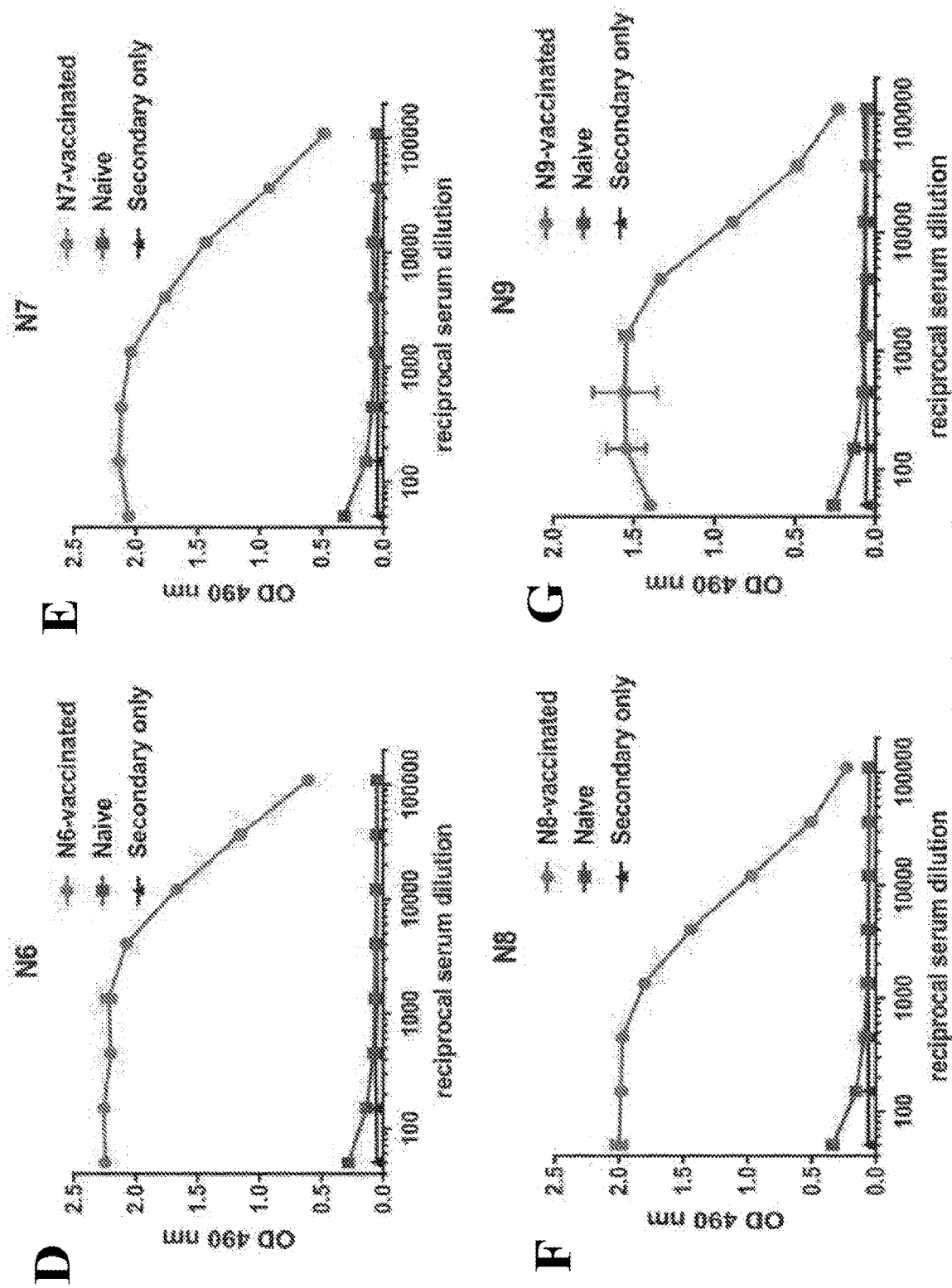

FIG. 17. Seroconversion of N3-, N4-, N5-, N6-, N7-, N8- and N9-vaccinated mice. Reactivity of N3—(FIG. 17A), N4—(FIG. 17B), N5—(FIG. 17C), N6—(FIG. 17D), N7—(FIG. 17E), N8—(FIG. 17F) and N9—(FIG. 17G) vaccinated mice was tested by ELISA against the homologous NA.

Figure 18:
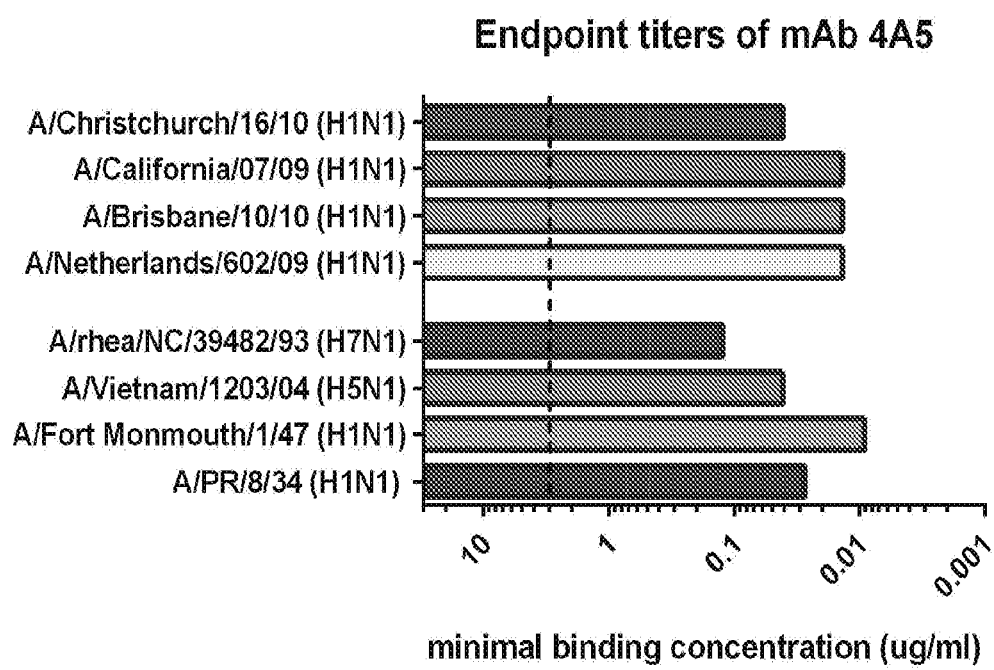

FIG. 18. Minimal binding concentration of mAb 4A5 to divergent N1 NAs. 4A5 binds to avian N1s from H5N1 and H7N1 as well as to human pre-pandemic and pandemic H1N1 isolates. The pandemic H1N1 viruses tested included the H1N1 components of the vaccines tested in FIG. 7. A/California/07/09 was a component of Fluzone and Flu-Laval, A/Brisbane/10/10 was a component of Flucelvax and A/Christchurch/16/10 was a component of Fluvirin. The dotted line indicates the 4A5 concentration used for ELISA quantification in FIG. 7 (3 ug/ml).

5. DETAILED DESCRIPTION

Described herein are immunization/vaccination regimens for inducing an immune response (e.g., an antibody response) against influenza virus. In specific aspects, the immunization regimens involve the administration of a chimeric hemagglutinin (HA), a headless HA or another influenza virus stem domain based construct (e.g., the HA stem domain or a fragment thereof) to a subject. In certain aspects, the immunization regimens also involve the administration of an influenza virus neuraminidase immunogen.

In one aspect, provided herein are regimens for immunization/vaccination of a subject (e.g., a human or other animal, such as a pig, horse, cow, dog, cat, and bird) against influenza virus. These immunization/vaccination regimens are designed to elicit highly potent and broadly neutralizing antibodies against the stem domain of an influenza virus hemagglutinin (HA) polypeptide. In specific embodiments, these immunization/vaccination regimens are designed to elicit highly potent and broadly neutralizing antibodies against the stem domain of an influenza virus HA polypeptide and elicit highly potent antibodies against an influenza virus neuraminidase (NA) polypeptide. In a specific embodiment, the immunization/vaccination regimens involve the use of a headless HA, chimeric HA, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). See, e.g., U.S. Pat. Nos. 8,673,314, 9,175,069, and 9,051,359, U.S. Patent Application Publication Nos. 20110027270, 20130129761, 20150297712, 20130209499, 20140328875, 20150335729 and 20150132330, and International Patent Publication Nos. WO 2010/117786, WO 2011/123495, WO 2011/103453, WO 2013/043729 and WO 2014/099931, which are incorporated herein by reference in their entireties, for examples of such constructs. In certain embodiments, the immunization/vaccination regimens also involve the use of an NA immunogen. The headless HA, chimeric HA, another influenza virus stem domain based construct, such as an influenza virus HA stem domain or a fragment of the stem domain of an influenza virus HA (e.g., the long alpha helix e.g., amino acids 76-130 of A/Hong Kong/1/1968, numbered according to the classic H3 subtype numbering system) and/or an NA immunogen may be administered to a subject (e.g., a human or other animal, such as a pig, horse, cow, dog, cat, and bird) in various forms, such as a live influenza viruses, inactivated influenza viruses, virus/viral-like particles ("VLPs"), subunit vaccines, split vaccines, DNA virus, polypeptides, etc. Without being bound by any theory, it is believed that the use of a chimeric HA, headless HA or other HA stem domain based construct breaks the immunodominance of the globular head domain of influenza virus HA and induces a more robust antibody response against the conserved HA stem domain of influenza virus (sometimes referred to herein as the "stalk domain") and, in certain embodiments, the influenza virus NA polypeptide.

In certain embodiments, a vaccine formulation comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation comprises a nucleic acid sequence (e.g., cDNA) encoding a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation comprises a nucleic acid sequence (e.g., cDNA) encoding a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and a nucleic acid sequence (e.g., cDNA) encoding an NA immunogen. In certain embodiments, a vaccine formulation is a live attenuated influenza virus engineered to express a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a live attenuated influenza virus engineered to express a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a chimeric HA polypeptide is expressed by an influenza virus that is heterologous to the HA globular head domain and/or the HA stem domain. For example, an influenza B virus may express a chimeric HA comprising a HA globular head domain from one influenza A virus HA and an HA stem domain from a heterologous influenza A virus. See, e.g., FIG. 9 and Example 2, infra.

In certain embodiments, a vaccine formulation is an inactivated influenza virus that comprises a chimeric HA polypeptide, headless HA polypeptide, or an influenza virus HA stem domain or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is an inactivated influenza virus that comprises a chimeric HA polypeptide, headless HA polypeptide, or an influenza virus HA stem domain or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and NA immunogen.

In certain embodiments, a vaccine formulation is a non-influenza viral vector engineered to express a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a non-influenza viral vector engineered to express a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation is an inactivated non-influenza viral vector that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is an inactivated non-influenza viral vector that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. See, e.g., Section 5.9, infra, for non-influenza viral vectors.

In certain embodiments, a vaccine formulation is a subunit vaccine that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a subunit vaccine that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation is a split vaccine that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a split vaccine that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation is a VLP that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a VLP that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation described herein further comprises an adjuvant.

Provided herein are immunization regimens involving a first immunization (e.g., priming) with a vaccine formulation described herein followed by one, two, or more additional immunizations (e.g., boostings) with a vaccine formulation. In a specific embodiment, the vaccine formulation used in the first immunization is the same type of vaccine formulation used in one, two or more additional immunizations. For example, if the vaccine formulation used in the first immunization is an inactivated influenza virus vaccine formulation, the vaccine formulation used for the one, two or more additional immunizations may be the same type of vaccine formulation, i.e., an inactivated influenza virus vaccine formulation. In other specific embodiments, the vaccine formulation used in the first immunization is different from the type of vaccine formulation used in one, two or more additional immunizations. For example, if the vaccine formulation used in the first immunization is a live influenza virus vaccine formulation, the vaccine formulation used in the one, two or more additional immunization is another type of vaccine formulation, such as an inactivated influenza virus. In certain embodiments, the vaccine formulation used in the additional immunizations changes. For example, if a live attenuated influenza virus vaccine formulation is used for one additional immunization, then one or more additional immunizations may use a different vaccine formulation, such as an inactivated vaccine formulation. See, e.g., the immunization scheme in FIG. 9 which is discussed in Example 2, infra. In a specific embodiment, if a vaccine formulation used in an immunization regimen described herein comprises a chimeric HA, then HA globular head domain of the chimeric HA changes with each immunization while the HA stem domain of the chimeric HA remains the same. In certain embodiments, an NA immunogen is used to supplement a vaccine formulation described herein. See, e.g., FIG. 8C and Example 2, infra, for examples of supplementing a vaccine formulation comprising a chimeric HA, headless HA or another HA stem domain based construct. Any route of administration known to one of skill in the art can be used to administer a vaccine formulation described herein to a subject. See, e.g., Example 1, infra, which describes the benefits of intranasal administration. In a specific embodiment, the live attenuated influenza virus and/or inactivated influenza virus are administered to the subject intranasally. In certain embodiments, the attenuated influenza virus and/or inactivated influenza virus are administered to the subject intramuscularly or subcutaneously.

In one embodiment, provided herein is a method of immunizing a subject against influenza virus, comprising:

(a) administering to the subject a live attenuated influenza virus engineered to express a headless HA or a chimeric HA; and (b) after a certain period of time (e.g., 1-6 months, 3-6 months, 6-9 months, 6-9 months, 9-12 months, etc.) administering to the subject an inactivated influenza virus engineered to express a headless HA or a chimeric HA. In a specific embodiment, if a chimeric HA is administered in steps (a) and (b), then the chimeric HA used in step (a) comprises a different HA globular head domain than the chimeric HA used in step (b). In certain embodiments, the method comprises administering to the subject one or more additional vaccine formulations described herein a certain period of time (e.g., 1-6 months, 3-6 months, 6-9 months, 6-9 months, 9-12 months, etc.) after step (b). In a specific embodiment, the method comprises administering the subject one or more additional inactivated influenza virus vaccine formulations described herein a certain period of time (e.g., 1-6 months, 3-6 months, 6-9 months, 6-9 months, 9-12 months, etc.) after step (b). In certain embodiments, the method comprises administering an NA immunogen prior to (e.g., 5 minutes, 10 minutes, 15 minutes, 30 minutes, 45 minutes or 1 hour prior to), concurrently or subsequent to (e.g., 5 minutes, 10 minutes, 15 minutes, 30 minutes, 45 minutes or 1 hour subsequent to) the administration of step (a) and/or step (b). In a specific embodiment, the live attenuated influenza virus and/or inactivated influenza virus are administered to the subject intranasally. See, e.g., Example 1, infra, which describes the benefits of intranasal administration. In certain embodiments, the attenuated influenza virus and/or inactivated influenza virus are administered to the subject intramuscularly or subcutaneously.

In another embodiment, provided herein is a method of immunizing a subject against influenza virus, comprising: (a) administering to the subject a live attenuated influenza virus engineered to express a headless HA or a chimeric HA; and (b) after a certain period of time (e.g., 1-6 months, 3-6 months, 6-9 months, 6-9 months, 9-12 months, etc.) administering to the subject a live attenuated influenza virus engineered to express a headless HA or a chimeric HA. In a specific embodiment, if a chimeric HA is administered in steps (a) and (b), then the chimeric HA used in step (a) comprises a different HA globular head domain than the chimeric HA used in step (b). In certain embodiments, the method comprises administering the subject one or more additional vaccine formulations described herein a certain period of time (e.g., 1-6 months, 3-6 months, 6-9 months, 6-9 months, 9-12 months, etc.) after step (b). In a specific embodiment, the method comprises administering the subject one or more additional inactivated influenza virus vaccine formulations described herein a certain period of time (e.g., 1-6 months, 3-6 months, 6-9 months, 6-9 months, 9-12 months, etc.) after step (b). In certain embodiments, the method comprising administering an NA immunogen prior to (e.g., 5 minutes, 10 minutes, 15 minutes, 30 minutes, 45 minutes or 1 hour prior to), concurrently or subsequent to (e.g., 5 minutes, 10 minutes, 15 minutes, 30 minutes, 45 minutes or 1 hour subsequent to) the administration of step (a) and/or step (b). In a specific embodiment, the live attenuated influenza virus and/or inactivated influenza virus are administered to the subject intranasally. See, e.g., Example 1, infra, which describes the benefits of intranasal administration. In certain embodiments, the attenuated influenza virus and/or inactivated influenza virus are administered to the subject intramuscularly or subcutaneously.

In another embodiment, provided herein is a method of immunizing a subject against influenza virus, comprising administering to the subject a vaccine formulation described herein (e.g., a vaccine formulation comprising a headless HA, a chimeric HA or another HA stem domain based construct (e.g., the long alpha helix)), in combination with an NA immunogen. The term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject. In some embodiments, two or more therapies are administered to a subject concurrently or within 1 hour of each other.

In a specific embodiment, an NA immunogen is an influenza virus NA from group 1 (e.g., N1, N4, N5 or N8) or a fragment thereof. In another embodiment, an NA immunogen is an influenza virus NA from group 2 (e.g., N2, N3, N6, N7 or N9) or fragment thereof. In a specific embodiment, an NA immunogen is an influenza B virus NA or a fragment thereof. In certain embodiments, an NA immunogen is a fusion protein comprising an influenza virus NA or a fragment thereof. In a specific embodiment, an NA immunogen is a soluble influenza virus NA protein. In another specific embodiment, an NA immunogen is a soluble influenza virus NA protein with N-terminal tetramerization domains and, optionally, a hexahistidine-tag(s). In certain embodiments, an NA immunogen is part of a viral vector, such as an influenza virus. The NA immunogen may be present naturally on the viral vector, or the viral vector may be engineered to express the NA immunogen. In some embodiments, an NA immunogen is not a part of a viral vector.

The headless HA and chimeric HA are designed to induce robust cross-neutralizing antibodies against the common stem domain of influenza virus HA. In a specific aspect, a headless HA is a polypeptide that lacks all or a fragment of the globular head domain of influenza HA, and maintains the stability of the pre-fusion conformation of influenza virus HA. In a specific embodiment, a headless HA comprises: (a) an influenza virus hemagglutinin HA1 domain that comprises an HA1 N-terminal stem segment covalently linked to a linker of a certain number of heterologous residues (e.g., 1 to 50 heterologous residues) that is in turn covalently linked an HA1 C-terminal stem segment; the HA1 domain in tertiary or quaternary association with (b) an influenza virus hemagglutinin HA2 domain. Headless HA constructs are disclosed in International Publication No. WO 2010/117786, U.S. Patent Application Publication No. 20130129761, International Publication No. WO 2011/123495, U.S. Patent Application Publication No. 20100297174, which issued as U.S. Pat. No. 9,051,359, and U.S. Patent Application Publication No. 20150297712, which are incorporated herein by in their entirety reference. In a specific embodiment, a headless HA used herein is a headless HA described in U.S. Patent Application Publication No. 20130129761 and International Publication No. WO 2011/123495, International Publication No. WO 2010/

117786, and U.S. Patent Application Publication No. 20100297174, which issued as U.S. Pat. No. 9,051,359, and U.S. Patent Application Publication No. 20150297712. In a specific embodiment, a headless HA construct is a stem domain polypeptide described in Section 5.3.1, infra.

A disulfide bond between cysteines 52 and 277 (H3 numbering) forms the demarcation line between the stem and globular head domains of HA. Amino acids between these two cysteines belong to the membrane distal globular head domain whereas amino acids of the HA ectodomain that are N-terminal of C52 and C-terminal of C277 belong to the stem domain.

In a specific aspect, a chimeric HA polypeptide comprises an influenza virus HA stem domain and an influenza virus HA globular head domain, wherein the influenza virus HA globular head domain is heterologous to the influenza virus HA stem domain (i.e., the globular head domain of the chimeric HA polypeptide is from a different strain or subtype of influenza virus than the stem domain of the chimeric HA polypeptide). In a specific embodiment, a chimeric HA used in the accordance with the methods described herein is a chimeric HA polypeptide described in International Publication No. WO 2013/043729 and/or U.S. patent application Ser. No. 14/345,816, which published as U.S. Patent Publication No. 20150132330, which are incorporated herein in their entirety (e.g., a chimeric HA described in Sections 3, 5.1, and/or 6 of International Publication No. WO 2013/043729 and U.S. patent application Ser. No. 14/345,816, which published as U.S. Patent Publication No. 20150132330) and/or in International Publication No. WO 2014/099931 and U.S. Patent Application Publication No. 20140328875, which are incorporated herein in their entirety (e.g., a chimeric HA described in Sections 3, 5.1 and/or 6 of International Publication No. WO 2014/099931 and U.S. Patent Application Publication No. 20140328875).

When designing the headless HA constructs or chimeric HA constructs, care should be taken to maintain the stability of the resulting protein. In this regard it is recommended that the cysteine residues identified as Ap and Aq in FIG. 14 be maintained since they contribute to the stability of the HA stalk domain. In a specific embodiment, the HA globular head domain of one influenza virus HA is swapped as a whole (between the Ap and Aq cysteine residues as shown in FIG. 14) with the HA globular head domain of heterologous influenza virus HA to maintain stability of resulting the chimeric HA since conformationally it would be closest to the native structure.

The influenza virus HA globular head domain of a chimeric HA might be based on (i.e., might have sequence identity to) the head domain of any influenza virus HA known to those of skill or later discovered. In certain embodiments, the influenza HA globular head domain of a chimeric HA is based on the globular head domain of an influenza A virus HA. In some embodiments, the influenza virus HA globular head domain of a chimeric HA is based on the globular head domain of an influenza A virus HA selected from the group consisting of H1, H2, H3, H4, H5, H6, H7, H8, H9, H10, H11, H12, H13, H14, H15, H16, H17, and H18 (See, e.g., Tong et al., 2013. *PLoS Path.* 9(10): e1003657. Doi:10.1371./journal.ppat.1003657 for examples of an influenza A virus hemagglutinin H18). In certain embodiments, the influenza virus HA globular head domain of a chimeric HA is based on the globular head domain of an influenza B virus HA. In some embodiments, the influenza virus HA globular head domain of a chimeric HA is based on the globular head domain of B/Seal/Netherlands/1/99. In a specific embodiment, the influenza virus HA globular head domain of a chimeric HA is based on the globular head domain of an influenza A hemagglutinin selected from an H5, H6, H7, or H9 group. In another specific embodiment, the influenza virus HA globular head domain of a chimeric HA is a globular head domain described in International Publication No. WO 2013/043729 and U.S. patent application Ser. No. 14/345,816, which published as U.S. Patent Publication No. 20150132330, which are incorporated herein in their entirety (e.g., a globular head domain described in Sections 3, 5.2 and/or 6 of International Publication No. WO 2013/043729 and U.S. patent application Ser. No. 14/345,816, which published as U.S. Patent Publication No. 20150132330) and/or in International Publication No. WO 2014/099931 and U.S. Patent Application Publication No. 20140328875, which are incorporated herein in their entirety (e.g., a globular head domain described in Sections 3, 5.1 and/or 6 of International Publication No. WO 2014/099931 and U.S. Patent Application No. 20140328875).

In certain embodiments, the influenza virus HA globular head domain of a chimeric HA comprises a deletion of one, two, three or more of the antigenic regions (e.g., a region of the head domain known to comprise or consist of an epitope) associated with the influenza virus HA globular head domain (e.g., antigenic sites A, B, C, and D, wherein the globular head domain is from subtype H3, or antigenic sites Sa, Sb, Ca and Cb, wherein the globular head domain is from subtype H1). In a specific embodiment, provided herein is an influenza virus HA globular head domain of a chimeric HA comprising a deletion of one, two or more antigenic region (e.g., a region of the globular head domain known to comprise or consist of an epitope). Those of skill in the art can readily determine the antigenic regions (e.g., epitopes) of influenza head domains known in the art or later identified using techniques known to those of skill in the art and described herein.

In certain embodiments, the influenza HA globular head domain of a chimeric HA comprises one, two, three, or more heterologous antigenic regions. In one embodiment, the influenza HA globular head domain of a chimeric HA comprises one, two, three, or more antigenic regions from the HA of a different influenza virus strain or subtype (e.g., an influenza virus strain or subtype to which all or part of the population is naïve). In a specific embodiment, the influenza HA globular head domain of a chimeric HA comprises one, two, three, or more antigenic regions from an influenza virus NA of the same or a different subtype as the globular head domain or stem domain of the chimeric HA. In accordance with this embodiment, the one, two, three or more NA antigenic regions may replace one, two, three or more HA antigenic regions. In another specific embodiment, the influenza HA globular head domain of a chimeric HA comprises the amino acid sequence ILRTQESEC, which is located between residues 222 and 230 (N2 numbering) in the enzymatic active site of NA. In certain embodiments, this amino acid sequence replaces one, two, three or more antigenic regions of the HA globular head domain of a chimeric HA. For example, the amino acid sequence may replace one, two, three or more of antigenic sites A, B, C, and D, wherein the globular head domain is from subtype H3. In another example, the amino acid sequence may replace one, two, three or more of antigenic sites Sa, Sb, Ca and Cb, wherein the globular head domain is from subtype H1.

In some embodiments, an influenza HA globular head domain of a chimeric HA comprises a non-antigenic polypeptide sequence(s) (e.g., a polypeptide sequence that is known to not induce an immune response or is known to generate an immune response that is not specific to influenza) in place of one or more of the antigenic regions (e.g., a region of the head domain known to comprise or consist of an epitope) associated with the influenza virus globular head domain. In certain embodiments, the influenza virus HA globular head domain of a chimeric HA contains additional or modified glycosylation sites, such as described in International Publication No. WO 2013/043729 and U.S. patent application Ser. No. 14/345,816, which published as U.S. Patent Publication No. 20150132330, which are incorporated herein in their entirety.

The influenza virus HA stem domain of a chimeric HA might be based on (i.e., might have sequence identity to) the head domain of any influenza virus HA known to those of skill or later discovered. In certain embodiments, the influenza HA stem domain of a chimeric HA is based on the stem domain of an influenza A virus HA. In some embodiments, the influenza virus HA stem domain of a chimeric HA is based on the stem domain of an influenza A virus HA selected from the group consisting of H1, H2, H3, H4, H5, H6, H7, H8, H9, H10, H11, H12, H13, H14, H15, H16, H17, and H18. In a specific embodiment, the influenza virus HA stem domain of a chimeric HA is a stem domain described in International Publication No. WO 2013/043729 (e.g., a stem domain described in Sections 3, 5.3, and/or 6 of International Publication No. WO 2013/043729) or in International Publication No. WO 2014/099931 (e.g., a stem domain described in Sections 3, 5.1, and/or 6 of International Publication No. WO 2014/099931). In a specific embodiment, the HA stem domain of a chimeric HA is the stem domain of an influenza A virus H1 or H3, or the stem domain of an influenza B virus. In certain embodiments, the influenza virus HA stem domain of a chimeric HA is deglycosylated, such as, e.g., described in International Publication No. WO 2013/043729 and U.S. patent application Ser. No. 14/345,816, which published as U.S. Patent Publication No. 20150132330, which are incorporated herein in their entirety, and/or using deglycosylation techniques known in the art (e.g., deglycosylation agents).

Nucleic acids, and methods for producing and expressing chimeric HA, headless HA, and other influenza virus stem domain based constructs (e.g., the HA stem domain or a fragment thereof) are described in U.S. Patent Application Publication No. 20100297174, U.S. Patent Application Publication No. 20130129761, U.S. patent application Ser. No. 14/345,816, which published as U.S. Patent Publication No. 20150132330, International Publication No. WO 2013/043729 International Publication No. WO 2013/043729, U.S. Patent Application Publication No. 20140328875, U.S. Pat. No. 8,673,314, U.S. Patent Application Publication No. 20130209499, and International Publication No. WO 2014/099931, which are incorporated herein by reference in their entirety. Examples of vaccine formulation/immunogenic compositions and methods for producing them which may be used in connection with the immunization regimens disclosed herein are described in U.S. Patent Application Publication No. 20100297174, U.S. Patent Application Publication No. 20130129761, U.S. patent application Ser. No. 14/345,816, which published as U.S. Patent Publication No. 20150132330, International Publication No. WO 2013/043729, U.S. Patent Application Publication No. 20140328875, U.S. Pat. No. 8,673,314, U.S. Patent Application Publication No. 20130209499, and International Publication No. WO 2014/099931 which are incorporated herein by reference in their entirety. Further, examples of modes of administration and dosages for administration of different vaccine formulations/immunogenic compositions which may be used in connection with the immunization regimens disclosed herein are described in U.S. Patent Application Publication No. 20100297174, U.S. Patent Application Publication No. 20130129761, U.S. patent application Ser. No. 14/345,816, which published as U.S. Patent Publication No. 20150132330, International Publication No. WO 2013/043729, U.S. Patent Application Publication No. 20140328875, U.S. Pat. No. 8,673,314, U.S. Patent Application Publication No. 20130209499, and International Publication No. WO 2014/099931, which are incorporated herein by reference in their entirety. Additionally, examples of subjects that may be administered vaccine formulations/immunogenic compositions are described in U.S. Patent Application Publication No. 20100297174, U.S. Patent Application Publication No. 20130129761, U.S. patent application Ser. No. 14/345,816, which published as U.S. Patent Publication No. 20150132330, International Publication No. WO 2013/043729, U.S. Patent Application Publication No. 20140328875, U.S. Pat. No. 8,673,314, U.S. Patent Application Publication No. 20130209499, and International Publication No. WO 2014/099931, which are incorporated herein by reference in their entirety.

In another aspect, provided herein is an immunization regimen comprising administering a seasonal influenza virus vaccine in combination with an NA immunogen. See, e.g., FIG. 8E and Example 2, infra, for examples of supplementing a seasonal vaccine with an NA immunogen. In another aspect, provided herein is an immunization regimen comprising administering an NA immunogen. See, e.g., FIG. 8D and Example 2, infra, for examples of immunization with NA immunogen. In certain embodiments, an NA immunogen lacks one or more naturally occurring glycosylation sites and/or has been deglycosylated (e.g., by a removing glycosylation sites and/or using a deglycosylation agent).

In certain embodiments, an NA immunogen or a vaccine formulation described herein which comprises an NA immunogen induces an immune response (e.g., an antibody response) that is cross-protective against a heterologous virus(es) within the same subtype. See, e.g., Example 1, infra, which describes such cross-protective antibodies. In some embodiments, a vaccine formulation described herein induces an immune response (e.g., an antibody response) that is cross-protective against one, two or more influenza viruses within the subtype and/or same group.

5.1 Chimeric Influenza Virus Hemagglutinin Polypeptides

Provided herein are chimeric influenza virus hemagglutinin polypeptides comprising or consisting of an influenza virus hemagglutinin head domain polypeptide and an influenza virus hemagglutinin stem domain polypeptide, wherein said influenza virus hemagglutinin head domain polypeptide is heterologous to said influenza virus hemagglutinin stem domain polypeptide (e.g., the influenza virus hemagglutinin head domain polypeptide and the influenza virus hemagglutinin stem domain polypeptide are derived from different influenza virus hemagglutinin subtypes). Influenza virus hemagglutinin head domain polypeptides are described in Section 5.2, infra, as well as in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety. Influenza virus hemagglutinin stem domain polypeptides, which are capable of forming stable, headless stem domains, are described in Section 5.3, infra, as well as in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety.

A full-length influenza hemagglutinin typically comprises an HA1 domain and an HA2 domain. The stem domain is formed by two segments of the HA1 domain and most or all of the HA2 domain. The two segments of the HA1 domain are separated, in primary sequence, by the globular head domain (see, e.g., the amino acid residues between the residues designated $A_p$ and $A_q$ in FIG. 14). In certain embodiments, the chimeric influenza virus hemagglutinin polypeptides described herein maintain such a structure. That is, in certain embodiments, the chimeric influenza virus hemagglutinin polypeptides described herein comprise a stable stem structure composed of an HA1 domain and an HA2 domain, and a globular head domain separating the two segments of the HA1 domain (in primary sequence), wherein said globular head domain is heterologous to the stem domain formed by the other segments of the HA1 domain and the HA2 domain.

In certain embodiments, a chimeric influenza virus hemagglutinin polypeptide described herein comprises or consists of (i) an influenza virus hemagglutinin stem domain polypeptide described herein (see, e.g., Section 5.3, infra) or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety, or an influenza virus hemagglutinin stem domain polypeptide from any known strain or subtype of influenza virus (e.g., any wild-type influenza virus hemagglutinin stem domain polypeptide such as the stem domain of the hemagglutinin of an influenza virus described in Section 5.8, infra) and (ii) an influenza virus hemagglutinin head domain polypeptide described herein (see, e.g., Sections 5.2 and 5.4.2, infra) or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety, or an influenza virus hemagglutinin head domain polypeptide from any known strain or subtype of influenza virus (e.g., any wild-type influenza virus hemagglutinin head domain polypeptide), wherein said influenza virus hemagglutinin head domain polypeptide is heterologous to said influenza virus hemagglutinin stem domain polypeptide. In specific embodiments, the influenza virus hemagglutinin head domain polypeptide is not an influenza virus hemagglutinin head domain polypeptide of influenza A virus subtype H1 or H3. In some embodiments, the influenza virus hemagglutinin head domain polypeptide is not an influenza virus hemagglutinin head domain polypeptide of influenza A virus subtype H2. In certain embodiments, the influenza virus hemagglutinin head domain polypeptide is not an influenza virus hemagglutinin head domain polypeptide of influenza A virus subtype H5.

In a specific embodiment, provided herein is a chimeric influenza virus hemagglutinin polypeptide comprising or consisting of (i) an influenza virus hemagglutinin stem domain polypeptide described herein (see, e.g., Sections 5.3 and 5.4.1, infra) or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety, or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide from influenza A virus subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide described herein (see, e.g., Sections 5.3 and 5.4.1, infra) or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330 which are incorporated herein by reference in their entirety, or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide from influenza A virus subtype H4, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide from influenza A virus subtype H1, H2, H3, H4, H5, H6, H7, H8, H9, H10, H11, H12, H13, H14, H15, H16, H17, or H18; and (ii) an influenza virus hemagglutinin head domain polypeptide described herein (see, e.g., Sections 5.2 and 5.4.2, infra) or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330, which are incorporated herein by reference in their entirety, or an influenza virus hemagglutinin head domain polypeptide from any known strain or subtype of influenza virus (e.g., any wild-type influenza virus hemagglutinin stem domain polypeptide), wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide from influenza A virus subtype H1, H2, H3, H4, H5, H6, H7, H8, H9, H10, H11, H12, H13, H14, H15, H16, H17, or H18; and (ii) an influenza virus hemagglutinin head domain polypeptide from influenza A virus subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide described herein (see, e.g., Sections 5.3 and 5.4.1, infra) or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330 which are incorporated herein by reference in their entirety, or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide from avian influenza virus subtype H1, H2, or H3, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide described herein (see, e.g., Sections 5.3 and 5.4.1, infra) or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330 which are incorporated herein by reference in their entirety, or an influenza virus hemagglutinin stem domain polypeptide from any known strain or subtype of influenza virus (e.g., any wild-type influenza virus hemagglutinin stem domain polypeptide) and (ii) an influenza virus hemagglutinin head domain polypeptide from horse influenza virus subtype H3, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide from an influenza A virus of subtype H1 and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, H16, H17, or H18. In another specific embodiment, the influenza virus hemagglutinin head domain polypeptide is not from an influenza A virus of subtype H1, H2, or H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from an influenza A virus of subtype H3 and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18 wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1, H2, or H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from an influenza A virus of subtype H2 and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18 wherein said influenza virus hemagglutinin head domain polypeptide is heterologous to said influenza virus hemagglutinin stem domain polypeptide. In a specific embodiment, the influenza virus hemagglutinin head domain polypeptide is not from an influenza A virus of subtype H1, H2, or H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from an influenza A virus of subtype H1, H2, H3, H4, H5, H6, H7, H8, H9, H10, H11, H12, H13, H14, H15, H16, H17, or H18 and (ii) an influenza virus hemagglutinin head domain polypeptide from an influenza B virus, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide from an influenza B virus and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H5, H6, H7, H8, H9, H10, H11, H12, H13, H14, H15, H16, H17, or H18. In another specific embodiment, the influenza virus hemagglutinin head domain polypeptide is not from an influenza A virus of subtype H1, H2, or H3. In another specific embodiment, the influenza virus hemagglutinin head domain polypeptide is not from an influenza A virus of subtype H5.

In another specific embodiment provided herein is a chimeric influenza virus hemagglutinin polypeptide comprising or consisting of (i) an influenza virus hemagglutinin stem domain polypeptide from an influenza B virus and (ii) an influenza virus hemagglutinin head domain polypeptide from an influenza B virus, wherein said influenza virus hemagglutinin head domain polypeptide is heterologous to said influenza virus hemagglutinin stem domain polypeptide.

In another specific embodiment, provided herein is a chimeric influenza virus hemagglutinin polypeptide comprising or consisting of (i) an influenza virus hemagglutinin stem domain polypeptide from influenza A virus A/California/7/2009 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/California/7/2009 (H1) and (ii) an influenza virus hemagglutinin head domain polypeptide from an influenza A virus of subtype H2, H4, H5, H6, H7, H8, H9, H10, H11, H12, H13, H14, H15, H16, H17, or H18. In a specific embodiment, the influenza virus hemagglutinin head domain polypeptide is from an influenza A virus of subtype H4. In a specific embodiment, the influenza virus hemagglutinin head domain polypeptide is from an influenza A virus of subtype H5. In a specific embodiment, the influenza virus hemagglutinin head domain polypeptide is from an influenza A virus of subtype H6. In a specific embodiment, the influenza virus hemagglutinin head domain polypeptide is from an influenza A virus of subtype H7. In a specific embodiment, the influenza virus hemagglutinin head domain polypeptide is from an influenza A virus of subtype H8. In a specific embodiment, the influenza virus hemagglutinin head domain polypeptide is from an influenza A virus of subtype H9. In a specific embodiment, the influenza virus hemagglutinin head domain polypeptide is from an influenza A virus of subtype H10. In a specific embodiment, the influenza virus hemagglutinin head domain polypeptide is from an influenza A virus of subtype H11. In a specific embodiment, the influenza virus hemagglutinin head domain polypeptide is from an influenza A virus of subtype H12. In a specific embodiment, the influenza virus hemagglutinin head domain polypeptide is from an influenza A virus of subtype H13. In a specific embodiment, the influenza virus hemagglutinin head domain polypeptide is from an influenza A virus of subtype H14. In a specific embodiment, the influenza virus hemagglutinin head domain polypeptide is from an influenza A virus of subtype H15. In a specific embodiment, the influenza virus hemagglutinin head domain polypeptide is from an influenza A virus of subtype H16.

In another specific embodiment, provided herein is a chimeric influenza virus hemagglutinin polypeptide comprising or consisting of (i) an influenza virus hemagglutinin stem domain polypeptide from influenza A virus A/Brisbane/59/2007-like (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/South Carolina/1918 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/USSR/92/1977 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/California/04/2009 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H5, H6, H8, H9, H11, H12, H13, or H16. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Perth/16/2009 (H3) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is from an influenza A virus of subtype H5. In another specific embodiment, the influenza virus hemagglutinin head domain polyp tide is from A/Viet Nam/1203/04 (H5). In another specific embodiment, the influenza virus hemagglutinin head domain polypeptide is from an influenza A virus of subtype H7. In another specific embodiment, the influenza virus hemagglutinin head domain polyp tide is from A/Alberta/24/01 (H7). In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Brisbane/10/2007-like (H3) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Hong Kong/1/1968 (H3) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/California/1/1988 (H3) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Ann Arbor/6/60 (H2) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H4, H7, H10, H14, or H15. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5.

In another specific embodiment, provided herein is a chimeric influenza virus hemagglutinin polypeptide comprising or consisting of (i) an influenza virus hemagglutinin stem domain polypeptide from influenza A virus A/Puerto Rico/8/1934 (H1) and (ii) an influenza virus hemagglutinin head domain polypeptide from an influenza A virus of subtype H1, H2, H3, H4, H5, H6, H7, H8, H9, H10, H11, H12, H13, H14, H15, H16, H17, or H18, wherein said influenza virus hemagglutinin head domain polypeptide is heterologous to said influenza virus hemagglutinin stem domain polypeptide. In a specific embodiment, the influenza virus hemagglutinin head domain polypeptide is from an influenza A virus of subtype H1, H2, H4, H5, H6, H7, H9, H10, H14, or H15. In another specific embodiment, the influenza virus hemagglutinin head domain polypeptide is from an influenza A virus of subtype H1, H2, H5, H6, or H9. In another specific embodiment, the influenza virus hemagglutinin head domain polypeptide is not from an influenza A virus of subtype H1. In another specific embodiment, the influenza virus hemagglutinin head domain polypeptide is not from an influenza A virus of subtype H2. In another specific embodiment, the influenza virus hemagglutinin head domain polypeptide is not from an influenza A virus of subtype H3. In another specific embodiment, the influenza virus hemagglutinin head domain polypeptide is not from an influenza A virus of subtype H5. In another specific embodiment, the influenza virus hemagglutinin head domain polypeptide is from an influenza A virus of subtype H5. In another specific embodiment, the influenza virus hemagglutinin head domain polyp tide is from A/Viet Nam/1203/04 (H5). In another specific embodiment, the influenza virus hemagglutinin head domain polypeptide is from an influenza A virus of subtype H6. In another specific embodiment, the influenza virus hemagglutinin head domain polypeptide is from A/mallard/Sweden/81/02 (H6). In another specific embodiment, the influenza virus hemagglutinin head domain polypeptide is from an influenza A virus of subtype H9. In another specific embodiment, the influenza virus hemagglutinin head domain polypeptide is from A/guinea fowl/Hong Kong/WF10/99 (H9).

In certain embodiments, a chimeric influenza hemagglutinin (HA) polypeptide provided herein comprises (i) the stem domain of the hemagglutinin from an influenza virus of the H1 subtype and (ii) the globular head domain of the hemagglutinin from an influenza virus of the H5 subtype (sometimes referred to herein as a "cH5/1 chimeric influenza hemagglutinin polypeptide"). In a specific embodiment, the stem domain of a cH5/1 chimeric influenza hemagglutinin polypeptide is the stem domain of A/California/4/2009 (H1N1) HA (or the stem domain of an A/California/4/2009-like influenza virus HA). In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Vietnam/1203/2004 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Indonesia/5/2005 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/Anhui/1/2005 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/bar headed goose/Quinghai/1A/2005 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/turkey/Turkey/1/2005 (H5) HA. In another specific embodiment, the stem domain of a cH5/1 chimeric influenza hemagglutinin polypeptide is the stem domain of A/California/4/2009 (H1N1) HA (or the stem domain of an A/California/4/2009-like influenza virus HA) and the globular head domain of the cH5/1 chimeric influenza hemagglutinin polypeptide is the globular head domain of A/whooperswan/Mongolia/244/2005 (H5) HA.

In certain embodiments, a chimeric influenza hemagglutinin (HA) polypeptide provided herein comprises (i) the stem domain of the hemagglutinin from an influenza virus of the H3 subtype and (ii) the globular head domain of the hemagglutinin from an influenza virus of the H5 subtype (sometimes referred to herein as a "cH5/3 chimeric influenza hemagglutinin polypeptide"). In a specific embodiment, the stem domain of a cH5/3 chimeric influenza hemagglutinin polypeptide is the stem domain of A/Victoria/361/2011 (H3N2) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/Vietnam/1203/2004 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/Indonesia/5/2005 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/Anhui/1/2005 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/bar headed goose/Quinghai/1A/2005 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/turkey/Turkey/1/2005 (H5) HA. In another specific embodiment, the stem domain of a cH5/3 chimeric influenza hemagglutinin polypeptide is the stem domain of A/Victoria/361/2011 (H3N2) HA and the globular head domain of the cH5/3 chimeric influenza hemagglutinin polypeptide is the globular head domain of A/whooperswan/Mongolia/244/2005 (H5) HA.

In another specific embodiment, the stem domain of a cH5/3 chimeric influenza hemagglutinin polypeptide is the stem domain of A/harbor seal/Massachusetts/1/2011 (H3N8) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/Vietnam/1203/2004 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/Indonesia/5/2005 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/Anhui/1/2005 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/bar headed goose/Quinghai/1A/2005 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/turkey/Turkey/1/2005 (H5) HA. In another specific embodiment, the stem domain of a cH5/3 chimeric influenza hemagglutinin polypeptide is the stem domain of A/harbor seal/Massachusetts/1/2011 (H3N8) HA and the globular head domain of the cH5/3 chimeric influenza hemagglutinin polypeptide is the globular head domain of A/whooperswan/Mongolia/244/2005 (H5) HA.

In another specific embodiment, the stem domain of a cH5/3 chimeric influenza hemagglutinin polypeptide is the stem domain of A/Indiana/10/2011 (H3N2) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/Vietnam/1203/2004 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/Indonesia/5/2005 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/Anhui/1/2005 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/bar headed goose/Quinghai/1A/2005 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/turkey/Turkey/1/2005 (H5) HA. In another specific embodiment, the stem domain of a cH5/3 chimeric influenza hemagglutinin polypeptide is the stem domain of A/Indiana/10/2011 (H3N2) HA and the globular head domain of the cH5/3 chimeric influenza hemagglutinin polypeptide is the globular head domain of A/whooperswan/Mongolia/244/2005 (H5) HA.

In a specific embodiment, a cH5/3 chimeric influenza hemagglutinin polypeptide provided herein does not comprise the globular head domain of A/Vietnam/1203/2004 (H5) HA. In another specific embodiment, a cH5/3 chimeric influenza hemagglutinin polypeptide does not comprise the stem domain of A/Perth/16/2009 (H3) HA.

In another specific embodiment, the stem domain of a cH5/3 chimeric influenza hemagglutinin polypeptide is the stem domain of A/Perth/16/2009 (H3N2) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/Vietnam/1203/2004 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/Indonesia/5/2005 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/Anhui/1/2005 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/bar headed goose/Quinghai/1A/2005 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/turkey/Turkey/1/2005 (H5) HA. In another specific embodiment, the stem domain of a cH5/3 chimeric influenza hemagglutinin polypeptide is the stem domain of A/Perth/16/2009 (H3N2) HA and the globular head domain of the cH5/3 chimeric influenza hemagglutinin polypeptide is the globular head domain of A/whooperswan/Mongolia/244/2005 (H5) HA.

In certain embodiments, a chimeric influenza hemagglutinin (HA) polypeptide provided herein comprises (i) the stem domain of the hemagglutinin from an influenza virus of the H3 subtype and (ii) the globular head domain of the hemagglutinin from an influenza virus of the H7 subtype (sometimes referred to herein as a "cH7/3 chimeric influenza hemagglutinin polypeptide"). In a specific embodiment, the stem domain of a cH7/3 chimeric influenza hemagglutinin polypeptide is the stem domain of A/Victoria/361/2011 (H3N2) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/Netherlands/219/03 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/Canada/504/04 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/Canada/444/04 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/chicken/Jalisco/CPA1/2012 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/mallard/Alberta/24/2001 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/rhea/NC/39482/93 (H7) HA. In another specific embodiment, the stem domain of a cH7/3 chimeric influenza hemagglutinin polypeptide is the stem domain of A/Victoria/361/2011 (H3N2) HA and the globular head domain of the cH7/3 chimeric influenza hemagglutinin polypeptide is the globular head domain of A/mallard/Netherlands/12/2000 (H7) HA.

In another specific embodiment, the stem domain of a cH7/3 chimeric influenza hemagglutinin polypeptide is the stem domain of A/harbor seal/Massachusetts/1/2011 (H3N8) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/Netherlands/219/03 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/Canada/504/04 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/Canada/444/04 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/chicken/Jalisco/CPA1/2012 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/mallard/Alberta/24/2001 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/rhea/NC/39482/93 (H7) HA. In another specific embodiment, the stem domain of a cH7/3 chimeric influenza hemagglutinin polypeptide is the stem domain of A/harbor seal/Massachusetts/1/2011 (H3N8) HA and the globular head domain of the cH7/3 chimeric influenza hemagglutinin polypeptide is the globular head domain of A/mallard/Netherlands/12/2000 (H7) HA.

In another specific embodiment, the stem domain of a cH7/3 chimeric influenza hemagglutinin polypeptide is the stem domain of A/Indiana/10/2011 (H3N2) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/Netherlands/219/03 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/Canada/504/04 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/Canada/444/04 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/chicken/Jalisco/CPA1/2012 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/mallard/Alberta/24/2001 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/rhea/NC/39482/93 (H7) HA. In another specific embodiment, the stem domain of a cH7/3 chimeric influenza hemagglutinin polypeptide is the stem domain of A/Indiana/10/2011 (H3N2) HA and the globular head domain of the cH7/3 chimeric influenza hemagglutinin polypeptide is the globular head domain of A/mallard/Netherlands/12/2000 (H7) HA.

In another specific embodiment, the stem domain of a cH7/3 chimeric influenza hemagglutinin polypeptide is the stem domain of A/Perth/16/2009 (H3N2) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/Netherlands/219/03 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/Canada/504/04 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/Canada/444/04 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/chicken/Jalisco/CPA1/2012 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/mallard/Alberta/24/2001 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/rhea/NC/39482/93 (H7) HA. In another specific embodiment, the stem domain of a cH7/3 chimeric influenza hemagglutinin polypeptide is the stem domain of A/Perth/16/2009 (H3N2) HA and the globular head domain of the cH7/3 chimeric influenza hemagglutinin polypeptide is the globular head domain of A/mallard/Netherlands/12/2000 (H7) HA.

In a specific embodiment, a cH7/3 chimeric influenza hemagglutinin polypeptide provided herein does not comprise the globular head domain of A/mallard/Alberta/24/2001 (H7) HA. In another specific embodiment, a cH7/3 chimeric influenza hemagglutinin polypeptide does not comprise the stem domain of A/Perth/16/2009 (H3) HA.

In certain embodiments, a chimeric influenza hemagglutinin (HA) polypeptide provided herein comprises (i) the stem domain of the hemagglutinin from an influenza B virus and (ii) the globular head domain of the hemagglutinin from an influenza virus of the H5 subtype (sometimes referred to herein as a "cH5/B chimeric influenza hemagglutinin polypeptide"). In a specific embodiment, the stem domain of a cH5/B chimeric influenza hemagglutinin polypeptide is the stem domain of B/Malaysia/2506/2004 HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/Vietnam/1203/2004 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/Indonesia/5/2005 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/Anhui/1/2005 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/bar headed goose/Quinghai/1A/2005 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/turkey/Turkey/1/2005 (H5) HA. In another specific embodiment, the stem domain of a cH5/B chimeric influenza hemagglutinin polypeptide is the stem domain of B/Malaysia/2506/2004 HA and the globular head domain of the cH5/B chimeric influenza hemagglutinin polypeptide is the globular head domain of A/whooperswan/Mongolia/244/2005 (H5) HA.

In another specific embodiment, the stem domain of a cH5/B chimeric influenza hemagglutinin polypeptide is the stem domain of B/Florida/4/2006 HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/Vietnam/1203/2004 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/Indonesia/5/2005 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/Anhui/1/2005 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/bar headed goose/Quinghai/1A/2005 (H5) HA. In another specific embodiment, the stem domain of a cH5/B chimeric influenza hemagglutinin polypeptide is the stem domain of B/Florida/4/2006 HA and the globular head domain of the cH5/B chimeric influenza hemagglutinin polypeptide is the globular head domain of A/turkey/Turkey/1/2005 (H5) HA. In another specific embodiment, the stem domain of a cH5/B chimeric influenza hemagglutinin polypeptide is the stem domain of B/Florida/4/2006 and the globular head domain of the cH5/B chimeric influenza hemagglutinin polypeptide is the globular head domain of A/whooperswan/Mongolia/244/2005 (H5) HA.

In another specific embodiment, the stem domain of a cH5/B chimeric influenza hemagglutinin polypeptide is the stem domain of B/Wisconsin/1/2010 HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/Vietnam/1203/2004 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/Indonesia/5/2005 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/Anhui/1/2005 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/bar headed goose/Quinghai/1A/2005 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/turkey/Turkey/1/2005 (H5) HA. In another specific embodiment, the stem domain of a cH5/B chimeric influenza hemagglutinin polypeptide is the stem domain of B/Wisconsin/1/2010 HA and the globular head domain of the cH5/B chimeric influenza hemagglutinin polypeptide is the globular head domain of A/whooperswan/Mongolia/244/2005 (H5) HA.

In another specific embodiment, the stem domain of a cH5/B chimeric influenza hemagglutinin polypeptide is the stem domain of B/Brisbane/60/2008 HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/Vietnam/1203/2004 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/Indonesia/5/2005 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/Anhui/1/2005 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/bar headed goose/Quinghai/1A/2005 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/turkey/Turkey/1/2005 (H5) HA. In another specific embodiment, the stem domain of a cH5/B chimeric influenza hemagglutinin polypeptide is the stem domain of B/Brisbane/60/2008 HA and the globular head domain of the cH5/B chimeric influenza hemagglutinin polypeptide is the globular head domain of A/whooperswan/Mongolia/244/2005 (H5) HA.

In certain embodiments, a chimeric influenza hemagglutinin (HA) polypeptide provided herein comprises (i) the stem domain of the hemagglutinin from an influenza B virus and (ii) the globular head domain of the hemagglutinin from an influenza virus of the H7 subtype (sometimes referred to herein as a "cH7/B chimeric influenza hemagglutinin polypeptide"). In a specific embodiment, the stem domain of a cH7/B chimeric influenza hemagglutinin polypeptide is the stem domain of B/Malaysia/2506/2004 HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/Netherlands/219/03 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/Canada/504/04 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/Canada/444/04 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/chicken/Jalisco/CPA1/2012 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/mallard/Alberta/24/2001 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/rhea/NC/39482/93 (H7) HA. In another specific embodiment, the stem domain of a cH7/B chimeric influenza hemagglutinin polypeptide is the stem domain of B/Malaysia/2506/2004 HA and the globular head domain of the cH7/B chimeric influenza hemagglutinin polypeptide is the globular head domain of A/mallard/Netherlands/12/2000 (H7) HA.

In another specific embodiment, the stem domain of a cH7/B chimeric influenza hemagglutinin polypeptide is the stem domain of B/Florida/4/2006 HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/Netherlands/219/03 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/Canada/504/04 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/Canada/444/04 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/chicken/Jalisco/CPA1/2012 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/mallard/Alberta/24/2001 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/rhea/NC/39482/93 (H7) HA. In another specific embodiment, the stem domain of a cH7/B chimeric influenza hemagglutinin polypeptide is the stem domain of B/Florida/4/2006 HA and the globular head domain of the cH7/B chimeric influenza hemagglutinin polypeptide is the globular head domain of A/mallard/Netherlands/12/2000 (H7) HA.

In another specific embodiment, the stem domain of a cH7/B chimeric influenza hemagglutinin polypeptide is the stem domain of B/Wisconsin/1/2010 HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/Netherlands/219/03 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/Canada/504/04 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/Canada/444/04 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/chicken/Jalisco/CPA1/2012 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/mallard/Alberta/24/2001 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/rhea/NC/39482/93 (H7) HA. In another specific embodiment, the stem domain of a cH7/B chimeric influenza hemagglutinin polypeptide is the stem domain of B/Wisconsin/1/2010 HA and the globular head domain of the cH7/B chimeric influenza hemagglutinin polypeptide is the globular head domain of A/mallard/Netherlands/12/2000 (H7) HA.

In another specific embodiment, the stem domain of a cH7/B chimeric influenza hemagglutinin polypeptide is the stem domain of B/Brisbane/60/2008 HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/Netherlands/219/03 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/Canada/504/04 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/Canada/444/04 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/chicken/Jalisco/CPA1/2012 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/mallard/Alberta/24/2001 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/rhea/NC/39482/93 (H7) HA. In another specific embodiment, the stem domain of a cH7/B chimeric influenza hemagglutinin polypeptide is the stem domain of B/Brisbane/60/2008 HA and the globular head domain of the cH7/B chimeric influenza hemagglutinin polypeptide is the globular head domain of A/mallard/Netherlands/12/2000 (H7) HA.

In certain embodiments, a chimeric influenza hemagglutinin (HA) polypeptide provided herein comprises (i) the stem domain of the hemagglutinin from an influenza B virus and (ii) the globular head domain of the hemagglutinin from a different influenza B virus strain (sometimes referred to herein as a "cB/B chimeric influenza hemagglutinin polypeptide"). In a specific embodiment, the stem domain of a cB/B chimeric influenza hemagglutinin polypeptide is the stem domain of B/Malaysia/2506/2004 HA. In another specific embodiment, the stem domain of a cB/B chimeric influenza hemagglutinin polypeptide is the stem domain of B/Malaysia/2506/2004 HA and the globular head domain of the cB/B chimeric influenza hemagglutinin polypeptide is the globular head domain of B/Lee/1940 HA. In another specific embodiment, the stem domain of a cB/B chimeric influenza hemagglutinin polypeptide is the stem domain of B/Malaysia/2506/2004 HA and the globular head domain of the cB/B chimeric influenza hemagglutinin polypeptide is the globular head domain of B/seal/Netherlands/1/99 HA (or a B/seal/Netherlands/1/99-like influenza virus).

In another specific embodiment, the stem domain of a cB/B chimeric influenza hemagglutinin polypeptide is the stem domain of B/Florida/4/2006 HA. In another specific embodiment, the stem domain of a cB/B chimeric influenza hemagglutinin polypeptide is the stem domain of B/Florida/4/2006 HA and the globular head domain of the cB/B chimeric influenza hemagglutinin polypeptide is the globular head domain of B/Lee/1940 HA. In another specific embodiment, the stem domain of a cB/B chimeric influenza hemagglutinin polypeptide is the stem domain of B/Florida/4/2006 HA and the globular head domain of the cB/B chimeric influenza hemagglutinin polypeptide is the globular head domain of B/seal/Netherlands/1/99 HA (or a B/seal/Netherlands/1/99-like influenza virus).

In another specific embodiment, the stem domain of a cB/B chimeric influenza hemagglutinin polypeptide is the stem domain of B/Wisconsin/1/2010 HA. In another specific embodiment, the stem domain of a cB/B chimeric influenza hemagglutinin polypeptide is the stem domain of B/Wisconsin/1/2010 HA and the globular head domain of the cB/B chimeric influenza hemagglutinin polypeptide is the globular head domain of B/Lee/1940 HA. In another specific embodiment, the stem domain of a cB/B chimeric influenza hemagglutinin polypeptide is the stem domain of B/Wisconsin/1/2010 HA and the globular head domain of the cB/B chimeric influenza hemagglutinin polypeptide is the globular head domain of B/seal/Netherlands/1/99 HA (or a B/seal/Netherlands/1/99-like influenza virus).

In another specific embodiment, the stem domain of a cB/B chimeric influenza hemagglutinin polypeptide is the stem domain of B/Brisbane/60/2008 HA. In another specific embodiment, the stem domain of a cB/B chimeric influenza hemagglutinin polypeptide is the stem domain of B/Brisbane/60/2008 HA and the globular head domain of the cB/B chimeric influenza hemagglutinin polypeptide is the globular head domain of B/Lee/1940 HA. In another specific embodiment, the stem domain of a cB/B chimeric influenza hemagglutinin polypeptide is the stem domain of B/Brisbane/60/2008 HA and the globular head domain of the cB/B chimeric influenza hemagglutinin polypeptide is the globular head domain of B/seal/Netherlands/1/99 HA (or a B/seal/Netherlands/1/99-like influenza virus).

In certain embodiments, a chimeric influenza hemagglutinin (HA) polypeptide provided herein comprises (i) the stem domain of the hemagglutinin from an influenza virus of the H3 subtype and (ii) the globular head domain of the hemagglutinin from an influenza virus of the H4 subtype (sometimes referred to herein as a "cH4/3 chimeric influenza hemagglutinin polypeptide"). In a specific embodiment, the stem domain of a cH4/3 chimeric influenza hemagglutinin polypeptide is the stem domain of A/Perth/16/09 HA (or the stem domain of an A/Perth/16/09-like influenza virus HA). In another specific embodiment, the stem domain of a cH4/3 chimeric influenza hemagglutinin polypeptide is the stem domain of A/Perth/16/09 HA (or the stem domain of an A/Perth/16/09-like influenza virus HA) and the globular head domain of the cH4/3 chimeric influenza hemagglutinin polypeptide is the globular head domain of A/duck/Czech/56 (or the globular head domain of an A/duck/Czech/56-like influenza virus HA).

In certain embodiments, a chimeric influenza virus hemagglutinin polypeptide provided herein comprises an influenza virus hemagglutinin stem domain polypeptide and an influenza virus hemagglutinin head domain polypeptide, wherein the influenza virus hemagglutinin head domain polypeptide is heterologous to the influenza virus hemagglutinin stem domain polypeptide, and wherein the chimeric influenza virus hemagglutinin polypeptide has a primary structure of, in the following order: an HA1 N-terminal stem segment, an influenza virus hemagglutinin head domain polypeptide, an HA1 C-terminal stem segment and an HA2. The primary sequence of a chimeric influenza virus hemagglutinin polypeptide provided herein might be formed by a single polypeptide, or it might be formed by multiple polypeptides. Typically, a single polypeptide is expressed by any technique deemed suitable by one of skill in the art.

In certain embodiments, a chimeric influenza virus hemagglutinin polypeptide provided herein is monomeric. In certain embodiments, a chimeric influenza virus hemagglutinin polypeptide provided herein is multimeric. In certain embodiments, a chimeric influenza virus hemagglutinin polypeptide provided herein is trimeric.

In certain embodiments, a chimeric influenza virus hemagglutinin polypeptide provided herein comprises a signal peptide. Typically, the signal peptide is cleaved during or after polypeptide expression and translation to yield a mature chimeric influenza virus hemagglutinin polypeptide. In certain embodiments, also provided herein are mature chimeric influenza virus hemagglutinin polypeptides that lack a signal peptide. In embodiments where a chimeric influenza virus hemagglutinin polypeptide provided herein comprises a signal peptide, the signal peptide might be based on any influenza virus signal peptide known to those of skill in the art. In certain embodiments, the signal peptides are based on influenza A signal peptides. In certain embodiments, the signal peptides are based on the signal peptide of an influenza A hemagglutinin selected from the group consisting of H1, H2, H3, H4, H5, H6, H7, H8, H9, H10, H11, H12, H13, H14, H15, H16, H17, and H18. In certain embodiments, the signal peptide might be any signal peptide deemed useful to one of skill in the art. In certain embodiments, the signal peptide is selected from SEQ ID NOS:18-33.

In certain embodiments, a chimeric influenza virus hemagglutinin polypeptide provided herein comprises a luminal domain. In embodiments where a chimeric influenza virus hemagglutinin polypeptide provided herein comprises a luminal domain, the luminal domain might be based on any influenza luminal domain known to those of skill in the art. In certain embodiments, the luminal domains are based on influenza A luminal domains. In certain embodiments, the luminal domains are based on the luminal domain of an influenza A hemagglutinin selected from the group consisting of H1, H2, H3, H4, H5, H6, H7, H8, H9, H10, H11, H12, H13, H14, H15, H16, H17, and H18. In certain embodiments, the luminal domain might be any luminal domain deemed useful to one of skill in the art. In certain embodiments, the luminal domain is selected from SEQ ID NOS: 51-66. In certain embodiments, the luminal domains are from the same hemagglutinin as the stem domain. In certain embodiments, the luminal domains are from influenza virus strain or subtype as the stem domain HA2 subunit.

In certain embodiments, a chimeric influenza virus hemagglutinin polypeptide provided herein comprises a transmembrane domain. In embodiments where a chimeric influenza virus hemagglutinin polypeptide provided herein comprises a transmembrane domain, the transmembrane domain might be based on any influenza transmembrane domain known to those of skill in the art. In certain embodiments, the transmembrane domains are based on influenza A transmembrane domains. In certain embodiments, the transmembrane domains are based on a transmembrane domain of an influenza A hemagglutinin selected from the group consisting of H1, H2, H3, H4, H5, H6, H7, H8, H9, H10, H11, H12, H13, H14, H15, H16, H17, and H18. In certain embodiments, the transmembrane domain might be any transmembrane domain deemed useful to one of skill in the art. In certain embodiments, the transmembrane domain is selected from SEQ ID NOS:67-82. In certain embodiments, the transmembrane domains are from the same hemagglutinin as the stem domain. In certain embodiments, the transmembrane domains are from influenza virus strain or subtype as the stem domain HA2 subunit.

In certain embodiments, a chimeric influenza virus hemagglutinin polypeptide provided herein comprises a cytoplasmic domain. In embodiments where a chimeric influenza virus hemagglutinin polypeptide provided herein comprises a cytoplasmic domain, the cytoplasmic domain might be based on any influenza cytoplasmic domain known to those of skill in the art. In certain embodiments, the cytoplasmic domains are based on influenza A cytoplasmic domains. In certain embodiments, the cytoplasmic domains are based on a cytoplasmic domain of an influenza A hemagglutinin selected from the group consisting of H1, H2, H3, H4, H5, H6, H7, H8, H9, H10, H11, H12, H13, H14, H15, H16, H17, and H18. In certain embodiments, the cytoplasmic domain might be any cytoplasmic domain deemed useful to one of skill in the art. In certain embodiments, the cytoplasmic domain is selected from SEQ ID NOS:83-98. In certain embodiments, the cytoplasmic domains are from the same hemagglutinin as the stem domain. In certain embodiments, the cytoplasmic domains are from influenza virus strain or subtype as the stem domain HA2 subunit.

In certain embodiments, the chimeric influenza virus hemagglutinin polypeptides provided herein further comprise one or more polypeptide domains. Useful polypeptide domains include domains that facilitate purification, folding and cleavage of portions of a polypeptide. For example, a His tag (His-His-His-His-His-His, SEQ ID NO:101), FLAG epitope or other purification tag can facilitate purification of a chimeric influenza virus hemagglutinin polypeptide provided herein. In some embodiments, the His tag has the sequence, (His)$_n$, wherein n is 2, 3, 4, 5, 6, 7, 8, 9, 10, 11, 12, 13, 14, 15, 16, 17, 18, 19, 20 or greater. In specific embodiments, the chimeric influenza virus hemagglutinin polypeptides provided herein comprise a foldon, or trimerization, domain from bacteriophage T4 fibritin. A foldon, or trimerization, domain from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. The foldon domain can have any foldon sequence known to those of skill in the art (see, e.g., Papanikolopoulou et al., 2004, J. Biol. Chem. 279(10):8991-8998, the contents of which are hereby incorporated by reference in their entirety. Examples include GSGYIPEAPRDGQAYVRKDGEWVLLSTFL (SEQ ID NO:102). A foldon domain can be useful to facilitate trimerization of soluble polypeptides provided herein. In specific embodiments, the chimeric influenza virus hemagglutinin polypeptides provided herein comprise a cleavage site. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50).

In certain embodiments, the chimeric influenza hemagglutinin polypeptides are soluble polypeptides, such as those described in Examples 6 and 9 of International Publication No. WO 2013/043729, which is incorporated herein by reference in its entirety.

In certain embodiments, the influenza hemagglutinin stem domain polypeptides of the chimeric influenza virus hemagglutinin polypeptides described herein maintain the cysteine residues identified in influenza hemagglutinin polypeptides as $A_p$ and $A_q$ in FIG. 14, i.e., the cysteine residues identified in influenza hemagglutinin polypeptides as $A_p$ and $A_q$ in FIG. 14 are maintained in the chimeric influenza virus hemagglutinin polypeptides described herein. Thus, in certain embodiments, in the primary sequence of a chimeric influenza virus hemagglutinin polypeptide described herein: (i) the N-terminal segment of an influenza hemagglutinin stem domain polypeptide ends at the cysteine residue identified as $A_p$ in FIG. 14, (ii) the C-terminal segment of an influenza hemagglutinin stem domain polypeptide begins at the cysteine residue identified as $A_q$ in FIG. 14; and (iii) the influenza hemagglutinin head domain polypeptide (which is heterologous to the influenza hemagglutinin stem domain polypeptide) is between the N-terminal and C-terminal segments of the influenza hemagglutinin stem domain polypeptide. Influenza hemagglutinin stem domain polypeptides are described in detail in Section 5.3, infra.

In certain embodiments, the HA1 N-terminal stem segment of the chimeric influenza virus hemagglutinin polypeptides described herein does not end exactly at $A_p$ (e.g., Cys$_{52}$ of an HA1 subunit from an H3 hemagglutinin (i.e., according to H3 numbering)), but at a residue in sequence and structural vicinity to $A_p$. For example, in certain embodiments, the HA1 N-terminal stem segment of the chimeric influenza virus hemagglutinin polypeptides described herein ends at $A_{p-1}$, $A_{p-2}$, $A_{p-3}$, $A_{p-4}$, $A_{p-5}$, $A_{p-6}$, $A_{p-7}$, $A_{p-8}$, $A_{p-9}$, $A_{p-10}$, $A_{p-11}$, $A_{p-12}$, $A_{p-13}$, $A_{p-14}$, $A_{p-15}$, $A_{p-16}$, $A_{p-17}$, $A_{p-18}$, $A_{p-19}$, $A_{p-20}$, $A_{p-21}$, $A_{p-22}$, $A_{p-23}$, $A_{p-23}$, $A_{p-24}$, $A_{p-25}$, $A_{p-26}$, $A_{p-27}$, $A_{p-28}$, $A_{p-29}$, $A_{p-30}$. In certain embodiments, the HA1 N-terminal stem segment of the chimeric influenza virus hemagglutinin polypeptides described herein ends in the range of $A_{p-1}$ to $A_{p-3}$, $A_{p-3}$ to $A_{p-5}$, $A_{p-5}$ to $A_{p-8}$, $A_{p-8}$ to $A_{p-10}$, $A_{p-10}$ to $A_{p-15}$, $A_{p-15}$ to $A_{p-20}$, $A_{p-20}$ to $A_{p-30}$, $A_{p-30}$ to $A_{p-40}$. For example, an HA1 N-terminal stem segment ending at $A_{p-10}$ would end at Leu42 of an H3 hemagglutinin. In certain embodiments, the HA1 N-terminal stem segment of the chimeric influenza virus hemagglutinin polypeptides described herein ends at $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, $A_{p+10}$, $A_{p+11}$, $A_{p+12}$, $A_{p+13}$, $A_{p+14}$, $A_{p+15}$, $A_{p+16}$, $A_{p+17}$, $A_{p+18}$, $A_{p+19}$, $A_{p+20}$, $A_{p+21}$, $A_{p+22}$, $A_{p+23}$, $A_{p+24}$, $A_{p+25}$, $A_{p+26}$, $A_{p+27}$, $A_{p+28}$, $A_{p+29}$, $A_{p+30}$, $A_{p+31}$, $A_{p+32}$, $A_{p+33}$, $A_{p+34}$, $A_{p+35}$, $A_{p+36}$, $A_{p+37}$, $A_{p+38}$, $A_{p+39}$, $A_{p+40}$. In certain embodiments, the HA1 N-terminal stem segment of the chimeric influenza virus hemagglutinin polypeptides described herein ends in the range of $A_{p+1}$ to $A_{p+5}$, $A_{p+5}$ to $A_{p+10}$, $A_{p+10}$ to $A_{p+15}$, $A_{p+15}$ to $A_{p+20}$, $A_{p+20}$ to $A_{p+25}$, $A_{p+25}$ to $A_{p+30}$, $A_{p+30}$ to $A_{p+35}$, $A_{p+35}$ to $A_{p+40}$, or $A_{p+40}$ to $A_{p+50}$. For example, an HA1 N-terminal stem segment ending at $A_{p+38}$ would end at Arg90 of an H3 hemagglutinin. The end of an HA1 N-terminal stem segment should be selected in conjunction with the end of the HA1 C-terminal stem segment and the influenza hemagglutinin head domain polypeptide so that the resulting chimeric influenza virus hemagglutinin polypeptide is capable of forming a three-dimensional structure similar to a wild-type influenza hemagglutinin. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the HA1 C-terminal stem segment of the chimeric influenza virus hemagglutinin polypeptides described herein does not start at $A_q$ (e.g., Cys$_{277}$ of an HA1 subunit from an H3 hemagglutinin (i.e., according to H3 numbering)), but at a residue in sequence and structural vicinity to $A_q$. For example, in certain embodiments, the HA1 C-terminal stem segment of the chimeric influenza virus hemagglutinin polypeptides described herein starts at about $A_{q-1}$, $A_{q-2}$, $A_{q-3}$, $A_{q-4}$, $A_{q-5}$, $A_{q-6}$, $A_{q-7}$, $A_{q-8}$, $A_{q-9}$, $A_{q-10}$, $A_{q-11}$, $A_{q-12}$, $A_{q-13}$, $A_{q-14}$, $A_{q-15}$, $A_{q-20}$, $A_{q-25}$, $A_{q-30}$, $A_{q-35}$, $A_{q-40}$, $A_{q-45}$, $A_{-50}$, $A_{q-55}$, $A_{q-60}$, $A_{q-65}$, $A_{q-70}$, $A_{q-75}$, or $A_{q-80}$. Iii certain embodiments, the HA1 C-terminal stem segment of the chimeric influenza virus hemagglutinin polypeptides described herein starts in the range of $A_{q-1}$ to $A_{q-5}$, $A_{q-5}$ to $A_{q-10}$, $A_{q-10}$ to $A_{q-15}$, $A_{q-15}$ to $A_{q-20}$, $A_{q-20}$ to $A_{q-25}$, $A_{q-25}$ to $A_{q-30}$, $A_{q-30}$ to $A_{q-35}$, $A_{q-35}$ to $A_{q-40}$, $A_{q-40}$ to $A_{q-45}$, $A_{q-45}$ to $A_{q-50}$, $A_{q-50}$ to $A_{q-55}$, $A_{q-55}$ to $A_{q-60}$, $A_{q-60}$ to $A_{q-65}$, $A_{q-65}$ to $A_{q-70}$, $A_{q-75}$ to $A_{q-80}$. For example, an HA1 C-terminal stem segment ending at $A_{q-77}$ would start at Gly200 of an H3 hemagglutinin; and an HA1 C-terminal stem segment ending at $A_{q-10}$ would start at Isoleucine267 of an H3 hemagglutinin. In certain embodiments, the HA1 C-terminal stem segment of the chimeric influenza virus hemagglutinin polypeptides described herein starts at $A_{q+1}$, $A_{q+2}$, $A_{q+3}$, $A_{q+4}$, $A_{q+5}$, $A_{q+6}$, $A_{q+7}$, $A_{q+8}$, $A_{q+9}$, $A_{q+10}$, $A_{q+11}$, $A_{q+12}$, $A_{q+13}$, $A_{q+14}$, $A_{q+15}$, $A_{q+16}$, $A_{q+17}$, $A_{q+18}$, $A_{q+19}$, $A_{q+20}$, $A_{q+21}$, $A_{q+22}$, $A_{q+23}$, $A_{q+24}$, $A_{q+25}$, $A_{q+26}$, $A_{q+27}$, $A_{q+28}$, $A_{q+29}$, $A_{q+30}$. In certain embodiments, the HA1 C-terminal stem segment of the chimeric influenza virus hemagglutinin polypeptides described herein starts in the range of $A_{q+1}$ to $A_{q+3}$, $A_{q+3}$ to $A_{q+5}$, $A_{q+5}$ to $A_{q+8}$, $A_{q+8}$ to $A_{q+10}$, $A_{q+10}$ to $A_{q+15}$, or $A_{q+15}$ to $A_{q+20}$. The end of an HA1 N-terminal stem segment should be selected in conjunction with the start of the HA1 C-terminal stem segment and the influenza hemagglutinin head domain polypeptide so that the resulting chimeric influenza virus hemagglutinin polypeptide is capable of forming a three-dimensional structure similar to a wild-type influenza hemagglutinin. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In one example, an HA1 N-terminal stem segment of a chimeric influenza virus hemagglutinin polypeptide described herein may end at any one of hemagglutinin amino acid positions 45-48 (using H3 numbering) and an HA1 C-terminal stem segment of the chimeric influenza virus hemagglutinin polypeptide may start at any one of hemagglutinin amino acid positions 285-290 (using H3 numbering); and the heterologous head domain may begin at any one of amino acid positions 46-49 and end at any one of amino acid position 284-289 (using H3 numbering). In another example, an HA1 N-terminal stem segment of a chimeric influenza virus hemagglutinin polypeptide described herein ends at hemagglutinin amino acid position 90 (using H3 numbering) and an HA1 C-terminal stem segment of the chimeric influenza virus hemagglutinin polypeptide starts hemagglutinin amino acid position 200 (using H3 numbering); and the heterologous head domain begins at amino acid position 91 and ends at amino acid position 199 (using H3 numbering).

In certain embodiments, the end of the N-terminal stem segment of a chimeric influenza virus hemagglutinin polypeptide described herein is $A_{p-1}$, and the start of the C-terminal stem segment of a chimeric influenza virus hemagglutinin polypeptide described herein is $A_{q-1}$. In certain embodiments, the end of the N-terminal stem segment of a chimeric influenza virus hemagglutinin polypeptide described herein is $A_{p-2}$, and the start of the C-terminal stem segment of a chimeric influenza virus hemagglutinin polypeptide described herein is $A_{q-2}$. In certain embodiments, the end of the N-terminal stem segment of a chimeric influenza virus hemagglutinin polypeptide described herein is $A_{p-3}$, and the start of the C-terminal stem segment of a chimeric influenza virus hemagglutinin polypeptide described herein is $A_{q-3}$. In certain embodiments, the end of the N-terminal stem segment of a chimeric influenza virus hemagglutinin polypeptide described herein is $A_{p-4}$, and the start of the C-terminal stem segment of a chimeric influenza virus hemagglutinin polypeptide described herein is $A_{q-4}$. In certain embodiments, the end of the N-terminal stem segment of a chimeric influenza virus hemagglutinin polypeptide described herein is $A_{p-5}$, and the start of the C-terminal stem segment of a chimeric influenza virus hemagglutinin polypeptide described herein is $A_{q-5}$. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the end of the N-terminal stem segment of a chimeric influenza virus hemagglutinin polypeptide described herein is $A_{p+1}$, and the start of the C-terminal stem segment is of a chimeric influenza virus hemagglutinin polypeptide described herein $A_{q+1}$. In certain embodiments, the end of the N-terminal stem segment of a chimeric influenza virus hemagglutinin polypeptide described herein is $A_{p+2}$, and the start of the C-terminal stem segment of a chimeric influenza virus hemagglutinin polypeptide described herein is $A_{q+2}$. In certain embodiments, the end of the N-terminal stem segment of a chimeric influenza virus hemagglutinin polypeptide described herein is $A_{p+3}$, and the start of the C-terminal stem segment is of a chimeric influenza virus hemagglutinin polypeptide described herein $A_{q+3}$. In certain embodiments, the end of the N-terminal stem segment of a chimeric influenza virus hemagglutinin polypeptide described herein is $A_{p+4}$, and the start of the C-terminal stem segment of a chimeric influenza virus hemagglutinin polypeptide described herein is $A_{q+4}$. In certain embodiments, the end of the N-terminal stem segment of a chimeric influenza virus hemagglutinin polypeptide described herein is $A_{p+5}$, and the start of the C-terminal stem segment of a chimeric influenza virus hemagglutinin polypeptide described herein is $A_{q+5}$. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the end of the N-terminal stem segment of a chimeric influenza virus hemagglutinin polypeptide described herein is $A_{p-1}$, and the start of the C-terminal stem segment of a chimeric influenza virus hemagglutinin polypeptide described herein is $A_{q+1}$. In certain embodiments, the end of the N-terminal stem segment of a chimeric influenza virus hemagglutinin polypeptide described herein is $A_{p-2}$, and the start of the C-terminal stem segment of a chimeric influenza virus hemagglutinin polypeptide described herein is $A_{q+2}$. In certain embodiments, the end of the N-terminal stem segment of a chimeric influenza virus hemagglutinin polypeptide described herein is $A_{p-3}$, and the start of the C-terminal stem segment is of a chimeric influenza virus hemagglutinin polypeptide described herein $A_{q+3}$. In certain embodiments, the end of the N-terminal stem segment of a chimeric influenza virus hemagglutinin polypeptide described herein is $A_{p-4}$, and the start of the C-terminal stem segment of a chimeric influenza virus hemagglutinin polypeptide described herein is $A_{q+4}$. In certain embodiments, the end of the N-terminal stem segment of a chimeric influenza virus hemagglutinin polypeptide described herein is $A_{p-5}$, and the start of the C-terminal stem segment of a chimeric influenza virus hemagglutinin polypeptide described herein is $A_{q+5}$. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

In certain embodiments, the end of the N-terminal stem segment of a chimeric influenza virus hemagglutinin polypeptide described herein is $A_{p+1}$, and the start of the C-terminal stem segment of a chimeric influenza virus hemagglutinin polypeptide described herein is $A_{q-1}$. In certain embodiments, the end of the N-terminal stem segment of a chimeric influenza virus hemagglutinin polypeptide described herein is $A_{p+2}$, and the start of the C-terminal stem segment of a chimeric influenza virus hemagglutinin polypeptide described herein is $A_{q-2}$. In certain embodiments, the end of the N-terminal stem segment of a chimeric influenza virus hemagglutinin polypeptide described herein is $A_{p+3}$, and the start of the C-terminal stem segment of a chimeric influenza virus hemagglutinin polypeptide described herein is $A_{q-3}$. In certain embodiments, the end of the N-terminal stem segment of a chimeric influenza virus hemagglutinin polypeptide described herein is $A_{p+4}$, and the start of the C-terminal stem segment of a chimeric influenza virus hemagglutinin polypeptide described herein is $A_{q-4}$. In certain embodiments, the end of the N-terminal stem segment of a chimeric influenza virus hemagglutinin polypeptide described herein is $A_{p+5}$, and the start of the C-terminal stem segment of a chimeric influenza virus hemagglutinin polypeptide described herein is $A_{q-5}$. In such embodiments, an influenza hemagglutinin head domain polypeptide (which is heterologous to the influenza hemagglutinin stem domain polypeptide) is located, in primary sequence, between the N-terminal and C-terminal segments of the influenza hemagglutinin stem domain polypeptide.

Also provided herein are chimeric influenza hemagglutinin polypeptides comprising an HA2 subunit and a chimeric HA1 subunit. In certain embodiments, the chimeric HA1 subunit comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 60, 51, 52, 53, 54, 55, 56, 57, 58, 59, 60, 61, 62, 63, 64, 65, 66, 67, 68, 69, 70, 71, 72, 73, 75, 75, 76, 77, 78, 79, or 80 amino acids of the HA1 subunit of a first influenza virus strain or subtype and the remainder of amino acids of the chimeric HA1 subunit are from a second influenza virus strain or subtype. In certain embodiments, the chimeric HA1 subunit comprises 1-10, 10-20, 20-30, 30-40, 40-50, 50-60, 60-70, 70-80, 80-90, or 90-100 amino acids of the HA1 subunit of a first influenza virus strain or subtype and the remainder of amino acids of the chimeric HA1 subunit are from a second influenza virus strain or subtype. In certain embodiments, the amino acids from the first influenza virus strain or subtype can be consecutive, or can represent portions of the N- and/or C-termini of a chimeric HA1 domain. In specific embodiments, the chimeric HA1 subunit comprises an influenza virus hemagglutinin head domain polypeptide comprising amino acids of two or more different subtypes or strains of influenza virus. In specific embodiments, the chimeric HA1 subunit comprises a globular head with amino acids of two or more different subtypes or strains of influenza virus.

In certain embodiments, one or more of glycosylation sites in a chimeric influenza virus hemagglutinin polypeptide provided herein are modified (e.g., by amino acid addition, deletion or substitution). In specific embodiments, the one or more glycosylation sites are modified such that glycosylation at these sites will not occur during processing and maturation of the polypeptide. Those of skill in the art will recognize that influenza HA typically comprises one or more glycosylation sites (e.g. Asn-Xaa-Ser/Thr/Cys, wherein Xaa is any amino acid or Asn-Xaa-Ser/Thr/Cys, or, in certain embodiments, wherein Xaa is any amino acid except Pro). In certain embodiments, the modified glycosylation site is located in the stem domain of the chimeric influenza virus hemagglutinin polypeptide. In certain embodiments, one or more amino acid residues in a glycosylation site are conservatively substituted with an amino acid residue that disrupts the glycosylation site. In certain embodiments, one or more amino acid residues in a glycosylation site are substituted with any amino acid residue that disrupts the glycosylation site. In certain embodiments, one or more asparagine residues in a glycosylation site is substituted with alanine. In a particular embodiment, the asparagine at position 38 of an H3 hemagglutinin is changed to an alanine. In certain embodiments, the chimeric influenza virus hemagglutinin polypeptide comprises one or more non-naturally occurring glycosylation sites in its globular head domain. In certain embodiments, the chimeric influenza virus hemagglutinin polypeptide comprises one or more modified glycosylation sites and/or non-naturally occurring glycosylation sites as discussed in Section 5.4, infra, or in International Publication Nos. WO 2010/117786, WO 2011/123495, WO 2013/043729, and WO 2014/099931, U.S. Publication Nos. 2010/0297174, 2013/0129761, 2014/0328875, and U.S. application Ser. No. 14/345,816, which published as U.S. Patent Publication No. 20150132330 which are incorporated herein by reference in their entirety.

In certain embodiments, the chimeric influenza virus hemagglutinin polypeptides provided herein are capable of forming a three dimensional structure that is similar to the three dimensional structure of a native influenza hemagglutinin. Structural similarity might be evaluated based on any technique deemed suitable by those of skill in the art. For instance, reaction, e.g. under non-denaturing conditions, of a chimeric influenza virus hemagglutinin polypeptide with a neutralizing antibody or antiserum that recognizes a native influenza hemagglutinin might indicate structural similarity. Useful neutralizing antibodies or antisera are described in, e.g. Sui, et al., 2009, *Nat. Struct. Mol. Biol.* 16(3):265-273, Ekiert et al., Feb. 26, 2009, Science [DOI: 10.1126/science.1171491], and Kashyap et al., 2008, *Proc. Natl. Acad. Sci. USA* 105(16):5986-5991, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a hemagglutinin.

In certain embodiments, a chimeric influenza hemagglutinin (HA) polypeptide described herein may be conjugated to heterologous proteins, e.g., a major histocompatibility complex (MHC) with or without heat shock proteins (e.g., Hsp10, Hsp20, Hsp30, Hsp40, Hsp60, Hsp70, Hsp90, or Hsp100). In certain embodiments, a chimeric influenza hemagglutinin (HA) polypeptide described herein may be conjugated to immunomodulatory molecules, such as proteins which would target the chimeric influenza hemagglutinin (HA) polypeptide to immune cells such as B cells (e.g., C3d) or T cells. In certain embodiments, chimeric influenza hemagglutinin (HA) polypeptide described herein may be conjugated to proteins which stimulate the innate immune system such as interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-β, TNFα, B7.1, B7.2, 4-1BB, CD40 ligand (CD40L), and drug-inducible CD40 (iCD40).

It will be understood by those of skill in the art that the chimeric influenza virus hemagglutinin polypeptides provided herein can be prepared according to any technique known by and deemed suitable to those of skill in the art, including the techniques described herein. In certain embodiments, the chimeric influenza virus hemagglutinin polypeptides are isolated.

5.2 Influenza Hemagglutinin Head Domain Polypeptides

Provided herein are influenza hemagglutinin head domain polypeptides for use in the generation of the flu HA polypeptides, including chimeric influenza virus hemagglutinin polypeptides, described herein.

Generally, the influenza hemagglutinin head domain polypeptides provided herein are polypeptides that comprise or consist essentially of the globular head domain of an influenza hemagglutinin polypeptide. The head domain of an influenza hemagglutinin polypeptide is the head domain that is generally recognized by those of skill in the art.

In certain embodiments, the influenza hemagglutinin head domain polypeptides provided herein comprise an influenza hemagglutinin head domain having at least 70%, 75%, 80%, 85%, 90%, 95%, 96%, 98%, or 99% amino acid sequence identity to an influenza hemagglutinin head domain known to those of skill in the art.

Also provided herein are influenza hemagglutinin head domain polypeptides comprising amino acids from two or more strains or subtypes of influenza virus. In certain embodiments, a chimeric HA1 subunit comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 60, 51, 52, 53, 54, 55, 56, 57, 58, 59, 60, 61, 62, 63, 64, 65, 66, 67, 68, 69, 70, 71, 72, 73, 75, 75, 76, 77, 78, 79, or 80 amino acids of the HA1 subunit of a first influenza virus strain or subtype and the remainder of amino acids of the chimeric HA1 subunit are from a second influenza virus strain or subtype. In certain embodiments, a chimeric HA1 subunit comprises 1-10, 10-20, 20-30, 30-40, 40-50, 50-60, 60-70, 70-80, 80-90, or 90-100 amino acids of the HA1 subunit of a first influenza virus strain or subtype and the remainder of amino acids of the chimeric HA1 subunit are from a second influenza virus strain or subtype. In certain embodiments, the amino acids from the first influenza virus strain or subtype can be consecutive, and/or can represent portions of the N- and/or C-termini of a chimeric HA1 domain.

Also provided herein are influenza hemagglutinin head domain polypeptides comprising deleted forms of a known influenza hemagglutinin head domain, wherein up to about 150, 145, 140, 135, 130, 125, 120, 115, 110, 105, 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from the head domain. Also provided herein are influenza hemagglutinin head domain polypeptides comprising deleted forms of a known influenza hemagglutinin head domain, wherein about 1-10, 10-20, 20-30, 30-40, 40-50, 50-60, 60-70, 70-80, 80-90, 90-100, 100-110, 110-120, 120-130, 130-140, or 140-150 amino acid residues are deleted from the head domain.

In certain embodiments, the influenza HA globular head domain of a chimeric HA comprises one, two, three, or more heterologous antigenic regions. In one embodiment, the influenza HA globular head domain of a chimeric HA comprises one, two, three, or more antigenic regions from the HA of a different influenza virus strain or subtype (e.g., an influenza virus strain or subtype to which all or part of the population is naïve). In a specific embodiment, the influenza HA globular head domain of a chimeric HA comprises one, two, three, or more antigenic regions from an influenza virus NA of the same or a different subtype as the globular head domain or stem domain of the chimeric HA. In accordance with this embodiment, the one, two, three or more NA antigenic regions may replace one, two, three or more HA antigenic regions. In another specific embodiment, the influenza HA globular head domain of a chimeric HA comprises the amino acid sequence ILRTQESEC, which is located between residues 222 and 230 (N2 numbering) in the enzymatic active site of NA. In certain embodiments, this amino acid sequence replaces one, two, three or more antigenic regions of the HA globular head domain of a chimeric HA. For example, the amino acid sequence may replace one, two, three or more of antigenic sites A, B, C, and D, wherein the globular head domain is from subtype H3. In another example, the amino acid sequence may replace one, two, three or more of antigenic sites Sa, Sb, Ca and Cb, wherein the globular head domain is from subtype H1.

Provided herein are influenza hemagglutinin head domain polypeptides comprising altered forms of a known influenza hemagglutinin head domain, wherein up to about 80, 75, 70 65, 60, 55, 50, 45, 40, 35, 30, 25, 20, 15, 10, 9, 8, 7, 6, 5, 4, 3, 2 or 1 amino acid residues of the head domain are substituted (e.g., conservatively substituted) with other amino acids. Also provided herein are influenza hemagglutinin head domain polypeptides comprising altered forms of a known influenza hemagglutinin head domain, wherein up to about 1-10, 10-20, 20-30, 30-40, 40-50, 50-60, 60-70, 70-80, 80-90, or 90-100 amino acid residues of the head domain are substituted (e.g., conservatively substituted) with other amino acids. Further provided herein are influenza hemagglutinin head domain polypeptides comprising altered forms of a known influenza hemagglutinin head domain, wherein up to about 80, 75, 70 65, 60, 55, 50, 45, 40, 35, 30, 25, 20, 15, 10, 9, 8, 7, 6, 5, 4, 3, 2 or 1 amino acid residues of the head domain are substituted with up to about 80, 75, 70 65, 60, 55, 50, 45, 40, 35, 30, 25, 20, 15, 10, 9, 8, 7, 6, 5, 4, 3, 2 or 1 amino acid residues of a known influenza neuraminidase. Also provided herein are influenza hemagglutinin head domain polypeptides comprising altered forms of a known influenza hemagglutinin head domain, wherein up to about 1-10, 10-20, 20-30, 30-40, 40-50, 50-60, 60-70, 70-80, 80-90, or 90-100 amino acid residues of the head domain are substituted with up to about 1-10, 10-20, 20-30, 30-40, 40-50, 50-60, 60-70, 70-80, 80-90, or 90-100 amino acid residues of a known influenza neuraminidase. Further provided herein are influenza hemagglutinin head domain polypeptides comprising altered forms of a known influenza hemagglutinin head domain, wherein up to about 80, 75, 70 65, 60, 55, 50, 45, 40, 35, 30, 25, 20, 15, 10, 9, 8, 7, 6, 5, 4, 3, 2 or 1 amino acid residues of a known influenza neuraminidase are inserted into the influenza hemagglutinin head domain polypeptide. Also provided herein are influenza hemagglutinin head domain polypeptides comprising altered forms of a known influenza hemagglutinin head domain, wherein up to about 1-10, 10-20, 20-30, 30-40, 40-50, 50-60, 60-70, 70-80, 80-90, or 90-100 amino acid residues of a known influenza neuraminidase are inserted into the influenza hemagglutinin head domain polypeptide. In certain embodiments, the up to about 80, 75, 70 65, 60, 55, 50, 45, 40, 35, 30, 25, 20, 15, 10, 9, 8, 7, 6, 5, 4, 3, 2 or 1 amino acid residues of a known influenza neuraminidase comprises the amino acid sequence ILRTQESEC (SEQ ID NO:107). In certain embodiments, the up to about 1-10, 10-20, 20-30, 30-40, 40-50, 50-60, 60-70, 70-80, 80-90, or 90-100 amino acid residues of a known influenza neuraminidase comprises the amino acid sequence ILRTQESEC (SEQ ID NO:107). In certain embodiments, up to 50, 60, or more amino acids are deleted from the N-terminus of an influenza hemagglutinin head domain (as viewed from the primary amino acid sequence) and up to 70, 80, or more amino acids are deleted from the C-terminus of an influenza hemagglutinin head domain (as viewed from the primary amino acid sequence). In certain embodiments, the influenza virus HA globular head domain comprises 1, 2, 3, 4, or more influenza virus neuraminidase antigenic peptides/influenza virus neuraminidase antigenic regions. See Section 5.5, infra, for examples of influenza virus neuraminidase antigenic peptides.

Also provided herein are influenza hemagglutinin head domain polypeptides comprising a deletion of one or more of the antigenic regions (e.g., a region of the head domain known to comprise or consist of an epitope) associated with the influenza hemagglutinin head domain (e.g., antigenic sites A, B, C, and D, wherein the head domain is from subtype H3 or antigenic sites Sa, Sb, Ca and Cb, wherein the head domain is from subtype H1). In a specific embodiment, provided herein is an influenza hemagglutinin head domain polypeptide comprising a deletion of one antigenic region (e.g., a region of the head domain known to comprise or consist of an epitope). In another specific embodiment, provided herein is an influenza hemagglutinin head domain polypeptide comprising a deletion of two antigenic region (e.g., two regions of the head domain known to comprise or consist of an epitope). In another specific embodiment, provided herein is an influenza hemagglutinin head domain polypeptide comprising a deletion of three antigenic region (e.g., three regions of the head domain known to comprise or consist of an epitope). In another specific embodiment, provided herein is an influenza hemagglutinin head domain polypeptide comprising a deletion of four antigenic regions (e.g., four regions of the head domain known to comprise or consist of an epitope). In another specific embodiment, provided herein is an influenza hemagglutinin head domain polypeptide comprising a deletion of five antigenic region (e.g., five regions of the head domain known to comprise or consist of an epitope). Those of skill in the art can readily determine the antigenic regions (e.g., epitopes) of influenza head domains known in the art or later identified using techniques known to those of skill in the art and described herein.

In certain embodiments, the influenza hemagglutinin head domain polypeptides of the chimeric influenza virus hemagglutinin polypeptides described herein comprise (i) one, two, three, or more antigenic regions from an influenza hemagglutinin head domain polypeptide that are homologous to the stem domain (i.e., derived from the same influenza virus strain or subtype) and (ii) one, two, three, or more antigenic regions from an influenza hemagglutinin head domain polypeptide that are heterologous to the stem domain (i.e., derived from a different influenza virus strain or subtype). In a specific embodiment, the C antigenic site/region of the head domain is homologous to the stem domain (i.e., derived from the same influenza virus strain or subtype). In another specific embodiment, the D antigenic site/region of the head domain is homologous to the stem domain (i.e., derived from the same influenza virus strain or subtype). In another specific embodiment, the C and D antigenic sites/regions of the head domain are homologous to the stem domain (i.e., derived from the same influenza virus strain or subtype). In yet another specific embodiment, the Ca and/or Cb antigenic sites/regions of the head domain are homologous to the stem domain (i.e., derived from the same influenza virus strain or subtype).

Also provided herein are influenza hemagglutinin head domain polypeptides comprising a replacement of one or more of the antigenic regions (e.g., a region of the head domain known to comprise or consist of an epitope) associated with the influenza hemagglutinin head domain with a non-antigenic polypeptide sequence (e.g., a polypeptide sequence that is known to not induce an immune response or is known to generate an immune response that is not specific to influenza). In a specific embodiment, provided herein is an influenza hemagglutinin head domain polypeptide comprising a replacement of one antigenic region (e.g., a region of the head domain known to comprise or consist of an epitope) with a non-antigenic polypeptide sequence (e.g., a polypeptide sequence that is known to not induce an immune response or is known to generate an immune response that is not specific to influenza). In another specific embodiment, provided herein is an influenza hemagglutinin head domain polypeptide comprising a replacement of two antigenic regions (e.g., two regions of the head domain known to comprise or consist of an epitope) with non-antigenic polypeptide sequences (e.g., polypeptide sequences that are known to not induce an immune response or are known to generate an immune response that is not specific to influenza). In another specific embodiment, provided herein is an influenza hemagglutinin head domain polypeptide comprising a replacement of three antigenic regions (e.g., three regions of the head domain known to comprise or consist of an epitope) with non-antigenic polypeptide sequences (e.g., polypeptide sequences that are known to not induce an immune response or are known to generate an immune response that is not specific to influenza). In another specific embodiment, provided herein is an influenza hemagglutinin head domain polypeptide comprising a replacement of four antigenic regions (e.g., four regions of the head domain known to comprise or consist of an epitope) with non-antigenic polypeptide sequences (e.g., polypeptide sequences that are known to not induce an immune response or are known to generate an immune response that is not specific to influenza). In another specific embodiment, provided herein is an influenza hemagglutinin head domain polypeptide comprising a replacement of five antigenic regions (e.g., five regions of the head domain known to comprise or consist of an epitope) with non-antigenic polypeptide sequences (e.g., polypeptide sequences that are known to not induce an immune response or are known to generate an immune response that is not specific to influenza). Those of skill in the art can readily determine the antigenic regions (e.g., epitopes) of influenza head domains known in the art or later identified using techniques known to those of skill in the art and described herein.

In another specific embodiment, provided herein is an influenza hemagglutinin head domain polypeptide comprising one, two, three, or more heterologous antigenic regions, i.e., one, two, three, or more antigenic regions from the hemagglutinin of a different influenza virus strain or subtype (e.g., an influenza virus strain or subtype to which all or part of the population is naïve). In another specific embodiment, the heterologous antigenic regions of the influenza hemagglutinin head domain polypeptide comprises one or more non-naturally occurring glycosylation sites as discussed, infra in Section 5.4.2. Without being bound by any particular theory of operation, it is believed that the immunogenicity of conserved subimmunodominant antigenic regions within the stem domain can be increased by the addition of one or more non-naturally occurring glycosylation sites in these immunodominant regions in the influenza hemagglutinin head domain. In specific embodiments, the influenza hemagglutinin head domain polypeptide comprises one, two, three, or more heterologous antigenic regions wherein the heterologous antigenic regions comprises one or more non-naturally occurring glycosylation sites.

The influenza hemagglutinin head domain polypeptides provided herein might be based on (i.e. might have sequence identity to) the head domain of any influenza hemagglutinin known to those of skill or later discovered. In certain embodiments, influenza hemagglutinin head domain polypeptides are based on the head domain of an influenza A hemagglutinin (e.g., the head domain of the hemagglutinin of an influenza A virus described in Section 5.4, infra). In certain embodiments, the influenza hemagglutinin head domain polypeptides are based on the head domain of an influenza A hemagglutinin selected from the group consisting of H1, H2, H3, H4, H5, H6, H7, H8, H9, H10, H11, H12, H13, H14, H15, H16, H17, and H18. In certain embodiments, influenza hemagglutinin head domain polypeptides are based on the head domain of an influenza B hemagglutinin (e.g., the head domain of the hemagglutinin of an influenza B virus described in Section 5.4, infra). In some embodiments, the influenza hemagglutinin head domain polypeptides are based on the head domain of B/Seal/Netherlands/1/99. In a specific embodiment, the influenza hemagglutinin head domain polypeptides are based on the head domain of an influenza A hemagglutinin selected from an H5, H6, and/or H9 group. In another specific embodiment, the influenza hemagglutinin head domain polypeptides are based on the head domain of an influenza A hemagglutinin selected from an H5, H7, and/or H9 group.

5.3 Influenza Hemagglutinin Stem Domain Polypeptides and Core Polypeptides 5.3.1 Influenza Hemagglutinin Stem Domain Polypeptides Provided herein are influenza hemagglutinin stem domain polypeptides for use in the generation of flu hemagglutinin polypeptides (e.g., chimeric influenza virus hemagglutinin polypeptides). While not intending to be bound by any particular theory of operation, it is believed that, in the context of the flu hemagglutinin polypeptides (e.g., chimeric influenza virus hemagglutinin polypeptides) provided herein, the influenza hemagglutinin stem domain polypeptides are useful for presenting one or more relatively conserved antigenic regions to a host immune system in order to generate an immune response that is capable of cross-reacting with a plurality of influenza strains. Since the one or more antigenic regions are well conserved across influenza hemagglutinin subtypes, such an immune response might cross-react with several subtypes of full-length influenza hemagglutinin polypeptides.

Generally, the influenza hemagglutinin stem domain polypeptides provided herein are polypeptides that comprise or consist essentially of the stem domain of an influenza hemagglutinin polypeptide. The stem domain of an influenza hemagglutinin polypeptide is the stem domain that is generally recognized by those of skill in the art.

In certain embodiments, the influenza hemagglutinin stem domain polypeptides provided herein comprise little or no globular head domain of an influenza hemagglutinin polypeptide. In certain embodiments, an influenza hemagglutinin stem domain polypeptide is an influenza hemagglutinin that has had its globular head domain deleted by any technique deemed suitable by one of skill in the art.

In certain embodiments, influenza hemagglutinin stem domain polypeptides described herein maintain the cysteine residues identified in influenza hemagglutinin polypeptides as $A_p$ and $A_q$ in FIG. 14. In certain embodiments, influenza hemagglutinin stem domain polypeptides described herein have greater stability at a pH lower than the hemagglutinin of a wild-type influenza virus (e.g., a pH less than 5.2, less than 5.1, less than 5.0, or less than 4.9, such as 4.8, 4.7, 4.6, 4.5, 4.4, 4.3, 4.2, 4.1, 4.0, 3.9, 3.8, etc.). In particular embodiments, influenza hemagglutinin stem domain polypeptides described herein undergo conformational changes from the pre-fusion to the fusion conformation at a pH lower than the hemagglutinin of wild-type influenza viruses. In some embodiments, influenza hemagglutinin stem domain polypeptides described herein comprise one or more amino acid substitutions, such as HA1 H17Y (H3 numbering) that increases the stability of the polypeptides at a low pH (e.g., a pH of between 4.9 to 5.2, 4.5 to 3.5, 3.5 to 2.5, 2.5 to 1.5, 1.5 to 0.5). The stability of influenza hemagglutinin stem domain polypeptides can be assessed using techniques known in the art, such as sensitivity of the hemagglutinin molecules to trypsin digestion, as described in, e.g., Thoennes et al., 2008, Virology 370: 403-414.

The influenza hemagglutinin stem domain polypeptides can be prepared according to any technique deemed suitable to one of skill in the art, including techniques described below. In certain embodiments, the stem domain polypeptides are isolated.

In some embodiments, the primary structure of an influenza hemagglutinin stem domain polypeptide comprises, in the following order: an HA1 N-terminal stem segment, a linker, an HA1 C-terminal stem segment and an HA2. In some embodiments, the primary structure of an influenza hemagglutinin stem domain polypeptide comprises, in the following order: an HA1 N-terminal stem segment, a linker, an HA1 C-terminal short stem segment and an HA2. In some embodiments, the primary structure of an influenza hemagglutinin stem domain polypeptide comprises, in the following order: an HA1 N-terminal long stem segment, a linker, an HA1 C-terminal long stem segment and an HA2. In some embodiments, the influenza hemagglutinin stem domain polypeptide comprises in the following order: an HA1 N-terminal stem segment, a linker, an HA1 intermediate stem segment, a second linker, an HA1 C-terminal stem segment and an HA2.

The primary sequence might be formed by a single polypeptide, or it might be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide might be cleaved, for example by a protease, under appropriate expression conditions to yield two polypeptides in quaternary association. The cleavage is typically between the HA1 C-terminal stem segment and the HA2. In certain embodiments, provided herein are multiple polypeptide, for example two polypeptide, influenza hemagglutinin stem domains. In multiple polypeptide embodiments, the HA1 segments and HA2 are in quaternary association.

In certain embodiments, an influenza hemagglutinin stem domain polypeptide provided herein is monomeric. In certain embodiments, an influenza hemagglutinin stem domain polypeptide provided herein is multimeric. In certain embodiments, an influenza hemagglutinin stem domain polypeptide provided herein is trimeric. Those of skill in the art will recognize that native influenza hemagglutinin polypeptides are capable of trimerization in vivo and that certain influenza hemagglutinin stem domain polypeptides provided herein are capable of trimerization. In particular embodiments described below, influenza hemagglutinin stem domain polypeptides provided herein comprise trimerization domains to facilitate trimerization.

In certain embodiments, an influenza hemagglutinin stem domain polypeptide comprises a signal peptide. Typically, the signal peptide is cleaved during or after polypeptide expression and translation to yield a mature influenza hemagglutinin stem domain polypeptide. The signal peptide might be advantageous for expression of the influenza hemagglutinin stem domain polypeptides. In certain embodiments, also provided herein are mature influenza hemagglutinin stem domain polypeptides that lack a signal peptide.

Influenza hemagglutinin HA2 typically comprises a stem domain, transmembrane domain and a cytoplasmic domain. In certain embodiments, provided herein are influenza hemagglutinin stem domain polypeptides that comprise an HA2 stem domain, an HA2 luminal domain, an HA2 transmembrane domain and an HA2 cytoplasmic domain. Such influenza hemagglutinin stem domain polypeptides might be expressed as membrane-bound antigens. In certain embodiments, provided herein are influenza hemagglutinin stem domain polypeptides that comprise an HA2 stem domain, an HA2 luminal domain, and an HA2 transmembrane domain but lack some or all of the typical cytoplasmic domain. Such influenza hemagglutinin stem domain polypeptides might be expressed as membrane-bound antigens. In certain embodiments, provided herein are influenza hemagglutinin stem domain polypeptides that comprise an HA2 stem domain and an HA2 luminal domain but lack both an HA2 transmembrane domain and an HA2 cytoplasmic domain. Such influenza hemagglutinin stem domain polypeptides might advantageously be expressed as soluble polypeptides. In certain embodiments, provided herein are influenza hemagglutinin stem domain polypeptides that comprise an HA2 stem domain but lack an HA2 luminal domain, an HA2 transmembrane domain and an HA2 cytoplasmic domain. Such influenza hemagglutinin stem domain polypeptides might advantageously be expressed as soluble polypeptides. In certain embodiments, the influenza hemagglutinin stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A and influenza B hemagglutinins are provided in the tables disclosed in International Publication No. WO 2010/117786, WO 2011/123495, and WO 2013/043729, U.S. Publication Nos. 2010/0297174, 2013/0129761, and U.S. application Ser. No. 14/345,816, which published as U.S. Patent Publication No. 20150132330 which are incorporated herein by reference in their entireties.

Also provided herein are influenza hemagglutinin stem domain polypeptides comprising deleted forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA2 stem domain. Further provided herein are influenza hemagglutinin stem domain polypeptides comprising altered forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin stem domain polypeptides comprising deleted and altered HA2 stem domains. In certain embodiments, the influenza hemagglutinin stem domain polypeptides comprises an HA2 stem domain comprising one or more modified glycosylation sites, wherein the modified glycosylation site comprises a modification of a naturally occurring glycosylation site that disrupts the ability of a glycan to attach to the modified glycosylation site, as described in Section 5.4.1, infra. Without being bound by any particular theory of operation, it is believed that immunogenicity and accessibility antigenic regions within the stem domain can be increased by modifying one or more glycosylation sites within the stem domain in a manner that disrupts the glycosylation (i.e. the attachment of a glycan) at the sites.

In certain embodiments, a stem domain polypeptide is deglycosylated using an agent. For example, in a specific embodiment, a stem domain polypeptide is deglycosylated using trifluoromethanesulfonic acid (Sigma), an enzyme, such as PNGase F, endoglycosidase H, exoglycosidase(s), or a Protein Deglycosylation Mix (e.g., the Protein Deglycosylation Mix sold by New England Biolabs Inc.).

In some embodiments, the primary structure of an influenza hemagglutinin stem domain polypeptide comprises, in the following order: an HA1 N-terminal stem segment, a linker, an HA1 C-terminal stem segment and an HA2. The HA1 N-terminal stem segment might be any HA1 N-terminal stem segment recognized by one of skill in the art based on the definition provided herein. Typically, an HA1 N-terminal stem segment corresponds to a polypeptide consisting of the N-terminal amino acid of a mature HA1 (i.e. an HA1 lacking a signal peptide) through the cysteine residue located in sequence at approximately the $52^{nd}$ residue of the HA1. This cysteine residue, termed $A_p$ herein, is generally capable of forming a disulfide bridge with a cysteine residue in the C-terminal stem segment of HA1. Sequences of 16 representative influenza A hemagglutinins are presented in FIG. 14, and residue $A_p$ is identified in each.

In certain embodiments, the HA1 N-terminal stem segment does not end exactly at $A_p$ (e.g., $Cys_{52}$ of an HA1 subunit from an H3 hemagglutinin (i.e., according to H3 numbering)), but at a residue in sequence and structural vicinity to $A_p$. For example, in certain embodiments, the HA1 N-terminal stem segment ends at $A_{p-1}$, $A_{p-2}$, $A_{p-3}$, $A_{p-4}$, $A_{p-5}$, $A_{p-6}$, $A_{p-7}$, $A_{p-8}$, $A_{p-9}$, $A_{p-10}$, $A_{p-11}$, $A_{p-12}$, $A_{p-13}$, $A_{p-14}$, $A_{p-15}$, $A_{p-16}$, $A_{p-17}$, $A_{p-18}$, $A_{p-19}$, $A_{p-20}$, $A_{p-21}$, $A_{p-22}$, $A_{p-23}$, $A_{p-23}$, $A_{p-24}$, $A_{p-25}$, $A_{p-26}$, $A_{p-27}$, $A_{p-28}$, $A_{p-29}$, $A^{p-30}$. In certain embodiments, the HA1 N-terminal stem segment of the flu hemagglutinin polypeptides described herein ends in the range of $A_{p-1}$ to $A_{p-3}$, $A_{p-3}$ to $A_{p-5}$, $A_{p-5}$ to $A_{p-8}$, $A_{p-8}$ to $A_{p-10}$, $A_{p-10}$ to $A_{p-15}$, $A_{p-15}$ to $A_{p-20}$, $A_{p-20}$ to $A_{p-30}$, $A_{p-30}$ to $A_{p-40}$. In other embodiments, the HA1 N-terminal stem segment ends at $A_{p+1}$, $A_{p+2}$, $A_{p+3}$, $A_{p+4}$, $A_{p+5}$, $A_{p+6}$, $A_{p+7}$, $A_{p+8}$, $A_{p+9}$, $A_{p+10}$, $A_{p+11}$, $A_{p+12}$, $A_{p+13}$, $A_{p+14}$, $A_{p+15}$, $A_{p+16}$, $A_{p+17}$, $A_{p+18}$, $A_{p+19}$, $A_{p+20}$, $A_{p+21}$, $A_{p+22}$, $A_{p+23}$, $A_{p+24}$, $A_{p+25}$, $A_{p+26}$, $A_{p+27}$, $A_{p+28}$, $A_{p+29}$, $A_{p+30}$, $A_{p+31}$, $A_{p+32}$, $A_{p+33}$, $A_{p+34}$, $A_{p+35}$, $A_{p+36}$, $A_{p+37}$, $A_{p+38}$, $A_{p+39}$, $A_{p+40}$. In certain embodiments, the HA1 N-terminal stem segment of the flu hemagglutinin polypeptides described herein ends in the range of $A_{p+1}$ to $A_{p+5}$, $A_{p+5}$ to $A_{p+10}$, $A_{p+10}$ to $A_{p+15}$, $A_{p+15}$ to $A_{p+20}$, $A_{p+20}$ to $A_{p+25}$, $A_{p+25}$ to $A_{p+30}$, $A_{p+30}$ to $A_{p+35}$, $A_{p+35}$ to $A_{p+40}$, or $A_{p+40}$ to $A_{p+50}$ The end of an HA1 N-terminal stem segment should be selected in conjunction with the end of the HA1 C-terminal stem segment and the linker so that the resulting linked HA1 stem domain is capable of forming a three-dimensional structure similar, as described below, to an influenza hemagglutinin stem domain.

In certain embodiments, the influenza hemagglutinin stem domain polypeptides comprise an HA1 N-terminal stem segment having at least 70%, 75%, 80%, 85%, 90%, 95%, 96% or 98% amino acid sequence identity to an influenza HA1 N-terminal stem segment known to those of skill in the art. Exemplary known HA1 N-terminal stem segments are provided in the tables disclosed in International Publication No. WO 2010/117786, WO 2011/123495, and WO 2013/043729, U.S. Publication Nos. 2010/0297174, 2013/0129761, and U.S. application Ser. No. 14/345,816, which published as U.S. Patent Publication No. 20150132330 which are incorporated herein by reference in their entireties.

Also provided herein are influenza hemagglutinin stem domain polypeptides comprising deleted forms of HA1 N-terminal stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 N-terminal stem segment. Also provided herein are influenza hemagglutinin stem domain polypeptides comprising deleted forms of a known influenza hemagglutinin stem domain, wherein about 1-10, 10-20, 20-30, 30-40, 40-50, 50-60, 60-70, 70-80, 80-90, 90-100 amino acid residues are deleted from the stem domain. In certain embodiments, provided herein are influenza hemagglutinin stem domain polypeptides that comprise expanded forms of HA1 N-terminal stem segments wherein 1, 2, 3, 4, 5, 6, 7, 8, 9, 10 or more residues are added to the C-terminus of the HA1 N-terminal stem segments; these added residues might be derived from the amino acid sequence of a globular head domain adjacent to an HA1 N-terminal stem segment. Further provided herein are influenza hemagglutinin stem domain polypeptides comprising altered forms of HA1 N-terminal stem segments wherein up to 80, 75, 70 65, 60, 55, 50, 45, 40, 35, 30, 25, 20, 15, 10, 9, 8, 7, 6, 5, 4, 3, 2 or 1 amino acid residues are conservatively substituted with other amino acids. Also provided herein are influenza hemagglutinin stem domain polypeptides comprising altered forms of a known influenza hemagglutinin stem domain, wherein up to about 1-10, 10-20, 20-30, 30-40, 40-50, 50-60, 60-70, 70-80, 80-90, or 90-100 amino acid residues of the stem domain are substituted (e.g., conservatively substituted) with other amino acids. Further provided are influenza hemagglutinin stem domain polypeptides comprising deleted and altered HA1 N-terminal stem segments. In certain embodiments, up to 50, 60, or more amino acids are deleted from the N-terminus of an influenza hemagglutinin stem domain (as viewed from the primary amino acid sequence) and up to 70, 80, or more amino acids are deleted from the C-terminus of an influenza hemagglutinin stem domain (as viewed from the primary amino acid sequence).

The HA1 C-terminal stem segment might be any HA1 C-terminal stem segment recognized by one of skill in the art based on the definition provided herein. Typically, an HA1 C-terminal stem segment corresponds to a polypeptide consisting of the cysteine residue located in sequence at approximately the $277^{th}$ residue of an HA1 (using H3 numbering) through the C-terminal amino acid of the HA1. This cysteine residue, termed $A_q$ herein, is generally capable of forming a disulfide bridge with cysteine residue $A_p$ in the N-terminal stem segment of HA1. Sequences of 17 representative influenza A hemagglutinins are presented in FIG. 14, and residue $A_q$ is identified in each.

In certain embodiments, the HA1 C-terminal stem segment does not start at $A_q$ (e.g., $Cys_{277}$ of an HA1 subunit from an H3 hemagglutinin (i.e., according to H3 numbering)), but at a residue in sequence and structural vicinity to $A_q$. For example, in certain embodiments, the HA1 C-terminal stem segment starts at about $A_{q-1}$, $A_{q-2}$, $A_{q-3}$, $A_{q-4}$, $A_{q-5}$, $A_{q-6}$, $A_{q-7}$, $A_{q-8}$, $A_{q-9}$, $A_{q-10}$, $A_{q-11}$, $A_{q-12}$, $A_{q-13}$, $A_{q-14}$, $A_{q-15}$, $A_{q-20}$, $A_{q-25}$, $A_{q-30}$, $A_{q-35}$, $A_{q-40}$, $A_{q-45}$, $A_{q-50}$, $A_{q-55}$, $A_{q-60}$, $A_{q-65}$, $A_{q-70}$, $A_{q-75}$, or $A_{q-80}$. In certain embodiments, the HA1 C-terminal stem segment starts at in the range of $A_{q-1}$ to $A_{q-5}$, $A_{q-5}$ to $A_{q-10}$, $A_{q-10}$ to $A_{q-15}$, $A_{q-15}$ to $A_{q-20}$, $A_{q-20}$ to $A_{q-25}$, $A_{q-25}$ to $A_{q-30}$, $A_{q-30}$ to $A_{q-35}$, $A_{q-35}$ to $A_{q-40}$, $A_{q-40}$ to $A_{q-45}$, $A_{q-45}$ to $A_{q-50}$, $A_{q-50}$ to $A_{q-55}$, $A_{q-55}$ to $A_{q-60}$, $A_{q-60}$ to $A_{q-65}$, $A_q-65$ to $A_{q-70}$, $A_{q-75}$ to $A_{q-80}$. In other embodiments, the HA1 C-terminal stem segment starts at $A_{q+1}$, $A_{q+2}$, $A_{q+3}$, $A_{q+4}$, $A_{q+5}$, $A_{q+6}$, $A_{q+7}$, $A_{q+8}$, $A_{q+9}$, or $A_{q+10}$. In certain embodiments, the HA1 C-terminal stem segment of the flu hemagglutinin polypeptides described herein starts in the range of $A_{q+1}$ to $A_{q+3}$, $A_{q+3}$ to $A_{q+5}$, $A_{q+5}$ to $A_{q+8}$, $A_{q+8}$ to $A_{q+10}$, $A_{q+10}$ to $A_{q+15}$, or $A_{q+15}$ to $A_{q+20}$. The end of an HA1 N-terminal stem segment should be selected in conjunction with the start of the HA1 C-terminal stem segment and the linker so that the resulting HA1 stem domain is capable of forming a three-dimensional structure similar, as described below, to an influenza hemagglutinin.

In certain embodiments, the influenza hemagglutinin stem domain polypeptides comprise an HA1 C-terminal stem segment having at least 70%, 75%, 80%, 85%, 90%, 95%, 96% or 98% amino acid sequence identity to an influenza HA1 C-terminal stem segment known to those of skill in the art. Exemplary known HA1 C-terminal stem segments are provided in the tables disclosed in International Publication No. WO 2010/117786, WO 2011/123495, and WO 2013/043729, U.S. Publication Nos. 2010/0297174, 2013/0129761, and U.S. application Ser. No. 14/345,816, which published as U.S. Patent Publication No. 20150132330 which are incorporated herein by reference in their entireties.

In certain embodiments, the end of the N-terminal stem segment is $A_{p-1}$, and the start of the C-terminal stem segment is $A_{q-1}$. In certain embodiments, the end of the N-terminal stem segment is $A_{p-2}$, and the start of the C-terminal stem segment is $A_{q-2}$. In certain embodiments, the end of the N-terminal stem segment is $A_{p-3}$, and the start of the C-terminal stem segment is $A_{q-3}$. In certain embodiments, the end of the N-terminal stem segment is $A_{p-4}$, and the start of the C-terminal stem segment is $A_{q-4}$. In certain embodiments, the end of the N-terminal stem segment is $A_{p-5}$, and the start of the C-terminal stem segment is $A_{q-5}$.

In certain embodiments, the end of the N-terminal stem segment is $A_{p+1}$, and the start of the C-terminal stem segment is $A_{q+1}$. In certain embodiments, the end of the N-terminal stem segment is $A_{p+2}$, and the start of the C-terminal stem segment is $A_{q+2}$. In certain embodiments, the end of the N-terminal stem segment is $A_{p+3}$, and the start of the C-terminal stem segment is $A_{q+3}$. In certain embodiments, the end of the N-terminal stem segment is $A_{p+4}$, and the start of the C-terminal stem segment is $A_{q+4}$. In certain embodiments, the end of the N-terminal stem segment is $A_{p+5}$, and the start of the C-terminal stem segment is $A_{q+5}$.

In certain embodiments, the end of the N-terminal stem segment is $A_{p-1}$, and the start of the C-terminal stem segment is $A_{q+1}$. In certain embodiments, the end of the N-terminal stem segment is $A_{p-2}$, and the start of the C-terminal stem segment is $A_{q+2}$. In certain embodiments, the end of the N-terminal stem segment is $A_{p-3}$, and the start of the C-terminal stem segment is $A_{q+3}$. In certain embodiments, the end of the N-terminal stem segment is $A_{p-4}$, and the start of the C-terminal stem segment is $A_{q+4}$. In certain embodiments, the end of the N-terminal stem segment is $A_{p-5}$, and the start of the C-terminal stem segment is $A_{q+5}$.

In certain embodiments, the end of the N-terminal stem segment is $A_{p+1}$, and the start of the C-terminal stem segment is $A_{q-1}$. In certain embodiments, the end of the N-terminal stem segment is $A_{p+2}$, and the start of the C-terminal stem segment is $A_{q-2}$. In certain embodiments, the end of the N-terminal stem segment is $A_{p+3}$, and the start of the C-terminal stem segment is $A_{q-3}$. In certain embodiments, the end of the N-terminal stem segment is $A_{p+4}$, and the start of the C-terminal stem segment is $A_{q-4}$. In certain embodiments, the end of the N-terminal stem segment is $A_{p+5}$, and the start of the C-terminal stem segment is $A_{q-5}$.

Also provided herein are influenza hemagglutinin stem domain polypeptides comprising deleted forms of HA1 C-terminal stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 C-terminal stem segment. Also provided herein are influenza hemagglutinin stem domain polypeptides comprising deleted forms of a known influenza hemagglutinin stem domain, wherein about 1-10, 10-20, 20-30, 30-40, 40-50, 50-60, 60-70, 70-80, 80-90, or 90-100 amino acid residues are deleted from the stem domain. In certain embodiments, provided herein are influenza hemagglutinin stem domain polypeptides that comprise expanded forms of HA1 C-terminal stem segments wherein 1, 2, 3, 4, 5, 6, 7, 8, 9, 10 or more residues are added to the N-terminus of the HA1 C-terminal stem segments; these added residues might be derived from the amino acid sequence of a globular head domain adjacent to an HA1 C-terminal stem segment. In particular embodiments, if one residue is added to the C-terminal stem segment, then one residue is added to the N-terminal stem segment; if two residues are added to the C-terminal stem segment, then two residues are added to the N-terminal stem segment; if three residues are added to the C-terminal stem segment, then three residues are added to the N-terminal stem segment. Further provided herein are influenza hemagglutinin stem domain polypeptides comprising altered forms of HA1 C-terminal stem segments wherein up to about 80, 75, 70 65, 60, 55, 50, 45, 40, 35, 30, 25, 20, 15, 10, 9, 8, 7, 6, 5, 4, 3, 2 or 1 amino acid residues are conservatively substituted with other amino acids. Also provided herein are influenza hemagglutinin stem domain polypeptides comprising altered forms of HA1 C-terminal stem segments, wherein up to about 1-10, 10-20, 20-30, 30-40, 40-50, 50-60, 60-70, 70-80, 80-90, or 90-100 amino acid residues of the HA1 C-terminal stem segment are substituted (e.g., conservatively substituted) with other amino acids. Further provided are influenza hemagglutinin stem domain polypeptides comprising deleted and altered HA1 C-terminal stem segments. In certain embodiments, the C-terminal stem segment comprises or more modified glycosylation sites. In certain embodiments, the N-terminal stem segment comprises or more modified glycosylation sites. In other embodiments, the C-terminal stem segment and N-terminal stem segment comprise one or more modified glycosylation sites.

In certain embodiments, the influenza hemagglutinin stem domain polypeptides provided herein comprise a chimeric/hybrid of the stem domain of the HA1 subunit. The chimeric of the stem domain of the HA1 subunit may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 60, 51, 52, 53, 54, 55, 56, 57, 58, 59, 60, 61, 62, 63, 64, 65, 66, 67, 68, 69, 70, 71, 72, 73, 75, 75, 76, 77, 78, 79, or 80 amino acids of the stem domain of the HA1 subunit of a first influenza virus strain or subtype and the remainder of amino acids of the chimeric of the stem domain of the HA1 subunit may be from a second influenza virus strain or subtype. In certain embodiments, the chimeric of the stem domain of the HA1 subunit comprises 1-10, 10-20, 20-30, 30-40, 40-50, 50-60, 60-70, 70-80, 80-90, or 90-100 amino acids of the stem domain of the HA1 subunit of a first influenza virus strain or subtype and the remainder of amino acids of the chimeric of the stem domain of the HA1 subunit are from a second influenza virus strain or subtype. In certain embodiments, the influenza hemagglutinin stem domain polypeptides provided herein comprise an HA2 subunit and a chimeric of the stem domain of the HA1 subunit. In certain embodiments, the influenza hemagglutinin stem domain polypeptide comprises a chimeric/hybrid of the stem domain of an HA1 subunit in which one or more naturally occurring glycosylation sites have been modified such that the modification, disrupts the ability of a glycan to attach to the modified glycosylation site, as described in Section 5.4.1, infra. Without being bound by any particular theory of operation, it is believed that immunogenicity and accessibility antigenic regions within the stem domain can be increased by modifying one or more glycosylation sites within the stem domain in a manner that disrupts the glycosylation (i.e. the attachment of a glycan) at the sites.

The influenza hemagglutinin stem domain polypeptides might be based on (i.e. might have sequence identity, as described above) any influenza hemagglutinin known to those of skill or later discovered. In certain embodiments, influenza hemagglutinin stem domain polypeptides are based on an influenza A hemagglutinin. In certain embodiments, the influenza hemagglutinin stem domain polypeptides are based on an influenza A hemagglutinin selected from the group consisting of H1, H2, H3, H4, H5, H6, H7, H8, H9, H10, H11, H12, H13, H14, H15, H16, H17, and H18. In certain embodiments, influenza hemagglutinin stem domain polypeptides are based on an influenza B hemagglutinin, as described in detail below.

The HA1 N-terminal stem segments might be based on (i.e. might have sequence identity, as described above) any HA1 N-terminal stem segments known to those of skill or later discovered. In certain embodiments, the HA1 N-terminal stem segments are based on influenza A HA1 N-terminal stem segments. In certain embodiments, the HA1 N-terminal stem segments are based on an influenza A hemagglutinin selected from the group consisting of H1, H2, H3, H4, H5, H6, H7, H8, H9, H10, H11, H12, H13, H14, H15, H16, H17, and H18. In certain embodiments, the HA1 N-terminal stem segment is or is based on the HA-1 N-terminal stem segment of an Ann Arbor/6/60, A/Puerto Rico/8/34, or A/Perth/16/2009 influenza virus.

The HA1 C-terminal stem segments might be based on (i.e. might have sequence identity, as described above) any HA1 C-terminal stem segments known to those of skill or later discovered. In certain embodiments, the HA1 C-terminal stem segments are based on influenza A HA1 C-terminal stem segments. In certain embodiments, the HA1 C-terminal stem segments are based on an influenza A hemagglutinin selected from the group consisting of H1, H2, H3, H4, H5, H6, H7, H8, H9, H10, H11, H12, H13, H14, H15, H16, H17, and H18. In certain embodiments, the HA1 C-terminal stem segment is or is based on the HA-1 N-terminal stem segment of an Ann Arbor/6/60, A/Puerto Rico/8/34, or A/Perth/16/2009 influenza virus.

The HA2 stem domains might be based on (i.e. might have sequence identity, as described above) any HA2 stem domains known to those of skill or later discovered. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15, H16, H17, and H18. In certain embodiments, the HA2 stem domain is selected from SEQ ID NOS:34-49. In certain embodiments, the HA2 stem domain is or is based on the HA stem domain of an A/Ann Arbor/6/60-like, A/Puerto Rico/8/1934-like, A/Perth/16/2009-like, A/California/07/2009- like, A/Brisbane/59/07-like, A/New Caledonia/20/1999-like or A/Victoria/361/201-like influenza virus. In certain embodiments, the HA2 stem domain is or is based on a later discovered HA2 stem domain.

In certain embodiments, the HA2 stem domains are from the same influenza virus strain or subtype as the stem domain of the HA1 subunit.

In embodiments comprising a signal peptide, the signal peptide might be based on any influenza virus signal peptide known to those of skill in the art. In certain embodiments, the signal peptides are based on influenza A signal peptides. In certain embodiments, the signal peptides are based on an influenza A hemagglutinin selected from the group consisting of H1, H2, H3, H4, H5, H6, H7, H8, H9, H10, H11, H12, H13, H14, H15 and H16. In certain embodiments, the signal peptide might be any signal peptide deemed useful to one of skill in the art.

In embodiments comprising a luminal domain, the luminal domain might be based on any influenza luminal domain known to those of skill in the art. In certain embodiments, the luminal domains are based on influenza A luminal domains. In certain embodiments, the HA2 luminal domains are based on an influenza A hemagglutinin selected from the group consisting of H1, H2, H3, H4, H5, H6, H7, H8, H9, H10, H11, H12, H13, H14, H15, H16, H17, and H18. In certain embodiments, the luminal domain might be any luminal domain deemed useful to one of skill in the art. In certain embodiments, the luminal domain is from the same influenza virus strain or subtype as the stem domain of the HA2 subunit.

In certain embodiments, the cytoplasmic, transmembrane and luminal domains are from the same influenza virus strain or subtype as the stem domain of the HA2 subunit. In other embodiments, the cytoplasmic and transmembrane domains are from the same influenza virus strain or subtype as the stem domain of the HA2 subunit. In certain embodiments, the cytoplasmic and luminal domain are from the same influenza virus strain or subtype as the stem domain of the HA2 subunit.

In embodiments comprising a transmembrane domain, the transmembrane domain might be based on any influenza transmembrane domain known to those of skill in the art. In certain embodiments, the transmembrane domains are based on influenza A transmembrane domains. In certain embodiments, the HA2 transmembrane domains are based on an influenza A hemagglutinin selected from the group consisting of H1, H2, H3, H4, H5, H6, H7, H8, H9, H10, H11, H12, H13, H14, H15, H16, H17, and H18. In certain embodiments, the transmembrane domain might be any transmembrane domain deemed useful to one of skill in the art. In certain embodiments, the transmembrane domain is selected from SEQ ID NOS:67-82. In certain embodiments, the transmembrane domains are from the same influenza virus strain or subtype as the stem domain of the HA2 subunit.

In embodiments comprising a cytoplasmic domain, the cytoplasmic domain might be based on any influenza cytoplasmic domain known to those of skill in the art. In certain embodiments, the cytoplasmic domains are based on influenza A cytoplasmic domains. In certain embodiments, the HA2 cytoplasmic domains are based on an influenza A hemagglutinin selected from the group consisting of H1, H2, H3, H4, H5, H6, H7, H8, H9, H10, H11, H12, H13, H14, H15, H16, H17, and H18. In certain embodiments, the cytoplasmic domain might be any cytoplasmic domain deemed useful to one of skill in the art. In certain embodiments, the cytoplasmic domain is selected from SEQ ID NOS:83-98. In certain embodiments, the cytoplasmic domains are from the same influenza virus strain or subtype as the stem domain of the HA2 subunit.

In certain embodiments, one or more of the glycosylation sites in the hemagglutinin stem domain are modified (e.g., by amino acid addition, deletion or substitution) such that glycosylation at these sites will not occur during processing and maturation of the polypeptide. Those of skill in the art will recognize that influenza HA typically comprises one or more glycosylation sites (e.g. Asn-Xaa-Ser/Thr/Cys, wherein Xaa is any amino acid or, in certain embodiments, wherein Xaa is any amino acid except Pro). In certain embodiments, one or more amino acid residues in a glycosylation site are conservatively substituted with an amino acid residue that disrupts the glycosylation site. In certain embodiments, one or more amino acid residues in a glycosylation site are substituted with any amino acid residue that disrupts the glycosylation site. In certain embodiments, one or more asparagine residues in a glycosylation sequence is substituted with alanine. In a particular embodiment, the asparagine at position 38 of an H3 hemagglutinin is changed to an alanine. In certain embodiments, one or more of the glycosylation sites in the hemagglutinin stem domain are modified by using a chemical (e.g., a deglycosylation agent), such that glycosylation at these sites will not occur during processing and maturation of the peptide. In certain embodiments, the hemagglutinin stem domain comprises one or more modified glycosylation sites as discussed in Section 5.4.1, infra.

In certain embodiments, the HA stem domain is as disclosed in International Publication Nos. WO 2011/123495, WO 2013/043729, and WO 2014/099931, U.S. Publication Nos. 2013/0129761, 2014/0328875, and U.S. application Ser. No. 14/345,816, which published as U.S. Patent Publication No. 20150132330 which are incorporated herein by reference in their entirety. In certain embodiments, the HA stem domain comprises amino acid sequences as described in Tables 6, 6A, 7, and 7A of International Publication No. WO 2011/123495 and WO 2013/043729, U.S. Publication No. 2013/0129761, and U.S. application Ser. No. 14/345,816, which published as U.S. Patent Publication No. 20150132330 which are incorporated by reference herein in their entirety, and Tables 1, 1A, and 2 of International Publication No. WO 2010/117786 and U.S. Publication No. 2010/0297174, which are incorporated herein by reference in their entirety.

In certain embodiments, the HA2 stem domains are based on an influenza B hemagglutinin. Exemplary residues for the end of an N-terminal stem segment and the end of a C-terminal stem segment of an influenza B hemagglutinin are indicated in FIG. 2 of International Publication No. WO 2013/043729, which is incorporated herein by reference in its entirety. In certain embodiments, the HA2 stem domain is according to SEQ ID NO:99, presented in Tables 3 and 4 as disclosed in International Publication No. WO 2013/043729, which is incorporated herein by reference in its entirety.

In particular embodiments, the boundaries of the influenza B virus HA1 N-terminal stem segment and influenza B virus HA1 C-terminal segment are defined with respect to six pairs of amino acid residues: $Arg_{50}$ and $Ser_{277}$; $Ala_{66}$ and $Trp_{271}$; $Lys_{80}$ and $Ser_{277}$, $Cys_{94}$ and $Cys_{143}$; $Cys_{178}$ and $Cys_{272}$ and $Cys_{54}$ and $Cys_{272}$. Positions of these six pairs of residues are also highlighted in FIG. 3 of International Publication No. WO 2013/043729, which is incorporated herein by reference in its entirety. The residue numbers are based on the numbering of the B-HA from influenza virus B as described in Protein Data Bank accession No. 3BT6. The amino acid sequence corresponding to the X-ray crystal structure of the B-HA protein in Protein Data Bank accession No. 3BT6 is aligned with representative H1 and H3 amino acid sequence and shown in FIG. 2 of International Publication No. WO 2013/043729, which is incorporated herein by reference in its entirety.

In certain embodiments, an influenza B virus HA1 N-terminal stem segment starts at residue 1 (based on numbering of an influenza B virus HA1 subunit as in PDB file 3BT6) and ends at $Arg_{50}$. In certain embodiments, an influenza B virus HA1 N-terminal stem segment starts at residue 1 and ends at $Ala_{66}$. In some embodiments, an influenza B virus HA1 N-terminal stem segment starts at residue 1 and ends at $Lys_{80}$. In some embodiments, an influenza B virus N-terminal stem segment starts at residue 1 and ends at $Arg_{80}$. In some embodiments, an influenza B virus N-terminal stem segment starts at residue 1 and ends at Cys54. In some embodiments, an influenza B virus N-terminal stem segment starts at residue 1 and ends at $Cys_{94}$. In some embodiments, an influenza B virus N-terminal stem segment starts at residue 1 and ends at $Cys_{178}$.

In certain embodiments, the influenza B virus HA2 domain is in tertiary or quaternary association with the influenza B virus HA1 domain through the influenza B virus HA1 N-terminal segment, the influenza B virus HA1 C-terminal segment, or both.

In some embodiments, the influenza B virus HA1 C-terminal segment and the influenza B virus HA2 subunit are covalently linked. For example, at its C-terminus (e.g., at the ending residue of the second sequence), the influenza B virus HA1 C-terminal segment is covalently linked to the influenza B virus HA2 domain in such embodiments. In some embodiments, the influenza B virus HA1 C-terminal segment and influenza B virus HA2 domain form a continuous polypeptide chain.

As illustrated in FIG. 14 and in FIG. 2 of International Publication No. WO 2013/043729, which is incorporated herein by reference in its entirety, HA1 N-terminal stem segments share sequence identity between influenza A and influenza B and additionally across influenza A subtypes. Similarly, HA1 C-terminal stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin stem domain polypeptide is a hybrid polypeptide that comprises or consists essentially of segments and/or domains from a plurality of influenza strains or subtypes. For example, an influenza hemagglutinin stem domain polypeptide might comprise HA1 N-terminal and HA1 C-terminal stem segments from different influenza A virus HA subtypes. In some embodiments, the HA1 N-terminal stem segment is from influenza A virus while the HA1 C-terminal stem segment is from influenza B virus. Similarly, HA2 may also be from influenza A virus while the HA1 N-terminal and/or C-terminal stem segment is from influenza B virus.

It will be understood that any combination of the sequence elements listed in Tables 1-4 of International Publication No. WO 2013/043729, which is incorporated herein in its entirety, or the variants thereof may be used to form the hemagglutinin HA stem domain polypeptides of the present invention.

In an influenza stem domain polypeptide provided herein, a linker covalently connects the HA1 N-terminal stem segment to the HA1 C-terminal stem segment. In certain embodiments, the linker is a direct bond. In certain embodiments, the linker is a globular head, or a fragment thereof, from an influenza virus heterologous to the influenza stem domain. In certain embodiments, the linker is a globular head, or a fragment thereof, from an influenza virus heterologous to the stem domain of the HA2 subunit of a chimeric influenza virus hemagglutinin. In certain embodiments, the linker is a globular head, or a fragment thereof, from an influenza virus heterologous to the stem domain of the HA1 and/or HA2 subunit of a chimeric influenza virus hemagglutinin. In certain embodiments, the linker is an antibody Fab region or fragment thereof. In other embodiments, the linker is a non-influenza, viral glycoprotein or fragment thereof. In certain embodiments, the linker is a peptide that comprises one amino acid residue, two or fewer amino acid residues, three or fewer amino acid residues, four or fewer amino acid residues, five or fewer amino acid residues, ten or fewer amino acid residues, 15 or fewer amino acid residues, 20 or fewer amino acid residues, 30 or fewer amino acid residues, 40 or fewer amino acid residues, or 50 or fewer amino acid residues. In certain embodiments, the linker peptide comprises 50 or more amino acid residues. In certain embodiments, the linker substantially lacks a globular head domain. In other words, the linker comprises no more than 10, 9, 8, 7, 6, 5 or 4 contiguous, sequential amino acid residues from the amino acid sequence of an influenza globular head domain. In certain embodiments, the linker is other than Lys-Leu-Asn-Gly-Ser-Gly-Ile-Met-Lys-Thr-Glu-Gly-Thr-Leu-Glu-Asn (SEQ ID NO:104). In certain embodiments, the linker is other than Asn-Asn-Ile-Asp-Thr (SEQ ID NO:105) or Lys-Leu-Asn-Gly-Ser-Gly-Ile-Met-Lys-Thr-Glu-Gly-Thr-Leu-Glu-Asn (SEQ ID NO:106). In certain embodiments, the linker is other than Asn-Asn-Ile-Asp-Thr (SEQ ID NO:105).

In certain embodiments, the linker is covalently connected, at one end, to the C-terminus of the HA1 N-terminal stem segment. The linker peptide is also covalently connected, at the other end, to the N-terminus of the HA1 C-terminal stem segment. In certain embodiments, one of the covalent links is an amide bond. In certain embodiments, both covalent links are amide bonds.

The linker might be any linker deemed suitable by one of skill in the art. In certain embodiments, the linker is selected based on the HA1 N-terminal stem segment and the HA1 C-terminal stem segment. In these embodiments, the linker might be selected with molecular modeling programs such as InsightII and Quanta, both from Accelrys. In certain embodiments, the linker is a structural motif that allows structural alignment of the HA1 N-terminal stem segment and the HA1 C-terminal stem segment that is consistent with the structure of a hemagglutinin stem domain as recognized by those of skill in the art. In certain embodiments, the linker is selected from a library of candidate linkers. In certain embodiments, the library includes three dimensional polypeptide structures in a publicly available database such as the Protein Data Bank (PDB) or the Macromolecular Structure Database at the European Molecular Biology Laboratory (EMBL) or European Bioinformatics Institute (EBI). In certain embodiments, the library includes proprietary three-dimensional polypeptide structures associated with commercial programs such as InsightII and Quanta, both from Accelrys. Additionally, any databases or collections of protein structures or structural elements can be used to select the linker. Exemplary database or collections of protein structural elements include but are not limited to the Structural Classification of Proteins (SCOP, maintained by and available through Cambridge University); the database of protein families (Pfam, maintained by and available through the Wellcome Trust Sanger Institute); the Universal Protein Resource (UniProt, maintained by and available through the UniProt Consortium); the Integrated resource for protein families (InterPro; maintained by and available through EMBL-EBI); the Class Architecture Topology Homologous superfamily (CATH, maintained by and available through Institute of Structural and Molecular Biology at the University College London); and the families of structurally similar proteins (FSSP, maintained by and available through EBI). Any algorithm deemed suitable by one of skill in the art may be used to select the linker, including but not limited by those used by SCOP, CATH and FSSP. Useful examples include but are not limited to Pymol (Delano Scientific LLC), InsightII and Quanta (both from Accelrys), MIDAS (University of California, San Francisco), SwissPDB viewer (Swiss Institute of Bioinformatics), TOPOFIT (Northeastern University), CB SU LOOPP (Cornell University), and SuperPose (University of Alberta, Edmonton). In certain embodiments, the linker is a direct bond. In certain embodiments, the linker is selected from the group consisting of Gly, Gly-Gly, Gly-Gly-Gly, Gly-Gly-Gly-Gly and Gly-Gly-Gly-Gly-Gly. In certain embodiments, the linker is selected from the group consisting of Gly-Pro and Pro-Gly. In certain embodiments, the linker is a 281 turn loop, e.g. having the sequence ITPNGSIPNDKPFQNVNKITYGA (SEQ ID NO:100).

In certain embodiments, the linker comprises a glycosylation sequence. In certain embodiments, the linker comprises an amino acid sequence according to Asn-Xaa-Ser/Thr/Cys where Xaa is any amino acid or, in certain embodiments, wherein Xaa is any amino acid except Pro and Ser/Thr/Cys is serine, threonine or cysteine. In certain embodiments, the linker comprises the amino acid sequence Asn-Ala-Ser. In certain embodiments, the linker is a glycosylation sequence. In certain embodiments, the linker is an amino acid sequence according to Asn-Xaa-Ser/Thr/Cys where Xaa is any amino acid or, in certain embodiments, wherein Xaa is any amino acid except Pro and Ser/Thr/Cys is serine, threonine or cysteine. In certain embodiments, the linker is the amino acid sequence Asn-Ala-Ser.

In certain embodiments, influenza hemagglutinin stem domain polypeptides are capable of forming a three dimensional structure that is similar to the three dimensional structure of the stem domain of a native influenza hemagglutinin. Structural similarity might be evaluated based on any technique deemed suitable by those of skill in the art. For instance, reaction, e.g. under non-denaturing conditions, of an influenza hemagglutinin stem domain polypeptide with a neutralizing antibody or antiserum that recognizes a native influenza hemagglutinin might indicate structural similarity. Useful neutralizing antibodies or antisera are described in, e.g. Sui, et al., 2009*, Nat. Struct. Mol. Biol.* 16(3):265-273, Ekiert et al., Feb. 26, 2009*, Science*[DOI: 10.1126/science.1171491], and Kashyap et al., 2008*, Proc. Natl. Acad. Sci. USA* 105(16):5986-5991, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a hemagglutinin.

In certain embodiments, structural similarity might be assessed by spectroscopic techniques such as circular dichroism, Raman spectroscopy, NMR, 3D NMR and X-ray crystallography. Known influenza hemagglutinin structures determined by X-ray crystallography are described in structural coordinates in Protein Data Bank files including but not limited to 1HGJ (an HA H3N2 strain) and 1RUZ (an HA H1N1 strain).

In certain embodiments, structural similarity is evaluated by RMS deviation between corresponding superimposed portions of two structures. In order to create a meaningful superimposition, in certain embodiments, the coordinates of at least 20 corresponding atoms, 25 corresponding atoms, 30 corresponding atoms, 40 corresponding atoms, 50 corresponding atoms, 60 corresponding atoms, 70 corresponding atoms, 80 corresponding atoms, 90 corresponding atoms, 100 corresponding atoms, 120 corresponding atoms, 150 corresponding atoms, 200 corresponding atoms, or 250 corresponding atoms are used to calculate an RMS deviation.

In certain embodiments, the coordinates of all corresponding atoms in amino acid backbones are used to calculate an RMS deviation. In certain embodiments, the coordinates of all corresponding alpha carbon-atoms in the amino acid backbones are used to calculate an RMS deviation. In certain embodiments, the coordinates of all corresponding identical residues, including side chains, are used to calculate an RMS deviation.

In certain embodiments, coordinates of all or a portion of the corresponding atoms in a HA1 N-terminal segment are used to calculate an RMS deviation. In certain embodiments, coordinates of all or a portion of the corresponding atoms in a HA1 C-terminal segment are used to calculate an RMS deviation. In certain embodiments, coordinates of all or a portion of the corresponding atoms in both a HA1 N-terminal segment and a C-terminal segment are used to calculate an RMS deviation. In certain embodiments, coordinates of all or a portion of corresponding atoms in HA2 domains are used to calculate an RMS deviation.

In certain embodiments, the RMS deviation between the structures of a influenza hemagglutinin stem domain polypeptide and corresponding portions of a known influenza A virus hemagglutinin stem domain (e.g., from 1HGJ or 1RUZ) is 5 Å or less, 4 Å or less, 3 Å or less, 2.5 Å or less, 2 Å or less, 1.5 Å or less, 1 Å or less, 0.75 Å or less, 0.5 Å or less, 0.3 Å or less, 0.2 Å or less, or 0.1 Å or less. Commercially available or open source software might be used to perform the structural superimpositions and/or RMS deviation calculations. Useful examples include but are not limited to Pymol (Delano Scientific LLC), InsightII and Quanta (both from Accelrys), MIDAS (University of California, San Francisco), SwissPDB viewer (Swiss Institute of Bioinformatics), TOPOFIT (Northeastern University), CBSU LOOPP (Cornell University), and SuperPose (University of Alberta, Edmonton).

In certain embodiments, any influenza hemagglutinin stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:101), FLAG epitope or other purification tag can facilitate purification of a polypeptide provided herein. In some embodiments, the His tag has the sequence, (His)n, wherein n is 2, 3, 4, 5, 6, 7, 8, 9, 10, 11, 12, 13, 14, 15, 16, 17, 18, 19, 20 or greater. A foldon, or trimerization, domain from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. The foldon domain can have any foldon sequence known to those of skill in the art (see, e.g., Papanikolopoulou et al., 2004, *J. Biol. Chem.* 279(10):8991-8998, the contents of which are hereby incorporated by reference in their entirety. Examples include GSGYIPEAPRDGQAYVRKDGEWVLLSTFL (SEQ ID NO:102). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50).

In certain embodiments, provided are influenza hemagglutinin stem domain polypeptides comprising an elastase cleavage site. Those of skill in the art will recognize that the trypsin cleavage site at the linkage between HA1 and HA2 can be mutated to an elastase cleavage site by substituting valine for the arginine or lysine at the HA1-HA2 cleavage site in a hemagglutinin sequence (see, e.g., Stech et al., 2005, *Nature Med.* 11(6):683-689). Accordingly, providesd herein are influenza hemagglutinin stem domain polypeptides having a valine substitution at the C-terminus of the C-terminal stem segment (i.e., the C-terminus of the HA1 domain).

In certain embodiments, provided herein are influenza virus hemagglutinin stem domain polypeptides comprising a modified multi-basic cleavage site. In a specific embodiment, an influenza virus stem domain polypeptide described herein does not contain a multi-basic cleavage site.

In certain embodiments, provided herein are influenza hemagglutinin stem domain polypeptides that are predicted to be resistant to protease cleavage at the junction between HA1 and HA2. Those of skill in the art should recognize that the Arg-Gly sequence spanning HA1 and HA2 is a recognition site for trypsin and is typically cleaved for hemagglutinin activation. Since the stem domain polypeptides described herein need not be activated, provided herein are influenza hemagglutinin stem domain polypeptides that are predicted to be resistant to protease cleavage. In certain embodiments, provided is any influenza hemagglutinin stem domain polypeptide described herein wherein the protease site spanning HA1 and HA2 is mutated to a sequence that is resistant to protease cleavage. In certain embodiments, provided is any influenza hemagglutinin stem domain polypeptide described herein wherein the C-terminal residue of the HA1 C-terminal stem segment is any residue other than Lys or Arg. In certain embodiments, provided is any influenza hemagglutinin stem domain polypeptide described herein wherein the N-terminal residue of the HA2 domain is proline. In certain embodiments, provided is any influenza hemagglutinin stem domain polypeptide described herein wherein the C-terminal residue of the HA1 C-terminal stem segment is Ala and the N-terminal residue of the HA2 domain is also Ala.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to, in sequence, a protease cleavage site, a trimerization domain, and a purification tag. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to, in sequence, a cleavage site, a trimerization domain and a purification tag. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to, in sequence, a protease cleavage site, a trimerization domain and a purification tag. In certain embodiments, the protease cleavage site is a thrombin cleavage site. In certain embodiments, the cleavage site has the amino acid sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is covalently linked to, in sequence, a cleavage site, a trimerization domain and a purification tag. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is covalently linked to, in sequence, a cleavage site, a trimerization domain and a purification tag. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is in turn covalently linked to an HA2 transmembrane domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain.

In certain embodiments, provided herein are influenza hemagglutinin stem domain polypeptides consisting of an HA1 N-terminal stem segment covalently linked to a linker, in turn covalently linked to an HA1 C-terminal stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin stem domain polypeptides consisting of an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin stem domain polypeptides consisting of a signal peptide covalently linked to an HA1 N-terminal stem segment covalently linked to a linker, in turn covalently linked to an HA1 C-terminal stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

In certain embodiments, the influenza hemagglutinin polypeptides described herein are not recognized by the antibody CR6261, CR6325, CR6329, CR6307, CR6323, 2A, D7, D8, F10, G17, H40, A66, D80, E88, E90, H98, C179 (produced by hybridoma FERM BP-4517; clones sold by Takara Bio, Inc. (Otsu, Shiga, Japan)), AI3C (FERM BP-4516), any other antibody described in Ekiert D C et al. (2009) Antibody Recognition of a Highly Conserved Influenza Virus Epitope. Science (published in Science Express Feb. 26, 2009); Kashyap et al. (2008), or any other similar antibodies.

5.3.1.1 Influenza Hemagglutinin Short Stem Domain Polypeptides

In certain embodiments, the influenza hemagglutinin stem domain polypeptide is an influenza hemagglutinin short stem domain polypeptide. In certain embodiments, the influenza hemagglutinin stem domain polypeptide is an influenza hemagglutinin short stem domain polypeptide as described in International Publication Nos. WO 2011/123495, WO 2013/043729, and WO 2014/099931, U.S. Publication Nos. 2013/0129761, 2014/0328875, and U.S. application Ser. No. 14/345,816, which published as U.S. Patent Publication No. 20150132330 which are incorporated herein by reference in their entirety. The typical primary structure of an influenza hemagglutinin short stem domain polypeptide provided herein comprises, in the following order: an HA1 N-terminal stem segment, a linker, an HA1 C-terminal short stem segment and an HA2. The primary sequence can be formed by a single polypeptide, or it can be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide can be cleaved, for example by a protease, under appropriate expression conditions to yield two polypeptides in quaternary association. The cleavage is typically between the HA1 C-terminal short stem segment and the HA2. In certain embodiments, provided herein are multiple polypeptides. In multiple polypeptide embodiments, the HA1 segments and HA2 are in quaternary association.

In certain embodiments, an influenza hemagglutinin short stem domain polypeptide provided herein is monomeric. In certain embodiments, an influenza hemagglutinin short stem domain polypeptide provided herein is multimeric. In certain embodiments, an influenza hemagglutinin short stem domain polypeptide provided herein is trimeric. Those of skill in the art will recognize that native influenza hemagglutinin polypeptides are capable of trimerization in vivo and that certain influenza hemagglutinin short stem domain polypeptides provided herein are capable of trimerization. In particular embodiments described below, influenza hemagglutinin short stem domain polypeptides provided herein comprise trimerization domains to facilitate trimerization.

In certain embodiments, an influenza hemagglutinin short stem domain polypeptide comprises a signal peptide. Typically, the signal peptide is cleaved during or after polypeptide expression and translation to yield a mature influenza hemagglutinin short stem domain polypeptide. The signal peptide can be advantageous for expression of the influenza hemagglutinin short stem domain polypeptides. In certain embodiments, also provided herein are mature influenza hemagglutinin short stem domain polypeptides that lack a signal peptide.

Influenza hemagglutinin HA2 typically comprises a stem domain, transmembrane domain and a cytoplasmic domain. In certain embodiments, provided herein are influenza hemagglutinin short stem domain polypeptides that comprise an HA2 stem domain, an HA2 luminal domain, an HA2 transmembrane domain and an HA2 cytoplasmic domain. In certain embodiments, provided herein are influenza hemagglutinin short stem domain polypeptides that comprise an HA2 stem domain, an HA2 luminal domain, and an HA2 transmembrane domain but lack some or all of the typical cytoplasmic domain. In certain embodiments, provided herein are influenza hemagglutinin short stem domain polypeptides that comprise an HA2 stem domain and an HA2 luminal domain but lack both an HA2 transmembrane domain and an HA2 cytoplasmic domain. In certain embodiments, provided herein are influenza hemagglutinin short stem domain polypeptides that comprise an HA2 stem domain but lack an HA2 luminal domain, an HA2 transmembrane domain and an HA2 cytoplasmic domain. In certain embodiments, the influenza hemagglutinin short stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A and influenza B hemagglutinins are provided in the tables disclosed in International Publication No. WO 2010/117786, WO 2011/123495, and WO 2013/043729, U.S. Publication Nos. 2010/0297174, 2013/0129761, and U.S. application Ser. No. 14/345,816, which published as U.S. Patent Publication No. 20150132330 which are incorporated herein by reference in their entireties.

Also provided herein are influenza hemagglutinin short stem domain polypeptides comprising deleted forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA2 stem domain. Further provided herein are influenza hemagglutinin short stem domain polypeptides comprising altered forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin short stem domain polypeptides comprising deleted and altered HA2 stem domains.

The HA1 N-terminal stem segment can be any HA1 N-terminal stem provided herein. Exemplary known HA1 N-terminal stem segments are provided in the tables disclosed in International Publication No. WO 2010/117786, WO 2011/123495, and WO 2013/043729, U.S. Publication Nos. 2010/0297174, 2013/0129761, and U.S. application Ser. No. 14/345,816, which published as U.S. Patent Publication No. 20150132330 which are incorporated herein by reference in their entireties.

The HA1 C-terminal short stem segment can be any HA1 C-terminal short stem segment recognized by one of skill in the art based on the definition provided herein. Typically, an HA1 C-terminal short stem segment corresponds to a polypeptide consisting of the cysteine residue located in sequence at approximately the $305^{th}$ residue of an HA1 (using H3 numbering) through the C-terminal amino acid of the HA1. This cysteine residue, termed $B_q$ herein, is capable of being linked to a cysteine residue $A_p$ in the N-terminal stem segment of HA1. Sequences of 17 representative influenza A hemagglutinins are presented in FIG. 14, and residue $B_q$ is identified in each.

In certain embodiments, the HA1 C-terminal short stem segment does not start at $B_q$ (e.g., $Cys_{305}$ of an HA1 subunit from an H3 hemagglutinin (i.e., according to H3 numbering)), but at a residue in sequence and structural vicinity to $B_q$. For example, in certain embodiments, the HA1 C-terminal short stem segment starts at $B_{q-1}$, $B_{q-2}$, $B_{q-3}$, $B_{q-5}$, $B_{q-6}$, $B_{q-7}$, $B_{q-8}$, $B_{q-9}$, $B_{q-10}$, $B_{q-11}$, $B_{q-12}$, $B_{q-13}$, $B_{q-14}$, $B_{q-15}$, $B_{q-20}$, $B_{q-25}$, $B_{q-30}$, $B_{q-35}$, $B_{q-40}$, $B_{q-45}$, $B_{q-50}$, $B_{q-55}$, $B_{q-60}$, $B_{q-65}$, $B_{q-70}$, $B_{q-75}$, or $B_{q-80}$. In other embodiments, the HA1 C-terminal short stem segment starts at $B_{q+1}$, $B_{q+2}$, $B_{q+3}$, $B_{q+4}$, $B_{q+5}$, $B_{q+6}$, $B_{q+7}$, $B_{q+8}$, $B_{q+9}$, or $B_{q+10}$. The end of an HA1 N-terminal stem segment should be selected in conjunction with the start of the HA1 C-terminal short stem segment and the linker so that the resulting HA1 stem domain is capable of forming a three-dimensional structure similar, as described below, to an influenza hemagglutinin.

In certain embodiments, the influenza hemagglutinin short stem domain polypeptides comprise an HA1 C-terminal short stem segment having at least 70%, 75%, 80%, 85%, 90%, 95%, 96% or 98% amino acid sequence identity to an influenza HA1 C-terminal short stem segment known to those of skill in the art. Exemplary known HA1 C-terminal short stem segments are provided in the tables disclosed in International Publication No. WO 2010/117786, WO 2011/123495, and WO 2013/043729, U.S. Publication Nos. 2010/0297174, 2013/0129761, and U.S. application Ser. No. 14/345,816, which published as U.S. Patent Publication No. 20150132330 which are incorporated herein by reference in their entireties.

In certain embodiments, the end of the N-terminal stem segment is $A_{p-1}$, and the start of the C-terminal short stem segment is $B_{q-1}$. In certain embodiments, the end of the N-terminal stem segment is $A_{p-2}$, and the start of the C-terminal short stem segment is $B_{q-2}$. In certain embodiments, the end of the N-terminal stem segment is $A_{p-3}$, and the start of the C-terminal short stem segment is $B_{q-3}$. In certain embodiments, the end of the N-terminal stem segment is $A_{p-4}$, and the start of the C-terminal short stem segment is $B_{q-4}$. In certain embodiments, the end of the N-terminal stem segment is $A_{p-5}$, and the start of the C-terminal short stem segment is $B_{q-5}$.

In certain embodiments, the end of the N-terminal stem segment is $A_{p+1}$, and the start of the C-terminal short stem segment is $B_{q+1}$. In certain embodiments, the end of the N-terminal stem segment is $A_{p+2}$, and the start of the C-terminal short stem segment is $B_{q+2}$. In certain embodiments, the end of the N-terminal stem segment is $A_{p+3}$, and the start of the C-terminal short stem segment is $B_{q+3}$. In certain embodiments, the end of the N-terminal stem segment is $A_{p+4}$, and the start of the C-terminal short stem segment is $B_{q+4}$. In certain embodiments, the end of the N-terminal stem segment is $A_{p+5}$, and the start of the C-terminal short stem segment is $B_{q+5}$.

In certain embodiments, the end of the N-terminal stem segment is $A_{p-1}$, and the start of the C-terminal short stem segment is $B_{q+1}$. In certain embodiments, the end of the N-terminal stem segment is $A_{p-2}$, and the start of the C-terminal short stem segment is $B_{q+2}$. In certain embodiments, the end of the N-terminal stem segment is $A_{p-3}$, and the start of the C-terminal short stem segment is $B_{q+3}$. In certain embodiments, the end of the N-terminal stem segment is $A_{p-4}$, and the start of the C-terminal short stem segment is $B_{q+4}$. In certain embodiments, the end of the N-terminal stem segment is $A_{p-5}$, and the start of the C-terminal short stem segment is $B_{q+5}$.

In certain embodiments, the end of the N-terminal stem segment is $A_p$ (i.e., the end of the N-terminal stem segment is Cysteine), and the start of the C-terminal stem segment is $A_q$ (i.e., the start of the C-terminal stem segment is Cysteine) In certain embodiments, the end of the N-terminal stem segment is $A_{p+1}$, and the start of the C-terminal short stem segment is $B_{q-1}$. In certain embodiments, the end of the N-terminal stem segment is $A_{p+2}$, and the start of the C-terminal short stem segment is $B_{q-2}$. In certain embodiments, the end of the N-terminal stem segment is $A_{p+3}$, and the start of the C-terminal short stem segment is $B_{q-3}$. In certain embodiments, the end of the N-terminal stem segment is $A_{p+4}$, and the start of the C-terminal short stem segment is $B_{q-4}$. In certain embodiments, the end of the N-terminal stem segment is $A_{p+5}$, and the start of the C-terminal short stem segment is $B_{q-5}$.

Also provided herein are influenza hemagglutinin short stem domain polypeptides comprising deleted forms of HA1 C-terminal short stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 C-terminal short stem segment. In certain embodiments, provided herein are influenza hemagglutinin short stem domain polypeptides that comprise expanded forms of HA1 C-terminal short stem segments wherein 1, 2, 3, 4, 5, 6, 7, 8, 9, 10 or more residues are added to the N-terminus of the HA1 C-terminal short stem segments. In particular embodiments, if one residue is added to the C-terminal short stem segment, then one residue is added to the N-terminal stem segment; if two residues are added to the C-terminal short stem segment, then two residues are added to the N-terminal stem segment; if three residues are added to the C-terminal short stem segment, then three residues are added to the N-terminal stem segment. Further provided herein are influenza hemagglutinin short stem domain polypeptides comprising altered forms of HA1 C-terminal short stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin short stem domain polypeptides comprising deleted and altered HA1 C-terminal short stem segments.

The influenza hemagglutinin short stem domain polypeptides can be based on (i.e. can have sequence identity, as described above) any influenza hemagglutinin known to those of skill or later discovered. In certain embodiments, influenza hemagglutinin short stem domain polypeptides are based on an influenza A hemagglutinin. In certain embodiments, the influenza hemagglutinin short stem domain polypeptides are based on an influenza A hemagglutinin selected from the group consisting of H1, H2, H3, H4, H5, H6, H7, H8, H9, H10, H11, H12, H13, H14, H15, H16, H17, and H18. In certain embodiments, influenza hemagglutinin short stem domain polypeptides are based on an influenza B hemagglutinin, as described in detail below.

The HA1 N-terminal stem segments can be based on (i.e. can have sequence identity, as described above) any HA1 N-terminal stem segments known to those of skill or later discovered. In certain embodiments, the HA1 N-terminal stem segments are based on influenza A HA1 N-terminal stem segments. In certain embodiments, the HA1 N-terminal stem segments are based on an influenza A hemagglutinin selected from the group consisting of H1, H2, H3, H4, H5, H6, H7, H8, H9, H10, H11, H12, H13, H14, H15, H16, H17, and H18.

The HA1 C-terminal short stem segments can be based on (i.e. can have sequence identity, as described above) any HA1 C-terminal short stem segments known to those of skill or later discovered. In certain embodiments, the HA1 C-terminal short stem segments are based on influenza A HA1 C-terminal short stem segments. In certain embodiments, the HA1 C-terminal short stem segments are based on an influenza A hemagglutinin selected from the group consisting of H1, H2, H3, H4, H5, H6, H7, H8, H9, H10, H11, H12, H13, H14, H15, H16, H17, and H18.

The HA2 stem domains can be based on (i.e. can have sequence identity, as described above) any HA2 stem domains known to those of skill, later discovered or described herein. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15, H16, H17, and H18.

In embodiments comprising a signal peptide, the signal peptide can be based on any influenza signal peptide known to those of skill in the art or described herein. In certain embodiments, the signal peptides are based on influenza A signal peptides.

In embodiments comprising a luminal domain, the luminal domain can be based on any influenza luminal domain known to those of skill in the art or described herein.

In embodiments comprising a transmembrane domain, the transmembrane domain can be based on any influenza transmembrane domain known to those of skill in the art or described herein.

In embodiments comprising a cytoplasmic domain, the cytoplasmic domain can be based on any influenza cytoplasmic domain known to those of skill in the art or described herein.

In certain embodiments, one or more of the glycosylation sites in the hemagglutinin short stem domain are modified (e.g., by amino acid addition, deletion or substitution) such that glycosylation at these sites will not occur during processing and maturation of the polypeptide. Those of skill in the art will recognize that influenza HA typically comprises one or more glycosylation sites (e.g. Ser/Thr/Cys, wherein Xaa is any amino acid, or, in certain embodiments, wherein Xaa is not Pro). In certain embodiments, one or more amino acid residues in a glycosylation sequence is conservatively substituted with an amino acid residue that disrupts the glycosylation site. In certain embodiments, one or more amino acid residues in a glycosylation site are substituted with any amino acid residue that disrupts the glycosylation site. In certain embodiments, one or more asparagine residues in a glycosylation sequence is substituted with alanine. In a particular embodiment, the asparagine at position 38 of an H3 hemagglutinin is changed to an alanine. In certain embodiments, the hemagglutinin short stem domain comprises one or more modified glycosylation sites as discussed in Section 5.4.1, infra.

In certain embodiments, the influenza virus hemagglutinin short stem domain polypeptide comprises one or more sequence as described in Table 6 of International Publication No. WO 2013/043729 and U.S. application Ser. No. 14/345,816, which published as U.S. Patent Publication No. 20150132330 which are incorporated herein by reference in their entirety.

In certain embodiments, the influenza hemagglutinin short stem domain polypeptides comprise one or more immunogenic epitopes in the tertiary or quaternary structure of an influenza hemagglutinin polypeptide.

As illustrated in FIG. 14 and in FIG. 2 of International Publication No. WO 2013/043729, which is incorporated herein by reference in its entirety, HA1 N-terminal stem segments share sequence identity between influenza A and influenza B and additionally across influenza A subtypes. Similarly, HA1 C-terminal short stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin short stem domain polypeptide is a hybrid polypeptide that comprises or consists essentially of segments and/or domains from a plurality of influenza strains or subtypes. For example, an influenza hemagglutinin short stem domain polypeptide can comprise HA1 N-terminal and HA1 C-terminal short stem segments from different influenza A virus HA subtypes. In some embodiments, the HA1 N-terminal stem segment is from influenza B virus while the HA1 C-terminal short stem segment is from influenza A virus. Similarly, HA2 and the HA1 C-terminal short stem segment may also be from influenza A virus while the HA1 N-terminal is from influenza B virus.

It will be understood that any combination of the sequence elements listed in Tables 2, 4, 5 of International Publication No. WO 2013/043729 and U.S. application Ser. No. 14/345,816, which published as U.S. Patent Publication No. 20150132330 which are incorporated herein by reference in their entirety, and sequences listed under the "Signal peptide," "HA1 N-terminal stem segment," and "HA2 Domain" columns of Table 3 of International Publication No. WO 2013/043729 and U.S. application Ser. No. 14/345,816, which published as U.S. Patent Publication No. 20150132330 which are incorporated herein by reference in their entirety, or the variants thereof may be used to form the hemagglutinin HA stem domain polypeptides of the present invention.

In an influenza hemagglutinin short stem domain polypeptide provided herein, a linker covalently connects the HA1 N-terminal stem segment to the HA1 C-terminal short stem segment. The linker can be any linker deemed suitable by one of skill in the art including, but not limited to, those linkers described herein. In certain embodiments, the linker is a globular head, or a fragment thereof, from an influenza virus heterologous to the influenza stem domain.

In certain embodiments, influenza hemagglutinin short stem domain polypeptides are capable of forming a three dimensional structure that is similar to the three dimensional structure of the stem domain of a native influenza hemagglutinin. Structural similarity can be evaluated based on any technique deemed suitable by those of skill in the art including, but not limited to, those techniques described herein.

In certain embodiments, any influenza hemagglutinin short stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:101), FLAG epitope or other purification tag can facilitate purification of a polypeptide provided herein. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

Any trimerization domain, including a foldon from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. The foldon domain can have any foldon sequence known to those of skill in the art (see, e.g., Papanikolopoulou et al., 2004, *J. Biol. Chem.* 279(10): 8991-8998, the contents of which are hereby incorporated by reference in their entirety. Examples include GSGYIPEAPRDGQAYVRKDGEWVLLSTFL (SEQ ID NO:102). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50).

In certain embodiments, provided herein are influenza hemagglutinin stem short domain polypeptides that are predicted to be resistant to protease cleavage at the junction between HA1 and HA2. In certain embodiments, provided is any influenza hemagglutinin short stem domain polypeptide described herein wherein the protease site spanning HA1 and HA2 is mutated to a sequence that is resistant to protease cleavage. In certain embodiments, provided is any influenza hemagglutinin short stem domain polypeptide described herein wherein the C-terminal residue of the HA1 C-terminal short stem segment is any residue other than Lys or Arg. In certain embodiments, provided is any influenza hemagglutinin short stem domain polypeptide described herein wherein the N-terminal residue of the HA2 domain is proline. In certain embodiments, provided is any influenza hemagglutinin short stem domain polypeptide described herein wherein the C-terminal residue of the HA1 C-terminal short stem segment is Ala and the N-terminal residue of the HA2 domain is also Ala.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to, in sequence, a cleavage site, a trimerization domain and a purification tag. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to, in sequence, a cleavage site, a trimerization domain and a purification tag. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is covalently linked to, in sequence, a cleavage site, a trimerization domain and a purification tag. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is covalently linked to, in sequence, a cleavage site, a trimerization domain and a purification tag. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is in turn covalently linked to an HA2 transmembrane domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain.

In certain embodiments, provided herein are influenza hemagglutinin short stem domain polypeptides consisting of an HA1 N-terminal stem segment covalently linked to a linker, in turn covalently linked to an HA1 C-terminal short stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin short stem domain polypeptides consisting of an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin short stem domain polypeptides consisting of a signal peptide covalently linked to an HA1 N-terminal stem segment covalently linked to a linker, in turn covalently linked to an HA1 C-terminal short stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

5.3.1.2 Influenza Hemagglutinin Long Stem Domain Polypeptides

In certain embodiments, the influenza hemagglutinin long stem domain polypeptide is an influenza hemagglutinin long stem domain polypeptide as described in International Publication Nos. WO 2011/123495, WO 2013/043729, and WO 2014/099931, U.S. Publication Nos. 2013/0129761, 2014/0328875, and U.S. application Ser. No. 14/345,816, which published as U.S. Patent Publication No. 20150132330 which are incorporated herein by reference in their entirety. In certain embodiments, the influenza hemagglutinin stem domain polypeptide is an influenza hemagglutinin long stem domain polypeptide. The typical primary structure of an influenza hemagglutinin long stem domain polypeptide provided herein comprises, in the following order: an HA1 N-terminal long stem segment, a linker, an HA1 C-terminal long stem segment and an HA2. The primary sequence can be formed by a single polypeptide, or it can be formed by multiple polypeptides. Typically, a single polypeptide is expressed by any technique deemed suitable by one of skill in the art. In single polypeptide embodiments, the HA1 segments and the HA2 are in tertiary association. As is known to those of skill in the art, a single HA polypeptide can be cleaved, for example by a protease, under appropriate expression conditions to yield two polypeptides in quaternary association. The cleavage is typically between the HA1 C-terminal short stem segment and the HA2. In certain embodiments, provided herein are multiple polypeptides. In multiple polypeptide embodiments, the HA1 segments and HA2 are in quaternary association.

In certain embodiments, an influenza hemagglutinin long stem domain polypeptide provided herein is monomeric. In certain embodiments, an influenza hemagglutinin long stem domain polypeptide provided herein is multimeric. In certain embodiments, an influenza hemagglutinin long stem domain polypeptide provided herein is trimeric. Those of skill in the art will recognize that native influenza hemagglutinin long stem domain polypeptides are capable of trimerization in vivo and that certain influenza hemagglutinin long stem domain polypeptides provided herein are capable of trimerization. In particular embodiments described below, influenza hemagglutinin long stem domain polypeptides provided herein comprise trimerization domains to facilitate trimerization.

In certain embodiments, an influenza hemagglutinin long stem domain polypeptide comprises a signal peptide. In certain embodiments, also provided herein are mature influenza hemagglutinin long stem domain polypeptides that lack a signal peptide.

In certain embodiments, provided herein are influenza hemagglutinin long stem domain polypeptides that comprise an HA2 stem domain, an HA2 luminal domain, an HA2 transmembrane domain and an HA2 cytoplasmic domain. In certain embodiments, provided herein are influenza hemagglutinin long stem domain polypeptides that comprise an HA2 stem domain, an HA2 luminal domain, and an HA2 transmembrane domain but lack some or all of the typical cytoplasmic domain. In certain embodiments, provided herein are influenza hemagglutinin long stem domain polypeptides that comprise an HA2 stem domain and an HA2 luminal domain but lack both an HA2 transmembrane domain and an HA2 cytoplasmic domain. In certain embodiments, provided herein are influenza hemagglutinin long stem domain polypeptides that comprise an HA2 stem domain but lack an HA2 luminal domain, an HA2 transmembrane domain and an HA2 cytoplasmic domain. In certain embodiments, the influenza hemagglutinin long stem domain polypeptides comprise an HA2 stem domain having at least 70%, 75%, 80%, 85%, 90%, 95%, 96% or 98% amino acid sequence identity to an influenza HA2 stem domain known to those of skill in the art. Exemplary known HA2 stem domains from known influenza A hemagglutinins are provided in International Publication Nos. WO 2011/123495, WO 2013/043729, and WO 2014/099931, U.S. Publication Nos. 2013/0129761, 2014/0328875, and U.S. application Ser. No. 14/345,816, which published as U.S. Patent Publication No. 20150132330 which are incorporated herein by reference in their entirety.

Also provided herein are influenza hemagglutinin long stem domain polypeptides comprising deleted forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA2 stem domain. Further provided herein are influenza hemagglutinin long stem domain polypeptides comprising altered forms of HA2 stem domains wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin long stem domain polypeptides comprising deleted and altered HA2 stem domains.

The HA1 N-terminal long stem segment can be any HA1 N-terminal long stem segment recognized by one of skill in the art based on the definition provided herein. Typically, an HA1 N-terminal long stem segment corresponds to a polypeptide consisting of the N-terminal amino acid of a mature HA1 (i.e. an HA1 lacking a signal peptide) through the cysteine residue located in sequence at approximately the $97^{th}$ residue of the HA1 (using H3 numbering). This cysteine residue, termed $C_p$ herein, is generally capable of being linked to a cysteine residue $C_q$ in the C-terminal long stem segment of HA1. Sequences of 17 representative influenza A hemagglutinins are presented in FIG. 14, and residue $C_p$ is identified in each.

In certain embodiments, the HA1 N-terminal long stem segment does not end exactly at $C_p$ (e.g., $Cys_{97}$ of an HA1 subunit from an H3 hemagglutinin (i.e., according to H3 numbering)), but at a residue in sequence and structural vicinity to $C_p$. For example, in certain embodiments, the HA1 N-terminal long stem segment ends at $C_{p-1}$, $C_{p-2}$, $C_{p-3}$, or $C_{p-4}$. In other embodiments, the HA1 N-terminal long stem segment ends at $C_{p+1}$, $C_{p+2}$, $C_{p+3}$, $C_{p+4}$ or $C_{p+5}$. The end of an HA1 N-terminal long stem segment should be selected in conjunction with the end of the HA1 C-terminal long stem segment and the linker so that the resulting linked HA1 stem domain is capable of forming a three-dimensional structure similar, as described below, to an influenza hemagglutinin stem domain.

In certain embodiments, the influenza hemagglutinin long stem domain polypeptides comprise an HA1 N-terminal long stem segment having at least 70%, 75%, 80%, 85%, 90%, 95%, 96% or 98% amino acid sequence identity to an influenza HA1 N-terminal long stem segment known to those of skill in the art. Exemplary known HA1 N-terminal long stem segments are provided in the tables disclosed in International Publication No. WO 2010/117786, WO 2011/123495, and WO 2013/043729, U.S. Publication Nos. 2010/0297174, 2013/0129761, and U.S. application Ser. No. 14/345,816, which published as U.S. Patent Publication No. 20150132330 which are incorporated herein by reference in their entireties.

Also provided herein are influenza hemagglutinin long stem domain polypeptides comprising deleted forms of HA1 N-terminal long stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 N-terminal long stem segment. In certain embodiments, provided herein are influenza hemagglutinin long stem domain polypeptides that comprise expanded forms of HA1 N-terminal long stem segments wherein 1, 2, 3, 4, 5, 6, 7, 8, 9, 10 or more residues are added to the C-terminus of the HA1 N-terminal long stem segments; these added residues can be derived from the amino acid sequence of a globular head domain adjacent to an HA1 N-terminal long stem segment. Further provided herein are influenza hemagglutinin long stem domain polypeptides comprising altered forms of HA1 N-terminal long stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin long stem domain polypeptides comprising deleted and altered HA1 N-terminal long stem segments.

The HA1 C-terminal long stem segment can be any HA1 C-terminal long stem segment recognized by one of skill in the art based on the definition provided herein. Typically, an HA1 C-terminal long stem segment corresponds to a polypeptide consisting of the alanine residue located in sequence at approximately the $253^{rd}$ residue of an HA1 (using H3 numbering) through the C-terminal amino acid of the HA1. This alanine residue, termed $C_q$ herein, is generally capable of being linked to a cysteine residue $C_p$ in the N-terminal long stem segment of HA1. Sequences of 16 representative influenza A hemagglutinins are presented in FIG. 14, and residue $C_q$ is identified in each.

In certain embodiments, the HA1 C-terminal long stem segment does not start at $C_q$ (e.g., $Ala_{253}$ of an HA1 subunit from an H3 hemagglutinin (i.e., according to H3 numbering)), but at a residue in sequence and structural vicinity to $C_q$. For example, in certain embodiments, the HA1 C-terminal long stem segment starts at $C_{q-1}$, $C_{q-2}$, $C_{q-3}$, or $C_{q-4}$. In other embodiments, the HA1 C-terminal long stem segment starts at $C_{q+1}$, $C_{q+2}$, $C_{q+3}$, $C_{q+4}$ or $C_{q+5}$. The end of an HA1 N-terminal long stem segment should be selected in conjunction with the start of the HA1 C-terminal long stem segment and the linker so that the resulting HA1 stem domain is capable of forming a three-dimensional structure similar, as described below, to an influenza hemagglutinin.

In certain embodiments, the influenza hemagglutinin long stem domain polypeptides comprise an HA1 C-terminal long stem segment having at least 70%, 75%, 80%, 85%, 90%, 95%, 96% or 98% amino acid sequence identity to an influenza HA1 C-terminal long stem segment known to those of skill in the art. Exemplary known HA1 C-terminal long stem segments are provided in the tables disclosed in International Publication No. WO 2010/117786, WO 2011/123495, and WO 2013/043729, U.S. Publication Nos. 2010/0297174, 2013/0129761, and U.S. application Ser. No. 14/345,816, which published as U.S. Patent Publication No. 20150132330 which are incorporated herein by reference in their entireties.

In certain embodiments, the end of the N-terminal long stem segment is $C_{p-1}$, and the start of the C-terminal long stem segment is $C_{q-1}$. In certain embodiments, the end of the N-terminal long stem segment is $A_{p-2}$, and the start of the C-terminal long stem segment is $C_{q-2}$. In certain embodiments, the end of the N-terminal long stem segment is $C_{p-3}$, and the start of the C-terminal long stem segment is $C_{q-3}$. In certain embodiments, the end of the N-terminal long stem segment is $C_{p-4}$, and the start of the C-terminal long stem segment is $C_{q-4}$. In certain embodiments, the end of the N-terminal long stem segment is $C_{p-5}$, and the start of the C-terminal long stem segment is $C_{q-5}$.

In certain embodiments, the end of the N-terminal long stem segment is $C_{p+1}$, and the start of the C-terminal long stem segment is $C_{q+1}$. In certain embodiments, the end of the N-terminal long stem segment is $C_{p+2}$, and the start of the C-terminal long stem segment is $C_{q+2}$ In certain embodiments, the end of the N-terminal long stem segment is $C_{p+3}$, and the start of the C-terminal long stem segment is $C_{q+3}$. In certain embodiments, the end of the N-terminal long stem segment is $C_{p+4}$, and the start of the C-terminal long stem segment is $C_{q+4}$. In certain embodiments, the end of the N-terminal long stem segment is $C_{p+5}$, and the start of the C-terminal long stem segment is $C_{q+5}$.

In certain embodiments, the end of the N-terminal long stem segment is $C_{p-1}$, and the start of the C-terminal long stem segment is $C_{q+1}$. In certain embodiments, the end of the N-terminal long stem segment is $C_{p-2}$, and the start of the C-terminal long stem segment is $C_{q+2}$. In certain embodiments, the end of the N-terminal long stem segment is $C_{p-3}$, and the start of the C-terminal long stem segment is $C_{q+3}$. In certain embodiments, the end of the N-terminal long stem segment is $C_{p-4}$, and the start of the C-terminal long stem segment is $C_{q+4}$. In certain embodiments, the end of the N-terminal long stem segment is $C_{p-5}$, and the start of the C-terminal long stem segment is $C_{q+5}$.

In certain embodiments, the end of the N-terminal long stem segment is $C_{p+1}$, and the start of the C-terminal long stem segment is $C_{q-1}$. In certain embodiments, the end of the N-terminal long stem segment is $C_{p+2}$, and the start of the C-terminal long stem segment is $C_{q-2}$ In certain embodiments, the end of the N-terminal long stem segment is $C_{p+3}$, and the start of the C-terminal long stem segment is $C_{q-3}$. In certain embodiments, the end of the N-terminal long stem segment is $C_{p+4}$, and the start of the C-terminal long stem segment is $C_{q-4}$. In certain embodiments, the end of the N-terminal long stem segment is $C_{p+5}$, and the start of the C-terminal long stem segment is $C_{q-5}$.

Also provided herein are influenza hemagglutinin long stem domain polypeptides comprising deleted forms of HA1 C-terminal long stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are deleted from either or both termini of the HA1 C-terminal long stem segment. In certain embodiments, provided herein are influenza hemagglutinin long stem domain polypeptides that comprise expanded forms of HA1 C-terminal long stem segments wherein 1, 2, 3, 4, 5, 6, 7, 8, 9, 10 or more residues are added to the N-terminus of the HA1 C-terminal long stem segments; these added residues can be derived from the amino acid sequence of a globular head domain adjacent to an HA1 C-terminal long stem segment. In particular embodiments, if one residue is added to the C-terminal long stem segment, then one residue is added to the N-terminal long stem segment; if two residues are added to the C-terminal long stem segment, then two residues are added to the N-terminal long stem segment; if three residues are added to the C-terminal long stem segment, then three residues are added to the N-terminal long stem segment. Further provided herein are influenza hemagglutinin long stem domain polypeptides comprising altered forms of HA1 C-terminal long stem segments wherein up to 100, 95, 90, 85, 80, 75, 70, 65, 60, 55, 50, 45, 40, 35, 30, 25, 20, 15, 10, 9, 8, 7, 6, 5, 4, 3, 2 or 1 amino acid residues are conservatively substituted with other amino acids. Further provided are influenza hemagglutinin long stem domain polypeptides comprising deleted and altered HA1 C-terminal long stem segments.

The influenza hemagglutinin long stem domain polypeptides can be based on (i.e. can have sequence identity, as described above) any influenza hemagglutinin known to those of skill or later discovered. In certain embodiments, influenza hemagglutinin long stem domain polypeptides are based on an influenza A hemagglutinin. In certain embodiments, the influenza hemagglutinin long stem domain polypeptides are based on an influenza A hemagglutinin selected from the group consisting of H1, H2, H3, H4, H5, H6, H7, H8, H9, H10, H11, H12, H13, H14, H15, H16, and H17, and H18. In certain embodiments, influenza hemagglutinin long stem domain polypeptides are based on an influenza B hemagglutinin, as described in detail below.

The HA1 N-terminal long stem segments can be based on (i.e. can have sequence identity, as described above) any HA1 N-terminal long stem segments known to those of skill or later discovered. In certain embodiments, the HA1 N-terminal long stem segments are based on influenza A HA1 N-terminal long stem segments. In certain embodiments, the HA1 N-terminal long stem segments are based on an influenza A hemagglutinin selected from the group consisting of H1, H2, H3, H4, H5, H6, H7, H8, H9, H10, H11, H12, H13, H14, H15, H16, and H17, and H18.

The HA1 C-terminal long stem segments can be based on (i.e. can have sequence identity, as described above) any HA1 C-terminal long stem segments known to those of skill or later discovered. In certain embodiments, the HA1 C-terminal long stem segments are based on influenza A HA1 C-terminal long stem segments. In certain embodiments, the HA1 C-terminal long stem segments are based on an influenza A hemagglutinin selected from the group consisting of H1, H2, H3, H4, H5, H6, H7, H8, H9, H10, H11, H12, H13, H14, H15, H16, and H17, and H18.

The HA2 stem domains can be based on (i.e. can have sequence identity, as described above) any HA2 stem domains known to those of skill, later discovered, or described herein. In certain embodiments, the HA2 stem domains are based on influenza A HA2 stem domains. In certain embodiments, the HA2 stem domains are based on an influenza A hemagglutinin selected from the group consisting of H1, H2, H3, H4, H5, H6, H7, H8, H9, H10, H11, H12, H13, H14, H15, H16, and H17, and H18.

In embodiments comprising a signal peptide, the signal peptide can be based on any influenza signal peptide known to those of skill in the art or described herein.

In embodiments comprising a luminal domain, the luminal domain can be based on any influenza luminal domain known to those of skill in the art or described herein.

In embodiments comprising a transmembrane domain, the transmembrane domain can be based on any influenza transmembrane domain known to those of skill in the art or described herein.

In embodiments comprising a cytoplasmic domain, the cytoplasmic domain can be based on any influenza cytoplasmic domain known to those of skill in the art or described herein.

In certain embodiments, one or more of the glycosylation sites in the hemagglutinin stem domain are modified (e.g., by amino acid addition, deletion or substitution) such that glycosylation at these sites will not occur during processing and maturation of the polypeptide. Those of skill in the art will recognize that influenza HA typically comprises one or more glycosylation sites (e.g. Asn-Xaa-Ser/Thr/Cys, wherein Xaa is any amino acid other, or, in certain embodiments, wherein Xaa is any amino acid except Pro). In certain embodiments, one or more amino acid residues in a glycosylation site are conservatively substituted with an amino acid residue that disrupts the glycosylation site. In certain embodiments, one or more amino acid residues in a glycosylation site are substituted with any amino acid residue that disrupts the glycosylation sequence. In certain embodiments, one or more asparagine residues in a glycosylation sequence is substituted with alanine. In a particular embodiment, the asparagine at position 38 of an H3 hemagglutinin is changed to an alanine. In certain embodiments, the hemagglutinin stem domain comprises one or more modified glycosylation sites as discussed in Section 5.4.1, infra.

In certain embodiments, the influenza virus hemagglutinin long stem domain polypeptide comprises one or more sequence as disclosed in Table 7 of International Publication Nos. WO 2013/043729 and U.S. application Ser. No. 14/345,816, which published as U.S. Patent Publication No. 20150132330 which are incorporated herein by reference in their entirety.

As illustrated in FIG. 14 and in FIG. 2 of International Publication No. WO 2013/043729, which is incorporated herein by reference in its entirety, HA1 N-terminal long stem segments share sequence identity between influenza A and influenza B and additionally across influenza A subtypes. Similarly, HA1 C-terminal long stem segments also share sequence identity between influenza A and influenza B and additionally across influenza A subtypes. Further, HA2 domains also share sequence identity between influenza A and influenza B and additionally across influenza A subtypes.

In some embodiments, the influenza hemagglutinin long stem domain polypeptide is a hybrid polypeptide that comprises or consists essentially of segments and/or domains from a plurality of influenza strains or subtypes. For example, an influenza hemagglutinin long stem domain polypeptide can comprise HA1 N-terminal and HA1 C-terminal long stem segments from different influenza A virus HA subtypes. In some embodiments, the HA1 N-terminal long stem segment is from influenza A virus while the HA1 C-terminal long stem segment is from influenza B virus. Similarly, HA2 may also be from influenza A virus while the HA1 N-terminal and/or C-terminal long stem segment is from influenza B virus.

It will be understood that any combination of the sequence elements listed in Tables 2-4, 6, 6a of International Publication No. WO 2013/043729 and U.S. application Ser. No. 14/345,816, which published as U.S. Patent Publication No. 20150132330 which are incorporated herein by reference in their entirety, or the variants thereof may be used to form the hemagglutinin HA long stem domain polypeptides of the present invention.

In an influenza stem domain polypeptide provided herein, a linker covalently connects the HA1 N-terminal long stem segment to the HA1 C-terminal long stem segment. The linker can be any linked deemed suitable by one of skill in the art including, but not limited to, those linkers described herein.

In certain embodiments, influenza hemagglutinin long stem domain polypeptides are capable of forming a three dimensional structure that is similar to the three dimensional structure of the stem domain of a native influenza hemagglutinin. Structural similarity can be evaluated based on any technique deemed suitable by those of skill in the art including, but not limited to, those techniques described herein.

In certain embodiments, any influenza hemagglutinin long stem domain polypeptide provided herein can further comprise one or more polypeptide domains deemed suitable to those of skill in the art. Useful polypeptide domains include domains that facilitate purification, folding and cleavage of portions of a polypeptide. For example, a His tag (His-His-His-His-His-His, SEQ ID NO:101), FLAG epitope or other purification tag can facilitate purification of a polypeptide provided herein. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

Any trimerization domain, including a foldon from bacteriophage T4 fibritin can facilitate trimerization of polypeptides provided herein. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. The foldon domain can have any foldon sequence known to those of skill in the art (see, e.g., Papanikolopoulou et al., 2004, *J. Biol. Chem.* 279(10): 8991-8998, the contents of which are hereby incorporated by reference in their entirety. Examples include GSGYIPEAPRDGQAYVRKDGEWVLLSTFL (SEQ ID NO:102). A foldon domain can be useful to facilitate trimerization of soluble polypeptides provided herein. Cleavage sites can be used to facilitate cleavage of a portion of a polypeptide, for example cleavage of a purification tag or foldon domain or both. Useful cleavage sites include a thrombin cleavage site, for example one with the sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50).

In certain embodiments, provided are influenza hemagglutinin long stem domain polypeptides comprising an elastase cleavage site as described herein.

In certain embodiments, provided herein are influenza hemagglutinin long stem domain polypeptides that are predicted to be resistant to protease cleavage at the junction between HA1 and HA2. Those of skill in the art should recognize that the Arg-Gly sequence spanning HA1 and HA2 is a recognition site for trypsin and is typically cleaved for hemagglutinin activation. Since the stem domain polypeptides described herein need not be activated, provided herein are influenza hemagglutinin long stem domain polypeptides that are predicted to be resistant to protease cleavage. In certain embodiments, provided is any influenza hemagglutinin long stem domain polypeptide described herein wherein the protease site spanning HA1 and HA2 is mutated to a sequence that is resistant to protease cleavage. In certain embodiments, provided is any influenza hemagglutinin long stem domain polypeptide described herein wherein the C-terminal residue of the HA1 C-terminal long stem segment is any residue other than Lys or Arg. In certain embodiments, provided is any influenza hemagglutinin long stem domain polypeptide described herein wherein the N-terminal residue of the HA2 domain is proline. In certain embodiments, provided is any influenza hemagglutinin long stem domain polypeptide described herein wherein the C-terminal residue of the HA1 C-terminal long stem segment is Ala and the N-terminal residue of the HA2 domain is also Ala. In certain embodiments, provided is any influenza hemagglutinin long stem domain polypeptide described herein wherein the N-terminal residue of the HA2 domain is any residue other than glycine.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain. In certain embodiments, the linker is a globular head, or a fragment thereof, from an influenza virus heterologous to the influenza stem domain. In certain embodiments, the linker is a globular head, or a fragment thereof, from an influenza virus heterologous to the stem domain of the HA2 subunit of the chimeric influenza virus hemagglutinin polypeptide. In certain embodiments, the linker is a globular head, or a fragment thereof, from an influenza virus heterologous to the stem domain of the HA1 and/or HA2 subunit of the chimeric influenza virus hemagglutinin.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain. In certain embodiments, the linker is a globular head, or a fragment thereof, from an influenza virus heterologous to the influenza stem domain. In certain embodiments, the linker is a globular head, or a fragment thereof, from an influenza virus heterologous to the stem domain of the HA2 subunit of the hemagglutinin. In certain embodiments, the linker is a globular head, or a fragment thereof, from an influenza virus heterologous to the stem domain of the HA1 and/or HA2 subunit of the hemagglutinin.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to, in sequence, a cleavage site, a trimerization domain and a purification tag. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to, in sequence, a cleavage site, a trimerization domain and a purification tag. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is covalently linked to, in sequence, a cleavage site, a trimerization domain and a purification tag. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is covalently linked to, in sequence, a cleavage site, a trimerization domain and a purification tag. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is covalently linked to, in sequence, a cleavage site, a trimerization domain and a purification tag. In certain embodiments, the protease cleavage site is a thrombin cleavage site. In certain embodiments, the cleavage site has the amino acid sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50). In certain embodiments, the trimerization domain is a foldon domain. In some embodiments, the trimerization domain comprises a wildtype GCN4pII trimerization heptad repeat or a modified GCN4pII trimerization heptad repeat that allows for the formation of trimeric or tetrameric coiled coils. See, e.g., Weldon et al., 2010, PLoSONE 5(9): e12466. In some embodiments, the purification tag is a His tag, having the sequence, (His)n, wherein n is 2, 3, 4, 5, 6, 7, 8, 9, 10, 11, 12, 13, 14, 15, 16, 17, 18, 19, 20 or greater.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is in turn covalently linked to an HA2 transmembrane domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain.

In certain embodiments, provided herein are influenza hemagglutinin long stem domain polypeptides consisting of an HA1 N-terminal long stem segment covalently linked to a linker, in turn covalently linked to an HA1 C-terminal long stem segment in binding association with an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin long stem domain polypeptides consisting of an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain that is in turn covalently linked to an HA2 cytoplasmic domain. In certain embodiments, provided herein are influenza hemagglutinin long stem domain polypeptides consisting of a signal peptide covalently linked to an HA1 N-terminal long stem segment covalently linked to a linker, in turn covalently linked to an HA1 C-terminal long stem segment, in turn covalently linked to an HA2 stem domain that is covalently linked to an HA2 luminal domain that is in turn covalently linked to an HA2 transmembrane domain that is in turn covalently linked to an HA2 cytoplasmic domain.

5.3.2 Core Polypeptides

In another embodiment, provided herein are influenza virus hemagglutinin core polypeptides. In certain embodiments, the influenza virus hemagglutinin core polypeptide is as described in International Publication No. WO 2011/103453 and U.S. Publication No. 2013/0209499, which are incorporated herein by reference in their entirety. In certain embodiments, the core polypeptide comprises one or more relatively conserved antigenic regions of the HA2 hemagglutinin subunit long alpha-helix. In a specific embodiment, the core polypeptide is capable of generating an immune response in a subject that is capable of cross reacting with, and preferably protecting against, a plurality of influenza virus strains from a single subtype, or strains from 2, 3, 4 or more subtypes. The ability of a core polypeptide to generate an immune response in a subject that is capable of cross reacting with, and preferably protecting against, a plurality of influenza virus strains from a single subtype, or strains from 2, 3, 4 or more subtypes can be assessed using methods known to those of skill in the art and described herein (see Sections 5.13 and 6 of International Publication No. WO 2011/103453 and U.S. Publication No. 2013/0209499, which are incorporated herein by reference in their entirety). In another specific embodiment, the core polypeptide is capable of generating an immune response in a subject that is capable of neutralizing a plurality of influenza virus strains from a single subtype, or strains from 2, 3, 4 or more subtypes. The ability of a core polypeptide to generate an immune response that is capable of neutralizing a plurality of influenza virus strains from a single subtype, or strains from 2, 3, 4 or more subtypes can be assessed using methods known to those of skill in the art and described herein (see Sections 5.13 and 6, of International Publication No. WO 2011/103453 and U.S. Publication No. 2013/0209499, which are incorporated herein by reference in their entirety). In another specific embodiment, the core polypeptide is capable of generating an immune response in a subject that is capable of inhibiting or reducing the replication of a plurality of influenza virus strains from a single subtype, or strains from 2, 3, 4 or more subtypes. The ability of a core polypeptide to generate an immune response that is capable of inhibiting or reducing the replication of a plurality of influenza virus strains from a single subtype, or strains from 2, 3, 4 or more subtypes can be assessed using methods known to those of skill in the art and described herein (see Sections 5.13 and 6, of International Publication No. WO 2011/103453 and U.S. Publication No. 2013/0209499, which are incorporated herein by reference in their entirety).

In a specific embodiment, a core polypeptide comprises the long alpha-helix of the HA2 hemagglutinin subunit of an influenza virus. In a specific embodiment, a core polypeptide comprises a portion of the long alpha-helix of the HA2 hemagglutinin subunit of an influenza virus. In a specific embodiment, a core polypeptide comprises a portion of the long alpha-helix of the HA2, wherein the native conformation of the portion is maintained. In a specific embodiment, a core polypeptide comprises a portion of the long alpha-helix of the HA2, wherein the portion maintains a native alpha-helix conformation. One of skill in the art can determine whether or not the alpha-helix conformation is maintained using any method known in the art such as, e.g., NMR, X-ray crystallographic methods, or secondary structure prediction methods, e.g., circular dichroism.

In specific embodiments, a core polypeptide does not include the amino acid sequence of a full length influenza virus hemagglutinin. In certain embodiments, a core polypeptide comprises or consists of between 25 to 50, 50 to 55, 50 to 60, 50 to 65, 50 to 70, 50 to 75, 50 to 80, 50 to 85, 50 to 90, 50 to 95, 50 to 100, 100 to 150, 100 to 200, or 100 to 250 amino acids. In other embodiments, a core polypeptide comprises or consists of between 50 to 55, 50 to 60, 50 to 65, 50 to 75, 50 to 80, 50 to 85, 50 to 90, 50 to 95, 50 to 100, 75 to 80, 75 to 85, 75 to 90, 75 to 95, or 75 to 100 amino acids In a specific embodiment, a core polypeptide comprises or consists of amino acids 1(±5) to 184(±5), 16(±5) to 184(±5), 30(±5) to 184(±5), 31(±5) to 184(±5), 46(±5) to 184(±5), 61(±5) to 184(±5), 70(±5) to 110(±5), 76(±5) to 106(±5), 76(±5) to 130(±5) or 76(±5) to 184(±5) of a hemagglutinin polypeptide numbered according to the classic H3 subtype numbering system. In some embodiments, a core polypeptide comprises or consists of amino acids 1(±5) to 184(±5), 16(±5) to 184(±5), 30(±5) to 184(±5), 31(±5) to 184(±5), 46(±5) to 184(±5), 61(±5) to 184(±5), 70(±5) to 184(±5), (70(±5) to 110(±5), 76(±5) to 106(±5), 76(±5) to 130(±5) or 76(±5) to 184(±5) of a hemagglutinin polypeptide numbered according to the classic H3 subtype numbering system, wherein the core polypeptide is less than 300, 275, 250, 200, 190, 185, or 180 amino acids in length. In a specific embodiment, a core polypeptide comprises or consists of amino acids 76 to 106 of a hemagglutinin polypeptide numbered according to the classic H3 subtype numbering system.

In another specific embodiment, a core polypeptide comprises amino acids 76 to 130 of a hemagglutinin polypeptide numbered according to the classic H3 subtype numbering system. In certain embodiments, a core polypeptide comprises or consists of amino acids 76 to 130 of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length. In another specific embodiment, a core polypeptide consists of amino acids 76 to 130 of a hemagglutinin polypeptide numbered according to the classic H3 subtype numbering system.

In a specific embodiment, a core polypeptide comprises or consists of amino acids 70(±5) to 125(±5), 80(±5) to 115(±5), 90(±5) to 105(±5), or 76(±5) to 95(±5) of a hemagglutinin polypeptide numbered according to the classic H3 subtype numbering system. In certain embodiments, a core polypeptide comprises or consists of amino acids 70(±5) to 125(±5), 80(±5) to 115(±5), 90(±5) to 105(±5), or 76(±5) to 95(±5) of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length.

In a specific embodiment, a core polypeptide comprises or consists of amino acids 70(±5) to 130(±5), 70(±5) to 120(±5), 70(±5) to 110(±5), 70(±5) to 100(±5), or 70(±5) to 95(±5) of a hemagglutinin polypeptide numbered according to the classic H3 subtype numbering system. In certain embodiments, a core polypeptide comprises or consists of amino acids 70(±5) to 130(±5), 70(±5) to 120(±5), 70(±5) to 110(±5), 70(±5) to 100(±5), or 70(±5) to 95(±5) of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length.

In a specific embodiment, a core polypeptide comprises or consists of amino acids 70(±5) to 130(±5), 80(±5) to 130(±5), 90(±5) to 130(±5), 100(±5) to 130(±5), or 110(±5) to 130(±5) of a hemagglutinin polypeptide numbered according to the classic H3 subtype numbering system. In certain embodiments, a core polypeptide comprises or consists of amino acids 70(±5) to 130(±5), 80(±5) to 130(±5), 90(±5) to 130(±5), 100(±5) to 130(±5), or 110(±5) to 130(±5) of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length.

In a specific embodiment, a core polypeptide comprises or consists of amino acids 1-184, 10(±5) to 184, 20(±5) to 184, 30(±5) to 184, 40(±5) to 184, 50(±5) to 184, 60(±5) to 184, 70(±5) to 184 or 80(±5) to 184 of a hemagglutinin polypeptide numbered according to the classic H3 subtype numbering system. In certain embodiments, a core polypeptide comprises or consists of amino acids 1-184, 10(±5) to 184, 20(±5) to 184, 30(±5) to 184, 40(±5) to 184, 50(±5) to 184, 60(±5) to 184, 70(±5) to 184 or 80(±5) to 184 of a hemagglutinin polypeptide numbered according to the classic H3 subtype numbering system, wherein the core polypeptide is less than 300, 275, 250, 200, 190, 185, 180, 175, 150, 145, 130, 130, 125, 100, or 75 amino acids in length.

5.4 Glycosylation Variants

In another aspect, provided herein are flu hemagglutinin (HA) polypeptides comprising one or more modified glycosylation sites and/or one or more non-naturally occurring glycosylation sites. In specific embodiments, the flu HA polypeptide is a chimeric influenza virus hemagglutinin polypeptide comprising one or more modified glycosylation sites and/or one or more non-naturally occurring glycosylation sites. As shown in FIGS. 19C and B of International Publication No. WO 2013/043729, which is incorporated herein by reference in its entirety, glycosylation of wild-type hemagglutinin occurs in both the globular head and stem domains. It is believed that glycosylation within these domains can mask antigenic regions, thereby allowing an influenza virus to evade a host immune system response. For example, seasonal influenza virus strains (e.g., H1N1 and H3N2) have been known to acquire additional glycosylation sites overtime in immunodominant antigenic regions of the globular head domain. Within the context of an influenza virus HA polypeptide described herein, however, glycosylation within the stem domain of the polypeptide can hinder or prevent desired immune responses against the conserved antigenic regions found in this domain.

Without being bound by any particular theory of operation, it is believed that an immune response to conserved antigenic regions within the stem domain of the influenza virus HA polypeptide provided herein can be increased by modifying one or more glycosylation sites within the stem domain in a manner that disrupts the glycosylation (i.e. the attachment of a glycan) at the sites. In addition, it is believed that masking of the immunodominant antigenic regions of the HA globular head domain by the addition of one or more non-naturally occurring glycosylation sites in these immunodominant regions can also increase the immunogenicity of conserved subimmunodominant antigenic regions within the stem domain. See FIG. 19C of International Publication No. WO 2013/043729, which is incorporated herein by reference in its entirety.

The flu hemagglutinin (HA) polypeptides comprising one or more modified glycosylation sites and/or one or more non-naturally occurring glycosylation sites can be used in accordance with the methods of vaccination described herein, i.e., such mutant HA polypeptides can be administered to a subject so as to elicit influenza virus stalk/stem domain-specific antibodies in the subject. To assess the ability of the mutant HA polypeptides to elicit such stalk-directed antibodies, subjects (e.g., mice) can be immunized with the mutant HA polypeptides described herein, or virus (e.g., influenza virus) expressing the mutant HA polypeptides described herein, and the ability of such mutant HA polypeptides or viruses expressing such mutant HA polypeptides to elicit the production stem/stalk domain specific antibodies can be assessed and compared to the ability of counterpart wild-type HA or wild-type viruses to elicit the production stem/stalk domain specific antibodies in the subject. For example, to assess the ability of the mutant HA polypeptides to elicit stalk-directed antibodies, mice can be immunized with a strain or subtype of wildtype influenza virus, influenza virus expressing HA mutants having glycosylation sites added to the head domain, and influenza virus expressing HA mutants with glycosylation sites removed from the stalk domain, and combinations thereof. Such mice then can be primed with influenza virus DNA or inoculated with viral protein. Three weeks later, such mice can be boosted with viral protein. Three weeks after being boosted with viral protein, the mice can be challenged with various influenza virus strains and monitored for weight loss and survival. The serum titers of anti-head and anti-stalk antibodies in infected mice can be assessed by ELISA as described below.

5.4.1 Modified Glycosylation Sites in the Stem Domain

In one embodiment, the flu hemagglutinin (HA) polypeptide provided herein comprises an HA stem domain comprising at least one modified glycosylation site, wherein the modified glycosylation site comprises a modification of a naturally occurring glycosylation site that disrupts the ability of a glycan to attach to the modified glycosylation site. In certain embodiments, the flu hemagglutinin (HA) polypeptide provided herein comprises an HA stem domain comprising at least one modified glycosylation site as provided in Section 5.4.1 of International Publication No. WO 2013/043729 and U.S. application Ser. No. 14/345,816, which published as U.S. Patent Publication No. 20150132330 which are incorporated herein by reference in their entirety. Without being bound by any particular theory of operation, it is believed that conserved antigenic regions within the stem domain of the flu HA polypeptide are shielded from a subject's immune system (e.g., an antibody response) by glycans that attach to these antigenic regions. Therefore, it is believed that immunogenicity of and accessibility to antigenic regions within the stem domain can be increased by modifying one or more glycosylation sites within the stem domain in a manner that disrupts the glycosylation (i.e. the attachment of a glycan) at the sites.

Modified glycosylation sites in which a naturally occurring glycosylation site is modified in a manner that disrupts the ability of a glycan to attach to the modified glycosylation site can be made by any technique apparent to one of skill in the art, including the methods described herein, including, for example, the site directed mutagenesis techniques discussed in Example 5 of International Publication No. WO 2013/043729, which is incorporated herein by reference in its entirety.

Modified glycosylation sites include, but are not limited to, N-linked and O-linked glycosylation sites. In certain embodiments, the modified glycosylation site is an N-linked glycosylation site. In other embodiments, the modified glycosylation site is an O-linked glycosylation site. In some embodiments, the modified glycosylation site is a modified N-linked glycosylation site having the amino acid motif Asn-Xaa-Ser/Thr/Cys, wherein Xaa is any amino acid or, in certain embodiments, wherein Xaa is any amino acid except Pro.

The modified glycosylation site can comprise any modification that can disrupt the ability of a glycan to attach to the modified glycosylation site. In preferred embodiments, the modification does not interfere with the proper folding of the flu hemagglutinin (HA) polypeptide and/or the ability of the flu hemagglutinin (HA) polypeptide to elicit an immune response in a subject. In certain embodiments, the modification comprises a deletion of one or more amino acid residues in a naturally occurring glycosylation site. In other embodiments, the modification comprises one or more amino acid substitutions in a naturally occurring glycosylation site.

In certain embodiments, the modified glycosylation site comprises one or more amino acid substitutions in a naturally occurring glycosylation site comprising the amino acid sequence Asn-Xaa-Ser/Thr/Cys, wherein Xaa is any amino acid or, in certain embodiments, wherein Xaa is any amino acid except Pro, and wherein the modification disrupts the ability of a glycan to attach to the modified glycosylation site. The modified glycosylation site can comprise any amino acid substitution know to one of skill in art that can disrupt the ability of a glycan to attach to the modified glycosylation site. In preferred embodiments, the one or more amino acid substitutions does not interfere with the ability of the flu hemagglutinin (HA) polypeptide to fold properly or elicit an immune response in a subject. In certain embodiments, the one or more amino acids of a naturally occurring glycosylation site is substituted for an Asn (N), Ser(s), Thr (T) or Asp (D) amino acid residue. Exemplary amino acid substitutions include, but are not limited to, substitution of an Asn (N) for a Lys (K) amino acid residue; substitution of a Ser(s) for an Asn (N) residue; and substitution of a Thr (T) for an Asp (D) residue. In specific embodiments, the modified glycosylation site comprises a substitution of an Asn (N) residue of a naturally occurring glycosylation site for a Lys (K) residue. In other embodiments, the modified glycosylation site comprises a substitution of a Ser(s) residue of a naturally occurring glycosylation site for an Asn (N) amino acid residue. In yet other embodiments, the modified glycosylation site comprises a substitution of a Thr (T) residue of a naturally occurring glycosylation site for an Asp (D) amino acid residue.

Conserved naturally occurring glycosylation sites in the HA stem domain include those shown in FIG. 20 of International Publication No. WO 2013/043729, which is incorporated herein by reference in its entirety. Exemplary naturally occurring N-glycosylation sites in group 1 hemagglutinins (H1, H2, H5, H6, H8, H9, H11, H12, H13, and H16) can be found at, but are not limited to, amino acid positions 20-22 (missing in H9), 21-23, 33-35 (missing in H8, H9, H12, H13, H16), 46-48 (missing in H1, H2, H5, H6, H8, H9, H11, H12), 289-291 (missing in H6, H11, H13, H16), 290-292 (missing in H1, H2, H5, H8, H9, H12), 296-298 (missing in H1, H2, H5, H11, H13, H16) and 481-483, wherein the amino acid positions are according to H3 numbering. In certain embodiments, one or more of the amino acids at these glycosylation sites may be modified.

Exemplary conserved N-glycosylation sites in group 2 hemagglutinins (H3, H4, H7, H10, H14, H15), can be found at, but are not limited to, amino acid positions, 8-10, 22-24, 38-40 (missing in H4, H14), 46-48 (missing in H3, H4, H7, H10, H14) 285-287 (missing in H4, H7, H10, H14, H15), 296-298 (missing in H3, H7, H15), 410-412 (missing in H3, H4, H14) and 481-483, wherein the amino acid positions are according to H3 numbering. In certain embodiments, one or more of the amino acids at these glycosylation sites may be modified.

The flu hemagglutinin polypeptide comprising a HA stem domain comprising at least one modified glycosylation site can be any flu hemagglutinin (HA) polypeptide comprising an HA stem domain described herein, including, but not limited to, a chimeric influenza virus hemagglutinin polypeptide, a non-chimeric influenza virus hemagglutinin polypeptide (i.e., an influenza virus hemagglutinin polypeptide comprising an HA stem domain and an HA head domain from the same subtype or strain), and an influenza virus hemagglutinin stem domain polypeptide.

In certain embodiments, the flu hemagglutinin (HA) polypeptide is a chimeric influenza virus hemagglutinin polypeptide. In specific embodiments, the chimeric influenza virus hemagglutinin (HA) polypeptide comprises an HA stem domain and an HA globular head domain, wherein the HA globular head domain is heterologous to the HA stem domain, and wherein the HA stem domain comprises at least one modified glycosylation site, wherein the modified glycosylation site comprises a modification of a naturally occurring glycosylation site that disrupts the ability of a glycan to attach to the modified glycosylation site. In specific embodiments, the modification comprises one or more amino acid substitutions in a naturally occurring glycosylation site having the amino acid sequence Asn-Xaa-Ser/Thr/Cys, wherein Xaa is any amino acid or, in certain embodiments, wherein Xaa is any amino acid except Pro.

In certain embodiments, the flu hemagglutinin (HA) polypeptide is a non-chimeric influenza virus hemagglutinin polypeptide. In specific embodiments, the non-chimeric influenza virus hemagglutinin polypeptide comprises an HA stem domain and an HA globular head domain, wherein the HA globular head domain is homologous to the HA stem domain (i.e., the globular head domain and stem domain are from the same influenza virus strain or subtype), and wherein the HA stem domain comprises at least one modified glycosylation site, wherein the modified glycosylation site comprises a modification of a naturally occurring glycosylation site that disrupts the ability of a glycan to attach to the modified glycosylation site. In specific embodiments, the modification comprises one or more amino acid substitutions in a naturally occurring glycosylation site having the amino acid sequence Asn-Xaa-Ser/Thr/Cys, wherein Xaa is any amino acid or, in certain embodiments, wherein Xaa is any amino acid except Pro. In certain embodiments, the non-chimeric influenza virus hemagglutinin polypeptide comprises an HA stem domain and HA globular head domain from the same influenza virus subtype. In specific embodiments, the influenza virus subtype is an H1, H2, H3, H4, H5, H6, H7, H8, H9, H10, H11, H12, H13, H14, H15, H16, H17, or H18 subtype. In specific embodiments, the non-chimeric influenza virus hemagglutinin polypeptide comprises an HA stem domain and HA globular head domain from the same influenza virus strain. In certain embodiments, the influenza virus strain is A/Netherlands/602/2009.

In certain embodiments, the flu hemagglutinin (HA) polypeptide is an influenza virus hemagglutinin stem domain polypeptide. Exemplary influenza virus hemagglutinin stem domain polypeptides are disclosed in Section 5.3, supra.

5.4.2 Non-Naturally Occurring Glycosylation Sites in the Globular Head Domain

In another embodiment, the flu hemagglutinin (HA) polypeptide provided herein comprises an HA globular head domain comprising at least one non-naturally occurring glycosylation site. In certain embodiments, the flu hemagglutinin (HA) polypeptide provided herein comprises an HA stem domain comprising at least one non-naturally occurring glycosylation site as provided in Section 5.4.2 of International Publication No. WO 2013/043729 and U.S. application Ser. No. 14/345,816, which published as U.S. Patent Publication No. 20150132330 which are incorporated herein by reference in their entirety. Without being bound by any particular theory of operation, it is believed that masking of the immunodominant antigenic regions of the HA globular head domain by the addition of one or more non-naturally occurring glycosylation sites in these immunodominant regions can also increase immunogenicity to the conserved subimmunodominant antigenic regions in the stem domain of the flu hemagglutinin (HA) polypeptide.

Non-naturally occurring glycosylation sites can be added to the HA globular head domain of the flu hemagglutinin (HA) polypeptide described herein using any known technique known to one of skill in the art, including, for example, the site directed mutagenesis techniques described in Example 5 of International Publication No. WO 2013/043729, which is incorporated herein by reference in its entirety. In preferred/specific embodiments, the non-naturally occurring glycosylation site does not interfere with the proper folding of the flu hemagglutinin (HA) polypeptide and/or interfere with the ability of the stem domain of the flu hemagglutinin (HA) polypeptide from eliciting an immune response (e.g., an antibody response) in a subject.

In certain embodiments, the non-naturally occurring glycosylation sites can be added to an HA globular head domain based on the head domain of an influenza A hemagglutinin. In certain embodiments, the HA globular head domain is based on the head domain of an influenza A hemagglutinin selected from the group consisting of H1, H2, H3, H4, H5, H6, H7, H8, H9, H10, H11, H12, H13, H14, H15, H16, and H17, and H18. In certain embodiments, the non-naturally occurring glycosylation sites can be added to an HA globular head domain based on the head domain of an influenza B hemagglutinin. In some embodiments, the HA globular head domain is based on the head domain of B/Seal/Netherlands/1/99.

The flu hemagglutinin (HA) polypeptide can comprise an HA globular head domain with one, two, three, four, five, six, seven, eight, nine, ten, eleven, twelve, thirteen, fourteen, fifteen, sixteen, seventeen, eighteen, nineteen, or twenty or more non-naturally occurring glycosylation sites. In some embodiments, the flu HA polypeptide comprises 2 to 5, 4 to 6, 5 to 10, or 10 to 15 non-naturally occurring glycosylation sites. In certain embodiments, the flu hemagglutinin (HA) polypeptide comprises an HA globular head domain with one non-naturally occurring glycosylation site. In other embodiments, the flu hemagglutinin (HA) polypeptide comprises an HA globular head domain with two non-naturally occurring glycosylation sites. In specific embodiments, the flu hemagglutinin (HA) polypeptide comprises an HA globular head domain with three non-naturally occurring glycosylation sites. In other embodiments, the flu hemagglutinin (HA) polypeptide comprises an HA globular head domain with four non-naturally occurring glycosylation sites. In certain embodiments, the flu hemagglutinin (HA) polypeptide comprises an HA globular head domain with five non-naturally occurring glycosylation sites. In other embodiments, the flu hemagglutinin (HA) polypeptide comprises an HA globular head domain with six non-naturally occurring glycosylation sites. In other embodiments, the flu hemagglutinin (HA) polypeptide comprises an HA globular head domain with seven non-naturally occurring glycosylation sites. In other embodiments, the flu hemagglutinin (HA) polypeptide comprises an HA globular head domain with eight non-naturally occurring glycosylation sites. In other embodiments, the flu hemagglutinin (HA) polypeptide comprises an HA globular head domain with nine non-naturally occurring glycosylation sites. In other embodiments, the flu hemagglutinin (HA) polypeptide comprises an HA globular head domain with ten non-naturally occurring glycosylation sites. In other embodiments, the flu hemagglutinin (HA) polypeptide an HA globular head domain with eleven non-naturally occurring glycosylation sites. In other embodiments, the flu hemagglutinin (HA) polypeptide comprises an HA globular head domain with twelve non-naturally occurring glycosylation sites. In certain embodiments, the flu hemagglutinin (HA) polypeptide comprises an HA globular head domain with thirteen non-naturally occurring glycosylation sites. In certain embodiments, the flu hemagglutinin (HA) polypeptide comprises an HA globular head domain with fourteen non-naturally occurring glycosylation sites. In other embodiments, the flu hemagglutinin (HA) polypeptide comprises an HA globular head domain with fifteen non-naturally occurring glycosylation sites. In other embodiments, the flu hemagglutinin (HA) polypeptide comprises an HA globular head domain with sixteen non-naturally occurring glycosylation sites. In certain embodiments, the flu hemagglutinin (HA) polypeptide comprises an HA globular head domain with seventeen non-naturally occurring glycosylation sites. In other embodiments, the flu hemagglutinin (HA) polypeptide comprises an HA globular head domain with eighteen non-naturally occurring glycosylation sites. In other embodiments, the flu hemagglutinin (HA) polypeptide comprises an HA globular head domain with nineteen non-naturally occurring glycosylation sites. In other embodiments, the flu hemagglutinin (HA) polypeptide comprises an HA globular head domain with twenty or more non-naturally occurring glycosylation sites.

The one or more non-naturally occurring glycosylation sites can be located at any amino acid positions within a globular head domain where a naturally occurring glycosylation site is not located with respect to a particular influenza virus subtype or strain. Exemplary mutations that introduce non-naturally occurring glycosylation sites into a globular head domain are shown in FIG. 21B of International Publication No. WO 2013/043729, which is incorporated herein by reference in its entirety. In certain embodiments, the non-naturally occurring glycosylation site is at amino acid positions 59-61, 128-130, 130-132, 158-160, and/or 163-165 according to the H3 numbering system. In certain embodiments, the non-naturally occurring glycosylation site is at amino acid positions 59-61, 81-83, 129-131, 143-145, 158-160, 165-167, 170-172, 187-189, 193-195, 197-199, and/or 208-210 according to the H3 numbering system. In some embodiments, the non-naturally occurring glycosylation site is at amino acid positions 59-61, according to H3 numbering. In other embodiments, the non-naturally occurring glycosylation site is at amino acid position 129-131, according to H3 numbering. In other embodiments, the non-naturally occurring glycosylation sites are at amino acid positions 129-131 and 158-160, according to H3 numbering. In some embodiments, the non-naturally occurring glycosylation sites are at amino acid positions 59-61, 129-131 and 165-167, according to H3 numbering. In some embodiments, the non-naturally occurring glycosylation sites are at amino acid positions 59-61, 129-131, 158-160 and 165-167, according to H3 numbering. In some embodiments, the non-naturally occurring glycosylation sites are at amino acid positions 81-83, 129-131, 158-160, 165-167, 170-172, 187-189 and 208-210, according to H3 numbering. In other embodiments, the non-naturally occurring glycosylation sites are at amino acid positions 81-83, 129-131, 158-160, 170-172, 187-189 and 208-210, according to H3 numbering. In still other embodiments, the non-naturally occurring glycosylation sites are at amino acid positions 129-131, 158-160, 165-167, 170-172, 187-189 and 208-210, according to H3 numbering.

In preferred embodiments, the non-naturally occurring glycosylation site is located in an antigenic region in the globular head domain, thereby shielding the antigenic region from eliciting an immune response. Exemplary antigenic regions in the globular domain include, but are not limited to the Sa, Sb, Ca and Cb antigenic site (FIG. 21A of International Publication No. WO 2013/043729, which is incorporated herein by reference in its entirety) in the H1 subtype and the A, B, C, D antigenic regions in the H3 subtype. In some embodiments, the flu hemagglutinin (HA) polypeptide comprises a non-naturally occurring glycosylation site located in the Sa antigenic region of an H1 subtype globular head domain. In certain embodiments, the flu hemagglutinin (HA) polypeptide comprises a non-naturally occurring glycosylation site located in the Sb antigenic region of an H1 subtype globular head domain. In other embodiments, the flu hemagglutinin (HA) polypeptide comprises a non-naturally occurring glycosylation site located in the Ca antigenic region of an H1 subtype globular head domain. In yet other embodiments, the flu hemagglutinin (HA) polypeptide comprises a non-naturally occurring glycosylation site located in the Cb antigenic region of an H1 subtype globular head domain. In another embodiment, the flu hemagglutinin (HA) polypeptide comprises a non-naturally occurring glycosylation site located in the Sa and Sb antigenic regions of an H1 subtype globular head domain. In another embodiment, the flu hemagglutinin (HA) polypeptide comprises a non-naturally occurring glycosylation site located in the Sa and Ca antigenic regions of an H1 subtype globular head domain. In another embodiment, the flu hemagglutinin (HA) polypeptide comprises a non-naturally occurring glycosylation site located in the Sa and Cb antigenic regions of an H1 subtype globular head domain. In another embodiment, the flu hemagglutinin (HA) polypeptide comprises a non-naturally occurring glycosylation site located in the Sb and Ca antigenic regions of an H1 subtype globular head domain. In another embodiment, the flu hemagglutinin (HA) polypeptide comprises a non-naturally occurring glycosylation site located in the Sb and Cb antigenic regions of an H1 subtype globular head domain. In another embodiment, the flu hemagglutinin (HA) polypeptide comprises a non-naturally occurring glycosylation site located in the Ca and Cb antigenic regions of an H1 subtype globular head domain. In another embodiment, the flu hemagglutinin (HA) polypeptide comprises a non-naturally occurring glycosylation site located in the Sa, Sb, and Ca antigenic regions of an H1 subtype globular head domain. In another embodiment, the flu hemagglutinin (HA) polypeptide comprises a non-naturally occurring glycosylation site located in the Sb, Ca and Cb antigenic regions of an H1 subtype globular head domain. In another embodiment, the flu hemagglutinin (HA) polypeptide comprises a non-naturally occurring glycosylation site located in the Sa, Sb, Ca and Cb antigenic regions of an H1 subtype globular head domain.

In some embodiments, the non-naturally occurring glycosylation site is in the A antigenic region of an H3 subtype globular head domain. In some embodiments, the non-naturally occurring glycosylation site is in the B antigenic region of an H3 subtype globular head domain. In some embodiments, the non-naturally occurring glycosylation site is in the C antigenic region of an H3 subtype globular head domain. In some embodiments, the non-naturally occurring glycosylation site is in the D antigenic region of an H3 subtype globular head domain. In another embodiment, the flu hemagglutinin (HA) polypeptide comprises a non-naturally occurring glycosylation site located in the A and B antigenic regions of an H3 subtype globular head domain. In another embodiment, the flu hemagglutinin (HA) polypeptide comprises a non-naturally occurring glycosylation site located in the A and C antigenic regions of an H3 subtype globular head domain. In another embodiment, the flu hemagglutinin (HA) polypeptide comprises a non-naturally occurring glycosylation site located in the A and D antigenic regions of an H3 subtype globular head domain. In another embodiment, the flu hemagglutinin (HA) polypeptide comprises a non-naturally occurring glycosylation site located in the B and C antigenic regions of an H3 subtype globular head domain. In another embodiment, the flu hemagglutinin (HA) polypeptide comprises a non-naturally occurring glycosylation site located in the B and D antigenic regions of an H3 subtype globular head domain. In another embodiment, the flu hemagglutinin (HA) polypeptide comprises a non-naturally occurring glycosylation site located in the C and D antigenic regions of an H3 subtype globular head domain. In another embodiment, the flu hemagglutinin (HA) polypeptide comprises a non-naturally occurring glycosylation site located in the A, B, and C antigenic regions of an H3 subtype globular head domain. In another embodiment, the flu hemagglutinin (HA) polypeptide comprises a non-naturally occurring glycosylation site located in the B, C, and D antigenic regions of an H3 subtype globular head domain. In another embodiment, the flu hemagglutinin (HA) polypeptide comprises a non-naturally occurring glycosylation site located in the A, B, C, and D antigenic regions of an H3 subtype globular head domain.

In other embodiments, a flu hemagglutinin (HA) polypeptide comprises one or more non-naturally occurring glycosylation sites in one or more antigenic regions of an H1, H2, H3, H4, H5, H6, H7, H8, H9, H10, H11, H12, H13, H14, H15, H16 or H17 globular head domain.

In certain embodiments, the flu hemagglutinin (HA) polypeptide comprising an HA globular head domain with one or more non-naturally occurring glycosylation sites is a chimeric influenza virus hemagglutinin polypeptide. In certain embodiments, the flu hemagglutinin (HA) polypeptide comprising an HA globular head domain with one or more non-naturally occurring glycosylation sites is a non-chimeric influenza virus hemagglutinin polypeptide.

5.4.3 Non-Naturally Occurring Glycosylation Sites in the Globular Head Domain and Modified Glycosylation Sites in the Stem Domain In another embodiment, the flu hemagglutinin (HA) polypeptide provided herein comprises an HA stem domain with one, two or more modified glycosylation sites and an HA globular head with one, two or more non-naturally occurring glycosylation sites, wherein the modified glycosylation sites comprises a modification of a naturally occurring glycosylation site that disrupts the ability of a glycan to attach to the modified glycosylation site. In certain embodiments, the flu hemagglutinin (HA) polypeptide provided herein comprises an HA stem domain with one, two or more modified glycosylation sites and an HA globular head with one, two or more non-naturally occurring glycosylation sites, wherein the modified glycosylation sites comprises a modification of a naturally occurring glycosylation site that disrupts the ability of a glycan to attach to the modified glycosylation site, as provided in Section 5.4.3 of International Publication No. WO 2013/043729 and U.S. application Ser. No. 14/345,816, which published as U.S. Patent Publication No. 20150132330 which are incorporated herein by reference in their entirety. The modified glycosylation sites and non-naturally occurring glycosylation sites can be produced using techniques known in the art and/or described herein. In specific embodiments, the modified glycosylation site(s) and non-naturally occurring glycosylation site(s) does not interfere with the proper folding of the flu HA polypeptide and/or interfere with the ability of the stem domain flu HA polypeptide from eliciting an immune response (e.g., an antibody response) in a subject. See, Sections 5.4.1 and 5.4.2, supra, for a description of modified glycosylation sites and non-naturally occurring glycosylation sites. The modified glycosylation sites and non-naturally occurring glycosylation sites described in Sections 5.4.1 and 5.4.2, supra, can both be incorporated into a flu HA polypeptide.

In certain embodiments, a flu hemagglutinin (HA) polypeptide provided herein comprises an HA stem domain with modified glycosylation sites at positions 33-35 and 289-291 according to H3 numbering; and an HA globular head domain comprising non-naturally occurring glycosylation sites at one, two, three, four, five, six or seven of the following positions: 129-131, 158-160, 165-167, 170-172, 187-189, and 208-210 according to H3 numbering.

In a specific embodiment, provided herein is a chimeric influenza hemagglutinin polypeptide comprising one or more non-naturally occurring glycosylation sites in the globular head domain and one or more modified glycosylation sites in the stem domain, wherein said modified glycosylation sites in the stem domain comprise a modification that disrupts glycosylation at the modified glycosylation site. In another specific embodiment, provided herein is a chimeric influenza hemagglutinin polypeptide comprising one or more non-naturally occurring glycosylation sites in the globular head domain and one or more modified glycosylation sites in the stem domain, wherein said modified glycosylation sites in the stem domain comprise a modification that disrupts glycosylation at the modified glycosylation site, and wherein (i) the non-naturally occurring glycosylation sites are at one, two, three, four, five, six, seven, or more of amino acid positions 81-83, 129-131, 158-160, 165-167, 170-172, 187-189 and 208-210, according to H3 numbering and (ii) the modified glycosylation sites are at one, two, three, or more of amino acid positions 20-23, 33-35, 271-273, 289-291, and/or 483-485 according to H3 numbering. In another specific embodiment, provided herein is a chimeric influenza hemagglutinin polypeptide comprising one or more non-naturally occurring glycosylation sites in the globular head domain and comprising one or more modified glycosylation sites in the stem domain, wherein said modified glycosylation sites in the stem domain comprise a modification that disrupts glycosylation at the modified glycosylation site, and wherein (i) the non-naturally occurring glycosylation sites are at amino acid positions 81-83, 129-131, 158-160, 170-172, 187-189 and 208-210, according to H3 numbering and (ii) the modified glycosylation sites are at amino acid positions 33-35 and 289-291, according to H3 numbering. In another specific embodiment, provided herein is a chimeric influenza hemagglutinin polypeptide comprising one or more non-naturally occurring glycosylation sites in the globular head domain comprising one or more modified glycosylation sites in the stem domain, wherein said modified glycosylation sites in the stem domain comprise a modification that disrupts glycosylation at the modified glycosylation site, and wherein (i) the non-naturally occurring glycosylation sites are at amino acid positions 81-83, 129-131, 158-160, 165-167, 170-172, 187-189 and 208-210, according to H3 numbering and (ii) the modified glycosylation sites are at amino acid positions 33-35 and 289-291, according to H3 numbering. In another specific embodiment, provided herein is a chimeric influenza hemagglutinin polypeptide comprising one or more non-naturally occurring glycosylation sites in the globular head domain comprising one or more modified glycosylation sites in the stem domain, wherein said modified glycosylation sites in the stem domain comprise a modification that disrupts glycosylation at the modified glycosylation site, and wherein (i) the non-naturally occurring glycosylation sites are at amino acid positions 129-131, 158-160, 165-167, 170-172, 187-189 and 208-210, according to H3 numbering and (ii) the modified glycosylation sites are at amino acid positions 33-35 and 289-291, according to H3 numbering. Exemplary chimeric influenza hemagglutinin polypeptide comprising modified glycosylation sites are described in Section 6.11 (Example 11) of International Publication No. WO 2013/043729, which is incorporated herein by reference in its entirety.

5.5 Influenza Virus Neuraminidase Immunogens

Provided herein are influenza virus neuraminidase (NA) immunogens (e.g., neuraminidase polypeptides). A full-length influenza neuraminidase typically comprises a cytoplasmic domain, a transmembrane domain, a stalk domain, and a globular head domain. In certain embodiments, the influenza virus neuraminidase polypeptides described herein maintain such a structure. That is, in certain embodiments, the influenza virus neuraminidase polypeptides described herein comprise a stable cytoplasmic domain, a transmembrane domain, a stalk domain, and a globular head domain. In certain embodiments, an influenza virus neuraminidase polypeptide described herein comprises a full-length influenza virus neuraminidase, e.g., comprises a cytoplasmic domain, a transmembrane domain, a stalk domain, and a globular head domain. In certain embodiments, an influenza virus neuraminidase polypeptide described herein comprises 1, 2, 3, or 4 domains of an influenza virus neuraminidase, e.g., comprises an influenza virus neuraminidase cytoplasmic domain, a transmembrane domain, a stalk domain, and/or a globular head domain. In certain embodiments, an influenza virus neuraminidase polypeptide described herein comprises an influenza virus neuraminidase cytoplasmic domain. In certain embodiments, an influenza virus neuraminidase polypeptide described herein comprises a fragment of an influenza virus neuraminidase cytoplasmic domain. In certain embodiments, an influenza virus neuraminidase polypeptide described herein comprises an influenza virus neuraminidase transmembrane domain. In certain embodiments, an influenza virus neuraminidase polypeptide described herein comprises a fragment of an influenza virus neuraminidase transmembrane domain. In certain embodiments, an influenza virus neuraminidase polypeptide described herein comprises an influenza virus neuraminidase stalk domain. In certain embodiments, an influenza virus neuraminidase polypeptide described herein comprises a fragment of an influenza virus neuraminidase stalk domain. In certain embodiments, an influenza virus neuraminidase polypeptide described herein comprises an influenza virus neuraminidase globular head domain. In certain embodiments, an influenza virus neuraminidase polypeptide described herein comprises a fragment of an influenza virus neuraminidase globular head domain.

In some embodiments, an influenza virus neuraminidase polypeptide described herein is a wild-type influenza virus neuraminidase polypeptide. In some embodiments, an influenza virus neuraminidase polypeptide described herein is an influenza A virus neuraminidase. In some embodiments, an influenza virus neuraminidase polypeptide described herein is an influenza B virus neuraminidase. In some embodiments, an influenza virus neuraminidase polypeptide described herein is an influenza C virus neuraminidase. In some embodiments, an influenza virus neuraminidase polypeptide described herein is an N1, N2, N3, N4, N5, N6, N7, N8, N9, N10, or N11 influenza virus neuraminidase. In some embodiments, an influenza virus neuraminidase polypeptide described herein is an N1, N2, N3, N4, N5, N6, N7, N8, or N9 influenza virus neuraminidase. In certain embodiments, an influenza virus neuraminidase polypeptide provided herein comprise an influenza neuraminidase head domain having at least 70%, 75%, 80%, 85%, 90%, 95%, 96%, 98%, or 99% amino acid sequence identity to an influenza neuraminidase head domain known to those of skill in the art.

In certain embodiments, an influenza virus neuraminidase polypeptide provided herein is a Group 1 influenza virus neuraminidase polypeptide, e.g., N1, N4, N5, and N8 influenza virus neuraminidase subtypes. In certain embodiments, an influenza virus neuraminidase polypeptide provided herein is an N1 subtype. In certain embodiments, an influenza virus neuraminidase polypeptide provided herein is an N4 subtype. In certain embodiments, an influenza virus neuraminidase polypeptide provided herein is an N5 subtype. In certain embodiments, an influenza virus neuraminidase polypeptide provided herein is an N8 subtype.

In certain embodiments, an influenza virus neuraminidase polypeptide is a Group 2 influenza virus neuraminidase polypeptide, e.g., N2, N3, N6, N7, and N9 influenza virus neuraminidase subtypes. In certain embodiments, an influenza virus neuraminidase polypeptide provided herein is an N2 subtype. In certain embodiments, an influenza virus neuraminidase polypeptide provided herein is an N3 subtype. In certain embodiments, an influenza virus neuraminidase polypeptide provided herein is an N6 subtype. In certain embodiments, an influenza virus neuraminidase polypeptide provided herein is an N7 subtype. In certain embodiments, an influenza virus neuraminidase polypeptide provided herein is an N9 subtype. In certain embodiments, an influenza virus neuraminidase polypeptide is a bat influenza virus neuraminidase polypeptide, e.g., N10 and N11 influenza virus neuraminidase subtypes. In certain embodiments, an influenza virus neuraminidase polypeptide provided herein is an N10 subtype. In certain embodiments, an influenza virus neuraminidase polypeptide provided herein is an N11 subtype.

GenBank™ Accession No. AAA43397.1 provides an exemplary amino acid sequence for a human influenza virus neuraminidase. GenBank™ Accession No. ABG23658.1 (GI: 108946273), GenBank™ Accession No. NP_040981.1 (GI: 8486128), GenBank™ Accession No. AAA43412.1 (GI: 324508), GenBank™ Accession No. ABE97720.1 (GI: 93008579), GenBank™ Accession No. ABE97719.1 (GI: 93008577), and GenBank™ Accession No. ABE97718.1 (GI: 93008575) provide exemplary amino acid sequences for human influenza virus neuraminidases. GenBank™ Accession No. CRI06477.1 provides an exemplary amino acid sequence for a swine influenza virus neuraminidase. GenBank™ Accession No. AAQ90293.1 provides an exemplary amino acid sequence for an equine influenza virus neuraminidase. GenBank™ Accession No. AEX30531.1 (GI: 371449652), GenBank™ Accession No. AEX30532.1 (GI: 371449654), GenBank™ Accession No. AIA62041.1 (GI: 641454926), GenBank™ Accession No. AII30325.1 (GI: 670605039), GenBank™ Accession No. AGO18161.1 (GI: 513130855), and GenBank™ Accession No. AAS89005.1 (GI: 46360357) provide exemplary amino acid sequences for avian influenza virus neuraminidases.

In certain embodiments, an influenza virus neuraminidase polypeptide is a human influenza virus neuraminidase polypeptide. Human influenza virus neuraminidase polypeptides are known in the art. In certain embodiments, an influenza virus neuraminidase polypeptide is a swine influenza virus neuraminidase polypeptide. Swine influenza virus neuraminidase polypeptides are known in the art. In certain embodiments, an influenza virus neuraminidase polypeptide is an equine influenza virus neuraminidase polypeptide. Equine influenza virus neuraminidase polypeptides are known in the art. In certain embodiments, an influenza virus neuraminidase is an avian influenza virus neuraminidase polypeptide. In certain embodiments, an influenza virus polypeptide provided herein is from a strain as described in Section 5.8, infra.

In certain embodiments, an influenza virus neuraminidase polypeptide provided herein is monomeric. In certain embodiments, an influenza virus neuraminidase polypeptide provided herein is multimeric. In certain embodiments, an influenza virus neuraminidase polypeptide provided herein is tetrameric.

In certain embodiments, one or more of glycosylation sites in an influenza virus neuraminidase polypeptide provided herein are modified (e.g., by amino acid addition, deletion or substitution). In specific embodiments, the one or more glycosylation sites are modified such that glycosylation at these sites will not occur during processing and maturation of the polypeptide. Those of skill in the art will recognize that influenza NA typically comprises one or more glycosylation sites (e.g. Asn-Xaa-Ser/Thr, wherein Xaa is any amino acid, or Asn-Xaa-Ser/Thr, wherein Xaa is any amino acid except Pro). In certain embodiments, the modified glycosylation site is located in the stalk domain of the influenza virus neuraminidase polypeptide. In certain embodiments, the modified glycosylation site is located in the globular head domain of the influenza virus neuraminidase polypeptide. In certain embodiments, one or more amino acid residues in a glycosylation site are conservatively substituted with an amino acid residue that disrupts the glycosylation site. In certain embodiments, one or more amino acid residues in a glycosylation site are substituted with any amino acid residue that disrupts the glycosylation site. In certain embodiments, one or more asparagine residues in a glycosylation site is substituted with alanine. In a particular embodiment, the asparagine at position is changed to an alanine. In certain embodiments, the influenza virus neuraminidase polypeptide comprises one or more non-naturally occurring glycosylation sites in its stalk domain. In certain embodiments, the influenza virus neuraminidase polypeptide comprises one or more non-naturally occurring glycosylation sites in its globular head domain. In certain embodiments, the influenza virus neuraminidase polypeptide lacks one or more naturally occurring glycosylation sites and/or has been deglycosylated (e.g., by a removing glycosylation sites and/or using a deglycosylation agent). Examples of deglycosylation agents include trifluoromethanesulfonic acid (Sigma), an enzyme, such as PNGase F, endoglycosidase H, exoglycosidase(s), and a Protein Deglycosylation Mix (e.g., the Protein Deglycosylation Mix sold by New England Biolabs Inc.).

In certain embodiments, the influenza virus neuraminidase polypeptides provided herein are capable of forming a three dimensional structure that is similar to the three dimensional structure of a native influenza neuraminidase. Structural similarity might be evaluated based on any technique deemed suitable by those of skill in the art. For instance, reaction, e.g. under non-denaturing conditions, of an influenza virus neuraminidase polypeptide with a neutralizing antibody or antiserum that recognizes a native influenza neuraminidase might indicate structural similarity. Useful neutralizing antibodies or antisera are described in, e.g., Shoji et al., Hum. Vaccines, 2011, 7:199-204, Wan et al., J. Virol. 2013, 87:9290-9300, Doyle et al. Antivir. Res. 2013, 100:567-574, and Doyle et al., Biochem. Biophys. Res. Commun. 2013, 441:226-229, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a neuraminidase.

In certain embodiments, the influenza virus neuraminidase polypeptides provided herein further comprise one or more polypeptide domains. Useful polypeptide domains include domains that facilitate purification, folding and cleavage of portions of a polypeptide. For example, a His tag (His-His-His-His-His-His, SEQ ID NO:101), FLAG epitope or other purification tag can facilitate purification of an influenza virus neuraminidase polypeptide provided herein. In some embodiments, the His tag has the sequence, (His)n, wherein n is 2, 3, 4, 5, 6, 7, 8, 9, 10, 11, 12, 13, 14, 15, 16, 17, 18, 19, 20 or greater. A tetramerization domain from Shaker-type voltage-gated potassium channels can facilitate tetramerization of neuraminidase polypeptides provided herein. In some embodiments, the tetramerization domain comprises a GCN4-LI domain or a modified GCN4-LI tetramerization domain that allows for the formation of tetrameric coiled coils. See, e.g., Zerangue et al., 2000, PNAS, 97(7): 3591-3595. The tetramerization domain can have any tetramerization sequence known to those of skill in the art (see, e.g., Papanikolopoulou et al., 2004, J. Biol. Chem. 279(10):8991-8998, the contents of which are hereby incorporated by reference in their entirety. Examples include GSGYIPEAPRDGQAYVRKDGEWVLLSTFL (SEQ ID NO:102). A tetramerization domain can be useful to facilitate tetramerization of soluble polypeptides provided herein. Cleavage sites can be used to facilitate cleavage of a portion of a polypeptide, for example cleavage of a purification tag or tetramerization domain or both. Useful cleavage sites include a thrombin cleavage site, for example one with the sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50).

In certain embodiments, the influenza neuraminidase polypeptides are soluble polypeptides. See, for example, Section 6.

When designing the influenza neuraminidase polypeptides, care should be taken to maintain the stability of the resulting protein. In this regard, it is recommended that cysteine residues capable of forming disulfide bonds be maintained since they contribute to the stability of the neuraminidase protein. See, e.g., Basler et al., 1999, Journal of Virology, 73(10):8095-8103 for non-limiting examples of influenza virus neuraminidase cysteine residues capable of forming disulfide bonds. In some embodiments, influenza neuraminidase polypeptides described herein comprise one or more amino acid substitutions, that increases the stability of the polypeptides at a low pH (e.g., a pH of between 4.9 to 5.2, 4.5 to 3.5, 3.5 to 2.5, 2.5 to 1.5, 1.5 to 0.5). The stability of influenza neuraminidase polypeptides can be assessed using techniques known in the art, such as sensitivity of the neuraminidase molecules to $Ca^{2+}$, as described in, e.g., Baker and Gandhi, 1976, Archives of Virology, 52:7-18.

In certain embodiments, the influenza virus neuraminidase polypeptide is a fragment of a neuraminidase polypeptide, such, for example, an influenza virus neuraminidase antigenic peptides. Generally, the influenza virus neuraminidase antigenic peptide comprises or consists of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 60, 51, 52, 53, 54, 55, 56, 57, 58, 59, 60, 61, 62, 63, 64, 65, 66, 67, 68, 69, 70, 71, 72, 73, 75, 75, 76, 77, 78, 79, 80, 81, 82, 83, 84, 85, 86, 87, 88, 89, 90, 91, 92, 93, 94, 95, 96, 97, 98, 99, or 100 amino acids from an influenza virus neuraminidase polypeptide. In certain embodiments, the influenza virus neuraminidase antigenic peptide comprises or consists of 3-10, 10-20, 20-30, 30-40, 40-50, 50-60, 60-70, 70-80, 80-90, or 90-100 amino acids from an influenza virus neuraminidase. In certain embodiments, the amino acids from the influenza virus neuraminidase are consecutive amino acids. In certain embodiments, the amino acids from the influenza virus neuraminidase are discontinuous amino acids.

In certain embodiments, an influenza virus neuraminidase antigenic peptide comprises amino acids from an influenza virus neuraminidase cytoplasmic domain. In certain embodiments, an influenza virus neuraminidase antigenic peptide described herein comprises amino acids from an influenza virus neuraminidase transmembrane domain. In certain embodiments, an influenza virus neuraminidase antigenic peptide described herein comprises amino acids from an influenza virus neuraminidase stalk domain. In certain embodiments, an influenza virus neuraminidase antigenic peptide described herein comprises amino acids from an influenza virus neuraminidase globular head domain.

In some embodiments, an influenza virus neuraminidase antigenic peptide described herein comprises 3-10, 10-20, 20-30, 30-40, 40-50, 50-60, 60-70, 70-80, 80-90, or 90-100 amino acids from an influenza A virus neuraminidase. In some embodiments, an influenza virus neuraminidase antigenic peptide described herein comprises 3-10, 10-20, 20-30, 30-40, 40-50, 50-60, 60-70, 70-80, 80-90, or 90-100 amino acids from an influenza B virus neuraminidase. In some embodiments, an influenza virus neuraminidase antigenic peptide described herein comprises 3-10, 10-20, 20-30, 30-40, 40-50, 50-60, 60-70, 70-80, 80-90, or 90-100 amino acids from an influenza C virus neuraminidase. In some embodiments, an influenza virus neuraminidase antigenic peptide described herein comprises 3-10, 10-20, 20-30, 30-40, 40-50, 50-60, 60-70, 70-80, 80-90, or 90-100 amino acids from an N1, N2, N3, N4, N5, N6, N7, N8, N9, N10, or N11 influenza virus neuraminidase. In some embodiments, an influenza virus neuraminidase antigenic peptide described herein comprises 3-10, 10-20, 20-30, 30-40, 40-50, 50-60, 60-70, 70-80, 80-90, or 90-100 amino acids from an N1, N2, N3, N4, N5, N6, N7, N8, or N9 influenza virus neuraminidase. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids having at least 70%, 75%, 80%, 85%, 90%, 95%, 96%, 98%, or 99% amino acid sequence identity to an influenza neuraminidase polypeptide known to those of skill in the art.

In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from a Group 1 influenza virus neuraminidase polypeptide, e.g., N1, N4, N5, and N8 influenza virus neuraminidase subtypes. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N1 subtype. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N4 subtype. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N5 subtype. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N8 subtype.

In certain embodiments, an influenza virus neuraminidase antigenic peptide comprises 3-10, 10-20, 20-30, 30-40, 40-50, 50-60, 60-70, 70-80, 80-90, or 90-100 amino acids from a Group 2 influenza virus neuraminidase polypeptide, e.g., N2, N3, N6, N7, and N9 influenza virus neuraminidase subtypes. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N2 subtype. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N3 subtype. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N6 subtype. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N7 subtype. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N9 subtype.

In certain embodiments, an influenza virus neuraminidase antigenic peptide comprises 3-10, 10-20, 20-30, 30-40, 40-50, 50-60, 60-70, 70-80, 80-90, or 90-100 amino acids from a bat influenza virus neuraminidase polypeptide, e.g., N10 and N11 influenza virus neuraminidase subtypes. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N10 subtype. In certain embodiments, an influenza virus neuraminidase antigenic peptide provided herein comprises 3-10, 10-20, 20-30, 30-40, 40-50, 50-60, 60-70, 70-80, 80-90, or 90-100 amino acids from an N11 subtype.

In certain embodiments, an influenza virus neuraminidase antigenic peptide comprises 3-10, 10-20, 20-30, 30-40, 40-50, 50-60, 60-70, 70-80, 80-90, or 90-100 amino acids from a human influenza virus neuraminidase polypeptide. In certain embodiments, an influenza virus neuraminidase antigenic peptide comprises 3-10, 10-20, 20-30, 30-40, 40-50, 50-60, 60-70, 70-80, 80-90, or 90-100 amino acids from a swine influenza virus neuraminidase polypeptide. In certain embodiments, an influenza virus neuraminidase antigenic peptide comprises 3-10, 10-20, 20-30, 30-40, 40-50, 50-60, 60-70, 70-80, 80-90, or 90-100 amino acids from an equine influenza virus neuraminidase polypeptide. Human, swine, and equine influenza virus neuraminidase polypeptides are known in the art. In certain embodiments, an influenza virus antigenic peptide provided herein comprises 3-10, 10-20, 20-30, 30-40, 40-50, 50-60, 60-70, 70-80, 80-90, or 90-100 amino acids from a strain as described in Section 5.8.

In certain embodiments, an influenza virus neuraminidase antigenic peptide comprises a conserved influenza virus neuraminidase epitope, e.g., an epitope that has at least 50%, 60%, 70%, 80%, 90%, or 100% sequence identity between same or different influenza virus neuraminidase strains and/or subtypes. In certain embodiments, the conserved influenza virus neuraminidase epitope has at least 50%, 60%, 70%, 80%, 90%, or 100% sequence identity between influenza A virus, influenza B virus, and/or influenza C virus neuraminidase. In certain embodiments, the conserved influenza virus neuraminidase epitope has at least 50%, 60%, 70%, 80%, 90%, or 100% sequence identity between influenza A virus and influenza B virus neuraminidase.

In certain embodiments, the conserved influenza virus neuraminidase epitope has at least 50%, 60%, 70%, 80%, 90%, or 100% sequence identity between influenza B virus neuraminidase strains as described in Section 5.8 or known in the art. In a specific embodiment, the conserved influenza virus neuraminidase epitope comprises or consists of the amino acid sequence ILRTQESEC (SEQ ID NO:107).

In certain embodiments, the conserved influenza virus neuraminidase epitope has at least 50%, 60%, 70%, 80%, 90%, or 100% sequence identity between Group 1, e.g., N1, N4, N5, and N8, and Group 2, e.g., N2, N3, N6, N7, and N9, influenza virus neuraminidase subtypes. In certain embodiments, the conserved influenza virus neuraminidase epitope has at least 50%, 60%, 70%, 80%, 90%, or 100% sequence identity between 1, 2, 3, 4, 5, 6, 7, 8, 9, 10, or more influenza virus neuraminidase subtypes, e.g., N1, N2, N3, N4, N5, N6, N7, N8, N9, N10, or N11. In certain embodiments, the conserved influenza virus neuraminidase epitope has at least 50%, 60%, 70%, 80%, 90%, or 100% sequence identity between 1, 2, 3, 4, 5, 6, 7, 8, 9, 10, or more influenza virus neuraminidase strains of the same or different subtype, e.g., 1, 2, 3, 4, 5, 6, 7, 8, 9, 10 or more influenza virus strains as described in Section 5.8 or known in the art. In a specific embodiment, the conserved influenza virus neuraminidase epitope comprises or consists of the amino acid sequence ILRTQESEC (SEQ ID NO:107).

In certain embodiments, an influenza virus neuraminidase antigenic peptide comprises or consists of the amino acid residues 222 to 230 or 226 to 230 of an influenza virus neuraminidase. In some embodiments, an influenza virus neuraminidase antigenic peptide comprises one, two, three, four, five, six, seven, eight, nine, ten or more of the following amino acid residues of an influenza virus neuraminidase 150, 198, 199, 220, 221, 253, 284, 329, 344, 346, 367, 368, 369, 370, 372, 400, 403, and/or 432 (according to N2 numbering). In certain embodiments, an influenza virus neuraminidase antigenic peptide comprises or consists of an epitope described in Huang et al, 2013, J. Transl. Med. 11:47 (see, e.g., Table 2 of Huang et al.), which is incorporated herein by reference in its entirety.

In certain embodiments, an influenza virus neuraminidase antigenic peptide provided herein is monomeric. In certain embodiments, an influenza virus neuraminidase antigenic peptide provided herein is multimeric. In certain embodiments, an influenza virus neuraminidase antigenic peptide provided herein is tetrameric.

In certain embodiments, one or more of glycosylation sites in an influenza virus neuraminidase antigenic peptide provided herein are modified (e.g., by amino acid addition, deletion or substitution). In specific embodiments, the one or more glycosylation sites are modified such that glycosylation at these sites will not occur during processing and maturation of the polypeptide. Those of skill in the art will recognize that influenza NA typically comprises one or more glycosylation sites (e.g. Asn-Xaa-Ser/Thr, wherein Xaa is any amino acid, or Asn-Xaa-Ser/Thr, wherein Xaa is any amino acid except Pro). In certain embodiments, the modified glycosylation site is located in the stalk domain of the influenza virus neuraminidase antigenic peptide. In certain embodiments, the modified glycosylation site is located in the globular head domain of the influenza virus neuraminidase antigenic peptide. In certain embodiments, one or more amino acid residues in a glycosylation site are conservatively substituted with an amino acid residue that disrupts the glycosylation site. In certain embodiments, one or more amino acid residues in a glycosylation site are substituted with any amino acid residue that disrupts the glycosylation site. In certain embodiments, one or more asparagine residues in a glycosylation site is substituted with alanine. In a particular embodiment, the asparagine at position is changed to an alanine. In certain embodiments, the influenza virus neuraminidase antigenic peptide comprises one or more non-naturally occurring glycosylation sites in its stalk domain. In certain embodiments, the influenza virus neuraminidase antigenic peptide comprises one or more non-naturally occurring glycosylation sites. In certain embodiments, the influenza virus neuraminidase antigenic peptides provided herein are capable of forming a three dimensional structure that is similar to the three dimensional structure of a native influenza neuraminidase. Structural similarity might be evaluated based on any technique deemed suitable by those of skill in the art. For instance, reaction, e.g., under non-denaturing conditions, of an influenza virus neuraminidase polypeptide with a neutralizing antibody or antiserum that recognizes a native influenza neuraminidase might indicate structural similarity. Useful neutralizing antibodies or antisera are described in, e.g., Shoji et al., Hum. Vaccines, 2011, 7:199-204, Wan et al., J. Virol. 2013, 87:9290-9300, Doyle et al. Antivir. Res. 2013, 100:567-574, and Doyle et al., Biochem. Biophys. Res. Commun. 2013, 441:226-229, the contents of which are hereby incorporated by reference in their entireties. In certain embodiments, the antibody or antiserum is an antibody or antiserum that reacts with a non-contiguous epitope (i.e., not contiguous in primary sequence) that is formed by the tertiary or quaternary structure of a neuraminidase.

In certain embodiments, the influenza virus neuraminidase antigenic peptides provided herein further comprise one or more polypeptide domains. Useful polypeptide domains include domains that facilitate purification, folding and cleavage of portions of a polypeptide. For example, a His tag (His-His-His-His-His-His, SEQ ID NO:101), FLAG epitope or other purification tag can facilitate purification of an influenza virus neuraminidase antigenic peptide provided herein. In some embodiments, the His tag has the sequence, (His)n, wherein n is 2, 3, 4, 5, 6, 7, 8, 9, 10, 11, 12, 13, 14, 15, 16, 17, 18, 19, 20 or greater. A tetramerization domain from Shaker-type voltage-gated potassium channels can facilitate tetramerization of neuraminidase antigenic peptides provided herein. In some embodiments, the tetramerization domain comprises a GCN4-LI domain or a modified GCN4-LI tetramerization domain that allows for the formation of tetrameric coiled coils. See, e.g., Zerangue et al., 2000, PNAS, 97(7): 3591-3595. The tetramerization domain can have any tetramerization sequence known to those of skill in the art (see, e.g., Papanikolopoulou et al., 2004, J. Biol. Chem. 279(10):8991-8998, the contents of which are hereby incorporated by reference in their entirety. Examples include GSGYIPEAPRDGQAYVRKDGEWVLLSTFL (SEQ ID NO:102). A tetramerization domain can be useful to facilitate tetramerization of soluble peptides provided herein. Cleavage sites can be used to facilitate cleavage of a portion of a peptide, for example cleavage of a purification tag or tetramerization domain or both. Useful cleavage sites include a thrombin cleavage site, for example one with the sequence LVPRGSP (SEQ ID NO:103). In certain embodiments, the cleavage site is a cleavage site recognized by Tobacco Etch Virus (TEV) protease (e.g., amino acid sequence Glu-Asn-Leu-Tyr-Phe-Gln-(Gly/Ser) (SEQ ID NO:50).

In certain embodiments, the influenza neuraminidase antigenic peptides are soluble polypeptides.

5.6 Nucleic Acids Encoding Flu Hemagglutinin (HA) Polypeptide and/or Influenza Virus Neuraminidase Polypeptides Provided herein are nucleic acids that encode the flu hemagglutinin (HA) polypeptides (e.g., chimeric influenza virus hemagglutinin polypeptides) and/or influenza virus neuraminidase polypeptides described herein. Due to the degeneracy of the genetic code, any nucleic acid that encodes a flu hemagglutinin (HA) polypeptide or an influenza virus neuraminidase polypeptide described herein is encompassed herein. In certain embodiments, nucleic acids corresponding to naturally occurring influenza virus nucleic acids encoding an HA1 N-terminal stem segment, an HA1 C-terminal stem segment, HA2 domain, HA luminal domain, HA transmembrane domain, and/or HA cytoplasmic domain are used to produce a flu hemagglutinin (HA) polypeptide (e.g., a chimeric influenza virus hemagglutinin polypeptide). In certain embodiments, nucleic acids corresponding to naturally occurring influenza virus nucleic acids encoding an NA cytoplasmic domain, an NA transmembrane domain, an NA stalk domain, and/or an NA globular head domain are used to produce an influenza virus neuraminidase polypeptide described herein.

Also provided herein are nucleic acids capable of hybridizing to a nucleic acid encoding a flu hemagglutinin (HA) polypeptide (e.g., a chimeric influenza virus hemagglutinin polypeptide) or an influenza virus neuraminidase polypeptide. In certain embodiments, provided herein are nucleic acids capable of hybridizing to a fragment of a nucleic acid encoding a flu hemagglutinin (HA) polypeptide (e.g., a chimeric influenza virus hemagglutinin polypeptide) or an influenza virus neuraminidase polypeptide. In other embodiments, provided herein are nucleic acids capable of hybridizing to the full length of a nucleic acid encoding a flu hemagglutinin (HA) polypeptide (e.g., a chimeric influenza virus hemagglutinin polypeptide) or to the full length of a nucleic acid encoding an influenza virus neuraminidase polypeptide. General parameters for hybridization conditions for nucleic acids are described in Sambrook et al., Molecular Cloning—A Laboratory Manual (2nd Ed.), Vols. 1-3, Cold Spring Harbor Laboratory, Cold Spring Harbor, N.Y. (1989), and in Ausubel et al., Current Protocols in Molecular Biology, vol. 2, Current Protocols Publishing, New York (1994). Hybridization may be performed under high stringency conditions, medium stringency conditions, or low stringency conditions. Those of skill in the art will understand that low, medium and high stringency conditions are contingent upon multiple factors all of which interact and are also dependent upon the nucleic acids in question. For example, high stringency conditions may include temperatures within 5° C. melting temperature of the nucleic acid(s), a low salt concentration (e.g., less than 250 mM), and a high co-solvent concentration (e.g., 1-20% of co-solvent, e.g., DMSO). Low stringency conditions, on the other hand, may include temperatures greater than 10° C.

below the melting temperature of the nucleic acid(s), a high salt concentration (e.g., greater than 1000 mM) and the absence of co-solvents.

In some embodiments, a nucleic acid encoding a flu hemagglutinin (HA) polypeptide (e.g., a chimeric influenza virus hemagglutinin polypeptide) or an influenza virus neuraminidase polypeptide is isolated. In certain embodiments, an "isolated" nucleic acid refers to a nucleic acid molecule which is separated from other nucleic acid molecules which are present in the natural source of the nucleic acid. In other words, the isolated nucleic acid can comprise heterologous nucleic acids that are not associated with it in nature. In other embodiments, an "isolated" nucleic acid, such as a cDNA molecule, can be substantially free of other cellular material, or culture medium when produced by recombinant techniques, or substantially free of chemical precursors or other chemicals when chemically synthesized. The term "substantially free of cellular material" includes preparations of nucleic acid in which the nucleic acid is separated from cellular components of the cells from which it is isolated or recombinantly produced. Thus, nucleic acid that is substantially free of cellular material includes preparations of nucleic acid having less than about 30%, 20%, 10%, or 5% (by dry weight) of other nucleic acids. The term "substantially free of culture medium" includes preparations of nucleic acid in which the culture medium represents less than about 50%, 20%, 10%, or 5% of the volume of the preparation. The term "substantially free of chemical precursors or other chemicals" includes preparations in which the nucleic acid is separated from chemical precursors or other chemicals which are involved in the synthesis of the nucleic acid. In specific embodiments, such preparations of the nucleic acid have less than about 50%, 30%, 20%, 10%, 5% (by dry weight) of chemical precursors or compounds other than the nucleic acid of interest.

In addition, provided herein are nucleic acids encoding the individual components of a chimeric influenza virus hemagglutinin polypeptide. In specific embodiments, nucleic acids encoding the globular head domain and/or the stem domain of the chimeric influenza virus hemagglutinin polypeptide are provided. Nucleic acids encoding components of a chimeric influenza virus hemagglutinin polypeptide may be assembled using standard molecular biology techniques known to one of skill in the art. In specific embodiments, the individual components of a chimeric influenza virus hemagglutinin polypeptide can be expressed by the same or different vector.

In addition, provided herein are nucleic acids encoding the individual components of an influenza hemagglutinin stem domain polypeptide. In specific embodiments, nucleic acids encoding an HA1 N-terminal stem segment, an HA1 C-terminal stem segment and/or HA2 domain are provided. Nucleic acids encoding components of an influenza hemagglutinin stem domain polypeptide may be assembled using standard molecular biology techniques known to the one of skill in the art. In specific embodiments, the individual components of an influenza hemagglutinin stem domain polypeptide can be expressed by the same or different vector.

In addition, provided herein are nucleic acids encoding the individual domains of an influenza virus neuraminidase polypeptide. In specific embodiments, nucleic acids encoding an NA cytoplasmic domain, an NA transmembrane domain, an NA stalk domain, and/or an NA globular head domain are provided. Nucleic acids encoding components of an influenza virus neuraminidase polypeptide may be assembled using standard molecular biology techniques known to one of skill in the art. In specific embodiments, the individual domains of an influenza virus neuraminidase polypeptide can be expressed by the same or different vector.

In addition, nucleic acids encoding a flu hemagglutinin polypeptide or a fragment thereof described herein and nucleic acids encoding an influenza virus neuraminidase polypeptide or a fragment thereof described herein can be expressed by the same or different vector. See Sections 5.8-5.12.

5.7 Expression of Flu Hemagglutinin (Ha) Polypeptide and/or Influenza Virus Neuraminidase Polypeptide Provided herein are vectors, including expression vectors, containing a nucleic acid encoding a flu hemagglutinin (HA) polypeptide (e.g., a chimeric influenza virus hemagglutinin polypeptide) described herein and/or an influenza virus neuraminidase polypeptide described herein. In a specific embodiment, the vector is an expression vector that is capable of directing the expression of a nucleic acid encoding a flu hemagglutinin (HA) polypeptide (e.g., a chimeric influenza virus hemagglutinin polypeptide) and/or a nucleic acid encoding an influenza virus neuraminidase polypeptide. Non-limiting examples of expression vectors include, but are not limited to, plasmids and viral vectors, such as replication defective retroviruses, adenoviruses, adeno-associated viruses and baculoviruses. Expression vectors also may include, without limitation, transgenic animals and non-mammalian cells/organisms, e.g., mammalian cells/organisms that have been engineered to perform mammalian N-linked glycosylation.

In some embodiments, provided herein are expression vectors encoding components of a flu hemagglutinin (HA) polypeptide (e.g., the stem domain and the head domain, or portions of either domain). In some embodiments, provided herein are expression vectors encoding components of an influenza virus neuraminidase polypeptide. In some embodiments, provided herein are expression vectors encoding components of a flu hemagglutinin (HA) polypeptide (e.g., the stem domain and the head domain, or portions of either domain) and/or the components of an influenza virus neuraminidase polypeptide. Such vectors may be used to express the components in one or more host cells and the components may be isolated and conjugated together with a linker using techniques known to one of skill in the art.

An expression vector comprises a nucleic acid encoding a flu hemagglutinin (HA) polypeptide described herein and/or a nucleic acid encoding an influenza virus neuraminidase polypeptide in a form suitable for expression of the nucleic acid in a host cell. In a specific embodiment, an expression vector includes one or more regulatory sequences, selected on the basis of the host cells to be used for expression, which is operably linked to the nucleic acid to be expressed. Within an expression vector, "operably linked" is intended to mean that a nucleic acid of interest is linked to the regulatory sequence(s) in a manner which allows for expression of the nucleic acid (e.g., in an in vitro transcription/translation system or in a host cell when the vector is introduced into the host cell). Regulatory sequences include promoters, enhancers and other expression control elements (e.g., polyadenylation signals). Regulatory sequences include those which direct constitutive expression of a nucleic acid in many types of host cells, those which direct expression of the nucleic acid only in certain host cells (e.g., tissue-specific regulatory sequences), and those which direct the expression of the nucleic acid upon stimulation with a particular agent (e.g., inducible regulatory sequences). It will be appreciated by those skilled in the art that the design of the expression vector can depend on such factors as the choice of the host cell to be transformed, the level of expression of protein desired, etc. The term "host cell" is intended to include a particular subject cell transformed or transfected with a nucleic acid and the progeny or potential progeny of such a cell. Progeny of such a cell may not be identical to the parent cell transformed or transfected with the nucleic acid due to mutations or environmental influences that may occur in succeeding generations or integration of the nucleic acid into the host cell genome. In specific embodiments, the host cell is a cell line.

Expression vectors can be designed for expression of a flu hemagglutinin (HA) polypeptide described herein and/or an influenza virus neuraminidase polypeptide described herein using prokaryotic (e.g., *E. coli*) or eukaryotic cells (e.g., insect cells (using baculovirus expression vectors, see, e.g., Treanor et al., 2007, JAMA, 297(14):1577-1582 incorporated by reference herein in its entirety), yeast cells, plant cells, algae, avian, or mammalian cells). Examples of yeast host cells include, but are not limited to *S. pombe* and *S. cerevisiae* and examples, infra. An example of avian cells includes, but is not limited to EB66 cells. Examples of mammalian host cells include, but are not limited to, Crucell Per.C6 cells, Vero cells, CHO cells, VERO cells, BHK cells, HeLa cells, COS cells, MDCK cells, 293 cells, 3T3 cells or WI38 cells. In certain embodiments, the hosts cells are myeloma cells, e.g., NS0 cells, 45.6 TG1.7 cells, AF-2 clone 9B5 cells, AF-2 clone 9B5 cells, J558L cells, MOPC 315 cells, MPC-11 cells, NCI-H929 cells, NP cells, NS0/1 cells, P3 NS1 Ag4 cells, P3/NS1/1-Ag4-1 cells, P3U1 cells, P3X63Ag8 cells, P3X63Ag8.653 cells, P3X63Ag8U.1 cells, RPMI 8226 cells, Sp20-Ag14 cells, U266B1 cells, X63AG8.653 cells, Y3.Ag.1.2.3 cells, and YO cells. Non-limiting examples of insect cells include Sf9, Sf21, *Trichoplusia ni, Spodoptera frugiperda* and *Bombyx mori*. In a particular embodiment, a mammalian cell culture system (e.g. Chinese hamster ovary or baby hamster kidney cells) is used for expression of a flu hemagglutinin (HA) polypeptide and/or an influenza virus neuraminidase polypeptide. In another embodiment, a plant cell culture system is used for expression of a flu hemagglutinin (HA) polypeptide and/or an influenza virus neuraminidase polypeptide. See, e.g., U.S. Pat. Nos. 7,504,560; 6,770,799; 6,551,820; 6,136,320; 6,034,298; 5,914,935; 5,612,487; and 5,484,719, and U.S. patent application publication Nos. 2009/0208477, 2009/0082548, 2009/0053762, 2008/0038232, 2007/0275014 and 2006/0204487 for plant cells and methods for the production of proteins utilizing plant cell culture systems. In specific embodiments, plant cell culture systems are not used for expression of a flu hemagglutinin (HA) polypeptide and/or an influenza virus neuraminidase polypeptide. The host cells comprising the nucleic acids that encode the flu hemagglutinin (HA) polypeptides (e.g., a chimeric influenza virus hemagglutinin polypeptides) described herein and/or nucleic acids that encode the influenza virus neuraminidase polypeptides described herein can be isolated, i.e., the cells are outside of the body of a subject. In certain embodiments, the cells are engineered to express nucleic acids that encode the flu hemagglutinin (HA) polypeptides (e.g., a chimeric influenza virus hemagglutinin polypeptides) described herein and/or the influenza virus neuraminidase polypeptides described herein. In specific embodiments, the host cells are cells from a cell line.

An expression vector can be introduced into host cells via conventional transformation or transfection techniques. Such techniques include, but are not limited to, calcium phosphate or calcium chloride co-precipitation, DEAE-dextran-mediated transfection, lipofection, and electroporation. Suitable methods for transforming or transfecting host cells can be found in Sambrook et al., 1989, Molecular Cloning—A Laboratory Manual, 2nd Edition, Cold Spring Harbor Press, New York, and other laboratory manuals. In certain embodiments, a host cell is transiently transfected with an expression vector containing a nucleic acid encoding a flu hemagglutinin (HA) polypeptide and/or a nucleic acid encoding an influenza virus neuraminidase polypeptide. In other embodiments, a host cell is stably transfected with an expression vector containing a nucleic acid encoding a flu hemagglutinin (HA) polypeptide and/or a nucleic acid encoding an influenza virus neuraminidase polypeptide.

For stable transfection of mammalian cells, it is known that, depending upon the expression vector and transfection technique used, only a small fraction of cells may integrate the foreign DNA into their genome. In order to identify and select these integrants, a nucleic acid that encodes a selectable marker (e.g., for resistance to antibiotics) is generally introduced into the host cells along with the nucleic acid of interest. Examples of selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

As an alternative to recombinant expression of a flu hemagglutinin (HA) polypeptide and/or an influenza virus neuraminidase polypeptide using a host cell, an expression vector containing a nucleic acid encoding a flu hemagglutinin (HA) polypeptide and/or a nucleic acid encoding an influenza virus neuraminidase polypeptide can be transcribed and translated in vitro using, e.g., T7 promoter regulatory sequences and T7 polymerase. In a specific embodiment, a coupled transcription/translation system, such as Promega TNT®, or a cell lysate or cell extract comprising the components necessary for transcription and translation may be used to produce a flu hemagglutinin (HA) polypeptide and/or an influenza virus neuraminidase polypeptide.

Once a flu hemagglutinin (HA) polypeptide and/or influenza virus neuraminidase polypeptide has been produced, it may be isolated or purified by any method known in the art for isolation or purification of a protein, for example, by chromatography (e.g., ion exchange, affinity, particularly by affinity for the specific antigen, by Protein A, and sizing column chromatography), centrifugation, differential solubility, or by any other standard technique for the isolation or purification of proteins. In certain embodiments, a flu hemagglutinin (HA) polypeptide and/or an influenza virus neuraminidase polypeptide may be conjugated to heterologous proteins, e.g., a major histocompatibility complex (MHC) with or without heat shock proteins (e.g., Hsp10, Hsp20, Hsp30, Hsp40, Hsp60, Hsp70, Hsp90, or Hsp100). In certain embodiments, a flu hemagglutinin (HA) polypeptide and/or an influenza virus neuraminidase polypeptide may be conjugated to immunomodulatory molecules, such as proteins which would target the flu hemagglutinin (HA) polypeptide and/or the influenza virus neuraminidase polypeptide to immune cells such as B cells (e.g., C3d) or T cells. In certain embodiments, a flu hemagglutinin (HA) polypeptide and/or an influenza virus neuraminidase polypeptide may be conjugated to proteins which stimulate the innate immune system such as interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-β, TNFα, B7.1, B7.2, 4-1BB, CD40 ligand (CD40L), and drug-inducible CD40 (iCD40).

Accordingly, provided herein are methods for producing a flu hemagglutinin (HA) polypeptide (e.g., a chimeric influenza virus hemagglutinin (HA) polypeptide) and/or an influenza virus neuraminidase polypeptide. In one embodiment, the method comprises culturing a host cell containing a nucleic acid encoding the polypeptide in a suitable medium such that the polypeptide is produced. In some embodiments, the method further comprises isolating the polypeptide from the medium or the host cell.

5.8 Influenza Virus Vectors

In one aspect, provided herein are influenza viruses containing a flu hemagglutinin (HA) polypeptide (e.g., a chimeric influenza virus hemagglutinin polypeptide) described herein and/or an influenza virus neuraminidase polypeptide. In a specific embodiment, the flu hemagglutinin (HA) polypeptide and/or the influenza virus neuraminidase polypeptide is incorporated into the virions of the influenza virus. The influenza viruses may be conjugated to moieties that target the viruses to particular cell types, such as immune cells. In some embodiments, the virions of the influenza virus have incorporated into them or express a heterologous polypeptide in addition to a flu hemagglutinin (HA) polypeptide and/or the influenza virus neuraminidase polypeptide. The heterologous polypeptide may be a polypeptide that has immunopotentiating activity, or that targets the influenza virus to a particular cell type, such as an antibody that binds to an antigen on a specific cell type or a ligand that binds a specific receptor on a specific cell type.

Influenza viruses containing a flu hemagglutinin (HA) polypeptide and/or an influenza virus neuraminidase polypeptide may be produced by supplying in trans the flu hemagglutinin (HA) polypeptide and/or the influenza virus neuraminidase polypeptide, respectively, during production of virions using techniques known to one skilled in the art, such as reverse genetics and helper-free plasmid rescue. Alternatively, the replication of a parental influenza virus comprising a genome engineered to express a flu hemagglutinin (HA) polypeptide and/or an influenza virus neuraminidase polypeptide in cells susceptible to infection with the virus wherein hemagglutinin and/or neuraminidase function is provided in trans will produce progeny influenza viruses containing the flu hemagglutinin (HA) polypeptide and/or the influenza virus neuraminidase polypeptide, respectively.

In another aspect, provided herein are influenza viruses comprising a genome engineered to express a flu hemagglutinin (HA) polypeptide and/or an influenza virus neuraminidase polypeptide. In a specific embodiment, the genome of a parental influenza virus is engineered to encode a flu hemagglutinin (HA) polypeptide and/or an influenza virus neuraminidase polypeptide, which is expressed by progeny influenza virus. In another specific embodiment, the genome of a parental influenza virus is engineered to encode a flu hemagglutinin (HA) polypeptide and/or an influenza virus neuraminidase polypeptide, which is expressed and incorporated into the virions of progeny influenza virus. Thus, the progeny influenza virus resulting from the replication of the parental influenza virus contain a flu hemagglutinin (HA) polypeptide and/or an influenza virus neuraminidase polypeptide. The virions of the parental influenza virus may have incorporated into them a flu hemagglutinin (HA) polypeptide and/or an influenza virus neuraminidase polypeptide that contains a stem or head domain from the same or a different type, subtype or strain of influenza virus. Alternatively, the virions of the parental influenza virus may have incorporated into them a moiety that is capable of functionally replacing one or more of the activities of influenza virus hemagglutinin polypeptide (e.g., the receptor binding and/or fusogenic activities of influenza virus hemagglutinin) and/or influenza virus neuraminidase polypeptide. In certain embodiments, one or more of the activities of the influenza virus hemagglutinin polypeptide is provided by a fusion protein comprising (i) an ectodomain of a polypeptide heterologous to influenza virus fused to (ii) a transmembrane domain, or a transmembrane domain and a cytoplasmic domain of an influenza virus hemagglutinin polypeptide. In a specific embodiment, the virions of the parental influenza virus may have incorporated into them a fusion protein comprising (i) an ectodomain of a receptor binding/fusogenic polypeptide of an infectious agent other than influenza virus fused to (ii) a transmembrane domain, or a transmembrane domain and a cytoplasmic domain of an influenza virus hemagglutinin. For a description of fusion proteins that provide one or more activities of an influenza virus hemagglutinin polypeptide and methods for the production of influenza viruses engineered to express such fusion proteins, see, e.g., International patent application Publication No. WO 2007/064802, published Jun. 7, 2007 and U.S. patent application Ser. No. 11/633,130, filed on Dec. 1, 2006, which published as U.S. Patent Application No. 2012/0122185; each of which is incorporated herein by reference in its entirety.

In certain embodiments, the influenza viruses engineered to express one or more of the flu hemagglutinin (HA) polypeptides described herein comprise a neuraminidase (NA), or fragment thereof, that is from the same source (e.g., influenza virus strain or subtype) as that from which the globular head of the flu hemagglutinin (HA) polypeptide is derived. In certain embodiments, the influenza viruses engineered to express one or more of the chimeric influenza virus hemagglutinin polypeptides described herein comprise a neuraminidase (NA), or fragment thereof, that is from the same source (e.g., influenza virus strain or subtype) as that from which the globular head of the chimeric influenza virus hemagglutinin polypeptide is derived, wherein the globular head is heterologous to the stem domain of the HA1 and/or HA2 subunits of the chimeric influenza virus hemagglutinin polypeptide. In certain embodiments, the influenza viruses engineered to express one or more of the flu hemagglutinin (HA) polypeptides described herein comprise a neuraminidase (NA), or fragment thereof, that is heterologous (e.g., from a different influenza virus strain or subtype) to the globular head of the flu hemagglutinin (HA) polypeptide.

In some embodiments, the virions of the parental influenza virus have incorporated into them a heterologous polypeptide. In certain embodiments, the genome of a parental influenza virus is engineered to encode a heterologous polypeptide and a flu hemagglutinin (HA) polypeptide and/or an influenza virus neuraminidase polypeptide, which are expressed by progeny influenza virus. In specific embodiments, the flu hemagglutinin (HA) polypeptide, the heterologous polypeptide or both are incorporated into virions of the progeny influenza virus. In specific embodiments, the influenza virus neuraminidase polypeptide, the heterologous polypeptide or both are incorporated into virions of the progeny influenza virus. In specific embodiments, the flu hemagglutinin (HA) polypeptide, the influenza virus neuraminidase polypeptide, the heterologous polypeptide or all three are incorporated into virions of the progeny influenza virus.

The heterologous polypeptide may be a polypeptide that targets the influenza virus to a particular cell type, such as an antibody that recognizes an antigen on a specific cell type or a ligand that binds a specific receptor on a specific cell type. In some embodiments, the targeting polypeptide replaces the target cell recognition function of the virus. In a specific embodiment, the heterologous polypeptide targets the influenza virus to the same cell types that influenza virus infects in nature. In other specific embodiments, the heterologous polypeptide targets the progeny influenza virus to immune cells, such as B cells, T cells, macrophages or dendritic cells. In some embodiments, the heterologous polypeptide recognizes and binds to cell-specific markers of antigen presenting cells, such as dendritic cells (e.g., such as CD44). In one embodiment, the heterologous polypeptide is DC-SIGN which targets the virus to dendritic cells. In another embodiment, the heterologous polypeptide is an antibody (e.g., a single-chain antibody) that targets the virus to an immune cell, which may be fused with a transmembrane domain from another polypeptide so that it is incorporated into the influenza virus virion. In some embodiments, the antibody is a CD20 antibody, a CD34 antibody, or an antibody against DEC-205. Techniques for engineering viruses to express polypeptides with targeting functions are known in the art. See, e.g., Yang et al., 2006, PNAS 103: 11479-11484 and United States patent application Publication No. 20080019998, published Jan. 24, 2008, and No. 20070020238, published Jan. 25, 2007, the contents of each of which are incorporated herein in their entirety.

In another embodiment, the heterologous polypeptide is a viral attachment protein. Non-limiting examples of viruses whose attachment protein(s) can be used in this aspect are viruses selected from the group of: Lassa fever virus, Hepatitis B virus, Rabies virus, Newcastle disease virus (NDV), a retrovirus such as human immunodeficiency virus, tick-borne encephalitis virus, vaccinia virus, herpesvirus, poliovirus, alphaviruses such as Semliki Forest virus, Ross River virus, and Aura virus (which comprise surface glycoproteins such as E1, E2, and E3), Borna disease virus, Hantaan virus, foamyvirus, and SARS-CoV virus.

In one embodiment, a flavivirus surface glycoprotein may be used, such as Dengue virus (DV) E protein. In some embodiments, a Sindbis virus glycoprotein from the alphavirus family is used (K. S. Wang, R. J. Kuhn, E. G. Strauss, S. Ou, J. H. Strauss, J. Virol. 66, 4992 (1992)). In certain embodiments, the heterologous polypeptide is derived from an NDV HN or F protein; a human immunodeficiency virus (HIV) gp160 (or a product thereof, such as gp41 or gp120); a hepatitis B virus surface antigen (HBsAg); a glycoprotein of herpesvirus (e.g., gD, gE); or VP1 of poliovirus.

In another embodiment, the heterologous polypeptide is derived from any non-viral targeting system known in the art. In certain embodiments, a protein of a nonviral pathogen such as an intracellular bacteria or protozoa is used. In some embodiments, the bacterial polypeptide is provided by, e.g., *Chlamydia, Rikettsia, Coxelia, Listeria, Brucella*, or *Legionella*. In some embodiments, protozoan polypeptide is provided by, e.g., Plasmodia species, *Leishmania* spp., *Toxoplasma gondii*, or *Trypanosoma cruzi*. Other exemplary targeting systems are described in Waehler et al., 2007, "Engineering targeted viral vectors for gene therapy," Nature Reviews Genetics 8: 573-587, which is incorporated herein in its entirety.

In certain embodiments, the heterologous polypeptide expressed by an influenza virus has immunopotentiating (immune stimulating) activity. Non-limiting examples of immunopotentiating polypeptides include, but are not limited to, stimulation molecules, cytokines, chemokines, antibodies and other agents such as Flt-3 ligands. Specific examples of polypeptides with immunopotentiating activity include: interferon type 1, alpha, beta, or gamma interferon, colony stimulating factors such as granulocyte-macrophage colony-stimulating factor (GM-CSF), interleukin (IL)-1, IL-2, IL-4, IL-5, IL-6, IL-7, IL-12, IL-15, IL-18, IL-21, IL-23, tumor necrosis factor (TNF)-β, TNFα, B7.1, B7.2, 4-1BB, CD40 ligand (CD40L), and drug-inducible CD40 (iCD40) (see, e.g., Hanks, B. A., et al. 2005. Nat Med 11:130-137, which is incorporated herein by reference in its entirety.)

Since the genome of influenza A and B viruses consist of eight (8) single-stranded, negative sense segments (influenza C viruses consist of seven (7) single-stranded, negative sense segments), the genome of a parental influenza virus may be engineered to express a flu hemagglutinin (HA) polypeptide (and any other polypeptide, such as a heterologous polypeptide) and/or an influenza virus neuraminidase polypeptide using a recombinant segment and techniques known to one skilled in the art, such a reverse genetics and helper-free plasmid rescue. In one embodiment, the recombinant segment comprises a nucleic acid encoding the flu hemagglutinin (HA) polypeptide as well as the 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, both of which are incorporated by reference herein in their entireties). In another embodiment, the recombinant segment comprises a nucleic acid encoding the influenza virus neuraminidase peptide as well as the 3' and 5' incorporation signals which are required for proper replication, transcription and packaging of the vRNAs (Fujii et al., 2003, Proc. Natl. Acad. Sci. USA 100:2002-2007; Zheng, et al., 1996, Virology 217:242-251, both of which are incorporated by reference herein in their entireties). In a specific embodiment, the recombinant segment uses the 3' and 5' noncoding and/or nontranslated sequences of segments of influenza viruses that are from a different or the same type, subtype or strain as the parental influenza virus. In some embodiments, the recombinant segment comprises the 3' noncoding region of an influenza virus hemagglutinin polypeptide, the untranslated regions of an influenza virus hemagglutinin polypeptide, and the 5' non-coding region of an influenza virus hemagglutinin polypeptide. In some embodiments, the recombinant segment comprises the 3' noncoding region of an influenza virus neuraminidase polypeptide, the untranslated regions of an influenza virus neuraminidase polypeptide, and the 5' non-coding region of an influenza virus neuraminidase polypeptide. In specific embodiments, the recombinant segment comprises the 3' and 5' noncoding and/or nontranslated sequences of the HA segment of an influenza virus that is the same type, subtype or strain as the influenza virus type, subtype or strain as the HA1 N-terminal stem segment, the HA1 C-terminal stem segment, the globular head domain, and/or the HA2 of a flu hemagglutinin (HA) polypeptide. In specific embodiments, the recombinant segment comprises the 3' and 5' noncoding and/or nontranslated sequences of the NA segment of an influenza virus that is the same type, subtype or strain as the influenza virus type, subtype or strain as the HA1 N-terminal stem segment, the HA1 C-terminal stem segment, the globular head domain, and/or the HA2 of a flu hemagglutinin (HA) polypeptide. In certain embodiments, the recombinant segment encoding the flu hemagglutinin (HA) polypeptide may replace the HA segment of a parental influenza virus. In certain embodiments, the recombinant segment encoding the influenza NA polypeptide may replace the NA segment of a parental influenza virus. In some embodiments, the recombinant segment encoding the flu hemagglutinin (HA) polypeptide may replace the NS1 gene of the parental influenza virus. In some embodiments, the recombinant segment encoding the influenza neuraminidase (NA) polypeptide may replace the NS1 gene of the parental influenza virus. In some embodiments, the recombinant segment encoding the flu hemagglutinin (HA) polypeptide may replace the NA gene of the parental influenza virus. In some embodiments, the recombinant segment encoding the influenza neuraminidase (NA) polypeptide may replace the NA gene of the parental influenza virus. Exemplary influenza virus strains that can be used to express the flu hemagglutinin (HA) polypeptides and/or the influenza virus neuraminidase polypeptides include Ann Arbor/1/50, A/Ann Arbor/6/60, A/Puerto Rico/8/34, A/South Dakota/6/2007, A/Uruguay/716/2007, A/California/07/2009, A/Perth/16/2009, A/Brisbane/59/2007, A/Brisbane/10/2007, and B/Brisbane/60/2008.

In some embodiments, a flu hemagglutinin gene segment encodes a flu hemagglutinin (HA) polypeptide. In specific embodiments, the flu hemagglutinin (HA) gene segment and at least one other influenza virus gene segment comprise packaging signals that enable the flu hemagglutinin (HA) gene segment and the at least one other gene segment to segregate together during replication of a recombinant influenza virus (see, Gao & Palese 2009, PNAS 106:15891-15896; and International Application Publication No. WO11/014645). In some embodiments, an influenza virus neuraminidase gene segment encodes an influenza virus neuraminidase polypeptide. In specific embodiments, the influenza virus neuraminidase gene segment and at least one other influenza virus gene segment comprise packaging signals that enable the influenza virus neuraminidase gene segment and the at least one other gene segment to segregate together during replication of a recombinant influenza virus (see, Gao & Palese 2009, PNAS 106:15891-15896; and International Application Publication No. WO11/014645).

In some embodiments, the genome of a parental influenza virus may be engineered to express a flu hemagglutinin (HA) polypeptide and/or an influenza virus neuraminidase polypeptide using a recombinant segment that is bicistronic. Bicistronic techniques allow the engineering of coding sequences of multiple proteins into a single mRNA through the use of internal ribosome entry site (IRES) sequences. IRES sequences direct the internal recruitment of ribosomes to the RNA molecule and allow downstream translation in a cap independent manner. Briefly, a coding region of one protein is inserted into the open reading frame (ORF) of a second protein. The insertion is flanked by an IRES and any untranslated signal sequences necessary for proper expression and/or function. The insertion must not disrupt the ORF, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which is hereby incorporated by reference in its entirety). See also, e.g., U.S. Pat. Nos. 6,887,699, 6,001,634, 5,854,037 and 5,820,871, each of which is incorporated herein by reference in its entirety. Any IRES known in the art or described herein may be used in accordance with the invention (e.g., the IRES of BiP gene, nucleotides 372 to 592 of GenBank database entry HUMGRP78; or the IRES of encephalomyocarditis virus (EMCV), nucleotides 1430-2115 of GenBank database entry CQ867238.). Thus, in certain embodiments, a parental influenza virus is engineered to contain a bicistronic RNA segment that expresses the flu hemagglutinin (HA) polypeptide or an influenza virus neuraminidase polypeptide and another polypeptide, such as a gene expressed by the parental influenza virus. In some embodiments, the parental influenza virus gene is the HA gene. In some embodiments, the parental influenza virus gene is the NA gene. In some embodiments, the parental influenza virus gene is the NS1 gene.

Techniques known to one skilled in the art may be used to produce an influenza virus containing a flu hemagglutinin (HA) polypeptide and/or an influenza virus neuraminidase polypeptide and an influenza virus comprising a genome engineered to express a flu hemagglutinin (HA) polypeptide and/or an influenza virus neuraminidase polypeptide. For example, reverse genetics techniques may be used to generate such an influenza virus. Briefly, reverse genetics techniques generally involve the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in European Patent Publication EP 0702085A1, published Feb. 20, 1996; in U.S. patent application Ser. No. 09/152,845; in International Patent Publications PCT WO 97/12032 published Apr. 3, 1997; WO 96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

Alternatively, helper-free plasmid technology may be used to produce an influenza virus containing a flu hemagglutinin (HA) polypeptide and/or an influenza neuraminidase polypeptide and an influenza virus comprising a genome engineered to express a flu hemagglutinin (HA) polypeptide and/or an influenza neuraminidase polypeptide. Briefly, full length cDNAs of viral segments are amplified using PCR with primers that include unique restriction sites, which allow the insertion of the PCR product into the plasmid vector (Flandorfer et al., 2003, J. Virol. 77:9116-9123; Nakaya et al., 2001, J. Virol. 75:11868-11873; both of which are incorporated herein by reference in their entireties). The plasmid vector is designed so that an exact negative (vRNA sense) transcript is expressed. For example, the plasmid vector may be designed to position the PCR product between a truncated human RNA polymerase I promoter and a hepatitis delta virus ribozyme sequence such that an exact negative (vRNA sense) transcript is produced from the polymerase I promoter. Separate plasmid vectors comprising each viral segment as well as expression vectors comprising necessary viral proteins may be transfected into cells leading to production of recombinant viral particles. In another example, plasmid vectors from which both the viral genomic RNA and mRNA encoding the necessary viral proteins are expressed may be used. For a detailed description of helper-free plasmid technology see, e.g., International Publication No. WO 01/04333; U.S. Pat. Nos. 6,951,754, 7,384,774, 6,649,372, and 7,312,064; Fodor et al., 1999, J. Virol. 73:9679-9682; Quinlivan et al., 2005, J. Virol. 79:8431-8439; Hoffmann et al., 2000, Proc. Natl. Acad. Sci. USA 97:6108-6113; and Neumann et al., 1999, Proc. Natl. Acad. Sci. USA 96:9345-9350, which are incorporated herein by reference in their entireties.

The influenza viruses described herein may be propagated in any substrate that allows the virus to grow to titers that permit their use in accordance with the methods described herein. In one embodiment, the substrate allows the viruses to grow to titers comparable to those determined for the corresponding wild-type viruses. In certain embodiments, the substrate is one which is biologically relevant to the influenza virus or to the virus from which the HA function is derived. In a specific embodiment, an attenuated influenza virus by virtue of, e.g., a mutation in the NS1 gene, may be propagated in an IFN-deficient substrate. For example, a suitable IFN-deficient substrate may be one that is defective in its ability to produce or respond to interferon, or is one which an IFN-deficient substrate may be used for the growth of any number of viruses which may require interferon-deficient growth environment. See, for example, U.S. Pat. No. 6,573,079, issued Jun. 3, 2003, U.S. Pat. No. 6,852,522, issued Feb. 8, 2005, and U.S. Pat. No. 7,494,808, issued Feb. 24, 2009, the entire contents of each of which is incorporated herein by reference in its entirety. In a specific embodiment, the virus is propagated in embryonated eggs (e.g., chicken eggs). In a specific embodiment, the virus is propagated in 8 day old, 9-day old, 8-10 day old, 10 day old, 11-day old, 10-12 day old, or 12-day old embryonated eggs (e.g., chicken eggs). In certain embodiments, the virus is propagated in MDCK cells, Vero cells, 293T cells, or other cell lines known in the art. In certain embodiments, the virus is propagated in cells derived from embryonated eggs.

The influenza viruses described herein may be isolated and purified by any method known to those of skill in the art. In one embodiment, the virus is removed from cell culture and separated from cellular components, typically by well known clarification procedures, e.g., such as gradient centrifugation and column chromatography, and may be further purified as desired using procedures well known to those skilled in the art, e.g., plaque assays.

In certain embodiments, the influenza viruses, or influenza virus polypeptides, genes or genome segments for use as described herein are obtained or derived from an influenza A virus. In certain embodiments, the influenza viruses, or influenza virus polypeptides, genes or genome segments for use as described herein are obtained or derived from a single influenza A virus subtype or strain. In other embodiments, the influenza viruses, or influenza virus polypeptides, genes or genome segments for use as described herein are obtained or derived from two or more influenza A virus subtypes or strains. In certain embodiments, the influenza viruses for use as described herein comprise a chimeric influenza virus hemagglutinin polypeptide described herein and a neuraminidase (NA), or fragment thereof, wherein the NA is from the same source (e.g., influenza virus strain or subtype) as that from which the globular head of the chimeric influenza virus hemagglutinin polypeptide is derived. In certain embodiments, the influenza viruses engineered to express one or more of the chimeric influenza virus hemagglutinin polypeptides described herein comprise a neuraminidase (NA), or fragment thereof, that is from the same source (e.g., influenza virus strain or subtype) as that from which the globular head of the chimeric influenza virus hemagglutinin polypeptide is derived, wherein the globular head is heterologous to the stem domain of the HA1 and/or HA2 subunits of the chimeric influenza virus hemagglutinin polypeptide.

In some embodiments, the influenza viruses, or influenza virus polypeptides, genes or genome segments for use as described herein are obtained or derived from an influenza B virus. In certain embodiments, the influenza viruses, or influenza virus polypeptides, genes or genome segments for use as described herein are obtained or derived from a single influenza B virus subtype or strain. In other embodiments, the influenza viruses, or influenza virus polypeptides, genes or genome segments for use as described herein are obtained or derived from two or more influenza B virus subtypes or strains. In other embodiments, the influenza viruses, or influenza virus polypeptides, genes or genome segments for use as described herein are obtained or derived from a combination of influenza A and influenza B virus subtypes or strains.

In some embodiments, the influenza viruses, or influenza virus polypeptides, genes or genome segments for use as described herein are obtained or derived from an influenza C virus. In certain embodiments, the influenza viruses, or influenza virus polypeptides, genes or genome segments for use as described herein are obtained or derived from a single influenza C virus subtype or strain. In other embodiments, the influenza viruses, or influenza virus polypeptides, genes or genome segments for use as described herein are obtained or derived from two or more influenza C virus subtypes or strains. In other embodiments, the influenza viruses, or influenza virus polypeptides, genes or genome segments for use as described herein are obtained or derived from a combination of influenza C virus and influenza A virus and/or influenza B virus subtypes or strains.

Non-limiting examples of influenza A viruses include subtype H10N4, subtype H10N5, subtype H10N7, subtype H10N8, subtype H10N9, subtype H11N1, subtype H11N13, subtype H11N2, subtype H11N4, subtype H11N6, subtype H11N8, subtype H11N9, subtype H12N1, subtype H12N4, subtype H12N5, subtype H12N8, subtype H13N2, subtype H13N3, subtype H13N6, subtype H13N7, subtype H14N5, subtype H14N6, subtype H15N8, subtype H15N9, subtype H16N3, subtype H1N1, subtype H1N2, subtype H1N3, subtype H1N6, subtype H1N9, subtype H2N1, subtype H2N2, subtype H2N3, subtype H2N5, subtype H2N7, subtype H2N8, subtype H2N9, subtype H3N1, subtype H3N2, subtype H3N3, subtype H3N4, subtype H3N5, subtype H3N6, subtype H3N8, subtype H3N9, subtype H4N1, subtype H4N2, subtype H4N3, subtype H4N4, subtype H4N5, subtype H4N6, subtype H4N8, subtype H4N9, subtype H5N1, subtype H5N2, subtype H5N3, subtype H5N4, subtype H5N6, subtype H5N7, subtype H5N8, subtype H5N9, subtype H6N1, subtype H6N2, subtype H6N3, subtype H6N4, subtype H6N5, subtype H6N6, subtype H6N7, subtype H6N8, subtype H6N9, subtype H7N1, subtype H7N2, subtype H7N3, subtype H7N4, subtype H7N5, subtype H7N7, subtype H7N8, subtype H7N9, subtype H8N4, subtype H8N5, subtype H9N1, subtype H9N2, subtype H9N3, subtype H9N5, subtype H9N6, subtype H9N7, subtype H9N8, and subtype H9N9.

Specific examples of strains of influenza A virus include, but are not limited to: A/Victoria/361/2011 (H3N2); A/California/4/2009 (H1N1); A/California/7/2009 (H1N1); A/Perth/16/2009 (H3N2); A/Brisbane/59/2007 (H1N1); A/Brisbane/10/2007 ((H3N2); A/sw/Iowa/15/30 (H1N1); A/WSN/33 (H1N1); A/eq/Prague/1/56 (H7N7); A/PR/8/34; A/mallard/Potsdam/178-4/83 (H2N2); A/herring gull/DE/

712/88 (H16N3); A/sw/Hong Kong/168/1993 (H1N1); A/mallard/Alberta/211/98 (H1N1); A/shorebird/Delaware/168/06 (H16N3); A/sw/Netherlands/25/80 (H1N1); A/sw/Germany/2/81 (H1N1); A/sw/Hannover/1/81 (H1N1); A/sw/Potsdam/1/81 (H1N1); A/sw/Potsdam/15/81 (H1N1); A/sw/Potsdam/268/81 (H1N1); A/sw/Finistere/2899/82 (H1N1); A/sw/Potsdam/35/82 (H3N2); A/sw/Cote d'Armor/3633/84 (H3N2); A/sw/Gent/1/84 (H3N2); A/sw/Netherlands/12/85 (H1N1); A/sw/Karrenzien/2/87 (H3N2); A/sw/Schwerin/103/89 (H1N1); A/turkey/Germany/3/91 (H1N1); A/sw/Germany/8533/91 (H1N1); A/sw/Belgium/220/92 (H3N2); A/sw/Gent/V230/92 (H1N1); A/sw/Leipzig/145/92 (H3N2); A/sw/Re220/92 hp (H3N2); A/sw/Bakum/909/93 (H3N2); A/sw/Schleswig-Holstein/1/93 (H1N1); A/sw/Scotland/419440/94 (H1N2); A/sw/Bakum/5/95 (H1N1); A/sw/Best/5C/96 (H1N1); A/sw/England/17394/96 (H1N2); A/sw/Jena/5/96 (H3N2); A/sw/Oedenrode/7C/96 (H3N2); A/sw/Lohne/1/97 (H3N2); A/sw/Cote d'Armor/790/97 (H1N2); A/sw/Bakum/1362/98 (H3N2); A/sw/Italy/1521/98 (H1N2); A/sw/Italy/1553-2/98 (H3N2); A/sw/Italy/1566/98 (H1N1); A/sw/Italy/1589/98 (H1N1); A/sw/Bakum/8602/99 (H3N2); A/sw/Cotes d'Armor/604/99 (H1N2); A/sw/Cote d'Armor/1482/99 (H1N1); A/sw/Gent/7625/99 (H1N2); A/Hong Kong/1774/99 (H3N2); A/sw/Hong Kong/5190/99 (H3N2); A/sw/Hong Kong/5200/99 (H3N2); A/sw/Hong Kong/5212/99 (H3N2); A/sw/Ille et Villaine/1455/99 (H1N1); A/sw/Italy/1654-1/99 (H1N2); A/sw/Italy/2034/99 (H1N1); A/sw/Italy/2064/99 (H1N2); A/sw/Berlin/1578/00 (H3N2); A/sw/Bakum/1832/00 (H1N2); A/sw/Bakum/1833/00 (H1N2); A/sw/Cote d'Armor/800/00 (H1N2); A/sw/Hong Kong/7982/00 (H3N2); A/sw/Italy/1081/00 (H1N2); A/sw/Belzig/2/01 (H1N1); A/sw/Belzig/54/01 (H3N2); A/sw/Hong Kong/9296/01 (H3N2); A/sw/Hong Kong/9745/01 (H3N2); A/sw/Spain/33601/01 (H3N2); A/sw/Hong Kong/1144/02 (H3N2); A/sw/Hong Kong/1197/02 (H3N2); A/sw/Spain/39139/02 (H3N2); A/sw/Spain/42386/02 (H3N2); A/Switzerland/8808/2002 (H1N1); A/sw/Bakum/1769/03 (H3N2); A/sw/Bissendorf/IDT1864/03 (H3N2); A/sw/Ehren/IDT2570/03 (H1N2); A/sw/Gescher/IDT2702/03 (H1N2); A/sw/Haselünne/2617/03 hp (H1N1); A/sw/Löningen/IDT2530/03 (H1N2); A/sw/IVD/IDT2674/03 (H1N2); A/sw/Nordkirchen/IDT1993/03 (H3N2); A/sw/Nordwalde/IDT2197/03 (H1N2); A/sw/Norden/IDT2308/03 (H1N2); A/sw/Spain/50047/03 (H1N1); A/sw/Spain/51915/03 (H1N1); A/sw/Vechta/2623/03 (H1N1); A/sw/Visbek/IDT2869/03 (H1N2); A/sw/Waltersdorf/IDT2527/03 (H1N2); A/sw/Damme/IDT2890/04 (H3N2); A/sw/Geldern/IDT2888/04 (H1N1); A/sw/Granstedt/IDT3475/04 (H1N2); A/sw/Greven/IDT2889/04 (H1N1); A/sw/Gudensberg/IDT2930/04 (H1N2); A/sw/Gudensberg/IDT2931/04 (H1N2); A/sw/Lohne/IDT3357/04 (H3N2); A/sw/Nortrup/IDT3685/04 (H1N2); A/sw/Seesen/IDT3055/04 (H3N2); A/sw/Spain/53207/04 (H1N1); A/sw/Spain/54008/04 (H3N2); A/sw/Stolzenau/IDT3296/04 (H1N2); A/sw/Wedel/IDT2965/04 (H1N1); A/sw/Bad Griesbach/IDT4191/05 (H3N2); A/sw/Cloppenburg/IDT4777/05 (H1N2); A/sw/Dötlingen/IDT3780/05 (H1N2); A/sw/Dötlingen/IDT4735/05 (H1N2); A/sw/Egglham/IDT5250/05 (H3N2); A/sw/Harkenblek/IDT4097/05 (H3N2); A/sw/Hertzen/IDT4317/05 (H3N2); A/sw/Krogel/IDT4192/05 (H1N1); A/sw/Laer/IDT3893/05 (H1N1); A/sw/Laer/IDT4126/05 (H3N2); A/sw/Merzen/IDT4114/05 (H3N2); A/sw/Muesleringen-S./IDT4263/05 (H3N2); A/sw/Osterhofen/IDT4004/05 (H3N2); A/sw/Sprenge/IDT3805/05 (H1N2); A/sw/Stadtlohn/IDT3853/05 (H1N2); A/sw/Voglarn/IDT4096/05 (H1N1); A/sw/Wohlerst/IDT4093/05 (H1N1); A/sw/Bad Griesbach/IDT5604/06 (H1N1); A/sw/Herzlake/IDT5335/06 (H3N2); A/sw/Herzlake/IDT5336/06 (H3N2); A/sw/Herzlake/IDT5337/06 (H3N2); and A/wild boar/Germany/R169/2006 (H3N2).

Other specific examples of strains of influenza A virus include, but are not limited to: A/Toronto/3141/2009 (H1N1); A/Regensburg/D6/2009 (H1N1); A/Bayern/62/2009 (H1N1); A/Bayern/62/2009 (H1N1); A/Bradenburg/19/2009 (H1N1); A/Bradenburg/20/2009 (H1N1); A/Distrito Federal/2611/2009 (H1N1); A/Mato Grosso/2329/2009 (H1N1); A/Sao Paulo/1454/2009 (H1N1); A/Sao Paulo/2233/2009 (H1N1); A/Stockholm/37/2009 (H1N1); A/Stockholm/41/2009 (H1N1); A/Stockholm/45/2009 (H1N1); A/swine/Alberta/OTH-33-1/2009 (H1N1); A/swine/Alberta/OTH-33-14/2009 (H1N1); A/swine/Alberta/OTH-33-2/2009 (H1N1); A/swine/Alberta/OTH-33-21/2009 (H1N1); A/swine/Alberta/OTH-33-22/2009 (H1N1); A/swine/Alberta/OTH-33-23/2009 (H1N1); A/swine/Alberta/OTH-33-24/2009 (H1N1); A/swine/Alberta/OTH-33-25/2009 (H1N1); A/swine/Alberta/OTH-33-3/2009 (H1N1); A/swine/Alberta/OTH-33-7/2009 (H1N1); A/Beijing/502/2009 (H1N1); A/Firenze/10/2009 (H1N1); A/Hong Kong/2369/2009 (H1N1); A/Italy/85/2009 (H1N1); A/Santo Domingo/572N/2009 (H1N1); A/Catalonia/385/2009 (H1N1); A/Catalonia/386/2009 (H1N1); A/Catalonia/387/2009 (H1N1); A/Catalonia/390/2009 (H1N1); A/Catalonia/394/2009 (H1N1); A/Catalonia/397/2009 (H1N1); A/Catalonia/398/2009 (H1N1); A/Catalonia/399/2009 (H1N1); A/Sao Paulo/2303/2009 (H1N1); A/Akita/1/2009 (H1N1); A/Castro/JXP/2009 (H1N1); A/Fukushima/1/2009 (H1N1); A/Israel/276/2009 (H1N1); A/Israel/277/2009 (H1N1); A/Israel/70/2009 (H1N1); A/Iwate/1/2009 (H1N1); A/Iwate/2/2009 (H1N1); A/Kagoshima/1/2009 (H1N1); A/Osaka/180/2009 (H1N1); A/Puerto Montt/Bio87/2009 (H1 N1); A/Sao Paulo/2303/2009 (H1N1); A/Sapporo/1/2009 (H1N1); A/Stockholm/30/2009 (H1N1); A/Stockholm/31/2009 (H1N1); A/Stockholm/32/2009 (H1N1); A/Stockholm/33/2009 (H1N1); A/Stockholm/34/2009 (H1N1); A/Stockholm/35/2009 (H1N1); A/Stockholm/36/2009 (H1N1); A/Stockholm/38/2009 (H1N1); A/Stockholm/39/2009 (H1N1); A/Stockholm/40/2009 (H1N1); A/Stockholm/42/2009 (H1N1); A/Stockholm/43/2009 (H1N1); A/Stockholm/44/2009 (H1N1); A/Utsunomiya/2/2009 (H1N1); A/WRAIR/0573N/2009 (H1N1); and A/Zhejiang/DTID-ZJU01/2009 (H1N1).

Non-limiting examples of influenza B viruses include strain Aichi/5/88, strain B/Brisbane/60/2008; Akita/27/2001, strain Akita/5/2001, strain Alaska/16/2000, strain Alaska/1777/2005, strain Argentina/69/2001, strain Arizona/146/2005, strain Arizona/148/2005, strain Bangkok/163/90, strain Bangkok/34/99, strain Bangkok/460/03, strain Bangkok/54/99, strain Barcelona/215/03, strain Beijing/15/84, strain Beijing/184/93, strain Beijing/243/97, strain Beijing/43/75, strain Beijing/5/76, strain Beijing/76/98, strain Belgium/WV106/2002, strain Belgium/WV107/2002, strain Belgium/WV109/2002, strain Belgium/WV114/2002, strain Belgium/WV122/2002, strain Bonn/43, strain Brazil/952/2001, strain Bucharest/795/03, strain Buenos Aires/161/00), strain Buenos Aires/9/95, strain Buenos Aires/SW16/97, strain Buenos Aires/VL518/99, strain Canada/464/2001, strain Canada/464/2002, strain Chaco/366/00, strain Chaco/R113/00, strain Cheju/303/03, strain Chiba/447/98, strain Chongqing/3/2000, strain clinical isolate SA1 Thailand/2002, strain clinical isolate SA10 Thailand/2002, strain clinical isolate SA100 Philippines/2002, strain clinical isolate SA101 Philippines/2002, strain clinical isolate SA110 Philippines/2002), strain clinical isolate SA112 Philippines/2002, strain clinical isolate SA113 Philippines/2002, strain clinical isolate SA114 Philippines/2002, strain clinical isolate SA2 Thailand/2002, strain clinical isolate SA20 Thailand/2002, strain clinical isolate SA38 Philippines/2002, strain clinical isolate SA39 Thailand/2002, strain clinical isolate SA99 Philippines/2002, strain CNIC/27/2001, strain Colorado/2597/2004, strain Cordoba/VA418/99, strain Czechoslovakia/16/89, strain Czechoslovakia/69/90, strain Daeku/10/97, strain Daeku/45/97, strain Daeku/47/97, strain Daeku/9/97, strain B/Du/4/78, strain B/Durban/39/98, strain Durban/43/98, strain Durban/44/98, strain B/Durban/52/98, strain Durban/55/98, strain Durban/56/98, strain England/1716/2005, strain England/2054/2005), strain England/23/04, strain Finland/154/2002, strain Finland/159/2002, strain Finland/160/2002, strain Finland/161/2002, strain Finland/162/03, strain Finland/162/2002, strain Finland/162/91, strain Finland/164/2003, strain Finland/172/91, strain Finland/173/2003, strain Finland/176/2003, strain Finland/184/91, strain Finland/188/2003, strain Finland/190/2003, strain Finland/220/2003, strain Finland/WV5/2002, strain Fujian/36/82, strain Geneva/5079/03, strain Genoa/11/02, strain Genoa/2/02, strain Genoa/21/02, strain Genova/54/02, strain Genova/55/02, strain Guangdong/05/94, strain Guangdong/08/93, strain Guangdong/5/94, strain Guangdong/55/89, strain Guangdong/8/93, strain Guangzhou/7/97, strain Guangzhou/86/92, strain Guangzhou/87/92, strain Gyeonggi/592/2005, strain Hannover/2/90, strain Harbin/07/94, strain Hawaii/10/2001, strain Hawaii/1990/2004, strain Hawaii/38/2001, strain Hawaii/9/2001, strain Hebei/19/94, strain Hebei/3/94), strain Henan/22/97, strain Hiroshima/23/2001, strain Hong Kong/110/99, strain Hong Kong/1115/2002, strain Hong Kong/112/2001, strain Hong Kong/123/2001, strain Hong Kong/1351/2002, strain Hong Kong/1434/2002, strain Hong Kong/147/99, strain Hong Kong/156/99, strain Hong Kong/157/99, strain Hong Kong/22/2001, strain Hong Kong/22/89, strain Hong Kong/336/2001, strain Hong Kong/666/2001, strain Hong Kong/9/89, strain Houston/1/91, strain Houston/1/96, strain Houston/2/96, strain Hunan/4/72, strain Ibaraki/2/85, strain ncheon/297/2005, strain India/3/89, strain India/77276/2001, strain Israel/95/03, strain Israel/WV187/2002, strain Japan/1224/2005, strain Jiangsu/10/03, strain Johannesburg/1/99, strain Johannesburg/96/01, strain Kadoma/1076/99, strain Kadoma/122/99, strain Kagoshima/15/94, strain Kansas/22992/99, strain Khazkov/224/91, strain Kobe/1/2002, strain, strain Kouchi/193/99, strain Lazio/1/02, strain Lee/40, strain Leningrad/129/91, strain Lissabon/2/90), strain Los Angeles/1/02, strain Lusaka/270/99, strain Lyon/1271/96, strain Malaysia/83077/2001, strain Maputo/1/99, strain Mar del Plata/595/99, strain Maryland/1/01, strain Memphis/1/01, strain Memphis/12/97-MA, strain Michigan/22572/99, strain Mie/1/93, strain Milano/1/01, strain Minsk/318/90, strain Moscow/3/03, strain Nagoya/20/99, strain Nanchang/1/00, strain Nashville/107/93, strain Nashville/45/91, strain Nebraska/2/01, strain Netherland/801/90, strain Netherlands/429/98, strain New York/1/2002, strain NIB/48/90, strain Ningxia/45/83, strain Norway/1/84, strain Oman/16299/2001, strain Osaka/1059/97, strain Osaka/983/97-V2, strain Oslo/1329/2002, strain Oslo/1846/2002, strain Panama/45/90, strain Paris/329/90, strain Parma/23/02, strain Perth/211/2001, strain Peru/1364/2004, strain Philippines/5072/2001, strain Pusan/270/99, strain Quebec/173/98, strain Quebec/465/98, strain Quebec/7/01, strain Roma/1/03, strain Saga/S172/99, strain Seoul/13/95, strain Seoul/37/91, strain Shangdong/7/97, strain Shanghai/361/2002), strain Shiga/T30/98, strain Sichuan/379/99, strain Singapore/222/79, strain Spain/WV27/2002, strain Stockholm/10/90, strain Switzerland/5441/90, strain Taiwan/0409/00, strain Taiwan/0722/02, strain Taiwan/97271/2001, strain Tehran/80/02, strain Tokyo/6/98, strain Trieste/28/02, strain Ulan Ude/4/02, strain United Kingdom/34304/99, strain USSR/100/83, strain Victoria/103/89, strain Vienna/1/99, strain Wuhan/356/2000, strain WV194/2002, strain Xuanwu/23/82, strain Yamagata/1311/2003, strain Yamagata/K500/2001, strain Alaska/12/96, strain GA/86, strain NAGASAKI/1/87, strain Tokyo/942/96, strain B/Wisconsin/1/2010; and strain Rochester/02/2001.

Non-limiting examples of influenza C viruses include strain Aichi/1/81, strain Ann Arbor/1/50, strain Aomori/74, strain California/78, strain England/83, strain Greece/79, strain Hiroshima/246/2000, strain Hiroshima/252/2000, strain Hyogo/1/83, strain Johannesburg/66, strain Kanagawa/1/76, strain Kyoto/1/79, strain Mississippi/80, strain Miyagi/1/97, strain Miyagi/5/2000, strain Miyagi/9/96, strain Nara/2/85, strain NewJersey/76, strain pig/Beijing/115/81, strain Saitama/3/2000), strain Shizuoka/79, strain Yamagata/2/98, strain Yamagata/6/2000, strain Yamagata/9/96, strain BERLIN/1/85, strain ENGLAND/892/8, strain GREAT LAKES/1167/54, strain JJ/50, strain PIG/BEIJING/10/81, strain PIG/BEIJING/439/82), strain TAYLOR/1233/47, and strain C/YAMAGATA/10/81.

In certain embodiments, the influenza viruses provided herein have an attenuated phenotype. In specific embodiments, the attenuated influenza virus is based on influenza A virus. In other embodiments, the attenuated influenza virus is based on influenza B virus. In yet other embodiments, the attenuated influenza virus is based on influenza C virus. In other embodiments, the attenuated influenza virus may comprise genes or genome segments from one or more strains or subtypes of influenza A, influenza B, and/or influenza C virus. In some embodiments, the attenuated backbone virus comprises genes from an influenza A virus and an influenza B virus.

In specific embodiments, attenuation of influenza virus is desired such that the virus remains, at least partially, infectious and can replicate in vivo, but only generate low titers resulting in subclinical levels of infection that are non-pathogenic. Such attenuated viruses are especially suited for embodiments described herein wherein the virus or an immunogenic composition thereof is administered to a subject to induce an immune response. Attenuation of the influenza virus can be accomplished according to any method known in the art, such as, e.g., selecting viral mutants generated by chemical mutagenesis, mutation of the genome by genetic engineering, selecting reassortant viruses that contain segments with attenuated function, or selecting for conditional virus mutants (e.g., cold-adapted viruses). Alternatively, naturally occurring attenuated influenza viruses may be used as influenza virus backbones for the influenza virus vectors.

In one embodiment, an influenza virus may be attenuated, at least in part, by virtue of substituting the HA gene of the parental influenza virus with a flu hemagglutinin (HA) polypeptide described herein and/or an influenza virus neuraminidase polypeptide. In some embodiments, an influenza virus may be attenuated, at least in part, by engineering the influenza virus to express a mutated NS1 gene that impairs the ability of the virus to antagonize the cellular interferon (IFN) response. Examples of the types of mutations that can be introduced into the influenza virus NS1 gene include deletions, substitutions, insertions and combinations thereof. One or more mutations can be introduced anywhere throughout the NS1 gene (e.g., the N-terminus, the C-terminus or somewhere in between) and/or the regulatory element of the NS1 gene. In one embodiment, an attenuated influenza virus comprises a genome having a mutation in an influenza virus NS1 gene resulting in a deletion consisting of 5, preferably 10, 15, 20, 25, 30, 35, 40, 45, 50, 55, 60, 65, 75, 80, 85, 90, 95, 99, 100, 105, 110, 115, 120, 125, 126, 130, 135, 140, 145, 150, 155, 160, 165, 170 or 175 amino acid residues from the C-terminus of NS1, or a deletion of between 5-170, 25-170, 50-170, 100-170, 100-160, or 105-160 amino acid residues from the C-terminus. In another embodiment, an attenuated influenza virus comprises a genome having a mutation in an influenza virus NS1 gene such that it encodes an NS1 protein of amino acid residues 1-130, amino acid residues 1-126, amino acid residues 1-120, amino acid residues 1-115, amino acid residues 1-110, amino acid residues 1-100, amino acid residues 1-99, amino acid residues 1-95, amino acid residues 1-85, amino acid residues 1-83, amino acid residues 1-80, amino acid residues 1-75, amino acid residues 1-73, amino acid residues 1-70, amino acid residues 1-65, or amino acid residues 1-60, wherein the N-terminus amino acid is number 1. For examples of NS1 mutations and influenza viruses comprising a mutated NS1, see, e.g., U.S. Pat. Nos. 6,468,544 and 6,669,943; and Li et al., 1999, J. Infect. Dis. 179:1132-1138, each of which is incorporated by reference herein in its entirety.

5.9 Non-Influenza Virus Vectors

In one aspect, provided herein are non-influenza viruses containing a flu hemagglutinin (HA) polypeptide (e.g., a chimeric influenza virus hemagglutinin (HA) polypeptide) and/or an influenza virus neuraminidase polypeptide. In a specific embodiment, the flu hemagglutinin (HA) polypeptide and/or the influenza virus neuraminidase polypeptide is incorporated into the virions of the non-influenza virus. In a specific embodiment, the flu hemagglutinin (HA) polypeptide (e.g., a chimeric influenza virus hemagglutinin polypeptide) and/or the influenza virus neuraminidase polypeptide is contained in/expressed by a purified (e.g., plaque purified) or isolated virus. The non-influenza viruses may be conjugated to moieties that target the viruses to particular cell types, such as immune cells. In some embodiments, the virions of the non-influenza virus have incorporated into them or express a heterologous polypeptide in addition to a flu hemagglutinin (HA) polypeptide and/or an influenza virus neuraminidase polypeptide. The heterologous polypeptide may be a polypeptide that has immunopotentiating activity, or that targets the non-influenza virus to a particular cell type, such as an antibody that recognizes an antigen on a specific cell type or a ligand that binds a specific receptor on a specific cell type.

Non-influenza viruses containing/expressing a flu hemagglutinin (HA) polypeptide and/or an influenza virus neuraminidase polypeptide can be produced using techniques known to those skilled in the art. Non-influenza viruses containing a flu hemagglutinin (HA) polypeptide and/or an influenza virus neuraminidase polypeptide may be produced by supplying in trans the flu hemagglutinin (HA) polypeptide and/or the influenza virus neuraminidase polypeptide, respectively, during production of virions using techniques known to one skilled in the art. Alternatively, the replication of a parental non-influenza virus comprising a genome engineered to express a flu hemagglutinin (HA) polypeptide and/or an influenza virus neuraminidase polypeptide in cells susceptible to infection with the virus wherein hemagglutinin function is provided in trans will produce progeny viruses containing the flu hemagglutinin (HA) polypeptide and/or the influenza virus neuraminidase polypeptide, respectively.

Any virus type, subtype or strain including, but not limited to, naturally occurring strains, variants or mutants, mutagenized viruses, reassortants and/or genetically modified viruses may be used as a non-influenza virus vector. In a specific embodiment, the parental non-influenza virus is not a naturally occurring virus. In another specific embodiment, the parental non-influenza virus is a genetically engineered virus. In certain embodiments, an enveloped virus is preferred for the expression of a membrane-bound flu hemagglutinin (HA) polypeptide described herein and/or a membrane-bound influenza virus neuraminidase polypeptide.

In an exemplary embodiment, the non-influenza virus vector is a Newcastle disease virus (NDV). In another embodiment, the non-influenza virus vector is a vaccinia virus. In other exemplary, non-limiting, embodiments, the non-influenza virus vector is adenovirus, adeno-associated virus (AAV), hepatitis B virus, retrovirus (such as, e.g., a gammaretrovirus such as Mouse Stem Cell Virus (MSCV) genome or Murine Leukemia Virus (MLV), e.g., Moloney murine leukemia virus, oncoretrovirus, or lentivirus), an alphavirus (e.g., Venezuelan equine encephalitis virus), a rhabdovirus, such as vesicular stomatitis virus or papillomaviruses, poxvirus (such as, e.g., vaccinia virus, a MVA-T7 vector, or fowlpox), metapneumovirus, measles virus, herpesvirus, such as herpes simplex virus, or foamyvirus. See, e.g., Lawrie and Tumin, 1993, Cur. Opin. Genet. Develop. 3, 102-109 (retroviral vectors); Bett et al., 1993, J. Virol. 67, 5911 (adenoviral vectors); Zhou et al., 1994, J. Exp. Med. 179, 1867 (adeno-associated virus vectors); Dubensky et al., 1996, J. Virol. 70, 508-519 (viral vectors from the pox family including vaccinia virus and the avian pox viruses and viral vectors from the alpha virus genus such as those derived from Sindbis and Semliki Forest Viruses); U.S. Pat. No. 5,643,576 (Venezuelan equine encephalitis virus); WO 96/34625 (VSV); Ohe et al., 1995, Human Gene Therapy 6, 325-333; Woo et al., WO 94/12629; Xiao & Brandsma, 1996, Nucleic Acids. Res. 24, 2630-2622 (papillomaviruses); and Bukreyev and Collins, 2008, Curr Opin Mol Ther. 10:46-55 (NDV), each of which is incorporated by reference herein in its entirety.

In a specific embodiment, the non-influenza virus vector is NDV. Any NDV type, subtype or strain may serve as the backbone that is engineered to express a flu hemagglutinin (HA) polypeptide and/or an influenza virus neuraminidase polypeptide, including, but not limited to, naturally-occurring strains, variants or mutants, mutagenized viruses, reassortants and/or genetically engineered viruses. In a specific embodiment, the NDV that serves as the backbone for genetic engineering is a naturally-occurring strain. In certain embodiments, the NDV that serves as the backbone for genetic engineering is a lytic strain. In other embodiments, the NDV that serves as the backbone for genetic engineering is a non-lytic strain. In certain embodiments, the NDV that serves as the backbone for genetic engineering is lentogenic strain. In some embodiments, the NDV that serves as the backbone for genetic engineering is a mesogenic strain. In other embodiments, the NDV that serves as the backbone for genetic engineering is a velogenic strain. Specific examples of NDV strains include, but are not limited to, the 73-T strain, Ulster strain, MTH-68 strain, Italien strain, Hickman strain, PV701 strain, Hitchner B1 strain, La Sota strain, YG97 strain, MET95 strain, and F48E9 strain. In a specific embodiment, the NDV that serves as the backbone for genetic engineering is the Hitchner B1 strain. In another specific embodiment, the NDV that serves as the backbone for genetic engineering is the La Sota strain.

In one embodiment, the NDV used as the backbone for a non-influenza virus vector is engineered to express a modified F protein in which the cleavage site of the F protein is replaced with one containing one or two extra arginine residues, allowing the mutant cleavage site to be activated by ubiquitously expressed proteases of the furin family. Specific examples of NDVs that express such a modified F protein include, but are not limited to, rNDV/F2aa and rNDV/F3aa. For a description of mutations introduced into a NDV F protein to produce a modified F protein with a mutated cleavage site, see, e.g., Park et al. (2006) "Engineered viral vaccine constructs with dual specificity: Avian influenza and Newcastle disease." PNAS USA 103: 8203-2808, which is incorporated herein by reference in its entirety.

In one embodiment, the non-influenza virus vector is a poxvirus. A poxvirus vector may be based on any member of the poxviridae, in particular, a vaccinia virus or an avipox virus (e.g., such as canarypox, fowlpox, etc.) that provides suitable sequences for vaccine vectors. In a specific embodiment, the poxviral vector is a vaccinia virus vector. Suitable vaccinia viruses include, but are not limited to, the Copenhagen (VC-2) strain (Goebel, et al., Virol 179: 247-266, 1990; Johnson, et al., Virol. 196: 381-401, 1993), modified Copenhagen strain (NYVAC) (U.S. Pat. No. 6,265,189), the WYETH strain and the modified Ankara (MVA) strain (Antoine, et al., Virol. 244: 365-396, 1998). Other suitable poxviruses include fowlpox strains such as ALVAC and TROVAC vectors that provide desirable properties and are highly attenuated (see, e.g. U.S. Pat. No. 6,265,189; Tartaglia et al., In AIDS Research Reviews, Koff, et al., eds., Vol. 3, Marcel Dekker, N.Y., 1993; and Tartaglia et al., 1990, Reviews in Immunology 10: 13-30, 1990).

Methods of engineering non-influenza viruses to express influenza polypeptides are well known in the art, as are methods for attenuating, propagating, and isolating and purifying such viruses. For such techniques with respect to NDV vectors, see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety. For such techniques with respect to poxviruses, see, e.g., Piccini, et al., Methods of Enzymology 153: 545-563, 1987; International Publication No. WO 96/11279; U.S. Pat. No. 4,769,330; U.S. Pat. No. 4,722,848; U.S. Pat. No. 4,769,330; U.S. Pat. No. 4,603,112; U.S. Pat. No. 5,110,587; U.S. Pat. No. 5,174,993; EP 83 286; EP 206 920; Mayr et al., Infection 3: 6-14, 1975; and Sutter and Moss, Proc. Natl. Acad. Sci. USA 89: 10847-10851, 1992. In certain embodiments, the non-influenza virus is attenuated.

Exemplary considerations for the selection of a non-influenza virus vector, particularly for use in compositions for administration to a subject, are safety, low toxicity, stability, cell type specificity, and immunogenicity, particularly, antigenicity of the flu hemagglutinin (HA) polypeptide and/or the influenza virus neuraminidase polypeptide expressed by the non-influenza virus vector.

5.10 Virus-Like Particles and Virosomes

The flu hemagglutinin (HA) polypeptides (e.g., chimeric influenza virus hemagglutinin polypeptides) described herein and/or the influenza virus neuraminidase polypeptides described herein can be incorporated into virus-like particle (VLP) vectors, e.g., purified/isolated VLPs. VLPs generally comprise a viral polypeptide(s) typically derived from a structural protein(s) of a virus. In some embodiments, the VLPs are not capable of replicating. In certain embodiments, the VLPs may lack the complete genome of a virus or comprise a portion of the genome of a virus. In some embodiments, the VLPs are not capable of infecting a cell. In some embodiments, the VLPs express on their surface one or more of viral (e.g., virus surface glycoprotein) or non-viral (e.g., antibody or protein) targeting moieties known to one skilled in the art or described herein. In some embodiments, the VLPs comprise a flu hemagglutinin (HA) polypeptide and/or an influenza virus neuraminidase polypeptide and a viral structural protein, such as HIV gag. In a specific embodiment, the VLPs comprise a flu hemagglutinin (HA) polypeptide and/or an influenza virus neuraminidase polypeptide, and an HIV gag polypeptide.

Methods for producing and characterizing recombinantly produced VLPs have been described based on several viruses, including influenza virus (Bright et al. (2007) Vaccine. 25:3871), human papilloma virus type 1 (Hagnesee et al. (1991) J. Virol. 67:315), human papilloma virus type 16 (Kirnbauer et al. Proc. Natl. Acad. Sci. (1992)89:12180), HIV-1 (Haffer et al., (1990) J. Virol. 64:2653), and hepatitis A (Winokur (1991) 65:5029), each of which is incorporated herein in its entirety. Methods for expressing VLPs that contain NDV proteins are provided by Pantua et al. (2006) J. Virol. 80:11062-11073, and in United States patent application Publication No. 20090068221, published Mar. 12, 2009, each of which is incorporated in its entirety herein. In a specific embodiment, the VLPs comprising flu hemagglutinin (HA) polypeptide described herein and/or the influenza virus neuraminidase polypeptides are generated using baculovirus, as described in the Examples section below. In other embodiments, the VLPs comprising flu hemagglutinin (HA) polypeptides described herein and/or the influenza virus neuraminidase polypeptides described herein are generated using 293T cells.

In specific embodiments, VLPs, e.g., VLPs comprising a flu hemagglutinin (HA) polypeptide and/or an influenza virus neuraminidase polypeptide, are expressed in cells (such as, e.g., mammalian cells (e.g., 293T cells) and insect cells (e.g., High Five cells and 519 cells). In certain embodiments, the VLPs are expressed in cells that express surface glycoproteins that comprise sialic acid. In accordance with such embodiments, the cells are cultured in the presence of neuraminidase (e.g., viral of bacterial neuraminidase). In certain embodiments, VLPs, e.g., VLPs comprising a flu hemagglutinin (HA) polypeptide and/or an influenza virus neuraminidase polypeptide, are expressed in cells that do not express surface glycoproteins that comprise sialic acid.

In a specific embodiment, a flu hemagglutinin (HA) polypeptide and/or an influenza virus neuraminidase polypeptide may be incorporated into a virosome. A virosome containing a flu hemagglutinin (HA) polypeptide and/or an influenza virus neuraminidase polypeptide may be produced using techniques known to those skilled in the art. For example, a virosome may be produced by disrupting a purified virus, extracting the genome, and reassembling particles with the viral proteins (e.g., a flu hemagglutinin (HA) polypeptide and/or an influenza virus neuraminidase polypeptide) and lipids to form lipid particles containing viral proteins.

5.11 Bacterial Vectors

In a specific embodiment, bacteria may be engineered to express a flu hemagglutinin (HA) polypeptide (e.g., chimeric influenza virus hemagglutinin polypeptide) described herein and/or an influenza virus neuraminidase polypeptide described herein. Suitable bacteria for expression of a flu hemagglutinin (HA) polypeptide and/or an influenza virus neuraminidase polypeptide include, but are not limited to,

*Listeria, Salmonella, Shigella* sp., *Mycobacterium tuberculosis, E. coli, Neisseria meningitides, Brucella abortus, Brucella melitensis, Borrelia burgdorferi, Lactobacillus, Campylobacter, Lactococcus, Bifidobacterium,* and *Francisella tularensis*. In a specific embodiment, the bacteria engineered to express a flu hemagglutinin (HA) polypeptide and/or an influenza virus neuraminidase polypeptide are attenuated. Techniques for the production of bacteria engineered to express a heterologous polypeptide are known in the art and can be applied to the expression of a flu hemagglutinin (HA) polypeptide and/or an influenza virus neuraminidase polypeptide. See, e.g., United States Patent Application Publication No. 20080248066, published Oct. 9, 2008, and United States Patent Application Publication No. 20070207171, published Sep. 6, 2007, each of which are incorporated by reference herein in their entirety. In certain embodiments, the bacterial vectors used herein possess the ability to perform N-linked glycosylation, e.g., such bacteria naturally possess N-glycosylation machinery (e.g., *Campylobacter*) or have been genetically engineered to possess N-glycosylation machinery.

5.12 Plant and Algae Vectors

In certain embodiments, plants (e.g., plants of the genus *Nicotiana*) may be engineered to express a flu hemagglutinin (HA) polypeptide described herein and/or an influenza virus neuraminidase polypeptide described herein. In specific embodiments, plants are engineered to express a flu hemagglutinin (HA) polypeptide (e.g., a chimeric influenza virus hemagglutinin polypeptide) described herein and/or an influenza virus neuraminidase polypeptide described herein via an agroinfiltration procedure using methods known in the art. For example, nucleic acids encoding a gene of interest, e.g., a gene encoding a flu hemagglutinin (HA) polypeptide described herein and/or an influenza virus neuraminidase polypeptide described herein, are introduced into a strain of *Agrobacterium*. Subsequently the strain is grown in a liquid culture and the resulting bacteria are washed and suspended into a buffer solution. The plants are then exposed (e.g., via injection or submersion) to the *Agrobacterium* that comprises the nucleic acids encoding a flu hemagglutinin (HA) polypeptide described herein such that the *Agrobacterium* transforms the gene of interest to a portion of the plant cells. The flu hemagglutinin (HA) polypeptide and/or the influenza virus neuraminidase polypeptide is then transiently expressed by the plant and can isolated using methods known in the art and described herein. (For specific examples see Shoji et al., 2008, Vaccine, 26(23):2930-2934; and D'Aoust et al., 2008, J. Plant Biotechnology, 6(9):930-940). In a specific embodiment, the plant is a tobacco plant (i.e., *Nicotiana tabacum*). In another specific embodiment, the plant is a relative of the tobacco plant (e.g., *Nicotiana benthamiana*). In another specific embodiment, the flu hemagglutinin (HA) polypeptides described herein and/or the influenza virus neuraminidase polypeptides described herein are expressed in a species of soy. In another specific embodiment, the flu hemagglutinin (HA) polypeptides described herein and/or the influenza virus neuraminidase polypeptides described herein are expressed in a species of corn. In another specific embodiment, the flu hemagglutinin (HA) polypeptides described herein and/or the influenza virus neuraminidase polypeptides described herein are expressed in a species of rice.

In other embodiments, algae (e.g., *Chlamydomonas reinhardtii*) may be engineered to express a flu hemagglutinin (HA) polypeptide described herein and/or an influenza virus neuraminidase polypeptide described herein (see, e.g., Rasala et al., 2010, Plant Biotechnology Journal (Published online Mar. 7, 2010)).

In certain embodiments, the plants used to express the flu hemagglutinin (HA) polypeptides described herein and/or an influenza virus neuraminidase polypeptide described herein are engineered to express components of an N-glycosylation system (e.g., a bacterial or mammalian N-glycosylation system), i.e., the plants can perform N-glycosylation.

Plant cells that can be used to express the flu hemagglutinin (HA) polypeptides and/or the influenza virus neuraminidase polypeptides and methods for the production of proteins utilizing plant cell culture systems are described in, e.g. U.S. Pat. Nos. 5,929,304; 7,504,560; 6,770,799; 6,551,820; 6,136,320; 6,034,298; 5,914,935; 5,612,487; and 5,484,719, U.S. patent application publication Nos. 2009/0208477, 2009/0082548, 2009/0053762, 2008/0038232, 2007/0275014 and 2006/0204487, and Shoji et al., 2008, Vaccine, 26(23):2930-2934, and D'Aoust et al., 2008, J. Plant Biotechnology, 6(9):930-940 (which are incorporated herein by reference in their entirety).

5.13 Generation of Antibodies Against Flu Hemagglutinin (HA) Polypeptides and/or Influenza Virus Neuraminidase Polypeptides The flu hemagglutinin (HA) polypeptides and/or the influenza virus neuraminidase polypeptides, nucleic acids encoding such polypeptides, or vectors comprising such nucleic acids or polypeptides described herein may be used to elicit neutralizing antibodies against influenza, for example, against the stalk region of an influenza virus hemagglutinin polypeptide and/or against neuraminidase, respectively. In a specific embodiment, the flu hemagglutinin (HA) polypeptide and/or the influenza virus neuraminidase polypeptide, nucleic acids encoding such polypeptides, or vectors comprising such nucleic acids or polypeptides described herein may be administered to a non-human subject (e.g., a mouse, rabbit, rat, guinea pig, etc.) to induce an immune response that includes the production of antibodies which may be isolated using techniques known to one of skill in the art (e.g., immunoaffinity chromatography, centrifugation, precipitation, etc.).

Alternatively, the flu hemagglutinin (HA) polypeptide described herein and/or the influenza virus neuraminidase polypeptide described herein may be used to screen for antibodies from antibody libraries. For example, an isolated flu hemagglutinin (HA) polypeptide and/or an isolated influenza virus neuraminidase polypeptide may be immobilized to a solid support (e.g., a silica gel, a resin, a derivatized plastic film, a glass bead, cotton, a plastic bead, a polystyrene bead, an alumina gel, or a polysaccharide, a magnetic bead), and screened for binding to antibodies. As an alternative, the antibodies may be immobilized to a solid support and screened for binding to the isolated flu hemagglutinin (HA) polypeptides and/or the influenza virus neuraminidase polypeptides. Any screening assay, such as a panning assay, ELISA, surface plasmon resonance, or other antibody screening assay known in the art may be used to screen for antibodies that bind to the flu hemagglutinin (HA) polypeptide and/or the influenza virus neuraminidase polypeptide. The antibody library screened may be a commercially available antibody library, an in vitro generated library, or a library obtained by identifying and cloning or isolating antibodies from an individual infected with influenza. In particular embodiments, the antibody library is generated from a survivor of an influenza virus outbreak. Antibody libraries may be generated in accordance with methods known in the art. In a particular embodiment, the antibody library is generated by cloning the antibodies and using them in phage display libraries or a phagemid display library.

Antibodies identified in the methods described herein may be tested for neutralizing activity and lack of autoreactivity using the biological assays known in the art or described herein. In one embodiment, an antibody isolated from a non-human animal or an antibody library neutralizes a hemagglutinin polypeptide from more than one influenza subtype. In some embodiments, an antibody elicited or identified using a flu hemagglutinin (HA) polypeptide and/or an influenza virus neuraminidase polypeptide, a nucleic acid encoding such a polypeptide(s), or a vector encoding such a nucleic acid or polypeptide neutralizes an influenza H3 virus. In some embodiments, an antibody elicited or identified using a flu hemagglutinin (HA) polypeptide and/or an influenza virus neuraminidase polypeptide, a nucleic acid encoding such a polypeptide(s), or a vector comprising such a nucleic acid or polypeptide neutralizes 1, 2, 3, 4, 5, 6, 7, 8, 9, 10, 11, 12, 13, 14, 15, or 16 or more subtypes or strains of influenza virus. In one embodiment, the neutralizing antibody neutralizes one or more influenza A viruses and one or more influenza B viruses. In particular embodiments, the neutralizing antibody is not, or does not bind the same epitope as CR6261, CR6325, CR6329, CR6307, CR6323, 2A, D7, D8, F10, G17, H40, A66, D80, E88, E90, H98, C179 (produced by hybridoma FERM BP-4517; clones sold by Takara Bio, Inc. (Otsu, Shiga, Japan)), and/or AI3C (FERM BP-4516); or any other antibody described in Ekiert D C et al. (2009) Antibody Recognition of a Highly Conserved Influenza Virus Epitope. Science (published in Science Express Feb. 26, 2009); Kashyap et al. (2008) Combinatorial antibody libraries from survivors of the Turkish H5N1 avian influenza outbreak reveal virus neutralization strategies. Proc Natl Acad Sci USA 105: 5986-5991; Sui et al. (2009) Structural and functional bases for broad-spectrum neutralization of avian and human influenza A viruses. Nat Struct Mol Biol 16: 265-273; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. In other embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9. In particular embodiments, the neutralizing antibody does not use the Ig VH1-69 segment. In some embodiments, the interaction of the neutralizing antibody with the antigen is not mediated exclusively by the heavy chain. In certain embodiments, the neutralizing antibody is a not 2B9 or any other antibody described in Shoji et al., Hum. Vaccines, 2011, 7:199-204. In certain embodiments, the neutralizing antibody is not 3A2, 4G2, 1H5, 2D9, or any other antibody described in Wan et al., J. Virol. 2013, 87:9290-9300. In certain embodiments, the neutralizing antibody is not HCA-2, or any other antibody described in Doyle et al. Antivir. Res. 2013, 100:567-574 or Doyle et al., Biochem. Biophys. Res. Commun. 2013, 441:226-229.

Antibodies identified or elicited using a flu hemagglutinin (HA) polypeptide and/or an influenza virus neuraminidase polypeptide, a nucleic acid encoding such a polypeptide(s), or a vector comprising such a nucleic acid or polypeptide include immunoglobulin molecules and immunologically active portions of immunoglobulin molecules, i.e., molecules that contain an antigen binding site that specifically binds to a hemagglutinin polypeptide and/or a neuraminidase polypeptide. The immunoglobulin molecules may be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass of immunoglobulin molecule. Antibodies include, but are not limited to, monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), and anti-idiotypic (anti-Id) antibodies (including, e.g., anti-Id antibodies to antibodies elicited or identified using a method described herein), and epitope-binding fragments of any of the above.

Antibodies elicited or identified using a flu hemagglutinin (HA) polypeptide and/or an influenza virus neuraminidase polypeptide, nucleic acids encoding such a polypeptide(s) or a vector comprising such a nucleic acid or polypeptide may be used in diagnostic immunoassays, passive immunotherapy, and generation of antiidiotypic antibodies. The antibodies before being used in passive immunotherapy may be modified, e.g., the antibodies may be chimerized or humanized. See, e.g., U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741, each of which is incorporated herein by reference in its entirety, for reviews on the generation of chimeric and humanized antibodies. In addition, the ability of the antibodies to neutralize hemagglutinin polypeptides and/or neuraminidase polypeptides and the specificity of the antibodies for the polypeptides may be tested prior to using the antibodies in passive immunotherapy. See Section 5.13, infra, for a discussion regarding use of neutralizing antibodies for the prevention or treatment of disease caused by influenza virus infection.

Antibodies elicited or identified using a flu hemagglutinin (HA) polypeptide and/or an influenza virus neuraminidase polypeptide, a nucleic acid encoding such a polypeptide(s), or a vector comprising such a nucleic acid or polypeptide may be used to monitor the efficacy of a therapy and/or disease progression. Without being bound by any particular theory, the level of antibodies elicited or identified using a flu hemagglutinin (HA) polypeptide and/or an influenza virus neuraminidase polypeptide may be indicative of the degree of protection against influenza virus disease: for example, a low level of influenza-specific antibodies may indicate that revaccination, or booster vaccination(s), are required. Any immunoassay system known in the art may be used for this purpose including, but not limited to, competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complement fixation assays, immunoradiometric assays, fluorescent immunoassays, protein A immunoassays and immunoelectrophoresis assays, to name but a few. Further, without being bound by any particular theory, elicited or identified can be utilized in an assay to determine the anti-influenza properties of the antibody(ies), which may be indicative of the level of protected provided by vaccination with the flu hemagglutinin (HA) polypeptide and/or the influenza virus neuraminidase polypeptide, the nucleic acid encoding such a polypeptide(s), or the vector comprising such a nucleic acid or polypeptide. Any assay known in the art for evaluating anti-influenza properties may be used for this purpose including, but not limited to, hemagglutinin inhibition assays, influenza virus growth curves, and plaque reduction assays, to name but a few.

Antibodies elicited or identified using a flu hemagglutinin (HA) polypeptide and/or an influenza virus neuraminidase polypeptide, a nucleic acid encoding such a polypeptide(s), or a vector comprising such a nucleic acid or polypeptide may be used in the production of antiidiotypic antibody. The antiidiotypic antibody can then in turn be used for immunization, in order to produce a subpopulation of antibodies that bind a particular antigen of influenza, e.g., a neutralizing epitope of a hemagglutinin polypeptide (Jerne, 1974, Ann. Immunol. (Paris) 125c:373; Jerne et al., 1982, EMBO J. 1:234, incorporated herein by reference in its entirety).

5.14 Stimulation of Cells with Flu Hemagglutinin (HA) Polypeptides and/or Influenza Virus Neuraminidase Polypeptides In another aspect, provided herein are methods for stimulating cells ex vivo with a flu hemagglutinin (HA) polypeptide (e.g., a chimeric influenza virus hemagglutinin polypeptide) described herein and/or an influenza virus neuraminidase polypeptide described herein. Such cells, e.g., dendritic cells, may be used in vitro to generate antibodies against the flu hemagglutinin (HA) polypeptide and/or the influenza virus neuraminidase polypeptide or may themselves be administered to a subject by, e.g., an adoptive transfer technique known in the art. See, e.g., United States patent application Publication No. 20080019998, published Jan. 24, 2008, which is incorporated herein by reference in its entirety, for a description of adoptive transfer techniques. In certain embodiments, when cells that have been stimulated ex vivo with a flu hemagglutinin (HA) polypeptide described herein and/or a influenza virus neuraminidase polypeptide described herein are administered to a subject, the cells are not mammalian cells (e.g., CB-1 cells).

In one non-limiting example, a vector, e.g., an influenza virus vector, engineered to express a flu hemagglutinin (HA) polypeptide described herein and/or an influenza virus neuraminidase polypeptide can be used to generate dendritic cells (DCs) that express the flu hemagglutinin (HA) polypeptide and/or the influenza virus neuraminidase polypeptide, respectively, and display immunostimulatory properties directed against an influenza virus hemagglutinin polypeptide. Such DCs may be used to expand memory T cells and are potent stimulators of T cells, including flu hemagglutinin (HA) polypeptide-specific cytotoxic T lymphocyte clones and/or influenza virus neuraminidase polypeptide-specific cytotoxic T lymphocyte clones. See Strobel et al., 2000, Human Gene Therapy 11:2207-2218, which is incorporated herein by reference in its entirety.

A flu hemagglutinin (HA) polypeptide described herein and/or an influenza virus neuraminidase polypeptide described herein may be delivered to a target cell in any way that allows the polypeptide to contact the target cell, e.g., a DC, and deliver the polypeptide to the target cell. In certain embodiments, the flu hemagglutinin (HA) polypeptide and/or the influenza virus neuraminidase polypeptide is delivered to a subject, as described herein. In some such embodiments, cells contacted with the polypeptide may be isolated and propagated.

In certain embodiments, a flu hemagglutinin (HA) polypeptide and/or an influenza virus neuraminidase polypeptide is delivered to a target cell in vitro. Techniques known to one of skill in the art may be used to deliver the polypeptide to target cells. For example, target cells may be contacted with the polypeptide in a tissue culture plate, tube or other container. The polypeptide may be suspended in media and added to the wells of a culture plate, tube or other container. The media containing the polypeptide may be added prior to plating of the cells or after the cells have been plated. The target cells are preferably incubated with the polypeptide for a sufficient amount of time to allow the polypeptide to contact the cells. In certain embodiments, the cells are incubated with the polypeptide for about 1 hour or more, about 5 hours or more, about 10 hours or more, about 12 hours or more, about 16 hours or more, about 24, hours or more, about 48 hours or more, about 1 hour to about 12 hours, about 3 hours to about 6 hours, about 6 hours to about 12 hours, about 12 hours to about 24 hours, or about 24 hours to about 48 hours. In certain embodiments, wherein the flu hemagglutinin (HA) polypeptide and/or the influenza virus neuraminidase polypeptide is in a virus, the contacting of the target cells comprises infecting the cells with the virus.

The target cells may be from any species, including, e.g., humans, mice, rats, rabbits and guinea pigs. In some embodiments, target cells are DCs obtained from a healthy subject or a subject in need of treatment. In certain embodiments, target cells are DCs obtained from a subject in whom it is desired to stimulate an immune response to the polypeptide. Methods of obtaining cells from a subject are well known in the art.

5.15 Compositions

The nucleic acids, vectors, polypeptides, bacteria, antibodies, or cells described herein (sometimes referred to herein as "active compounds") may be incorporated into compositions. In specific embodiments, an active compound described herein is a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s). In a specific embodiment, the compositions are pharmaceutical compositions, such as immunogenic compositions (e.g., vaccine formulations). The pharmaceutical compositions provided herein can be in any form that allows for the composition to be administered to a subject. In a specific embodiment, the pharmaceutical compositions are suitable for veterinary and/or human administration. The compositions may be used in methods of preventing or treating an influenza virus disease.

In one embodiment, a pharmaceutical composition comprises a flu hemagglutinin (HA) polypeptide (e.g., a chimeric influenza virus hemagglutinin polypeptide) and/or an influenza virus neuraminidase polypeptide, in an admixture with a pharmaceutically acceptable carrier. In another embodiment, a pharmaceutical composition comprises a nucleic acid encoding a flu hemagglutinin (HA) polypeptide described herein and/or a nucleic acid encoding an influenza virus neuraminidase polypeptide, in an admixture with a pharmaceutically acceptable carrier. In another embodiment, a pharmaceutical composition comprises an expression vector comprising a nucleic acid encoding a flu hemagglutinin (HA) polypeptide and/or a nucleic acid encoding an influenza virus neuraminidase polypeptide, in an admixture with a pharmaceutically acceptable carrier. In another embodiment, a pharmaceutical composition comprises an influenza virus or non-influenza virus containing a flu hemagglutinin (HA) polypeptide and/or an influenza virus or non-influenza virus containing an influenza virus neuraminidase polypeptide, in an admixture with a pharmaceutically acceptable carrier. In another embodiment, a pharmaceutical composition comprises an influenza virus or non-influenza virus having a genome engineered to express a flu hemagglutinin (HA) polypeptide and/or an influenza virus or non-influenza virus having a genome engineered to express an influenza virus neuraminidase polypeptide, in admixture with a pharmaceutically acceptable carrier. In another embodiment, a pharmaceutical composition comprises a virus-like particle or virosome containing a flu hemagglutinin (HA) polypeptide and/or a virus-like particle or virosome containing an influenza virus neuraminidase polypeptide, in an admixture with a pharmaceutically acceptable carrier. In another embodiment, a pharmaceutical composition comprises a bacteria expressing or engineered to express a flu hemagglutinin (HA) polypeptide and/or a bacteria expressing or engineered to express an influenza virus neuraminidase polypeptide, in an admixture with a pharmaceutically acceptable carrier. In another embodiment, a pharmaceutical composition comprises cells stimulated with a flu hemagglutinin (HA) polypeptide and/or cells stimulated with an influenza virus neuraminidase polypeptide, in an admixture with a pharmaceutically acceptable carrier. In another embodiment, a pharmaceutical composition comprises a seasonal influenza virus vaccine supplemented with influenza neuraminidase polypeptide, in an admixture with a pharmaceutically acceptable carrier. Non-limiting examples of seasonal influenza virus vaccines include Afluria (CSL Limited), Fluarix Quadrivalent (GlaxoSmithKline Biologicals SA), Flublock (Protein Sciences Corporation), Flucelvax (Novartis Vaccines and Diagnostics, Inc.), Flulaval (ID Biomedical Corporation of Quebec), FluMist Quadrivalent (MedImmune, LLC), Fluzone (Sanofi Pasteur Inc.), Fluzone High-Dose (Sanofi Pasteur Inc.), Fluzone Intradermal (Sanofi Pasteur Inc), and Fluzone Quadrivalent (Sanofi Pasteur Inc.). In another embodiment, a pharmaceutical composition comprises (i) a flu hemagglutinin (HA) polypeptide described herein or an expression vector expressing a flu hemagglutinin (HA) polypeptide described herein, or a nucleic acid encoding a flu hemagglutinin (HA) polypeptide described herein, and (ii) influenza neuraminidase polypeptide, in an admixture with a pharmaceutically acceptable carrier.

In some embodiments, a pharmaceutical composition may comprise one or more other therapies in addition to a therapy that utilizes a flu hemagglutinin (HA) polypeptide described herein and/or an influenza virus neuraminidase polypeptide described herein.

As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, pharmaceutical compositions are formulated to be suitable for the intended route of administration to a subject. For example, the pharmaceutical composition may be formulated to be suitable for parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration.

In certain embodiments, biodegradable polymers, such as ethylene vinyl acetate, polyanhydrides, polyethylene glycol (PEGylation), polymethyl methacrylate polymers, polylactides, poly(lactide-co-glycolides), polyglycolic acid, collagen, polyorthoesters, and polylactic acid, may be used as carriers. In some embodiments, the active compounds are prepared with carriers that increase the protection of the compound against rapid elimination from the body, such as a controlled release formulation, including implants and microencapsulated delivery systems. Methods for preparation of such formulations will be apparent to those skilled in the art. Liposomes or micelles can also be used as pharmaceutically acceptable carriers. These can be prepared according to methods known to those skilled in the art, for example, as described in U.S. Pat. No. 4,522,811. In certain embodiments, the pharmaceutical compositions comprise one or more adjuvants.

In specific embodiments, immunogenic compositions described herein are monovalent formulations. In other embodiments, immunogenic compositions described herein are multivalent formulations. In one example, a multivalent formulation comprises more than one vector expressing a flu hemagglutinin (HA) polypeptide and/or an influenza virus neuraminidase polypeptide. In certain embodiments, a multivalent formulation may comprise one or more different flu hemagglutinin (HA) polypeptides and/or influenza virus neuraminidase polypeptides expressed using a single vector.

In certain embodiments, the pharmaceutical compositions described herein additionally comprise a preservative, e.g., the mercury derivative thimerosal. In a specific embodiment, the pharmaceutical compositions described herein comprises 0.001% to 0.01% thimerosal. In other embodiments, the pharmaceutical compositions described herein do not comprise a preservative. In a specific embodiment, thimerosal is used during the manufacture of a pharmaceutical composition described herein and the thimerosal is removed via purification steps following production of the pharmaceutical composition, i.e., the pharmaceutical composition contains trace amounts of thimerosal (<0.3 µg of mercury per dose after purification; such pharmaceutical compositions are considered thimerosal-free products).

In certain embodiments, the pharmaceutical compositions described herein additionally comprise egg protein (e.g., ovalbumin or other egg proteins). The amount of egg protein in the pharmaceutical compositions described herein may range from about 0.0005 to about 1.2. µg of egg protein to 1 ml of pharmaceutical composition. In other embodiments, the pharmaceutical compositions described herein do not comprise egg protein.

In certain embodiments, the pharmaceutical compositions described herein additionally comprise one or more antimicrobial agents (e.g., antibiotics) including, but not limited to gentamicin, neomycin, polymyxin (e.g., polymyxin B), and kanamycin, streptomycin. In other embodiments, the pharmaceutical compositions described herein do not comprise any antibiotics.

In certain embodiments, the pharmaceutical compositions described herein additionally comprise one or more components used to inactivate a virus, e.g., formalin or formaldehyde or a detergent such as sodium deoxycholate, octoxynol 9 (Triton X-100), and octoxynol 10. In other embodiments, the pharmaceutical compositions described herein do not comprise any components used to inactivate a virus.

In certain embodiments, the pharmaceutical compositions described herein additionally comprise gelatin. In other embodiments, the pharmaceutical compositions described herein do not comprise gelatin.

In certain embodiments, the pharmaceutical compositions described herein additionally comprise one or more buffers, e.g., phosphate buffer and sucrose phosphate glutamate buffer. In other embodiments, the pharmaceutical compositions described herein do not comprise buffers.

In certain embodiments, the pharmaceutical compositions described herein additionally comprise one or more salts, e.g., sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts). In other embodiments, the pharmaceutical compositions described herein do not comprise salts.

In specific embodiments, the pharmaceutical compositions described herein are low-additive influenza virus vaccines, i.e., the pharmaceutical compositions do not comprise one or more additives commonly found in influenza virus vaccines. Low-additive influenza vaccines have been described (see, e.g., International Application No. PCT/IB2008/002238 published as International Publication No. WO 09/001217 which is herein incorporated by reference in its entirety).

The pharmaceutical compositions described herein can be included in a container, pack, or dispenser together with instructions for administration.

The pharmaceutical compositions described herein can be stored before use, e.g., the pharmaceutical compositions can be stored frozen (e.g., at about −20° C. or at about −70° C.); stored in refrigerated conditions (e.g., at about 4° C.); or stored at room temperature (see International Application No. PCT/IB2007/001149 published as International Publication No. WO 07/110776, which is herein incorporated by reference in its entirety, for methods of storing compositions comprising influenza vaccines without refrigeration).

In certain embodiments, when the active compound in a pharmaceutical composition described herein is a cell engineered to express a flu hemagglutinin (HA) polypeptide and/or a cell engineered to express an influenza virus neuraminidase polypeptide, the cells in the pharmaceutical composition are not mammalian cells (e.g., CB-1 cells).

In certain embodiments, a vaccine formulation comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation comprises a nucleic acid sequence (e.g., cDNA) encoding a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation comprises a nucleic acid sequence (e.g., cDNA) encoding a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and a nucleic acid sequence (e.g., cDNA) encoding an NA immunogen. In certain embodiments, a vaccine formulation is a live attenuated influenza virus engineered to express a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a live attenuated influenza virus engineered to express a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a chimeric HA polypeptide is expressed by an influenza virus that is heterologous to the HA globular head domain and/or the HA stem domain. For example, an influenza B virus may express a chimeric HA comprising a HA globular head domain from one influenza A virus HA and an HA stem domain from a heterologous influenza A virus. See, e.g., FIG. 9 and Example 2, infra.

In certain embodiments, a vaccine formulation is an inactivated influenza virus that comprises a chimeric HA polypeptide, headless HA polypeptide, or an influenza virus HA stem domain or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is an inactivated influenza virus that comprises a chimeric HA polypeptide, headless HA polypeptide, or an influenza virus HA stem domain or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and NA immunogen.

In certain embodiments, a vaccine formulation is a non-influenza viral vector engineered to express a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a non-influenza viral vector engineered to express a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation is an inactivated non-influenza viral vector that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is an inactivated non-influenza viral vector that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen.

In certain embodiments, a vaccine formulation is a subunit vaccine that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a subunit vaccine that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation is a split vaccine that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a split vaccine that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation is a VLP that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system). In some embodiments, a vaccine formulation is a VLP that comprises a chimeric HA polypeptide, headless HA polypeptide, or another influenza virus stem domain based construct, such as an influenza virus HA stem domain or a fragment of the stem domain of an influenza virus HA (e.g., the long alpha helix, e.g., amino acids 76-130 of A/Hong Kong/1/1968, numbered according to the classic H3 subtype numbering system) and an NA immunogen. In certain embodiments, a vaccine formulation described herein further comprises an adjuvant.

In certain embodiments, a vaccine formulation is multivalent. In one embodiment, a vaccine formulation comprises three chimeric HAs, wherein the first chimeric HA comprises a stem domain polypeptide from an H1 influenza virus and a first HA globular head domain, the second chimeric HA comprises a stem domain polypeptide from an H3 influenza virus and a second HA globular head domain, and the third chimeric HA comprises a stem domain polypeptide from an influenza B virus and a third HA globular head domain, wherein the first, second and third HA globular head domains are each from a different subtype or strain of influenza virus hemagglutinin, and wherein the HA globular head domain of each chimeric HA is heterologous to the stem domain polypeptide of each chimeric HA. In some embodiments, this vaccine formulation further comprises one, two, three or more NA immunogens. For example, in a specific embodiment, the vaccine formulation further comprises an influenza virus neuraminidase polypeptide from an N1, an influenza virus neuraminidase polypeptide from an N2, and an influenza virus neuraminidase polypeptide from an influenza B virus.

In one embodiment, a vaccine formulation comprises three vectors, wherein each vector comprises a chimeric HA, wherein the first vector comprises a first chimeric HA comprising a stem domain polypeptide from an H1 influenza virus and a first HA globular head domain, the second vector comprises a second chimeric HA comprising a stem domain polypeptide from an H3 influenza virus and a second HA globular head domain, and the third vector comprises a third chimeric HA comprising a stem domain polypeptide from an influenza B virus and a third HA globular head domain, wherein the first, second and third HA globular head domains are each from a different subtype or strain of influenza virus hemagglutinin, and wherein the HA globular head domain of each chimeric HA is heterologous to the stem domain polypeptide of each chimeric HA. In certain embodiments, the vector is a viral vector or VLP. See, e.g., Sections 5.8 and 5.9, supra, for examples of influenza virus vectors and non-influenza virus vectors. In some embodiments, the viral vectors may be live attenuated viral vectors or inactivated. In some embodiments, this vaccine formulation further comprises one, two, three or more NA immunogens. For example, in a specific embodiment, the vaccine formulation further comprises an influenza virus neuraminidase polypeptide from an N1, an influenza virus neuraminidase polypeptide from an N2, and an influenza virus neuraminidase polypeptide from an influenza B virus.

In one embodiment, a vaccine formulation comprises three headless HAs, wherein the first headless HA comprises a stem domain polypeptide from an H1 influenza virus, the second headless HA comprises a stem domain polypeptide from an H3 influenza virus, and the third headless HA comprises a stem domain polypeptide from an influenza B virus. In some embodiments, this vaccine formulation further comprises one, two, three or more NA immunogens. For example, in a specific embodiment, the vaccine formulation further comprises an influenza virus neuraminidase polypeptide from an N1, an influenza virus neuraminidase polypeptide from an N2, and an influenza virus neuraminidase polypeptide from an influenza B virus.

In one embodiment, a vaccine formulation comprises three vectors, wherein each vector comprises a headless HA, wherein the first viral vector comprises a first headless HA comprising a stem domain polypeptide from an H1 influenza virus, the second vector comprises a second headless HA comprising a stem domain polypeptide from an H3 influenza virus, and the third vector comprises the third headless HA comprising a stem domain polypeptide from an influenza B virus. In certain embodiments, the vector is a viral vector or VLP. See, e.g., Sections 5.8 and 5.9, supra, for examples of influenza virus vectors and non-influenza virus vectors. In some embodiments, the viral vectors may be live attenuated viral vectors or inactivated. In some embodiments, this vaccine formulation further comprises one, two, three or more NA immunogens. For example, in a specific embodiment, the vaccine formulation comprises an influenza virus neuraminidase polypeptide from an N1, an influenza virus neuraminidase polypeptide from an N2, and an influenza virus neuraminidase polypeptide from an influenza B virus.

In a specific embodiment, a vaccine formulation comprises one, two, three or more NA immunogens. In certain embodiments, a vaccine formulation comprises an influenza virus neuraminidase polypeptide from an N1, an influenza virus neuraminidase polypeptide from an N2, and an influenza virus neuraminidase polypeptide from an influenza B virus.

5.15.1 Subunit Vaccines

In a specific embodiment, provided herein are subunit vaccines comprising a flu hemagglutinin (HA) polypeptide (e.g., a chimeric influenza virus hemagglutinin polypeptide) described herein and/or an influenza virus neuraminidase polypeptide described herein. In some embodiments, a subunit vaccine comprises a flu hemagglutinin (HA) polypeptide and/or an influenza virus neuraminidase polypeptide, and one or more surface glycoproteins (e.g., influenza virus neuraminidase), other targeting moieties, or adjuvants. In specific embodiments, a subunit vaccine comprises a single flu hemagglutinin (HA) polypeptide and/or a single influenza virus neuraminidase polypeptide. In other embodiments, a subunit vaccine comprises two, three, four or more flu hemagglutinin (HA) polypeptides and/or two, three, four or more influenza virus neuraminidase polypeptides. In specific embodiments, the flu hemagglutinin (HA) polypeptide(s) and/or the influenza virus neuraminidase polypeptide(s) used in a subunit vaccine are not membrane-bound, i.e., are soluble.

In certain embodiments, provided herein are subunit vaccines comprising about 10 µg to about 60 µg of one or more flu hemagglutinin (HA) polypeptides described herein and/or one or more influenza virus neuraminidase polypeptides described herein, about 0.001% to 0.01% thimerosal, about 0.1 µg to about 1.0 µg chicken egg protein, about 1.0 µg to about 5.0 polymyxin, about 1.0 µg to about 5.0 µg neomycin, about 0.1 µg to about 0.5 betapropiolactone, and about 0.001 to about 0.05% w/v of nonylphenol ethoxylate per dose.

In a specific embodiment, a subunit vaccine provided herein comprises or consists of a 0.5 ml dose that comprises 45 µg of flu hemagglutinin (HA) polypeptide(s) provided herein and/or 45 µg of influenza virus neuraminidase polypeptide(s) provided herein, ≤1.0 µg of mercury (from thimerosal), ≤1.0 µg chicken egg protein (i.e., ovalbumin), ≤3.75 µg polymyxin, and ≤2.5 µg neomycin. In some embodiments, a subunit vaccine provided herein additionally comprises or consists of not more than 0.5 µg betapropiolactone, and not more than 0.015% w/v of nonylphenol ethoxylate per dose. In some embodiments, the 0.5 ml dose subunit vaccine is packaged in a pre-filled syringe.

In a specific embodiment, a subunit vaccine provided herein consists of a 5.0 ml multidose vial (0.5 ml per dose) that comprises 45 µg of flu hemagglutinin (HA) polypeptide(s) provided herein and/or 45 µg of influenza virus neuraminidase polypeptide(s) provided herein, 25.0 µg of mercury (from thimerosal), <1.0 µg chicken egg protein (i.e., ovalbumin), <3.75 µg polymyxin, and <2.5 µg neomycin. In some embodiments, a subunit vaccine provided herein additionally comprises or consists of not more than 0.5 µg betapropiolactone, and not more than 0.015% w/v of nonylphenol ethoxylate per dose.

In a specific embodiment, the subunit vaccine is prepared using influenza virus that was propagated in embryonated chicken eggs (i.e., the components of the subunit vaccine (e.g., a flu hemagglutinin (HA) polypeptide and/or an influenza virus neuraminidase polypeptide) are isolated from virus that was propagated in embryonated chicken eggs). In another specific embodiment, the subunit vaccine is prepared using influenza virus that was not propagated in embryonated chicken eggs (i.e., the components of the subunit vaccine (e.g., a flu hemagglutinin (HA) polypeptide and/or an influenza virus neuraminidase polypeptide) are isolated from virus that was not propagated in embryonated chicken eggs). In another specific embodiment, the subunit vaccine is prepared using influenza virus that was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) (i.e., the components of the subunit vaccine (e.g., a flu hemagglutinin (HA) polypeptide and/or an influenza virus neuraminidase polypeptide) are isolated from virus that was propagated in mammalian cells). In another specific embodiment, the flu hemagglutinin (HA) polypeptide(s) and/or the influenza virus neuraminidase polypeptide(s) in a subunit vaccine are prepared using an expression vector, e.g., a viral vector, plant vector or a bacterial vector (i.e., the flu hemagglutinin (HA) polypeptide(s) and/or the influenza virus neuraminidase polypeptide(s) in the subunit vaccine are obtained/isolated from an expression vector).

5.15.2 Live Virus Vaccines

In one embodiment, provided herein are immunogenic compositions (e.g., vaccines) comprising live virus containing a flu hemagglutinin (HA) polypeptide (e.g., a chimeric influenza virus hemagglutinin polypeptide) and/or an influenza virus neuraminidase polypeptide. In another embodiment, provided herein are immunogenic compositions (e.g., vaccines) comprising live virus that is engineered to encode a flu hemagglutinin (HA) polypeptide and/or an influenza virus neuraminidase polypeptide, which is expressed by progeny virus produced in the subjects administered the compositions. In specific embodiments, the flu hemagglutinin (HA) polypeptide and/or the influenza virus neuraminidase polypeptide is membrane-bound. In other specific embodiments, the flu hemagglutinin (HA) polypeptide and/or the influenza virus neuraminidase polypeptide is not membrane-bound, i.e., it is soluble. In particular embodiments, the live virus is an influenza virus, such as described in Section 5.8. In other embodiments, the live virus is a non-influenza virus, such as described in Section 5.9. In some embodiments, the live virus is attenuated. In some embodiments, an immunogenic composition comprises two, three, four or more live viruses containing or engineered to express two, three, four or more different flu hemagglutinin (HA) polypeptides and/or two, three, four or more different influenza virus neuraminidase polypeptides.

In certain embodiments, provided herein are immunogenic compositions (e.g., vaccines) comprising about $10^5$ to about $10^{10}$ fluorescent focus units (FFU) of live attenuated influenza virus containing one or more flu hemagglutinin (HA) polypeptides described herein and/or one or more influenza virus neuraminidase polypeptides described herein, about 0.1 to about 0.5 mg monosodium glutamate, about 1.0 to about 5.0 mg hydrolyzed porcine gelatin, about 1.0 to about 5.0 mg arginine, about 10 to about 15 mg sucrose, about 1.0 to about 5.0 mg dibasic potassium phosphate, about 0.5 to about 2.0 mg monobasic potassium phosphate, and about 0.001 to about 0.05 µg/ml gentamicin sulfate per dose. In some embodiments, the immunogenic compositions (e.g., vaccines) are packaged as pre-filled sprayers containing single 0.2 ml doses.

In a specific embodiment, provided herein are immunogenic compositions (e.g., vaccines) comprising $10^{6.5}$ to $10^{7.5}$ FFU of live attenuated influenza virus containing one or more flu hemagglutinin (HA) polypeptides described herein and/or one or more influenza virus neuraminidase polypeptides described herein, 0.188 mg monosodium glutamate, 2.0 mg hydrolyzed porcine gelatin, 2.42 mg arginine, 13.68 mg sucrose, 2.26 mg dibasic potassium phosphate, 0.96 mg monobasic potassium phosphate, and <0.015 µg/ml gentamicin sulfate per dose. In some embodiments, the immunogenic compositions (e.g., vaccines) are packaged as pre-filled sprayers containing single 0.2 ml doses.

In a specific embodiment, the live virus that contains a flu hemagglutinin (HA) polypeptide and/or an influenza virus neuraminidase polypeptide is propagated in embryonated chicken eggs before its use in an immunogenic composition described herein. In another specific embodiment, the live virus that contains a flu hemagglutinin (HA) polypeptide and/or an influenza virus neuraminidase polypeptide is not propagated in embryonated chicken eggs before its use in an immunogenic composition described herein. In another specific embodiment, the live virus that contains a flu hemagglutinin (HA) polypeptide and/or an influenza virus neuraminidase polypeptide is propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its use in an immunogenic composition described herein.

An immunogenic composition comprising a live virus for administration to a subject may be preferred because multiplication of the virus in the subject may lead to a prolonged stimulus of similar kind and magnitude to that occurring in natural infections, and therefore, confer substantial, long lasting immunity.

5.15.3 Inactivated Virus Vaccines

In one embodiment, provided herein are immunogenic compositions (e.g., vaccines) comprising an inactivated virus containing a flu hemagglutinin (HA) polypeptide (e.g., a chimeric influenza virus hemagglutinin polypeptide) and/or an influenza virus neuraminidase polypeptide. In specific embodiments, the flu hemagglutinin (HA) polypeptide and/or the influenza virus neuraminidase polypeptide is membrane-bound. In particular embodiments, the inactivated virus is an influenza virus, such as described in Section 5.8. In other embodiments, the inactivated virus is a non-influenza virus, such as described in Section 5.9. In some embodiments, an immunogenic composition comprises two, three, four or more inactivated viruses containing two, three, four or more different flu hemagglutinin (HA) polypeptides and/or two, three, four or more different influenza virus neuraminidase polypeptides. In certain embodiments, the inactivated virus immunogenic compositions comprise one or more adjuvants.

Techniques known to one of skill in the art may be used to inactivate viruses containing a flu hemagglutinin (HA) polypeptide and/or an influenza virus neuraminidase polypeptide. Common methods use formalin, heat, or detergent for inactivation. See, e.g., U.S. Pat. No. 6,635,246, which is herein incorporated by reference in its entirety. Other methods include those described in U.S. Pat. Nos. 5,891,705; 5,106,619 and 4,693,981, which are incorporated herein by reference in their entireties.

In certain embodiments, provided herein are immunogenic compositions (e.g., vaccines) comprising inactivated influenza virus such that each dose of the immunogenic composition comprises about 15 to about 60 µg of a flu hemagglutinin (HA) polypeptide described herein and/or of an influenza virus neuraminidase polypeptide described herein, about 1.0 to about 5.0 mg sodium chloride, about 20 to about 100 µg monobasic sodium phosphate, about 100 to about 500 µg dibasic sodium phosphate, about 5 to about 30 µg monobasic potassium phosphate, about 5 to about 30 µg potassium chloride, and about 0.5 to about 3.0 µg calcium chloride. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In certain embodiments, provided herein are immunogenic compositions (e.g., vaccines) comprising inactivated influenza virus such that each dose of the immunogenic composition comprises about 15 to about 60 µg of a flu hemagglutinin (HA) polypeptide described herein and/or of an influenza virus neuraminidase polypeptide described herein, about 0.001% to 0.01% thimerosal, about 1.0 to about 5.0 mg sodium chloride, about 20 to about 100 µg monobasic sodium phosphate, about 100 to about 500 µg dibasic sodium phosphate, about 5 to about 30 µg monobasic potassium phosphate, about 5 to about 30 µg potassium chloride, and about 0.5 to about 3.0 µg calcium chloride per dose. In some embodiments, the immunogenic compositions (e.g., vaccines) are packaged as single 0.25 ml or single 0.5 ml doses. In other embodiments, the immunogenic compositions (e.g., vaccines) are packaged as multi-dose formulations.

In a specific embodiment, immunogenic compositions (e.g., vaccines) provided herein are packaged as single 0.25 ml doses and comprise 22.5 µg of a flu hemagglutinin (HA) polypeptide described herein and/or of an influenza virus neuraminidase polypeptide described herein, 2.05 mg sodium chloride, 40 µg monobasic sodium phosphate, 150 µg dibasic sodium phosphate, 10 µg monobasic potassium phosphate, 10 µg potassium chloride, and 0.75 µg calcium chloride per dose.

In a specific embodiment, immunogenic compositions (e.g., vaccines) provided herein are packaged as single 0.5 ml doses and comprise 45 µg of a flu hemagglutinin (HA) polypeptide described herein and/or of an influenza virus neuraminidase polypeptide described herein, 4.1 mg sodium chloride, 80 µg monobasic sodium phosphate, 300 µg dibasic sodium phosphate, 20 µg monobasic potassium phosphate, 20 µg potassium chloride, and 1.5 µg calcium chloride per dose.

In a specific embodiment, immunogenic compositions (e.g., vaccines) are packaged as multi-dose formulations comprising or consisting of 5.0 ml of vaccine (0.5 ml per dose) and comprise 24.5 µg of mercury (from thimerosal), 45 µg of a flu hemagglutinin (HA) polypeptide described herein and/or of an influenza virus neuraminidase polypeptide described herein, 4.1 mg sodium chloride, 80 µg monobasic sodium phosphate, 300 µg dibasic sodium phosphate, 20 µg monobasic potassium phosphate, 20 µg potassium chloride, and 1.5 µg calcium chloride per dose.

In a specific embodiment, the inactivated virus that contains a flu hemagglutinin (HA) polypeptide and/or an influenza virus neuraminidase polypeptide was propagated in embryonated chicken eggs before its inactivation and subsequent use in an immunogenic composition described herein. In another specific embodiment, the inactivated virus that contains a flu hemagglutinin (HA) polypeptide and/or an influenza virus neuraminidase polypeptide was not propagated in embryonated chicken eggs before its inactivation and subsequent use in an immunogenic composition described herein. In another specific embodiment, the inactivated virus that contains a flu hemagglutinin (HA) polypeptide and/or an influenza virus neuraminidase polypeptide was propagated in mammalian cells, e.g., immortalized human cells (see, e.g., International Application No. PCT/EP2006/067566 published as International Publication No. WO 07/045674 which is herein incorporated by reference in its entirety) or canine kidney cells such as MDCK cells (see, e.g., International Application No. PCT/IB2007/003536 published as International Publication No. WO 08/032219 which is herein incorporated by reference in its entirety) before its inactivation and subsequent use in an immunogenic composition described herein.

5.15.4 Split Virus Vaccines

In one embodiment, an immunogenic composition comprising a flu hemagglutinin (HA) polypeptide (e.g., a chimeric influenza virus hemagglutinin polypeptide) and/or an influenza virus neuraminidase polypeptide is a split virus vaccine. In some embodiments, split virus vaccine contains two, three, four or more different flu hemagglutinin (HA) polypeptides and/or two, three, four or more different influenza virus neuraminidase polypeptides. In certain embodiments, the flu hemagglutinin (HA) polypeptide and/or the influenza virus neuraminidase polypeptide is/was membrane-bound. In certain embodiments, the split virus vaccines comprise one or more adjuvants.

Techniques for producing split virus vaccines are known to those skilled in the art. By way of non-limiting example, an influenza virus split vaccine may be prepared using inactivated particles disrupted with detergents. One example of a split virus vaccine that can be adapted for use in accordance with the methods described herein is the Fluzone®, Influenza Virus Vaccine (Zonal Purified, Subvirion) for intramuscular use, which is formulated as a sterile suspension prepared from influenza viruses propagated in embryonated chicken eggs. The virus-containing fluids are harvested and inactivated with formaldehyde. Influenza virus is concentrated and purified in a linear sucrose density gradient solution using a continuous flow centrifuge. The virus is then chemically disrupted using a nonionic surfactant, octoxinol-9, (Triton® X-100—A registered trademark of Union Carbide, Co.) producing a "split virus." The split virus is then further purified by chemical means and suspended in sodium phosphate-buffered isotonic sodium chloride solution.

In certain embodiments, provided herein are split virus vaccines comprising about 10 µg to about 60 µg of one or more flu hemagglutinin (HA) polypeptides described herein and/or of one or more influenza virus neuraminidase polypeptides described herein, about 0.01 to about 1.0 mg octoxynol-10 (TRITON X-100®, about 0.5 to 0.5 mg a-tocopheryl hydrogen succinate, about 0.1 to 1.0 mg polysorbate 80 (Tween 80), about 0.001 to about 0.003 hydrocortisone, about 0.05 to about 0.3 µg gentamcin sulfate, about 0.5 to about 2.0 µg chicken egg protein (ovalbumin), about 25 to 75 µg formaldehyde, and about 25 to 75 µg sodium deoxycholate.

In a specific embodiment, a split virus vaccine provided herein comprises or consists of a 0.5 ml dose that comprises 45 µg of a flu hemagglutinin (HA) polypeptide(s) provided herein and/or of an influenza virus neuraminidase polypeptide described herein, <0.085 mg octoxynol-10 (TRITON X-100®, ≤0.1 mg α-tocopheryl hydrogen succinate, ≤0.415 mg polysorbate 80 (Tween 80), ≤0.0016 µg hydrocortisone, ≤0.15 µg gentamcin sulfate, ≤1.0 chicken egg protein (ovalbumin), ≤50 µg formaldehyde, and ≤50 µg sodium deoxycholate. In some embodiments, the 0.5 ml dose subunit vaccine is packaged in a pre-filled syringe.

In a specific embodiment, the split virus vaccine is prepared using influenza virus that was propagated in embryonated chicken eggs. In another specific embodiment, the split virus vaccine is prepared using influenza virus that was not propagated in embryonated chicken eggs. In another specific embodiment, the split virus vaccine is prepared using influenza virus that was propagated in mammalian cells, e.g., immortalized human cells (see, e.g., PCT/EP2006/067566 published as WO 07/045674 which is herein incorporated by reference in its entirety) or canine kidney cells such as MDCK cells (see, e.g., PCT/M2007/003536 published as WO 08/032219 which is herein incorporated by reference in its entirety).

5.15.5 Adjuvants

In certain embodiments, the compositions described herein comprise, or are administered in combination with, an adjuvant. The adjuvant for administration in combination with a composition described herein may be administered before, concomitantly with, or after administration of said composition. In some embodiments, the term "adjuvant" refers to a compound that when administered in conjunction with or as part of a composition described herein augments, enhances and/or boosts the immune response to a flu hemagglutinin (HA) polypeptide (e.g., a chimeric influenza virus hemagglutinin polypeptide) and/or an influenza virus neuraminidase polypeptide, but when the compound is administered alone does not generate an immune response to the polypeptide. In some embodiments, the adjuvant generates an immune response to the polypeptide and does not produce an allergy or other adverse reaction. Adjuvants can enhance an immune response by several mechanisms including, e.g., lymphocyte recruitment, stimulation of B and/or T cells, and stimulation of macrophages.

In certain embodiments, an adjuvant augments the intrinsic response to the flu hemagglutinin (HA) polypeptide and/or the influenza virus neuraminidase polypeptide without causing conformational changes in the polypeptide that affect the qualitative form of the response. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N Y, 1995); U.S. Pat. No. 5,057, 540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG (Bioworld Today, Nov. 15, 1998). Such adjuvants can be used with or without other specific immunostimulating agents such as MPL or 3-DMP, QS21, polymeric or monomeric amino acids such as polyglutamic acid or polylysine, or other immunopotentiating agents. It should be understood that different formulations of flu hemagglutinin (HA) polypeptides and/or influenza virus neuraminidase polypeptides may comprise different adjuvants or may comprise the same adjuvant.

5.16 Prophylactic and Therapeutic Uses

In one aspect, provided herein are methods for inducing an immune response in a subject utilizing an active compound (e.g., a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or a composition described herein. In a specific embodiment, a method for inducing an immune response to an influenza virus hemagglutinin polypeptide and/or an influenza virus neuraminidase polypeptide in a subject comprises administering to a subject in need thereof an effective amount of a flu hemagglutinin (HA) polypeptide described herein and/or an influenza virus neuraminidase polypeptide, respectively, or an immunogenic composition thereof. In another embodiment, a method for inducing an immune response to an influenza virus hemagglutinin polypeptide and/or an influenza virus neuraminidase polypeptide in a subject comprises administering to a subject in need thereof an effective amount of a nucleic acid encoding a flu hemagglutinin (HA) polypeptide described herein and/or an influenza virus neuraminidase polypeptide described herein, respectively, or an immunogenic composition thereof. In another embodiment, a method for inducing an immune response to an influenza virus hemagglutinin polypeptide and/or an influenza virus neuraminidase polypeptide in a subject comprises administering to a subject in need thereof an effective amount of a viral vector containing or expressing a flu hemagglutinin (HA) polypeptide described herein and/or an influenza virus neuraminidase polypeptide described herein, respectively, or an immunogenic composition thereof. In yet another embodiment, a method for inducing an immune response to an influenza virus hemagglutinin polypeptide and/or an influenza virus neuraminidase polypeptide in a subject comprises administering to a subject in need thereof an effective amount of cells stimulated with a flu hemagglutinin (HA) polypeptide described herein and/or an influenza virus neuraminidase polypeptide described herein, respectively, or a pharmaceutical composition thereof. In certain embodiments, a flu hemagglutinin (HA) polypeptide described herein and/or an influenza virus neuraminidase polypeptide described herein used in the method is a purified flu hemagglutinin (HA) polypeptide described herein and/or an influenza virus neuraminidase polypeptide, respectively, derived from a mammalian cell, a plant cell, or an insect cell.

In a specific embodiment, a method for inducing an immune response to an influenza virus hemagglutinin polypeptide and/or an influenza virus neuraminidase polypeptide in a subject comprises administering to a subject in need thereof a subunit vaccine described herein. In another embodiment, a method for inducing an immune response to an influenza virus hemagglutinin polypeptide and/or an influenza virus neuraminidase polypeptide in a subject comprises administering to a subject in need thereof a live virus vaccine described herein. In particular embodiments, the live virus vaccine comprises an attenuated virus. In another embodiment, a method for inducing an immune response to an influenza virus hemagglutinin polypeptide and/or an influenza virus neuraminidase polypeptide in a subject comprises administering to a subject in need thereof an inactivated virus vaccine described herein. In another embodiment, a method for inducing an immune response to an influenza virus hemagglutinin polypeptide and/or an influenza virus neuraminidase polypeptide in a subject comprises administering to a subject in need thereof a split virus vaccine described herein. In another embodiment, a method for inducing an immune response to an influenza virus hemagglutinin polypeptide and/or an influenza virus neuraminidase polypeptide in a subject comprises administering to a subject in need thereof a virus-like particle vaccine described herein. In another embodiment, a method for inducing an immune response to an influenza hemagglutinin polypeptide and/or an influenza virus neuraminidase polypeptide comprises administering to a subject in need thereof a virosome described herein. In another embodiment, a method for inducing an immune response to an influenza hemagglutinin polypeptide and/or an influenza virus neuraminidase polypeptide comprises administering to a subject in need thereof a bacteria expressing or engineered to express a flu hemagglutinin (HA) polypeptide described herein and/or an influenza virus neuraminidase polypeptide described herein, or a composition thereof. In certain embodiments, a flu hemagglutinin (HA) polypeptide described herein and/or an influenza virus neuraminidase polypeptide described herein used in the method is a purified flu hemagglutinin (HA) polypeptide described herein and/or a purified influenza virus neuraminidase polypeptide, respectively, derived from a mammalian cell, a plant cell, or an insect cell.

In a specific embodiment, a method for inducing an immune response to an influenza virus hemagglutinin polypeptide and/or an influenza virus neuraminidase polypeptide in a subject comprises administering to a subject in need thereof (a) a live influenza virus vaccine comprising a chimeric HA; and (b) an inactivated seasonal influenza virus vaccine. In certain embodiments, the live influenza virus vaccine is supplemented with NA immunogen(s). In certain embodiments, the inactivated influenza virus vaccine is supplemented with NA immunogen(s). In a specific embodiment, a method for inducing an immune response to an influenza virus hemagglutinin polypeptide and/or an influenza virus neuraminidase polypeptide in a subject comprises administering to a subject in need thereof (a) a live influenza virus vaccine comprising a headless HA; and (b) and an inactivated seasonal influenza virus vaccine. In certain embodiments, the live influenza virus vaccine is supplemented with NA immunogen(s). In certain embodiments, the inactivated influenza virus vaccine is supplemented with NA immunogen(s). In a specific embodiment, a method for inducing an immune response to an influenza virus hemagglutinin polypeptide and/or an influenza virus neuraminidase polypeptide in a subject comprises administering to a subject in need thereof (a) a live influenza virus vaccine comprising a flu HA polypeptide; and (b) an inactivated seasonal influenza virus vaccine. In certain embodiments, the live influenza virus vaccine is supplemented with NA immunogen(s). In certain embodiments, the inactivated influenza virus vaccine is supplemented with NA immunogen(s). In a specific embodiment, a method for inducing an immune response to an influenza virus hemagglutinin polypeptide and/or an influenza virus neuraminidase polypeptide in a subject comprises administering to a subject in need thereof (a) a live influenza virus vaccine comprising a flu HA polypeptide; and (b) a seasonal NA immunogen. In certain embodiments, the live influenza virus vaccine is supplemented with NA immunogen(s). In a specific embodiment, a method for inducing an immune response to an influenza virus hemagglutinin polypeptide and/or an influenza virus neuraminidase polypeptide in a subject comprises administering to a subject in need thereof (a) a seasonal influenza virus vaccine; and (b) an NA immunogen. In certain embodiments, the seasonal influenza virus vaccine is supplemented with NA immunogen(s). In certain embodiments, the method for inducing an immune response to an influenza virus hemagglutinin polypeptide and/or an influenza virus neuraminidase immunogen further comprises administering to the subject one or more additional boosters, of, e.g., an HA construct described herein or vector thereof, and/or an NA immunogen described herein.

In some embodiments, the immune response induced by an active compound (e.g., a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or a composition described herein is effective to prevent and/or treat an influenza virus infection caused by any subtype or strain of influenza virus. In certain embodiments, the immune response induced by an active compound or a composition described herein is effective to prevent and/or treat an influenza virus infection caused by a subtype of influenza virus that belongs to one HA group (e.g., Group 1, which comprises H1, H2, H5, H6, H8, H9, H11, H12, H13, and H16) and not the other HA group (e.g., Group 2, which comprises H3, H4, H7, H10, H14, and H15). For example, the immune response induced may be effective to prevent and/or treat an influenza virus infection caused by an influenza virus that belongs to the HA group consisting of H11, H13, H16, H9, H8, H12, H6, H1, H5 and H2. Alternatively, the immune response induced may be effective to prevent and/or treat an influenza virus infection caused by an influenza virus that belongs to the HA group consisting of H3, H4, H14, H10, H15 and H7. In certain embodiments, the immune response induced by an active compound or a composition described herein is effective to prevent and/or treat an influenza virus infection caused by a subtype of influenza virus that belongs to one NA group (e.g., Group 1, which comprises N1, N4, N5, and N8) and not the other NA group (e.g., Group 2, which comprises N2, N3, N6, N7, and N9). For example, the immune response induced may be effective to prevent and/or treat an influenza virus infection caused by an influenza virus that belongs to the NA group consisting of N1, N4, N5, and N8. Alternatively, the immune response induced may be effective to prevent and/or treat an influenza virus infection caused by an influenza virus that belongs to the NA group consisting of N2, N3, N6, N7, and N9.

In some embodiments, the immune response induced by an active compound or a composition described herein is effective to prevent and/or treat an influenza virus infection caused by one, two, three, four or five subtypes of influenza virus. In certain embodiments, the immune response induced by an active compound or a composition described herein is effective to prevent and/or treat an influenza virus infection caused by six, seven, eight, nine, ten, eleven, twelve, thirteen, fourteen or fifteen subtypes of influenza virus. In some embodiments, the immune response induced by an active compound or a composition described herein is effective to prevent and/or treat an influenza virus infection caused by one or more variants within the same subtype of influenza virus.

In some embodiments, the immune response induced by an active compound (e.g., a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or a composition described herein is effective to prevent and/or treat an influenza virus infection caused by both H1N1 and H2N2 subtypes. In other embodiments, the immune response induced by an active compound or a composition described herein is not effective to prevent and/or treat an influenza virus infection caused by both H1N1 and H2N2 subtypes. In some embodiments, the immune response induced by an active compound or a composition described herein is effective to prevent and/or treat an influenza virus infection caused by H1N1, H2N2, and H3N2 subtypes. In some embodiments, the immune response induced by an active compound or a composition described herein is effective to prevent and/or treat an influenza virus infection caused by H3N2 subtypes. In other embodiments, the immune response induced by an active compound or a composition described herein is not effective to prevent and/or treat an influenza virus infection caused by H3N2 subtypes.

In some embodiments, the immune response induced by an active compound (e.g., a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or a composition described herein is effective to prevent and/or treat an influenza virus disease caused by any subtype or strain of influenza virus. In certain embodiments, the immune response induced by an active compound or a composition described herein is effective to prevent and/or treat an influenza virus disease caused by a subtype of influenza virus that belongs to one HA group and not the other HA group. For example, the immune response induced may be effective to prevent and/or treat an influenza virus disease caused by an influenza virus that belongs to the HA group consisting of H11, H13, H16, H9, H8, H12, H6, H1, H5 and H2. Alternatively, the immune response induced may be effective to prevent and/or treat an influenza virus disease caused by an influenza virus that belongs to the HA group consisting of H3, H4, H14, H10, H15 and H7. In certain embodiments, the immune response induced by an active compound or a composition described herein is effective to prevent and/or treat an influenza virus disease caused by a subtype of influenza virus that belongs to one NA group and not the other NA group. For example, the immune response induced may be effective to prevent and/or treat an influenza virus disease caused by an influenza virus that belongs to the NA group consisting of N1, N4, N5, and N8. Alternatively, the immune response induced may be effective to prevent and/or treat an influenza virus disease caused by an influenza virus that belongs to the NA group consisting of N2, N3, N6, N7, and N9. In some embodiments, the immune response induced by an active compound or a composition described herein is effective to prevent and/or treat an influenza virus disease caused by any of one, two, three, four or five subtypes of influenza virus. In certain embodiments, the immune response induced by an active compound or a composition described herein is effective to prevent and/or treat an influenza virus disease caused by any of six, seven, eight, nine, ten, eleven, twelve, thirteen, fourteen or fifteen subtypes of influenza virus. In some embodiments, the immune response induced by an active compound or a composition described herein is effective to prevent and/or treat an influenza virus disease caused by one or more variants within the same subtype of influenza virus.

In some embodiments, the immune response induced by an active compound (e.g., a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or a composition described herein is effective to reduce symptoms resulting from an influenza virus disease/infection. Symptoms of influenza virus disease/infection include, but are not limited to, body aches (especially joints and throat), fever, nausea, headaches, irritated eyes, fatigue, sore throat, reddened eyes or skin, and abdominal pain.

In some embodiments, the immune response induced by an active compound (e.g., a flu hemagglutinin (HA) polypeptide described herein and/or an influenza virus neuraminidase polypeptide, a nucleic acid encoding such a polypeptide(s), a vector (e.g., a viral vector, or a bacteria) containing or expressing such a polypeptide(s), cells stimulated with such a polypeptide(s)) or a composition described herein is effective to reduce the hospitalization of a subject suffering from an influenza virus disease/infection. In some embodiments, the immune response induced by an active compound or a composition described herein is effective to reduce the duration of hospitalization of a subject suffering from an influenza virus disease/infection.

In another aspect, provided herein are methods for preventing and/or treating an influenza virus infection in a subject utilizing an active compound (e.g., a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or a composition described herein. In one embodiment, a method for preventing or treating an influenza virus infection in a subject comprises administering to a subject in need thereof a flu hemagglutinin (HA) polypeptide and/or an influenza virus neuraminidase polypeptide, a nucleic acid encoding such a polypeptide(s), a vector containing or expressing such a polypeptide(s), or a composition of any one of the foregoing. In a specific embodiment, a method for preventing or treating an influenza virus infection in a subject comprises administering to a subject in need thereof a subunit vaccine, a live virus vaccine, an inactivated virus vaccine, a split virus vaccine or a virus-like particle vaccine.

In another aspect, provided herein are methods for preventing and/or treating an influenza virus disease in a subject utilizing a flu hemagglutinin (HA) polypeptide described herein and/or an influenza virus neuraminidase polypeptide described herein, a nucleic acid encoding such a polypeptide(s), a vector containing or expressing such a polypeptide(s), or cells stimulated with such a polypeptide(s). In a specific embodiment, a method for preventing or treating an influenza virus disease in a subject comprises administering to a subject in need thereof an effective amount of a flu hemagglutinin (HA) polypeptide and/or an influenza virus neuraminidase polypeptide or an immunogenic composition thereof. In another embodiment, a method for preventing or treating an influenza virus disease in a subject comprises administering to a subject in need thereof an effective amount of a nucleic acid encoding a flu hemagglutinin (HA) polypeptide and/or a nucleic acid encoding an influenza virus neuraminidase polypeptide or an immunogenic composition thereof. In another embodiment, a method for preventing or treating an influenza virus disease in a subject comprises administering to a subject in need thereof an effective amount of a viral vector containing or expressing a flu hemagglutinin (HA) polypeptide and/or a viral vector containing or expressing an influenza virus neuraminidase polypeptide or an immunogenic composition thereof. In yet another embodiment, a method for preventing or treating an influenza virus disease in a subject comprises administering to a subject in need thereof an effective amount of cells stimulated with a flu hemagglutinin (HA) polypeptide and/or cells stimulated with an influenza virus neuraminidase polypeptide or a pharmaceutical composition thereof.

In a specific embodiment, a method for preventing and/or treating an influenza virus disease in a subject comprises administering to a subject in need thereof (a) a live influenza virus vaccine comprising a chimeric HA; and (b) an inactivated influenza virus vaccine comprising a seasonal NA polypeptide. In certain embodiments, the live influenza virus vaccine is supplemented with NA polypeptide(s). In certain embodiments, the inactivated influenza virus vaccine is supplemented with NA polypeptide(s). In a specific embodiment, a method for preventing and/or treating an influenza virus disease in a subject comprises administering to a subject in need thereof (a) a live influenza virus vaccine comprising a headless HA; and (b) and an inactivated influenza virus vaccine comprising a seasonal NA polypeptide. In certain embodiments, the live influenza virus vaccine is supplemented with NA polypeptide(s). In certain embodiments, the inactivated influenza virus vaccine is supplemented with NA polypeptide(s). In a specific embodiment, a method for preventing and/or treating an influenza virus disease in a subject comprises administering to a subject in need thereof (a) a live influenza virus vaccine comprising a flu HA polypeptide; and (b) and an inactivated influenza virus vaccine comprising a seasonal NA polypeptide. In certain embodiments, the live influenza virus vaccine is supplemented with NA polypeptide(s). In certain embodiments, the inactivated influenza virus vaccine is supplemented with NA polypeptide(s). In a specific embodiment, a method for preventing and/or treating an influenza virus disease in a subject comprises administering to a subject in need thereof (a) a live influenza virus vaccine comprising a flu HA polypeptide; and (b) a seasonal NA polypeptide. In certain embodiments, the live influenza virus vaccine is supplemented with NA polypeptide(s). In a specific embodiment, a method for preventing and/or treating an influenza virus disease in a subject comprises administering to a subject in need thereof (a) a seasonal influenza virus vaccine; and (b) an NA polypeptide. In certain embodiments, the seasonal influenza virus vaccine is supplemented with NA polypeptide(s). In certain embodiments, the method for preventing and/or treating an influenza virus disease further comprises administering to the subject one or more additional boosters.

In a specific embodiment, a method for preventing or treating an influenza virus disease in a subject comprises administering to a subject in need thereof a subunit vaccine described herein. In another embodiment, a method for preventing or treating an influenza virus disease in a subject comprises administering to a subject in need thereof a live virus vaccine described herein. In particular embodiments, the live virus vaccine comprises an attenuated virus. In another embodiment, a method for preventing or treating an influenza virus disease in a subject comprises administering to a subject in need thereof an inactivated virus vaccine described herein. In another embodiment, a method for preventing or treating an influenza virus disease in a subject comprises administering to a subject in need thereof a split virus vaccine described herein. In another embodiment, a method for preventing or treating an influenza virus disease comprises administering to a subject in need thereof a virus-like particle vaccine described herein. In another embodiment, a method for preventing or treating an influenza virus disease in a subject, comprising administering to a subject in need thereof a virosome described herein. In another embodiment, a method for preventing or treating an influenza virus disease in a subject comprising administering to a subject in need thereof a bacteria expressing or engineered to express a flu hemagglutinin (HA) polypeptide and/or a bacteria expressing or engineered to express an influenza virus neuraminidase polypeptide or a composition thereof In another aspect, provided herein are methods of immunizing a subject against an influenza virus disease or infection comprising exposing the subject to the hemagglutinin and/or the neuraminidase of an influenza virus to which the subject is naive, i.e., the subject has not previously been exposed to the influenza virus and/or the hemagglutinin and/or the neuraminidase, respectively, of the influenza virus.

In one embodiment, provided herein is a method of immunizing a subject against an influenza virus disease or infection comprising administering to said subject one or more influenza viruses, wherein each of said one or more influenza viruses comprises a hemagglutinin polypeptide and/or neuraminidase polypeptide to which the subject is naive, i.e., the subject has not previously been exposed to the one or more influenza viruses. In a specific embodiment, the one or more influenza viruses is an influenza virus of subtype H2, H4, H5, H6, H7, H8, H9, H10, H11, H12, H13, H14, H15, H16, and/or H17. In another specific embodiment, the method comprises (i) a first administration of an influenza virus of subtype H2, H4, H5, H6, H7, H8, H9, H10, H11, H12, H13, H14, H15, H16, H17, or H18 and (ii) a second administration of an influenza virus of subtype H2, H4, H5, H6, H7, H8, H9, H10, H11, H12, H13, H14, H15, H16, H17, or H18, wherein the influenza virus of the first administration is of a different subtype than the influenza virus of the second administration. The first and second administrations may be separated by at least 1 day, 2 days, 3 days, 5 days, 10 days, 15 days, 30 days, 45 days, 2 months, 75 days, 3 months, or at least 6 months. In another specific embodiment, the method comprises (i) a first administration of an influenza virus of subtype H2, H4, H5, H6, H7, H8, H9, H10, H11, H12, H13, H14, H15, H16, H17, or H18; (ii) a second administration of an influenza virus of subtype H2, H4, H5, H6, H7, H8, H9, H10, H11, H12, H13, H14, H15, H16, H17, or H18; and (iii) a third administration of an influenza virus of subtype H2, H4, H5, H6, H7, H8, H9, H10, H11, H12, H13, H14, H15, H16, H17, or H18, wherein the influenza viruses of the first, second, and third administrations are of different subtypes. The first, second, and third administrations may be separated by at least 1 day, 2 days, 3 days, 5 days, 10 days, 15 days, 30 days, 45 days, 2 months, 75 days, 3 months, or at least 6 months. In a specific embodiment, the one or more influenza viruses is an influenza virus of subtype N1, N2, N3, N4, N5, N6, N7, N8, N9, N10 and/or H11. In another specific embodiment, the method comprises (i) a first administration of an influenza virus of subtype N1, N2, N3, N4, N5, N6, N7, N8, N9, N10, or N11 and (ii) a second administration of an influenza virus of subtype N1, N2, N3, N4, N5, N6, N7, N8, N9, N10, or N11, wherein the influenza virus of the first administration is of a different subtype than the influenza virus of the second administration. The first and second administrations may be separated by at least 1 day, 2 days, 3 days, 5 days, 10 days, 15 days, 30 days, 45 days, 2 months, 75 days, 3 months, or at least 6 months. In another specific embodiment, the method comprises (i) a first administration of an influenza virus of N1, N2, N3, N4, N5, N6, N7, N8, N9, N10, or N11; (ii) a second administration of an influenza virus of subtype N1, N2, N3, N4, N5, N6, N7, N8, N9, N10, or N11; and (iii) a third administration of an influenza virus of subtype N1, N2, N3, N4, N5, N6, N7, N8, N9, N10, or N11, wherein the influenza viruses of the first, second, and third administrations are of different subtypes. The first, second, and third administrations may be separated by at least 1 day, 2 days, 3 days, 5 days, 10 days, 15 days, 30 days, 45 days, 2 months, 75 days, 3 months, or at least 6 months.

In another embodiment, provided herein is a method of immunizing a subject against an influenza virus disease or infection comprising administering to said subject one or more influenza virus hemagglutinin polypeptides to which the subject is naive, i.e., the subject has not previously been exposed to the one or more influenza virus hemagglutinin polypeptides. In certain embodiments, said one or more influenza virus hemagglutinin polypeptides to which the subject is naive are in a composition (e.g., a composition comprising a vaccine). In certain embodiments, one or more influenza virus hemagglutinin polypeptides to which the subject is naive are in a vector, e.g., an influenza virus vector. In certain embodiments, one or more influenza virus hemagglutinin polypeptides to which the subject is naive are in a VLP. In certain embodiments, one or more influenza virus hemagglutinin polypeptides to which the subject is naive are in a virosome. In a specific embodiment, the one or more influenza viruses hemagglutinin polypeptides is an influenza virus hemagglutinin polypeptide from an influenza virus of subtype H2, H4, H5, H6, H7, H8, H9, H10, H11, H12, H13, H14, H15, H16, and/or H17. In another specific embodiment, the method comprises (i) a first administration of an influenza virus hemagglutinin polypeptide of subtype H2, H4, H5, H6, H7, H8, H9, H10, H11, H12, H13, H14, H15, H16, H17, or H18 and (ii) a second administration of an influenza virus hemagglutinin polypeptide of subtype H2, H4, H5, H6, H7, H8, H9, H10, H11, H12, H13, H14, H15, H16, H17, or H18, wherein the influenza virus hemagglutinin polypeptide of the first administration is of a different subtype than the influenza virus hemagglutinin polypeptide of the second administration. The first and second administrations may be separated by at least 1 day, 2 days, 3 days, 5 days, 10 days, 15 days, 30 days, 45 days, 2 months, 75 days, 3 months, or at least 6 months. In another specific embodiment, the method comprises (i) a first administration of an influenza virus hemagglutinin polypeptide of subtype H2, H4, H5, H6, H7, H8, H9, H10, H11, H12, H13, H14, H15, H16, H17, or H18; (ii) a second administration of an influenza virus hemagglutinin polypeptide of subtype H2, H4, H5, H6, H7, H8, H9, H10, H11, H12, H13, H14, H15, H16, H17, or H18; and (iii) a third administration of an influenza virus hemagglutinin polypeptide of subtype H2, H4, H5, H6, H7, H8, H9, H10, H11, H12, H13, H14, H15, H16, H17, or H18, wherein the influenza virus hemagglutinin polypeptides of the first, second, and third administrations are from different influenza virus subtypes. The first, second, and third administrations may be separated by at least 1 day, 2 days, 3 days, 5 days, 10 days, 15 days, 30 days, 45 days, 2 months, 75 days, 3 months, or at least 6 months.

In another embodiment, provided herein is a method of immunizing a subject against an influenza virus disease or infection comprising administering to said subject one or more influenza virus neuraminidase polypeptides to which the subject is naive, i.e., the subject has not previously been exposed to the one or more influenza virus neuraminidase polypeptides. In certain embodiments, said one or more influenza virus neuraminidase polypeptides to which the subject is naive are in a composition (e.g., a composition comprising a vaccine). In certain embodiments, one or more influenza virus neuraminidase polypeptides to which the subject is naive are in a vector, e.g., an influenza virus vector. In certain embodiments, one or more influenza virus neuraminidase polypeptides to which the subject is naive are in a VLP. In certain embodiments, one or more influenza virus hemagglutinin polypeptides to which the subject is naive are in a virosome. In a specific embodiment, the one or more influenza virus neuraminidase polypeptides is an influenza virus neuraminidase polypeptide from an influenza virus of subtype N1, N2, N3, N4, N5, N6, N7, N8, N9, N10, and/or N11, and/or an influenza B virus neuraminidase polypeptide. In another specific embodiment, the method comprises (i) a first administration of an influenza virus neuraminidase polypeptide of subtype N1, N2, N3, N4, N5, N6, N7, N8, N9, N10, or N11, or an influenza B virus neuraminidase polypeptide and (ii) a second administration of an influenza virus neuraminidase polypeptide of subtype N1, N2, N3, N4, N5, N6, N7, N8, N9, N10, or N11, or an influenza B virus neuraminidase polypeptide, wherein the influenza virus neuraminidase polypeptide of the first administration is of a different subtype than the influenza virus neuraminidase polypeptide of the second administration. The first and second administrations may be separated by at least 1 day, 2 days, 3 days, 5 days, 10 days, 15 days, 30 days, 45 days, 2 months, 75 days, 3 months, or at least 6 months. In another specific embodiment, the method comprises (i) a first administration of an influenza virus neuraminidase polypeptide of subtype N1, N2, N3, N4, N5, N6, N7, N8, N9, N10, or N11, or an influenza B virus neuraminidase polypeptide; (ii) a second administration of an influenza virus neuraminidase polypeptide of subtype N1, N2, N3, N4, N5, N6, N7, N8, N9, N10, or N11, or an influenza B virus neuraminidase polypeptide; and (iii) a third administration of an influenza virus neuraminidase polypeptide of subtype N1, N2, N3, N4, N5, N6, N7, N8, N9, N10, or N11, or an influenza B virus neuraminidase polypeptide, wherein the influenza virus neuraminidase polypeptides of the first, second, and third administrations are from different influenza virus subtypes. The first, second, and third administrations may be separated by at least 1 day, 2 days, 3 days, 5 days, 10 days, 15 days, 30 days, 45 days, 2 months, 75 days, 3 months, or at least 6 months. In certain embodiments, the influenza virus neuraminidase polypeptides of the first and second administrations are from different influenza virus subtypes.

In another embodiment, the method of immunizing a subject against an influenza virus disease or infection comprises (i) a first administration of a first flu HA polypeptide described herein (e.g., a chimeric influenza virus hemagglutinin polypeptide) and/or a first influenza virus neuraminidase polypeptide, a nucleic acid encoding such a polypeptide(s), a vector containing or expressing such a polypeptide(s); and (ii) a second administration of a second flu HA polypeptide described herein (e.g., a chimeric influenza virus hemagglutinin polypeptide) and/or a second influenza virus neuraminidase polypeptide, wherein the first and second flu HA polypeptides have the same stem domain. In certain embodiments, the globular head domain of the first and second flu HA polypeptides are different. In certain embodiments, the globular head domain of the first and second flu HA polypeptides are from the same strain. In certain embodiments, the first flu HA polypeptide and/or the first influenza virus neuraminidase polypeptide are expressed by a first non-influenza virus vector. In certain embodiments, the second flu HA polypeptide and/or the second influenza virus neuraminidase polypeptide are expressed by a second non-influenza virus vector. In certain embodiments, the first and second non-influenza virus vectors are the same. In certain embodiments, the first and second non-influenza virus vectors are different. The first and second administrations may be separated by at least 1 day, 2 days, 3 days, 5 days, 10 days, 15 days, 30 days, 45 days, 2 months, 75 days, 3 months, or at least 6 months. In certain embodiments, booster inoculations may be administered to the subject at 6 to 12 month intervals following the second inoculation.

In another embodiment, the method of immunizing a subject against an influenza virus disease or infection comprises (i) a first administration of a first influenza virus neuraminidase polypeptide, a nucleic acid encoding such a polypeptide, a vector containing or expressing such a polypeptide; and (ii) a second administration of a second influenza virus neuraminidase polypeptide. In certain embodiments, the first and second influenza virus neuraminidase polypeptides are the same. In certain embodiments, the first and second influenza virus neuraminidase polypeptides are different. In certain embodiments, the first influenza virus neuraminidase polypeptide is expressed by a first non-influenza virus vector. In certain embodiments, the second influenza virus neuraminidase polypeptide is expressed by a second non-influenza virus vector. In certain embodiments, the first and second non-influenza virus vectors are the same. In certain embodiments, the first and second non-influenza virus vectors are different. The first and second administrations may be separated by at least 1 day, 2 days, 3 days, 5 days, 10 days, 15 days, 30 days, 45 days, 2 months, 75 days, 3 months, or at least 6 months. In certain embodiments, booster inoculations may be administered to the subject at 6 to 12 month intervals following the second inoculation.

In another embodiment, the method of immunizing a subject against an influenza virus disease or infection comprises (i) a first administration of a first flu HA polypeptide, a nucleic acid encoding such a polypeptide(s), or a vector encoding such a nucleic acid; and (ii) a second administration of (a) an influenza neuraminidase polypeptide, a nucleic acid encoding such a polypeptide(s), or a vector encoding such a nucleic acid, and (b) a second flu HA polypeptide, a nucleic acid encoding such a polypeptide(s), or a vector encoding such a nucleic acid. In certain embodiments, the first and second flu HA polypeptide are the same. In certain embodiments, the first and second flu HA polypeptide are different.

In another embodiment, the method of immunizing a subject against an influenza virus disease or infection comprises (i) a first administration of an influenza virus to the subject; and (ii) a second administration of a flu HA polypeptide described herein (e.g., a chimeric influenza virus hemagglutinin polypeptide) and/or an influenza virus neuraminidase polypeptide to the subject, wherein the influenza virus and the flu HA polypeptides have the same stem domain. In certain embodiments, the globular head domain of the influenza virus and the flu HA polypeptides are different. The first and second administrations may be separated by at least 1 day, 2 days, 3 days, 5 days, 10 days, 15 days, 30 days, 45 days, 2 months, 75 days, 3 months, or at least 6 months. In certain embodiments, booster inoculations may be administered to the subject at 6 to 12 month intervals following the second inoculation.

In another embodiment, the method of immunizing a subject against an influenza virus disease or infection comprises: (i) a first administration of a flu HA polypeptide described herein (e.g., a chimeric influenza virus hemagglutinin polypeptide or headless HA); and (ii) a second administration of an influenza virus neuraminidase to the subject. In certain embodiments, the first and second administrations are 1 to 3 months, 3 to 6 months, or 6 to 12 months apart. In other embodiments, the first and second administrations are about 2 months, 3 months, 4 months, 5 months, 6 months, 7 months, 8 months or 9 months apart.

In another embodiment, provided herein are immunization regimens involving a first immunization (e.g., priming) with a vaccine formulation described herein followed by one, two, or more additional immunizations (e.g., boostings) with a vaccine formulation. In a specific embodiment, the vaccine formulation used in the first immunization is the same type of vaccine formulation used in one, two or more additional immunizations. For example, if the vaccine formulation used in the first immunization is an inactivated influenza virus vaccine formulation, the vaccine formulation used for the one, two or more additional immunizations may be the same type of vaccine formulation, i.e., an inactivated influenza virus vaccine formulation. In other specific embodiments, the vaccine formulation used in the first immunization is different from the type of vaccine formulation used in one, two or more additional immunizations. For example, if the vaccine formulation used in the first immunization is a live influenza virus vaccine formulation, the vaccine formulation used in the one, two or more additional immunization is another type of vaccine formulation, such as an inactivated influenza virus. In certain embodiments, the vaccine formulation used in the additional immunizations changes. For example, if a live attenuated influenza virus vaccine formulation is used for one additional immunization, then one or more additional immunizations may use a different vaccine formulation, such as an inactivated vaccine formulation. See, e.g., the immunization scheme in FIG. 9 which is discussed in Example 2, infra. In a specific embodiment, if a vaccine formulation used in an immunization regimen described herein comprises a chimeric HA, then HA globular head domain of the chimeric HA changes with each immunization while the HA stem domain of the chimeric HA remains the same. In certain embodiments, an NA immunogen is used to supplement a vaccine formulation described herein. See, e.g., FIG. 8C and Example 2, infra, for examples of supplementing a vaccine formulation comprising a chimeric HA, headless HA or another HA stem domain based construct. Any route of administration known to one of skill in the art can be used to administer a vaccine formulation described herein to a subject. See, e.g., Example 1, infra, which describes the benefits of intranasal administration. In a specific embodiment, the live attenuated influenza virus and/or inactivated influenza virus are administered to the subject intranasally. In certain embodiments, the attenuated influenza virus and/or inactivated influenza virus are administered to the subject intramuscularly or subcutaneously.

In specific embodiments, provided herein is a method of immunizing a subject against influenza virus, comprising: (a) administering to the subject a live attenuated influenza virus; and (b) after a certain period of time (e.g., 1-6 months, 3-6 months, 6-9 months, 6-9 months, 9-12 months, etc.) administering to the subject a headless HA or a chimeric HA or vector comprising the same. In a specific embodiment, the stem domain of the hemagglutinin of the live attenuated influenza virus administered in step (a) is the same subtype or strain as the stem domain polypeptide of the headless HA or chimeric HA administered in step (b), and, if a chimeric HA is utilized in step (b), the globular head domain of the hemagglutinin of the live attenuated influenza virus administered in step (a) is heterologous to the globular head domain of the chimeric HA used in step (b). In certain embodiments, the method comprises step (c), which comprises administering to the subject one or more additional vaccine formulations described herein a certain period of time (e.g., 1-6 months, 3-6 months, 6-9 months, 6-9 months, 9-12 months, etc.) after step (b). In certain embodiments, the one or more additional vaccine formulations comprise a chimeric HA or a headless HA, or a vector comprising the same. In a specific embodiment, the stem domain of the hemagglutinin of the live attenuated influenza virus administered in step (a) and the stem domain polypeptide of the headless HA or chimeric HA in step (b) are the same subtype or strain as the stem domain polypeptide of the headless HA or chimeric HA administered in step (c), and, if a chimeric HA is utilized in step (c), the globular head domain of the hemagglutinin of the live attenuated influenza virus administered in step (a) and the globular head domain of the chimeric HA administered in step (b) are heterologous to the globular head domain of the chimeric HA used in step (c). In a specific embodiment, the one or more additional vaccine formulations comprises an inactivated influenza virus vector comprising the same. In certain embodiments, the method comprises administering an NA immunogen prior to (e.g., 5 minutes, 10 minutes, 15 minutes, 30 minutes, 45 minutes, 1 hour, 2 hours, 3 hours, 6 hours, 12 hours, 24 hours, 2 days, 5 days, 7 days, two weeks, three weeks, 1 month, 2 months, 3 months, 4 months, 5 months, 6 months, 7 months, 8 months or 9 months prior to), concurrently or subsequent to (e.g., 5 minutes, 10 minutes, 15 minutes, 30 minutes, 45 minutes, 1 hour, 2 hours, 3 hours, 6 hours, 12 hours, 24 hours, 2 days, 5 days, 7 days, two weeks, three weeks, 1 month, 2 months, 3 months, 4 months, 5 months, 6 months, 7 months, 8 months or 9 months subsequent to) the administration of step (a) and/or step (b) and/or step (c). In a specific embodiment, the live attenuated influenza virus and/or inactivated influenza virus are administered to the subject intranasally. See, e.g., Example 1, infra, which describes the benefits of intranasal administration. In certain embodiments, the attenuated influenza virus and/or inactivated influenza virus are administered to the subject intramuscularly or subcutaneously.

In specific embodiments, provided herein is a method of immunizing a subject against influenza virus, comprising: (a) administering to the subject an inactivated influenza virus; and (b) after a certain period of time (e.g., 1-6 months, 3-6 months, 6-9 months, 6-9 months, 9-12 months, etc.) administering to the subject a headless HA or a chimeric HA or vector comprising the same. In a specific embodiment, the stem domain of the hemagglutinin of the inactivated influenza virus administered in step (a) is the same subtype or strain as the stem domain polypeptide of the headless HA or chimeric HA administered in step (b), and, if a chimeric HA is utilized in step (b), the globular head domain of the hemagglutinin of the inactivated influenza virus administered in step (a) is heterologous to the globular head domain of the chimeric HA used in step (b). In certain embodiments, the method comprises step (c), which comprises administering to the subject one or more additional vaccine formulations described herein a certain period of time (e.g., 1-6 months, 3-6 months, 6-9 months, 6-9 months, 9-12 months, etc.) after step (b). In certain embodiment, the one or more additional vaccine formulations comprise a chimeric HA or headless HA, or vector comprising the same. In a specific embodiment, the stem domain of the hemagglutinin of the inactivated influenza virus administered in step (a) and the stem domain polypeptide of the headless HA or chimeric HA administered in step (b) are the same subtype or strain as the stem domain polypeptide of the headless HA or chimeric HA administered in step (c), and, if a chimeric HA is utilized in step (c), the globular head domain of the hemagglutinin of the inactivated influenza virus administered in step (a) and the globular head domain of the chimeric HA administered in step (b) are heterologous to the globular head domain of the chimeric HA used in step (c). In a specific embodiment, the one or more additional vaccine formulations comprises an inactivated influenza virus or live attenuated influenza virus. In certain embodiments, the method comprises administering an NA immunogen prior to (e.g., 5 minutes, 10 minutes, 15 minutes, 30 minutes, 45 minutes, 1 hour, 2 hours, 3 hours, 6 hours, 12 hours, 24 hours, 2 days, 5 days, 7 days, two weeks, three weeks, 1 month, 2 months, 3 months, 4 months, 5 months, 6 months, 7 months, 8 months or 9 months prior to), concurrently or subsequent to (e.g., 5 minutes, 10 minutes, 15 minutes, 30 minutes, 45 minutes, 1 hour, 2 hours, 3 hours, 6 hours, 12 hours, 24 hours, 2 days, 5 days, 7 days, two weeks, three weeks, 1 month, 2 months, 3 months, 4 months, 5 months, 6 months, 7 months, 8 months or 9 months subsequent to) the administration of step (a) and/or step (b) and/or step (c). In a specific embodiment, the inactivated influenza virus and/or inactivated influenza virus are administered to the subject intranasally. See, e.g., Example 1, infra, which describes the benefits of intranasal administration. In certain embodiments, the attenuated influenza virus and/or inactivated influenza virus are administered to the subject intramuscularly or subcutaneously.

In one embodiment, provided herein is a method of immunizing a subject against influenza virus, comprising: (a) administering to the subject a live attenuated influenza virus engineered to express a headless HA or a chimeric HA; and (b) after a certain period of time (e.g., 1-6 months, 3-6 months, 6-9 months, 6-9 months, 9-12 months, etc.) administering to the subject an inactivated influenza virus engineered to express a headless HA or a chimeric HA. In a specific embodiment, if a chimeric HA is administered in steps (a) and (b), then the chimeric HA used in step (a) comprises a different HA globular head domain than the chimeric HA used in step (b). In a specific embodiment, the stem domain polypeptide of the headless HA or the chimeric HA of step (a) is the same subtype or strain as the stem domain polypeptide of the headless HA or chimeric HA administered in step (b). In certain embodiments, the method comprises administering to the subject one or more additional vaccine formulations described herein a certain period of time (e.g., 1-6 months, 3-6 months, 6-9 months, 6-9 months, 9-12 months, etc.) after step (b). In a specific embodiment, the method comprises administering the subject one or more additional inactivated influenza virus vaccine formulations described herein a certain period of time (e.g., 1-6 months, 3-6 months, 6-9 months, 6-9 months, 9-12 months, etc.) after step (b). In certain embodiments, the method comprises administering an NA immunogen prior to (e.g., 5 minutes, 10 minutes, 15 minutes, 30 minutes, 45 minutes, 1 hour, 2 hours, 3 hours, 6 hours, 12 hours, 24 hours, 2 days, 5 days, 7 days, two weeks, three weeks, 1 month, 2 months, 3 months, 4 months, 5 months, 6 months, 7 months, 8 months or 9 months prior to), concurrently or subsequent to (e.g., 5 minutes, 10 minutes, 15 minutes, 30 minutes, 45 minutes, 1 hour, 2 hours, 3 hours, 6 hours, 12 hours, 24 hours, 2 days, 5 days, 7 days, two weeks, three weeks, 1 month, 2 months, 3 months, 4 months, 5 months, 6 months, 7 months, 8 months or 9 months subsequent to) the administration of step (a) and/or step (b). In a specific embodiment, the live attenuated influenza virus and/or inactivated influenza virus are administered to the subject intranasally. See, e.g., Example 1, infra, which describes the benefits of intranasal administration. In certain embodiments, the attenuated influenza virus and/or inactivated influenza virus are administered to the subject intramuscularly or subcutaneously.

In another embodiment, provided herein is a method of immunizing a subject against influenza virus, comprising: (a) administering to the subject a live attenuated influenza virus engineered to express and/or containing a headless HA or a chimeric HA; and (b) after a certain period of time (e.g., 1-6 months, 3-6 months, 6-9 months, 6-9 months, 9-12 months, etc.) administering to the subject a live attenuated influenza virus engineered to express a headless HA or a chimeric HA. In a specific embodiment, if a chimeric HA is administered in steps (a) and (b), then the chimeric HA used in step (a) comprises a different HA globular head domain than the chimeric HA used in step (b). In a specific embodiment, the stem domain polypeptide of the headless HA or the chimeric HA of step (a) is the same subtype or strain as the stem domain polypeptide of the headless HA or chimeric HA administered in step (b). In certain embodiments, the method comprises administering the subject one or more additional vaccine formulations described herein a certain period of time (e.g., 1-6 months, 3-6 months, 6-9 months, 6-9 months, 9-12 months, etc.) after step (b). In a specific embodiment, the method comprises administering the subject one or more additional inactivated influenza virus vaccine formulations described herein a certain period of time (e.g., 1-6 months, 3-6 months, 6-9 months, 6-9 months, 9-12 months, etc.) after step (b). In certain embodiments, the method comprising administering an NA immunogen prior to (e.g., 5 minutes, 10 minutes, 15 minutes, 30 minutes, 45 minutes, 1 hour, 2 hours, 3 hours, 6 hours, 12 hours, 24 hours, 2 days, 5 days, 7 days, two weeks, three weeks, 1 month, 2 months, 3 months, 4 months, 5 months, 6 months, 7 months, 8 months or 9 months prior to), concurrently or subsequent to (e.g., 5 minutes, 10 minutes, 15 minutes, 30 minutes, 45 minutes, 1 hour, 2 hours, 3 hours, 6 hours, 12 hours, 24 hours, 2 days, 5 days, 7 days, two weeks, three weeks, 1 month, 2 months, 3 months, 4 months, 5 months, 6 months, 7 months, 8 months or 9 months subsequent to) the administration of step (a) and/or step (b). In a specific embodiment, the live attenuated influenza virus and/or inactivated influenza virus are administered to the subject intranasally. See, e.g., Example 1, infra, which describes the benefits of intranasal administration. In certain embodiments, the attenuated influenza virus and/or inactivated influenza virus are administered to the subject intramuscularly or subcutaneously.

In another embodiment, provided herein is a method of immunizing a subject against influenza virus, comprising administering to the subject a vaccine formulation described herein (e.g., a vaccine formulation comprising a headless HA, a chimeric HA or another HA stem domain based construct (e.g., the long alpha helix)), in combination with an NA immunogen. In certain embodiments, the NA immunogen is a polypeptide as described in Section 5.5, above. The term "in combination," in the context of the administration of two or more therapies to a subject, refers to the use of more than one therapy (e.g., more than one prophylactic agent and/or therapeutic agent). The use of the term "in combination" does not restrict the order in which therapies are administered to a subject. For example, a first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject. In some embodiments, two or more therapies are administered to a subject concurrently or within 1 hour of each other.

In another aspect, provided herein is an immunization regimen comprising administering a seasonal influenza virus vaccine in combination with an NA immunogen. See, e.g., FIG. 8E and Example 2, infra, for examples of supplementing a seasonal vaccine with an NA immunogen. In another aspect, provided herein is an immunization regimen comprising administering an NA immunogen. See, e.g., FIG. 8D and Example 2, infra, for examples of immunization with an NA immunogen. In certain embodiments, an NA immunogen lacks one or more naturally occurring glycosylation sites and/or has been deglycosylated (e.g., by a removing glycosylation sites and/or using a deglycosylation agent).

In certain embodiments, an NA immunogen or a vaccine formulation described herein which comprises an NA immunogen induces an immune response (e.g., an antibody response) that is cross-protective against a heterologous virus(es) within the same subtype. See, e.g., Example 1, infra, which describes such cross-protective antibodies. In some embodiments, a vaccine formulation described herein induces an immune response (e.g., an antibody response) that is cross-protective against one, two or more influenza viruses within the subtype and/or same group.

In another aspect, provided herein are methods of preventing and/or treating an influenza virus disease in a subject by administering neutralizing antibodies described herein. In a specific embodiment, a method for preventing or treating an influenza virus disease in a subject comprises administering to a subject in need thereof an effective amount of a neutralizing antibody described herein, or a pharmaceutical composition thereof. In particular embodiments, the neutralizing antibody is a monoclonal antibody. In certain embodiments, the neutralizing antibody is not CR6261, CR6325, CR6329, CR6307, CR6323, 2A, D7, D8, F10, G17, H40, A66, D80, E88, E90, H98, C179 (FERM BP-4517), AI3C (FERM BP-4516) or any other antibody described in Ekiert D C et al. (2009) Antibody Recognition of a Highly Conserved Influenza Virus Epitope. Science (published in Science Express Feb. 26, 2009); Kashyap et al. (2008) Combinatorial antibody libraries from survivors of the Turkish H5N1 avian influenza outbreak reveal virus neutralization strategies. Proc Natl Acad Sci USA 105: 5986-5991; Sui et al. (2009) Structural and functional bases for broad-spectrum neutralization of avian and human influenza A viruses. Nat Struct Mol Biol 16: 265-273; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. In other embodiments, the neutralizing antibody is not an antibody described in Wang et al. (2010) "Broadly Protective Monoclonal Antibodies against H3 Influenza Viruses following Sequential Immunization with Different Hemagglutinins," PLOS Pathogens 6(2):1-9. In certain embodiments, the neutralizing antibody is a not 2B9 or any other antibody described in Shoji et al., Hum. Vaccines, 2011, 7:199-204. In certain embodiments, the neutralizing antibody is not 3A2, 4G2, 1H5, 2D9, or any other antibody described in Wan et al., J. Virol. 2013, 87:9290-9300. In certain embodiments, the neutralizing antibody is not HCA-2, or any other antibody described in Doyle et al. Antivir. Res. 2013, 100:567-574 or Doyle et al., Biochem. Biophys. Res. Commun. 2013, 441:226-229.

In certain embodiments, the methods for preventing or treating an influenza virus disease or infection in a subject (e.g., a human or non-human animal) provided herein result in a reduction in the replication of the influenza virus in the subject as measured by in vivo and in vitro assays known to those of skill in the art and described herein. In some embodiments, the replication of the influenza virus is reduced by approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Example 9 of International Publication No. WO 2013/043729, which is incorporated herein by reference in its entirety, sets forth how chimeric influenza virus HA polypeptides may be used to vaccinate subjects against influenza virus infection.

5.16.1 Combination Therapies

In various embodiments, a flu hemagglutinin (HA) polypeptide (e.g., a chimeric influenza virus hemagglutinin polypeptide) described herein and/or an influenza virus neuraminidase polypeptide, a nucleic acid encoding such a polypeptide(s), a vector (e.g., a viral vector or a bacteria) containing or expressing such a polypeptide(s), cells stimulated with such a polypeptide(s), or a neutralizing antibody may be administered to a subject in combination with one or more other therapies (e.g., antiviral, antibacterial, or immunomodulatory therapies). In some embodiments, a pharmaceutical composition (e.g., an immunogenic composition) described herein may be administered to a subject in combination with one or more therapies. The one or more other therapies may be beneficial in the treatment or prevention of an influenza virus disease or may ameliorate a symptom or condition associated with an influenza virus disease. In some embodiments, the one or more other therapies are pain relievers, anti-fever medications, or therapies that alleviate or assist with breathing. In certain embodiments, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In specific embodiments, two or more therapies are administered within the same patent visit.

Any anti-viral agents well-known to one of skill in the art may used in combination with an active compound (e.g., a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or pharmaceutical composition described herein. Non-limiting examples of anti-viral agents include proteins, polypeptides, peptides, fusion proteins antibodies, nucleic acid molecules, organic molecules, inorganic molecules, and small molecules that inhibit and/or reduce the attachment of a virus to its receptor, the internalization of a virus into a cell, the replication of a virus, or release of virus from a cell. In particular, anti-viral agents include, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, zanamivir (Relenza®), and oseltamivir (Tamiflu®). Other anti-viral agents include influenza virus vaccines, e.g., Fluarix® (GlaxoSmithKline), FluMist® (MedImmune Vaccines), Fluvirin® (Chiron Corporation), Flulaval® (GlaxoSmithKline), Afluria® (CSL Biotherapies Inc.), Agriflu® (Novartis) or Fluzone® (Aventis Pasteur).

In specific embodiments, the anti-viral agent is an immunomodulatory agent that is specific for a viral antigen. In particular embodiments, the viral antigen is an influenza virus polypeptide other than a hemagglutinin polypeptide. In other embodiments, the viral antigen is an influenza virus hemagglutinin polypeptide.

Any anti-bacterial agents known to one of skill in the art may used in combination with an active compound (e.g., a flu hemagglutinin (HA) polypeptide described herein and/or an influenza virus neuraminidase polypeptide, a nucleic acid encoding such a polypeptide(s), a vector (e.g., a viral vector, or a bacteria) containing or expressing such a polypeptide(s), cells stimulated with such a polypeptide(s)) or pharmaceutical composition described herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazone-sulbactam, Cefotaxime, Cefoxitin, Cefpirome, Cefpodoxime, Cefpodoxime-clavulanic acid, Cefpodoxime-sulbactam, Cefprozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

In some embodiments, a combination therapy comprises active immunization with a flu hemagglutinin (HA) polypeptide described herein and/or an influenza virus neuraminidase polypeptide described herein, or one or more vectors described in Sections 5.8-5.12 and passive immunization with one or more neutralizing antibodies described in Section 5.13. In some embodiments, a combination therapy comprises immunization with one or more vectors described in Sections 5.8-5.12 and administration of cells (e.g., by adoptive transfer) described in Section 5.13.

In some embodiments, a combination therapy comprises administration of two or more different vectors described in Sections 5.8-5.12.

In some embodiments, a combination therapy comprises active immunization with an active compound (e.g., a flu hemagglutinin (HA) polypeptide described herein, a nucleic acid encoding such a polypeptide(s), a vector (e.g., a viral vector, or a bacteria) containing or expressing such a polypeptide(s), cells stimulated with such a polypeptide(s)) that induces an immune response to one, two, three, or more HA subtypes in one HA group (e.g., Group 1) in combination with an active compound (e.g., a flu hemagglutinin (HA) polypeptide described herein, a nucleic acid encoding such a polypeptide(s), a vector (e.g., a viral vector, or a bacteria) containing or expressing such a polypeptide(s), cells stimulated with such a polypeptide(s)) that induces an immune response to one, two, three, or more HA subtypes in the other HA group (e.g., Group 2).

In some embodiments, a combination therapy comprises active immunization with an active compound (e.g., an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) that induces an immune response to one, two, three, or more NA subtypes in one NA group (e.g., Group 1) in combination with an active compound (e.g., an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) that induces an immune response to one, two, three, or more NA subtypes in the other NA group (e.g., Group 2).

In some embodiments, a combination therapy comprises active immunization with two or more flu hemagglutinin (HA) polypeptides and/or two or more influenza virus neuraminidase polypeptides described herein.

5.16.2 Patient Populations

In certain embodiments, an active compound (e.g., a flu hemagglutinin (HA) polypeptide (e.g., a chimeric influenza virus hemagglutinin polypeptide) or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein may be administered to a naïve subject, i.e., a subject that does not have a disease caused by influenza virus infection or has not been and is not currently infected with an influenza virus infection. In one embodiment, an active compound or composition described herein is administered to a naïve subject that is at risk of acquiring an influenza virus infection. In one embodiment, an active compound or composition described herein is administered to a subject that does not have a disease caused by the specific influenza virus, or has not been and is not infected with the specific influenza virus to which the flu hemagglutinin (HA) polypeptide and/or influenza virus neuraminidase polypeptide induces an immune response. An active compound or composition described herein may also be administered to a subject that is and/or has been infected with the influenza virus or another type, subtype or strain of the influenza virus to which the flu hemagglutinin (HA) polypeptide and/or influenza virus neuraminidase polypeptide induces an immune response.

In certain embodiments, an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is administered to a patient who has been diagnosed with an influenza virus infection. In some embodiments, an active compound or composition described herein is administered to a patient infected with an influenza virus before symptoms manifest or symptoms become severe (e.g., before the patient requires hospitalization). In some embodiments, an active compound or composition described herein is administered to a patient that is infected with or has been diagnosed with a different type of influenza virus than that of the influenza virus from which the head domain of the flu hemagglutinin (HA) polypeptide or the influenza virus neuraminidase polypeptide of the active compound or composition was derived.

In certain embodiments, an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is administered to a patient that may be or is infected with an influenza virus that belongs to the same HA group as that of the head domain of the flu hemagglutinin (HA) polypeptide and/or the same NA group as that of the influenza virus neuraminidase polypeptide. In certain embodiments, an active compound or composition described herein is administered to a patient that may be or is infected with an influenza virus of the same subtype as that of the head domain of the flu hemagglutinin (HA) polypeptide and/or as that of the influenza virus neuraminidase polypeptide.

In some embodiments, a subject to be administered an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is an animal. In certain embodiments, the animal is a bird. In certain embodiments, the animal is a canine. In certain embodiments, the animal is a feline. In certain embodiments, the animal is a horse. In certain embodiments, the animal is a cow. In certain embodiments, the animal is a mammal, e.g., a horse, swine, mouse, or primate, preferably a human.

In certain embodiments, a subject to be administered an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is a human adult. In certain embodiments, a subject to be administered an active compound or composition described herein is a human adult more than 50 years old. In certain embodiments, a subject to be administered an active compound or composition described herein is an elderly human subject.

In certain embodiments, a subject to be administered an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is a human child. In certain embodiments, a subject to be administered an active compound or composition described herein is a human infant. In certain embodiments, a subject to whom an active compound or composition described herein is administered is not an infant of less than 6 months old. In a specific embodiment, a subject to be administered an active compound or composition described herein is 2 years old or younger.

In specific embodiments, a subject to be administered an active compound (i.e., a flu hemagglutinin (HA) polypeptide or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is any infant or child more than 6 months of age and any adult over 50 years of age. In other embodiments, the subject is an individual who is pregnant. In another embodiment, the subject is an individual who may or will be pregnant during the influenza season (e.g., November to April). In specific embodiments, a subject to be administered an active compound or composition described herein is a woman who has given birth 1, 2, 3, 4, 5, 6, 7, or 8 weeks earlier.

In some embodiments, the human subject to be administered an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is any individual at increased risk of influenza virus infection or disease resulting from influenza virus infection (e.g., an immunocompromised or immunodeficient individual). In some embodiments, the human subject to be administered an active compound or composition described herein is any individual in close contact with an individual with increased risk of influenza virus infection or disease resulting from influenza virus infection (e.g., immunocompromised or immunosuppressed individuals).

In some embodiments, the human subject to be administered an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is an individual affected by any condition that increases susceptibility to influenza virus infection or complications or disease resulting from influenza virus infection. In other embodiments, an active compound or composition described herein is administered to a subject in which an influenza virus infection has the potential to increase complications of another condition that the individual is affected by, or for which they are at risk. In particular embodiments, such conditions that increase susceptibility to influenza virus complications or for which influenza virus increases complications associated with the condition are, e.g., conditions that affect the lung, such as cystic fibrosis, emphysema, asthma, or bacterial infections (e.g., infections caused by *Haemophilus influenzae, Streptococcus pneumoniae, Legionella pneumophila*, and *Chlamydia trachomatus*); cardiovascular disease (e.g., congenital heart disease, congestive heart failure, and coronary artery disease); endocrine disorders (e.g., diabetes), neurological and neuron-developmental conditions (e.g., disorders of the brain, the spinal cord, the peripheral nerve, and muscle (such as cerebral palsy, epilepsy (seizure disorders), stroke, intellectual disability (e.g., mental retardation), muscular dystrophy, and spinal cord injury)).

In some embodiments, the human subject to be administered an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is an individual that resides in a group home, such as a nursing home. In some embodiments, the human subject to be administered an active compound or composition described herein works in, or spends a significant amount of time in, a group home, e.g., a nursing home. In some embodiments, the human subject to be administered an active compound or composition described herein is a health care worker (e.g., a doctor or nurse). In some embodiments, the human subject to be administered an active compound or composition described herein is a smoker. In a specific embodiment, the human subject to be administered an active compound or composition described herein is immunocompromised or immunosuppressed.

In addition, subjects at increased risk of developing complications from influenza who may be administered an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein include: any individual who can transmit influenza viruses to those at high risk for complications, such as, e.g., members of households with high-risk individuals, including households that will include infants younger than 6 months, individuals coming into contact with infants less than 6 months of age, or individuals who will come into contact with individuals who live in nursing homes or other long-term care facilities; individuals with long-term disorders of the lungs, heart, or circulation; individuals with metabolic diseases (e.g., diabetes); individuals with kidney disorders; individuals with blood disorders (including anemia or sickle cell disease); individuals with weakened immune systems (including immunosuppression caused by medications, malignancies such as cancer, organ transplant, or HIV infection); children who receive long-term aspirin therapy (and therefore have a higher chance of developing Reye syndrome if infected with influenza).

In other embodiments, subjects for administration of an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein include healthy individuals six months of age or older, who: plan to travel to foreign countries and areas where flu outbreaks may be occurring, such, e.g., as the tropics and the Southern Hemisphere from April through September; travel as a part of large organized tourist groups that may include persons from areas of the world where influenza viruses are circulating; attend school or college and reside in dormitories, or reside in institutional settings; or wish to reduce their risk of becoming ill with influenza.

In some embodiments, a subject for whom administration of an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition described herein is contraindicated include any individual for whom influenza vaccination is contraindicated, such as: infants younger than six months of age; and individuals who have had an anaphylactic reaction (allergic reactions that cause difficulty breathing, which is often followed by shock) to eggs, egg products, or other components used in the production of the immunogenic formulation. In certain embodiments, when administration of an active compound or composition described herein is contraindicated due to one or more components used in the production of the immunogenic formulation (e.g., due to the presence of egg or egg products), the active compound or composition may be produced in a manner that does not include the component that causes the administration of an active compound or composition to be contraindicated (e.g., the active compound or composition may be produced without the use of eggs or egg products).

In some embodiments, it may be advisable not to administer a live virus vaccine to one or more of the following patient populations: elderly humans; infants younger than 6 months old; pregnant individuals; infants under the age of 1 years old; children under the age of 2 years old; children under the age of 3 years old; children under the age of 4 years old; children under the age of 5 years old; adults under the age of 20 years old; adults under the age of 25 years old; adults under the age of 30 years old; adults under the age of 35 years old; adults under the age of 40 years old; adults under the age of 45 years old; adults under the age of 50 years old; elderly humans over the age of 70 years old; elderly humans over the age of 75 years old; elderly humans over the age of 80 years old; elderly humans over the age of 85 years old; elderly humans over the age of 90 years old; elderly humans over the age of 95 years old; children and adolescents (2-17 years of age) receiving aspirin or aspirin-containing medications, because of the complications associated with aspirin and wild-type influenza virus infections in this age group; individuals with a history of asthma or other reactive airway diseases; individuals with chronic underlying medical conditions that may predispose them to severe influenza infections; individuals with a history of Guillain-Barre syndrome; individuals with acute serious illness with fever; or individuals who are moderately or severely ill. For such individuals, administration of inactivated virus vaccines, split virus vaccines, subunit vaccines, virosomes, virus-like particles or the non-viral vectors described herein may be preferred. In certain embodiments, subjects preferably administered a live virus vaccine may include healthy children and adolescents, ages 2-17 years, and healthy adults, ages 18-49.

In certain embodiments, an immunogenic formulation comprising a live virus vector is not given concurrently with other live-virus vaccines.

5.17 Modes of Administration 5.17.1 Routes of Delivery

An active compound (e.g., a flu hemagglutinin (HA) polypeptide and/or an influenza virus neuraminidase polypeptide described herein (e.g., a chimeric influenza virus hemagglutinin polypeptide), a nucleic acid encoding such a polypeptide(s), a vector (e.g., a viral vector, or a bacteria) containing or expressing such a polypeptide(s), cells stimulated with such a polypeptide(s)) or composition described herein may be delivered to a subject by a variety of routes. These include, but are not limited to, intranasal, intratracheal, oral, intradermal, intramuscular, intraperitoneal, transdermal, intravenous, conjunctival and subcutaneous routes. In some embodiments, a composition is formulated for topical administration, for example, for application to the skin. In specific embodiments, the route of administration is nasal, e.g., as part of a nasal spray. In certain embodiments, a composition is formulated for intramuscular administration. In some embodiments, a composition is formulated for subcutaneous administration. In certain embodiments, a composition is not formulated for administration by injection. In specific embodiments for live virus vaccines, the vaccine is formulated for administration by a route other than injection.

In cases where the antigen is a viral vector, a virus-like particle vector, or a bacterial vector, for example, it may be preferable to introduce an immunogenic composition via the natural route of infection of the backbone virus or bacteria from which the vector was derived. Alternatively, it may be preferable to introduce a flu hemagglutinin (HA) polypeptide or an influenza virus neuraminidase polypeptide via the natural route of infection of the influenza virus from which polypeptide is derived. The ability of an antigen, particularly a viral vector, to induce a vigorous secretory and cellular immune response can be used advantageously. For example, infection of the respiratory tract by a viral vector may induce a strong secretory immune response, for example in the urogenital system, with concomitant protection against an influenza virus. In addition, in a preferred embodiment it may be desirable to introduce the pharmaceutical compositions into the lungs by any suitable route. Pulmonary administration can also be employed, e.g., by use of an inhaler or nebulizer, and formulation with an aerosolizing agent for use as a spray.

In a specific embodiment, a subunit vaccine is administered intramuscularly. In another embodiment, a live influenza virus vaccine is administered intranasally. In another embodiment, an inactivated influenza virus vaccine, or a split influenza virus vaccine is administered intramuscularly. In another embodiment, a virus-like particle or composition thereof is administered intramuscularly.

In some embodiments, cells stimulated with a flu hemagglutinin (HA) polypeptide or an influenza virus neuraminidase polypeptide described herein in vitro may be introduced (or re-introduced) into a subject using techniques known to one of skill in the art. In some embodiments, the cells can be introduced into the dermis, under the dermis, or into the peripheral blood stream. In some embodiments, the cells introduced into a subject are preferably cells derived from that subject, to avoid an adverse immune response. In other embodiments, cells also can be used that are derived from a donor host having a similar immune background. Other cells also can be used, including those designed to avoid an adverse immunogenic response.

5.17.2 Dosage and Frequency of Administration

The amount of an active compound (e.g., a flu hemagglutinin (HA) polypeptide and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition which will be effective in the treatment and/or prevention of an influenza virus infection or an influenza virus disease will depend on the nature of the disease, and can be determined by standard clinical techniques.

The precise dose to be employed in the formulation will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, health), whether the patient is human or an animal, other medications administered, and whether treatment is prophylactic or therapeutic. Usually, the patient is a human but nonhuman mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Exemplary doses for nucleic acids encoding a flu hemagglutinin (HA) polypeptide or an influenza virus neuraminidase polypeptide described herein range from about 10 ng to 1 g, 100 ng to 100 mg, 1 µg to 10 mg, or 30-300 µg nucleic acid, e.g., DNA, per patient.

In certain embodiments, exemplary doses for a flu hemagglutinin (HA) polypeptide described herein (e.g., as provided in split virus vaccines and subunit vaccines) range from about 5 µg to 100 mg, 15 µg to 50 mg, 15 µg to 25 mg, 15 µg to 10 mg, 15 µg to 5 mg, 15 µg to 1 mg, 15 µg to 100 µg, 15 µg to 75 µg, 5 µg to 50 µg, 10 µg to 50 µg, 15 µg to 45 µg, 20 µg to 40 or 25 to 35 µg per kilogram of the patient. In certain embodiments, exemplary doses for an influenza neuraminidase polypeptide described herein (e.g., as provided in split virus vaccines and subunit vaccines) range from about 0.1 µg to 20 µg, 1 µg to 15 µg, 5 µg to 10 µg, 0.5

µg to 20 µg, 0.5 µg to 15 µg, or 0.5 µg to 10 µg per kilogram of the patient. In other embodiments, exemplary doses for flu hemagglutinin (HA) polypeptide range from about 1 µg to about 50 mg, about 5 µg to about 50 mg, about 1 µg to about 100 mg, about 5 µg to about 100 mg, about 15 µg to about 50 mg, about 15 µg to about 25 mg, about 15 µg to about 10 mg, about 15 µg to about 5 mg, about 15 µg to about 1 mg, about 15 µg to about 100 µg, about 15 µg to about 75 µg, about 5 µg to about 50 µg, about 10 µg to about 50 µg, about 15 µg to about 45 µg, about 20 µg to about 40 µg, or about 25 to about 35 µg of flu hemagglutinin (HA) polypeptide per kilogram of the patient and exemplary doses for influenza virus neuraminidase polypeptide range from about 0.1 µg to about 20 µg, about 1 µg to about 15 µg, about 5 µg to about 10 µg, about 0.5 µg to about 20 µg, about 0.5 µg to about 15 µg, or about 0.5 µg to about 10 µg of influenza virus neuraminidase polypeptide per kilogram of the patient, and can be administered to a subject once, twice, three or more times with intervals as often as needed.

Doses for infectious viral vectors may vary from 10-100, or more, virions per dose. In some embodiments, suitable dosages of a virus vector are $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and can be administered to a subject once, twice, three or more times with intervals as often as needed.

In certain embodiments, exemplary doses for VLPs range from about 0.01 µg to about 100 mg, about 0.1 µg to about 100 mg, about 5 µg to about 100 mg, about 15 µg to about 50 mg, about 15 µg to about 25 mg, about 15 µg to about 10 mg, about 15 µg to about 5 mg, about 15 µg to about 1 mg, about 15 µg to about 100 µg, about 15 µg to about 75 µg, about 5 µg to about 50 µg, about 10 µg to about 50 µg, about 15 µg to about 45m, about 20 µg to about 40 µg, or about 25 to about 35 µg per kilogram of the patient.

In one embodiment, an inactivated vaccine is formulated such that it contains about 5 µg to about 50m, about 10 µg to about 50m, about 15 µg to about 100m, about 15 µg to about 75m, about 15 µg to about 50m, about 15 µg to about 30m, about 20 µg to about 50 µg, about 25 µg to about 40m, about 25 µg to about 35 µg of a flu hemagglutinin (HA) polypeptide or an influenza virus neuraminidase polypeptide.

In certain embodiments, an active compound, e.g., a flu hemagglutinin (HA) polypeptide or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s), or composition is administered to a subject once as a single dose.

In certain embodiments, an active compound or composition is administered to a subject as a single dose followed by a second dose 3 to 6 weeks later. In certain embodiments, an active compound or composition is administered to a subject as a single dose followed by a second dose 3 to 6 weeks later, which is followed by administration of a third dose 3 to 6 weeks later. In certain embodiments, the second and/or third administrations may utilize a different active compound or composition. In accordance with these embodiments, booster inoculations may be administered to the subject at 3 to 6 week intervals following the second inoculation. In certain embodiments, an active compound or composition is administered to a subject as a single dose followed by a second dose 3 to 6 months later. In certain embodiments, an active compound or composition is administered to a subject as a single dose followed by a second dose 3 to 6 months later, which is followed by administration of a third dose 3 to 6 months later. In certain embodiments, the second and/or third administrations may utilize a different active compound or composition. In accordance with these embodiments, booster inoculations may be administered to the subject at 3 to 6 month intervals following the second inoculation.

In certain embodiments, the booster inoculations may utilize a different active compound or composition. In certain embodiments, the first (priming) administration comprises a full-length hemagglutinin or fragment thereof (or a nucleic acid encoding the same) and/or an influenza virus neuraminidase polypeptide and the second (booster) administration comprises administration of a flu hemagglutinin (HA) polypeptide described herein and/or an influenza virus neuraminidase polypeptide described herein (or a nucleic acid encoding the same, a VLP comprising the same, or a virus or bacteria expressing the same). In some embodiments, the administration of the same active compound or composition may be repeated and the administrations may be separated by at least 1 day, 2 days, 3 days, 5 days, 10 days, 15 days, 30 days, 45 days, 2 months, 75 days, 3 months, or at least 6 months. In certain embodiments, an active compound or composition is administered to a subject as a single dose once per year.

In specific embodiments for administration to children, two doses of an active compound (e.g., a flu hemagglutinin (HA) polypeptide described herein and/or an influenza virus neuraminidase polypeptide described herein, a nucleic acid encoding such a polypeptide(s), a vector (e.g., a viral vector, or a bacteria) containing or expressing such a polypeptide(s), cells stimulated with such a polypeptide(s)) or composition, given at least one month apart, are administered to a child. In specific embodiments for administration to adults, a single dose is given. In another embodiment, two doses of an active compound or composition, given at least one month apart, are administered to an adult. In another embodiment, a young child (six months to nine years old) may be administered an active compound or composition for the first time in two doses given one month apart. In a particular embodiment, a child who received only one dose in their first year of vaccination should receive two doses in the following year. In some embodiments, two doses administered 4 weeks apart are preferred for children 2-8 years of age who are administered an influenza vaccine, e.g., an immunogenic formulation described herein, for the first time. In certain embodiments, for children 6-35 months of age, a half dose (0.25 ml) may be preferred, in contrast to 0.5 ml which may be preferred for subjects over three years of age.

In a specific embodiment, for administration to human infants, two doses of flu hemagglutinin (HA) polypeptides described herein (see Section 5.1, infra) or a composition thereof and/or one or more of the nucleic acids, vectors, VLPs, or virosomes described herein, are administered to an infant, wherein the influenza virus hemagglutinin head domain of the flu hemagglutinin (HA) polypeptide used in the first dose is from a different strain or subtype than the influenza virus hemagglutinin head domain of the flu hemagglutinin (HA) polypeptide used in the second dose. The first and second administrations may be separated by at least 1 day, 2 days, 3 days, 5 days, 10 days, 15 days, 30 days, 45 days, 2 months, 75 days, 3 months, or at least 6 months.

In a specific embodiment, for administration to human infants, three doses of flu hemagglutinin (HA) polypeptides described herein (see Section 5.1, infra) or a composition thereof and/or one or more of the nucleic acids, vectors, VLPs, or virosomes described herein, are administered to an infant, wherein the influenza virus hemagglutinin head domains of the flu hemagglutinin (HA) polypeptides used in the first, second, and third doses are from different strains or subtypes of influenza virus. The first, second, and third administrations may be separated by at least 1 day, 2 days, 3 days, 5 days, 10 days, 15 days, 30 days, 45 days, 2 months, 75 days, 3 months, or at least 6 months.

In particular embodiments, an active compound (e.g., a flu hemagglutinin (HA) polypeptide described herein and/or an influenza virus neuraminidase polypeptide, a nucleic acid encoding such a polypeptide(s), a vector (e.g., a viral vector, or a bacteria) containing or expressing such a polypeptide(s), cells stimulated with such a polypeptide(s)) or composition is administered to a subject in the fall or winter, i.e., prior to or during the influenza season in each hemisphere. In one embodiment, children are administered their first dose early in the season, e.g., late September or early October in the Northern hemisphere, so that the second dose can be given prior to the peak of the influenza season.

For passive immunization with an antibody, the dosage ranges from about 0.0001 to 100 mg/kg, and more usually 0.01 to 5 mg/kg, of the patient body weight. For example, dosages can be 1 mg/kg body weight or 10 mg/kg body weight or within the range of 1-10 mg/kg or in other words, 70 mg or 700 mg or within the range of 70-700 mg, respectively, for a 70 kg patient. An exemplary treatment regime entails administration once per every two weeks or once a month or once every 3 to 6 months for a period of one year or over several years, or over several year-intervals. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to the flu hemagglutinin (HA) polypeptide and/or to the influenza virus neuraminidase polypeptide in the patient.

5.18 Biological Assays 5.18.1 Assays for Testing Activity of Chimeric Influenza Virus Hemagglutinin Polypeptides and/or Influenza Virus Neuraminidase Polypeptides Assays for testing the expression of a flu hemagglutinin (HA) polypeptide and/or an influenza virus neuraminidase polypeptide in a vector disclosed herein may be conducted using any assay known in the art. For example, an assay for incorporation into a viral vector comprises growing the virus as described in this section or Sections 5.8 or 5.9, purifying the viral particles by centrifugation through a sucrose cushion, and subsequent analysis for flu hemagglutinin (HA) polypeptide and/or influenza virus neuraminidase polypeptide expression by an immunoassay, such as Western blotting, using methods well known in the art. Methods for determining whether a hemagglutinin polypeptide is chimeric are known to those of skill in the art (see, e.g., the Examples 3 and 4 of International Publication No. WO 2013/043729, which is incorporated herein by reference in its entirety).

In one embodiment, a flu hemagglutinin (HA) polypeptide disclosed herein and/or an influenza virus neuraminidase polypeptide is assayed for proper folding and functionality by testing its ability to bind specifically to a neutralizing antibody directed to an influenza virus hemagglutinin polypeptide, such as the stalk region of the polypeptide, and/or and influenza virus neuraminidase polypeptide, respectively, using any assay for antibody-antigen interaction known in the art. Neutralizing antibodies for use in such assays include, for example, the neutralizing antibodies described in Ekiert et al., 2009, Science Express, 26 Feb. 2009; Kashyap et al., 2008, Proc Natl Acad Sci USA 105: 5986-5991; Sui et al. 2009, Nature Structural and Molecular Biology, 16:265-273; Wang et al., 2010, PLOS Pathogens 6(2):1-9; U.S. Pat. Nos. 5,589,174, 5,631,350, 6,337,070, and 6,720,409; International Application No. PCT/US2007/068983 published as International Publication No. WO 2007/134237; International Application No. PCT/US2008/075998 published as International Publication No. WO 2009/036157; International Application No. PCT/EP2007/059356 published as International Publication No. WO 2008/028946; and International Application No. PCT/US2008/085876 published as International Publication No. WO 2009/079259. These antibodies include CR6261, CR6325, CR6329, CR6307, CR6323, 2A, D7, D8, F10, G17, H40, A66, D80, E88, E90, H98, C179 (FERM BP-4517), AI3C (FERM BP-4516), among others.

In another embodiment, a flu hemagglutinin (HA) polypeptide and/or an influenza virus neuraminidase polypeptide disclosed herein is assayed for proper folding by determination of the structure or conformation of the flu hemagglutinin (HA) polypeptide and/or influenza virus neuraminidase polypeptide, respectively, using any method known in the art such as, e.g., NMR, X-ray crystallographic methods, or secondary structure prediction methods, e.g., circular dichroism.

5.18.2 Assays for Testing Activity of Antibodies Generated Using Chimeric Influenza Virus Hemagglutinin Polypeptides or Influenza Virus Neuraminidase Polypeptides Antibodies described herein may be characterized in a variety of ways known to one of skill in the art (e.g. ELISA, Surface Plasmon resonance display (BIAcore), Western blot, immunofluorescence, immunostaining and/or microneutralization assays). In some embodiments, antibodies are assayed for the ability to specifically bind to an influenza virus neuraminidase polypeptide, a vector comprising said influenza virus neuraminidase polypeptide, flu hemagglutinin (HA) polypeptide, and/or a vector comprising said flu hemagglutinin (HA) polypeptide. In some embodiments, antibodies are assayed for the ability to specifically bind to influenza virus neuraminidase polypeptide, or a vector comprising said polypeptide. In some embodiments, antibodies are assayed for the ability to specifically bind to a flu hemagglutinin (HA) polypeptide, or a vector comprising said polypeptide. Such an assay may be performed in solution (e.g., Houghten, 1992, Bio/Techniques 13:412 421), on beads (Lam, 1991, Nature 354:82 84), on chips (Fodor, 1993, Nature 364:555 556), on bacteria (U.S. Pat. No. 5,223,409), on spores (U.S. Pat. Nos. 5,571,698; 5,403, 484; and 5,223,409), on plasmids (Cull et al., 1992, Proc. Natl. Acad. Sci. USA 89:1865 1869) or on phage (Scott and Smith, 1990, Science 249:386 390; Cwirla et al., 1990, Proc. Natl. Acad. Sci. USA 87:6378 6382; and Felici, 1991, J. Mol. Biol. 222:301 310) (each of these references is incorporated herein in its entirety by reference).

Specific binding of an antibody to the influenza virus neuraminidase polypeptide and/or to the flu hemagglutinin (HA) polypeptide and cross-reactivity with other antigens can be assessed by any method known in the art. Specific binding of an antibody to the influenza virus neuraminidase polypeptide and cross-reactivity with other antigens can be assessed by any method known in the art. Specific binding of an antibody to the flu hemagglutinin (HA) polypeptide and cross-reactivity with other antigens can be assessed by any method known in the art. Immunoassays which can be used to analyze specific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety).

The binding affinity of an antibody to a flu hemagglutinin (HA) polypeptide and/or to an influenza virus neuraminidase polypeptide and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody for a flu hemagglutinin (HA) polypeptide and/or for an influenza virus neuraminidase polypeptide and the binding off-rates can be determined from the data by Scatchard plot analysis. Competition with a second antibody can also be determined using radioimmunoassays. In this case, a flu hemagglutinin (HA) polypeptide and/or an influenza virus neuraminidase polypeptide is incubated with the test antibody conjugated to a labeled compound (e.g., $^3$H or $^{125}$I) in the presence of increasing amounts of an unlabeled second antibody.

In certain embodiments, antibody binding affinity and rate constants are measured using the KinExA 3000 System (Sapidyne Instruments, Boise, Id.). In some embodiments, surface plasmon resonance (e.g., BIAcore kinetic) analysis is used to determine the binding on and off rates of the antibodies to an influenza virus hemagglutinin polypeptide. BIAcore kinetic analysis comprises analyzing the binding and dissociation of a flu hemagglutinin (HA) polypeptide and/or an influenza virus neuraminidase polypeptide from chips with immobilized antibodies to a flu hemagglutinin (HA) polypeptide and/or to an influenza virus neuraminidase polypeptide, respectively, on their surface. A typical BIAcore kinetic study involves the injection of 250 µL of an antibody reagent (mAb, Fab) at varying concentration in HBS buffer containing 0.005% Tween-20 over a sensor chip surface, onto which has been immobilized the flu hemagglutinin (HA) polypeptide and/or the influenza virus neuraminidase polypeptide. The flow rate is maintained constant at 75 µL/min. Dissociation data is collected for 15 min or longer as necessary. Following each injection/dissociation cycle, the bound antibody is removed from the influenza virus hemagglutinin polypeptide surface using brief, 1 min pulses of dilute acid, typically 10-100 mM HCl, though other regenerants are employed as the circumstances warrant. More specifically, for measurement of the rates of association, $k_{on}$, and dissociation, $k_{off}$, the polypeptide is directly immobilized onto the sensor chip surface through the use of standard amine coupling chemistries, namely the EDC/NHS method (EDC=N-diethylaminopropyl)-carbodiimide). Briefly, a 5-100 nM solution of the polypeptide in 10 mM NaOAc, pH 4 or pH 5 is prepared and passed over the EDC/NHS-activated surface until approximately 30-50 RU's worth of polypeptide are immobilized. Following this, the unreacted active esters are "capped" off with an injection of 1M Et-NH$_2$. A blank surface, containing no polypeptide, is prepared under identical immobilization conditions for reference purposes. Once an appropriate surface has been prepared, a suitable dilution series of each one of the antibody reagents is prepared in HBS/Tween-20, and passed over both the polypeptide and reference cell surfaces, which are connected in series. The range of antibody concentrations that are prepared varies, depending on what the equilibrium binding constant, $K_D$, is estimated to be. As described above, the bound antibody is removed after each injection/dissociation cycle using an appropriate regenerant.

The neutralizing activity of an antibody can be determined utilizing any assay known to one skilled in the art. Antibodies described herein can be assayed for their ability to inhibit the binding of an influenza virus, or any other composition comprising a flu hemagglutinin (HA) polypeptide and/or an influenza virus neuraminidase polypeptide (e.g., a VLP, liposome, or detergent extract), to its host cell receptor (i.e., sialic acid) using techniques known to those of skill in the art. For example, cells expressing influenza virus receptors can be contacted with a composition comprising a flu hemagglutinin (HA) polypeptide and/or an influenza virus neuraminidase polypeptide in the presence or absence of the antibody and the ability of the antibody to inhibit the antigen's binding can measured by, for example, flow cytometry or a scintillation assay. The composition comprising a flu hemagglutinin (HA) polypeptide and/or an influenza virus neuraminidase polypeptide or the antibody can be labeled with a detectable compound such as a radioactive label (e.g., $^{32}$P, $^{35}$S, and $^{125}$I) or a fluorescent label (e.g., fluorescein isothiocyanate, rhodamine, phycoerythrin, phycocyanin, allophycocyanin, o-phthaldehyde and fluorescamine) to enable detection of an interaction between the composition comprising a flu hemagglutinin (HA) polypeptide and/or influenza virus neuraminidase polypeptide and a cell receptor. Alternatively, the ability of antibodies to inhibit a flu hemagglutinin (HA) polypeptide and/or an influenza virus neuraminidase polypeptide from binding to its receptor can be determined in cell-free assays. For example, a composition comprising an influenza virus hemagglutinin polypeptide and/or an influenza virus neuraminidase polypeptide can be contacted with an antibody and the ability of the antibody to inhibit the composition comprising a flu hemagglutinin (HA) polypeptide and/or an influenza virus neuraminidase polypeptide from binding to a cell receptor can be determined. In a specific embodiment, the antibody is immobilized on a solid support and the composition comprising an influenza virus hemagglutinin polypeptide and/or an influenza virus neuraminidase polypeptide is labeled with a detectable compound. Alternatively, a composition comprising a flu hemagglutinin (HA) polypeptide and/or an influenza virus neuraminidase polypeptide is immobilized on a solid support and the antibody is labeled with a detectable compound. In certain embodiments, the ability of an antibody to inhibit a flu hemagglutinin (HA) polypeptide and/or an influenza virus neuraminidase polypeptide from binding to a cell receptor is determined by assessing the percentage of binding inhibition of the antibody relative to a control (e.g., an antibody known to inhibit the flu hemagglutinin (HA) polypeptide and/or an influenza virus neuraminidase polypeptide from binding to the cell receptor).

In other embodiments, an antibody suitable for use in the methods described herein does not inhibit influenza virus receptor binding, yet is still found to be neutralizing in an assay described herein. In some embodiments, an antibody suitable for use in accordance with the methods described herein reduces or inhibits virus-host membrane fusion in an assay known in the art or described herein.

In one embodiment, virus-host membrane fusion is assayed in an in vitro assay using an influenza virus containing a reporter and a host cell capable of being infected with the virus. An antibody inhibits fusion if reporter activity is inhibited or reduced compared to a negative control (e.g., reporter activity in the presence of a control antibody or in the absence of antibody).

In one embodiment, virus-host membrane fusion is detected using a model system of cell fusion. In an exemplary cell fusion assay, cells (e.g., HeLa cells) are transfected with a plasmid encoding a flu hemagglutinin (HA) polypeptide and contacted and exposed to a buffer that allows the flu hemagglutinin (HA) polypeptide fusion function (e.g., pH 5.0 buffer) in the presence of an antibody. An antibody is neutralizing if it reduces or inhibits syncytia formation compared to a negative control (e.g., syncytia formation in the presence of a control antibody or in the absence of antibody).

In other embodiments, virus-host membrane fusion is assayed using an in vitro liposome-based assay. In an exemplary assay, the host cell receptor is reconstituted into liposomes containing one half of a reporter. A flu hemagglutinin (HA) polypeptide is reconstituted into another set of liposomes containing another half of a reporter. When the two liposome populations are mixed together, fusion is detected by reconstitution of the reporter, for example, an enzymatic reaction that can be detected colorimetrically. The antibody inhibits fusion if reporter activity is reduced or inhibited compared to reporter activity in an assay conducted in the absence of antibody or in the presence of a control antibody. In certain embodiments, the ability of an antibody to inhibit fusion is determined by assessing the percentage of fusion in the presence of the antibody relative to the percentage of fusion in the presence a control.

5.18.3 Assays for Testing Activity of Stimulated Cells

Cells stimulated in accordance with the methods described herein may be analyzed, for example, for integration, transcription and/or expression of the polynucleotide or gene(s) of interest, the number of copies of the gene integrated, and the location of the integration. Such analysis may be carried out at any time and may be carried out by any methods known in the art. In other embodiments, successful stimulation of the target cell with an influenza virus neuraminidase (NA) polypeptide described herein and/or a flu hemagglutinin (HA) polypeptide described herein is determined by detecting production of neutralizing antibodies against the influenza virus neuraminidase (NA) polypeptide and/or the flu hemagglutinin (HA) polypeptide, respectively, using methods known in the art or described herein. In other embodiments, successful stimulation of the target cell with an influenza virus neuraminidase (NA) polypeptide described herein is determined by detecting production of neutralizing antibodies against the influenza virus neuraminidase (NA) polypeptide using methods known in the art or described herein. In other embodiments, successful stimulation of the target cell with a flu hemagglutinin (HA) polypeptide described herein is determined by detecting production of neutralizing antibodies against the flu hemagglutinin (HA) polypeptide using methods known in the art or described herein.

In certain embodiments, subjects in which the stimulated cells, e.g., DCs, are administered can be analyzed for location of the cells, expression of a vector-delivered polynucleotide or gene encoding the influenza virus neuraminidase (NA) polypeptide described herein and/or the flu hemagglutinin (HA) polypeptide described herein, stimulation of an immune response (e.g., production of neutralizing antibodies against the influenza virus neuraminidase (NA) polypeptide described herein and/or the flu hemagglutinin (HA) polypeptide described herein, respectively), and/or monitored for symptoms associated with influenza virus infection or a disease associated therewith by any methods known in the art or described herein. In certain embodiments, subjects in which the stimulated cells, e.g., DCs, are administered can be analyzed for location of the cells, expression of a vector-delivered polynucleotide or gene encoding the influenza virus neuraminidase (NA) polypeptide, stimulation of an immune response (e.g., production of neutralizing antibodies against the influenza virus neuraminidase (NA) polypeptide), and/or monitored for symptoms associated with influenza virus infection or a disease associated therewith by any methods known in the art or described herein. In certain embodiments, subjects in which the stimulated cells, e.g., DCs, are administered can be analyzed for location of the cells, expression of a vector-delivered polynucleotide or gene encoding the flu hemagglutinin (HA) polypeptide, stimulation of an immune response (e.g., production of neutralizing antibodies against the flu hemagglutinin (HA) polypeptide), and/or monitored for symptoms associated with influenza virus infection or a disease associated therewith by any methods known in the art or described herein.

Reporter assays can be used to determine the specificity of the targeting of the influenza virus neuraminidase (NA) polypeptide and/or flu hemagglutinin (HA) polypeptide. For example, a mixed population of bone marrow cells can be obtained from a subject and cultured in vitro. The influenza virus neuraminidase (NA) polypeptide and/or the flu hemagglutinin (HA) polypeptide can be administered to the mixed population of bone marrow cells, and expression of a reporter gene associated with the influenza virus neuraminidase (NA) polypeptide and/or the flu hemagglutinin (HA) polypeptide can be assayed in the cultured cells. In some embodiments, at least about 50%, more preferably at least about 60%, 70%, 80% or 90%, still more preferably at least about 95% of stimulated cells in the mixed cell population are dendritic cells.

5.18.4 Antiviral Activity Assays

Antibodies described herein or compositions thereof can be assessed in vitro for antiviral activity. In one embodiment, the antibodies or compositions thereof are tested in vitro for their effect on growth of an influenza virus. Growth of influenza virus can be assessed by any method known in the art or described herein (e.g. in cell culture). In a specific embodiment, cells are infected at a MOI of 0.0005 and 0.001, 0.001 and 0.01, 0.01 and 0.1, 0.1 and 1, or 1 and 10, or a MOI of 0.0005, 0.001, 0.005, 0.01, 0.05, 0.1, 0.5, 1, 5 or 10 and incubated with serum free media supplemented. Viral titers are determined in the supernatant by hemagglutinin plaques or any other viral assay described herein. Cells in which viral titers can be assessed include, but are not limited to, EFK-2 cells, Vero cells, MDCK cells, primary human umbilical vein endothelial cells (HUVEC), H292 human epithelial cell line and HeLa cells. In vitro assays include those that measure altered viral replication (as determined, e.g., by plaque formation) or the production of viral proteins (as determined, e.g., by Western blot analysis) or viral RNAs (as determined, e.g., by RT-PCR or northern blot analysis) in cultured cells in vitro using methods which are well known in the art or described herein.

In one non-limiting example, a monolayer of the target mammalian cell line is infected with different amounts (e.g., multiplicity of 3 plaque forming units (pfu) or 5 pfu) of virus (e.g., influenza) and subsequently cultured in the presence or absence of various dilutions of antibodies (e.g., 0.1 µg/ml, 1 µg/ml, 5 µg/ml, or 10 µg/ml). Infected cultures are harvested 48 hours or 72 hours post infection and titered by standard plaque assays known in the art on the appropriate target cell line (e.g., Vero cells).

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments an inhibitor results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs in influenza virus titer in the subject. The log-reduction in Influenza virus titer may be as compared to a negative control, as compared to another treatment, or as compared to the titer in the patient prior to antibody administration.

In a non-limiting example of a hemagglutination assay, cells are contacted with an antibody and are concurrently or subsequently infected with the virus (e.g., at an MOI of 1) and the virus is incubated under conditions to permit virus replication (e.g., 20-24 hours). The antibodies are preferably present throughout the course of infection. Viral replication and release of viral particles is then determined by hemagglutination assays using 0.5% chicken red blood cells. See, e.g., Kashyap et al., PNAS USA 105: 5986-5991. In some embodiments, a compound is considered an inhibitor of viral replication if it reduces viral replication by at least 2 wells of HA, which equals approximately a 75% reduction in viral titer. In specific embodiments, an inhibitor reduces viral titer in this assay by 50% or more, by 55% or more, by 60% or more, by 65% or more, by 70% or more, by 75% or more, by 80% or more, by 85% or more, by 90% or more, or by 95% or more. In other specific embodiments an inhibitor results in a reduction of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs in influenza virus titer in the subject. The log-reduction in Influenza virus titer may be as compared to a negative control, as compared to another treatment, or as compared to the titer in the patient prior to antibody administration.

In a non-limiting example of a neuraminidase inhibition assay (NI assay), flat-bottom nonsterile Immulon 4 HBX 96-well plates (Thermo Scientific) are coated (pH 9.4 carbonate-bicarbonate coating buffer) with 150 µl of fetuin (Sigma) at a concentration of 50 µg/µl and refrigerated at 4° C. overnight. The coating buffer is discarded and wells are blocked for 1 hour at room temperature with 200 µl blocking solution (PBS containing 5% BSA). While plates are blocking, virus stocks are serially diluted 1:2 in a separate sterile flat-bottom 96-well tissue culture plate (Sigma) using PBS containing 1% BSA. After blocking for 1 hour, the plates are washed 6 times using TPBS (225 µl/well). After the last wash, plates are forcefully tapped on clean paper towels to ensure no residual wash buffer remained (this technique was repeated for all subsequent wash steps). 100 µl of the viral dilutions are transferred in parallel to the fetuin coated plates, after which the plates are incubated at 37° C. for 2 hours. Plates are again washed 6 times using TPBS (225 µl/well) and a secondary solution of peanut agglutinin (PNA) conjugated to HRP (PNA-HRP; Sigma) at a concentration of 5 µg/ml in PBS was added to the plates (100 µl/well). After a 1.75 hour incubation in the dark, plates are again washed 6 times using TBPS (225 µl/well) and developed with 100 µl SigmaFast OPD. The developing process is stopped after 7 min with 3M HCl and the reaction was read at an absorbance of 490 nm with a synergy H1 hybrid multimode microplate reader (BioTek). In order to determine the optimal concentration of virus to use for subsequent NI assays, ELISA data from the NA assay for each virus is plotted in GraphPad Prism 6 software and fit to a non-linear curve. In this way, an EC50-like value can be obtained. Two times this concentration (2EC50) is used for subsequent NI assays. To perform NI assays, ELISA plates are coated and blocked in an identical fashion to the NA assay. While plates are blocking, mouse serum samples are serially diluted 1:2 in separate sterile flat-bottom 96-well tissue culture plates using PBS, starting with a 1:50 dilution, and ensuring that the final volume in all wells was 75 µl. Virus stocks are diluted to the determined, optimal 2EC50 concentrations in PBS containing 1% BSA. After virus is added to the antibody plates (75 µl/well), the plates re briefly tapped (for mixing) and incubated at room temperature for 1 h 40 min. Immediately before the incubation time expires, the blocked plates are washed 6 times using TPBS (225 µl/well). 100 µl of the virus/serum mixture is transferred in parallel to the fetuin coated plates, after which the plates are incubated at 37° C. for 2 h. Plates are again washed 6 times using TPBS (225 µl/well) and a secondary solution of peanut agglutinin (PNA) conjugated to HRP (PNA-HRP; Sigma) at a concentration of 5 µg/ml in PBS was added to the plates (100 µl/well). Values obtained from the plate reader re divided by the average of virus only control wells and then multiplied by a factor of 100 to obtain the NA activity. Percent inhibition is calculated by subtracting the NA activity from 100.

5.18.5 Cytotoxicity Assays

Many assays well-known in the art can be used to assess viability of cells (infected or uninfected) or cell lines following exposure to an active compound or a composition thereof and, thus, determine the cytotoxicity of the compound or composition. For example, cell proliferation can be assayed by measuring Bromodeoxyuridine (BrdU) incorporation (See, e.g., Hoshino et al., 1986, Int. J. Cancer 38, 369;

Campana et al., 1988, J. Immunol. Meth. 107:79), (3H) thymidine incorporation (See, e.g., Chen, J., 1996, Oncogene 13:1395-403; Jeoung, J., 1995, J. Biol. Chem. 270: 18367 73), by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes. These changes are given a designation of T (100% toxic), PVH (partially toxic—very heavy—80%), PH (partially toxic—heavy—60%), P (partially toxic—40%), Ps (partially toxic—slight—20%), or 0 (no toxicity—0%), conforming to the degree of cytotoxicity seen. A 50% cell inhibitory (cytotoxic) concentration ($IC_{50}$) is determined by regression analysis of these data.

In a specific embodiment, the cells used in the cytotoxicity assay are animal cells, including primary cells and cell lines. In some embodiments, the cells are human cells. In certain embodiments, cytotoxicity is assessed in one or more of the following cell lines: U937, a human monocyte cell line; primary peripheral blood mononuclear cells (PBMC); Huh7, a human hepatoblastoma cell line; 293T, a human embryonic kidney cell line; and THP-1, monocyte cells. In certain embodiments, cytotoxicity is assessed in one or more of the following cell lines: MDCK, MEF, Huh 7.5, Detroit, or human tracheobronchial epithelial (HTBE) cells.

Active compounds or compositions thereof can be tested for in vivo toxicity in animal models. For example, animal models, described herein and/or others known in the art, used to test the activities of active compounds can also be used to determine the in vivo toxicity of these compounds. For example, animals are administered a range of concentrations of active compounds. Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an active compound can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An active compound that exhibits large therapeutic indices is preferred. While an active compound that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of an active compound for use in humans. The dosage of such agents lies preferably within a range of circulating concentrations that include the $ED_{50}$ with little or no toxicity. The dosage may vary within this range depending upon the dosage form employed and the route of administration utilized. For any active compound used in a method described herein, the effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high-performance liquid chromatography. Additional information concerning dosage determination is provided herein.

Further, any assays known to those skilled in the art can be used to evaluate the prophylactic and/or therapeutic utility of the active compounds and compositions described herein, for example, by measuring viral infection or a condition or symptoms associated therewith.

5.18.6 In Vivo Antiviral Activity

Active compounds and compositions thereof are preferably assayed in vivo for the desired therapeutic or prophylactic activity prior to use in humans. For example, in vivo assays can be used to determine whether it is preferable to administer an active compound or composition thereof and/ or another therapy. For example, to assess the use of an active compound or composition thereof to prevent an influenza virus disease, the composition can be administered before the animal is infected with influenza virus. Alternatively, or in addition, an active compound or composition thereof can be administered to the animal at the same time that the animal is infected with influenza virus. To assess the use of an active compound or composition thereof to treat an influenza virus infection or disease associated therewith, the compound or composition may be administered after infecting the animal with influenza virus. In a specific embodiment, an active compound or composition thereof is administered to the animal more than one time.

Active compounds and compositions thereof can be tested for antiviral activity in animal model systems including, but are not limited to, rats, mice, chicken, cows, monkeys, pigs, ferrets, goats, sheep, dogs, rabbits, guinea pigs, etc. In a specific embodiment, active compounds and compositions thereof are tested in a mouse model system. Such model systems are widely used and well-known to the skilled artisan. In a specific embodiment, active compounds and compositions thereof are tested in a mouse model system. Non-limiting examples of animal models for influenza virus are provided in this section.

In general, animals are infected with influenza virus and concurrently or subsequently treated with an active compound or composition thereof, or placebo. Alternatively, animals are treated with an active compound or composition thereof or placebo and subsequently infected with influenza virus. Samples obtained from these animals (e.g., serum, urine, sputum, semen, saliva, plasma, or tissue sample) can be tested for viral replication via well known methods in the art, e.g., those that measure altered viral titers (as determined, e.g., by plaque formation), the production of viral proteins (as determined, e.g., by Western blot, ELISA, or flow cytometry analysis) or the production of viral nucleic acids (as determined, e.g., by RT-PCR or northern blot analysis). For quantitation of virus in tissue samples, tissue samples are homogenized in phosphate-buffered saline (PBS), and dilutions of clarified homogenates are adsorbed for 1 hour at 37° C. onto monolayers of cells (e.g., Vero, CEF or MDCK cells). In other assays, histopathologic evaluations are performed after infection, preferably evaluations of the organ(s) the virus is known to target for infection. Virus immunohistochemistry can be performed using a viral-specific monoclonal antibody.

The effect of an active compound or composition thereof on the virulence of a virus can also be determined using in vivo assays in which the titer of the virus in an infected subject administered an active compound or composition thereof, the length of survival of an infected subject administered an active compound or composition thereof, the immune response in an infected subject administered an active compound or composition thereof, the number, duration and/or severity of the symptoms in an infected subject administered an active compound or composition thereof, and/or the time period before onset of one or more symptoms in an infected subject administered an active compound or composition thereof, is assessed. Techniques known to one of skill in the art can be used to measure such effects. In certain embodiments, an active compound or composition thereof results in a 0.5 fold, 1 fold, 2 fold, 4 fold, 6 fold, 8 fold, 10 fold, 15 fold, 20 fold, 25 fold, 50 fold, 75 fold, 100 fold, 125 fold, 150 fold, 175 fold, 200 fold, 300 fold, 400 fold, 500 fold, 750 fold, or 1,000 fold or greater reduction in titer of influenza virus relative to an untreated subject. In some embodiments, an active compound or composition thereof results in a reduction in titer of influenza virus relative to an untreated subject of approximately 1 log or more, approximately 2 logs or more, approximately 3 logs or more, approximately 4 logs or more, approximately 5 logs or more, approximately 6 logs or more, approximately 7 logs or more, approximately 8 logs or more, approximately 9 logs or more, approximately 10 logs or more, 1 to 3 logs, 1 to 5 logs, 1 to 8 logs, 1 to 9 logs, 2 to 10 logs, 2 to 5 logs, 2 to 7 logs, 2 logs to 8 logs, 2 to 9 logs, 2 to 10 logs 3 to 5 logs, 3 to 7 logs, 3 to 8 logs, 3 to 9 logs, 4 to 6 logs, 4 to 8 logs, 4 to 9 logs, 5 to 6 logs, 5 to 7 logs, 5 to 8 logs, 5 to 9 logs, 6 to 7 logs, 6 to 8 logs, 6 to 9 logs, 7 to 8 logs, 7 to 9 logs, or 8 to 9 logs.

Influenza virus animal models, such as ferret, mouse, guinea pig, squirrel monkey, macaque, and chicken, developed for use to test antiviral agents against influenza virus have been described. See, e.g., Sidwell et al., Antiviral Res., 2000, 48:1-16; Lowen A. C. et al. PNAS., 2006, 103: 9988-92; and McCauley et al., Antiviral Res., 1995, 27:179-186 and Rimmelzwann et al., Avian Diseases, 2003, 47:931-933. For mouse models of influenza, non-limiting examples of parameters that can be used to assay antiviral activity of active compounds administered to the influenza-infected mice include pneumonia-associated death, serum al-acid glycoprotein increase, animal weight, lung virus assayed by hemagglutinin, lung virus assayed by plaque assays, and histopathological change in the lung. Statistical analysis is carried out to calculate significance (e.g., a P value of 0.05 or less).

In other assays, histopathologic evaluations are performed after infection of an animal model subject. Nasal turbinates and trachea may be examined for epithelial changes and subepithelial inflammation. The lungs may be examined for bronchiolar epithelial changes and peribronchiolar inflammation in large, medium, and small or terminal bronchioles. The alveoli are also evaluated for inflammatory changes. The medium bronchioles are graded on a scale of 0 to 3+ as follows: 0 (normal: lined by medium to tall columnar epithelial cells with ciliated apical borders and basal pseudostratified nuclei; minimal inflammation); 1+(epithelial layer columnar and even in outline with only slightly increased proliferation; cilia still visible on many cells); 2+(prominent changes in the epithelial layer ranging from attenuation to marked proliferation; cells disorganized and layer outline irregular at the luminal border); 3+(epithelial layer markedly disrupted and disorganized with necrotic cells visible in the lumen; some bronchioles attenuated and others in marked reactive proliferation).

The trachea is graded on a scale of 0 to 2.5+ as follows: 0 (normal: Lined by medium to tall columnar epithelial cells with ciliated apical border, nuclei basal and pseudostratified. Cytoplasm evident between apical border and nucleus. Occasional small focus with squamous cells); 1+ (focal squamous metaplasia of the epithelial layer); 2+ (diffuse squamous metaplasia of much of the epithelial layer, cilia may be evident focally); 2.5+ (diffuse squamous metaplasia with very few cilia evident).

Virus immunohistochemistry is performed using a viral-specific monoclonal antibody (e.g. NP-, N- or HN-specific monoclonal antibodies). Staining is graded 0 to 3+ as follows: 0 (no infected cells); 0.5+ (few infected cells); 1+ (few infected cells, as widely separated individual cells); 1.5+ (few infected cells, as widely separated singles and in small clusters); 2+ (moderate numbers of infected cells, usually affecting clusters of adjacent cells in portions of the epithelial layer lining bronchioles, or in small sublobular foci in alveoli); 3+ (numerous infected cells, affecting most of the epithelial layer in bronchioles, or widespread in large sublobular foci in alveoli).

In one example, the ability to induce lung lesions and cause infection in an animal model of virus infection is compared using wild-type virus and mock virus. Lung lesions can be assessed as a percentage of lung lobes that are healthy by visual inspection. Animals are euthanized 5 days p.i. by intravenous administration of pentobarbital, and their lungs are removed in toto. The percentage of the surface of each pulmonary lobe that is affected by macroscopic lesions is estimated visually. The percentages are averaged to obtain a mean value for the 7 pulmonary lobes of each animal. In other assays, nasal swabs can be tested to determine virus burden or titer. Nasal swabs can be taken during necropsy to determine viral burden post-infection.

In one embodiment, virus is quantified in tissue samples. For example, tissue samples are homogenized in phosphate-buffered saline (PBS), and dilutions of clarified homogenates adsorbed for 1 h at 37° C. onto monolayers of cells (e.g., MDCK cells). Infected monolayers are then overlaid with a solution of minimal essential medium containing 0.1% bovine serum albumin (BSA), 0.01% DEAE-dextran, 0.1% $NaHCO_3$, and 1% agar. Plates are incubated 2 to 3 days until plaques could be visualized. Tissue culture infectious dose (TCID) assays to titrate virus from PR8-infected samples are carried out as follows. Confluent monolayers of cells (e.g., MDCK cells) in 96-well plates are incubated with log dilutions of clarified tissue homogenates in media. Two to three days after inoculation, 0.05-ml aliquots from each well are assessed for viral growth by hemagglutination assay (HA assay).

5.18.6.1.1 Assays in Humans

In one embodiment, an active compound or composition thereof that modulates replication of an influenza virus are assessed in infected human subjects. In accordance with this embodiment, an active compound or composition thereof is administered to the human subject, and the effect of the active compound or composition on viral replication is determined by, e.g., analyzing the level of the virus or viral nucleic acids in a biological sample (e.g., serum or plasma). An active compound or composition thereof that alters virus replication can be identified by comparing the level of virus replication in a subject or group of subjects treated with a control to that in a subject or group of subjects treated with an active compound or composition thereof. Alternatively, alterations in viral replication can be identified by comparing the level of the virus replication in a subject or group of subjects before and after the administration of an active compound or composition thereof. Techniques known to those of skill in the art can be used to obtain the biological sample and analyze the mRNA or protein expression.

In another embodiment, the effect of an active compound or composition thereof on the severity of one or more symptoms associated with an influenza virus infection/disease are assessed in an infected subject. In accordance with this embodiment, an active compound or composition thereof or a control is administered to a human subject suffering from influenza virus infection and the effect of the active compound or composition on one or more symptoms of the virus infection is determined. An active compound or composition thereof that reduces one or more symptoms can be identified by comparing the subjects treated with a control to the subjects treated with the active compound or composition. In a specific embodiment, administration of an active compound (e.g., a flu hemagglutinin (HA) polypeptide described herein and/or an influenza virus neuraminidase (NA) polypeptide described herein) or composition thereof results in a decrease in hospitalization of a human or population of humans caused by influenza virus disease or infection. In another specific embodiment, administration of an active compound (e.g., a flu hemagglutinin (HA) polypeptide described herein and/or an influenza virus neuraminidase (NA) polypeptide described herein) or composition thereof results in a reduced need for respiratory/breathing assistance in a human or population of humans with an influenza virus disease or infection. In another specific embodiment, administration of an active compound (e.g., a flu hemagglutinin (HA) polypeptide described herein and/or an influenza virus neuraminidase (NA) polypeptide described herein) or composition thereof results in a reduced length of illness of a human or population of humans with an influenza virus disease or infection. In another specific embodiment, administration of an active compound (e.g., a flu hemagglutinin (HA) polypeptide described herein and/or an influenza virus neuraminidase (NA) polypeptide described herein) or composition thereof results in improvement (e.g., an increase) in lung volume as assessed by, e.g., whole body or lung plethysmography. In another embodiment, an active compound or composition thereof is administered to a healthy human subject and monitored for efficacy as a vaccine (e.g., the subject is monitored for the onset of symptoms of influenza virus infection; the ability of influenza virus to infect the subject; and/or a reduction in/absence of one or more symptoms associated with influenza virus infection). Techniques known to physicians familiar with infectious diseases can be used to determine whether an active compound or composition thereof reduces one or more symptoms associated with the influenza virus disease.

5.19 Assessment of Antibodies in a Subject

In another aspect, an influenza virus neuraminidase (NA) polypeptide described herein, or virus expressing an influenza virus neuraminidase (NA) polypeptide described herein, can be used to assess the antibody response of a subject (e.g., a naive subject or an immunized/vaccinated subject) or a population of subjects to an influenza virus neuraminidase polypeptide described herein (see, e.g., the Examples in Section 6 of International Publication No. WO 2013/043729, which is incorporated herein by reference in its entirety). In specific embodiments, an influenza virus neuraminidase (NA) polypeptide or a virus expressing an influenza virus neuraminidase (NA) polypeptide can be used to assess the presence of conserved epitope-specific antibodies in the subject or population of subjects. In specific embodiments, the influenza virus NA polypeptide comprises one or more modified glycosylations sites in the NA stem domain and/or one or more non-naturally occurring glycosylation sites in the globular head domain.

In a specific embodiment, the antibody response of a subject or a population of subjects that has been an immunized/vaccinated with an influenza virus neuraminidase polypeptide described herein, or a virus expressing an influenza virus neuraminidase (NA) polypeptide described herein, is assessed to identify the types of NA-specific antibodies in the subject or population of subjects. Such an assessment may allow for the identification surrogate markers/endpoints important in determining the clinical response to administration of an influenza virus NA polypeptide(s) described herein, or a virus expressing an influenza virus NA polypeptide(s) described herein. In such an approach, a biological sample, e.g., blood, from the subject or population of subjects may be isolated and tested directly for the presence of antibodies, or may be processed (e.g., to obtain sera) and subsequently tested for the presence of antibodies.

In another specific embodiment, the antibody profile of a naive subject (i.e., a subject that has not been immunized/vaccinated with an influenza virus NA polypeptide(s) described herein or a virus expressing an influenza virus NA polypeptide(s)) or a population of naive subjects is assessed to determine whether said subject or population of subjects possesses NA globular head-specific and/or NA stem specific antibodies against various influenza virus strains or subtypes. Such an assessment may allow for the generation of an influenza virus neuraminidase (NA) polypeptide described herein, or viruses expressing an influenza virus neuraminidase (NA) polypeptide described herein, that are suitable for administration to said subject or population of subjects, e.g., influenza virus neuraminidase (NA) polypeptides comprising a globular head or stalk domain to which said subject or population of subjects is naive (does not have antibodies against). Such an assessment may determine an immunization strategy for the patient.

In another aspect, a flu hemagglutinin (HA) polypeptide (e.g., a chimeric influenza virus hemagglutinin polypeptide) described herein, or virus expressing a flu hemagglutinin (HA) polypeptide (e.g., a chimeric influenza virus hemagglutinin polypeptide) described herein, can be used to assess the antibody response of a subject (e.g., a naive subject or an immunized/vaccinated subject) or a population of subjects to an influenza virus hemagglutinin polypeptide (e.g., a flu HA polypeptide, such as a chimeric influenza virus hemagglutinin polypeptide (see, e.g., Example 8 of International Publication No. WO 2013/043729, which is incorporated herein by reference in its entirety). In specific embodiments, a chimeric influenza virus hemagglutinin polypeptide or a virus expressing a chimeric influenza virus hemagglutinin polypeptide can be used to assess the presence of stem-specific antibodies in the subject or population of subjects. In specific embodiments, the chimeric influenza virus HA polypeptide comprises one or more modified glycosylations sites in the HA stem domain and/or one or more non-naturally occurring glycosylation sites in the globular head domain.

In a specific embodiment, the antibody response of a subject or a population of subjects that has been an immunized/vaccinated with an influenza virus hemagglutinin polypeptide (e.g., a flu hemagglutinin (HA) polypeptide(s) described herein, such as a chimeric influenza virus hemagglutinin polypeptide, or a virus expressing a flu hemagglutinin (HA) polypeptide described herein, such as a chimeric influenza virus hemagglutinin polypeptide), is assessed to identify the types of stalk-specific antibodies in the subject or population of subjects. Such an assessment may allow for the identification surrogate markers/endpoints important in determining the clinical response to administration of an influenza virus HA polypeptide(s) (e.g., a flu HA polypeptide such as a chimeric influenza virus hemagglutinin polypeptide) described herein, or a virus expressing a influenza virus HA polypeptide(s) (e.g., a flu HA polypeptide such as a chimeric influenza virus hemagglutinin polypeptide) described herein. In such an approach, a biological sample, e.g., blood, from the subject or population of subjects may be isolated and tested directly for the presence of antibodies, or may be processed (e.g., to obtain sera) and subsequently tested for the presence of antibodies.

In another specific embodiment, the antibody profile of a naive subject (i.e., a subject that has not been immunized/vaccinated with an influenza virus HA polypeptide(s) (e.g., a flu HA polypeptide such as a chimeric influenza virus hemagglutinin polypeptide described herein), or a virus expressing an influenza virus HA polypeptide polypeptide(s) (e.g., a flu HA polypeptide such as a chimeric influenza virus hemagglutinin polypeptide)) or a population of naive subjects is assessed to determine whether said subject or population of subjects possesses globular head-specific and/or stem specific antibodies against various influenza virus strains or subtypes. Such an assessment may allow for the generation of a flu hemagglutinin (HA) polypeptide (e.g., a chimeric influenza virus hemagglutinin polypeptide), or viruses expressing flu hemagglutinin (HA) polypeptide (e.g., a chimeric influenza virus hemagglutinin polypeptide), that are suitable for administration to said subject or population of subjects, e.g., flu hemagglutinin (HA) polypeptides, such as a chimeric influenza virus hemagglutinin polypeptide, comprising a head domain to which said subject or population of subjects is naive (does not have antibodies against). Such an assessment may determine an immunization strategy for the patient.

In another specific embodiment, provided herein is a method of assessing/detecting the presence of antibodies in a subject that are specific for a stem domain of a particular influenza virus strain or subtype comprising contacting in vitro a biological sample (e.g., blood, sera) from said subject with a chimeric influenza virus hemagglutinin polypeptide described herein, wherein said chimeric influenza virus hemagglutinin polypeptide comprises a stem domain from the strain or subtype of interest. See Examples 6-8 of International Publication No. WO 2013/043729, which is incorporated herein by reference in its entirety, for methods for assessing/detecting the presence of antibodies specific for a stem domain of a particular influenza virus strain or subtype. In another specific embodiment, provided herein is a method of assessing/detecting the presence of antibodies in a subject that are specific for a stem domain of a particular influenza virus strain or subtype comprising contacting in vitro a biological sample (e.g., blood, sera) from said subject with a virus expressing/containing a chimeric influenza virus hemagglutinin polypeptide described herein, wherein said chimeric influenza virus hemagglutinin polypeptide comprises a stem domain from the strain or subtype of interest.

In another aspect, a flu hemagglutinin (HA) polypeptide (e.g., a chimeric influenza virus hemagglutinin polypeptide) described herein, virus expressing a flu hemagglutinin (HA) polypeptide (e.g., a chimeric influenza virus hemagglutinin polypeptide) described herein, an influenza virus neuraminidase (NA) polypeptide described herein, virus expressing an influenza virus neuraminidase (NA) polypeptide described herein, or virus expressing a flu hemagglutinin (HA) polypeptide (e.g., a chimeric influenza virus hemagglutinin polypeptide) described herein and an influenza virus neuraminidase (NA) polypeptide described herein can be used to assess the antibody response of a subject (e.g., a naive subject or an immunized/vaccinated subject) or a population of subjects to an influenza virus hemagglutinin polypeptide (e.g., a flu HA polypeptide, such as a chimeric influenza virus hemagglutinin polypeptide (see, e.g., Example 8 of International Publication No. WO 2013/043729, which is incorporated herein by reference in its entirety) and/or to an influenza virus neuraminidase polypeptide. In specific embodiments, a chimeric influenza virus hemagglutinin polypeptide or a virus expressing a chimeric influenza virus hemagglutinin polypeptide can be used to assess the presence of stem-specific antibodies in the subject or population of subjects. In specific embodiments, the chimeric influenza virus HA polypeptide comprises one or more modified glycosylations sites in the HA stem domain and/or one or more non-naturally occurring glycosylation sites in the globular head domain. In specific embodiments, an influenza virus neuraminidase (NA) polypeptide or a virus expressing an influenza virus neuraminidase (NA) polypeptide can be used to assess the presence of conserved epitope-specific antibodies in the subject or population of subjects. In specific embodiments, the influenza virus NA polypeptide comprises one or more modified glycosylations sites in the NA stem domain and/or one or more non-naturally occurring glycosylation sites in the globular head domain.

In a specific embodiment, the antibody response of a subject or a population of subjects that has been an immunized/vaccinated with an influenza virus hemagglutinin polypeptide (e.g., a flu hemagglutinin (HA) polypeptide(s) described herein, such as a chimeric influenza virus hemagglutinin polypeptide, or a virus expressing a flu hemagglutinin (HA) polypeptide described herein, such as a chimeric influenza virus hemagglutinin polypeptide) and/or an influenza virus neuraminidase polypeptide described herein, is assessed to identify the types of HA stalk-specific antibodies in the subject or population of subjects and/or to identify the types of NA-specific antibodies in the subject or population of subjects. Such an assessment may allow for the identification surrogate markers/endpoints important in determining the clinical response to administration of an influenza virus HA polypeptide(s) (e.g., a flu HA polypeptide such as a chimeric influenza virus hemagglutinin polypeptide) described herein, a virus expressing an influenza virus HA polypeptide(s) (e.g., a flu HA polypeptide such as a chimeric influenza virus hemagglutinin polypeptide) described herein, an influenza virus NA polypeptide(s) described herein, a virus expressing an influenza virus NA polypeptide(s) described herein, or a virus expressing an influenza virus hemagglutinin polypeptide (e.g., a flu hemagglutinin (HA) polypeptide(s) described herein, such as a chimeric influenza virus hemagglutinin polypeptide) and an influenza virus NA polypeptide described herein. In such an approach, a biological sample, e.g., blood, from the subject or population of subjects may be isolated and tested directly for the presence of antibodies, or may be processed (e.g., to obtain sera) and subsequently tested for the presence of antibodies.

In another specific embodiment, the antibody profile of a naive subject (i.e., a subject that has not been immunized/vaccinated with an influenza virus HA polypeptide(s) (e.g., a flu HA polypeptide such as a chimeric influenza virus hemagglutinin polypeptide described herein), or a virus expressing an influenza virus HA polypeptide(s) (e.g., a flu HA polypeptide such as a chimeric influenza virus hemagglutinin polypeptide)) and/or with an influenza virus NA polypeptide(s) described herein, or a virus expressing an influenza virus NA polypeptide(s) described herein, and/or a virus expressing an influenza virus HA polypeptide(s) (e.g., a flu HA polypeptide such as a chimeric influenza virus hemagglutinin polypeptide described herein) and an influenza virus NA polypeptide(s) described herein, or a population of naive subjects is assessed to determine whether said subject or population of subjects possesses HA globular head-specific antibodies, HA stem-specific antibodies, NA globular head-specific antibodies, and/or NA stem-specific antibodies against various influenza virus strains or subtypes. Such an assessment may allow for the generation of a flu hemagglutinin (HA) polypeptide (e.g., a chimeric influenza virus hemagglutinin polypeptide), viruses expressing flu hemagglutinin (HA) polypeptide (e.g., a chimeric influenza virus hemagglutinin polypeptide), an influenza virus neuraminidase (NA) polypeptide, viruses expressing an influenza virus neuraminidase (NA) polypeptide, and/or viruses expressing flu hemagglutinin (HA) polypeptide (e.g., a chimeric influenza virus hemagglutinin polypeptide) and an influenza virus neuraminidase (NA) polypeptide that are suitable for administration to said subject or population of subjects, e.g., flu hemagglutinin (HA) polypeptides, such as a chimeric influenza virus hemagglutinin polypeptide, comprising a head domain to which said subject or population of subjects is naive (does not have antibodies against) and/or influenza virus neuraminidase (NA) polypeptide to which said subject or population of subjects is naive (does not have antibodies against). Such an assessment may determine an immunization strategy for the patient.

In another specific embodiment, provided herein is a method of assessing/detecting the presence of antibodies in a subject that are specific for an HA stem domain of a particular influenza virus strain or subtype and/or NA domain of a particular influenza virus strain or subtype comprising contacting in vitro a biological sample (e.g., blood, sera) from said subject with a chimeric influenza virus hemagglutinin polypeptide described herein, wherein said chimeric influenza virus hemagglutinin polypeptide comprises an HA stem domain from the strain or subtype of interest, and/or contacting in vitro a biological sample (e.g., blood, sera) from said subject with an influenza virus neuraminidase polypeptide described herein, wherein said influenza virus neuraminidase polypeptide comprises an NA stem domain from the strain or subtype of interest. See Examples 6-8 of International Publication No. WO 2013/043729, which is incorporated herein by reference in its entirety, for methods for assessing/detecting the presence of antibodies specific for a hemagluttinin stem domain of a particular influenza virus strain or subtype. In another specific embodiment, provided herein is a method of assessing/detecting the presence of antibodies in a subject that are specific for an HA stem domain of a particular influenza virus strain or subtype and/or for an NA domain of a particular influenza virus strain or subtype, comprising contacting in vitro a biological sample (e.g., blood, sera) from said subject with a virus expressing/containing a chimeric influenza virus hemagglutinin polypeptide described herein and/or an influenza virus neuraminidase polypeptide described herein, wherein said chimeric influenza virus hemagglutinin polypeptide comprises a stem domain from the strain or subtype of interest and wherein said influenza virus neuraminidase polypeptide comprises a domain from the strain or subtype of interest.

5.20 Kits

Provided herein is a pharmaceutical pack or kit comprising one or more containers filled with one or more of the ingredients of the pharmaceutical/immunogenic compositions described herein, such as one or more active compounds provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in accordance with the methods described herein. In one embodiment, a kit comprises an active compound described herein, preferably one or more flu hemagglutinin (HA) polypeptides (e.g., one or more chimeric influenza virus hemagglutinin polypeptides) and/or one or more influenza virus neuraminidase (NA) polypeptides, in one or more containers. In one embodiment, a kit comprises an active compound described herein, preferably one or more influenza virus neuraminidase (NA) polypeptides, in one or more containers. In one embodiment, a kit comprises an active compound described herein, preferably one or more flu hemagglutinin (HA) polypeptides (e.g., one or more chimeric influenza virus hemagglutinin polypeptides), in one or more containers. In certain embodiments, a kit comprises a vaccine described herein, e.g., a split virus vaccine, a subunit vaccine, an inactivated influenza virus vaccine, or a live influenza virus vaccine, wherein said vaccine comprises one or more flu hemagglutinin (HA) polypeptides described herein (e.g., one or more chimeric influenza virus hemagglutinin polypeptides) and/or one or more influenza virus neuraminidase (NA) polypeptides described herein. In certain embodiments, a kit comprises a vaccine described herein, e.g., a split virus vaccine, a subunit vaccine, an inactivated influenza virus vaccine, or a live influenza virus vaccine, wherein said vaccine comprises one or more influenza virus neuraminidase (NA) polypeptides described herein. In certain embodiments, a kit comprises a vaccine described herein, e.g., a split virus vaccine, a subunit vaccine, an inactivated influenza virus vaccine, or a live influenza virus vaccine, wherein said vaccine comprises one or more flu hemagglutinin (HA) polypeptides described herein (e.g., one or more chimeric influenza virus hemagglutinin polypeptides). In certain embodiments, a kit comprises a vaccine described herein, e.g., a split virus vaccine, a subunit vaccine, an inactivated influenza virus vaccine, or a live influenza virus vaccine, and one or more flu neuraminidase (NA) polypeptides described herein. In certain embodiments, a kit comprises a vaccine described herein, e.g., a split virus vaccine, a subunit vaccine, an inactivated influenza virus vaccine, or a live influenza virus vaccine, and one or more influenza virus neuraminidase (NA) polypeptides described herein, wherein said vaccine comprises one or more flu hemagglutinin (HA) polypeptides described herein (e.g., one or more chimeric influenza virus hemagglutinin polypeptides) and/or one or more influenza virus neuraminidase (NA) polypeptides described herein. In certain embodiments, a kit comprises a vaccine described herein, e.g., a split virus vaccine, a subunit vaccine, an inactivated influenza virus vaccine, or a live influenza virus vaccine, and one or more influenza virus neuraminidase (NA) polypeptides described herein, wherein said vaccine comprises one or more influenza virus neuraminidase (NA) polypeptides described herein. In certain embodiments, a kit comprises a vaccine described herein, e.g., a split virus vaccine, a subunit vaccine, an inactivated influenza virus vaccine, or a live influenza virus vaccine, and one or more influenza virus neuraminidase (NA) polypeptides described herein, wherein said vaccine comprises one or more flu hemagglutinin (HA) polypeptides described herein (e.g., one or more chimeric influenza virus hemagglutinin polypeptides). In a specific embodiment, provided herein are kits comprising a chimeric influenza virus hemagglutinin polypeptide described herein and/or an influenza virus neuraminidase polypeptide described herein and instructions for using the chimeric influenza virus hemagglutinin polypeptide and/or the influenza virus neuraminidase polypeptide described herein to assess the antibodies present in a subject. In a specific embodiment, provided herein are kits comprising an influenza virus neuraminidase polypeptide described herein and instructions for using the influenza virus neuraminidase polypeptide to assess the antibodies present in a subject. In a specific embodiment, provided herein are kits comprising a chimeric influenza virus hemagglutinin polypeptide described herein and instructions for using the chimeric influenza virus hemagglutinin polypeptide to assess the antibodies present in a subject.

6. EXAMPLES

6.1 Example 1

Vaccination with Adjuvanted Recombinant Neuraminidase Induces Broad Heterologous—but not Heterosubtypic—Cross-Protection Against Influenza Virus Infection in Mice 6.1.1 Introduction Despite the existence of vaccine prophylaxis and antiviral therapeutics, the influenza virus continues to have a detrimental impact on the morbidity and mortality of the human population, emphasizing the continued need for research in the field. While the majority of influenza vaccine strategies target the hemagglutinin—the immunodominant antigen on the surface of the influenza virion—antibodies against the viral neuraminidase have been correlated with less severe disease and decreased viral shedding in humans. Nevertheless, the amount of NA is not standardized in current seasonal vaccines, and the exact breadth of NA-based protection is unknown. Greater insight into the cross-protective potential of the influenza virus NA as a vaccine antigen may pave the way for the development of influenza vaccines of greater breadth and efficacy.

Seasonal influenza virus infections cause significant morbidity and mortality worldwide (1). If well matched to currently circulating strains, influenza virus vaccines are efficient tools in protecting the human population from influenza virus infection. Although effective, these vaccines have a suboptimal efficacy (74 percent) in healthy adults for well matched strains (2), and this value may drop sharply when the vaccine is mismatched (3). Furthermore, the seasonal vaccine is not protective against pandemic influenza viruses. Immune responses following vaccination with inactivated influenza virus are predominantly raised to the viral hemagglutinin (HA), the major glycoprotein on the surface of the influenza virion. The majority of antibodies are directed against the immunodominant globular head domain of the molecule (4-7). These antibodies are highly potent in inhibiting virus replication and are often strain specific. Thus, the main focus of influenza virus vaccine development, production, and efficacy testing is on the HA. Inactivated influenza virus vaccines (IIVs) are standardized based on their HA content and vaccine efficacy is measured based on the induction of hemagglutination-inhibiting antibodies (8). The second influenza surface glycoprotein, the neuraminidase (NA), has enzymatic activity that is crucial for the virus and is the target of small molecule NA inhibitors (9). While many studies propose the usefulness of NA as a vaccine antigen (10-19), the viral neuraminidase is mostly ignored in the context of influenza vaccine development, and the NA content of IIVs is not even measured.

6.1.2 Materials and Methods 6.1.2.1 Viruses and cells

Madin Darby Canine Kidney (MDCK) cells were grown in complete Dulbecco's modified Eagles medium (DMEM, Life Technologies) supplemented with antibiotics (100 units/ml of penicillin-100 μg/ml of streptomycin; Pen-Strep, Gibco) and 10% fetal bovine serum (FBS, Hyclone). Sf9 insect cells were grown in TNM-FH insect medium (Gemini Bioproducts) supplemented with antibiotics (Pen-Strep) and 10% FBS and High Five (BTI-TN-5B1-4, Vienna Institute of BioTechnology subclone (23)) cells were grown in serum free SFX-insect media (Hyclone) supplemented with antibiotics (Pen-Strep). Influenza viruses (A/Puerto Rico/8/34 (PR8; H1N1), X-31 (HK68/X-31; H3N2; PR8 internal genes and HA and NA from A/Hong Kong/1/68), A/Netherlands/602/09 (NL09; pandemic H1N1), X-79 (Phil82/X-79; H3N2; PR8 internal genes and HA and NA from A/Philippines/2/82), low pathogenicity A/Vietnam/1203/04 (VN04; H5N1; PR8 internal genes and HA and NA from A/Vietnam/1203/04 with polybasic cleavage site of the HA deleted), B/Victoria/2/87 (Vic87), B/Yamagata/16/88 (Yam88) and B/Malaysia/2506/04 (Mal04)) were grown in 8-10 day old embryonated chicken eggs and titered on MDCK cells in the presence of tosyl phenylalanyl chloromethyl ketone (TPCK) treated trypsin. For ELISAs influenza viruses were concentrated through a 30% buffered sucrose cushion by ultracentrifugation (Beckmann L7-65 Ultracentrifuge, SW-28 rotor, 25,000 rpm). Recombinant baculoviruses expressing neuraminidases were generated as described before and grown in Sf9 cells (24).

6.1.2.2 Recombinant Proteins

Recombinant neuraminidase proteins (PR8 N1, HK68 N2, A/Texas/91 N1, A/New Caledonia/20/99 N1, A/California/4/09 (Ca109) N1, A/Panama/2007/99 N2, Yam88 B NA, A/swine/Missouri/4296424/06 N3, A/mallard/Sweden/24/02 N4, A/mallard/Sweden/86/03 N5, A/mallard/Netherlands/1/99 N6, A/mallard/Interior Alaska/10BM01929/10 N7, A/mallard/Sweden/50/02 N8, and A/Anhui/1/13 (N9) were expressed in High Five cells and purified from cell culture supernatants as described before (24, 25). Briefly, cultures were infected with recombinant baculoviruses at a multiplicity of infection (MOI) of 10. Supernatants were then harvested by low speed centrifugation 72 hours post infection and were purified via Ni-NTA resin (Qiagen) using a published protocol (24).

6.1.2.3 Vaccination and Challenge Studies

Six- to eight-week old female BALB/c mice were used for all vaccination and challenge studies. For standard challenge experiments mice (n=5-10) were anesthetized (0.15 mg/kg ketamine and 0.03 mg/kg xylazine intraperitoneally) and received recombinant NA adjuvanted with polyI:C (5 µg rNA and 5 µg polyI:C in 50 µl of PBS intranasally (IN) plus 5 rNA and 5 µg polyI:C in 50 µl of PBS intramuscularly (IM)), bovine serum albumin (BSA) adjuvanted with polyI:C (negative control; 5 µg BSA and 5 µg polyI:C in 50 µl of PBS IN plus 5 ug BSA and 5 µg polyI:C in 50 µl of PBS IM), matched inactivated whole or split virus vaccines (positive control; 1 µg intramuscularly in 50 µl of PBS) and in most cases a mismatched rNA from a different subtype as additional negative control (5 µg rNA and 5 µg polyI:C in 50 µl of PBS IN plus 5 µg rNA and 5 µg polyI:C in 50 µl of PBS IM). A boost using the same formulations and routes was given three weeks post prime. Animals dedicated for IN versus IM experiments were either vaccinated twice with 5 µg of rNA plus 5 µg of polyI:C IN or IM at the same intervals and volumes as described above. Four weeks post boost animals were anesthetized and intranasally challenged with 10 (homologous) or 5 (heterologous) murine lethal doses 50 (mLD50) of virus in 50 µl of PBS. An exception was the Yam88 experiment where mice were challenged with a sublethal dose ($1.1 \times 10^6$ plaque forming units (PFU)) of virus due to the low pathogenicity of the isolate. Weight was monitored for a period of 14 days.

Animals for lung titer experiments were vaccinated via the IN and IM route as described above and lungs were harvested 3 and 6 days post challenge. Lungs were then homogenized using a BeadBlaster 24 (Benchmark) homogenizer and the virus lung titer was measured using a plaque assay in MDCK cells.

For the passive transfer experiments animals (recombinant HK68 N2, BSA and positive control groups) were anaesthetized and terminally bled. Serum was harvested and transferred into naive mice (200 µl per mouse, intraperitoneally, n=5 per group). Two hours post transfer the mice were then challenged with 5 mLD50 of X-31 virus as described above. Weight was monitored for a period of 14 days.

All animal procedures were performed in accordance with the Icahn School of Medicine at Mount Sinai Institutional Animal Care and Use Committee.

6.1.2.4 Human Sera

Human sera were obtained from a clinical trial performed at the University of Bergen, Norway with the 2004-2005 trivalent influenza vaccine Fluarix® vaccine (Glaxo-Smith-Kline) (A/Caledonia/20/99 (H1N1), A/Wyoming/3/03 (H3N2) and B/Jiangsu/10/03) (26). Serum samples were taken 14 days post vaccination. The trial was approved by the regional ethics committee (REK Vest, approval #170-04) and the Norwegian Medicines Agency.

6.1.2.5 Mouse Serum Preparation

Sera collected in all vaccination studies were stored long term at −20° C. until use. In all serological assays, serum samples from individual mice within an experimental group were pooled and inactivated by heating in a 56° C. water bath for 1 h.

6.1.2.6 Enzyme Linked Immunosorbent Assay (ELISA)

For mouse ELISAs, plates (Immulon 4 HBX, Thermo Scientific) were coated over night with 5 µg/ml (50 µl per well) of concentrated influenza virus in coating buffer (pH 9.4 carbonate-bicarbonate buffer) at 4° C. Plates were then blocked using 3% milk in PBS containing 0.1% Tween 20 (TPBS) for 1 hour at room temperature. Serum samples were diluted in 1:3 steps starting with a 1:100 dilution in 1% TPBS. Plates were then incubated with the serum samples for 1 hour at room temperature. After three washes with TPBS (3×100W/well) plates were incubated for another hour at RT with an anti-mouse HRP labeled antibody (1:3000, GE Healthcare) and developed using SigmaFast OPD (o-phenylenediamine dihydrochloride, 100 W per well, Sigma) after another round of extensive washing. Plates were developed for 10 minutes and stopped with 3 M hydrochloric acid (HCL) (50 µl/well) and read at OD490 on a Synergy 4 (BioTek) plate reader.

The procedure for human ELISAs was similar but the following modifications were made. Plates were coated with recombinant HA or NA (2 µg/ml, 50 µl per well) and blocking was performed in TPBS containing 3% goat serum and 0.5% milk (GM-TPBS). GM-TPBS was also used for making serum dilutions (1:2 steps starting with 1:100) and for diluting the secondary anti-human IgG horseradish peroxidase (HRP)-labeled secondary antibody (1:3000, Sigma). Endpoint titers were calculated using blank values plus three times their standard deviation as cut-off. Results are shown as fold-induction, which was calculated by dividing post-vaccination endpoint titers by pre-vaccination endpoint titers as described before (27).

Endpoint titer ELISAs were performed with mAb 4A5. A/Brisbane/10/10 (NIBSC#11/134) and A/Christchurch/16/10 (NIBSC#10/258) antigen preparations were purchased from the National Institute for Biological Standards and Control (NIBSC, Potters Bar, UK). FluLaval vaccine preparation was used as A/California/07/09 substrate. All other substrates were purified and concentrated viruses grown in house. As cutoff for the endpoint titer we used the average values from secondary antibody only control rows plus three times the standard deviation of these wells. The last 4A5 dilution that produced a value above the cutoff was determined to be the endpoint titer.

6.1.2.7 NA*Star Assay

The NA*Star assay (Applied Biosystems) was performed as described in the manufacturer's instructions. Briefly, recombinant NA was mixed with NA*Star assay buffer at a concentration of 1 µg/ml. The mix was then incubated at 37° C. for 15 minutes. Then 10 µl of NA*Star substrate diluted in NA*buffer was added and the mix was incubated at room temperature in the dark for 30 minutes. Shortly before reading out bioluminescence on a microplate reader (BioTek) 60 µl NA*Star accelerator was added to each well.

6.1.2.8 Enzyme Linked Lectin Assay (ELLA) to Determine Neuraminidase Inhibition In order to determine the ideal virus concentration to be used in the NI assay, NA assays were first performed for all virus stocks. In brief, flat-bottom nonsterile Immulon 4 HBX 96-well plates (Thermo Scientific) were coated (pH 9.4 carbonate-bicarbonate coating buffer) with 150 µl of fetuin (Sigma) at a concentration of 50 µg/µl and refrigerated at 4° C. overnight. The coating buffer was discarded and wells were blocked for 1 h at room temperature with 200 µl blocking solution (PBS containing 5% BSA). While plates were blocking, virus stocks were serially diluted 1:2 in a separate sterile flat-bottom 96-well tissue culture plate (Sigma) using PBS containing 1% BSA. Dilutions were made horizontally across the plate, starting with undiluted stock and ensuring that the final volume in all wells was 150 µl. After blocking for 1 h, the plates were washed 6 times using TPBS (225 µl/well). After the last wash, plates were forcefully tapped on clean paper towels to ensure no residual wash buffer remained (this technique was repeated for all subsequent wash steps). 100 μl of the viral dilutions were transferred in parallel to the fetuin coated plates, after which the plates are incubated at 37° C. for 2 h. Plates were again washed 6 times using TPBS (225 μl/well) and a secondary solution of peanut agglutinin (PNA) conjugated to HRP (PNA-HRP; Sigma) at a concentration of 5 μg/ml in PBS was added to the plates (100 μl/well). After a 1 h 45 min incubation in the dark, plates were again washed 6 times using TBPS (225 μl/well) and developed with 100 μl SigmaFast OPD. The developing process was stopped after 7 min with 3M HCl and the reaction was read at an absorbance of 490 nm with a synergy H1 hybrid multimode microplate reader (BioTek). In order to determine the optimal concentration of virus to use for subsequent NI assays, ELISA data from the NA assay for each virus was plotted in GraphPad Prism 6 software and fit to a non-linear curve. In this way, an EC50-like value could be obtained (in this case, the concentration of virus at which half the maximal OD reading was obtained). Two times this concentration (2EC50) was used for subsequent NI assays.

To perform NI assays, ELISA plates were coated and blocked in an identical fashion to the NA assay. While plates were blocking, mouse serum samples were serially diluted 1:2 in separate sterile flat-bottom 96-well tissue culture plates using PBS, starting with a 1:50 dilution, and ensuring that the final volume in all wells was 75 μl. Virus stocks were diluted to the determined, optimal 2EC50 concentrations in PBS containing 1% BSA. After virus was added to the antibody plates (75 μl/well), the plates were briefly tapped (for mixing) and incubated at room temperature for 1 h 40 min. Immediately before the incubation time expired, the blocked plates were washed 6 times using TPBS (225 μl/well). 100 μl of the virus/serum mixture was transferred in parallel to the fetuin coated plates, after which the plates were incubated at 37° C. for 2 h. Plates were again washed 6 times using TPBS (225 μl/well) and a secondary solution of peanut agglutinin (PNA) conjugated to HRP (PNA-HRP; Sigma) at a concentration of 5 μg/ml in PBS was added to the plates (100 μl/well). The rest of the NI assay protocol is identical to that of the NA assay. Values obtained from the plate reader were divided by the average of virus only control wells and then multiplied by a factor of 100 to obtain the NA activity. Percent inhibition was calculated by subtracting the NA activity from 100.

Western Blot and Quantitative Elisa Analysis

Four different brands of FDA-licensed influenza vaccines intended for use in the 2013-2014 flu season were obtained from either the Mount Sinai hospital pharmacy, local pharmacies, or directly from the manufacturer. The trade names of the vaccines (and their respective manufacturers, lot numbers, and included H1N1 strain names) were as follows: Fluvirin (Novartis Vaccines and Manufacturers, 13472P, A/Christchurch/16/2010), Flucelvax (Novartis Vaccines and Manufacturers, 161281, A/Brisbane/10/2010), Fluzone (Sanofi Pasteur, UH953AA, A/California/07/2009 X-179A), and FluLaval (ID Biomedical Corporation of Quebec, a subsidiary of GlaxoSmithKline, 597FZ, A/California/07/2009). All of the brands obtained are trivalent, egg-derived vaccines with the exception of Flucelvax, which is produced in a suspension MDCK cell line. Using a small initial volume of each vaccine, 5-fold serial dilutions were prepared in PBS, mixed with an equal volume of 2× Laemmli buffer with 2% beta-mercaptoethanol (BME), and heated for 30 minutes at 100° C. 12 μL of each dilution was loaded on polyacrylamide gels (5-20% gradient, Bio-Rad). As a standard control, equivalent-volume dilutions of recombinant, baculovirus-expressed, purified Cal09 N1, with a known starting concentration of 0.672 mg/mL (as measured by Bradford Protein Assay, Bio-Rad) were loaded on the same gel, adjacent to the vaccine dilutions (each unique vaccine was run on a separate gel, however). After transferring for 40 min at 0.11 A using a semidry transfer apparatus (Bio-Rad, Owl), blots were washed 3 times for 3 min in PBS (all subsequent wash steps were done in this way) and blocked with 3% milk in TBPS for 1 h at room temperature. Blocking solution was removed and a primary antibody solution of mAb 4A5 (1:3000 in 1% milk TBPS) was added to the blots in enough volume so they were completely submerged and blots were incubated for 1 h at room temperature. The mAb 4A5 is an antibody that specifically binds NA of 2009 pandemic H1N1 viruses. After removing the primary antibody solution and washing, blots were incubated for 1 h at room temperature with an anti-mouse HRP labeled antibody (1:6000, GE Healthcare). Secondary solution was removed, blots were washed, and developing solution was added (1 mL of Enhanced Luminol Reagent+1 mL of oxidizing agent; Western Lightning—ECL, PerkinElmer). After—30 seconds in the developing solution, blots were developed on standard autoradiography film (HyBlot Cl, Denville Scientific) using a 1 minute exposure time (Konika Minolta SRX-101A).

In order to approximately quantify the amount of Cal09 NA contained in vaccine formulations, flat-bottom nonsterile Immulon 4 HBX 96-well plates (Thermo Scientific) were coated with triplicate, serial 1:2 dilutions of each vaccine sample in coating buffer (see above), starting with a 1:2 dilution and diluting horizontally across the plate. As a standard, recombinant, baculovirus-expressed, purified Cal09 N1 was coated in an identical fashion, starting with a known concentration of 16 μg/ml. Plates were incubated at 4° C. overnight. The general mouse ELISA protocol (as detailed above) was performed, except the primary antibody used was mAb 4A5, added at a constant concentration of 3 μg/ml (in 3% milk TPBS, 100 μl/well). ELISA data was transferred to Microsoft Excel, the average of each triplicate reading was calculated, and the points were plotted (dilution vs. OD reading) in order to determine the portion of each sample curve that was most linear (using R-squared regression analysis). For the recombinant Cal09 curve, this best-fit linear equation was used to calculate the unknown N1 concentrations of the 4 vaccine formulations. The values were averaged and are reported in FIG. 7B.

6.1.3 Results 6.1.3.1 Expression of Recombinant NA Proteins

Influenza virus NA has been found to be immunosubdominant when administered in association with the influenza virus HA in animal models (28-30). Accordingly, baculovirus-expressed NA antigens were utilized to investigate the protective efficacy and breadth of divergent NAs. Recombinant NAs (rNAs) included an N-terminal hexahistidine-tag to facilitate purification, a tetramerization domain to guarantee optimal folding and are secreted into the cell supernatant allowing posttranslational modification to occur in the endoplasmic reticulum and in the Golgi-network (24, 25). All NAs were obtained at high purity and exhibited enzymatic activity (FIG. 15 and FIG. 16). Expression levels varied between approximately 0.1 and 5 mg/liter culture.

Figure 2B:
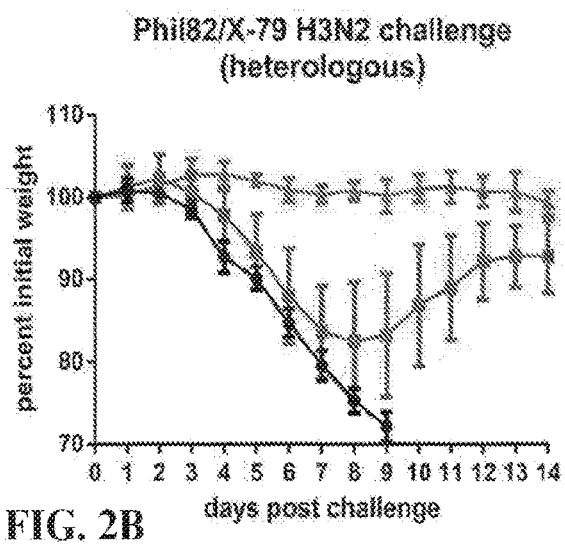
Figure 2C:
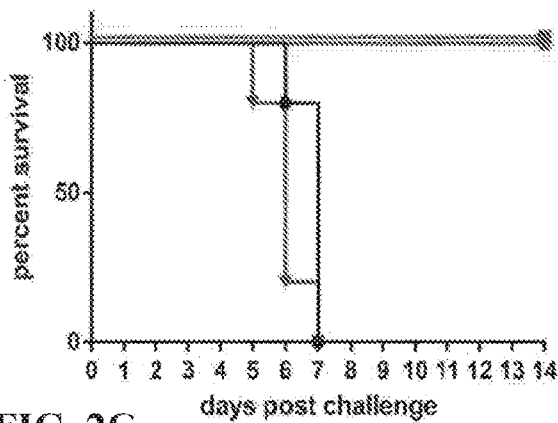

6.1.3.2 Recombinant Influenza Virus NA Immunogens Protect Mice from Homologous Virus Challenge To assess the protective efficacy of N1, N2 and B NAs, mice were vaccinated twice at a 3-week interval with N1 NA from PR8 or N2 NA from HK68 or B NA from Yam88. The vaccine was administered IM and IN (5 μg adjuvanted with 5 μg of polyI:C each) because the contribution of mucosal vs. systemic immunity for NA-based protection was unclear. Four weeks post-boost animals were challenged with 10 mLD50 of homologous virus or 1.1×10⁶ PFU for Yam88. Animals that received PR8 N1 were fully protected from weight loss and mortality comparable to the positive control animals, which received inactivated matched whole virus vaccine (FIG. 1A and FIG. 1D), while control animals vaccinated with BSA or rN2 lost weight rapidly and succumbed to infection by days 8 and 9 post infection, respectively. Similarly, animals vaccinated with HK68 N2 were completely protected from homologous lethal HK68/X-31 challenge while control animals (BSA and rN1 vaccinated) lost weight and succumbed to infection by day 7 (FIG. 2A and FIG. 2C). N2 vaccination significantly reduced virus infection in the lungs of these mice on day 3 post infection and only one out of five mice had detectable amounts of virus in the lungs on day 6 post infection (FIG. 3B). N2 vaccination did not induce sterilizing immunity—as did two vaccinations with inactivated homologous virus—but reduced lung titers 1,000 fold on day 3 and 100,000 fold on day 6 as compared to the BSA control group. Finally, vaccination with recombinant Yam88 influenza B NA protected completely against a non-lethal challenge with Yam88 while control animals (BSA and rN2 vaccinated) lost approximately 20% of their initial weight and had survival rates of only 80% (FIG. 4A and FIG. 4D) showing that influenza B NA is as protective as influenza A NA.

6.1.3.3 Protection is Mediated by NA-reactive Antibodies

Figure 2D:
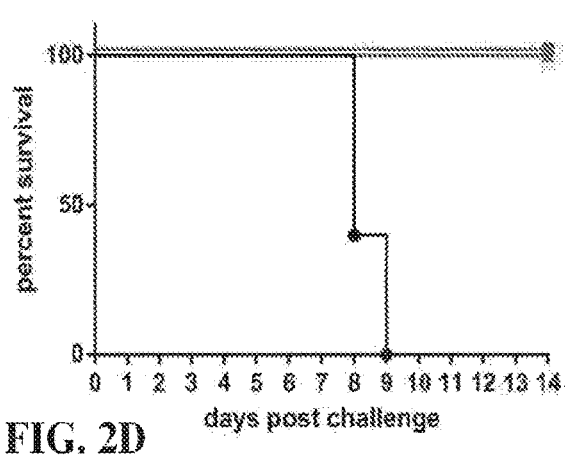
Figures 2E, 2F:
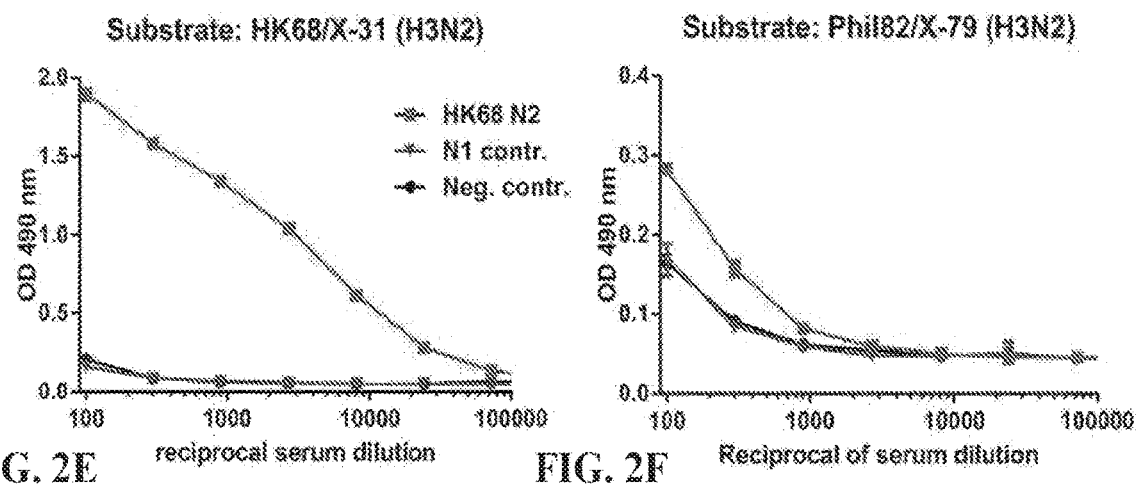
Figures 2G, 2H:
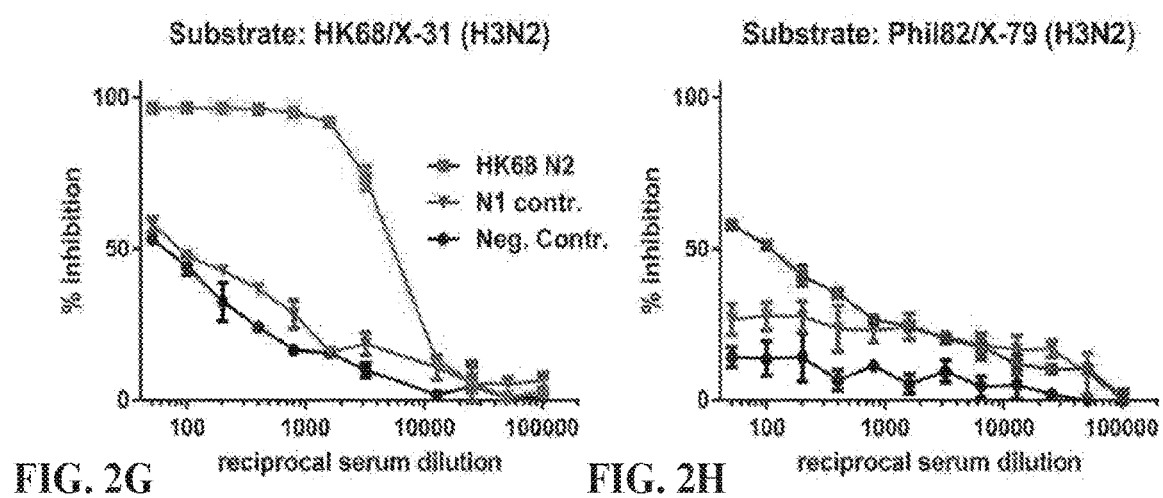

To investigate the mechanism of protection, anti-NA titers were measured using ELISA with purified whole virus as substrate. In all three cases, high levels of reactivity against the homologous virus were detected (FIG. 1G, FIG. 2E and FIG. 4G). To assess the functionality of this antibody response, NI titers against the respective homologous viruses were determined using ELLA and demonstrated high activity in all three cases (FIG. 1J, FIG. 2G and FIG. 4J). To confirm the role of antibodies as a contributing mechanism of protection, a passive transfer challenge experiment was performed. Sera from a positive control group vaccinated twice with HK68/X-31 whole inactivated vaccine, a group that received rN2, and a group that received BSA were transferred into three sets of naive mice, respectively. Two hours post transfer, the animals were challenged with 5 mLD50 of HK68/X-31 virus. No difference in weight loss was observed between N2 and positive control mice; both groups showed modest weight loss of approximately 10 percent of their initial weight and all mice in both groups survived the infection, while control mice lost weight rapidly and succumbed to infection on day 8 post challenge (FIG. 3A).

6.1.3.4 Mucosal NA Vaccination Confers Better Protection than Intramuscular NA Vaccination Without being bound by any theory, NA antibodies may impact at least two important steps of the influenza virus life cycle: virus release from infected cells (9) and transport of incoming virus particles through mucins on the mucosa (9, 31). As such, the efficacy of intramuscular versus intranasal vaccination was compared, since intranasal vaccination also induces mucosal antibodies. Mice were vaccinated twice with rN2 at a 3 week interval intranasally or intramuscularly (5 μg rN2 plus 5 μg of polyI:C per dose). Control animals received BSA (IN and IM) or rN1 via IN or IM administration. Four weeks post vaccination, mice were challenged with 10 mLD50 of HK68/X-31. Although a small difference in weight loss could be observed on days 4-7 post vaccination, no statistically significant difference between the IN and IM routes could be established (FIG. 3C). All rN2 vaccinated animals (both, IN and IM vaccinated animals) survived the infection while all control animals succumbed to infection between days 6 and 7, regardless of the vaccination route. The experiment was repeated with a higher challenge dose of 25 mLD50, indicating that IN vaccination provided significantly better protection against weight loss than IM vaccination (FIG. 3D). However, systemic anti-N2 antibody levels were similar in the three experimental groups, suggesting an important role of mucosal immunity, most likely mucosal IgA, in NA based protection (FIG. 3E).

6.1.3.5 NA Immunogens Partially Protect Against Heterologous but not Against Heterosubtypic Influenza a Virus Challenge To assess the breadth that NA-based immunity can afford, animals were vaccinated with PR8 N1 and then challenged with 5 mLD50 of either NL09 H1N1 (2009 pandemic strain) or VN04 H5N1. Both viruses carry N1 NAs which belong to a different N1 clade than PR8 N1, which falls into the human N1 clade (9). PR8 N1 was able to provide partial protection against weight loss (as compared to BSA and N2 control animals) and mortality (80% survival in both cases) (FIG. 1B, FIG. 1C, FIG. 1E and FIG. 1F). However, when challenged with a higher dose (10 mLD50) of NL09 virus, all PR8 N1-vaccinated mice succumbed to infection, indicating the limit of crossprotection. Specific reactivity to purified NL09 and VN04 virus particles were detected by ELISA, potentially explaining the observed cross-protection (FIG. 1H and FIG. 1I). However, only low specific NI activity could be detected against NL09 and no activity above background was detected for VN04 (FIG. 1K and FIG. 1L). Cross-reactivity of the N2 was tested using the heterologous Phil82 H3N2 strain that is separated from HK68 by 14 years of antigenic drift. Animals challenged with a 5 mLD50 dose of virus were completely protected from mortality but showed a body weight loss of approximately 80% (FIG. 2B and FIG. 2D). With a higher challenge dose of 10 mLD50 survival dropped to 20%. HK68 N2 sera showed low specific cross-reactivity to Phil82 virus in ELISA and detectable, but low, NI activity (FIG. 2F and FIG. 2H).

In the experiments described above, rN2-vaccinated mice were used as controls for challenge with viruses expressing N1 NAs and vice versa without observing protection in the controls. This indicated the absence of heterosubtypic immunity between N1 and N2. However, there are currently nine subtypes of true influenza A NA subtypes known (those with demonstrated NA enzymatic activity) and it was unclear if any of them would share protective epitopes with either N1 or N2 NA. To explore whether any of the NA subtypes would share protective epitopes, mice were vaccinated twice with rN3, rN4, rN5, rN6, rN7, rN8 or rN9 NA and challenged them with 5 mLD50 of either PR8 (H1N1) or HK68 (H3N2). All animals seroconverted to the respective NAs (FIG. 17), but lost weight rapidly after infection with PR8 (FIG. 5A) or HK68 (FIG. 5B). Survival was 0% in most cases, but in the rN5 and rN7 PR8 challenge groups and in the rN6 HK68 challenge group, survival was 20% (one animal). However, survival of a low percentage of animals is expected with a challenge dose of 5 mLD50. Without being bound by any theory, these data indicate that vaccination with influenza A virus NA does not induce heterosubtypic immunity.

6.1.3.6 Vaccination with Influenza B NA Induces Broad Protection Against Heterologous Virus Challenge Genetic diversity of influenza B virus HAs and NAs is limited as compared to influenza A virus (9, 32). To assess the breadth of NA-based immunity against influenza B viruses, animals were vaccinated with NA from Yam88, the lineage-defining strain of the Yamagata lineage. These animals were subsequently challenged with Vic87 and Mal04—both viruses that belong to the antigenically distinct (based on HA) Victoria lineage. Interestingly, vaccination with Yam88 NA protected against weight loss and mortality after challenge with the two heterologous strains (FIG. 4B, FIG. 4C, FIG. 4E and FIG. 4F). NA cross-reactivity could be detected against both viruses, although reactivity to Vic87 was higher than reactivity to Mal04 (FIG. 4H and FIG. 4I). Yam88 NA vaccination induced robust NI titers against Vic87 (FIG. 4K). NI activity against Mal04 was low but still detectable (FIG. 4L).

6.1.3.7 IIV does not Efficiently Induce N1 and N2 Reactive Antibody Responses in Humans Previous studies have indicated that the anti-NA response to IIV in humans is low. To assess the anti-NA response to IIV in humans, a quantitative ELISA method based on recombinant HA and NA proteins was utilized. The H1N1 vaccine component of the vaccine was NC99. Immunity was assessed using homologous HA and NA reagents. Pre-existing immunity against NC99 H1 HA was found to be relatively high at baseline and increased greatly after vaccination (24-fold) (FIG. 6A and FIG. 6E). Pre-existing antibody levels against the NC99 N1 were found to be low and did not significantly increase after vaccination (1.1 fold) (FIG. 6B and FIG. 6E). The H3N2 component of the vaccine strains was A/Wyoming/3/03. However, due to the lack of homologous reagents, HA and NA proteins of a closely related H3N2 strain, A/Panama/2007/99, were utilized. The H3 baseline titer was lower than the baseline titer of H1 and vaccination resulted in a 6.4-fold induction (FIG. 6C and FIG. 6E). The N2 baseline titer was higher than the one for N1 and increased 2-fold upon vaccination (FIG. 6D and FIG. 6E). IIV induced a significantly stronger immune response against HA than against NA for both influenza A components of the vaccine with $p=0.0003$ for H1N1 and $p=0.0240$ for H3N2 (FIG. 6E).

6.1.3.8 The N1 NA Content of Inactivated Influenza Virus Vaccines is Highly Variable To evaluate the role of the amount of NA present in IIVs in the induction of anti-NA antibodies as compared to HA-antibodies, the N1 NA content was quantified in current IIVs. Using the broadly N1-reactive monoclonal antibody 4A5 (FIG. 18), a semi-quantitative Western blot analysis of four 2013-2014 seasonal vaccines was quantified to measure their N1 content. Three out of four vaccines showed robust levels of NA while one vaccine, Flucelvax (Novartis), only showed a very weak band (FIG. 7A). Interestingly, although the dominant band was running between 50 and 80 kDa, multiple and diverse higher molecular weight species were detected in the three egg-derived vaccines (FIG. 7A). The N1 NA content of the four tested vaccines was quantified using an ELISA-based assay and linear regression. The highest N1 NA content was measured in Fluzone (10.5 μg/vaccine dose), followed by Fluvirin (5.0 μg/vaccine dose) and FluLaval (4.4 μg/vaccine dose). The cell-culture derived Flucelvax appeared to have only minimal amounts of NA (0.02 μg/vaccine dose). Since only one cell-culture-derived vaccine (the only one on the market as of 2014/2015) was tested, it is unclear if the low N1 content of this vaccine is caused by the virus production method or by steps downstream in the production process.

6.1.4 Discussion

In an attempt to assess the cross-protective potential of the influenza virus NA as a vaccine antigen, different subtypes of recombinant NA were expressed in a baculovirus system and used to vaccinate mice prior to lethal challenge with homologous, heterologous, or heterosubtypic viral challenge. Mice immunized with N2 were completely protected from morbidity and mortality in a homologous challenge and displayed significantly reduced viral lung titers. Heterologous challenge with a drifted strain resulted in morbidity but no mortality. Similar results were obtained for challenge experiments with N1 NA. Mice immunized with influenza B NA (from B/Yamagata/16/88) displayed no morbidity when sub-lethally infected with the homologous strain and, importantly, were completely protected from morbidity and mortality when lethally challenged with a Victoria lineage strain and a more recent Yamagata lineage strain. Analysis of the NA content in 4 different inactivated vaccine formulations from the 2013-2014 season via Western blot and ELISA quantification indicated that the amount of NA across vaccine brands is indeed variable. HA and NA endpoint titers in pre- and post-vaccination human serum samples from individuals that received a trivalent inactivated seasonal influenza vaccine from 2004-2005 were measured: the induction of NA titers was statistically less pronounced than that of HA titers. Without being bound by any theory, the demonstrated homologous and heterologous protective capacity of recombinant NA suggests that supplementing vaccine formulations with a standard amount of NA may offer increased protection against influenza virus infection.

Inactivated influenza virus vaccines, both seasonal and pandemic, are standardized based on their included amounts of the major surface glycoprotein HA (8). Consequently, only an HA based surrogate measure of protection, HI activity, is used to assess efficacy of influenza virus vaccines (33). Importantly, IIV only induces a relatively narrow immune response, and protection is mostly limited to viral strains closely related to the vaccine strain (4-6). The IIV induced immune response in humans against the NA is significantly weaker than the response against the HA (9, 22, 27-29, 34). This example demonstrates that, in certain cases, no response against the NA can be detected at all, despite high induction of antibodies against the corresponding HA. There are several factors that could contribute to the low immunogenicity of the NA as compared to that of the HA. First, NA seems to be inherently immunosubdominant to the HA when both antigens are administered in conjunction (22, 28, 29). Second, HA is more abundant on the virus surface than NA (35), and third, the NA could be lost to some extent during the manufacturing of the vaccine. To investigate the third factor, the N1 NA content of four licensed IIVs produced by three manufacturers from the 2013/14 season was assessed. Interestingly, all egg-derived vaccines had robust amounts of NA, while the cell culture-derived preparation contained only minimal amounts of N1. Without being bound by any theory, since most licensed IIVs are derived from eggs (including the one used for measuring human HA and NA titers above in FIG. 6), the low NA content of vaccines is an unlikely as explanation for the low immunogenicity.

It has been hypothesized that robust immune responses against NA could contribute to protection against both homologous and heterologous virus strains. Recombinant NA-based immunogens in mice were utilized to study the protective potential of NA. Interestingly, there was robust protection against homologous challenge, comparable to vaccination with whole inactivated virus. Complete protection against morbidity and mortality was observed even at high challenge doses when the vaccine was given intranasally. Intramuscular vaccination still resulted in full protection against mortality at high challenge doses but significant weight loss was observed, suggesting that mucosal immunity can play an important role in NA-based protection. In contrast to whole virus inactivated vaccines, vaccination with NA antigens did not result in sterilizing immunity but reduced lung titers drastically, which is in line with historic studies in humans and animal models (10, 20). However, two vaccinations with whole virus vaccines were necessary to induce sterilizing immunity. Without being bound by any theory, humoral immunity is sufficient for protection, since passive transfer of sera from vaccinated mice protected naive mice from challenge, although the contribution of cellular immunity to NA-based protection cannot be ruled out.

Previous studies have identified an epitope that is highly conserved among influenza A virus NAs (36). An antibody that recognized this epitope was also effective in inhibiting the influenza B virus neuraminidase (36, 37). However, the antibody has relatively low effective concentrations as compared to specific anti-NA antibodies (15, 36, 37) and it is unknown if similar antibodies against the same epitope can be induced by natural infection or vaccination with influenza virus vaccines. Vaccination with N3-N9 NAs did not induce protective immunity against H1N1 or H3N2 challenge. Also, N1 antigens did not protect against challenge with N2-expressing viruses (and vice versa). However, limited heterologous (within the subtype) cross-protection for influenza A viruses was observed. N1 antigens from an early human isolate partially protected against challenge with a pandemic H1N1 and an H5N1 strain, both of which carry avian-type N1 NAs that are phylogenetically distinct from the human N1 lineage (9). This finding is supported by reports of N1 cross-reactive monoclonal antibodies (15) and cross-protection against H5N1 induced by H1N1 exposure (13, 14, 16, 17, 38). Full cross-protection, in terms of mortality, for the N2 immunogen was observed when mice were challenged with an H3N2 strain that had drifted 14 years. This cross-protection was limited to lower challenge doses; no cross-protection was observed for either N1 or N2 at high challenge doses. Cross-protection was observed for influenza B viruses; an NA immunogen from Yam88 (Yamagata lineage) was able to fully protect against two Victoria lineage strains. Importantly, the influenza B NA has not diverged into two lineages, as has the influenza B HA.

In conclusion, NA-based immunity is able to provide robust protection against homologous influenza virus infection in mice. Cross-protection is confined within the same subtype with no displayed intersubtypic protection, as seen with HA stalk-reactive antibodies (27, 39). However, subtype-specific cross-reactive antibodies have the potential to contribute to protection against drifted seasonal viruses in cases where the vaccine is mismatched, as in the 2014-2015 season (40). Without being bound by any theory, strong N1- and N2-based immunity might be beneficial in the case of a new pandemic virus that may carry a heterologous N2 of N1 NA, such as H2N2 or H5N1. Current seasonal IIV is sub-optimal in inducing robust immunity against NA. Without being bound by any theory, NA could be rendered more immunogenic by presenting it in context of a novel HA globular head domain or chimeric HA to which humans are naive (7, 22). Alternatively, IIV could be supplemented with purified NA or purified NA could be given as an extra vaccine in addition to IIV.

6.1.5 References Cited in Example 1

1. Jayasundara K, Soobiah C, Thommes E, Tricco A C, Chit A. 2014. Natural attack rate of influenza in unvaccinated children and adults: a meta-regression analysis. BMC Infect Dis 14:670.

2. Tricco A C, Chit A, Soobiah C, Hallett D, Meier G, Chen M H, Tashkandi M, Bauch C T, Loeb M. 2013. Comparing influenza vaccine efficacy against mismatched and matched strains: a systematic review and meta-analysis. BMC Med 11:153.

3. de Jong J C, Beyer W E, Palache A M, Rimmelzwaan G F, Osterhaus A D. 2000. Mismatch between the 1997/1998 influenza vaccine and the major epidemic A(H3N2) virus strain as the cause of an inadequate vaccine-induced antibody response to this strain in the elderly. J Med Virol 61:94-99.

4. Wrammert J, Smith K, Miller J, Langley W A, Kokko K, Larsen C, Zheng N Y, Mays I, Garman L, Helms C, James J, Air G M, Capra J D, Ahmed R, Wilson P C. 2008. Rapid cloning of high-affinity human monoclonal antibodies against influenza virus. Nature 453:667-671.

5. Moody M A, Zhang R, Walter E B, Woods C W, Ginsburg G S, McClain M T, Denny T N, Chen X, Munshaw S, Marshall D J, Whitesides J F, Drinker M S, Amos J D, Gurley T C, Eudailey J A, Foulger A, DeRosa K R, Parks R, Meyerhoff R R, Yu J S, Kozink D M, Barefoot B E, Ramsburg E A, Khurana S, Golding H, Vandergrift N A, Alam S M, Tomaras G D, Kepler T B, Kelsoe G, Liao H X, Haynes B F. 2011. H3N2 influenza infection elicits more cross-reactive and less clonally expanded anti-hemagglutinin antibodies than influenza vaccination. PLoS One 6:e25797.

6. Margine I, Hai R, Albrecht R A, Obermoser G, Harrod A C, Banchereau J, Palucka K, Garcia-Sastre A, Palese P, Treanor J J, Krammer F. 2013. H3N2 influenza virus infection induces broadly reactive hemagglutinin stalk antibodies in humans and mice. J Virol 87:4728-4737.

7. Krammer F, Palese P. 2013. Influenza virus hemagglutinin stalk-based antibodies and vaccines. Curr Opin Virol 3:521-530.

8. Gerdil C. 2003. The annual production cycle for influenza vaccine. Vaccine 21:1776-1779.

9. Wohlbold T J, Krammer F. 2014. In the shadow of hemagglutinin: a growing interest in influenza viral neuraminidase and its role as a vaccine antigen. Viruses 6:2465-2494.

10. Schulman J L, Khakpour M, Kilbourne E D. 1968. Protective effects of specific immunity to viral neuraminidase on influenza virus infection of mice. J Virol 2:778-786.

11. Chen Z, Kadowaki S, Hagiwara Y, Yoshikawa T, Matsuo K, Kurata T, Tamura S. 2000. Cross-protection against a lethal influenza virus infection by DNA vaccine to neuraminidase. Vaccine 18:3214-3222.

12. Sylte M J, Hubby B, Suarez D L. 2007. Influenza neuraminidase antibodies provide partial protection for chickens against high pathogenic avian influenza infection. Vaccine 25:3763-3772.

13. Rockman S, Brown L E, Barr I G, Gilbertson B, Lowther S, Kachurin A, Kachurina O, Klippel J, Bodle J, Pearse M, Middleton D. 2013. Neuraminidase-inhibiting antibody is a correlate of cross-protection against lethal H5N1 influenza virus in ferrets immunized with seasonal influenza vaccine. J Virol 87:3053-3061.

14. Van Reeth K, Braeckmans D, Cox E, Van Borm S, van den Berg T, Goddeeris B, De Vleeschauwer A. 2009. Prior infection with an H1N1 swine influenza virus partially protects pigs against a low pathogenic H5N1 avian influenza virus. Vaccine 27:6330-6339.

15. Wan H, Gao J, Xu K, Chen H, Couzens L K, Rivers K H, Easterbrook J D, Yang K, Zhong L, Raj abi M, Ye J, Sultana I, Wan X F, Liu X, Perez D R, Taubenberger J K, Eichelberger M C. 2013. Molecular Basis for Broad Neuraminidase Immunity: Conserved Epitopes in Seasonal and Pandemic H1N1 as Well as H5N1 Influenza Viruses. J Virol 87:9290-9300.

16. Easterbrook J D, Schwartzman L M, Gao J, Kash J C, Morens D M, Couzens L, Wan H, Eichelberger M C, Taubenberger J K. 2012. Protection against a lethal H5N1 influenza challenge by intranasal immunization with virus-like particles containing 2009 pandemic H1N1 neuraminidase in mice. Virology 432:39-44.

17. Chen Z, Kim L, Subbarao K, Jin H. 2012. The 2009 pandemic H1N1 virus induces anti-neuraminidase (N A) antibodies that cross-react with the N A of H5N1 viruses in ferrets. Vaccine 30:2516-2522.

18. Halbherr S J, Ludersdorfer T H, Ricklin M, Locher S, Berger Rentsch M, Summerfield A, Zimmer G. 2014. Biological and protective properties of immune sera directed to influenza virus neuraminidase. J Virol.

19. He B, Chang H, Liu Z, Huang C, Liu X, Zheng D, Fang F, Sun B, Chen Z. 2014. Infection of influenza virus neuraminidase-vaccinated mice with homologous influenza virus leads to strong protection against heterologous influenza viruses. J Gen Virol 95:2627-2637.

20. Couch R B, Kasel J A, Gerin J L, Schulman J L, Kilbourne E D. 1974. Induction of partial immunity to influenza by a neuraminidase-specific vaccine. J Infect Dis 129:411-420.

21. Dowdle W R, Coleman M T, Mostow S R, Kaye H S, Schoenbaum S C. 1973. Inactivated influenza vaccines. 2. Laboratory indices of protection. Postgrad Med J 49:159-163.

22. Kilbourne E D, Cerini C P, Khan M W, Mitchell J W, Ogra P L. 1987. Immunologic response to the influenza virus neuraminidase is influenced by prior experience with the associated viral hemagglutinin. I. Studies in human vaccinees. J Immunol 138:3010-3013.

23. Krammer F, Schinko T, Palmberger D, Tauer C, Messner P, Grabherr R. 2010. *Trichoplusia ni* cells (High Five) are highly efficient for the production of influenza A virus-like particles: a comparison of two insect cell lines as production platforms for influenza vaccines. Mol Biotechnol 45:226-234.

24. Margine I, Palese P, Krammer F. 2013. Expression of Functional Recombinant Hemagglutinin and Neuraminidase Proteins from the Novel H7N9 Influenza Virus Using the Baculovirus Expression System. J Vis Exp.

25. Xu X, Zhu X, Dwek R A, Stevens J, Wilson I A. 2008. Structural characterization of the 1918 influenza virus H1N1 neuraminidase. J Virol 82:10493-10501.

26. Eriksson J C, Cox R J, Szyszko E, Davidsson A, Brokstad K A. 2007. Local and systemic cytokine and chemokine responses after parenteral influenza vaccination. Influenza Other Respir Viruses 1:139-146.

27. Nachbagauer R, Wohlbold T J, Hirsh A, Hai R, Sjursen H, Palese P, Cox R J, Krammer F. 2014. Induction of broadly reactive anti-hemagglutinin stalk antibodies by an H5N1 vaccine in humans. J Virol 88:13260-13268.

28. Johansson B E, Moran T M, Kilbourne E D. 1987. Antigen-presenting B cells and helper T cells cooperatively mediate intravirionic antigenic competition between influenza A virus surface glycoproteins. Proc Natl Acad Sci USA 84:6869-6873.

29. Johansson B E, Kilbourne E D. 1993. Dissociation of influenza virus hemagglutinin and neuraminidase eliminates their intravirionic antigenic competition. J Virol 67:5721-5723.

30. Johansson B E, Kilbourne E D. 1994. Immunization with purified N1 and N2 influenza virus neuraminidases demonstrates cross-reactivity without antigenic competition. Proc Natl Acad Sci USA 91:2358-2361.

31. Yang X, Steukers L, Forier K, Xiong R, Braeckmans K, Van Reeth K, Nauwynck H. 2014. A Beneficiary Role for Neuraminidase in Influenza Virus Penetration through the Respiratory Mucus. PLoS One 9:e110026.

32. Palese P, Shaw M L (ed). 2007. Fields' virology. Lippincott Williams & Wilkins, Philadelphia.

33. Hobson D, Curry R L, Beare A S, Ward-Gardner A. 1972. The role of serum haemagglutination-inhibiting antibody in protection against challenge infection with influenza A2 and B viruses. J Hyg (Lond) 70:767-777.

34. Krammer F, Jul-Larsen A, Margine I, Hirsh A, Sjursen H, Zambon M, Cox R J. 2014. An H7N1 Influenza Virus Vaccine Induces Broadly Reactive Antibody Responses against H7N9 in Humans. Clin Vaccine Immunol 21:1153-1163.

35. Harris A, Cardone G, Winkler D, Heymann J, Brecher M, White J, Steven A. 2006. Influenza virus pleiomorphy characterized by cryoelectron tomography. Proc Natl Acad Sci USA 103:1912319127.

36. Doyle T M, Hashem A M, Li C, Van Domselaar G, Larocque L, Wang J, Smith D, Cyr T, Farnsworth A, He R, Hurt A C, Brown E G, Li X. 2013. Universal anti-neuraminidase antibody inhibiting all influenza A subtypes. Antiviral Res 100:567-574.

37. Doyle T M, Li C, Bucher D J, Hashem A M, Van Domselaar G, Wang J, Farnsworth A, She Y M, Cyr T, He R, Brown E G, Hurt A C, Li X. 2013. A monoclonal antibody targeting a highly conserved epitope in influenza B neuraminidase provides protection against drug resistant strains. Biochem Biophys Res Commun 441:226-229.

38. Sandbulte M R, Jimenez G S, Boon A C, Smith L R, Treanor J J, Webby R J. 2007. Cross-reactive neuraminidase antibodies afford partial protection against H5N1 in mice and are present in unexposed humans. PLoS Med 4:e59.

39. Krammer F, Pica N, Hai R, Margine I, Palese P. 2013. Chimeric hemagglutinin influenza virus vaccine constructs elicit broadly protective stalk-specific antibodies. J Virol 87:6542-6550.

40. Rolfes M, Blanton L, Brammer L, Smith S, Mustaquim D, Steffens C, Cohen J, Leon M, Chaves S S, Abd Elal A I, Gubareva L, Hall H, Wallis T, Villanueva J, Bresee J, Cox N, Finelli L 2014. Update: influenza activity—United States, Sep. 28-Dec. 6, 2014. MMWR Morb Mortal Wkly Rep 63:1189-1194.

6.2 Example 2

Enhancing the Immune Response Against NA in Influenza Virus Vaccines

Influenza virus infection continues to be a major public health problem worldwide. Current influenza virus vaccines are thought to protect mainly by eliciting neutralizing antibodies against the immunodominant globular head domain of the major viral surface glycoprotein hemagglutinin (HA). These antibodies are strain specific and attach near or at the receptor binding site and block attachment of the virus particle to cellular receptors, thus preventing infection. Antibodies directed towards the head of the hemagglutinin provide immunogenic pressure that results in the selection of fixed mutations at defined antigenic sites, a process known as "antigenic drift" (Palese and Shaw, 2006, Fields Virology, Philadelphia, Lippincott Williams & Wilkins, 1648-1689). It is through this process that new influenza viruses emerge in the human population, and the reason that the vaccine must be updated annually, in order to provide protection against the strain that is thought to circulate in the coming influenza season. Additionally, influenza virus strains of more than one subtype are co-circulating in the human population. Antibodies elicited by conventional vaccines against one strain are not sufficiently cross-protective against other, distinct strains, drifted strains or other subtypes. Therefore, typical seasonal influenza virus vaccines have to contain antigens that protect against two influenza A strains, H1 and H3, and an influenza B strain as well.

The dominant immune response against influenza HA is directed towards the "head" of the glycoprotein, specifically towards defined antigenic regions (antigenic sites).

Antibodies against these sites are known to be quite potent, and can neutralize virus binding to host substrates. An immune response can also be directed against the immunosubdominant "stem" or "stalk" of the influenza virus HA, the membrane proximal portion of the glycoprotein. Although antibodies against the stalk are usually less potent than antibodies directed towards the head domain they are broadly protective due to the conserved nature of the stalk domain.

Antibodies against the second virus surface glycoprotein, the neuraminidase (NA), can be highly protective against influenza virus challenge (see, Example 1, Section 6.1). Anti-NA antibodies provide substantial and broad cross-reactivity within NA subtypes (see, Example 1, Section 6.1). In a mouse model, recombinant N1 NA from the isolate A/PR/8/34 (H1N1) was able to protect against challenge with the homologous virus strain, and was also protective against pandemic H1N1 and H5N1 challenge (see, Example 1, Section 6.1). Similarly, N2 NA from A/Hong Kong/1/68 (H3N2) was able to protect against challenge with the drift variant A/Philippines/2/82 (H3N2). The strongest effect was seen with recombinant influenza B NA from B/Yamagata/16/88 which cross-protected against challenge with divergent influenza B virus isolates (see, Example 1, Section 6.1).

Accordingly, NA can be used in several different ways as broadly protective antigen (FIG. 8). In association with HA, the viral NA is immunologically subdominant and the majority of the immune response is directed against the HA globular head domain. Without being bound by any theory, immune responses against NA are enhanced by presenting NA in the context of a chimeric HA vaccine to break the immunodominance of the HA globular head domain and therefore enhances the immune response against the HA stalk domain and the NA (FIG. 8B and FIG. 9). In this context, the NA comes from inactivated viruses used to prepare the chimeric HA vaccine or additional NA could be added (FIG. 8B).

For example, ferrets immunized with influenza B virus expressing cH9/1 (referred to as "B-cH9/1" in the vaccination scheme in FIG. 9), boosted with a live attenuated influenza A virus (N1 subtype) expressing cH8/1 (referred to as "cH8/1-LAIV" in the vaccination scheme in FIG. 9), and boosted with an inactivated influenza A virus (N1 subtype) expressing cH5/1 (cH5/1-IIV) (referred to as the "cH8/1 LAIV-cH5/1 IIV" vaccination scheme in FIG. 9) exhibited enhanced influenza virus anti-NA (N1 subtype) titers as compared to ferrets immunized with a trivalent influenza virus vaccine (referred to as the "TIV" vaccination scheme in FIG. 9) or ferrets immunized with B-cH9/1, boosted with an inactivated influenza A virus (N1 subtype) expressing cH8/1 (referred to as "cH8/1-IIV" in the vaccination scheme in FIG. 9), and boosted with cH5/1-IIV (referred to as the "cH8/1 IIV-cH5/1 IIV" vaccination scheme in FIG. 9) or ferrets immunized with B-cH9/1 only. See FIG. 9 and FIG. 10. In particular, the anti-NA titers in the H8/1 LAIV-cH5/1 IIV vaccination scheme were increased after the first and second boosts as compared to the anti-NA titers in the cH8/1 IIV-cH5/1 IIV vaccination scheme (compare "post-cH8/1 IIV" with "post-cH8/1 LAIV" and "post-cH5/1 IIV" with "post-cH5/1 IIV" in FIG. 10). Ferrets immunized with B-cH9/1 and boosted with cH8/1 IIV, as well as ferrets immunized with B-cH9/1 and boosted with cH8/1-LAIV had increased anti-N1 titers compared to TIN. Ferrets which received the regular inactivated influenza virus vaccine did not have increased anti-NA titers (FIG. 10B).

Without being bound by any theory, immune responses against NA are enhanced by using NA in conjunction with HA stalk antigens (e.g., headless HA) to enhance breadth and potency of the protection (FIG. 8C). Without being bound by any theory, immune responses against NA are enhanced by using NA as a stand-alone vaccine (adjuvanted or unadjuvanted, FIG. 8D). Without being bound by any theory, immune responses against NA are enhanced by adding NA to regular inactivated influenza virus vaccines (FIG. 8E).

The NA can be expressed by, for example, recombinant viral vectors, as soluble NA proteins with N-terminal tetramerization domains and hexahistidine-tags, as full length recombinant proteins, as virus-like particles or, in conjunction with chimeric HA based vaccines, directly by an influenza virus. The vaccination strategies to enhance NA-based immunity (FIG. 8) can be used to prepare human and veterinarian universal influenza virus vaccines that broadly protect from viruses with NA subtypes which are included in the vaccine preparation. A vaccine based on NA could be a chimeric HA based universal vaccines that induce high titers of anti-NA antibodies, a universal influenza virus vaccine constructs (e.g., chimeric HA or headless HA based) supplemented with NA, a 'stand-alone' vaccine or regular seasonal inactivated vaccine supplemented with NA. Additionally, NA can be utilized as an additive to regular TIV (FluNhance—Protein Sciences). Moreover, to improve efficacy of vaccines, a LAIV or DNA vaccine prime followed by an IIV boost vaccination strategy can be utilized. Without being bound by any theory, the LAIV or DNA vaccine immunologically primes subjects, very often without a measurable seroconversion, and this immune response can then be recalled later by administering an IIV boost.

Conventional influenza virus vaccines elicit strain specific antibodies against the globular head domain of the viral HA. Although these antibodies are potently neutralizing the influenza virus strain they were raised against, they are not able to recognize slightly drifted variants of the same influenza virus subtype. Therefore, conventional influenza virus vaccines have to be updated/adjusted to circulating strains every year. The vaccination strategies described herein aim to induce antibodies against the viral NA which can form the basis of subtype-specific (e.g., N1, N2, B NA etc.) broad protection. NA can be used, most importantly, in conjunction with chimeric HA based vaccines, HA stalk-based constructs, as 'stand alone' vaccine or as supplement to existing seasonal influenza virus vaccines. Without being

6.3 Example 3

Stalk Immunity Reduces Influenza Virus Replication Following Naturally Acquired Infection The currently licensed inactivated and live attenuated influenza virus vaccines are proven to reduce the burden of influenza virus infections. However, epidemics of seasonal influenza still occur in the globally resulting in significant morbidity (13) and mortality (2). Humoral responses induced by these licensed vaccines are typically focused on the immunodominant globular head domains of hemagglutinin (HA), are specific for the respective vaccine strains, but are suboptimal against antigenically drifted influenza virus strains. Thus, annual influenza virus vaccination is required to keep pace with an antigenically "moving target" (18). This limitation of currently licensed vaccines is additionally complicated by the emergence of pandemic influenza virus strains which are difficult to predict. Upon the emergence of a pandemic, redirection of commercial vaccine manufacture is unlikely to occur in a sufficiently timely fashion to limit viral spread, as was the case during the 2009 H1N1 influenza pandemic (3, 4). HA-specific universal influenza virus vaccines focus humoral immune responses on the antigenically conserved, but immunosubdominant, stalk region thereby overcoming these limitations. Universal vaccines stimulating stalk-specific antibody responses would confer protection against homologous and drifted influenza virus strains, eliminate the requirement for reformulation of annual influenza vaccines, and confer increased protection against influenza viruses with pandemic potential (8, 17, 19). The level of protection conferred by hemagglutinin stalk-based immunity against influenza virus infection by aerosol transmission in a ferret model was assessed, which constitutes a natural route of infection.

Five month old male Fitch ferrets (Triple F Farms; Sayre Pa.) were immunized with viral vectors expressing chimeric hemagglutinin (cHA) as described previously (6). Ferrets (n=4) were primed by intranasal infection with $2 \times 10^7$ PFU of an influenza B virus vector expressing cH9/1 HA (B-cH9/1). The ferrets were then boosted by an intramuscular administration of $1 \times 10^7$ PFU of a recombinant VSV vector expressing cH5/1 HA (VSV-cH5/1, 0.5 ml intramuscular) followed with a second boost with $1 \times 10^9$ PFU of a replication deficient recombinant adenovirus 5 vector expressing cH6/1 HA (Adv-cH6/1, intranasal administration and intramuscular, 0.5 ml respectively) (6). Without being bound by any theory, by sequential vaccination with immunogens that have the same conserved stalk domain but divergent head domains, it is possible to specifically induce high levels of stalk-reactive antibodies. Control ferrets (n=4) received the same empty virus vectors by the same immunization routes in the same sequence. Seroconversion of the immunized ferrets to the hemagglutinin globular head expressed by the indicated viral vector was assessed by hemagglutination inhibition (HI) assay (1, 16). Although priming of ferrets with influenza B virus expressing-cH9/1 resulted in detectable serum responses (Table 1), no seroconversion was detected by HI following boosting with either VSV-cH5/1 HA or Adv-cH6/1. Importantly, during the course of the vaccine regimen, the stalk-immunized and control-immunized ferrets did not develop HI titers against the pandemic H1 globular head domain (Table 1).

TABLE 1

|  | Control-immunized | | Stalk-immunized | |
| --- | --- | --- | --- | --- |
|  | Pre- | Post- | Pre- | Post- |
| H9 HI titers* | 5 (—) | 5 (—) | 5 (—) | 190.2(±69.2) |
| H5 HI titers | 5 (—) | 5 (—) | 5 (—) | 5 (—) |
| H6 HI titers | 5 (—) | 5 (—) | 5 (—) | 5 (—) |
| H1 HI titers | 5 (—) | 5 (—) | 5 (—) | 5 (—) |

*HI titers reported as Geometric Mean Titers (±S.D.)

Following prime/boost vaccination, a stalk immunized ferret and a control immunized ferret were co-housed together with a ferret directly infected with $10^6$ PFU of pandemic H1N1 influenza virus A/California/4/2009 under conditions that permitted only aerosol transmission to occur (FIG. 11). However, the stalk-immunized and the control-immunized ferrets were kept in the same chamber and contact transmission between these two animals was possible (FIG. 11). On days 2, 4, 6, 8, and 10 post-infection, nasal washes were then taken from the directly infected and aerosol contacts for determination of virus titers by plaque assay. Direct intranasal infection of naïve ferrets with the pandemic H1N1 influenza virus resulted in high virus titers at day 2 post-infection (average of 5.7 log 10 PFU/mL) that declined to below detectable limits by day 6 post-infection (FIG. 12). All control immunized ferrets became infected and uniformly shed virus between days 2 to 8 post-infection (days 1 to 7 post-aerosol contact) with peak nasal wash titers (peak average of 6.0 log 10 PFU/mL on day 6 post-infection). All stalk-immunized ferrets also became infected, but shed virus less uniformly. Importantly, the virus titers detected in the nasal wash samples from the stalk-immunized ferrets were substantially lower (peak average of 3.8 log 10 PFU/mL on day 8 post-infection) than for the control-immunized ferrets. Additionally, the time frame by which the stalk-immunized ferrets shed influenza virus (days 6 to 10 post-infection) was delayed as compared to the control-vaccinated ferrets. The experimental design (FIG. 11) did not permit assessment of pure aerosol transmission, as virus could also transmit by direct contact from aerosol infected control vaccinated animals to their stalk vaccinated cage mates. Based on the delayed onset of virus replication in stalk vaccinated ferrets, it is likely that this group was actually not infected by aerosol from the directly infected animals but by contact from their cage mates. This outcome suggests that stalk vaccination might actually protect from infection via the aerosol route. Stalk-immunized and control immunized ferrets exhibited minimal weight loss during the aerosol transmission experiment (data not shown).

The cHA based universal influenza virus vaccine strategy stimulated readily detectable levels of H1 stalk-reactive antibody responses (cHA vaccinated pre-challenge; FIG. 13). H1N1 infection following aerosol transmission had a boosting effect on these H1 stalk-reactive antibody responses (cHA vaccinated post-challenge; FIG. 13). This boost in stalk-reactive antibodies (approx. 3-fold) might further enhance broad protection against future infections. Importantly, serum from naïve ferrets or from control-immunized ferrets lacked detectable levels of H1 stalk-reactive antibodies.

In this study, the ferret model of influenza virus transmission was utilized to assess the level of protection conferred by group 1 HA stalk-specific antibodies against natural infection with pandemic H1N1 by an aerosol route of transmission. Ferrets were immunized using a universal influenza virus vaccine strategy in which the animals were vaccinated with viral vectors expressing chimeric HAs that induce stalk-reactive antibodies. This aerosol transmission study revealed that group 1 stalk-specific antibodies could reduce of the magnitude and duration of influenza virus shedding from the nasal cavity of HA stalk-immunized ferrets following infection by an aerosol route of influenza virus transmission. Without being bound by any theory, given the set-up of the experiment and the delay in transmission, the stalk-vaccinated ferrets were likely protected from aerosol transmission but became infected by direct contact with their cage mates. These data provide additional evidence that ferrets produce HA stalk reactive antibodies following vaccination with chimeric HAs as observed previously (6), and that stalk reactive antibodies provide protection from influenza virus infection by a natural route of transmission. Importantly, hemagglutinin stalk-immunized ferrets did not exhibit any clinical signs of antibody-enhanced disease as has been reported for the pig model (5). Collectively, these findings, along with previous observations (6, 9-11), provide compelling evidence that a universal influenza virus vaccine strategy that stimulates robust HA stalk-focused immunity would reduce severity of influenza virus replication and disease burden following natural transmission routes of virus infection. The novelty and significance of the current findings described in this example support the development of vaccines stimulating stalk-specific antibody responses and the transition from investigations on universal influenza vaccines in research laboratories to clinical settings (14).

6.3.1 References Cited in Example 3

1. Baker, S. F., H. Guo, R. A. Albrecht, A. Garcia-Sastre, D. J. Topham, and L. Martinez-Sobrido. 2013. Protection against lethal influenza with a viral mimic. Journal of virology 87:8591-8605.

2. Centers for Disease, C., and Prevention. 2010. Estimates of deaths associated with seasonal influenza—United States, 1976-2007. MMWR. Morbidity and mortality weekly report 59:1057-1062.

3. Centers for Disease, C., and Prevention. 2009. Swine influenza A (H1N1) infection in two children—Southern California, March-April 2009. MMWR. Morbidity and mortality weekly report 58:400-402.

4. Centers for Disease, C., and Prevention. 2009. Update on influenza A (H1N1) 2009 monovalent vaccines. MMWR. Morbidity and mortality weekly report 58:1100-1101.

5. Khurana, S., C. L. Loving, J. Manischewitz, L. R. King, P. C. Gauger, J. Henningson, A. L. Vincent, and H. Golding. 2013. Vaccine-induced anti-HA2 antibodies promote virus fusion and enhance influenza virus respiratory disease. Science translational medicine 5:200ra114.

6. Krammer, F., R. Hai, M. Yondola, G. S. Tan, V. H. Leyva-Grado, A. B. Ryder, M. S. Miller, J. K. Rose, P. Palese, A. Garcia-Sastre, and R. A. Albrecht. 2014. Assessment of influenza virus hemagglutinin stalk-based immunity in ferrets. Journal of virology 88:3432-3442.

7. Krammer, F., I. Margine, G. S. Tan, N. Pica, J. C. Krause, and P. Palese. 2012. A carboxy-terminal trimerization domain stabilizes conformational epitopes on the stalk domain of soluble recombinant hemagglutinin substrates. PloS one 7:e43603.

8. Krammer, F., and P. Palese. 2013. Influenza virus hemagglutinin stalk-based antibodies and vaccines. Current opinion in virology 3:521-530.

9. Krammer, F., N. Pica, R. Hai, I. Margine, and P. Palese. 2013. Chimeric hemagglutinin influenza virus vaccine constructs elicit broadly protective stalk-specific antibodies. Journal of virology 87:6542-6550.

10. Krammer, F., N. Pica, R. Hai, G. S. Tan, and P. Palese. 2012. Hemagglutinin Stalk-Reactive Antibodies Are Boosted following Sequential Infection with Seasonal and Pandemic H1N1 Influenza Virus in Mice. Journal of virology 86:10302-10307.

11. Mallajosyula, V. V., M. Citron, F. Ferrara, X. Lu, C. Callahan, G. J. Heidecker, S. P. Sarma, J. A. Flynn, N. J. Temperton, X. Liang, and R. Varadarajan. 2014. Influenza hemagglutinin stem-fragment immunogen elicits broadly neutralizing antibodies and confers heterologous protection. Proceedings of the National Academy of Sciences of the United States of America.

12. Martinez-Romero, C., E. de Vries, A. Belicha-Villanueva, I. Mena, D. M. Tscherne, V. L. Gillespie, R. A. Albrecht, C. A. de Haan, and A. Garcia-Sastre. 2013. Substitutions T200A and E227A in the hemagglutinin of pandemic 2009 influenza A virus increase lethality but decrease transmission. Journal of virology 87:6507-6511.

13. Molinari, N. A., I. R. Ortega-Sanchez, M. L. Messonnier, W. W. Thompson, P. M. Wortley, E. Weintraub, and C. B. Bridges. 2007. The annual impact of seasonal influenza in the US: measuring disease burden and costs. Vaccine 25:5086-5096.

14. Oxford, J. S. 2013. Towards a universal influenza vaccine: volunteer virus challenge studies in quarantine to speed the development and subsequent licensing. British journal of clinical pharmacology 76:210-216.

15. Seibert, C. W., M. Kaminski, J. Philipp, D. Rubbenstroth, R. A. Albrecht, F. Schwalm, S. Stertz, R. A. Medina, G. Kochs, A. Garcia-Sastre, P. Staeheli, and P. Palese. 2010. Oseltamivir-resistant variants of the 2009 pandemic H1N1 influenza A virus are not attenuated in the guinea pig and ferret transmission models. Journal of virology 84:11219-11226.

16. Seibert, C. W., S. Rahmat, J. C. Krause, D. Eggink, R. A. Albrecht, P. H. Goff, F. Krammer, J. A. Duty, N. M. Bouvier, A. Garcia-Sastre, and P. Palese. 2013. Recombinant IgA is sufficient to prevent influenza virus transmission in guinea pigs. Journal of virology 87:7793-7804.

17. Subbarao, K., and Y. Matsuoka. 2013. The prospects and challenges of universal vaccines for influenza. Trends in microbiology 21:350-358.

18. Wang, T. T., and P. Palese. 2011. Biochemistry. Catching a moving target. Science 333:834-835.

19. Yewdell, J. W. 2013. To dream the impossible dream: universal influenza vaccination. Current opinion in virology 3:316-321.

6.4 Example 4

Comparing Seasonal Vaccine to Other Vaccines

Experiment 1: A first group of ferrets are intranasally administered a vaccine formulation comprising a chimeric HA protein comprising an HA globular head domain of an H5 influenza virus (e.g., A/Vietname/1203/04) and a stem domain polypeptide of an H1 (e.g., A/California/4/2009) and a soluble form of influenza virus neuraminidase from A/California/4/2009 (an H1N1 influenza virus). A second group of ferrets are intranasally administered a vaccine formulation comprising a seasonal influenza virus vaccine (e.g., an inactivated influenza virus vaccine or live attenuated influenza virus vaccine) that comprises an HA of an influenza virus H1 and an NA of an influenza virus N1. A certain period of time after administration of the vaccine formulations to the two groups of ferrets, serum from both groups of ferrets is obtained and assessed for antibody titers against an H1N1 influenza virus (e.g., A/California/4/2009 or the 1918 pandemic H1N1 influenza virus) or an H6N1 influenza virus. The antibody titers from both groups are compared to assess which group has the higher antibody titer. As an alternative to ferrets, mice may be used. In addition, as alternative route of administration, intramuscular may be used rather than intranasal. In addition, an adjuvant may be added the vaccine formulation administered to the first group of animals.

The two groups of animals may also be challenged with an H1N1 influenza virus (e.g., A/California/4/2009 and/or the 1918 pandemic H1N1 influenza virus) or an H6N1 influenza virus a certain period after administration of the vaccine formulations to the animals, and the health of the animals assessed to see which of the two vaccine formulations offers better protection to the animals.

Experiment 2: A first group of ferrets are intranasally administered a vaccine formulation comprising a non-influenza virus vector (e.g., adenovirus or VSV) comprising chimeric HA and an influenza virus neuraminidase polypeptide from A/California/4/2009 (an H1N1 influenza virus), wherein the chimeric HA comprises an HA globular head domain of an H5 influenza virus (e.g., A/Vietnam/1203/04) and a stem domain polypeptide of an H1 (e.g., A/California/4/2009). A second group of ferrets are intranasally administered a vaccine formulation comprising a seasonal influenza virus vaccine (e.g., an inactivated influenza virus vaccine or live attenuated influenza virus vaccine) that comprises an HA of an influenza virus H1 and an NA of an influenza virus N1. A certain period of time after administration of the vaccine formulations to the two groups of ferrets, serum from both groups of ferrets is obtained and assessed for antibody titers against an H1N1 influenza virus (e.g., A/California/4/2009 or the 1918 pandemic H1N1 influenza virus) or an H6N1 influenza virus. The antibody titers from both groups are compared to assess which group has the higher antibody titer. As an alternative to ferrets, mice may be used. In addition, as alternative route of administration, intramuscular may be used rather than intranasal.

The two groups of animals may also be challenged with an H1N1 influenza virus (e.g., A/California/4/2009 and/or the 1918 pandemic H1N1 influenza virus) or an H6N1 influenza virus a certain period after administration of the vaccine formulations to the animals, and the health of the animals assessed to see which of the two vaccine formulations offers better protection to the animals.

7. DESCRIPTION OF SEQUENCES

TABLE 2

Description of Sequences.

| SEQ ID NO | Description | Sequence |
|---|---|---|
| 1 | Exemplary H1 HA | MKANLLVLLCALAAADADTICIGYHANNSTDTVDTVLEK NVTVTHSVNLLEDSHNGKLCRLKGIAPLQLGKCNIAGWL LGNPECDPLLPVRSWSYIVETPNSENGICYPGDFIDYEELR EQLSSVSSFERFEIFPKESSWPNHNTNGVTAACSHEGKSSF YRNLLWLTEKEGSYPKLKNSYVNKKGKEVLVLWGIHHP PNSKEQQNLYQNENAYVSVVTSNYNRRFTPEIAERPKVR DQAGRMNYYWTLLKPGDTIIFEANGNLIAPMYAFALSRG FGSGIITSNASMHECNTKCQTPLGAINSSLPYQNIHPVTIGE CPKYVRSAKLRMVTGLRNNPSIQSRGLFGAIAGFIEGGWT GMIDGWYGYHHQNEQGSGYAADQKSTQNAINGITNKVN TVIEKMNIQFTAVGKEFNKLEKRMENLNKKVDDGFLDIW TYNAELLVLLENERTLDFHDSNVKNLYEKVKSQLKNNAK EIGNGCFEFYHKCDNECMESVRNGTYDYPKYSEESKLNR EKVDGVKLESMGIYQILAIYSTVASSLVLLVSLGAISFWM CSNGSLQCRICI |
| 2 | Exemplary H2 HA | MAIIYLILLFTAVRGDQICIGYHSNNSTEKVDTILERNVTV THAQNILEKTHNGKLCKLNGIPPLELGDCSIAGWLLGNPE CDRLLTVPEWSYIMEKENPRNGLCYPGSFNDYEELKHLLS SVTHFEKVKILPKDRWTQHTTTGGSRACAVSGNPSFFRN MVWLTKKGSNYPIAKGSYNNTSGEQMLIIWGVHHPSNDE TEQRTLYQNVGTYVSIGTSTLNKRSIPVIATRPKVNGQGG RMEFSWTILDIWDTINFESTGNLIAPEYGFRISKRGSSGIM KTEGTLENCETKCQTPLGAINTTLPFHNVHPLTIGECPKYV KSERLVLATGLRNVPQIESRGLFGAIAGFIEGGWQGMIDG WYGYHHSNDQGSGYAADKESTQKAIDGITNRVNSVIEK MNTQFEAVGKEFSNLEKRLENLNKKMEDGFLDVWTYNA ELLVLMENERTLDFHDSNVKNLYDRVRMQLRDNAKELG NGCFEFYHKCDDECMNSVKNGTYDYPKYEEESKLNRNEI KGVKLSNMGVYQILAIYATVAGSLSLAIMIAGISLWMCSN GSLQCRICI |
| 3 | Exemplary H3 HA | MKTIIALSYIFCLALGQDLPGNDNSTATLCLGHHAVPNGT LVKTITDDQIEVTNATELVQSSSTGKICNNPHRILDGIDCT LIDALLGDPHCDVFQNETWDLFVERSKAFSNCYPYDVPD YASLRSLVASSGTLEFITEGFTWTGVTQNGGSNACKRGPG NGFFSRLNWLTKSGSTYPVLNVTMPNNDNFDKLYIWGV HHPSTNQEQTSLYVQESGRVTVSTRRSQQSIIPNIGSRPWV RGQSSRISIYWTIVKPGDVLVINSNGNLIAPRGYFKMRTG |

TABLE 2-continued

Description of Sequences.

| SEQ ID NO | Description | Sequence |
|---|---|---|
| | | KSSIMSSDAPIDTCISECITPNGSIPNDKPFQNVNKITYGAC PKYVKQNTLKLATGMRNVPEKQTRGLFGAIAGFIENGWE GMIDGWYGFRHQNSEGTGQAADLKSTQAAIDQINGKLN RVIEKTNEKFHQIEKEFSEVEGRIQDLEKYVEDTKIDLWSY NAELLVALENQHTIDLTDSEMNKLFEKTRRQLRENAEDM GNGCFKIYHKCDNACIESIRNGTYDHDVYRDEALNNRFQI KGVELKSGYKDWILWISFAISCFLLCVVLLGFIMWACQRG NIRCNICI |
| 4 | Exemplary H4 HA | MLSIVILFLLIAENSSQNYTGNPVICMGHHAVANGTMVKT LADDQVEVVTAQELVESQNLPELCPSPLRLVDGQTCDIIN GALGSPGCDHLNGAEWDVFIERPNAVDTCYPFDVPEYQS LRSILANNGKFEFIAEEFQWNTVKQNGKSGACKRANVDD FFNRLNWLVKSDGNAYPLQNLTKINNGDYARLYIWGVH HPSTSTEQTNLYKNNPGRVTVSTKTSQTSVVPDIGSRPLV RGQSGRVSFYWTIVEPGDLIVFNTIGNLIAPRGHYKLNNQ KKSTILNTAIPIGSCVSKCHTDKGSLSTTKPFQNISRIAVGD CPRYVKQGSLKLATGMRNIPEKASRGLFGAIAGFIENGW QGLIDGWYGFRHQNAEGTGTAADLKSTQAAIDQINGKLN RLIEKTNDKYHQIEKEFEQVEGRIQDLENYVEDTKIDLWS YNAELLVALENQHTIDVTDSEMNKLFERVRRQLRENAED KGNGCFEIFHKCDNNCIESIRNGTYDHDIYRDEAINNRFQI QGVKLTQGYKDIILWISFSISCFLLVALLLAFILWACQNGN IRCQICI |
| 5 | Exemplary H5 HA | MERIVLLLAIVSLVKSDQICIGYHANKSTKQVDTIMEKNV TVTHAQDILERTHNGKLCSLNGVKPLILRDCSVAGWLLG NPMCDEFLNLPEWLYIVEKDNPINSLCYPGDFNDYEELKY LLSSTNHFEKIRIIPRSSWSNHDASSGVSSACPYIGRSSFLR NVVWLIKKNNTYPTIKRSYNNTNQEDLLILWGIHHPNDA AEQTKLYQNPTTYVSVGTSTLNQRSIPEIATRPKVNGQSG RMEFFWTILKPNDAINFESNGNFIAPRYAYKIVKKGDSAI MKSGLAYGNCDTKCQTPVGEINSSMPFHNIHPHTIGECPK YVKSDRLVLATGLRNVPQRKKRGLFGAIAGFIEGGWQG MVDGWYGYHHSNEQGSGYAADKESTQKAIDGITNKVNS IIDKMNTRFEAVGKEFNNLERRVENLNKKMEDGFLDVWT YNVELLVLMENERTLDFHDSNVNNLYDKVRLQLKDNAR ELGNGCFEFYHKCDNECMESVRNGTYDPQYSEEARLNR EEISGVKLESMGVYQILSIYSTVASSLALAIMIAGLSFWMC SNGSLQCRICI |
| 6 | Exemplary H6 HA | MIAIIVVAILATAGRSDKICIGYHANNSTTQIDTILEKNVTV THSVELLENQKEERFCKILKKAPLDLKGCTIEGWILGNPQ CDLLLGDQSWSYIVERPTAQNGICYPGVLNEVEELKALIG SGERVERFEMFPKSTWTGVDTSSGVTRACPYNSGSSFYR NLLWIIKTKSAAYSVIKGAYNNTGNQPILYFWGVHHPPDT NEQNTLYGSGDRYVRMGTESMNFAKSPEIAARPAVNGQ RGRIDYYWSILKPGETLNVESNGNLIAPWYAFRFVSTSNK GAVFKSNLPIENCDATCQTVAGVLRTNKTFQNVSPLWIGE CPKYVKSESLRLATGLRNVPQIETRGLFGAIAGFIEGGWT GMIDGWYGYHHENSQGSGYAADRESTQKAVDGITNKVN SIIDKMNTQFEAVDHEFSNLERRIDNLNKRMEDGFLDVW TYNAELLVLLENERTLDLHDANVKNLYERVKSQLRDNA MILGNGCFEFWHKCDDECMESVKNGTYDYPKYQDESKL NRQEIESVKLESLGVYQILAIYSTVSSSLVLVGLIIAVGLW MCSNGSMQCRICI |
| 7 | Exemplary H7 HA | MNTQILVFALVAVIPTNADKICLGHHAVSNGTKVNTLTER GVEVVNATETVERTNIPKICSKGKRTTDLGQCGLLGTITG PPQCDQFLEFSADLIIERREGNDVCYPGKFVNEEALRQILR GSGGIDKETMGFTYSGIRTNGTTSACRRSGSSFYAEMEWL LSNTDNASFPQMTKSYKNTRRESALIVWGIBESGSTTEQT KLYGSGNKLITVGSSKYHQSFVPSPGTRPQINGQSGRIDFH WLILDPNDTVTFSFNGAFIAPNRASFLRGKSMGIQSDVQV DANCEGECYHSGGTITSRLPFQNINSRAVGKCPRYVKQES LLLATGMKNVPEPSKKRKKRGLFGAIAGFIENGWEGLVD GWYGFRHQNAQGEGTAADYKSTQSAIDQITGKLNRLIEK TNQQFELIDNEFTEVEKQIGNLINWTKDSITEVWSYNAELI VAMENQHTIDLADSEMNRLYERVRKQLRENAEEDGTGC FEIFHKCDDDCMASIRNNTYDHSKYREEAMQNRIQIDPVK LSSGYKDVILWFSFGASCFLLLAIAMGLVFICVKNGNMRC TICI |

TABLE 2-continued

Description of Sequences.

| SEQ ID NO | Description | Sequence |
|---|---|---|
| 8 | Exemplary H8 HA | MEKFIAIATLASTNAYDRICIGYQSNNSTDTVNTLIEQNVP VTQTMELVETEKHPAYCNTDLGAPLELRDCKIEAVIYGNP KCDIHLKDQGWSYIVERPSAPEGMCYPGSVENLEELRFVF SSAASYKRIRLFDYSRWNVTRSGTSKACNASTGGQSFYRS INWLTKKEPDTYDFNEGAYVNNEDGDIIFLWGIHHPPDTK EQTTLYKNANTLSSVTTNTINRSFQPNIGPRPLVRGQQGR MDYYWGILKRGETLKIRTNGNLIAPEFGYLLKGESYGRII QNEDIPIGNCNTKCQTYAGAINSSKPFQNASRHYMGECPK YVKKASLRLAVGLRNTPSVEPRGLFGAIAGFIEGGWSGMI DGWYGFHHSNSEGTGMAADQKSTQEAIDKITNKVNNIVD KMNREFEVVNHEFSEVEKRINMINDKIDDQIEDLWAYNA ELLVLLENQKTLDEHDSNVKNLFDEVKRRLSANAIDAGN GCFDILHKCDNECMETIKNGTYDHKEYEEEAKLERSKING VKLEENTTYKILSIYSTVAASLCLAILIAGGLILGMQNGSC RCMFCI |
| 9 | Exemplary H9 HA | METKAIIAALLMVTAANADKICIGYQSTNSTETVDTLTES NVPVTHTKELLHTEHNGMLCATDLGHPLILDTCTIEGLIY GNPSCDILLGGKEWSYIVERSSAVNGMCYPGNVENLEEL RSLFSSAKSYKRIQIFPDKTWNVTYSGTSRACSNSFYRSM RWLTHKSNSYPEQNAHYTNNERENILEMWGIHEIPPTDTE QTDLYKNADTTTSVTTEDINRTFKPVIGPRPLVNGQQGRI DYYWSVLKPGQTLRIRSNGNLIAPWYGHVLTGESHGRIL KTDLNNGNCVVQCQTEKGGLNTTLPFHNISKYAFGNCPK YVGVKSLKLPVGLRNVPAVSSRGLEGAIAGFIEGGWPGL VAGWYGFQHSNDQGVGMAADKGSTQKAIDKITSKVNNII DKMNKQYEVIDHEFNELEARLNMINNKIDDQIQDIWAYN AELLVLLENQKTLDEHDANVNNLYNKVKRALGSNAVED GNGCFELYHKCDDQCMETIRNGTYDRQKYQEESRLERQ KIEGVKLESEGTYKILTIYSTVASSLVLAMGEAAELFWAM SNGSCRCNICI |
| 10 | Exemplary H10 HA | MYKVVVIIALLGAVKGLDRICLGHHAVANGTIVKTLTNE QEEVTNATETVESTNLNKLCMKGRSYKDLGNCHPVGMLI GTPVCDPHLTGTWDTLIERENAIAHCYPGATINEEALRQK IMESGGISKMSTGFTYGSSITSAGTTKACMRNGGDSFYAE LKWLVSKTKGQNFPQTTNTYRNTDTAEHLIIWGIHHPSST QEKNDLYGTQSLSISVESSTYQNNFVPVVGARPQVNGQS GRIDFHWTLVQPGDNITFSDNGGLIAPSRVSKLTGRDLGIQ SEALIDNSCESKCFWRGGSINTKLPFQNLSPRTVGQCPKY VNQRSLLLATGMRNVPEVVQGRGLFGAIAGFIENGWEG MVDGWYGFRHQNAQGTGQAADYKSTQAAIDQITGKLNR LIEKTNTEFESIESEESETEHQIGNVINWTKDSITDIWTYNA ELLVAMENQHTIDMADSEMLNLYERVRKQLRQNAEEDG KGCFEIYHTCDDSCMESIRNNTYDHSQYREEALLNRLNIN PVKLSSGYKDIILWFSFGESCFVLLAVVMGLVEFCLKNGN MRCTICI |
| 11 | Exemplary H11 HA | MEKTLLEAAIELCVKADEICIGYLSNNSTDKVDTIIENNVT VTSSVELVETEHTGSFCSINGKQPISLGDCSFAGWILGNPM CDELIGKTSWSYIVEKPNPTNGICYPGTLESEEELRLKFSG VLEENKEEVETSNGWGAVNSGVGVTAACKEGGSNSFERN MVWLIHQSGTYPVIKRTFNNTKGRDVLIVWGIHHPATLTE HQDLYKKDSSYVAVGSETYNRRFTPEINTRPRVNGQAGR MTFYWKIVKPGESITFESNGAFLAPRYAFEIVSVGNGKLF RSELNIESCSTKCQTEIGGINTNKSFHNVHRNTIGDCPKYV NVKSLKLATGPRNVPAIASRGLFGAIAGFIEGGWPGLING WYGFQHRDEEGTGIAADKESTQKAIDQITSKVNNIVDRM NTNFESVQHEFSEIEERINQLSKHVDDSVVDIWSYNAQLL VLLENEKTLDLHDSNVRNLHEKVRRMLKDNAKDEGNGC FTEYHKCDNKCIERVRNGTYDHKEFEEESKINRQEIEGVK LDSSGNVYKILSIYSCIASSLVLAALIMGFMFWACSNGSCR CTICI |
| 12 | Exemplary H12 HA | MEKFIILSTVLAASFAYDKICIGYQTNNSTETVNTLSEQNV PVTQVEELVHRGIDPILCGTELGSPLVLDDCSLEGLILGNP KCDLYLNGREWSYIVERPKEMEGVCYPGSIENQEELRSLF SSIKKYERVKMFDFTKWNVTYTGTSKACNNTSNQGSFYR SMRWLTLKSGQFPVQTDEYKNTRDSDIVFTWAIHHPPTS DEQVKLYKNPDTLSSVTTVEINRSFKPNIGPRPLVRGQQG RMDYYWAVLKPGQTVKIQTNGNLIAPEYGHLITGKSHGR ILKNNLPMGQCVTECQLNEGVMNTSKPFQNTSKHYIGKC PKYIPSGSLKLAIGLRNVPQVQDRGLFGAIAGFIEGGWPGL |

TABLE 2-continued

Description of Sequences.

| SEQ ID NO | Description | Sequence |
|---|---|---|
| | | VAGWYGFQHQNAEGTGIAADRDSTQRAIDNMQNKLNNV IDKMNKQFEVVNHEFSEVESRINMINSKIDDQITDIWAYN AELLVLLENQKTLDEHDANVRNLHDRVRRVLRENAIDTG DGCFEILHKCDNNCMDTIRNGTYNHKEYEEESKIERQKV NGVKLEENSTYKILSIYSSVASSLVLLLMIIGGFIFGCQNGN VRCTFCI |
| 13 | Exemplary H13 HA | MALNVIATLTLISVCVHADRICVGYLSTNSSERVDTLLEN GVPVTSSIDLIETNHTGTYCSLNGVSPVHLGDCSFEGWIV GNPACTSNFGIREWSYLIEDPAAPHGLCYPGELNNNGELR HLFSGIRSFSRTELIPPTSWGEVLDGTTSACRDNTGTNSFY RNLVWFIKKNTRYPVISKTYNNTTGRDVLVLWGIHHPVS VDETKTLYVNSDPYTLVSTKSWSEKYKLETGVRPGYNGQ RSWMKIYWSLIHPGEMITFESNGGFLAPRYGYIIEEYGKG RIFQSRIRMSRCNTKCQTSVGGINTNRTFQNIDKNALGDC PKYIKSGQLKLATGLRNVPAISNRGLFGAIAGFIEGGWPG LINGWYGFQHQNEQGTGIAADKESTQKAIDQITTKINNIID KMNGNYDSIRGEFNQVEKRINMLADRIDDAVTDIWSYNA KLLVLLENDKTLDMHDANVKNLHEQVRRELKDNAIDEG NGCFELLHKCNDSCMETIRNGTYDHTEYAEESKLKRQEID GIKLKSEDNVYKALSIYSCIASSVVLVGLILSFIMWACSSG NCRFNVCI |
| 14 | Exemplary H14 HA | MIALILVALALSHTAYSQITNGTTGNPIICLGHHAVENGTS VKTLTDNHVEVVSAKELVETNHTDELCPSPLKLVDGQDC HLINGALGSPGCDRLQDTTWDVFIERPTAVDTCYPFDVPD YQSLRSILASSGSLEFIAEQFTWNGVKVDGSSSACLRGGR NSFFSRLNWLTKATNGNYGPINVTKENTGSYVRLYLWGV HHPSSDNEQTDLYKVATGRVTVSTRSDQISIVPNIGSRPRV RNQSGRISIYWTLVNPGDSIIFNSIGNLIAPRGHYKISKSTK STVLKSDKRIGSCTSPCLTDKGSIQSDKPFQNVSRIAIGNCP KYVKQGSLMLATGMRNIPGKQAKGLFGAIAGFIENGWQ GLIDGWYGFRHQNAEGTGTAADLKSTQAAIDQINGKLNR LIEKTNEKYHQIEKEFEQVEGRIQDLEKYVEDTKIDLWSY NAELLVALENQHTIDVTDSEMNKLFERVRRQLRENAEDQ GNGCFEIFHQCDNNCIESIRNGTYDHNIYRDEAINNRIKINP VTLTMGYKDIILWISFSMSCFVFVALILGFVLWACQNGNI RCQICI |
| 15 | Exemplary H15 HA | MNTQIIVILVLGLSMVKSDKICLGHHAVANGTKVNTLTER GVEVVNATETVEITGIDKVCTKGKKAVDLGSCGILGTIIGP PQCDLHLEFKADLIIERRNSSDICYPGRFTNEEALRQTIRES GGIDKESMGFRYSGIRTDGATSACKRTVSSFYSEMKWLSS SMNNQVFPQLNQTYRNTRKEPALIVWGVHHSSSLDEQNK LYGTGNKLITVGSSKYQQSFSPSPGARPKVNGQAGRIDFH WMLLDPGDTVTFTFNGAFIAPDRATFLRSNAPSGIEYNGK SLGIQSDAQIDESCEGECFYSGGTINSPLPFQNIDSRAVGK CPRYVKQSSLPLALGMKNVPEKIRTRGLFGAIAGFIENGW EGLIDGWYGFRHQNAQGQGTAADYKSTQAAIDQITGKLN RLIEKTNKQFELIDNEFTEVEQQIGNVINWTRDSLTEIWSY NAELLVAMENQHTIDLADSEMNKLYERVRRQLRENAEE DGTGCFEIFHRCDDQCMESIRNNTYNHTEYRQEALQNRI MINPVKLSSGYKDVILWFSFGASCVMLLAIAMGLIFMCV KNGNLRCTICI |
| 16 | Exemplary H16 HA | MMIKVLYFLIIVLGRYSKADKICIGYLSNNSSDTVDTLTEN GVPVTSSVDLVETNHTGTYCSLNGISPIHLGDCSFEGWIV GNPSCATNINIREWSYLIEDPNAPNKFCYPGELDNNGELR HLFSGVNSFSRTELINPSKWGNVLDGVTASCLDRGASSFY RNLVWIVKKDEKYPVIKGDYNNTTGRDVLVLWGIREIPD TETTATNLYVNKNPYTLVSTKEWSKRYELEIGTRIGDGQR SWMKLYWHLMHPGERIMFESNGGLIAPRYGYIIEKYGTG RIFQSGVRMARCNTKCQTSLGGINTNKTFQNIERNALGDC PKYIKSGQLKLATGLRNVPSIGERGLFGAIAGFIEGGWPGL INGWYGFQHQNEQGTGIAADKASTQKAINEITTKINNIIEK MNGNYDSIRGEFNQVEKRINMLADRVDDAVTDIWSYNA KLLVLLENDRTLDLHDANVRNLHDQVKRALKSNAIDEG DGCFNLLHKCNDSCMETIRNGTYNHEDYREESQLKRQEI EGIKLKTEDNVYKVLSIYSCIASSIVLVGLILAFIMWACSN GSCRFNVCI |
| 17 | Exemplary H17 HA | DRICTGITSSNSPHVVKTATQGEVNVTGVIPLTTTPTKSHF ANLKGTQTRGKLCPNCLNCTDLDVALGRPKCMGTIPSAK ASILHEVKPVTSGCFPIMHDRTKIRQLPNLLRGYENIRLSA |

TABLE 2-continued

| Description of Sequences. | | |
|---|---|---|
| SEQ ID NO | Description | Sequence |
| | | RNVTNAETAPGGPYIVGTSGSCPNVTNGNGFFATMAWA VPKNKTATNPLTVEVPYICTKGEDQITVWGFHSDDETQM VKLYGDSKPQKFTSSANGVTTHYVSQIGGFPNQAEDEGL PQSGRIVVDYMVQKPGKTGTIAYQRGVLLPQKVWCASG RSKVIKGSLPLIGEADCLHEKYGGLNKSKPYYTGEHAKAI GNCPIWVKTPLKLANGTKYRPPAKLLK |
| 18 | Exemplary influenza A HA subtype H1 signal peptide | MKANLLVLLCALAAADA |
| 19 | Exemplary influenza A HA subtype H2 signal peptide | MAIIYLILLFTAVRG |
| 20 | Exemplary influenza A HA subtype H3 signal peptide | MKTIIALSYIFCLALG |
| 21 | Exemplary influenza A HA subtype H4 signal peptide | MLSIVILFLLIAENSS |
| 22 | Exemplary influenza A HA subtype H5 signal peptide | MLSIVILFLLIAENSS |
| 23 | Exemplary influenza A HA subtype H6 signal peptide | MIAIIVVAILATAGRS |
| 24 | Exemplary influenza A HA subtype H7 signal peptide | MNTQILVFALVAVIPTNA |
| 25 | Exemplary influenza A HA subtype H8 signal peptide | MEKFIAIATLASTNAY |
| 26 | Exemplary influenza A HA subtype H9 signal peptide | METKAIIAALLMVTAA |
| 27 | Exemplary influenza A HA subtype H10 signal peptide | MYKVVVIIALLGAVKG |
| 28 | Exemplary influenza A HA subtype H11 signal peptide | MEKTLLFAAIFLCVKA |
| 29 | Exemplary influenza A HA subtype H12 signal peptide | MEKFIILSTVLAASFAY |
| 30 | Exemplary influenza A HA subtype H13 signal peptide | MALNVIATLTLISVCVHA |
| 31 | Exemplary influenza A HA subtype H14 signal peptide | MIALILVALALSHTAYS |
| 32 | Exemplary influenza A HA subtype H15 signal peptide | MNTQIIVILVLGLSMVKS |
| 33 | Exemplary influenza A HA subtype H16 signal peptide | MMIKVLYFLIIVLGRYSKA |

TABLE 2-continued

Description of Sequences.

| SEQ ID NO | Description | Sequence |
|---|---|---|
| 34 | Exemplary influenza A HA2 domain subtype H1 st

TABLE 2-continued

Description of Sequences.

| SEQ ID NO | Description | Sequence |
|---|---|---|
| 46 | Exemplary influenza A HA2 domain subtype H13 stem domain | GLFGAIAGFIEGGWPGLINGWYGFQHNEQGTGIAADKE STQKAIDQITTKINNIIDKMNGNYDSIRGEFNQVEKRINML ADRIDDAVTDIWSYNAKLLVLLENDKTLDMHDANVKNL HEQVRRELKDNAIDEGNGCFELLHKCNDSCMETIRNGTY DHTEYAEESKLKRQEIDGIKLKSE |
| 47 | Exemplary influenza A HA2 domain subtype H14 stem domain | GLFGAIAGFIENGWQGLIDGWYGFRHQNAEGTGTAADLK STQAAIDQINGKLNRLIEKTNEKYHQIEKEFEQVEGRIQDL EKYVEDTKIDLWSYNAELLVALENQHTIDVTDSEMNKLF ERVRRQLRENAEDQGNGCFEIFHQCDNNCIESIRNGTYDH NIYRDEAINNRIKINPVTLT |
| 48 | Exemplary influenza A HA2 domain subtype H15 stem domain | GLFGAIAGFIENGWEGLIDGWYGFRHQNAQGQGTAADY KSTQAAIDQITGKLNRLIEKTNKQFELIDNEFTEVEQQIGN VINWTRDSLTEIWSYNAELLVAMENQHTIDLADSEMNKL YERVRRQLRENAEEDGTGCFEIFHRCDDQCMESIRNNTY NHTEYRQEALQNRIMINPVKLS |
| 49 | Exemplary influenza A HA2 domain subtype H16 stem domain | GLFGAIAGFIEGGWPGLINGWYGFQHNEQGTGIAADKA STQKAINEITTKINNIIEKMNGNYDSIRGEFNQVEKRINML ADRVDDAVTDIWSYNAKLLVLLENDRTLDLHDANVRNL HDQVKRALKSNAIDEGDGCFNLLHKCNDSCMETIRNGTY NHEDYREESQLKRQEIEGIKLKTE |
| 50 | Exemplary cleavage site | ENLYFQX Where in X is G or S |
| 51 | Exemplary influenza A HA2 domain subtype H1 Luminal domain | MGIYQ |
| 52 | Exemplary influenza A HA2 domain subtype H2 Luminal domain | MGVYQ |
| 53 | Exemplary influenza A HA2 domain subtype H3 Luminal domain | SGYKD |
| 54 | Exemplary influenza A HA2 domain subtype H4 Luminal domain | QGYKD |
| 55 | Exemplary influenza A HA2 domain subtype H5 Luminal domain | MGVYQ |
| 56 | Exemplary influenza A HA2 domain subtype H6 Luminal domain | LGVYQ |
| 57 | Exemplary influenza A HA2 domain subtype H7 Luminal domain | SGYKD |
| 58 | Exemplary influenza A HA2 domain subtype H8 Luminal domain | NTTYK |
| 59 | Exemplary influenza A HA2 domain subtype H9 Luminal domain | EGTYK |

TABLE 2-continued

Description of Sequences.

| SEQ ID NO | Description | Sequence |
|---|---|---|
| 60 | Exemplary influenza A HA2 domain subtype H10 Luminal domain | SGYKD |
| 61 | Exemplary influenza A HA2 domain subtype H11 Luminal domain | GNVYK |
| 62 | Exemplary influenza A HA2 domain subtype H12 Luminal domain | NSTYK |
| 63 | Exemplary influenza A HA2 domain subtype H13 Luminal domain | DNVYK |
| 64 | Exemplary influenza A HA2 domain subtype H14 Luminal domain | MGYKD |
| 65 | Exemplary influenza A HA2 domain subtype H15 Luminal domain | SGYKD |
| 66 | Exemplary influenza A HA2 domain subtype H16 Luminal domain | DNVYK |
| 67 | Exemplary influenza A HA2 domain subtype H1 Transmembrane domain | ILAIYSTVASSLVLLVSLGAISFWMCS |
| 68 | Exemplary influenza A HA2 domain subtype H2 Transmembrane domain | ILAIYATVAGSLSLAIMIAGISLWMCS |
| 69 | Exemplary influenza A HA2 domain subtype H3 Transmembrane domain | WILWISFAISCFLLCVVLLGFIMWACQ |
| 70 | Exemplary influenza A HA2 domain subtype H4 Transmembrane domain | IILWISFSISCFLLVALLLAFILWACQ |
| 71 | Exemplary influenza A HA2 domain subtype H5 Transmembrane domain | ILSIYSTVASSLALAIMIAGLSFWMCS |
| 72 | Exemplary influenza A HA2 domain subtype H6 Transmembrane domain | ILAIYSTVSSSLVLVGLIIAVGLWMCS |

TABLE 2-continued

Description of Sequences.

| SEQ ID NO | Description | Sequence |
|---|---|---|
| 73 | Exemplary influenza A HA2 domain subtype H7 Transmembrane domain | VILWFSFGASCFLLLAIAMGLVFICVK |
| 74 | Exemplary influenza A HA2 domain subtype H8 Transmembrane domain | ILSIYSTVAASLCLAILIAGGLILGMQ |
| 75 | Exemplary influenza A HA2 domain subtype H9 Transmembrane domain | ILTIYSTVASSLVLAMGFAAFLFWAMS |
| 76 | Exemplary influenza A HA2 domain subtype H10 Transmembrane domain | IILWFSFGESCFVLLAVVMGLVFFCLK |
| 77 | Exemplary influenza A HA2 domain subtype H11 Transmembrane domain | ILSIYSCIASSLVLAALIMGFMFWACS |
| 78 | Exemplary influenza A HA2 domain subtype H12 Transmembrane domain | ILSIYSSVASSLVLLLMIIGGFIFGCQN |
| 79 | Exemplary influenza A HA2 domain subtype H13 Transmembrane domain | ALSIYSCIASSVVLVGLILSFIMWACSS |
| 80 | Exemplary influenza A HA2 domain subtype H14 Transmembrane domain | IILWISFSMSCFVFVALILGFVLWACQ |
| 81 | Exemplary influenza A HA2 domain subtype H15 Transmembrane domain | VILWFSFGASCVMLLAIAMGLIFMCVKN |
| 82 | Exemplary influenza A HA2 domain subtype H16 Transmembrane domain | VLSIYSCIASSIVLVGLILAFIMWACS |
| 83 | Exemplary influenza A HA2 domain subtype H1 Cytoplasmic domain | NGSLQCRICI |
| 84 | Exemplary influenza A HA2 domain subtype H2 Cytoplasmic domain | NGSLQCRICI |

TABLE 2-continued

Description of Sequences.

| SEQ ID NO | Description | Sequence |
|---|---|---|
| 85 | Exemplary influenza A HA2 domain subtype H3 Cytoplasmic domain | RGNIRCNICI |
| 86 | Exemplary influenza A HA2 domain subtype H4 Cytoplasmic domain | NGNIRCQICI |
| 87 | Exemplary influenza A HA2 domain subtype H5 Cytoplasmic domain | NGSLQCRICI |
| 88 | Exemplary influenza A HA2 domain subtype H6 Cytoplasmic domain | NGSMQCRICI |
| 89 | Exemplary influenza A HA2 domain subtype H7 Cytoplasmic domain | NGNMRCTICI |
| 90 | Exemplary influenza A HA2 domain subtype H8 Cytoplasmic domain | NGSCRCMFCI |
| 91 | Exemplary influenza A HA2 domain subtype H9 Cytoplasmic domain | NGSCRCNICI |
| 92 | Exemplary influenza A HA2 domain subtype H10 Cytoplasmic domain | NGNMRCTICI |
| 93 | Exemplary influenza A HA2 domain subtype H11 Cytoplasmic domain | NGSCRCTICI |
| 94 | Exemplary influenza A HA2 domain subtype H12 Cytoplasmic domain | GNVRCTFCI |
| 95 | Exemplary influenza A HA2 domain subtype H13 Cytoplasmic domain | GNCRFNVCI |
| 96 | Exemplary influenza A HA2 domain subtype H14 Cytoplasmic domain | NGNIRCQICI |
| 97 | Exemplary influenza A HA2 domain subtype H15 Cytoplasmic domain | GNLRCTICI |
| 98 | Exemplary influenza A HA2 domain subtype H16 Cytoplasmic domain | NGSCRFNVCI |
| 99 | HA2 Domain of Influenza B HA construct variant | GFFGAIAGFLEGGWEGMIAGWHGYTSHGAHGVAVAADL KSTQEAINKITKNLNSLSELEVKNLQRLSGAMDELHNEIL ELDEKVDDLRADTISSQIELAVLLSNEGIINSEDEHLLALE |

TABLE 2-continued

| Description of Sequences. | | |
|---|---|---|
| SEQ ID NO | Description | Sequence |
| | Arg50-Ser277 | RKLKKMLGPSAVEIGNGCFETKHKCNQTCLDRIAAGTFD AGEFSLPTFDSLNITAASLNDDGLDNHTILLYYSTAASSLA VTLMIAIFVVYMVSRDNVSCSICL |
| 100 | 281 turn loop linker | ITPNGSIPNDKPFQNVNKITYGA |
| 101 | 6xHi stag | HHHHHH |
| 102 | Exemplary foldon domain sequence | GSGYIPEAPRDGQAYVRKDGEWVLLSTFL |
| 103 | Exemplary thrombin cleavage site | LVPRGSP |
| 104 | Exemplary linker sequence | KLNGSGIMKTEGTLEN |
| 105 | Exemplary linker sequence | NNIDT |
| 106 | Exemplary linker sequence | KLNGSGIMKTEGTLEN |
| 107 | Conserved NA epitope | ILRTQESEC |

8. EQUIVALENTS

All publications, patents and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A vaccine formulation comprising three vectors, an influenza virus neuraminidase polypeptide from an N1, an influenza virus neuraminidase polypeptide from an N2, and an influenza virus neuraminidase polypeptide from an influenza B virus, wherein each vector comprises a chimeric HA, wherein the first vector comprises a first chimeric HA comprising an HA stem domain polypeptide from an H1 influenza virus HA and a first HA globular head domain, the second vector comprises a second chimeric HA comprising an HA stem domain polypeptide from an H3 influenza virus HA and a second HA globular head domain, and the third vector comprises a third chimeric HA comprising an HA stem domain polypeptide from an influenza B virus HA and a third HA globular head domain, wherein the first, second and third HA globular head domains are each from a different subtype or strain of influenza virus hemagglutinin, and wherein the HA globular head domain of each chimeric HA is heterologous to the HA stem domain polypeptide of each chimeric HA.

2. The vaccine formulation of claim 1, wherein one or more of the vectors is a viral vector.

3. The vaccine formulation of claim 2, wherein each viral vector is an inactivated viral vector, or a live attenuated viral vector.

4. The vaccine formulation of claim 1, which is a split virus vaccine.

5. The vaccine formulation of claim 1, wherein one or more of the vectors is an influenza virus.

6. The vaccine of claim 4, wherein each of the vectors is an influenza virus.

7. A vaccine formulation of comprising three vectors, an influenza virus neuraminidase polypeptide from an N1, an influenza virus neuraminidase polypeptide from an N2 and an influenza virus neuraminidase polypeptide from an influenza B virus, wherein each vector comprises a chimeric HA, wherein the first vector comprises a first chimeric HA comprising an HA stem domain polypeptide from an H1 influenza virus HA and a first HA globular head domain, the second vector comprises a second chimeric HA comprising an HA stem domain polypeptide from an H3 influenza virus HA and a second HA globular head domain, and the third vector comprises a third chimeric HA comprising an HA stem domain polypeptide from an influenza B virus HA and a third HA globular head domain, wherein the first, second and third HA globular head domains are each from a different subtype or strain of influenza virus hemagglutinin, wherein the HA globular head domain of each chimeric HA is heterologous to the HA stem domain polypeptide of each chimeric HA, and wherein one or more of the vectors is a Newcastle disease virus, an adeno-associated virus, vesicular stomatitis virus, a poxvirus, or an adenovirus.

8. The vaccine formulation of claim 1, wherein each vector is an influenza virus.

9. A vaccine formulation of comprising three vectors, an influenza virus neuraminidase polypeptide from an N1, an influenza virus neuraminidase polypeptide from an N2, and an influenza virus neuraminidase polypeptide from an influenza B virus, wherein each vector comprises a chimeric HA, wherein the first vector comprises a first chimeric HA comprising an HA stem domain polypeptide from an H1 influenza virus HA and a first HA globular head domain, the second vector comprises a second chimeric HA comprising an HA stem domain polypeptide from an H3 influenza virus HA and a second HA globular head domain, and the third vector comprises a third chimeric HA comprising an HA stem domain polypeptide from an influenza B virus HA and a third HA globular head domain, wherein the first, second and third HA globular head domains are each from a different subtype or strain of influenza virus hemagglutinin, wherein the HA globular head domain of each chimeric HA is heterologous to the HA stem domain polypeptide of each chimeric HA, and wherein each vector is a Newcastle disease virus, an adeno-associated virus, vesicular stomatitis virus, a poxvirus, or an adenovirus.

10. The vaccine formulation of claim 1, wherein the HA stem domain polypeptides of the H1 and H3 influenza viruses each comprise an HA1 N-terminal stem segment, an HA1 C-terminal stem segment, an HA2 stem domain; wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

11. The vaccine formulation of claim 10, wherein the first and second influenza virus HA globular head domains consist of the amino acid residues intervening Ap and Aq.

12. The vaccine formulation of claim 1, wherein the first chimeric HA further comprises the H1 influenza virus HA transmembrane and cytoplasmic domains, the second chimeric HA further comprises the H3 influenza virus HA transmembrane and cytoplasmic domains, and the third chimeric HA further comprises the influenza B virus transmembrane and cytoplasmic domains.

13. The vaccine formulation of claim 1, wherein the H1 influenza virus is A/California/4/2009 and the H3 influenza virus is A/Perth/16/09.

14. The vaccine formulation of claim 1, wherein the first and second globular head domains are selected from an H4, H5, H7, H8, H11, H12, H14 and H15 subtype.

15. A method for immunizing against influenza virus in a human subject, comprising administering the vaccine formulation of claim 1.

16. The vaccine formulation of claim 12, wherein each vector is an influenza virus.

17. The vaccine formulation of claim 11, wherein the first chimeric HA further comprises the H1 influenza virus HA transmembrane and cytoplasmic domains, the second chimeric HA further comprises the H3 influenza virus HA transmembrane and cytoplasmic domains, and the third chimeric HA further comprises the influenza B virus transmembrane and cytoplasmic domains.

18. The vaccine formulation of claim 17, wherein each vector is an influenza virus.

19. The vaccine formulation of claim 18, wherein the influenza virus is inactivated.

20. The vaccine formulation of claim 18, wherein the influenza virus is live attenuated.

21. The vaccine formulation of claim 7, wherein the HA stem domain polypeptides of the H1 and H3 influenza viruses each comprise an HA1 N-terminal stem segment, an HA1 C-terminal stem segment, an HA2 stem domain; wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

22. The vaccine formulation of claim 21, wherein the first and second influenza virus HA globular head domains consist of the amino acid residues intervening $A_p$ and $A_q$.

23. The vaccine formulation of claim 9, wherein the HA stem domain polypeptides of the H1 and H3 influenza viruses each comprise an HA1 N-terminal stem segment, an HA1 C-terminal stem segment, an HA2 stem domain; wherein the HA1 N-terminal stem segment consists of amino acid residues $HA_{N\text{-}term}$ through $A_p$ of an influenza virus hemagglutinin HA1 domain, and wherein the HA1 C-terminal stem segment consists of amino acid residues $A_q$ through $HA_{C\text{-}term}$ of an influenza virus hemagglutinin HA1 domain, wherein $HA_{N\text{-}term}$ is the N-terminal amino acid of a mature HA0 protein lacking a signal peptide, wherein $HA_{C\text{-}term}$ is the C-terminal amino acid of the HA1 domain, wherein $A_p$ is Cys that corresponds to amino acid position 52 of an influenza virus hemagglutinin HA1 domain according to H3 numbering, and wherein $A_q$ is Cys that corresponds to amino acid position 277 of an influenza virus hemagglutinin HA1 domain of an H3 hemagglutinin according to H3 numbering.

24. The vaccine formulation of claim 23, wherein the first and second influenza virus HA globular head domains consist of the amino acid residues intervening $A_p$ and $A_q$.

* * * * *